United States Patent
Gogliotti et al.

(10) Patent No.: US 10,807,959 B2
(45) Date of Patent: Oct. 20, 2020

(54) WDR5-MLL1 INHIBITORS AND MODULATORS

(71) Applicant: Vanderbilt University, Nashville, TN (US)

(72) Inventors: Rocco D. Gogliotti, Kingston Springs, TN (US); Shaun R. Stauffer, Brentwood, TN (US); KyuOk Jeon, Nashville, TN (US); James M. Salovich, Nashville, TN (US); Jonathan D. Macdonald, Nashville, TN (US); Jonathan J. Mills, Nashville, TN (US); Kenneth M. Meyers, Nashville, TN (US); Joseph R. Alvarado, Cleveland Heights, OH (US); Changho Han, Nashville, TN (US); Stephen W. Fesik, Nashville, TN (US); Taekyu Lee, Brentwood, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 16/543,303

(22) Filed: Aug. 16, 2019

(65) Prior Publication Data
US 2020/0055824 A1 Feb. 20, 2020

Related U.S. Application Data

(60) Provisional application No. 62/764,756, filed on Aug. 16, 2018.

(51) Int. Cl.
| | |
|---|---|
| C07D 233/48 | (2006.01) |
| C07D 401/12 | (2006.01) |
| C07D 401/14 | (2006.01) |
| C07D 207/22 | (2006.01) |
| C07D 401/06 | (2006.01) |
| C07D 405/12 | (2006.01) |
| C07D 233/26 | (2006.01) |
| C07D 413/12 | (2006.01) |
| C07D 263/28 | (2006.01) |
| C07D 213/58 | (2006.01) |

(52) U.S. Cl.
CPC ......... *C07D 233/48* (2013.01); *C07D 207/22* (2013.01); *C07D 213/58* (2013.01); *C07D 233/26* (2013.01); *C07D 263/28* (2013.01); *C07D 401/06* (2013.01); *C07D 401/12* (2013.01); *C07D 401/14* (2013.01); *C07D 405/12* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 7,476,688 B2 | 1/2009 | Suzuki et al. | |
| 10,160,763 B2 | 12/2018 | Fesik et al. | |
| 2004/0242627 A1 | 12/2004 | Suzuki et al. | |
| 2019/0084988 A1 | 3/2019 | Fesik et al. | |

FOREIGN PATENT DOCUMENTS

| | | | |
|---|---|---|---|
| WO | 200198276 A1 | 12/2001 | |
| WO | 2002088092 A1 | 11/2002 | |
| WO | WO-2009110985 A2 * | 9/2009 | ........... C07D 401/12 |
| WO | 2017147700 A1 | 9/2017 | |
| WO | 2017147701 A1 | 9/2017 | |
| WO | 2019046944 A1 | 3/2019 | |

OTHER PUBLICATIONS

Cantekin et al, Chemical Abstracts 2012:701057(Abstract of Angewandte Chemie, International Edition, 51(26), 6426-6431) (Year: 2012).*
Aho et al., "Displacement of WDR5 from Chromatin by a WIN Site Inhibitor with Picomolar Affinity", Cell Reports 26, 2019, pp. 2916-2928.
Balgobind et al., "The heterogeneity of pediatric MLL-rearranged acute myeloid leukemia," Leukemia, 2011, 8, 1239-1248.
Cao et al. "Targeting MLL1 H3 K4 methyltransferase activity in MLL leukemia," Molecular Cell, 2014, 53, 247-261.
Carugo et al., "In Vivo Functional Platform Targeting Patient Derived Xenografts Identifies WDR5-Myc Association as a Critical Determinant of Pancreatic Cancer," Cell Reports, 2016, 16, 133-147.
Caslini et al., "Interaction of MLL Amino Terminal Sequences with Menin Is Required for Transformation," Cancer Res., 2007, 67, 7275-83.
Chen et al., "Upregulated WDR5 promotes proliferation, self-renewal and chemoresistance in bladder cancer via mediating H3K4 trimethylation," Scientific Reports, 2015, 5:8293, 1-12.
Dai et al., "WDR5 Expression Is Prognostic of Breast Cancer Outcome," PLoSOne, Sep. 10, 2015, 15 pages.
Dias et al., "Structural analysis of the KANSL1/WDR5/KANSL2 complex reveals that WDR5 is required for efficient assembly and chromatin targeting of the NSL complex," Genes & Development, 2014, 28, 929-942.
Dimartino et al., "Mll rearrangements in human malignancies: lessons from clinical and biological studies," Br. J. Haematol. 1999, 106, 614-626.
Ee et al., "An Embryonic Stem Cell-Specific NuRD Complex Functions through Interaction with WDR5," Stem Cell Reports, 2017, 8, 1488-96.
Karatas et al., "Discovery of a Highly Potent, Cell-Permeable Macrocyclic Peptidomimetic (MM-589) Targeting the WD Repeat Domain 5 Protein (WDR5)-Mixed Lineage Leukemia (MLL) Protein—Protein Interaction," J. Med. Chem., 2017, 60, 4818-4839.

(Continued)

*Primary Examiner* — Zinna Northington Davis
(74) *Attorney, Agent, or Firm* — Michael Best & Friedrich LLP

(57) ABSTRACT

Benzamides and picolinamides that are meta-substituted with imino-, guanidino-, or heterocycle-containing groups disrupt the WDR5-MLL1 protein-protein interaction, and have use in pharmaceutical compositions and in treating proliferative disorders and conditions in a subject, such as cancer.

18 Claims, No Drawings

(56) References Cited

OTHER PUBLICATIONS

Li et al., "MOF and H4 K16 acetylation play important roles in DNA damage repair by modulating recruitment of DNA damage repair protein Mdc1.," Molecular and Cellular Biology, 2010, 30, 5335-47.

Marschalek, "Mechanisms of leukemogenesis by MLL fusion proteins," Br. J. Haematol. 2011, 152, 141-54.

Milne et al., "Leukemogenic MLL Fusion Proteins Bind across a Broad Region of the Hox a9 Locus, Promoting Transcription and Multiple Histone Modifications," Cancer Res., 2005, 65, 11367-74.

Milne et al., "MLL Targets Set Domain Methyltransferase Activity to Hox Gene Promoters," Mol. Cell, 2002, 10, 1107-17.

Nakamura et al., "ALL-1 Is a Histone Methyltransferase that Assembles a Supercomplex of Proteins Involved in Transcriptional Regulation," Mol. Cell, 2002, 10, 1119-28.

Patel et al., "On the Mechanism of Multiple Lysine Methylation by the Human Mixed Lineage Leukemia Protein-1 (MLL1) Core Complex," J. Biol. Chem., 2009, 284, 24242-56.

Pigazzi et al., "MLL partner genes drive distinct gene expression profiles and genomic alterations in pediatric acute myeloid leukemia: an AIEOP study," Leukemia, 2011, 25, 560-563.

Pui et al., "Clinical heterogeneity in childhood acute lymphoblastic leukemia with 11q23 rearrangements," Leukemia, 2003, 4, 700-706.

Senisterra et al., "Small-molecule inhibition of MLL activity by disruption of its interaction with WDR5." Biochem. J., 2013, 449, 151-159.

Slany, "The molecular biology of mixed lineage leukemia," Haematologica, 2009, 94, 984-993.

Sun et al., "WDR5 Supports an N-Myc Transcriptional Complex That Drives a Protumorigenic Gene Expression Signature in Neuroblastoma," Cancer Research, 2015, 75, 5143-54.

Tamai etal., "11q23/MLL Acute Leukemia : Update of Clinical Aspects," J. Clin. Exp. Hematop., 2010, 50, 91-98.

Tan et al., "PI3K/AKT-mediated upregulation of WDR5 promotes colorectal cancer metastasis by directly targeting ZNF407," Cell Death & Disease, 2017, 8, 1-12.

Thachuk et al., "Involvement of a homolog of *Drosophila trithorax* by 11q23 chromosomal translocations in acute leukemias," Cell, 1992, 71, 691-700.

Thomas et al., "Interaction with WDR5 Promotes Target Gene Recognition and Tumorigenesis by MYC," Molecular Cell, 2015, 58, 440-52.

Tomizawa et al., "Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group," Leukemia, 2007, 21, 2258-63.

Yokoyama et al., "Leukemia proto-oncoprotein MLL forms a SET1-like histone methyltransferase complex with menin to regulate Hox gene expression," Mol. Cell Biol., 2004, 24, 5639-49.

Yokoyama et al., "The menin tumor suppressor protein is an essential oncogenic cofactor for MLL-associated leukemogenesis," Cell, 2005, 123, 207-18.

Yu et al., "MLL, a mammalian trithorax-group gene, functions as a transcriptional maintenance factor in morphogenesis," Proc. Natl. Acad. Sci., 1998, 95, 10632-10636.

Song et al., "WDR5 Interacts with Mixed Lineage Leukemia (MLL) Protein via the Histone HS-binding Pocket", The Journal of Biological Chemistry, vol. 283 No. 50, Dec. 12, 2008, pp. 35258-35264.

United States Patent Office Non Final Office Action for U.S. Appl. No. 16/441,854 dated Apr. 1, 2020 (24 pages).

* cited by examiner

WDR5-MLL1 INHIBITORS AND MODULATORS

RELATED APPLICATIONS

This application claims priority to U.S. Provisional Application No. 62/764,756, filed Aug. 16, 2018, which is hereby incorporated by reference in its entirety.

STATEMENT OF GOVERNMENT INTEREST

This invention was made with government support under Contract No. HHSN261200800001E, awarded by the National Institutes of Health. The government has certain rights in the invention.

TECHNICAL FIELD

The present invention relates generally to compounds that inhibit the binding of transcription factors, regulatory regulators, and chromatin to WDR5 and methods of use thereof. In particular embodiments, the present invention provides compositions comprising benzamide compounds and methods of use thereof to inhibit or modulate the interaction of WDR5 with chromatin, cognate transcription and other regulatory factors, including for example the histone methyltransferase MLL1, for the treatment of leukemia, solid cancers and other diseases dependent on activity of WDR5.

BACKGROUND

Mixed lineage leukemia (MLL) presents a heterogeneous group of acute myeloid leukemia and acute lymphoblastic leukemia bearing features of more than one hematopoietic cell lineage. MLL accounts for about 80% of infant acute leukemia cases (Tomizawa, D.; et. al. *Leukemia,* 2007, 21, 2258-63.) and 10% of all acute leukemia cases (Marschalek, R. *Br. J. Haematol.* 2011, 152, 141-54.). MLL leukemia patients have a poor prognosis with overall 5-year survival ratio around 35% (Dimartino, J. F.; Cleary, M. L., *Br. J. Haematol.* 1999, 106, 614-626; Pui, C., et al. *Leukemia,* 2003, 4, 700-706.; Tomizawa, D.; et. al. *Leukemia,* 2007, 21, 2258-63.).

MLL is composed of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of Drosophila trithorax (Trx) (Thachuk, D. C.; et al. *Cell,* 1992, 71, 691-700.). Wild type MLL binds to regulatory regions of homeox (HOX) genes (Milne, T. A.; et al. *Cancer Res.,* 2005, 65, 11367-74.) through the amino terminal fragment while the catalytic C-terminal domain catalyzes the Histone 3 lysine 4 (H3K4) methylation via interaction with WDR5 and up regulates target gene transcription (Nakamura, T.; et al. *Mol. Cell,* 2002, 10, 1119-28; Yokoyama, A. et al. *Mol. Cell Biol.,* 2004, 24, 5639-49.; Milne, T. A.; et al. *Mol. Cell,* 2002, 10, 1107-17). Wild type MLL in conjunction with WDR5 is required for maintenance HOX genes expression and is widely expressed not only during embryo development but also in adult tissues including myeloid and lymphoid cells (Yu, B. D.; et al. *Proc. Natl. Acad. Sci.,* 1998, 95, 10632-10636.). Reciprocal translocations of MLL gene result in-frame fusion of the 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, C., et al. *Leukemia,* 2003, 4, 700-706; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, C.; et al. *Cancer Res.,* 2007, 67, 7275-83.; Yokoyama, A.; et al. *Cell,* 2005, 123, 207-18.). The numerous chromosomal translocations of MLL gene and partner genes add to the complexity of MLL leukemia treatment. Although HOX9 and MEIS1 overexpression are commonly observed among MLL leukemia patients, each rearrangement leads to distinct dysregulated target gene expression patterns and downstream events (Slany, R. K., *Haematologica,* 2009, 94, 984-993). Clinical studies reveal that MLL of different chromosomal translocations are associated with different prognosis and are treated differently under current protocols (Tamai, H., et al. *J. Clin. Exp. Hematop.,* 2010, 50, 91-98; Balgobind, B. V., et al. *Leukemia,* 2011, 8, 1239-1248; Pigazzi, M.; et al. Leukemia, 2011, 25, 560-563).

Intrinsic histone methyltransferase (HMT) activity of MLL1 is extremely low and requires a complex assembly of WDR5, RbBP5, ASH2L, and DPY30 protein partners for effective H3K4 trimethylation, the so-called WRAD complex (Patel, A.; et al. *J. Biol. Chem.,* 2009, 284, 24242-56). The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, F.; et al. *Molecular Cell,* 2014, 53, 247-61., Karatas, H.; et al. *J. Med. Chem.,* 2017, 60, 4818-4839.). In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. In addition to the highly characterized WDR5-MLL1 interaction, disruption of WDR5 with other recent transcription factors or displacement from chromatin itself could have a desirable benefit as a cancer treatment strategy. For example, WDR5 acts as a scaffold protein with the following chromatin complexes/structures, including histone H3 (via R2 residues, e.g. see Song, J.-J., et al. *J. Biol. Chem.* 2008, 283, 35258-64), NSL/MOF (Li, X., et al. Molecular and Cellular Biology, 2010, 30, 5335-47., Dias, J., et al. *Genes & Development,* 2014, 28, 929-942.), C/EBPα p30 (Senisterra, G., et al. *Biochem. J.,* 2013, 449, 151-159.), c-MYC (Thomas, L. R.; et al. *Molecular Cell,* 2015, 58, 440-52., herein incorporated by reference in its entirety), and the NuRD complex (Ee, L.-S., et al. Stem Cell Reports, 2017, 8, 1488-96.). In addition, WDR5 expression levels have been reported to be correlative and connected to patient prognosis in several other cancer types, including neuroblastoma (Sun, Y. et al. *Cancer Research,* 2015, 75, 5143-54.), breast cancer (Dai, X. et al. *PLoSOne,* 2015, 10, PMC4565643), bladder cancer (Chen, X. et al. *Scientific Reports,* 2015, 5, 8293.), and colorectal cancer (Tan, X. et al. *Cell Death & Disease,*

2017, 8, PMC5386518). In addition, in an unbiased shRNA screen in human xenografts, WDR5 was identified as an important target in pancreatic cancer (Carugo, A. et al. *Cell Reports,* 2016, 16, 133-147.). Based on the growing number of complexes found which utilize WDR5 to maintain tumor fitness and growth, the emerging importance of WDR5 in several cancer types is not unexpected. In the case of the c-MYC-WDR5 interaction, the MYC oncoprotein utilizes a molecularly defined interaction with WDR5 to bind to its target genes on chromatin. MYC is overexpressed in a majority of malignancies and contributes to an estimated 70,000-100,000 cancer deaths per year in the United States. Thus, disruption of WDR5 from chromatin as a strategy to displace MYC from its target genes may provide a beneficial strategy to treat MYC-driven tumors.

SUMMARY

The molecules described herein can inhibit or modulate the interaction of WDR5 with chromatin, cognate transcription and other regulatory factors, including for example the histone methyltransferase MLL1, and can provide a therapeutic approach to treat cancers associated with such interactions (e.g., the MLL1-WDR5 interaction).

The molecules described herein target the WIN-site interaction and provide a therapeutic approach to treat leukemias with translocations of MLL gene, other leukemias with upregulation of target genes, and other solid tumor and diseases dependent on WDR5. As such, the WIN-site inhibitors described herein may have utility through mechanisms of action involving both direct competitive WIN-site antagonism and allosteric disruption of higher complexes wherein WDR5 is dependent for their proliferative activity, tumor formation, and tumor maintenance.

In one aspect, the invention provides compounds of formula (I)

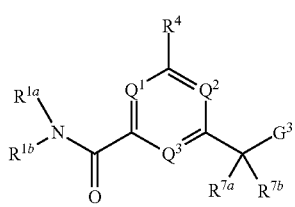

(I)

or a pharmaceutically acceptable salt or tautomer thereof, wherein:

$Q^1$ is N or $CR^3$;
$Q^2$ is N or $CR^5$;
$Q^3$ is N or $CR^2$;
$R^{1a}$ is $C_1$-$C_4$alkyl, $G^1$ or —$(CR^aR^b)_n$-$G^1$;
n is 1, 2, or 3;
$R^a$ is hydrogen, $C_1$-$C_4$alkyl, $C_1$-$C_4$haloalkyl, $C_3$-$C_6$carbocycle, or —$C_1$-$C_3$alkylene-C(O)$YR^{20}$;
Y is O, NH, or $NC_1$-$C_4$alkyl;
$R^{20}$ is H, $C_1$-$C_4$alkyl, $C_3$-$C_6$cycloalkyl, or —$C_1$-$C_3$alkylene-$R^{30}$;
$R^{30}$ is $C(O)C_1$-$C_4$alkyl, $C(O)C_3$-$C_6$cycloalkyl, or phenyl, wherein the $C_3$-$C_6$cycloalkyl and phenyl are optionally substituted with 1-4 substituents independently selected from the group consisting of halogen, $C_1$-$C_4$alkyl, —$OC_1$-$C_4$alkyl, and $C_1$-$C_4$haloalkyl;
$R^b$ is hydrogen or $C_1$-$C_4$alkyl;

optionally $R^a$ and $R^b$ together with the carbon atom to which they are attached form a ring selected from the group consisting of a 3-8 membered saturated or partially unsaturated carbocyclic ring and a 3-8 membered saturated or partially unsaturated heterocyclic ring having 1-4 heteroatoms independently selected from the group consisting of nitrogen, oxygen, or sulfur;
optionally $R^a$ and $R^b$ are taken together to form an oxo group;
$R^{1b}$ is hydrogen, $C_1$-$C_4$alkyl, $C_3$-$C_6$cycloalkyl, or —$C_1$-$C_3$alkylene-$C_3$-$C_6$cycloalkyl;
$G^1$ is 6- to 12-membered aryl, a 5- to 12-membered heteroaryl, a 4- to 12-membered heterocyclyl, or a $C_3$-$C_{10}$carbocycle optionally fused to a phenyl or to a 5- to 6-membered heteroaryl, wherein $G^1$ is optionally substituted with 1-5 substituents independently selected from the group consisting of $C_1$-$C_4$hydroxyalkyl, halogen, $C_1$-$C_6$alkyl, $C_1$-$C_6$haloalkyl, oxo, —$OR^{1c}$, —$N^{1c}R^{1d}$, —$SR^{1c}$, cyano, —$C(O)OR^{1c}$, —$C(O)NR^{1c}R^{1d}$, —$C(O)R^{1e}$, —$SOR^{1e}$, —$SO_2R^{1e}$, —$SO_2NR^{1c}R^{1d}$, —$NR^{1c}C(O)R^{1e}$, —$NR^{1c}C(O)OR^{1d}$, —$NR^{1c}C(O)NR^{1c}R^{1d}$, —$NR^{1c}S(O)_2R^{1e}$, —$NR^{1c}S(O)_2NR^{1c}R^{1d}$, $C_3$-$C_8$cycloalkyl, and —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;
$R^2$ is hydrogen, halo, $C_1$-$C_4$ alkyl, or $C_1$-$C_4$ haloalkyl;
$R^3$ is hydrogen, halo, $C_1$-$C_4$ alkyl, $C_1$-$C_4$ haloalkyl, —$OR^{3a}$, —$NR^{3a}R^{3b}$, —$SR^{3a}$, cyano, —$C(O)OR^{3a}$, —$C(O)NR^{3a}R^{3b}$, —$C(O)R^{3c}$, —$SOR^{3c}$, —$SO_2R^{3c}$, —$SO_2NR^{3a}R^{3b}$, —$NR^{3a}C(O)R^{3c}$, —$NR^{3a}C(O)OR^{3b}$, —$NR^{3a}C(O)NR^{3a}R^{3b}$, —$NR^{3a}S(O)_2R^{3c}$, —$NR^{3a}S(O)_2NR^{3a}R^{3b}$, $C_3$-$C_8$cycloalkyl, or —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;
$R^4$ is hydrogen, halo, $C_1$-$C_6$ alkyl, $C_1$-$C_6$ haloalkyl, $C_1$-$C_6$haloalkenyl, -L-$R^x$, $G^2$, -L-$G^2$, or -L-$C_1$-$C_3$alkylene-$G^2$;
L is O, S, —$NR^{4a}$—, —S(O)—, —$S(O)_2$—, —$S(O)_2NR^{4a}$—, —$C(O)NR^{4a}$—, —C(O)—, —$NR^{4a}C(O)$—, —$NR^{4a}C(O)O$—, —$NR^{4a}C(O)NR^{4a}$—, —$NR^{4a}S(O)_2$—, or —$NR^{4a}S(O)_2NR^{4a}$—;
$R^x$ is hydrogen, $C_1$-$C_6$alkyl, or $C_1$-$C_6$haloalkyl;
$G^2$ is a $C_3$-$C_{10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of $C_1$-$C_4$hydroxyalkyl, halogen, $C_1$-$C_6$alkyl, $C_1$-$C_6$haloalkyl, oxo, —$OR^{4b}$, —$NR^{4b}R^{4c}$, —$SR^{4b}$, cyano, —$C(O)OR^{4b}$, —$C(O)NR^{4b}R^{4c}$, —$C(O)R^{4d}$, —$SOR^{4d}$, —$SO_2R^{4d}$, —$SO_2NR^{4b}R^{4c}$, —$NR^{4b}C(O)R^{4d}$, —$NR^{4b}C(O)OR^{4c}$, —$NR^{4b}C(O)NR^{4b}R^{4c}$, —$NR^{4b}S(O)_2R^{4d}$, —$NR^{4b}S(O)_2NR^{4b}R^{4c}$, $C_3$-$C_8$cycloalkyl, and —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;
$R^5$ is hydrogen, halo, $C_1$-$C_4$ alkyl, $C_1$-$C_4$ haloalkyl, —$OR^{5a}$, —$NR^{5a}R^{5b}$, —$SR^{5a}$, cyano, —$C(O)OR^{5a}$, —$C(O)NR^{5a}R^{5b}$, —$C(O)R^{5c}$, —$SOR^{5c}$, —$SO_2R^{5c}$, —$SO_2NR^{5a}R^{5b}$, —$NR^{5a}C(O)R^{5c}$, —$NR^{5a}C(O)OR^{5b}$, —$NR^{5a}C(O)NR^{5a}R^{5b}$, —$NR^{5a}S(O)_2R^{5c}$, —$NR^{5a}S(O)_2NR^{5a}R^{5b}$, $C_3$-$C_8$cycloalkyl, or —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;

$G^3$ is

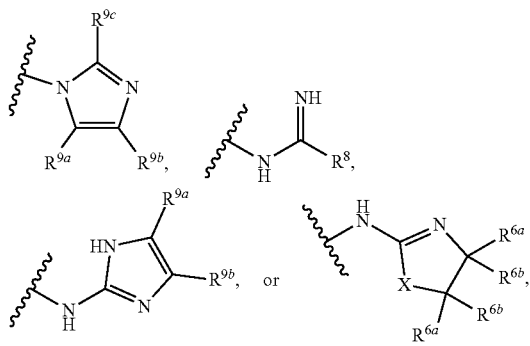

provided that $R^4$ is not hydrogen when $G^3$ is

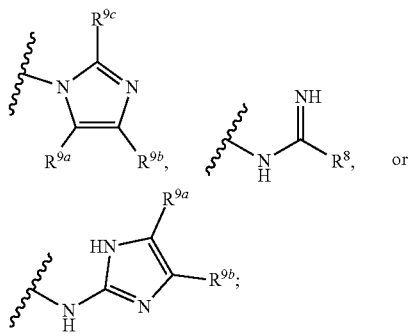

X is O, NR or $(CR^{6a}R^{6b})_{1-2}$;

R is independently hydrogen or $C_1$-$C_4$ alkyl;

$R^{6a}$ and $R^{6b}$, at each occurrence, are each independently hydrogen, $C_1$-$C_4$alkyl, $C_1$-$C_4$haloalkyl, $G^{3a}$, or —$C_1$-$C_3$alkylene-$G^{3a}$, wherein optionally each $R^{6a}$ and $R^{6b}$, independently, are taken together to form an oxo group, a 3-8 membered saturated or partially unsaturated carbocyclic ring, or a 3-8 membered saturated or partially unsaturated heterocyclic ring having 1-4 heteroatoms independently selected from the group consisting of nitrogen, oxygen, and sulfur;

$R^{7a}$ and $R^{7b}$ are independently hydrogen, halogen, $C_1$-$C_4$alkyl, or $C_1$-$C_4$haloalkyl, or $R^{7a}$ and $R^{7b}$ are taken together to form an oxo group;

$R^8$ is —$NR^{8a}R^{8b}$, $C_1$-$C_6$alkyl, $C_1$-$C_6$haloalkyl, $G^{3a}$, or —$C_1$-$C_3$alkylene-$G^{3a}$;

$R^{8a}$ and $R^{8b}$ are independently hydrogen, $C_1$-$C_6$alkyl, $C_1$-$C_6$haloalkyl, $G^{3a}$, or —$C_1$-$C_3$alkylene-$G^{3a}$;

$R^{9a}$, $R^{9b}$, and $R^{9c}$, are each independently hydrogen, halogen, $C_1$-$C_4$alkyl, $C_1$-$C_4$haloalkyl, or $C_3$-$C_{10}$carbocycle, wherein the $C_3$-$C_{10}$carbocycle is optionally substituted with 1-4 substituents independently selected from the group consisting of halogen, $C_1$-$C_4$alkyl, $C_1$-$C_4$haloalkyl, OH, and —$OC_1$-$C_4$alkyl;

$G^{3a}$ is $C_3$-$C_{10}$carbocycle, a 6- to 12-membered aryl, a 5- to 12-membered heteroaryl, or a 4- to 12-membered heterocycle, wherein $G^{3a}$ is optionally substituted with 1-4 substituents independently selected from the group consisting of halogen, $C_1$-$C_4$alkyl, $C_1$-$C_4$haloalkyl, OH, and —$OC_1$-$C_4$alkyl;

and $R^{1c}$, $R^{1d}$, $R^{1e}$, $R^{3a}$, $R^{3b}$, $R^{3c}$, $R^{4a}$, $R^{4b}$, $R^{4c}$, $R^{4d}$, $R^{5a}$, $R^{5b}$, and $R^{5c}$, at each occurrence, are independently hydrogen, $C_1$-$C_6$alkyl, $C_1$-$C_6$haloalkyl, $C_3$-$C_8$cycloalkyl, or —$C_1$-$C_6$alkylene-$C_3$-$C_8$cycloalkyl, wherein the $C_3$-$C_8$cycloalkyl and —$C_1$-$C_6$alkylene-$C_3$-$C_8$cycloalkyl are optionally substituted with 1-4 substituents independently selected from the group consisting of $C_1$-$C_4$alkyl and halogen, wherein alternatively $R^{1c}$ and $R^{1d}$, $R^{3a}$ and $R^{3b}$, $R^{4b}$ and $R^{4c}$, and/or $R^{5a}$ and $R^{5b}$, each together with a common nitrogen atom to which each attaches form a 4- to 8-membered saturated or partially unsaturated heterocyclic ring, optionally substituted with 1-4 substituents independently selected from the group consisting of $C_1$-$C_4$alkyl, $C_1$-$C_4$haloalkyl, oxo, —OH, and —$OC_1$-$C_4$alkyl.

In another aspect, the invention provides a pharmaceutical composition comprising a compound of formula (I), or a pharmaceutically acceptable salt or tautomer thereof, and a pharmaceutically acceptable carrier.

In another aspect, the invention provides a method for the treatment of cancer, comprising administering to a subject in need thereof a therapeutically effective amount of a compound of formula (I), or a pharmaceutically acceptable salt, tautomer, or composition thereof.

In another aspect, the invention provides a method for inhibiting the binding of MLL1 to WDR5, comprising administering to a subject in need thereof a therapeutically effective amount of a compound of formula (I), or a pharmaceutically acceptable salt, tautomer, or composition thereof.

In another aspect, the invention provides a compound of formula (I), or a pharmaceutically acceptable salt, tautomer, or composition thereof, for use in the treatment of cancer.

In another aspect, the invention provides a compound of formula (I), or a pharmaceutically acceptable salt, tautomer, or composition thereof, for use in the inhibition of binding of MLL1 to WDR5.

In another aspect, the invention provides the use of a compound of formula (I), or a pharmaceutically acceptable salt, tautomer, or composition thereof, in the manufacture of a medicament for the treatment of cancer.

In another aspect, the invention provides the use of a compound of formula (I), or a pharmaceutically acceptable salt, tautomer, or composition thereof, in the manufacture of a medicament for the inhibition of binding of MLL1 to WDR5.

In another aspect, the invention provides a kit comprising a compound of formula (I), or a pharmaceutically acceptable salt, tautomer, or composition thereof, and instructions for use.

In other aspects are provided pharmaceutical compositions comprising the compounds, methods of making the compounds, and methods of using the compounds for inhibiting the binding of WDR5 to chromatin and cognate transcription and other regulatory factors (e.g., the histone methyltransferase MLL1). Also provided are methods of treating cancer, comprising administration of a therapeutically effective amount of a compound of formula (I), or a pharmaceutically acceptable salt thereof to a subject in need thereof.

DETAILED DESCRIPTION

Disclosed herein are inhibitors of WDR5 which bind at the WDR5 interaction or WIN-site. The inhibitors can be compounds of formula (I). Compounds of formula (I) can be used to treat cancers associated with the MLL1-WDR5 interaction. In one aspect, disclosed are compounds of formula (I) as WDR5-WIN-site inhibitors.

Disclosed herein are inhibitors or disruptors of the MLL1-WDR5 protein-protein interaction. The inhibitors can be compounds of formula (I) or (II). Compounds of formula (I) or (II) can be used to treat cancers associated with the MLL1-WDR5 interaction. In one aspect, disclosed are compounds of formula (I) as WDR5-WIN-site inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to the group —O-alkyl. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_1$-$C_6$alkyl" means a straight or branched chain hydrocarbon containing from 1 to 6 carbon atoms. The term "$C_1$-$C_4$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —NR$_x$R$_y$, wherein R$_x$ and R$_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NR$_x$—, wherein R$_x$ may be hydrogen, alkyl, cycloalkyl, aryl, heteroaryl, heterocycle, alkenyl, or heteroalkyl.

The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a saturated ring system containing all carbon atoms as ring members and zero double bonds. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl," as used herein, means a non-aromatic monocyclic or multicyclic ring system containing all carbon atoms as ring members and at least one carbon-carbon double bond and preferably having from 5-10 carbon atoms per ring. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl.

The term "carbocyclyl" or "carbocycle" includes both a "cycloalkyl" and a "cycloalkenyl."

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from the group consisting of S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from the group consisting of O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a monocyclic aromatic or carbocyclic ring, a monocyclic heteroaryl, or a monocyclic heterocycle. The bicyclic heteroaryl group includes a 9-membered fused bicyclic aromatic ring system having four double bonds and at least one heteroatom contributing a lone electron pair to a fully aromatic $10\pi$ electron system, such as ring systems with a nitrogen atom at the ring junction (e.g., imidazopyridine) or a benzoxadiazolyl. The bicyclic heteroaryl is attached to the parent molecular moiety at an aromatic ring atom. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a monocyclic heterocycle fused to a monocyclic heteroaryl, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a non-aromatic ring atom (e.g., 2-oxaspiro[3.3]heptan-6-yl, indolin-1-yl, hexahydro-cyclopenta[b]pyrrol-1(2H)-yl). Representative examples of bicyclic heterocycles include, but are not limited to, benzo-pyranyl, benzothiopyranyl, chromanyl, 2,3-dihydrobenzo-furanyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1] hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methano-cyclopenta[c]furan, aza-adamantane (1-azatricyclo [3.3.1.1³,⁷]decane), and oxa-adamantane (2-oxatricyclo [3.3.1.1³,⁷]decane). The monocyclic, bicyclic, and tricyclic heterocycles are connected to the parent molecular moiety at a non-aromatic ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituted" refers to a group that may be further substituted with one or more non-hydrogen substituent groups. Substituent groups may include, for example, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, compounds have formula (I), wherein $G^3$, $R^{1a}$, $R^{1b}$, $Q^1$, $Q^2$, $Q^3$, $R^4$, $R^{7a}$, and $R^{7b}$ are as defined herein. Embodiments of formula (I) include the following descriptions of $G^3$, $R^{1a}$, $R^{1b}$, $Q^1$, $Q^2$, $Q^3$, $R^4$, $R^{7a}$, and $R^{7b}$ and any combinations thereof.

In some embodiments, $R^4$ is halo, $C_1$-$C_6$ alkyl, $C_1$-$C_6$ haloalkyl, $C_1$-$C_6$haloalkenyl, -L-$R^x$, $G^2$, -L-$G^2$, or -L-$C_1$-$C_3$alkylene-$G^2$, wherein L, $R^x$, and $G^2$ are as defined herein. In further embodiments, $R^4$ is halogen, $C_1$-$C_6$alkyl, $C_1$-$C_6$haloalkyl, —O—$C_1$-$C_6$alkyl, $G^2$, or —O-$G^2$, wherein $G^2$ is as defined herein. In still further embodiments, $G^2$ is a $C_3$-$C_7$carbocycle, a 6- to 10-membered aryl, a 5- to 10-membered heteroaryl, or a 4- to 10-membered heterocycle, wherein $G^2$ is optionally substituted with 1-3 substituents independently selected from the group consisting of $C_1$-$C_4$hydroxyalkyl, halogen, $C_1$-$C_6$alkyl, $C_1$-$C_6$haloalkyl, oxo, —OR$^{4b}$, cyano, —C(O)OR$^{4b}$, —C(O)NR$^{4b}$R$^{4c}$, and $C_3$-$C_8$cycloalkyl, wherein the $C_3$-$C_8$cycloalkyl is optionally substituted with 1-4 substituents independently selected from the group consisting of $C_1$-$C_4$alkyl and halogen, and R$^{4b-4c}$ are as defined herein. In still further embodiments, $R^4$ is halogen, $C_1$-$C_4$alkyl, $C_1$-$C_4$haloalkyl, —O—$C_1$-$C_4$alkyl, $G^{2a}$, or —O-$G^{2b}$; $G^{2a}$ is phenyl, a 5- to 6-membered heteroaryl, or a 4-8-membered heterocycle, wherein $G^{1a}$ is optionally substituted with 1-3 substituents independently selected from the group consisting of $C_1$-$C_4$hydroxyalkyl, halogen, $C_1$-$C_4$alkyl, $C_1$-$C_4$haloalkyl, oxo, —OR$^{4b}$, and —C(O)NR$^{4b}$R$^{4c}$; and $G^{2b}$ is $C_3$-$C_7$cycloalkyl or phenyl, wherein $G^{2b}$ is optionally substituted with $C_1$-$C_4$alkyl, and R$^{4b-4c}$ are as defined herein. In yet further embodiments, $G^{2a}$ is a) phenyl optionally substituted with 1-3 substituents independently selected from the group consisting of $C_1$-$C_4$hydroxyalkyl, halogen, $C_1$-$C_4$alkyl, $C_1$-$C_4$haloalkyl, —OR$^{4b}$, and —C(O)NR$^{4b}$R$^{4c}$; b) a pyrazolyl, pyrrolyl, furanyl, or pyridinyl, optionally substituted with 1-3 substituents independently selected from the group consisting of $C_1$-$C_4$hydroxyalkyl, halogen, $C_1$-$C_4$alkyl, $C_1$-$C_4$haloalkyl, —OR$^{4b}$, and —C(O)NR$^{4b}$R$^{4c}$; or c) pyrrolidinyl or morpholinyl, optionally substituted with 1-3 substituents independently selected from the group consisting of halogen, $C_1$-$C_4$alkyl, and $C_1$-$C_4$haloalkyl, and R$^{4b-4c}$ are as defined herein. In yet further embodiments, $R^4$ is

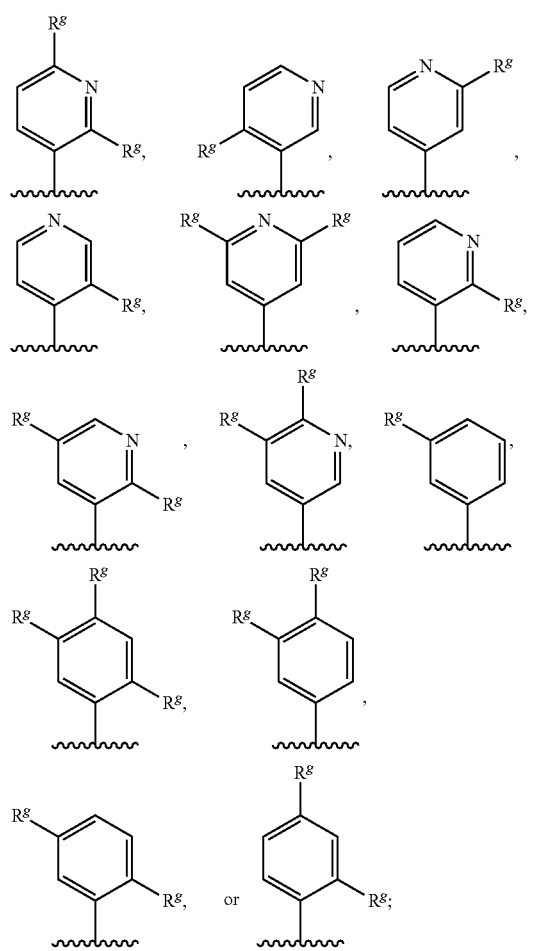
and R$^g$, at each occurrence, is independently halo, C$_1$-C$_4$ alkyl, C$_1$-C$_4$ haloalkyl, or C$_1$-C$_4$ alkoxy. In yet further embodiments, R$^4$ is
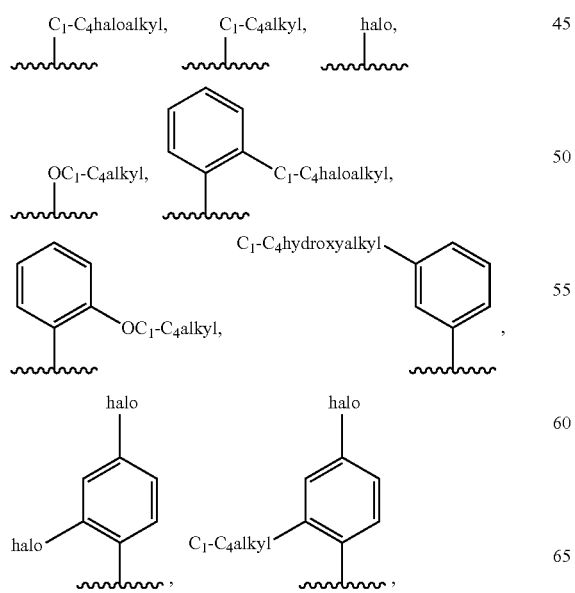
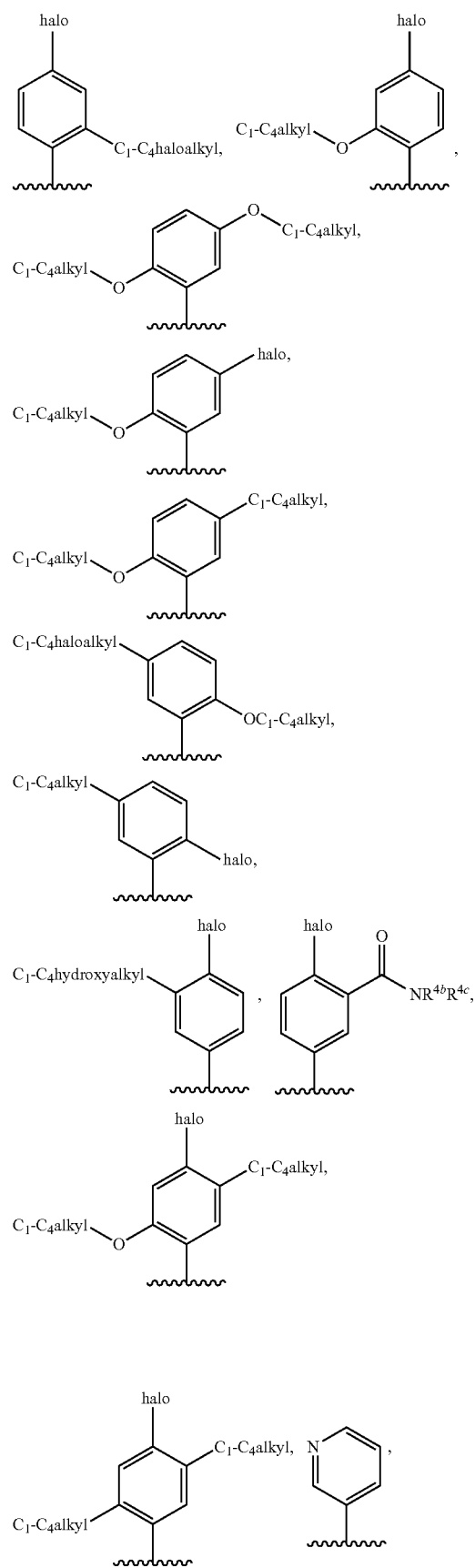

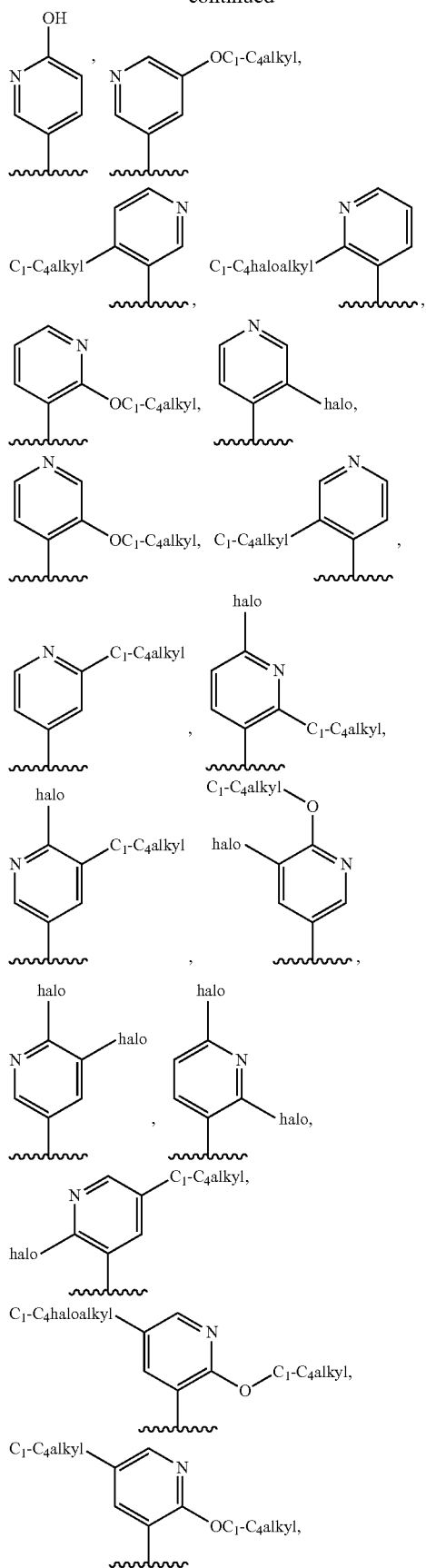

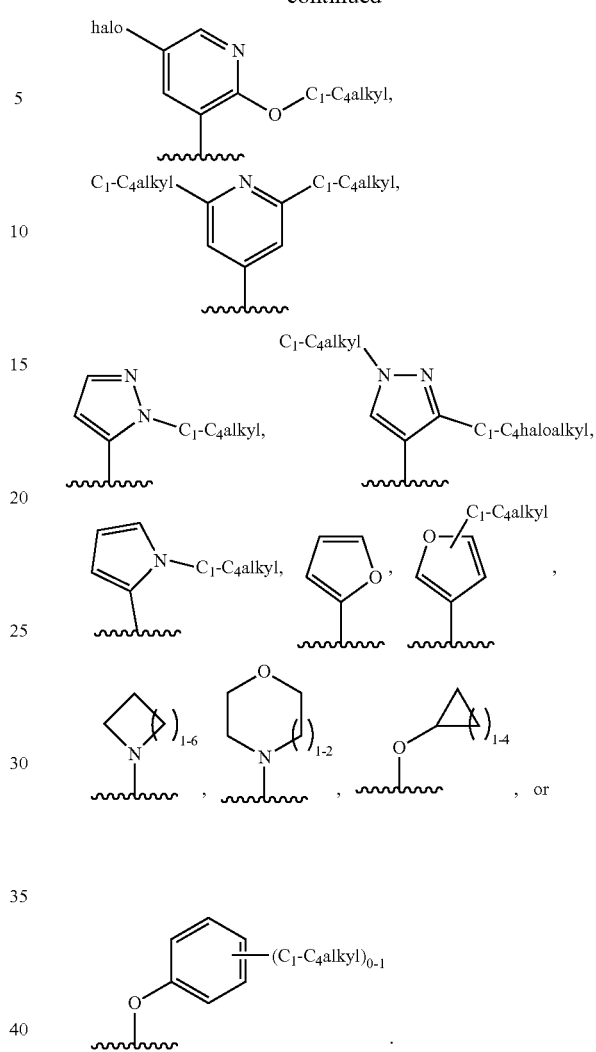

In some embodiments, $G^3$ is

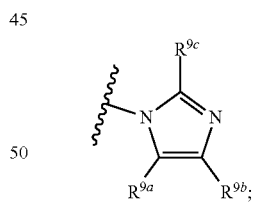

and $R^{9a}$, $R^{9b}$, and $R^{9c}$, are each independently hydrogen, $C_1$-$C_4$alkyl, $C_1$-$C_4$haloalkyl, or $C_3$-$C_6$carbocycle, wherein the $C_3$-$C_6$carbocycle is optionally substituted with 1-4 substituents independently selected from the group consisting of halogen, $C_1$-$C_4$alkyl, $C_1$-$C_4$haloalkyl, OH, and —O$C_1$-$C_4$alkyl. In further embodiments, $R^{9a}$ and $R^{9b}$ are hydrogen; and $R^{9c}$ is hydrogen, $C_1$-$C_4$alkyl, $C_1$-$C_4$haloalkyl, or $C_3$-$C_6$cycloalkyl, wherein the $C_3$-$C_6$cycloalkyl is optionally substituted with 1-4 substituents independently selected from the group consisting of halogen, $C_1$-$C_4$alkyl, $C_1$-$C_4$haloalkyl, OH, and —O$C_1$-$C_4$alkyl. In still further embodiments, $R^{9c}$ is hydrogen, methyl, trifluoromethyl, or cyclopropyl, and $R^{9a-9b}$ are as defined herein.

In some embodiments, G³ is

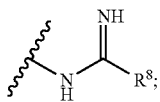

R⁸ is —NR⁸ᵃR⁸ᵇ, G³ᵃ, or —C₁-C₃alkylene-G³ᵃ; R⁸ᵃ and R⁸ᵇ are hydrogen; and G³ᵃ is C₃-C₆carbocycle or a 4- to 8-membered heterocycle, wherein G³ᵃ is optionally substituted with 1-4 substituents independently selected from the group consisting of halogen, C₁-C₄alkyl, C₁-C₄haloalkyl, OH, and —OC₁-C₄alkyl. In further embodiments, G³ᵃ is C₃-C₆cycloalkyl or a 4- to 8-membered heterocycle containing one oxygen atom, wherein G³ᵃ is optionally substituted with 1-4 substituents independently selected from the group consisting of halogen, C₁-C₄alkyl, C₁-C₄haloalkyl, OH, and —OC₁-C₄alkyl. In still further embodiments, R⁸ is —NH₂, cyclopropyl, cyclobutyl, —CH₂-cyclopropyl, 1-methylcycloprop-1-yl, or tetrahydrofuran-3-yl.

In some embodiments, G³ is

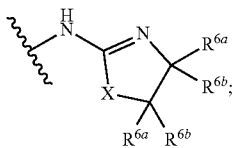

X is NR, and R⁶ᵃ⁻⁶ᵇ are as defined herein.

In some embodiments, G³ is

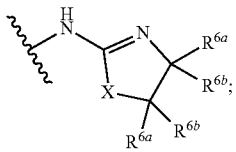

X is CH₂, and R⁶ᵃ⁻⁶ᵇ are as defined herein.

In some embodiments, G³ is

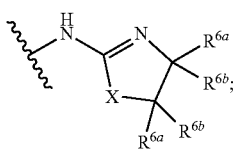

X is O, and R⁶ᵃ⁻⁶ᵇ are as defined herein.

In some embodiments, G³ is

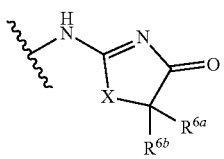

and X and R⁶ᵃ⁻⁶ᵇ are as defined herein.

In the embodiments herein are further embodiments wherein R⁶ᵃ and R⁶ᵇ, at each occurrence, are each hydrogen.

In some embodiments, Q¹ is CR³; Q² is CR⁵; Q³ is CR², and R², R³, and R⁵ are as defined herein.

In some embodiments, Q¹ is N; Q² is CR⁵; Q³ is CR², and R³ and R⁵ are as defined herein.

In the embodiments herein are further embodiments wherein R² is hydrogen.

In the embodiments herein are further embodiments wherein R³ is hydrogen, —NR³ᵃR³ᵇ, or —NR³ᵃC(O)R³ᶜ, and R³ᵃ⁻³ᶜ are as defined herein.

In the embodiments herein are further embodiments wherein R⁵ is hydrogen, halogen, or —OR⁵ᵃ, and R⁵ᵃ is as defined herein.

In some embodiments, R¹ᵃ is G¹ᵃ or —(CRᵃRᵇ)-G¹ᵇ; G¹ᵃ is C₃-C₇carbocycle wherein G¹ᵃ is optionally substituted with 1-4 substituents independently selected from the group consisting of halogen, C₁-C₆alkyl, C₁-C₆haloalkyl, oxo, —NR¹ᶜR¹ᵈ, —SR¹ᶜ, cyano, —C(O)OR¹ᶜ, —C(O)NR¹ᶜR¹ᵈ, —C(O)R¹ᵉ, —SOR¹ᵉ, —SO₂R¹ᵉ, —SO₂NR¹ᶜR¹ᵈ, —NR¹ᶜC(O)R¹ᵉ, —NR¹ᶜC(O)OR¹ᵈ, —NR¹ᶜC(O)NR¹ᶜR¹ᵈ, —NR¹ᶜS(O)₂R¹ᵉ, —NR¹ᶜS(O)₂NR¹ᶜR¹ᵈ, C₃-C₈cycloalkyl, and —C₁-C₃alkylene-C₃-C₈cycloalkyl, wherein the C₃-C₈cycloalkyl and —C₁-C₃alkylene-C₃-C₈cycloalkyl are optionally substituted with 1-4 substituents independently selected from the group consisting of C₁-C₄alkyl and halogen; and G¹ᵇ is C₃-C₇carbocycle, phenyl, or a 5- to 6-membered heteroaryl, wherein G¹ᵇ is optionally substituted with 1-4 substituents independently selected from the group consisting of halogen, C₁-C₆alkyl, C₁-C₆haloalkyl, oxo, —OR¹ᶜ, —NR¹ᶜR¹ᵈ, —SR¹ᶜ, cyano, —C(O)OR¹ᶜ, —C(O)NR¹ᶜR¹ᵈ, —C(O)R¹ᵉ, —SOR¹ᵉ, —SO₂R¹ᵉ, —SO₂NR¹ᶜR¹ᵈ, —NR¹ᶜC(O)R¹ᵉ, —NR¹ᶜC(O)OR¹ᵈ, —NR¹ᶜC(O)NR¹ᶜR¹ᵈ, —NR¹ᶜS(O)₂R¹ᵉ, —N¹ᶜS(O)₂NR¹ᶜR¹ᵈ, C₃-C₈cycloalkyl, and —C₁-C₃alkylene-C₃-C₈cycloalkyl, wherein the C₃-C₈cycloalkyl and —C₁-C₃alkylene-C₃-C₈cycloalkyl are optionally substituted with 1-4 substituents independently selected from the group consisting of C₁-C₄alkyl and halogen; and Rᵃ, Rᵇ, R¹ᶜ, R¹ᵈ, and R¹ᵉ are as defined herein. In further embodiments, G¹ᵃ is C₃-C₇cycloalkyl optionally substituted with 1-4 substituents independently selected from the group consisting of halogen, C₁-C₄alkyl, and C₁-C₄haloalkyl; and G¹ᵇ is C₃-C₇cycloalkyl, phenyl, or a 6-membered heteroaryl containing 1-3 nitrogen atoms, wherein G¹ᵇ is optionally substituted with 1-4 substituents independently selected from the group consisting of halogen, C₁-C₄alkyl, C₁-C₄haloalkyl, and —OR¹ᶜ; and R¹ᶜ is as defined herein. In still further embodiments, R¹ᵃ is G¹ᵃ and G¹ᵃ is C₃-C₇cycloalkyl optionally substituted with C₁-C₄alkyl. In other further embodiments, R¹ᵃ is —(CRᵃRᵇ)-G¹ᵇ; and G¹ᵇ is

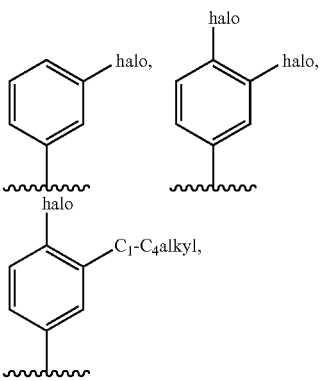

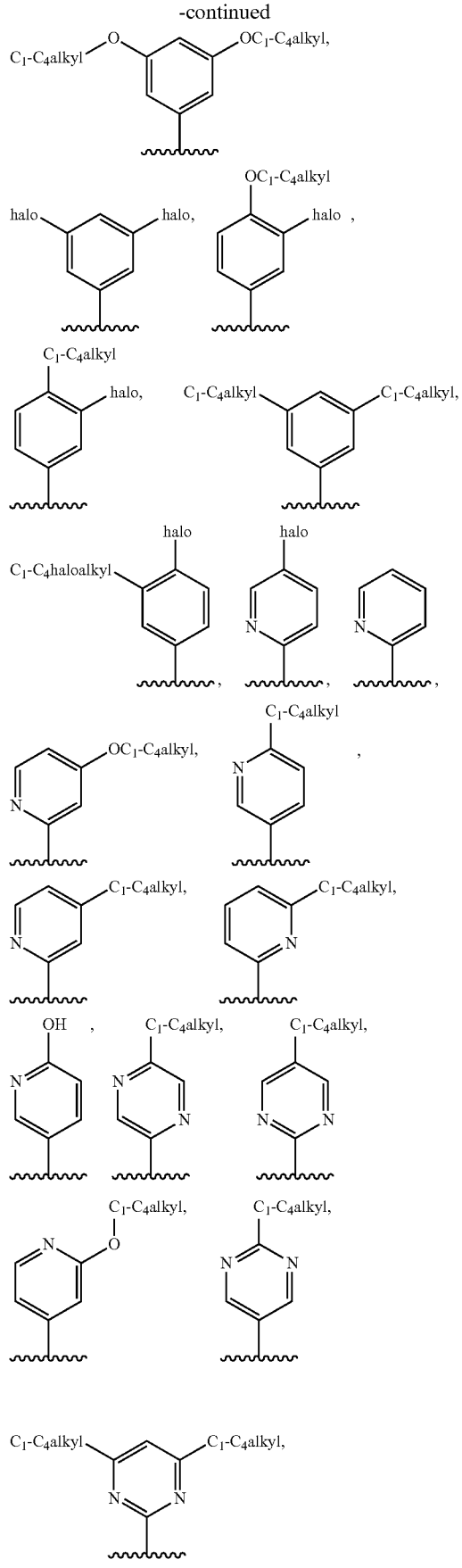

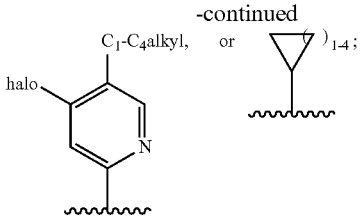

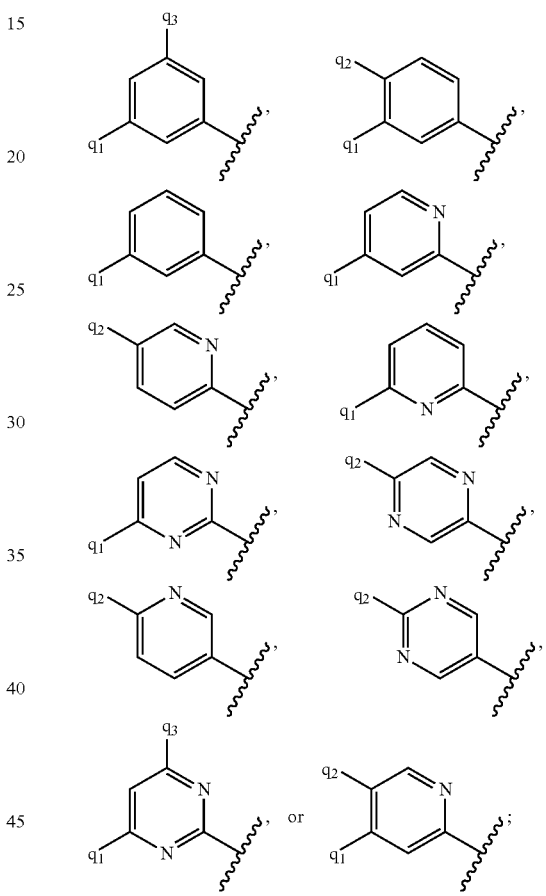

and $R^a$ and $R^b$ are as defined herein. In other further embodiments, $R^{1a}$ is —$(CR^aR^b)$-$G^{1b}$; $G^{1b}$ is and $q_1$, $q_2$, and $q_3$ are independently selected from the group consisting of halo, $C_1$-$C_4$ alkyl, and $C_1$-$C_4$ alkoxy; and $R^a$ and $R^b$ are as defined herein.

In the embodiments herein are further embodiments wherein $R^a$ is hydrogen, $C_1$-$C_4$alkyl, $C_3$-$C_6$carbocycle, —$C_1$-$C_3$alkylene-C(O)OH, or —$C_1$-$C_3$alkylene-C(O)OC$_1$-C$_4$alkyl. In further embodiments, $R^a$ is hydrogen, $C_1$-$C_2$alkyl, $C_3$-$C_4$cycloalkyl, or —$C_1$-$C_3$alkylene-C(O)OC$_1$-$C_4$alkyl.

In the embodiments herein are further embodiments wherein $R^b$ is hydrogen or $C_1$-$C_4$alkyl.

In the embodiments herein are further embodiments wherein $R^{1b}$ is hydrogen or $C_1$-$C_4$alkyl.

In the embodiments herein are further embodiments wherein $R^{1c}$, $R^{1d}$, $R^{1e}$, $R^{3a}$, $R^{3b}$, $R^{3c}$, $R^{4a}$, $R^{4b}$, $R^{4c}$, $R^{4d}$, $R^{5a}$, $R^{5b}$, and $R^{5c}$, at each occurrence, are independently hydrogen or $C_1$-$C_4$alkyl.

In another aspect, compounds of formula (I) have formula (I'), wherein X, $R^{1a}$, $R^{1b}$, $R^2$, $R^3$, $R^4$, $R^5$, $R^{6a}$, and $R^{6b}$ are as defined herein.

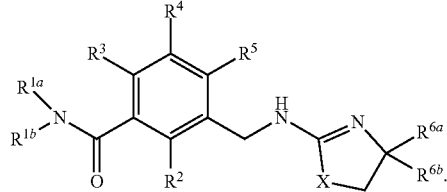

(I')

In some embodiments, X is NR and R is H or $C_1$-$C_4$ alkyl. For example, X may be NH or $NCH_3$. In other embodiments, X is $CH_2$. In other embodiments, X is O.

In some embodiments, $R^{1a}$ is selected from the group consisting of $C_1$-$C_4$ alkyl, —($CR^aR^b$)-aryl, —($CR^aR^b$)-heteroaryl, and —($CR^aR^b$)—$C_3$-$C_6$-cycloalkyl (e.g., cyclopropyl); $R^{1b}$ is selected from the group consisting of hydrogen and $C_1$-$C_4$ alkyl; $R^a$ is selected from the group consisting of hydrogen, $C_1$-$C_4$ alkyl, and $C_3$-$C_6$-cycloalkyl (e.g., cyclopropyl); and $R^b$ is hydrogen, wherein the heteroaryl is a 5- or 6-membered heteroaryl having 1, 2, or 3 heteroatoms independently selected from the group consisting of N, O and S, and the aryl and heteroaryl are unsubstituted or substituted with 1, 2, or 3 substituents independently selected from the group consisting of halo, $C_1$-$C_4$ alkyl, $C_1$-$C_4$ haloalkyl, $C_1$-$C_4$ alkoxy, and $C_1$-$C_4$ hydroxyalkyl. In some embodiments, $R^a$ is hydrogen. In some embodiments, $R^a$ is cyclopropyl. In some embodiments, $R^a$ is methyl. In some embodiments, $R^{1a}$ is —($CR^aR^b$)-cyclopropyl, $R^b$ is hydrogen, and $R^a$ is cyclopropyl.

In some embodiments, $R^{1a}$ is —($CR^aR^b$)-aryl, wherein the aryl is

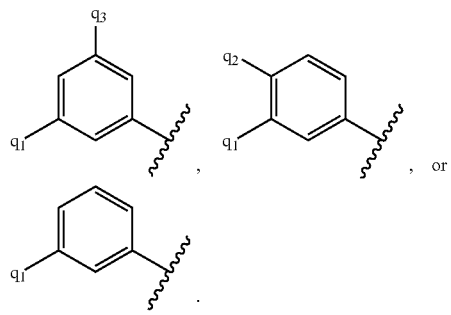

In some embodiments, $R^{1a}$ is —($CR^aR^b$)-heteroaryl, wherein the heteroaryl is

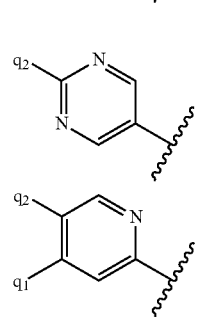

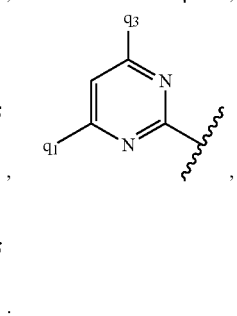

-continued

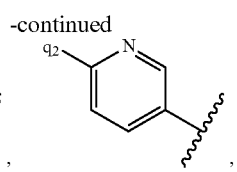

The substituents $q_1$, $q_2$, and $q_3$ are independently selected from the group consisting of halo, $C_1$-$C_4$ alkyl, and $C_1$-$C_4$ alkoxy. In some embodiments, $q_1$, $q_2$, and $q_3$ are independently selected from the group consisting of fluoro, chloro, methyl, and methoxy.

In some embodiments, $R^2$ is hydrogen. In other embodiments, $R^2$ is halogen (e.g., fluoro, chloro).

In some embodiments, $R^3$ is hydrogen. In other embodiments, $R^3$ is halogen (e.g., fluoro, chloro). In other embodiments, $R^3$ is hydrogen, —$NR^{3a}R^{3b}$, or —$NR^{3a}C(O)R^{3c}$, wherein $R^{3a}$, $R^{3b}$, and $R^{3c}$ are as defined herein (e.g., hydrogen or $C_1$-$C_4$alkyl).

In some embodiments, $R^4$ is hydrogen. In other embodiments, $R^4$ is halogen (e.g., fluoro, chloro). In other embodiments, $R^4$ is $C_1$-$C_4$ haloalkyl (e.g., $CF_3$). In other embodiments, $R^4$ is an optionally substituted aryl (e.g., optionally substituted phenyl). In other embodiments, $R^4$ is an optionally substituted 5- or 6-membered heteroaryl (e.g., optionally substituted pyridinyl, pyrrolyl). In other embodiments, $R^4$ is an optionally substituted —O-aryl (e.g., —O-phenyl, where the phenyl is optionally substituted). In other embodiments, $R^4$ is an optionally substituted —O-heteroaryl. The aryl and 5- or 6-membered heteroaryl are independently optionally substituted with 1, 2, or 3 substituents independently selected from the group consisting of halo, $C_1$-$C_4$ alkyl, $C_1$-$C_4$ haloalkyl, $C_1$-$C_4$ alkoxy, and $C_1$-$C_4$ hydroxyalkyl. In some embodiments, $R^4$ is aryl or 5- or 6-membered heteroaryl, wherein the aryl or heteroaryl is unsubstituted or substituted with 1, 2, or 3 substituents independently selected from the group consisting of halo, $C_1$-$C_4$ alkyl, $C_1$-$C_4$ haloalkyl, $C_1$-$C_4$ alkoxy, and $C_1$-$C_4$ hydroxyalkyl. In some embodiments, $R^4$ is selected from the group consisting of phenyl, pyridyl, and pyrrolyl, each of which is unsubstituted or substituted with 1, 2, or 3 substituents independently selected from the group consisting of fluoro, chloro, methyl, isopropyl, methoxy, trifluoromethyl, and hydroxymethyl. In some embodiments, the aryl and heteroaryl substituents at $R^4$ are selected from the group consisting of fluoro, chloro, methyl, methoxy, ethoxy, and trifluoromethyl.

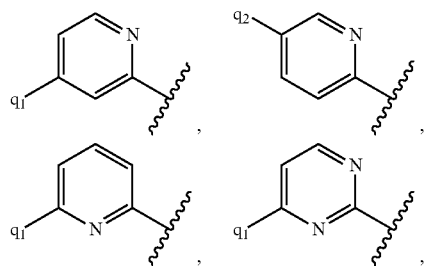

For example, $R^4$ may be
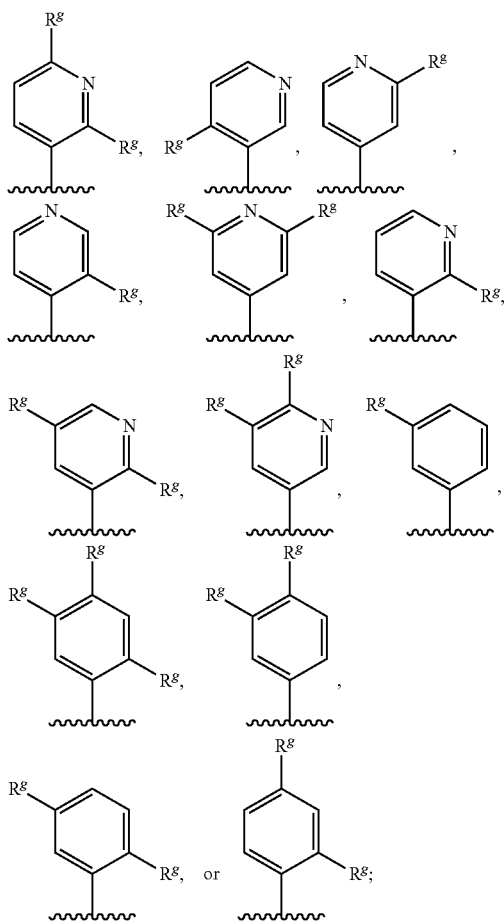
and $R^g$, at each occurrence, is independently halo, $C_1$-$C_4$ alkyl, $C_1$-$C_4$ haloalkyl, or $C_1$-$C_4$ alkoxy. In some embodiments, $R^g$, at each occurrence is selected from the group consisting of fluoro, chloro, methyl, methoxy, ethoxy, and trifluoromethyl.
In further examples, the aryl at $R^4$ may be
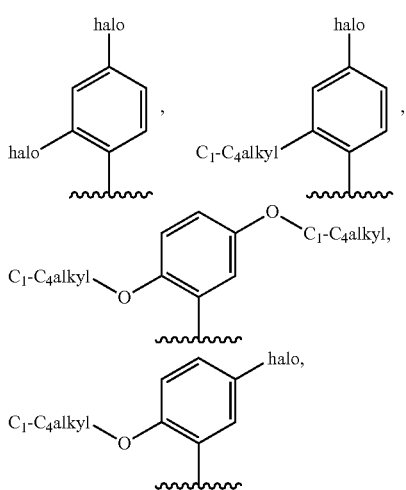
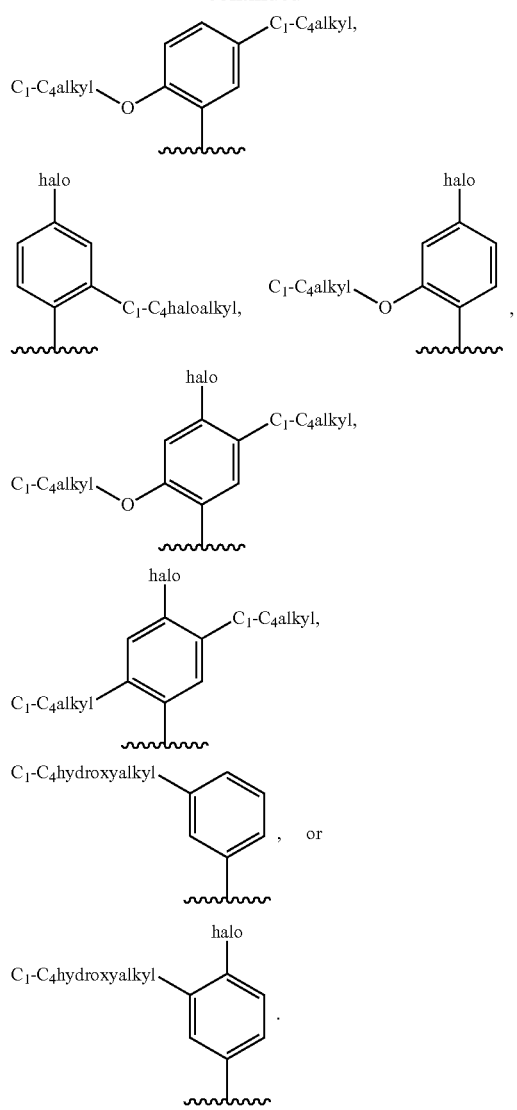
Specific exemplary aryl $R^4$ include
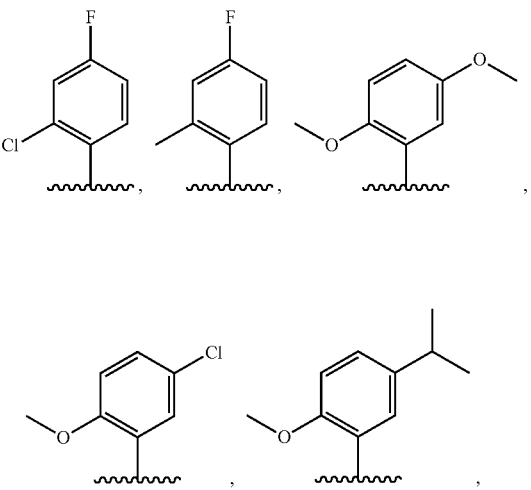

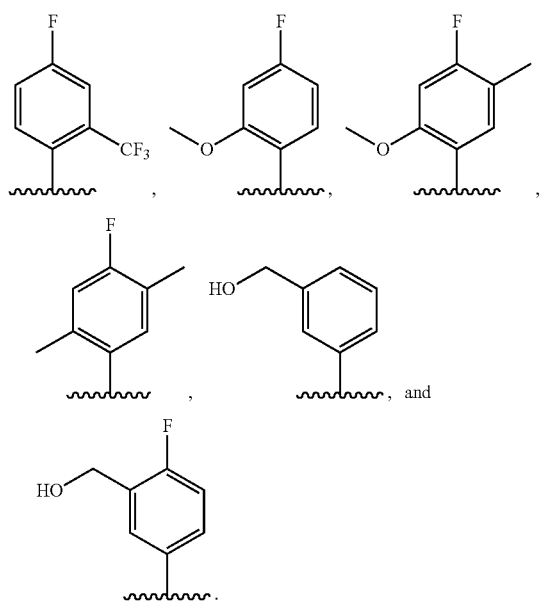
In the embodiments described herein the heteroaryl at $R^4$ may be
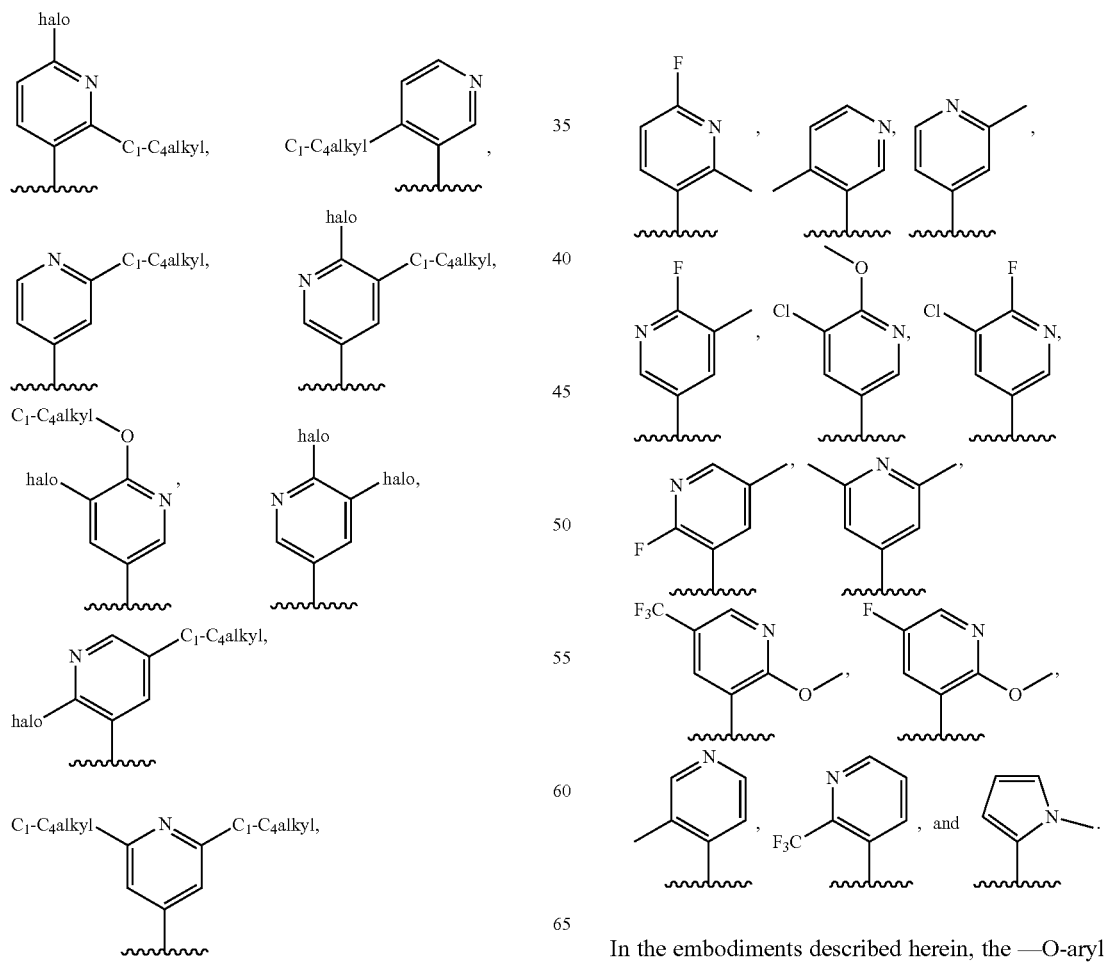
Specific exemplary heteroaryl $R^4$ include
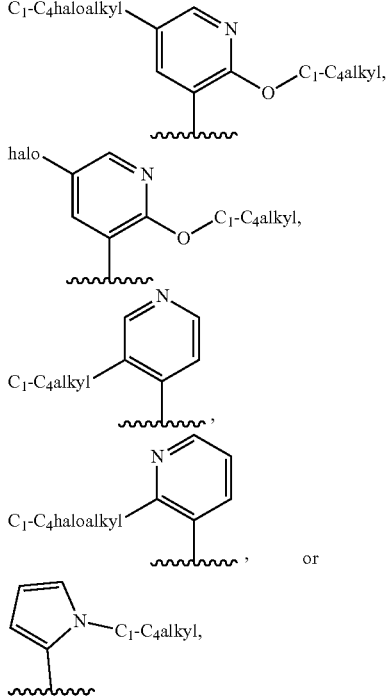
In the embodiments described herein, the —O-aryl at $R^4$ may be

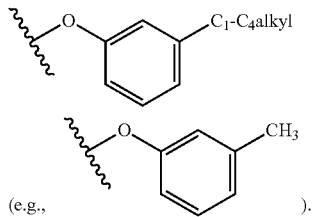

(e.g., ).

In some embodiments, $R^4$ is a 4- to 12-membered heterocyclyl containing one nitrogen atom and optionally 1-2 additional heteroatoms selected from the group consisting of nitrogen, oxygen, and sulfur, the heterocyclyl being monocyclic (e.g., pyrrolidinyl, piperidinyl, morpholinyl, thiomorpholinyl), fused bicyclic (e.g., 3-azabicyclo[3.2.0]heptanyl), spirocyclic (e.g., 5-azaspiro[2.4]heptanyl), or bridged (e.g., 2-azabicyclo[2.2.1]heptanyl) and optionally substituted with 1-4 substituents independently selected from the group consisting of halo, $C_1$-$C_4$ alkyl (e.g., $CH_3$), $C_1$-$C_4$ haloalkyl (e.g., $CF_3$), $C_1$-$C_4$ alkoxy, OH, and oxo. In some embodiments, the heterocyclyl is attached through a ring nitrogen atom (e.g., pyrrolidin-1-yl, piperidin-1-yl, morpholin-4-yl, thiomorpholin-4-yl, 3-azabicyclo[3.2.0]heptan-3-yl, 5-azaspiro[2.4]heptan-5-yl, 2-azabicyclo[2.2.1]heptan-2-yl). In some embodiments, the heterocyclyl is attached through a ring nitrogen and substituted in the 2-position of the heterocyclyl (e.g., 2-($C_1$-$C_3$haloalkyl)pyrrolidin-1-yl, 2-(trifluoromethyl)pyrrolidin-1-yl, 2-(2,2,2-trifluoroethyl)pyrrolidin-1-yl, 2-($C_1$-$C_3$alkyl)pyrrolidin-1-yl, 2-methylpyrrolidin-1-yl, 2-ethylpyrrolidin-1-yl, 2-($C_1$-$C_3$haloalkyl)piperidin-1-yl, 2-(trifluoromethyl)piperidin-1-yl, 2-($C_1$-$C_3$alkyl)piperidin-1-yl, 2-methylpiperidin-1-yl).

In some embodiments, $R^5$ is hydrogen. In other embodiments, $R^5$ is halogen (e.g., fluoro, chloro). In other embodiments, $R^5$ is —OR (e.g., —O$C_1$-$C_4$alkyl).

In some embodiments, $R^2$, $R^3$, $R^4$, and $R^5$ are each hydrogen. In other embodiments, $R^2$ is halogen and $R^3$, $R^4$, and $R^5$ are hydrogen. In other embodiments, $R^3$ is halogen and $R^2$, $R^4$, and $R^5$ are hydrogen. In other embodiments, $R^4$ is halogen and $R^2$, $R^3$, and $R^5$ are hydrogen. In other embodiments $R^5$ is halogen and $R^2$, $R^3$, and $R^4$ are hydrogen. In other embodiments $R^4$ and $R^5$ are halogen (e.g., fluoro) and $R^2$ and $R^3$ are hydrogen. In other embodiments $R^3$ and $R^5$ are halogen and $R^2$ and $R^4$ are hydrogen.

In other embodiments, $R^4$ is an optionally substituted aryl and $R^2$, $R^3$, and $R^5$ are hydrogen. In other embodiments, $R^4$ is an optionally substituted 5- or 6-membered heteroaryl and $R^2$, $R^3$, and $R^5$ are hydrogen. In other embodiments, $R^4$ is an optionally substituted —O-aryl and $R^2$, $R^3$, and $R^5$ are hydrogen. In other embodiments, $R^4$ is $C_1$-$C_4$ haloalkyl and $R^2$, $R^3$, and $R^5$ are hydrogen.

In other embodiments $R^5$ is —O$C_1$-$C_4$alkyl and $R^2$, $R^3$, and $R^4$ are hydrogen.

In some embodiments, $R^{6a}$ and $R^{6b}$ are each hydrogen. In other embodiments, $R^{6a}$ and $R^{6b}$ are taken together to form an oxo group.

In some embodiments, X is N—$C_1$-$C_4$alkyl and $R^{6a}$ and $R^{6b}$ together form an oxo group. In other embodiments, X is NH and $R^{6a}$ and $R^{6b}$ are each hydrogen. In other embodiments, X is $CH_2$ and $R^{6a}$ and $R^{6b}$ are each hydrogen. In other embodiments, X is O and $R^{6a}$ and $R^{6b}$ are each hydrogen.

In some embodiments, the compound of formula (I') is a compound of formula (Ia'):

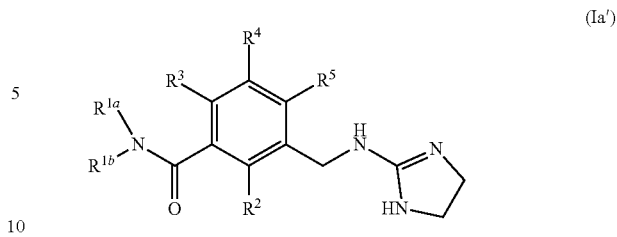

(Ia')

wherein $R^{1a}$, $R^{1b}$, $R^2$, $R^3$, $R^4$, and $R^5$ are as described in the embodiments and combinations thereof herein. In some embodiments of formula (Ia'), $R^2$ is selected from the group consisting of hydrogen and halo; $R^3$ is selected from the group consisting of hydrogen and halo; $R^4$ is selected from the group consisting of hydrogen and halo; $R^5$ is selected from the group consisting of hydrogen, halo, and —OR, and $R^{1a}$ and $R^{1b}$ are as described herein.

In some embodiments, the compound of formula (I') is a compound of formula (Ib'):

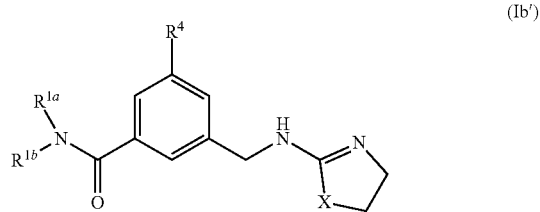

(Ib')

wherein X, $R^{1a}$, $R^{1b}$, and $R^4$ are as described in the embodiments and combinations thereof herein.

In some embodiments, the compound of formula (I') is selected from the group consisting of:
N-(3,5-dichlorobenzyl)-3-(((4,5-dihydro-1H-imidazol-2-yl)amino)methyl)benzamide;
N-(3-chlorobenzyl)-3-(((4,5-dihydro-1H-imidazol-2-yl)amino)methyl)-N-isopropylbenzamide;
N-(3,4-dichlorobenzyl)-3-(((4,5-dihydro-1H-imidazol-2-yl)amino)methyl)benzamide;
N-(4-chloro-3-methylbenzyl)-3-(((4,5-dihydro-1H-imidazol-2-yl)amino)methyl)benzamide;
N-(1-(3-chlorophenyl)ethyl)-3-(((4,5-dihydro-1H-imidazol-2-yl)amino)methyl)benzamide;
N-(3,4-dichlorobenzyl)-3-(((4,5-dihydro-1H-imidazol-2-yl)amino)methyl)-4-fluorobenzamide;
3-(((4,5-dihydro-1H-imidazol-2-yl)amino)methyl)-N-(3,5-dimethylbenzyl)-4-fluorobenzamide;
3-chloro-N-(3,4-dichlorobenzyl)-5-(((4,5-dihydro-1H-imidazol-2-yl)amino)methyl)benzamide;
3-chloro-N-(3,5-dichlorobenzyl)-5-(((4,5-dihydro-1H-imidazol-2-yl)amino)methyl)benzamide;
3-chloro-N-(3-chloro-4-methylbenzyl)-5-(((4,5-dihydro-1H-imidazol-2-yl)amino)methyl)benzamide;
3-chloro-5-(((4,5-dihydro-1H-imidazol-2-yl)amino)methyl)-N-(3,5-dimethylbenzyl)benzamide;
3-chloro-N-(1-(3-chlorophenyl)ethyl)-5-(((4,5-dihydro-1H-imidazol-2-yl)amino)methyl)benzamide;
4-chloro-3-(((4,5-dihydro-1H-imidazol-2-yl)amino)methyl)-N-(3,5-dimethoxybenzyl)benzamide;
4-chloro-N-(3,5-dichlorobenzyl)-3-(((4,5-dihydro-1H-imidazol-2-yl)amino)methyl)benzamide;
3-(((4,5-dihydro-1H-imidazol-2-yl)amino)methyl)-N-(3,5-dimethoxybenzyl)-4-fluorobenzamide;

N-((4-chloropyridin-2-yl)methyl)-3-(((4,5-dihydro-1H-imidazol-2-yl)amino)methyl)-4-fluorobenzamide;
N-(3,5-dichlorobenzyl)-3-(((4,5-dihydro-1H-imidazol-2-yl)amino)methyl)-4-fluorobenzamide;
3-(((4,5-dihydro-1H-imidazol-2-yl)amino)methyl)-N-(1-(3,5-dimethoxyphenyl)ethyl)-4-fluorobenzamide;
3-(((4,5-dihydro-1H-imidazol-2-yl)amino)methyl)-N-(3,4-dimethoxybenzyl)-4-fluorobenzamide;
N-(cyclopropyl(4-methylpyridin-2-yl)methyl)-3-(((4,5-dihydro-1H-imidazol-2-yl)amino)methyl)-4-fluorobenzamide;
3-(((4,5-dihydro-1H-imidazol-2-yl)amino)methyl)-N-(3,5-dimethoxybenzyl)-2-fluorobenzamide;
3-(((4,5-dihydro-1H-imidazol-2-yl)amino)methyl)-4-fluoro-N-((4-methoxypyridin-2-yl)methyl)benzamide;
N-((5-chloropyridin-2-yl)methyl)-3-(((4,5-dihydro-1H-imidazol-2-yl)amino)methyl)-4-fluorobenzamide;
3-(((4,5-dihydro-1H-imidazol-2-yl)amino)methyl)-N-(3,5-dimethoxybenzyl)-4-fluoro-N-methylbenzamide;
3-(((4,5-dihydro-1H-imidazol-2-yl)amino)methyl)-4-fluoro-N-((6-methoxypyridin-2-yl)methyl)benzamide;
N-(3-chloro-4-methoxybenzyl)-3-(((4,5-dihydro-1H-imidazol-2-yl)amino)methyl)-4-fluorobenzamide;
3-(((4,5-dihydro-1H-imidazol-2-yl)amino)methyl)-N-(3,5-dimethoxybenzyl)-4-methoxybenzamide;
N-(3,4-dichlorobenzyl)-3-(((4,5-dihydro-1H-imidazol-2-yl)amino)methyl)-4-methoxybenzamide;
3-(((4,5-dihydro-1H-imidazol-2-yl)amino)methyl)-4-fluoro-N-((4-methylpyridin-2-yl)methyl)benzamide;
3-(((4,5-dihydro-1H-imidazol-2-yl)amino)methyl)-N-(3,5-dimethoxybenzyl)-4,5-difluorobenzamide;
3-(((4,5-dihydro-1H-imidazol-2-yl)amino)methyl)-N-(3,5-dimethylbenzyl)-4,5-difluorobenzamide;
N-(3-chloro-4-methoxybenzyl)-3-(((4,5-dihydro-1H-imidazol-2-yl)amino)methyl)-4,5-difluorobenzamide;
N-(3,4-dichlorobenzyl)-3-(((4,5-dihydro-1H-imidazol-2-yl)amino)methyl)-4,5-difluorobenzamide;
3-(((4,5-dihydro-1H-imidazol-2-yl)amino)methyl)-4,5-difluoro-N-((4-methoxypyridin-2-yl)methyl)benzamide;
3-(((4,5-dihydro-1H-imidazol-2-yl)amino)methyl)-N-(1-(3,5-dimethoxyphenyl)ethyl)-4,5-difluorobenzamide;
N-(3,4-dichlorobenzyl)-5-(((4,5-dihydro-1H-imidazol-2-yl)amino)methyl)-2-fluorobenzamide;
5-(((4,5-dihydro-1H-imidazol-2-yl)amino)methyl)-N-(3,5-dimethoxybenzyl)-2-fluorobenzamide;
N-(4-chloro-3-methoxybenzyl)-3-(((4,5-dihydro-1H-imidazol-2-yl)amino)methyl)-4-methoxybenzamide;
N-((4-chloropyridin-2-yl)methyl)-3-(((4,5-dihydro-1H-imidazol-2-yl)amino)methyl)-4-methoxybenzamide;
3-(((4,5-dihydro-1H-imidazol-2-yl)amino)methyl)-4-methoxy-N-((4-methoxypyridin-2-yl)methyl)benzamide;
N-(4-chloro-3-fluorobenzyl)-3-(((4,5-dihydro-1H-imidazol-2-yl)amino)methyl)-4-methoxybenzamide;
N-(4-chloro-3-methylbenzyl)-3-(((4,5-dihydro-1H-imidazol-2-yl)amino)methyl)-4-methoxybenzamide;
3-(((4,5-dihydro-1H-imidazol-2-yl)amino)methyl)-N-(1-(3,5-dimethoxyphenyl)ethyl)-4-methoxybenzamide;
N-((5-chloropyridin-2-yl)methyl)-3-(((4,5-dihydro-1H-imidazol-2-yl)amino)methyl)-4-methoxybenzamide;
3-(((4,5-dihydro-1H-imidazol-2-yl)amino)methyl)-N-((4,6-dimethylpyrimidin-2-yl)methyl)-4-fluorobenzamide;
3-(((4,5-dihydro-1H-imidazol-2-yl)amino)methyl)-4-fluoro-N-((5-methylpyrazin-2-yl)methyl)benzamide;
N-(4-chloro-3-methylbenzyl)-3-(((4,5-dihydro-1H-imidazol-2-yl)amino)methyl)-4-fluorobenzamide;
N-(cyclopropyl(4-methylpyridin-2-yl)methyl)-5-(((4,5-dihydro-1H-imidazol-2-yl)amino)methyl)-2,4-difluorobenzamide;
5-(((4,5-dihydro-1H-imidazol-2-yl)amino)methyl)-N-(1-(3,5-dimethoxyphenyl)ethyl)-2,4-difluorobenzamide;
N-(cyclopropyl(4-methylpyridin-2-yl)methyl)-3-(((4,5-dihydro-1H-imidazol-2-yl)amino)methyl)-4-ethoxybenzamide;
3-(((4,5-dihydro-1H-imidazol-2-yl)amino)methyl)-N-(1-(3,5-dimethoxyphenyl)ethyl)-4-ethoxybenzamide;
3-(((4,5-dihydro-1H-imidazol-2-yl)amino)methyl)-N-(1-(3,5-dimethoxyphenyl)ethyl)-4-isopropoxybenzamide;
N-(3,4-dichlorobenzyl)-3-(((4,5-dihydro-1H-imidazol-2-yl)amino)methyl)-4-isopropoxybenzamide;
2'-chloro-N-(3,4-dichlorobenzyl)-5-(((4,5-dihydro-1H-imidazol-2-yl)amino)methyl)-4'-fluoro-[1,1'-biphenyl]-3-carboxamide;
2'-chloro-5-(((4,5-dihydro-1H-imidazol-2-yl)amino)methyl)-N-(3,5-dimethylbenzyl)-4'-fluoro-[1,1'-biphenyl]-3-carboxamide;
2'-chloro-N-(dicyclopropylmethyl)-5-(((4,5-dihydro-1H-imidazol-2-yl)amino)methyl)-4'-fluoro-[1,1'-biphenyl]-3-carboxamide;
2'-chloro-5-(((4,5-dihydro-1H-imidazol-2-yl)amino)methyl)-N-(3,5-dimethoxybenzyl)-4'-fluoro-[1,1'-biphenyl]-3-carboxamide;
2'-chloro-N-(4-chloro-3-methylbenzyl)-5-(((4,5-dihydro-1H-imidazol-2-yl)amino)methyl)-4'-fluoro-[1,1'-biphenyl]-3-carboxamide;
3-(((4,5-dihydro-1H-imidazol-2-yl)amino)methyl)-N-(3,4-dimethoxybenzyl)-5-(6-fluoro-2-methylpyridin-3-yl)benzamide;
N-(4-chloro-3-methylbenzyl)-3-(((4,5-dihydro-1H-imidazol-2-yl)amino)methyl)-5-(6-fluoro-2-methylpyridin-3-yl)benzamide;
3-(((4,5-dihydro-1H-imidazol-2-yl)amino)methyl)-N-(3,5-dimethylbenzyl)-5-(6-fluoro-2-methylpyridin-3-yl)benzamide;
3-(((4,5-dihydro-1H-imidazol-2-yl)amino)methyl)-N-(1-(3,5-dimethoxyphenyl)ethyl)-5-(6-fluoro-2-methylpyridin-3-yl)benzamide;
3-(((4,5-dihydro-1H-imidazol-2-yl)amino)methyl)-N-(3,5-dimethoxybenzyl)-5-(6-fluoro-2-methylpyridin-3-yl)benzamide;
N-(3,4-dichlorobenzyl)-3-(((4,5-dihydro-1H-imidazol-2-yl)amino)methyl)-5-(6-fluoro-2-methylpyridin-3-yl)benzamide;
3-(((4,5-dihydro-1H-imidazol-2-yl)amino)methyl)-N-(3,5-dimethoxybenzyl)-5-(6-fluoro-2-methylpyridin-3-yl)-N-methylbenzamide;
N-(cyclopropyl(4-methylpyridin-2-yl)methyl)-3-(((4,5-dihydro-1H-imidazol-2-yl)amino)methyl)-5-(6-fluoro-2-methylpyridin-3-yl)benzamide;
N-(dicyclopropylmethyl)-3-(((4,5-dihydro-1H-imidazol-2-yl)amino)methyl)-5-(6-fluoro-2-methylpyridin-3-yl)benzamide;
3-(((4,5-dihydro-1H-imidazol-2-yl)amino)methyl)-5-(6-fluoro-2-methylpyridin-3-yl)-N-((4-methoxypyridin-2-yl)methyl)benzamide;
N-(3,4-dichlorobenzyl)-3-(((4,5-dihydro-1H-imidazol-2-yl)amino)methyl)-5-(4-methylpyridin-3-yl)benzamide;
3-(((4,5-dihydro-1H-imidazol-2-yl)amino)methyl)-N-(3,5-dimethoxybenzyl)-5-(4-methylpyridin-3-yl)benzamide;
N-(3-chloro-4-methoxybenzyl)-3-(((4,5-dihydro-1H-imidazol-2-yl)amino)methyl)-5-(4-methylpyridin-3-yl)benzamide;

3-(((4,5-dihydro-1H-imidazol-2-yl)amino)methyl)-N-(3,5-dimethoxybenzyl)-5-(2-methylpyridin-4-yl)benzamide;

3-(((4,5-dihydro-1H-imidazol-2-yl)amino)methyl)-N-(3,4-dimethoxybenzyl)-5-(2-methylpyridin-4-yl)benzamide;

N-(3,4-dichlorobenzyl)-3-(((4,5-dihydro-1H-imidazol-2-yl)amino)methyl)-5-(2-methylpyridin-4-yl)benzamide;

N-(3-chloro-5-fluorobenzyl)-3-(((4,5-dihydro-1H-imidazol-2-yl)amino)methyl)-5-(2-methylpyridin-4-yl)benzamide;

N-(4-chloro-3-methoxybenzyl)-3-(((4,5-dihydro-1H-imidazol-2-yl)amino)methyl)-5-(2-methylpyridin-4-yl)benzamide;

N-(4-chloro-3-methoxybenzyl)-3-(((4,5-dihydro-1H-imidazol-2-yl)amino)methyl)-5-(4-methylpyridin-3-yl)benzamide;

3-(((4,5-dihydro-1H-imidazol-2-yl)amino)methyl)-N-((4-methoxypyridin-2-yl)methyl)-5-(4-methylpyridin-3-yl)benzamide;

3-(((4,5-dihydro-1H-imidazol-2-yl)amino)methyl)-N-(1-(3,5-dimethoxyphenyl)ethyl)-5-(4-methylpyridin-3-yl)benzamide;

3-(((4,5-dihydro-1H-imidazol-2-yl)amino)methyl)-N-((4-methoxypyridin-2-yl)methyl)-5-(2-methylpyridin-4-yl)benzamide;

N-(3,5-dichlorobenzyl)-3-(((4,5-dihydro-1H-imidazol-2-yl)amino)methyl)-5-(2-methylpyridin-4-yl)benzamide;

N-((4-chloropyridin-2-yl)methyl)-3-(((4,5-dihydro-1H-imidazol-2-yl)amino)methyl)-5-(2-methylpyridin-4-yl)benzamide;

N-(3-chloro-4-methoxybenzyl)-3-(((4,5-dihydro-1H-imidazol-2-yl)amino)methyl)-5-(2-methylpyridin-4-yl)benzamide;

N-(4-chloro-3-methylbenzyl)-3-(((4,5-dihydro-1H-imidazol-2-yl)amino)methyl)-5-(2-methylpyridin-4-yl)benzamide;

N-(3-chloro-5-fluorobenzyl)-3-(((4,5-dihydro-1H-imidazol-2-yl)amino)methyl)-5-(4-methylpyridin-3-yl)benzamide;

N-(cyclopropyl(4-methylpyridin-2-yl)methyl)-3-(((4,5-dihydro-1H-imidazol-2-yl)amino)methyl)-5-(4-methylpyridin-3-yl)benzamide;

N-(3,5-dichlorobenzyl)-3-(((4,5-dihydro-1H-imidazol-2-yl)amino)methyl)-5-(4-methylpyridin-3-yl)benzamide;

N-(4-chloro-3-methylbenzyl)-3-(((4,5-dihydro-1H-imidazol-2-yl)amino)methyl)-5-(4-methylpyridin-3-yl)benzamide;

3-(((4,5-dihydro-1H-imidazol-2-yl)amino)methyl)-N-((6-fluoropyridin-2-yl)methyl)-5-(4-methylpyridin-3-yl)benzamide;

3-(((4,5-dihydro-1H-imidazol-2-yl)amino)methyl)-N-(3,5-dimethylbenzyl)-5-(2-methylpyridin-4-yl)benzamide;

3-(((4,5-dihydro-1H-imidazol-2-yl)amino)methyl)-N-((6-methylpyridin-3-yl)methyl)-5-(2-methylpyridin-4-yl)benzamide;

N-((5-chloropyridin-2-yl)methyl)-3-(((4,5-dihydro-1H-imidazol-2-yl)amino)methyl)-5-(2-methylpyridin-4-yl)benzamide;

N-(dicyclopropylmethyl)-3-(((4,5-dihydro-1H-imidazol-2-yl)amino)methyl)-5-(4-methylpyridin-3-yl)benzamide;

3-(((4,5-dihydro-1H-imidazol-2-yl)amino)methyl)-5-(4-methylpyridin-3-yl)-N-((6-methylpyridin-3-yl)methyl)benzamide;

3-(((4,5-dihydro-1H-imidazol-2-yl)amino)methyl)-N-((6-fluoropyridin-2-yl)methyl)-5-(2-methylpyridin-4-yl)benzamide;

3-(((4,5-dihydro-1H-imidazol-2-yl)amino)methyl)-5-(2-methylpyridin-4-yl)-N-((4-methylpyrimidin-2-yl)methyl)benzamide;

3-(((4,5-dihydro-1H-imidazol-2-yl)amino)methyl)-N-(3,5-dimethoxybenzyl)-5-(6-fluoro-5-methylpyridin-3-yl)benzamide;

N-(4-chloro-3-methylbenzyl)-3-(((4,5-dihydro-1H-imidazol-2-yl)amino)methyl)-5-(6-fluoro-5-methylpyridin-3-yl)benzamide;

N-(3,4-dichlorobenzyl)-3-(((4,5-dihydro-1H-imidazol-2-yl)amino)methyl)-5-(6-fluoro-5-methylpyridin-3-yl)benzamide;

N-(3,4-dichlorobenzyl)-3-(((4,5-dihydro-1H-imidazol-2-yl)amino)methyl)-5-(m-tolyloxy)benzamide;

3-(((4,5-dihydro-1H-imidazol-2-yl)amino)methyl)-N-(1-(3,5-dimethoxyphenyl)ethyl)-5-(trifluoromethyl)benzamide;

3-(5-chloro-6-methoxypyridin-3-yl)-5-(((4,5-dihydro-1H-imidazol-2-yl)amino)methyl)-N-(3,5-dimethoxybenzyl)benzamide;

3-(5-chloro-6-fluoropyridin-3-yl)-5-(((4,5-dihydro-1H-imidazol-2-yl)amino)methyl)-N-(3,5-dimethoxybenzyl)benzamide;

3-(((4,5-dihydro-1H-imidazol-2-yl)amino)methyl)-5-(6-fluoro-2-methylpyridin-3-yl)-N-((5-methylpyrazin-2-yl)methyl)benzamide;

3-(((4,5-dihydro-1H-imidazol-2-yl)amino)methyl)-5-(6-fluoro-2-methylpyridin-3-yl)-N-((2-methylpyrimidin-5-yl)methyl)benzamide;

N-((4-chloropyridin-2-yl)methyl)-3-(((4,5-dihydro-1H-imidazol-2-yl)amino)methyl)-5-(2-fluoro-5-methylpyridin-3-yl)benzamide;

3-(((4,5-dihydro-1H-imidazol-2-yl)amino)methyl)-N-(3,4-dimethoxybenzyl)-5-(2-fluoro-5-methylpyridin-3-yl)benzamide;

N-(cyclopropyl(4-methylpyridin-2-yl)methyl)-3-(((4,5-dihydro-1H-imidazol-2-yl)amino)methyl)-5-(2-fluoro-5-methylpyridin-3-yl)benzamide;

3-(((4,5-dihydro-1H-imidazol-2-yl)amino)methyl)-N-(3,5-dimethoxybenzyl)-5-(2-fluoro-5-methylpyridin-3-yl)benzamide;

3-(((4,5-dihydro-1H-imidazol-2-yl)amino)methyl)-5-(2-fluoro-5-methylpyridin-3-yl)-N,N-dimethylbenzamide;

N-((4-chloropyridin-2-yl)methyl)-3-(((4,5-dihydro-1H-imidazol-2-yl)amino)methyl)-5-(2,6-dimethylpyridin-4-yl)benzamide;

N-(4-chloro-3-methylbenzyl)-3-(((4,5-dihydro-1H-imidazol-2-yl)amino)methyl)-5-(2,6-dimethylpyridin-4-yl)benzamide;

N-(4-chloro-3-methylbenzyl)-3-(((4,5-dihydro-1H-imidazol-2-yl)amino)methyl)-5-(2-fluoro-5-methylpyridin-3-yl)benzamide;

5-(((4,5-dihydro-1H-imidazol-2-yl)amino)methyl)-4'-fluoro-N-((4-methoxypyridin-2-yl)methyl)-2'-methyl-[1,1'-biphenyl]-3-carboxamide;

5-(((4,5-dihydro-1H-imidazol-2-yl)amino)methyl)-2',5'-dimethoxy-N-((4-methoxypyridin-2-yl)methyl)-[1,1'-biphenyl]-3-carboxamide;

5'-chloro-5-(((4,5-dihydro-1H-imidazol-2-yl)amino)methyl)-2'-methoxy-N-((4-methoxypyridin-2-yl)methyl)-[1,1'-biphenyl]-3-carboxamide;

5-(((4,5-dihydro-1H-imidazol-2-yl)amino)methyl)-5'-isopropyl-2'-methoxy-N-((4-methoxypyridin-2-yl)methyl)-[1,1'-biphenyl]-3-carboxamide;

3-(((4,5-dihydro-1H-imidazol-2-yl)amino)methyl)-5-(2-methoxy-5-(trifluoromethyl)pyridin-3-yl)-N-((4-methoxypyridin-2-yl)methyl)benzamide;

5-(((4,5-dihydro-1H-imidazol-2-yl)amino)methyl)-4'-fluoro-N-((4-methoxypyridin-2-yl)methyl)-2'-(trifluoromethyl)-[1,1'-biphenyl]-3-carboxamide;

3-(((4,5-dihydro-1H-imidazol-2-yl)amino)methyl)-5-(5-fluoro-2-methoxypyridin-3-yl)-N-((4-methoxypyridin-2-yl)methyl)benzamide;
5-(((4,5-dihydro-1H-imidazol-2-yl)amino)methyl)-4'-fluoro-2'-methoxy-N-((4-methoxypyridin-2-yl)methyl)-[1,1'-biphenyl]-3-carboxamide;
5-(((4,5-dihydro-1H-imidazol-2-yl)amino)methyl)-4'-fluoro-2'-methoxy-N-((4-methoxypyridin-2-yl)methyl)-5'-methyl-[1,1'-biphenyl]-3-carboxamide;
5-(((4,5-dihydro-1H-imidazol-2-yl)amino)methyl)-4'-fluoro-N-((4-methoxypyridin-2-yl)methyl)-2',5'-dimethyl-[1,1'-biphenyl]-3-carboxamide;
3-(((3,4-dihydro-2H-pyrrol-5-yl)amino)methyl)-N-(1-(3,5-dimethoxyphenyl)ethyl)-4-isopropoxybenzamide;
N-(3,4-dichlorobenzyl)-3-(((3,4-dihydro-2H-pyrrol-5-yl)amino)methyl)-4-isopropoxybenzamide;
N-(3,4-dichlorobenzyl)-3-(((3,4-dihydro-2H-pyrrol-5-yl)amino)methyl)-5-(6-fluoro-2-methylpyridin-3-yl)benzamide;
3-(((3,4-dihydro-2H-pyrrol-5-yl)amino)methyl)-5-(6-fluoro-2-methylpyridin-3-yl)-N-((4-methoxypyridin-2-yl)methyl)benzamide;
N-(1-(5-chloro-4-methylpyridin-2-yl)ethyl)-3-(((3,4-dihydro-2H-pyrrol-5-yl)amino)methyl)-5-(6-fluoro-2-methylpyridin-3-yl)benzamide;
N-(4-chloro-3-methylbenzyl)-3-(((3,4-dihydro-2H-pyrrol-5-yl)amino)methyl)-5-(6-fluoro-2-methylpyridin-3-yl)benzamide;
3-(((3,4-dihydro-2H-pyrrol-5-yl)amino)methyl)-N-(1-(3,5-dimethoxyphenyl)ethyl)-5-(6-fluoro-2-methylpyridin-3-yl)benzamide;
3-(((3,4-dihydro-2H-pyrrol-5-yl)amino)methyl)-N-(3,5-dimethoxybenzyl)-5-(6-fluoro-2-methylpyridin-3-yl)-N-methylbenzamide;
3-(((3,4-dihydro-2H-pyrrol-5-yl)amino)methyl)-N-(3,5-dimethoxybenzyl)-5-(2-methylpyridin-4-yl)benzamide;
3-(((3,4-dihydro-2H-pyrrol-5-yl)amino)methyl)-N-(3,5-dimethoxybenzyl)-5-(1-methyl-1H-pyrrol-2-yl)benzamide;
5-(((3,4-dihydro-2H-pyrrol-5-yl)amino)methyl)-N-(3,5-dimethoxybenzyl)-4'-fluoro-2'-methyl-[1,1'-biphenyl]-3-carboxamide;
3-(((3,4-dihydro-2H-pyrrol-5-yl)amino)methyl)-N-(3,5-dimethoxybenzyl)-5-(6-fluoro-2-methylpyridin-3-yl)benzamide;
3-(((3,4-dihydro-2H-pyrrol-5-yl)amino)methyl)-N-(3,5-dimethoxybenzyl)-5-(3-methylpyridin-4-yl)benzamide;
5-(((3,4-dihydro-2H-pyrrol-5-yl)amino)methyl)-N-(3,5-dimethoxybenzyl)-4'-fluoro-2',5'-dimethyl-[1,1'-biphenyl]-3-carboxamide;
N-(4-chloro-3-methylbenzyl)-5-(((3,4-dihydro-2H-pyrrol-5-yl)amino)methyl)-3'-(hydroxymethyl)-[1,1'-biphenyl]-3-carboxamide;
N-(4-chloro-3-methylbenzyl)-5-(((3,4-dihydro-2H-pyrrol-5-yl)amino)methyl)-4'-fluoro-2'-methyl-[1,1'-biphenyl]-3-carboxamide;
N-(4-chloro-3-methylbenzyl)-5-(((3,4-dihydro-2H-pyrrol-5-yl)amino)methyl)-4'-fluoro-3'-(hydroxymethyl)-[1,1'-biphenyl]-3-carboxamide;
N-(4-chloro-3-methylbenzyl)-5-(((3,4-dihydro-2H-pyrrol-5-yl)amino)methyl)-4'-fluoro-2',5'-dimethyl-[1,1'-biphenyl]-3-carboxamide;
N-(4-chloro-3-methylbenzyl)-3-(((3,4-dihydro-2H-pyrrol-5-yl)amino)methyl)-5-(2-(trifluoromethyl)pyridin-3-yl)benzamide;
N-(4-chloro-3-methylbenzyl)-5-(((3,4-dihydro-2H-pyrrol-5-yl)amino)methyl)-4'-fluoro-2'-(trifluoromethyl)-[1,1'-biphenyl]-3-carboxamide;
N-(4-chloro-3-methylbenzyl)-5-(((3,4-dihydro-2H-pyrrol-5-yl)amino)methyl)-4'-fluoro-2'-methoxy-5'-methyl-[1,1'-biphenyl]-3-carboxamide;
N-(4-chloro-3-methylbenzyl)-5-(((3,4-dihydro-2H-pyrrol-5-yl)amino)methyl)-4'-fluoro-2'-methoxy-[1,1'-biphenyl]-3-carboxamide;
N-(4-chloro-3-methylbenzyl)-3-(6-fluoro-2-methylpyridin-3-yl)-5-(((1-methyl-4-oxo-4,5-dihydro-1H-imidazol-2-yl)amino)methyl)benzamide;
N-(1-(3,5-dimethoxyphenyl)ethyl)-3-(6-fluoro-2-methylpyridin-3-yl)-5-(((1-methyl-4-oxo-4,5-dihydro-1H-imidazol-2-yl)amino)methyl)benzamide;
N-(3,4-dichlorobenzyl)-3-(6-fluoro-2-methylpyridin-3-yl)-5-(((1-methyl-4-oxo-4,5-dihydro-1H-imidazol-2-yl)amino)methyl)benzamide;
5-(((4,5-dihydro-1H-imidazol-2-yl)amino)methyl)-N-(1-(3,5-dimethoxyphenyl)ethyl)-4'-fluoro-2'-methyl-[1,1'-biphenyl]-3-carboxamide;
2-amino-5-(((3,4-dihydro-2H-pyrrol-5-yl)amino)methyl)-N-(3,5-dimethoxybenzyl)-4'-fluoro-2'-methyl-[1,1'-biphenyl]-3-carboxamide;
2-amino-5-(((4,5-dihydro-1H-imidazol-2-yl)amino)methyl)-N-(3,5-dimethoxybenzyl)-4'-fluoro-2'-methyl-[1,1'-biphenyl]-3-carboxamide;
5-(((3,4-dihydro-2H-pyrrol-5-yl)amino)methyl)-N-(3,5-dimethoxybenzyl)-4'-fluoro-N,2'-dimethyl-2-(methylamino)-[1,1'-biphenyl]-3-carboxamide;
5-(((4,5-dihydro-1H-imidazol-2-yl)amino)methyl)-N-(3,5-dimethoxybenzyl)-4'-fluoro-N,2'-dimethyl-2-(methylamino)-[1,1'-biphenyl]-3-carboxamide;
2-acetamido-5-(((3,4-dihydro-2H-pyrrol-5-yl)amino)methyl)-N-(3,5-dimethoxybenzyl)-4'-fluoro-2'-methyl-[1,1'-biphenyl]-3-carboxamide;
2-acetamido-5-(((4,5-dihydro-1H-imidazol-2-yl)amino)methyl)-N-(3,5-dimethoxybenzyl)-4'-fluoro-2'-methyl-[1,1'-biphenyl]-3-carboxamide;
(S)—N-(cyclopropyl(4-fluoro-3-methylphenyl)methyl)-5-(((4,5-dihydrooxazol-2-yl)amino)methyl)-4'-fluoro-2'-(trifluoromethyl)-[1,1'-biphenyl]-3-carboxamide; and
(S)—N-(cyclopropyl(4-fluoro-3-methylphenyl)methyl)-3-(((4,5-dihydrooxazol-2-yl)amino)methyl)-5-(1-ethyl-3-(trifluoromethyl)-1H-pyrazol-4-yl)benzamide;
or a pharmaceutically acceptable salt or tautomer thereof.

In another aspect, compounds of formula (I) have formula (I″), wherein $Q^1$ is N or $CR^3$; and $Q^2$ is N or $CR^5$; provided that at least one of $Q^1$ and $Q^2$ is N, and X, $R^{1a}$, $R^{1b}$, $R^2$, $R^4$, $R^{6a}$, and $R^{6b}$ are as defined herein.

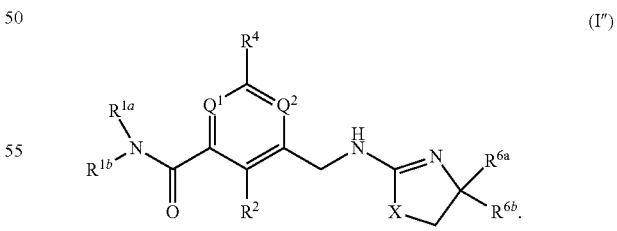

(I″)

In some embodiments, X is NR and R is H or $C_1$-$C_4$alkyl. For example, X may be NH or $NCH_3$.

In other embodiments, X is $CH_2$.

In some embodiments, $R^{1a}$ is selected from the group consisting of $C_1$-$C_4$ alkyl, —$(CR^aR^b)$-aryl, —$(CR^aR^b)$-heteroaryl, and —$(CR^aR^b)$—$C_3$-$C_6$-cycloalkyl (e.g., cyclopropyl); $R^{1b}$ is selected from the group consisting of hydrogen and $C_1$-$C_4$ alkyl; $R^a$ is selected from the group consisting of hydrogen, $C_1$-$C_4$ alkyl, and $C_3$-$C_6$-cycloalkyl (e.g., cyclopropyl); and $R^b$ is hydrogen, wherein the heteroaryl is a 5- or 6-membered heteroaryl having 1, 2, or 3 heteroatoms independently selected from the group consisting of N, O and S, and the aryl and heteroaryl are unsubstituted or substituted with 1, 2, or 3 substituents independently selected from the group consisting of halo, $C_1$-$C_4$ alkyl, $C_1$-$C_4$ haloalkyl, $C_1$-$C_4$ alkoxy, OH, and $C_1$-$C_4$ hydroxyalkyl. In some embodiments, $R^{1a}$ is selected from the group consisting of —(CR$^a$R$^b$)-aryl and —(CR$^a$R$^b$)heteroaryl; $R^{1b}$ is hydrogen; $R^a$ is selected from the group consisting of hydrogen, $C_1$-$C_4$ alkyl, and $C_3$-$C_6$-cycloalkyl (e.g., cyclopropyl); and $R^b$ is hydrogen, wherein the heteroaryl is a 5- or 6-membered heteroaryl having 1, 2, or 3 heteroatoms independently selected from the group consisting of N, O and S, and the aryl and heteroaryl are unsubstituted or substituted with 1, 2, or 3 substituents independently selected from the group consisting of halo, $C_1$-$C_4$ alkyl, $C_1$-$C_4$ haloalkyl, $C_1$-$C_4$ alkoxy, and OH. In some embodiments, $R^a$ is hydrogen. In some embodiments, $R^a$ is cyclopropyl. In some embodiments, $R^a$ is methyl. In some embodiments, $R^{1a}$ is —(CR$^a$R$^b$)-cyclopropyl, $R^b$ is hydrogen, and $R^a$ is cyclopropyl.

In some embodiments, $R^{1a}$ is —(CR$^a$R$^b$)-aryl, wherein the aryl is

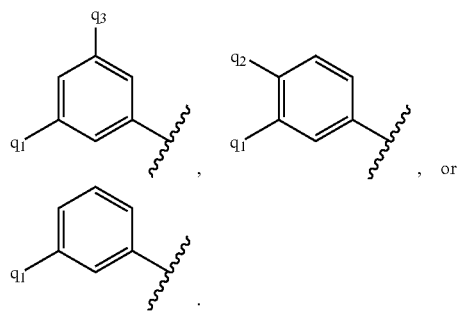

In some embodiments, $R^{1a}$ is —(CR$^a$R$^b$)-heteroaryl, wherein the heteroaryl is

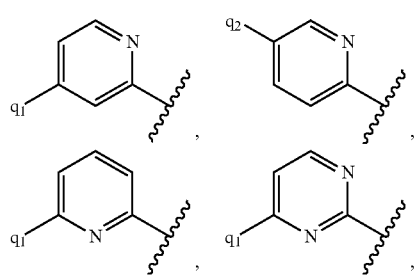

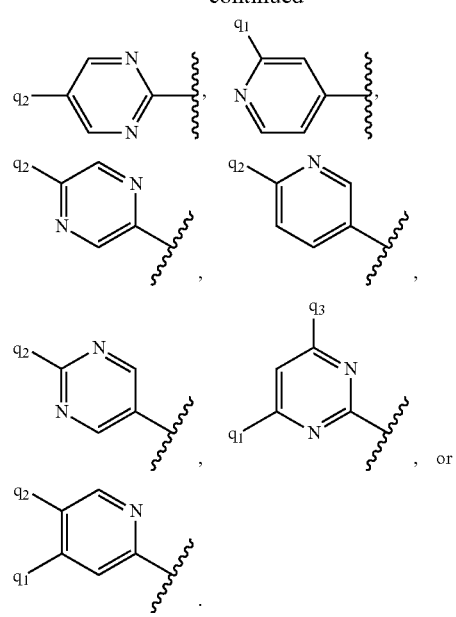

In some embodiments, the heteroaryl in $R^{1a}$ is

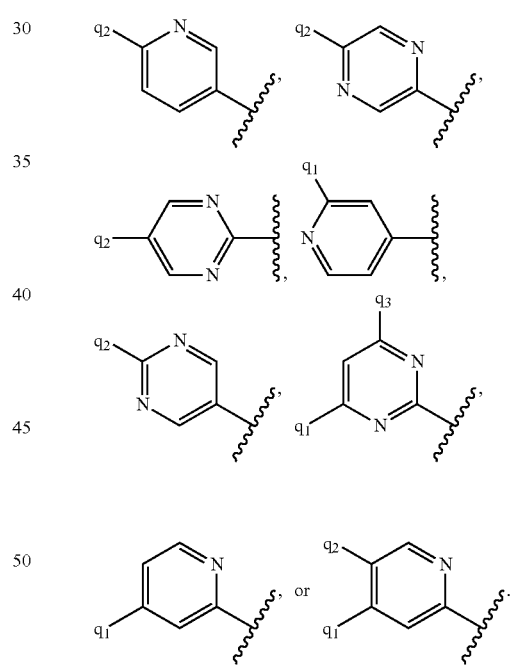

In some embodiments, the aryl in $R^{1a}$ is

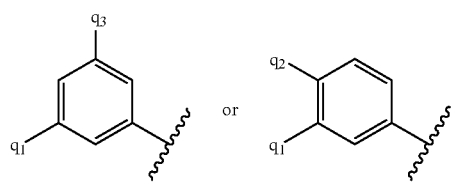

The substituents $q_1$, $q_2$, and $q_3$ are independently selected from the group consisting of halo, $C_1$-$C_4$ alkyl, $C_1$-$C_4$ haloalkyl, $C_1$-$C_4$ alkoxy, OH, and $C_1$-$C_4$ hydroxyalkyl. In some embodiments, $q_1$, $q_2$, and $q_3$ are independently selected from the group consisting of halo, $C_1$-$C_4$ alkyl, $C_1$-$C_4$ haloalkyl, $C_1$-$C_4$ alkoxy, and OH. In some embodiments, $q_1$, $q_2$, and $q_3$ are independently selected from the group consisting of halo, $C_1$-$C_4$ alkyl, and $C_1$-$C_4$ alkoxy. In some embodiments, $q_1$, $q_2$, and $q_3$ are independently selected from the group consisting of fluoro, chloro, methyl, $CF_3$, OH, and methoxy.

In further embodiments, the aryl in $R^{1a}$ is

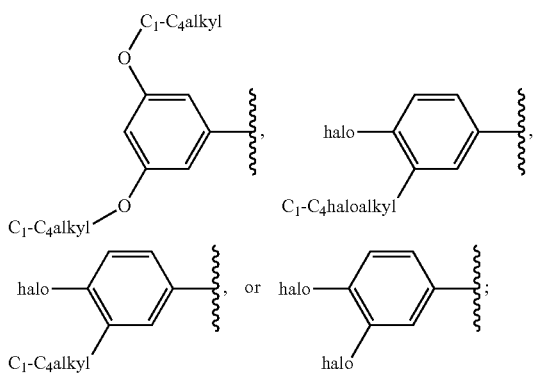

and the heteroaryl in $R^{1a}$ is

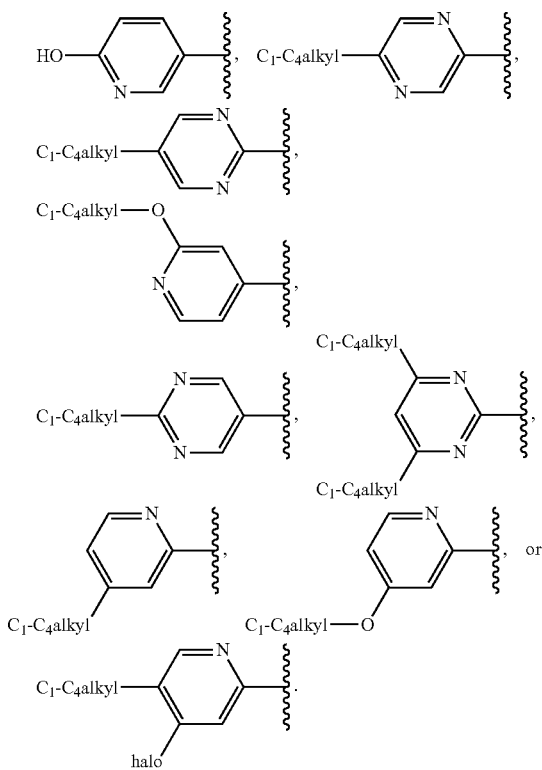

The heteroaryl

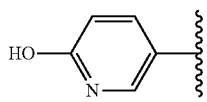

also represents the tautomeric form

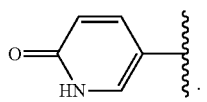

In some embodiments, $R^2$ is hydrogen. In other embodiments, $R^2$ is halogen (e.g., fluoro, chloro).

In some embodiments, $R^4$ is hydrogen. In other embodiments, $R^4$ is halogen (e.g., fluoro, chloro). In other embodiments, $R^4$ is $C_1$-$C_4$ haloalkyl (e.g., $CF_3$). In other embodiments, $R^4$ is an optionally substituted aryl (e.g., optionally substituted phenyl). In other embodiments, $R^4$ is an optionally substituted 5- to 6-membered heteroaryl having 1, 2, or 3 heteroatoms independently selected from the group consisting of N, O and S (e.g., optionally substituted pyridinyl, pyrrolyl) In other embodiments, $R^4$ is an optionally substituted —O-aryl (e.g., —O-phenyl, where the phenyl is optionally substituted). In other embodiments, $R^4$ is an optionally substituted —O-heteroaryl, wherein the heteroaryl is an optionally substituted 5- to 6-membered heteroaryl. The aryl and 5- or 6-membered heteroaryl at $R^4$ are independently optionally substituted with 1, 2, or 3 substituents independently selected from the group consisting of halo, $C_1$-$C_4$ alkyl, $C_1$-$C_4$ haloalkyl, $C_1$-$C_4$ alkoxy, and $C_1$-$C_4$ hydroxyalkyl. In some embodiments, $R^4$ is aryl or 5- to 6-membered heteroaryl having 1, 2, or 3 heteroatoms independently selected from the group consisting of N, O and S, wherein the aryl or heteroaryl is unsubstituted or substituted with 1, 2 or 3 substituents independently selected from the group consisting of halo, $C_1$-$C_4$ alkyl, $C_1$-$C_4$ haloalkyl, and $C_1$-$C_4$ alkoxy. In some embodiments, $R^4$ is selected from the group consisting of phenyl and pyridyl, each of which is unsubstituted or substituted with 1, 2, or 3 substituents as described herein. In some embodiments, the aryl and heteroaryl substituents at $R^4$ are selected from the group consisting of fluoro, chloro, methyl, methoxy, ethoxy, and trifluoromethyl.

For example, $R^4$ may be

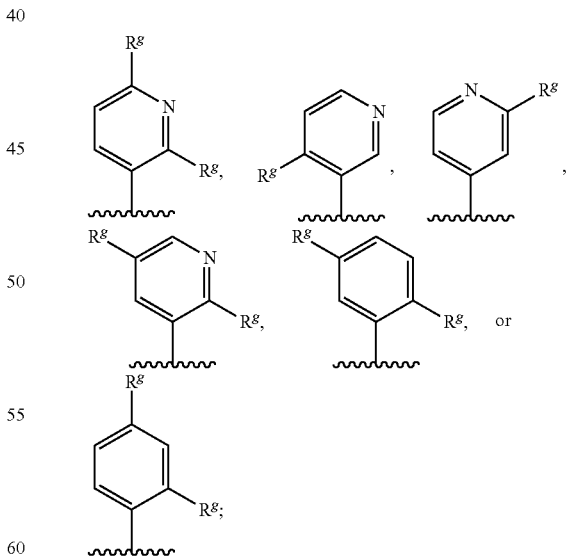

and $R^g$, at each occurrence, is independently halo, $C_1$-$C_4$ alkyl, $C_1$-$C_4$ haloalkyl, or $C_1$-$C_4$ alkoxy. In some embodiments, $R^g$, at each occurrence is selected from the group consisting of fluoro, chloro, methyl, methoxy, ethoxy, and trifluoromethyl.

In further examples, $R^4$ may be

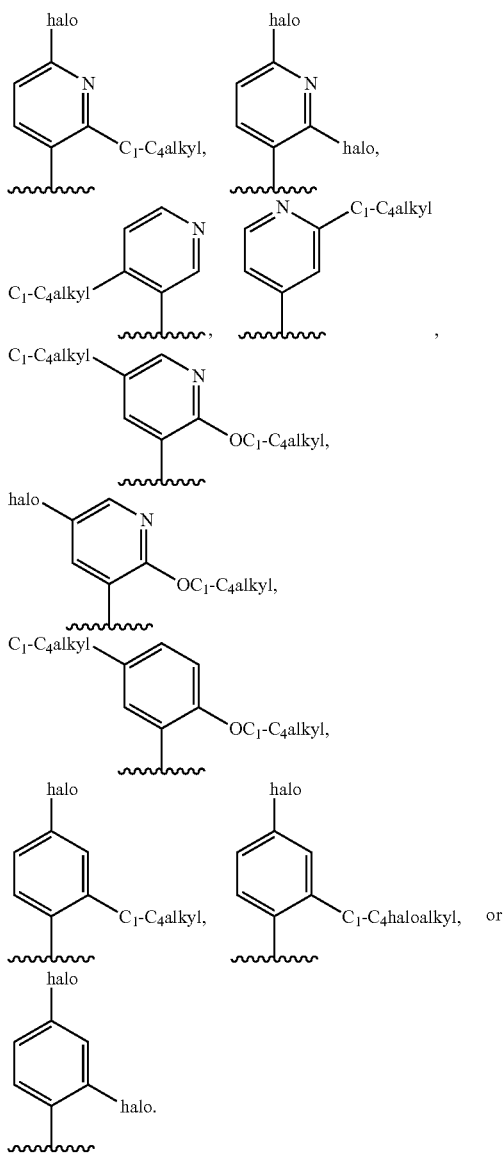

Specific exemplary aryl $R^4$ include

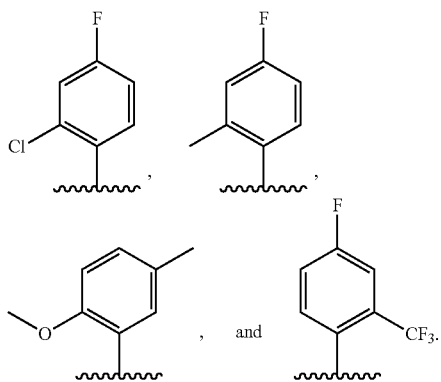

Specific exemplary heteroaryl $R^4$ include

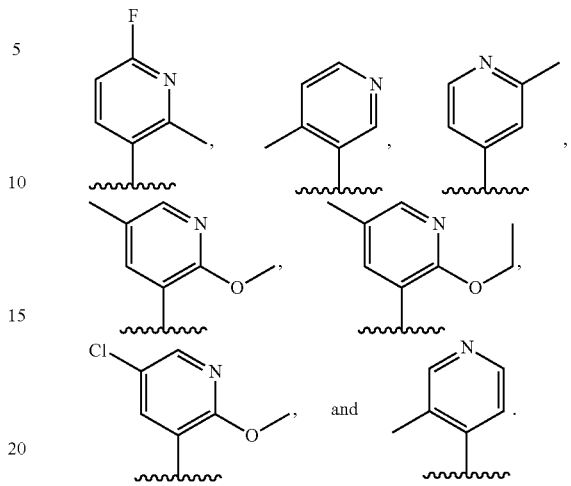

In some embodiments, $R^4$ is a 4- to 12-membered heterocyclyl containing one nitrogen atom and optionally 1-2 additional heteroatoms selected from the group consisting of nitrogen, oxygen, and sulfur, the heterocyclyl being monocyclic (e.g., pyrrolidinyl, piperidinyl, morpholinyl, thiomorpholinyl), fused bicyclic (e.g., 3-azabicyclo[3.2.0]heptanyl), spirocyclic (e.g., 5-azaspiro[2.4]heptanyl), or bridged (e.g., 2-azabicyclo[2.2.1]heptanyl) and optionally substituted with 1-4 substituents independently selected from the group consisting of halo, $C_1$-$C_4$ alkyl (e.g., $CH_3$), $C_1$-$C_4$ haloalkyl (e.g., $CF_3$), $C_1$-$C_4$ alkoxy, OH, and oxo. In some embodiments, the heterocyclyl is attached through a ring nitrogen atom (e.g., pyrrolidin-1-yl, piperidin-1-yl, morpholin-4-yl, thiomorpholin-4-yl, 3-azabicyclo[3.2.0]heptan-3-yl, 5-azaspiro[2.4]heptan-5-yl, 2-azabicyclo[2.2.1]heptan-2-yl). In some embodiments, the heterocyclyl is attached through a ring nitrogen and substituted in the 2-position of the heterocyclyl (e.g., 2-($C_1$-$C_3$haloalkyl)pyrrolidin-1-yl, 2-(trifluoromethyl)pyrrolidin-1-yl, 2-(2,2,2-trifluoroethyl)pyrrolidin-1-yl, 2-($C_1$-$C_3$alkyl)pyrrolidin-1-yl, 2-methylpyrrolidin-1-yl, 2-ethylpyrrolidin-1-yl, 2-($C_1$-$C_3$haloalkyl)piperidin-1-yl, 2-(trifluoromethyl)piperidin-1-yl, 2-(($C_1$-$C_3$alkyl)piperidin-1-yl, 2-methylpiperidin-1-yl).

In some embodiments, $Q^1$ is N, $Q^2$ is $CR^5$, and $R^5$ is hydrogen, halo (e.g., fluoro, chloro), $C_1$-$C_4$ alkyl (e.g., methyl, ethyl), $C_1$-$C_4$ haloalkyl (e.g., $CF_3$), —OH, or —O($C_1$-$C_4$ alkyl (e.g., methoxy). In some embodiments, $Q^1$ is N, $Q^2$ is $CR^5$, and $R^2$, $R^4$, and $R^5$ are each hydrogen.

In other embodiments, $Q^2$ is N, $Q^1$ is $CR^3$, and $R^3$ is hydrogen, halo (e.g., fluoro, chloro), $C_1$-$C_4$ alkyl (e.g., methyl, ethyl), $C_1$-$C_4$ haloalkyl (e.g., $CF_3$), —OH, or —O$C_1$-$C_4$ alkyl (e.g., methoxy). In other embodiments, $Q^2$ is N, $Q^1$ is $CR^3$, and $R^2$, $R^3$, and $R^4$ are each hydrogen.

In other embodiments, $Q^1$ is N, $Q^2$ is $CR^5$, $R^4$ is optionally substituted aryl, as defined herein, and $R^2$ and $R^5$ are hydrogen. In other embodiments, $R^4$ is an optionally substituted 5- to 6-membered heteroaryl, as defined herein, and $R^2$ and $R^5$ are hydrogen.

In other embodiments, $Q^1$ and $Q^2$ are each N.

In some embodiments, $R^{6a}$ and $R^{6b}$ are each hydrogen. In other embodiments, $R^{6a}$ and $R^{6b}$ are taken together to form an oxo group.

In some embodiments, X is N—$C_1$-$C_4$alkyl and $R^{6a}$ and $R^{6b}$ together form an oxo group. In other embodiments, X is NH and $R^{6a}$ and $R^{6b}$ are each hydrogen. In other embodiments, X is $CH_2$ and $R^{6a}$ and $R^{6b}$ are each hydrogen.

In some embodiments, the compound of formula (I") is a compound of formula (Ia"):

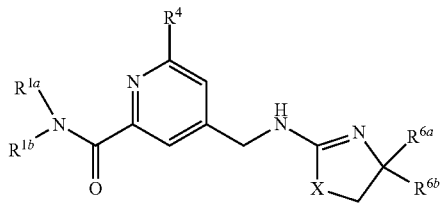

(Ia")

wherein $R^{1a}$, $R^{1b}$, $R^4$, $R^{6a}$, $R^{6b}$, and X are as described in the embodiments and combinations thereof herein. For example, in some embodiments of formula (Ia"), $R^{1a}$ is selected from the group consisting of —$(CR^aR^b)$-aryl and —$(CR^aR^b)$-heteroaryl, wherein the heteroaryl is a 5- or 6-membered heteroaryl having 1, 2 or 3 heteroatoms independently selected from the group consisting of N, O and S, and the aryl and heteroaryl are unsubstituted or substituted with 1, 2, or 3 substituents independently selected from the group consisting of halo, $C_1$-$C_4$ alkyl, $C_1$-$C_4$ haloalkyl, $C_1$-$C_4$ alkoxy, and OH; $R^{1b}$ is hydrogen; $R^a$ is selected from the group consisting of hydrogen, $C_1$-$C_4$ alkyl, and $C_3$-$C_6$-cycloalkyl; $R^b$ is hydrogen; X is NH, NCH$_3$, or CH$_2$; $R^{6a}$ and $R^{6b}$ are as defined herein; and $R^4$ is aryl or a 5- to 6-membered heteroaryl having 1, 2, or 3 heteroatoms independently selected from the group consisting of N, O and S, wherein the aryl or heteroaryl are unsubstituted or substituted with 1, 2 or 3 substituents independently selected from the group consisting of halo, $C_1$-$C_4$ alkyl, $C_1$-$C_4$ haloalkyl, and $C_1$-$C_4$ alkoxy. In further embodiments, the aryl and heteroaryl at $R^{1a}$ and $R^4$ are as defined in the embodiments above.

In some embodiments, the compound of formula (I") is a compound of formula (Ib"):

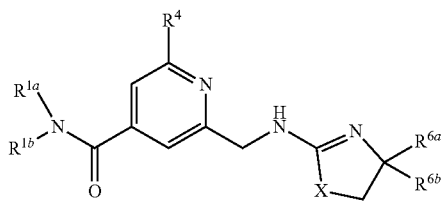

(Ib")

$R^{1a}$, $R^{1b}$, $R^4$, $R^{6a}$, $R^{6b}$, and X are as described in the embodiments and combinations thereof herein. For example, in some embodiments of formula (Ib"), $R^{1a}$ is selected from the group consisting of —$(CR^aR^b)$-aryl and —$(CR^aR^b)$-heteroaryl, wherein the heteroaryl is a 5- or 6-membered heteroaryl having 1, 2, or 3 heteroatoms independently selected from the group consisting of N, O and S, and the aryl and heteroaryl are unsubstituted or substituted with 1, 2, or 3 substituents independently selected from the group consisting of halo, $C_1$-$C_4$ alkyl, $C_1$-$C_4$ haloalkyl, $C_1$-$C_4$ alkoxy, and OH; $R^{1b}$ is hydrogen; $R^a$ is selected from the group consisting of hydrogen, $C_1$-$C_4$ alkyl, and $C_3$-$C_6$-cycloalkyl; $R^b$ is hydrogen; X is NH, NCH$_3$, or CH$_2$; $R^{6a}$ and $R^{6b}$ are as defined herein; and $R^4$ is aryl or a 5- to 6-membered heteroaryl having 1, 2, or 3 heteroatoms independently selected from the group consisting of N, O and S, wherein the aryl or heteroaryl are unsubstituted or substituted with 1, 2, or 3 substituents independently selected from the group consisting of halo, $C_1$-$C_4$ alkyl, $C_1$-$C_4$ haloalkyl, and $C_1$-$C_4$ alkoxy. In further embodiments, the aryl and heteroaryl at $R^{1a}$ and $R^4$ are as defined in the embodiments above.

In some embodiments, the compound of formula (I") is selected from the group consisting of:
N-(3,4-dichlorobenzyl)-4-(((4,5-dihydro-1H-imidazol-2-yl)amino)methyl)-6'-fluoro-2'-methyl-[2,3'-bipyridine]-6-carboxamide;
N-(3,4-dichlorobenzyl)-4-(((4,5-dihydro-1H-imidazol-2-yl)amino)methyl)-2',6'-difluoro-[2,3'-bipyridine]-6-carboxamide;
N-(4-chloro-3-fluorobenzyl)-4-(((4,5-dihydro-1H-imidazol-2-yl)amino)methyl)-6'-fluoro-2'-methyl-[2,3'-bipyridine]-6-carboxamide;
4-(((4,5-dihydro-1H-imidazol-2-yl)amino)methyl)-6'-fluoro-2'-methyl-N-((6-oxo-1,6-dihydropyridin-3-yl)methyl)-[2,3'-bipyridine]-6-carboxamide;
N-(4-chloro-3-methylbenzyl)-4-(((4,5-dihydro-1H-imidazol-2-yl)amino)methyl)-6'-fluoro-2'-methyl-[2,3'-bipyridine]-6-carboxamide;
4-(((4,5-dihydro-1H-imidazol-2-yl)amino)methyl)-N-(1-(3,5-dimethoxyphenyl)ethyl)-6'-fluoro-2'-methyl-[2,3'-bipyridine]-6-carboxamide;
4-(((4,5-dihydro-1H-imidazol-2-yl)amino)methyl)-6'-fluoro-2'-methyl-N-((5-methylpyrazin-2-yl)methyl)-[2,3'-bipyridine]-6-carboxamide;
4-(((4,5-dihydro-1H-imidazol-2-yl)amino)methyl)-6'-fluoro-2'-methyl-N-((5-methylpyrimidin-2-yl)methyl)-[2,3'-bipyridine]-6-carboxamide;
4-(((4,5-dihydro-1H-imidazol-2-yl)amino)methyl)-N-(3,5-dimethoxybenzyl)-6'-fluoro-2'-methyl-[2,3'-bipyridine]-6-carboxamide;
4-(((4,5-dihydro-1H-imidazol-2-yl)amino)methyl)-6'-fluoro-N-((2-methoxypyridin-4-yl)methyl)-2'-methyl-[2,3'-bipyridine]-6-carboxamide;
4-(((4,5-dihydro-1H-imidazol-2-yl)amino)methyl)-6'-fluoro-2'-methyl-N-((2-methylpyrimidin-5-yl)methyl)-[2,3'-bipyridine]-6-carboxamide;
N-(3,4-dichlorobenzyl)-4-(((4,5-dihydro-1H-imidazol-2-yl)amino)methyl)-4'-methyl-[2,3'-bipyridine]-6-carboxamide;
N-(3,4-dichlorobenzyl)-4-(((4,5-dihydro-1H-imidazol-2-yl)amino)methyl)-2'-methyl-[2,4'-bipyridine]-6-carboxamide;
N-(3,4-dichlorobenzyl)-4-(((4,5-dihydro-1H-imidazol-2-yl)amino)methyl)-2'-methoxy-5'-methyl-[2,3'-bipyridine]-6-carboxamide;
N-(3,4-dichlorobenzyl)-4-(((4,5-dihydro-1H-imidazol-2-yl)amino)methyl)-3'-methyl-[2,4'-bipyridine]-6-carboxamide;
4-(((4,5-dihydro-1H-imidazol-2-yl)amino)methyl)-N-((4,6-dimethylpyrimidin-2-yl)methyl)-6'-fluoro-2'-methyl-[2,3'-bipyridine]-6-carboxamide;
5'-chloro-N-(3,4-dichlorobenzyl)-4-(((4,5-dihydro-1H-imidazol-2-yl)amino)methyl)-2'-methoxy-[2,3'-bipyridine]-6-carboxamide;
N-(3,4-dichlorobenzyl)-4-(((4,5-dihydro-1H-imidazol-2-yl)amino)methyl)-6-(2-methoxy-5-methylphenyl)picolinamide;
N-(3,4-dichlorobenzyl)-4-(((4,5-dihydro-1H-imidazol-2-yl)amino)methyl)-2'-ethoxy-5'-methyl-[2,3'-bipyridine]-6-carboxamide;
4-(((4,5-dihydro-1H-imidazol-2-yl)amino)methyl)-N-(1-(3,5-dimethoxyphenyl)ethyl)picolinamide;
4-(((3,4-dihydro-2H-pyrrol-5-yl)amino)methyl)-N-(1-(3,5-dimethoxyphenyl)ethyl)picolinamide;

N-(3,4-dichlorobenzyl)-4-(((3,4-dihydro-2H-pyrrol-5-yl) amino)methyl)-6-(4-fluoro-2-methylphenyl)picolinamide;

N-(4-chloro-3-methylbenzyl)-4-(((3,4-dihydro-2H-pyrrol-5-yl)amino)methyl)-6-(4-fluoro-2-methylphenyl)picolinamide;

4-(((3,4-dihydro-2H-pyrrol-5-yl)amino)methyl)-N-(3,5-dimethoxybenzyl)-6-(4-fluoro-2-methylphenyl)picolinamide;

N-(3,4-dichlorobenzyl)-4-(((3,4-dihydro-2H-pyrrol-5-yl) amino)methyl)-6-(4-fluoro-2-(trifluoromethyl)phenyl)picolinamide;

N-(cyclopropyl(4-methylpyridin-2-yl)methyl)-4-(((3,4-dihydro-2H-pyrrol-5-yl)amino)methyl)-6-(4-fluoro-2-(trifluoromethyl)phenyl)picolinamide;

2-(((3,4-dihydro-2H-pyrrol-5-yl)amino)methyl)-N-(3,5-dimethoxybenzyl)-6-(4-fluoro-2-(trifluoromethyl)phenyl) isonicotinamide;

4-(((3,4-dihydro-2H-pyrrol-5-yl)amino)methyl)-N-(3,5-dimethoxybenzyl)-6-(4-fluoro-2-(trifluoromethyl)phenyl) picolinamide;

(S)—N-(1-(4-chloro-3-methylphenyl)ethyl)-4-(((3,4-dihydro-2H-pyrrol-5-yl)amino)methyl)-6-(4-fluoro-2-(trifluoromethyl)phenyl)picolinamide;

4-(((3,4-dihydro-2H-pyrrol-5-yl)amino)methyl)-N-(1-(3,5-dimethoxyphenyl)ethyl)-6-(4-fluoro-2-(trifluoromethyl) phenyl)picolinamide;

4-(((3,4-dihydro-2H-pyrrol-5-yl)amino)methyl)-6-(4-fluoro-2-(trifluoromethyl)phenyl)-N-((4-methoxypyridin-2-yl)methyl)picolinamide;

N-(cyclopropyl(4-methylpyridin-2-yl)methyl)-4-(((3,4-dihydro-2H-pyrrol-5-yl)amino)methyl)-6-(4-fluoro-2-methylphenyl)picolinamide;

N-(1-(5-chloro-4-methylpyridin-2-yl)ethyl)-4-(((3,4-dihydro-2H-pyrrol-5-yl)amino)methyl)-6-(4-fluoro-2-(trifluoromethyl)phenyl)picolinamide;

N-(1-(4-chloro-5-methylpyridin-2-yl)ethyl)-4-(((3,4-dihydro-2H-pyrrol-5-yl)amino)methyl)-6-(4-fluoro-2-(trifluoromethyl)phenyl)picolinamide;

(S)-4-(((3,4-dihydro-2H-pyrrol-5-yl)amino)methyl)-6-(4-fluoro-2-methylphenyl)-N-(1-(4-fluoro-3-(trifluoromethyl)phenyl)ethyl)picolinamide;

2-(((4,5-dihydro-1H-imidazol-2-yl)amino)methyl)-N-(1-(3,5-dimethoxyphenyl)ethyl)isonicotinamide;

2-(((3,4-dihydro-2H-pyrrol-5-yl)amino)methyl)-N-(1-(3,5-dimethoxyphenyl)ethyl)isonicotinamide;

(S)-6-(2-chloro-4-fluorophenyl)-4-(((3,4-dihydro-2H-pyrrol-5-yl)amino)methyl)-N-(1-(4-fluoro-3-methylphenyl) ethyl)picolinamide;

(S)-6-(2-chloro-4-fluorophenyl)-N-(cyclopropyl(4-fluoro-3-methylphenyl)methyl)-4-(((3,4-dihydro-2H-pyrrol-5-yl)amino)methyl)picolinamide;

(S)-6-(2-chloro-4-fluorophenyl)-N-(1-(4-fluoro-3-methylphenyl)ethyl)-4-(((1-methyl-4-oxo-4,5-dihydro-1H-imidazol-2-yl)amino)methyl)picolinamide;

(S)-6-(2-chloro-4-fluorophenyl)-N-(cyclopropyl(4-fluoro-3-methylphenyl)methyl)-4-(((1-methyl-4-oxo-4,5-dihydro-1H-imidazol-2-yl)amino)methyl)picolinamide;

or a pharmaceutically acceptable salt or tautomer thereof.

In some embodiments of formula (I) and its subformulas (I'), (I"), etc., $R^4$ is

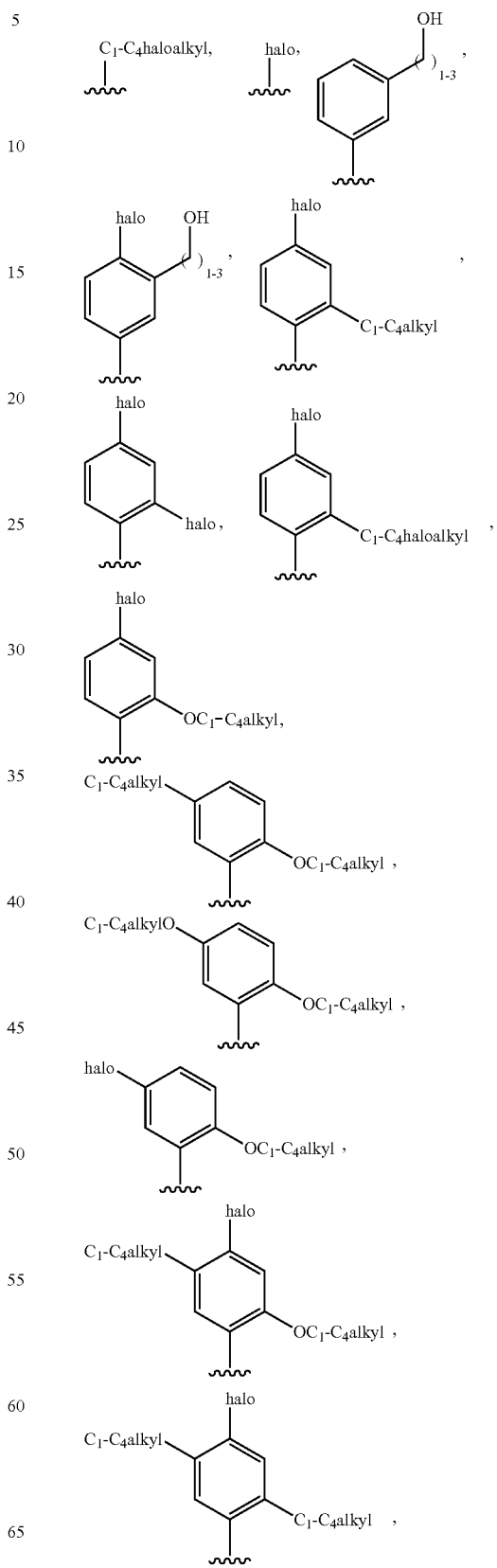

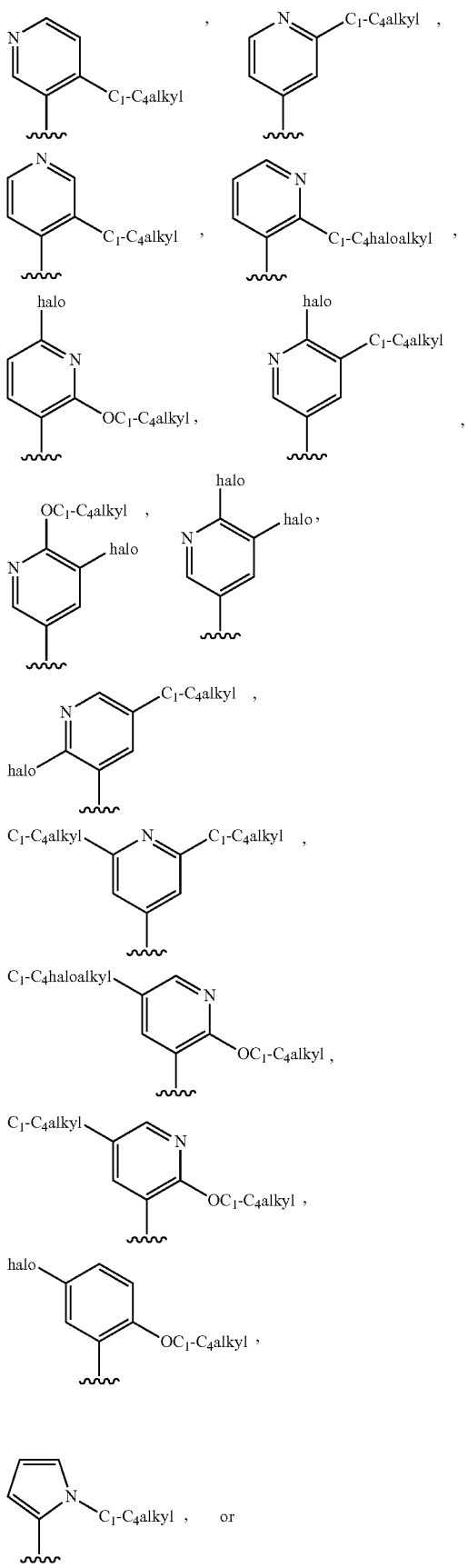
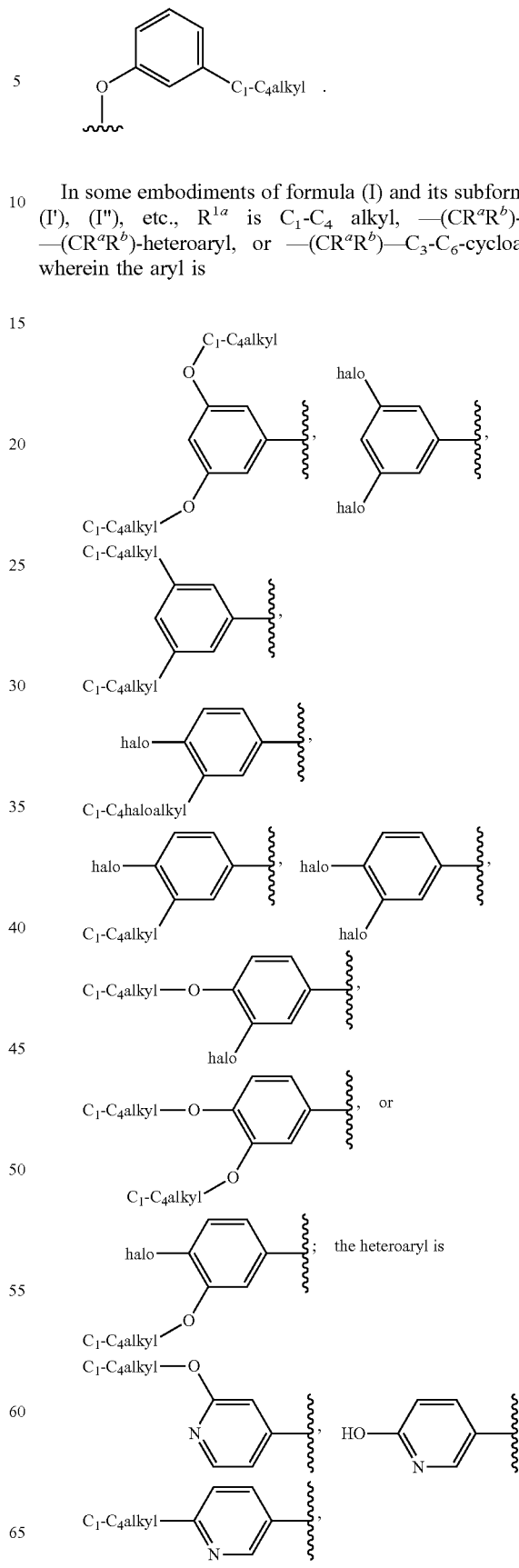
In some embodiments of formula (I) and its subformulas (I'), (I''), etc., $R^{1a}$ is $C_1$-$C_4$ alkyl, —$(CR^aR^b)$-aryl, —$(CR^aR^b)$-heteroaryl, or —$(CR^aR^b)$—$C_3$-$C_6$-cycloalkyl, wherein the aryl is
; the heteroaryl is -continued

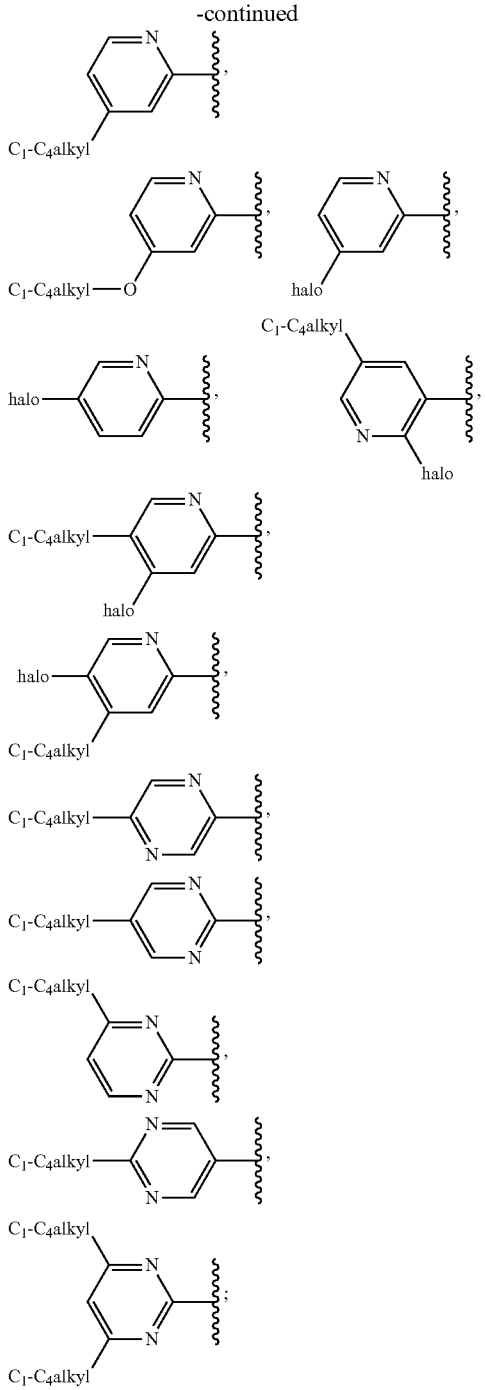

and the cycloalkyl is

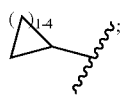

$R^{1b}$ is hydrogen or $C_1$-$C_4$ alkyl; $R^a$ is hydrogen, $C_1$-$C_4$ alkyl, or $C_3$-$C_6$-cycloalkyl; and $R^b$ is hydrogen.

In another aspect of the invention compounds of formula (I) have formula (II)

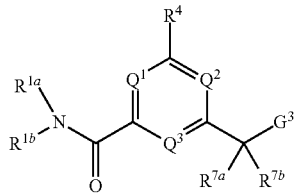

(II)

wherein
$Q^1$ is N or $CR^3$;
$Q^2$ is N or $CR^5$;
$Q^3$ is N or $CR^2$;
$R^{1a}$ is $G^1$ or —$(CR^aR^b)_n$-$G^1$;
n is 1, 2, or 3;
$R^a$ is hydrogen, $C_1$-$C_4$alkyl, $C_1$-$C_4$haloalkyl, $C_3$-$C_6$carbocycle, or —$C_1$-$C_3$alkylene-C(O)YR$^{20}$;
Y is O, NH, or NC$_1$-$C_4$alkyl;
$R^{20}$ is H, $C_1$-$C_4$alkyl, $C_3$-$C_6$cycloalkyl, or —$C_1$-$C_3$alkylene-$R^{30}$;
$R^{30}$ is C(O)C$_1$-$C_4$alkyl, C(O)C$_3$-$C_6$cycloalkyl, or phenyl, wherein the $C_3$-$C_6$cycloalkyl and phenyl are optionally substituted with 1-4 substituents independently selected from the group consisting of halogen, $C_1$-$C_4$alkyl, —OC$_1$-$C_4$alkyl, and $C_1$-$C_4$haloalkyl;
$R^b$ is hydrogen or $C_1$-$C_4$alkyl;
or alternatively $R^a$ and $R^b$ together with the carbon atom to which they are attached form a ring selected from the group consisting of a 3-8 membered saturated or partially unsaturated carbocyclic ring and a 3-8 membered saturated or partially unsaturated heterocyclic ring having 1-4 heteroatoms independently selected from the group consisting of nitrogen, oxygen, or sulfur;
or alternatively $R^a$ and $R^b$ are taken together to form an oxo group;
$R^{1b}$ is hydrogen, $C_1$-$C_4$alkyl, $C_3$-$C_6$cycloalkyl, or —$C_1$-$C_3$alkylene-$C_3$-$C_6$cycloalkyl;
$G^1$ is 6- to 12-membered aryl, a 5- to 12-membered heteroaryl, a 4- to 12-membered heterocyclyl, or a $C_3$-$C_{10}$carbocycle optionally fused to a phenyl or to a 5- to 6-membered heteroaryl, wherein $G^1$ is optionally substituted with 1-5 substituents independently selected from the group consisting of $C_1$-$C_4$hydroxyalkyl, halogen, $C_1$-$C_6$alkyl, $C_1$-$C_6$haloalkyl, oxo, —OR$^{1c}$, —NR$^{1c}$R$^{1d}$, —SR$^{1c}$, cyano, —C(O)OR$^{1c}$, —C(O)NR$^{1c}$R$^{1d}$, —C(O)R$_{1e}$, —SOR$^{1e}$, —SO$_2$R$^{1e}$, —SO$_2$NR$^{1c}$R$^{1d}$, —NR$^{1c}$C(O)R$^{1e}$, —NR$^{1c}$C(O)OR$^{1d}$, —NR$^{1c}$C(O)NR$^{1c}$R$^{1d}$, —NR$^{1c}$S(O)$_2$R$^{1e}$, —NR$^{1c}$S(O)$_2$NR$^{1c}$R$^{1d}$, $C_3$-$C_8$cycloalkyl, and —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;
$R^2$ is hydrogen, halogen, $C_1$-$C_4$alkyl, or $C_1$-$C_4$haloalkyl;
$R^3$ is hydrogen, halo, $C_1$-$C_4$ alkyl, $C_1$-$C_4$ haloalkyl, —OR$^{3a}$, —NR$^{3a}$R$^{3b}$, —SR$^{3a}$, cyano, —C(O)OR$^{3a}$, —C(O)NR$^{3a}$R$^{3b}$, —C(O)R$^{3c}$, —SOR$^{3c}$, —SO$_2$R$^{3c}$, —SO$_2$NR$^{3a}$R$^{3b}$, —NR$^{3a}$C(O)R$^{3c}$, —NR$^{3a}$C(O)OR$^{3b}$, —NR$^{3a}$C(O)NR$^{3a}$R$^{3b}$, —NR$^{3a}$S(O)$_2$R$^{3c}$, —NR$^{3a}$S(O)$_2$NR$^{3a}$R$^{3b}$, $C_3$-$C_8$cycloalkyl, or —(C$_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;

R⁴ is halogen, $C_1$-$C_6$alkyl, $C_1$-$C_6$haloalkyl, $C_1$-$C_6$haloalkenyl, -L-$R^x$, $G^2$, -L-$G^2$, or -L-$C_1$-$C_3$alkylene-$G^2$;

L is O, S, —$NR^{4a}$—, —S(O)—, —S(O)$_2$—, —S(O)$_2$$NR^{4a}$—, —C(O)$NR^{4a}$—, —C(O)—, —$NR^{4a}$C(O)—, —$NR_{4a}$C(O)O—, —$NR_{4a}$C(O)$NR_{4a}$$NR_{4a}$—, —$NR^{4a}$S(O)$_2$—, or —$NR^{4a}$S(O)$_2$$NR^{4a}$—;

$R^x$ is hydrogen, $C_1$-$C_6$alkyl, or $C_1$-$C_6$haloalkyl;

$G^2$ is a $C_3$-$C_{10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of $C_1$-$C_4$hydroxyalkyl, halogen, $C_1$-$C_6$alkyl, $C_1$-$C_6$haloalkyl, oxo, —$OR^{4b}$, —$NR^{4b}R^{4c}$, —$SR^{4b}$, cyano, —$C(O)OR^{4b}$, —$C(O)NR^{4b}R^{4c}$, —$C(O)R^{4d}$, —$SOR^{4d}$, —$SO_2R^{4d}$, —$SO_2NR^{4b}R^{4c}$, —$NR^{4b}C(O)R^{4d}$, —$NR^{4b}C(O)OR^{4c}$, —$NR^{4b}C(O)NR^{4b}R^{4c}$, —$NR^{4b}S(O)_2R^{4d}$, —$NR^{4b}S(O)_2NR^{4b}R^{4c}$, $C_3$-$C_8$cycloalkyl, and —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;

$R^5$ is hydrogen, halo, $C_1$-$C_4$ alkyl, $C_1$-$C_4$ haloalkyl, —$OR^{5a}$, —$NR^{5a}R^{5b}$, —$SR^{5a}$, cyano, —$C(O)OR^{5a}$, —$C(O)NR^{5a}R^{5b}$, —$C(O)R^{5c}$, —$SOR^{5c}$, —$SO_2R^{5c}$, —$SO_2NR^{5a}R^{5b}$, —$NR^{5a}C(O)R^{5c}$, —$NR^{5a}C(O)OR^{5b}$, —$NR^{5a}C(O)NR^{5a}R^{5b}$, —$NR^{5a}S(O)_2R^{5c}$, —$NR^{5a}S(O)_2NR^{5a}R^{5b}$, $C_3$-$C_8$cycloalkyl, or —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;

$R^{7a}$ and $R^{7b}$ are independently hydrogen, halogen, $C_1$-$C_4$alkyl, or $C_1$-$C_4$haloalkyl, or $R^{7a}$ and $R^{7b}$ are taken together to form an oxo group;

$G^3$ is

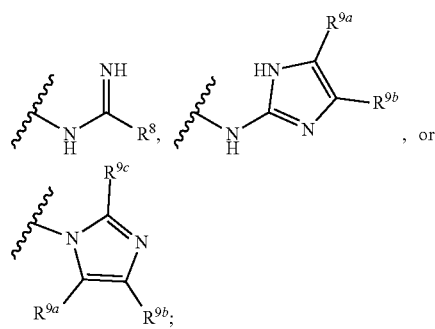

$R^8$ is $NR^{8a}R^{8b}$, $C_1$-$C_6$alkyl, $C_1$-$C_6$haloalkyl, $G^{3a}$, or —$C_1$-$C_3$alkylene-$G^{3a}$;

$R^{8a}$ and $R^{8b}$ are independently hydrogen, $C_1$-$C_6$alkyl, $C_1$-$C_6$haloalkyl, $G^{3a}$, or —$C_1$-$C_3$alkylene-$G^{3a}$;

$G^{3a}$ is $C_3$-$C_{10}$carbocycle, a 6- to 12-membered aryl, a 5- to 12-membered heteroaryl, or a 4- to 12-membered heterocycle, wherein $G^{3a}$ is optionally substituted with 1-4 substituents independently selected from the group consisting of halogen, $C_1$-$C_4$alkyl, $C_1$-$C_4$haloalkyl, OH, and —$OC_1$-$C_4$alkyl;

$R^{9a}$, $R^{9b}$, and $R^{9c}$, are each independently hydrogen, halogen, $C_1$-$C_4$alkyl, $C_1$-$C_4$haloalkyl, or $C_3$-$C_{10}$carbocycle, wherein the $C_3$-$C_{10}$carbocycle is optionally substituted with 1-4 substituents independently selected from the group consisting of halogen, $C_1$-$C_4$alkyl, $C_1$-$C_4$haloalkyl, OH, and —$OC_1$-$C_4$alkyl; and $R^{1c}$, $R^{1d}$, $R^{1e}$, $R^{3a}$, $R^{3b}$, $R^{3c}$, $R^{4a}$, $R^{4b}$, $R^{4c}$, $R^{4d}$, $R^{5a}$, $R^{5b}$, and $R^{5c}$, at each occurrence, are independently hydrogen, $C_1$-$C_6$alkyl, $C_1$-$C_6$haloalkyl, $C_3$-$C_8$cycloalkyl, or —$C_1$-$C_6$alkylene-$C_3$-$C_8$cycloalkyl, wherein the $C_3$-$C_8$cycloalkyl and —$C_1$-$C_6$alkylene-$C_3$-$C_8$cycloalkyl are optionally substituted with 1-4 substituents independently selected from the group consisting of $C_1$-$C_4$alkyl and halogen, wherein alternatively $R^{1c}$ and $R^{1d}$, $R^{3a}$ and $R^{3b}$, $R^{4b}$ and $R^{4c}$, and/or $R^{5a}$ and $R^{5b}$, each together with a common nitrogen atom to which each attaches form a 4- to 8-membered saturated or partially unsaturated heterocyclic ring, optionally substituted with 1-4 substituents independently selected from the group consisting of $C_1$-$C_4$alkyl, $C_1$-$C_4$haloalkyl, oxo, —OH, and —$OC_1$-$C_4$alkyl.

In some embodiments, $G^3$ is

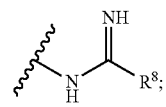

$R^8$ is —$NR^{8a}R^{8b}$, $G^{3a}$, or —$C_1$-$C_3$alkylene-$G^{3a}$; $R^{8a}$ and $R^{8b}$ are hydrogen; and $G^{3a}$ is $C_3$-$C_6$carbocycle or a 4- to 8-membered heterocycle (e.g., a 4- to 8-membered monocyclic nitrogen-containing heterocycle attached at a nitrogen atom, such as pyrrolidin-1-yl), wherein $G^{3a}$ is optionally substituted with 1-4 substituents independently selected from the group consisting of halogen, $C_1$-$C_4$alkyl, $C_1$-$C_4$haloalkyl, OH, and —$OC_1$-$C_4$alkyl. In further embodiments, $G^{3a}$ is $C_3$-$C_6$cycloalkyl or a 4- to 8-membered heterocycle containing one oxygen atom, wherein $G^{3a}$ is optionally substituted with 1-4 substituents independently selected from the group consisting of halogen, $C_1$-$C_4$alkyl, $C_1$-$C_4$haloalkyl, OH, and —$OC_1$-$C_4$alkyl. In still further embodiments, $R^8$ is —$NH_2$, cyclopropyl, cyclobutyl, —$CH_2$-cyclopropyl, 1-methylcycloprop-1-yl, or tetrahydrofuran-3-yl.

In some embodiments, $G^3$ is

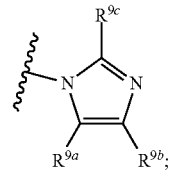

and $R^{9a}$, $R^{9b}$, and $R^{9c}$, are each independently hydrogen, $C_1$-$C_4$alkyl, $C_1$-$C_4$haloalkyl, or $C_3$-$C_6$carbocycle, wherein the $C_3$-$C_6$carbocycle is optionally substituted with 1-4 substituents independently selected from the group consisting of halogen, $C_1$-$C_4$alkyl, $C_1$-$C_4$haloalkyl, OH, and —$OC_1$-$C_4$alkyl. In further embodiments, $R^{9a}$ and $R^{9b}$ are hydrogen; and $R^{9c}$ is hydrogen, $C_1$-$C_4$alkyl, $C_1$-$C_4$haloalkyl, or $C_3$-$C_6$cycloalkyl, wherein the $C_3$-$C_6$cycloalkyl is optionally substituted with 1-4 substituents independently selected from the group consisting of halogen, $C_1$-$C_4$alkyl, $C_1$-$C_4$haloalkyl, OH, and —$OC_1$-$C_4$alkyl. In still further embodiments, $R^{9c}$ is hydrogen, methyl, trifluoromethyl, or cyclopropyl.

In some embodiments, $R^{1a}$ is $G^{1a}$ or —$(CR^aR^b)$-$G^{1b}$, $G^{1a}$ is $C_3$-$C_7$carbocycle wherein $G^{1a}$ is optionally substituted with 1-4 substituents independently selected from the group consisting of halogen, $C_1$-$C_6$alkyl, $C_1$-$C_6$haloalkyl, oxo, —$OR^{1c}$, —$NR^{1c}R^{1d}$, —$SR^{1c}$, cyano, —$C(O)OR^{1c}$, —$C(O)NR^{1c}C(O)R^{1e}$, —$SOR^{1e}$, —$SO_2R^{1e}$, —$SO_2NR^{1c}R^{1d}$, $NR^{1c}C(O)R^{1e}$, $NR^{1c}C(O)OR^{1d}$, —$NR^{1c}C(O)NR^{1c}R^{1d}$, —$NR^{1c}S(O)_2R^{1e}$, —$NR^{1c}S(O)_2NR^{1c}R^{1d}$, $C_3$-$C_8$cycloalkyl, and —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen; and $G^{1b}$ is $C_3$-$C_7$carbocycle, phenyl, or a 5- to 6-membered heteroaryl, wherein $G^{1b}$ is optionally substituted with 1-4 substituents independently selected from the group consisting of halogen, $C_1$-$C_6$alkyl, $C_1$-$C_6$haloalkyl, oxo, —$OR^{1c}$, —$NR^{1c}R^{1d}$, —$SR^{1c}$, cyano, —$C(O)OR^{1c}$, —$C(O)NR^{1a}R^{1d}$, —$SOR^{1e}$, —$SO_2R^{1e}$, —$SO_2NR^{1c}R^{1d}$, —$NR^{1c}C(O)R^{1e}$, —$NR^{1c}C(O)OR^{1d}$, —$NR_{1c}C(O)NR^{1c}R^{1d}$, —$NR^{1c}S(O)_2R^{1e}$, —$NR^{1c}S(O)_2NR^{1c}R^{1d}$, $C_1$-$C_8$cycloalkyl, and —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen. In further embodiments, $G^{1a}$ is $C_3$-$C_7$cycloalkyl optionally substituted with 1-4 substituents independently selected from the group consisting of halogen, $C_1$-$C_4$alkyl, and $C_1$-$C_4$haloalkyl; and $G^{1b}$ is $C_3$-$C_7$cycloalkyl, phenyl, or a 5- to 6-membered heteroaryl, wherein $G^{1b}$ is optionally substituted with 1-4 substituents independently selected from the group consisting of halogen, $C_1$-$C_4$alkyl, $C_1$-$C_4$haloalkyl, oxo, and —$OR^{1c}$ (e.g., $OCH_3$). In other embodiments, $R^{1a}$ is $G^{1a}$ and $G^{1a}$ is $C_3$-$C_7$cycloalkyl optionally substituted with $C_1$-$C_4$alkyl (e.g., 1-methylcyclopent-1-yl). In other embodiments, $R^{1a}$ is —$(CR^aR^b)$-$G^{1b}$; and $G^{1b}$ is

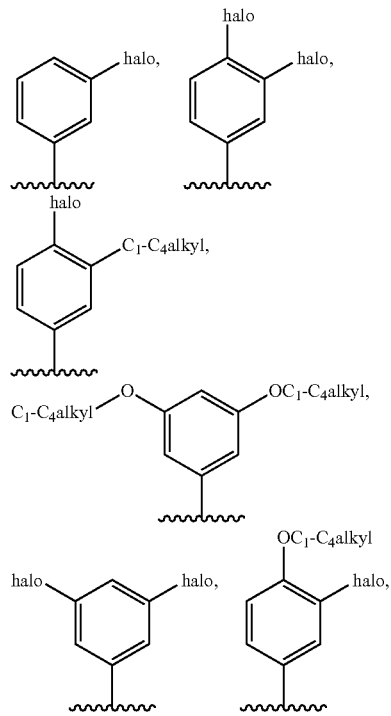

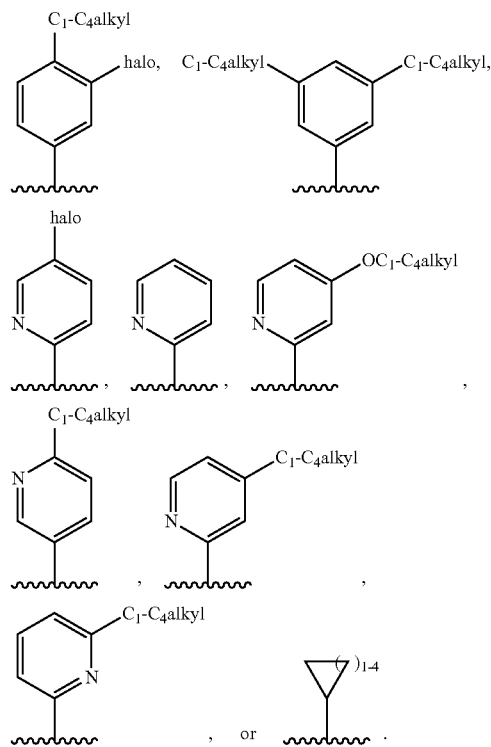

In further embodiments, $G^{1b}$ is

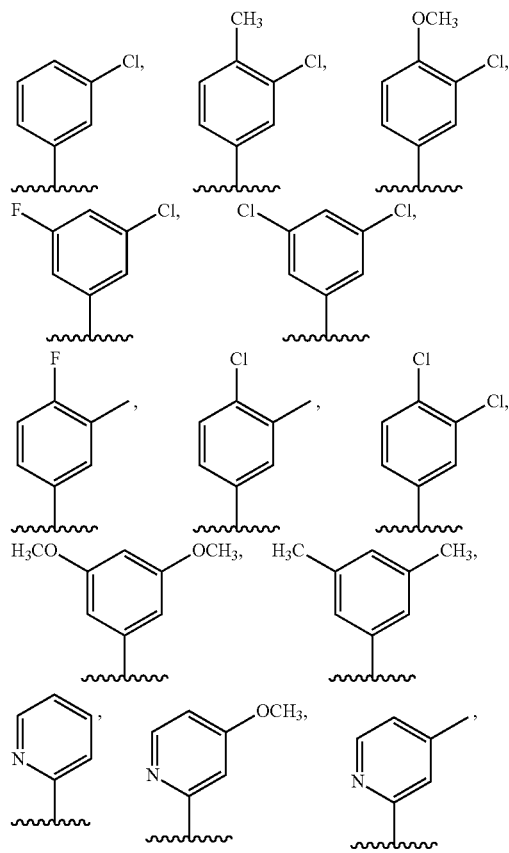

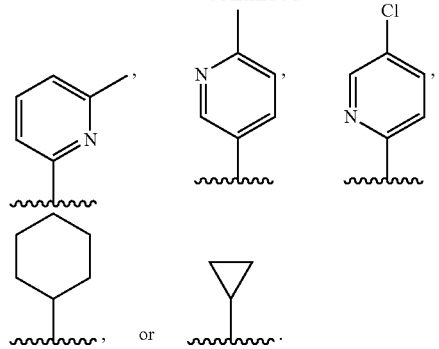

In the embodiments herein are further embodiments wherein $R^a$ is hydrogen, $C_1$-$C_4$alkyl, $C_3$-$C_6$carbocycle, —$C_1$-$C_3$alkylene-C(O)OH, or —$C_1$-$C_3$alkylene-C(O)O$C_1$-$C_4$alkyl (e.g., $CH_2C(O)OC_1$-$C_4$alkyl). Included are further embodiments wherein $R^a$ is hydrogen, $C_1$-$C_2$alkyl, $C_3$-$C_4$cycloalkyl, or —$C_1$-$C_3$alkylene-C(O)O$C_1$-$C_4$alkyl. Still further included are embodiments wherein $R^a$ is hydrogen, $C_1$-$C_2$alkyl, or $C_3$-$C_4$cycloalkyl.

In the embodiments herein are further embodiments wherein $R^b$ is hydrogen or $C_1$-$C_4$alkyl.

In the embodiments herein are further embodiments wherein $R^{1b}$ is hydrogen or $C_1$-$C_4$alkyl. Included are embodiments wherein $R^{1b}$ is hydrogen.

In the embodiments herein are further embodiments wherein $R^4$ is halogen (e.g., chloro), $C_1$-$C_6$alkyl (e.g., methyl), $C_1$-$C_6$haloalkyl, —O—$C_1$-$C_6$alkyl (e.g., —$OCH_3$), $G^2$, or —O-$G^2$. In further embodiments, $G^2$ is a $C_3$-$C_7$carbocycle, a 6- to 10-membered aryl, a 5- to 10-membered heteroaryl, or a 4- to 10-membered heterocycle, wherein $G^2$ is optionally substituted with 1-3 substituents independently selected from the group consisting of $C_1$-$C_4$hydroxyalkyl, halogen, $C_1$-$C_6$alkyl, $C_1$-$C_6$haloalkyl, oxo, —$OR^{4b}$, cyano, —$C(O)OR^{4b}$, —$C(O)NR^{4b}R^{4c}$, and $C_3$-$C_8$cycloalkyl, wherein the $C_3$-$C_8$cycloalkyl is optionally substituted with 1-4 substituents independently selected from the group consisting of $C_1$-$C_4$alkyl and halogen. In further embodiments, $R^4$ is halogen, $C_1$-$C_4$alkyl, $C_1$-$C_4$haloalkyl, $G^{2a}$, or —O-$G^{2b}$; $G^{2a}$ is phenyl, a 5- to 6-membered heteroaryl, or a 4-8-membered heterocycle, wherein $G^{2a}$ is optionally substituted with 1-3 substituents independently selected from the group consisting of $C_1$-$C_4$ hydroxyalkyl, halogen, $C_1$-$C_4$alkyl, $C_1$-$C_4$haloalkyl, oxo, —$OR^{4b}$, and —$C(O)NR^{4b}R^{4c}$; and $G^{2b}$ is $C_3$-$C_7$cycloalkyl or phenyl, wherein $G^{2b}$ is optionally substituted with $C_1$-$C_4$alkyl. In still further embodiments, $G^{2a}$ is a) phenyl optionally substituted with 1-3 substituents independently selected from the group consisting of $C_1$-$C_4$hydroxyalkyl, halogen, $C_1$-$C_4$alkyl, $C_1$-$C_4$haloalkyl, —$OR^{4b}$, and —$C(O)NR^{4b}R^{4c}$, b) a pyrazolyl, furanyl, or pyridinyl, optionally substituted with 1-3 substituents independently selected from the group consisting of $C_1$-$C_4$hydroxyalkyl, halogen, $C_1$-$C_4$alkyl, $C_1$-$C_4$haloalkyl, —$OR^{4b}$, and —$C(O)NR^{4b}R^{4c}$, or c) pyrrolidinyl or morpholinyl, optionally substituted with 1-3 substituents independently selected from the group consisting of halogen, $C_1$-$C_4$alkyl, and $C_1$-$C_4$haloalkyl. In still further embodiments, $R^4$ is

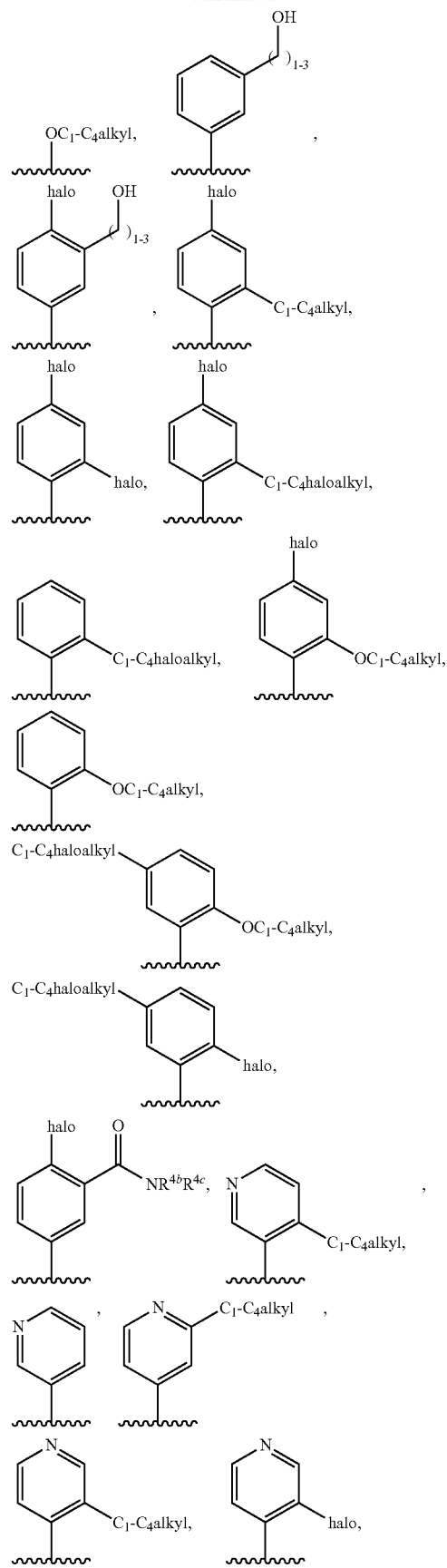

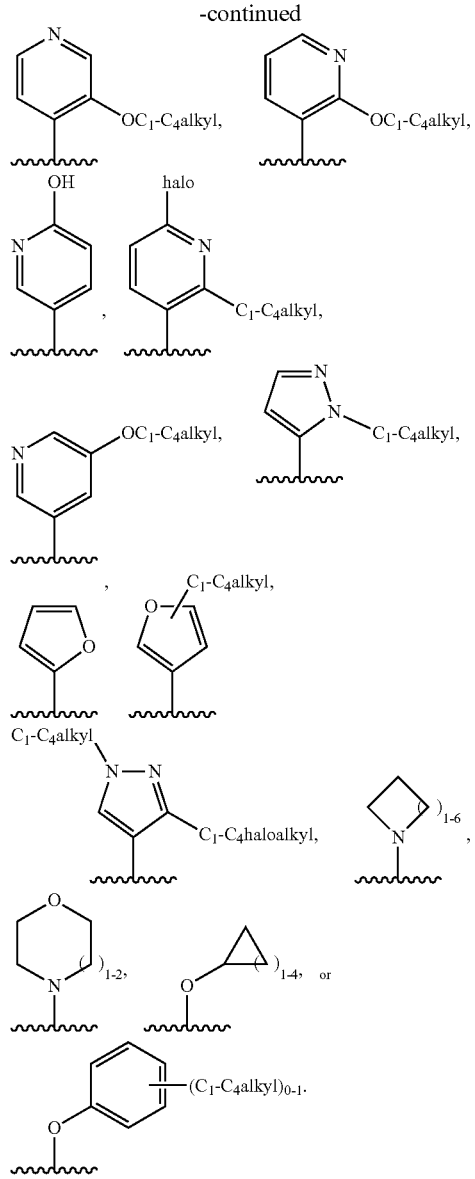
In still further embodiments, $R^4$ is
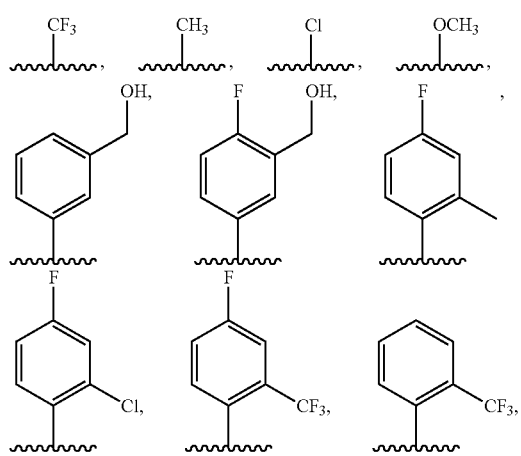
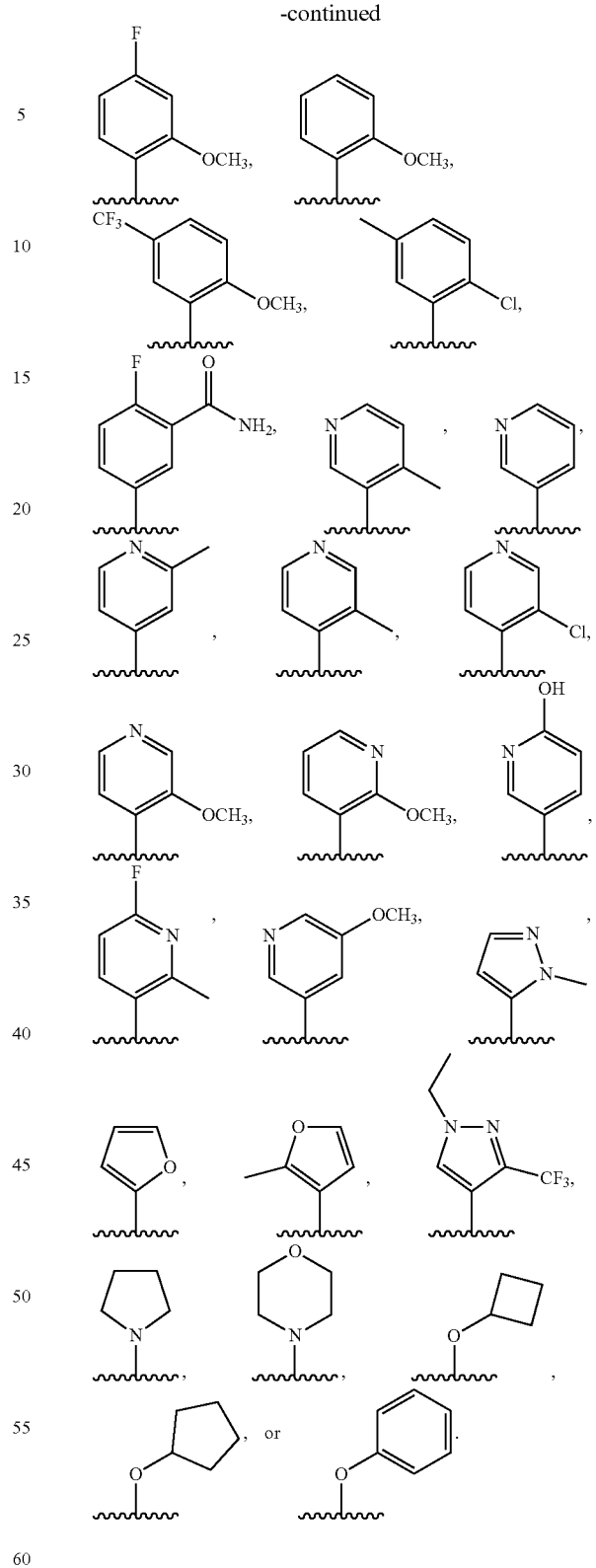
In the embodiments herein are further embodiments wherein $Q^1$ is $CR^3$; $Q^2$ is $CR^5$; and $Q^3$ is $CR^2$. In further embodiments, $R^3$ is hydrogen.
In the embodiments herein are further embodiments wherein $Q^1$ is N; $Q^2$ is $CR^5$; and $Q^3$ is $CR^2$.
In the embodiments herein are further embodiments wherein $R^2$ is hydrogen.

In the embodiments herein are further embodiments wherein $R^5$ is hydrogen or $-OR^{5a}$ (e.g., $-OC_1-C_4$alkyl).

In the embodiments herein are further embodiments wherein only one of $Q^1$, $Q^2$, and $Q^3$ is N.

In the embodiments herein are further embodiments wherein $R^{1c}$, $R^{1d}$, $R^{1e}$, $R^{3a}$, $R^{3b}$, $R^{3c}$, $R^4$, $R^{4b}$, $R^{4c}$, $R^{4d}$, $R^{5a}$, $R^{5b}$, and $R^{5c}$, at each occurrence, are independently hydrogen or $C_1-C_4$alkyl.

In some embodiments, the compound of formula (II) is selected from the group consisting of:

N-(3,5-dimethoxybenzyl)-3-(guanidinomethyl)-5-(2-methylpyridin-4-yl)benzamide;
N-(3-chloro-5-fluorobenzyl)-3-(guanidinomethyl)-5-(2-methylpyridin-4-yl)benzamide;
N-(3-chloro-4-methoxybenzyl)-3-(guanidinomethyl)-5-(2-methylpyridin-4-yl)benzamide;
3-(guanidinomethyl)-N-((4-methoxypyridin-2-yl)methyl)-5-(2-methylpyridin-4-yl)benzamide;
N-((5-chloropyridin-2-yl)methyl)-3-(guanidinomethyl)-5-(2-methylpyridin-4-yl)benzamide;
3-(guanidinomethyl)-N-((6-methylpyridin-3-yl)methyl)-5-(2-methylpyridin-4-yl)benzamide;
(S)-3-(cyclopropanecarboximidamidomethyl)-N-(cyclopropyl(4-fluoro-3-methylphenyl)methyl)-5-(1-ethyl-3-(trifluoromethyl)-1H-pyrazol-4-yl)benzamide;
(S)-3-(cyclobutanecarboximidamidomethyl)-N-(cyclopropyl(4-fluoro-3-methylphenyl)methyl)-5-(1-ethyl-3-(trifluoromethyl)-1H-pyrazol-4-yl)benzamide;
(S)—N-(cyclopropyl(4-fluoro-3-methylphenyl)methyl)-3-((2-cyclopropylacetimidamido)methyl)-5-(1-ethyl-3-(trifluoromethyl)-1H-pyrazol-4-yl)benzamide;
N—((S)-cyclopropyl(4-fluoro-3-methylphenyl)methyl)-3-(1-ethyl-3-(trifluoromethyl)-1H-pyrazol-4-yl)-5-((tetrahydrofuran-3-carboximidamido)methyl)benzamide;
(S)—N-(cyclopropyl(4-fluoro-3-methylphenyl)methyl)-3-(1-ethyl-3-(trifluoromethyl)-1H-pyrazol-4-yl)-5-(1-methylcyclopropane-1-carboximidamido)methyl)benzamide;
3-((1H-imidazol-1-yl)methyl)-5-chloro-N-(3,5-dichlorobenzyl)benzamide;
3-((1H-imidazol-1-yl)methyl)-5-chloro-N-(3,5-dimethoxybenzyl)benzamide;
3-((1H-imidazol-1-yl)methyl)-5-chloro-N-(3-chloro-4-methylbenzyl)benzamide;
3-((1H-imidazol-1-yl)methyl)-N-(4-chloro-3-methylbenzyl)-5-methoxybenzamide;
methyl 3-(3-((1H-imidazol-1-yl)methyl)-5-chlorobenzamido)-3-(3-chlorophenyl)propanoate;
3-((1H-imidazol-1-yl)methyl)-N-(4-chloro-3-methylbenzyl)-5-(cyclopentyloxy)benzamide;
5-((1H-imidazol-1-yl)methyl)-2'-chloro-N-(3,4-dichlorobenzyl)-4'-fluoro-[1,1'-biphenyl]-3-carboxamide;
5-((1H-imidazol-1-yl)methyl)-N-(3,4-dichlorobenzyl)-2'-methoxy-[1,1'-biphenyl]-3-carboxamide;
3-((1H-imidazol-1-yl)methyl)-N-(3,4-dichlorobenzyl)-5-(pyridin-3-yl)benzamide;
3-((1H-imidazol-1-yl)methyl)-N-(3,4-dichlorobenzyl)-5-(furan-2-yl)benzamide;
3-((1H-imidazol-1-yl)methyl)-N-(3,5-dimethoxybenzyl)-5-phenoxybenzamide;
3-((1H-imidazol-1-yl)methyl)-N-(3,4-dichlorobenzyl)-5-(4-methylpyridin-3-yl)benzamide;
5-((1H-imidazol-1-yl)methyl)-2'-chloro-N-(3,4-dichlorobenzyl)-5'-methyl-[1,1'-biphenyl]-3-carboxamide;
3-((1H-imidazol-1-yl)methyl)-N-(3,4-dichlorobenzyl)-5-(2-methylpyridin-4-yl)benzamide;
5-((1H-imidazol-1-yl)methyl)-N-(3,4-dichlorobenzyl)-2'-(trifluoromethyl)-[1,1'-biphenyl]-3-carboxamide;
3-((1H-imidazol-1-yl)methyl)-5-(3-chloropyridin-4-yl)-N-(3,4-dichlorobenzyl)benzamide;
3-((1H-imidazol-1-yl)methyl)-N-(3,4-dichlorobenzyl)-5-(6-fluoro-2-methylpyridin-3-yl)benzamide;
5-((1H-imidazol-1-yl)methyl)-N-(3,4-dichlorobenzyl)-4'-fluoro-2'-(trifluoromethyl)-[1,1'-biphenyl]-3-carboxamide;
3-((1H-imidazol-1-yl)methyl)-N-(3,4-dichlorobenzyl)-5-(5-methoxypyridin-3-yl)benzamide;
3-((1H-imidazol-1-yl)methyl)-N-(3,4-dichlorobenzyl)-5-(3-methoxypyridin-4-yl)benzamide;
3-((1H-imidazol-1-yl)methyl)-N-(3,5-dimethoxybenzyl)-5-(2-methylfuran-3-yl)benzamide;
3-((1H-imidazol-1-yl)methyl)-N-(3,4-dichlorobenzyl)-5-(1-methyl-1H-pyrazol-5-yl)benzamide;
3-((1H-imidazol-1-yl)methyl)-N-(1-cyclohexylethyl)-5-(6-fluoro-2-methylpyridin-3-yl)benzamide;
3-((1H-imidazol-1-yl)methyl)-N-(dicyclopropylmethyl)-5-(6-fluoro-2-methylpyridin-3-yl)benzamide;
2'-chloro-N-(3,4-dichlorobenzyl)-4'-fluoro-5-((2-methyl-1H-imidazol-1-yl)methyl)-[1,1'-biphenyl]-3-carboxamide;
2'-chloro-N-(3,4-dichlorobenzyl)-4'-fluoro-5-((2-(trifluoromethyl)-1H-imidazol-1-yl)methyl)-[1,1'-biphenyl]-3-carboxamide;
3-((1H-imidazol-1-yl)methyl)-N-(3,4-dichlorobenzyl)-5-(pyrrolidin-1-yl)benzamide;
3-((1H-imidazol-1-yl)methyl)-N-(cyclopropyl(4-methylpyridin-2-yl)methyl)-5-(6-fluoro-2-methylpyridin-3-yl)benzamide;
5-((1H-imidazol-1-yl)methyl)-2'-chloro-4'-fluoro-N-(1-methylcyclopentyl)-[1,1'-biphenyl]-3-carboxamide;
3-((2-cyclopropyl-1H-imidazol-1-yl)methyl)-N-(3,4-dichlorobenzyl)-5-(6-fluoro-2-methylpyridin-3-yl)benzamide;
3-((1H-imidazol-1-yl)methyl)-N-(3,5-dimethoxybenzyl)-5-(6-fluoro-2-methylpyridin-3-yl)-N-methylbenzamide;
3-((1H-imidazol-1-yl)methyl)-N-(3,4-dichlorobenzyl)-5-(trifluoromethyl)benzamide;
3-((1H-imidazol-1-yl)methyl)-5-cyclobutoxy-N-(3,4-dichlorobenzyl)benzamide;
3-cyclobutoxy-N-(3,4-dichlorobenzyl)-5-((2-methyl-1H-imidazol-1-yl)methyl)benzamide;
N-(cyclopropyl(4-methylpyridin-2-yl)methyl)-3-((2-methyl-1H-imidazol-1-yl)methyl)-5-morpholinobenzamide;
3-((1H-imidazol-1-yl)methyl)-N-(3,5-dimethoxybenzyl)-5-(6-oxo-1,6-dihydropyridin-3-yl)benzamide;
4-methoxy-N-((4-methoxypyridin-2-yl)methyl)-3-methyl-5-((2-methyl-1H-imidazol-1-yl)methyl)benzamide;
N-(3,4-dichlorobenzyl)-3'-(hydroxymethyl)-5-((2-methyl-1H-imidazol-1-yl)methyl)-[1,1'-biphenyl]-3-carboxamide;
4-((1H-imidazol-1-yl)methyl)-6-(2-chloro-4-fluorophenyl)-N-(3,5-dichlorobenzyl)picolinamide;
4-((1H-imidazol-1-yl)methyl)-6-(2-chloro-4-fluorophenyl)-N-(2-cyclopropylpropan-2-yl)picolinamide;
4-((1H-imidazol-1-yl)methyl)-6-(2-chloro-4-fluorophenyl)-N-(cyclopropyl(4-methylpyridin-2-yl)methyl)picolinamide;
4-((1H-imidazol-1-yl)methyl)-6-(2-chloro-4-fluorophenyl)-N-((6-methylpyridin-2-yl)methyl)picolinamide;
4-((1H-imidazol-1-yl)methyl)-6-(2-chloro-4-fluorophenyl)-N-(1-cyclopropylpropyl)picolinamide;
4-((1H-imidazol-1-yl)methyl)-6-(2-chloro-4-fluorophenyl)-N-(3,5-dimethylbenzyl)picolinamide;

4-((1H-imidazol-1-yl)methyl)-6-(2-chloro-4-fluorophenyl)-
N-(1-(3,5-dimethoxyphenyl)ethyl)picolinamide;
4-((1H-imidazol-1-yl)methyl)-6-(2-chloro-4-fluorophenyl)-
N-(1-(pyridin-2-yl)ethyl)picolinamide;
N-(3,4-dichlorobenzyl)-6-(4-fluoro-2-methylphenyl)-4-((2-
methyl-1H-imidazol-1-yl)methyl)picolinamide;
N-(1-(3,5-dimethoxyphenyl)ethyl)-6-(3-(hydroxymethyl)
phenyl)-4-((2-methyl-1H-imidazol-1-yl)methyl)picolina-
mide;
N-(1-(3,5-dimethoxyphenyl)ethyl)-6-(4-fluoro-2-methoxy-
phenyl)-4-((2-methyl-1H-imidazol-1-yl)methyl)picolina-
mide;
N-(1-(3,5-dimethoxyphenyl)ethyl)-6'-fluoro-2'-methyl-4-
((2-methyl-1H-imidazol-1-yl)methyl)-[2,3'-bipyridine]-
6-carboxamide;
N-(1-(3,5-dimethoxyphenyl)ethyl)-6-(2-methoxy-5-(trifluo-
romethyl)phenyl)-4-((2-methyl-1H-imidazol-1-yl)
methyl)picolinamide;
6-(3-carbamoyl-4-fluorophenyl)-N-(1-(3,5-dimethoxyphe-
nyl)ethyl)-4-((2-methyl-1H-imidazol-1-yl)methyl)pico-
linamide;
N-(3,4-dichlorobenzyl)-2'-methoxy-4-((2-methyl-1H-imi-
dazol-1-yl)methyl)-[2,3'-bipyridine]-6-carboxamide;
N-(1-(3,5-dimethoxyphenyl)ethyl)-6-(4-fluoro-3-(hy-
droxymethyl)phenyl)-4-((2-methyl-1H-imidazol-1-yl)
methyl)picolinamide;
N-(3,4-dichlorobenzyl)-6'-fluoro-2'-methyl-4-((2-methyl-
1H-imidazol-1-yl)methyl)-[2,3'-bipyridine]-6-carboxam-
ide;
N-(3,4-dichlorobenzyl)-6-(4-fluoro-2-methoxyphenyl)-4-
((2-methyl-1H-imidazol-1-yl)methyl)picolinamide;
N-(3,4-dichlorobenzyl)-3'-methyl-4-((2-methyl-1H-imida-
zol-1-yl)methyl)-[2,4'-bipyridine]-6-carboxamide; and
6-(3-carbamoyl-4-fluorophenyl)-N-(3,4-dichlorobenzyl)-4-
((2-methyl-1H-imidazol-1-yl)methyl)picolinamide;
or a pharmaceutically acceptable salt or tautomer thereof.

In certain embodiments, the compound of formula (I) is selected from the group consisting of the compounds in Table 1, or a pharmaceutically acceptable salt or tautomer thereof.

TABLE 1

Exemplary compounds.

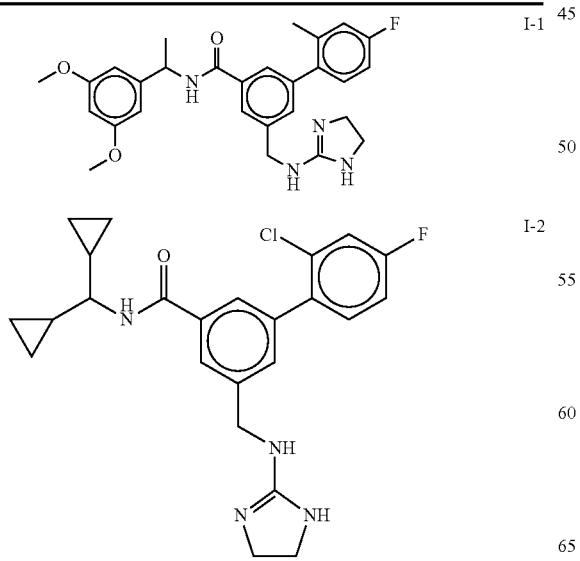

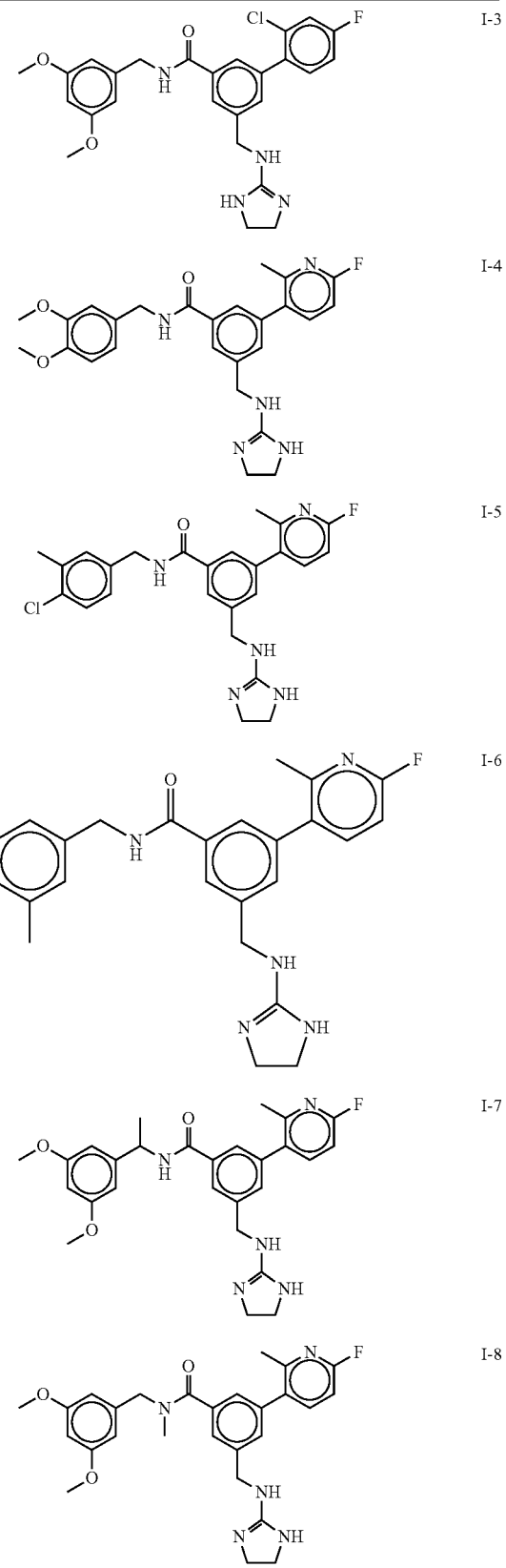

TABLE 1-continued
Exemplary compounds.
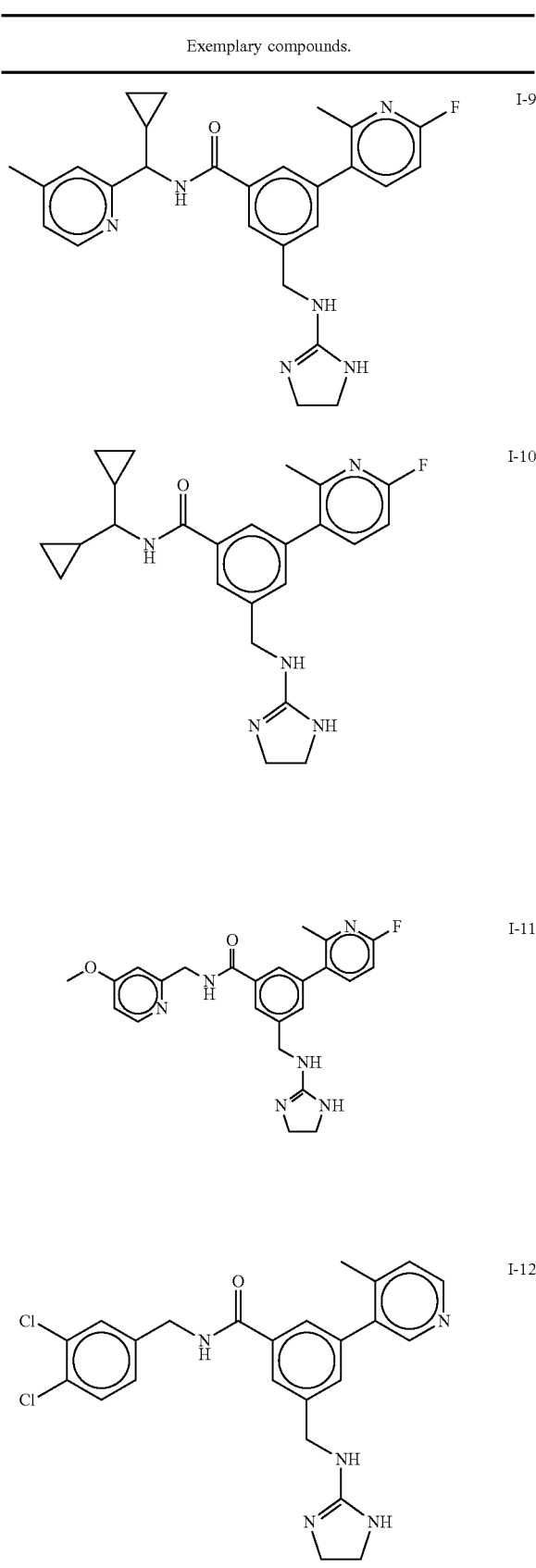
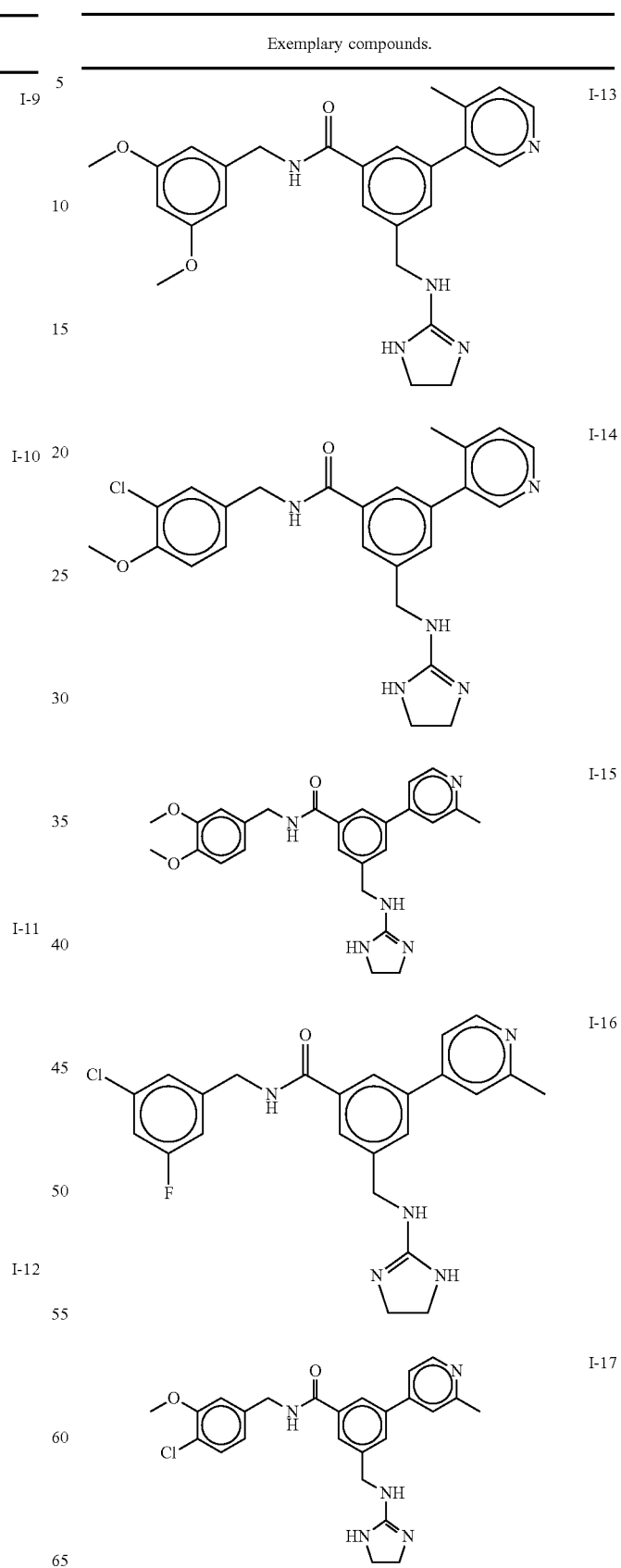

TABLE 1-continued

Exemplary compounds.

TABLE 1-continued
Exemplary compounds.
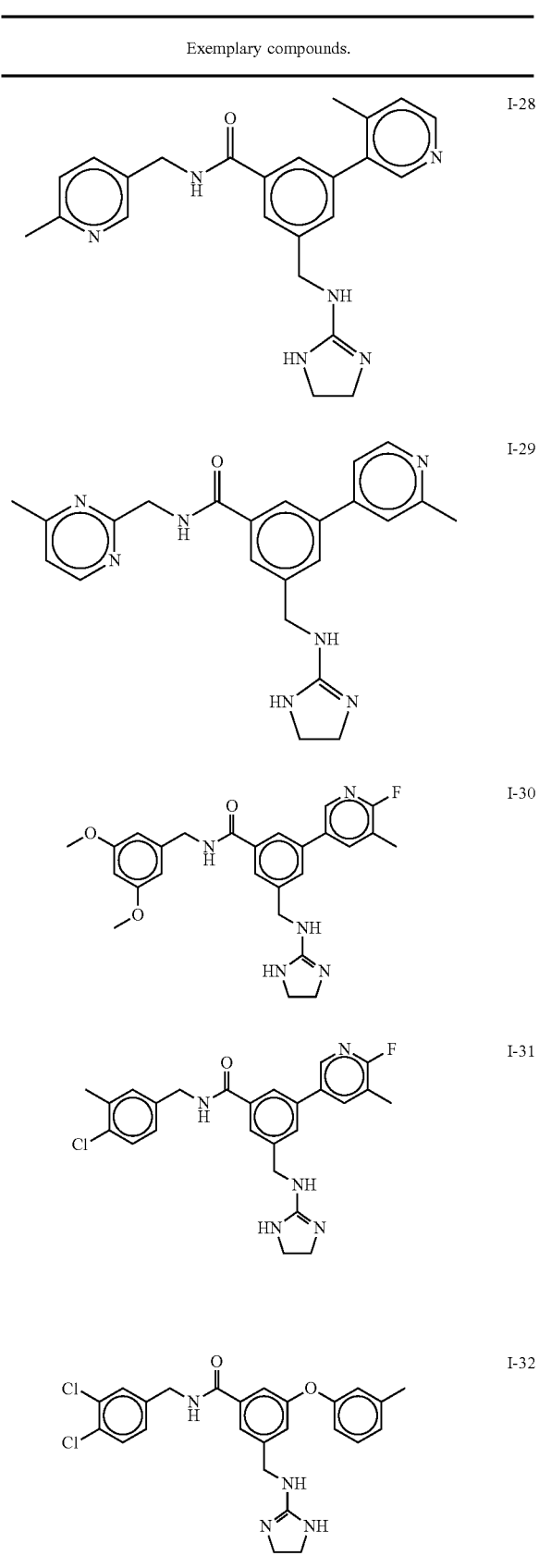
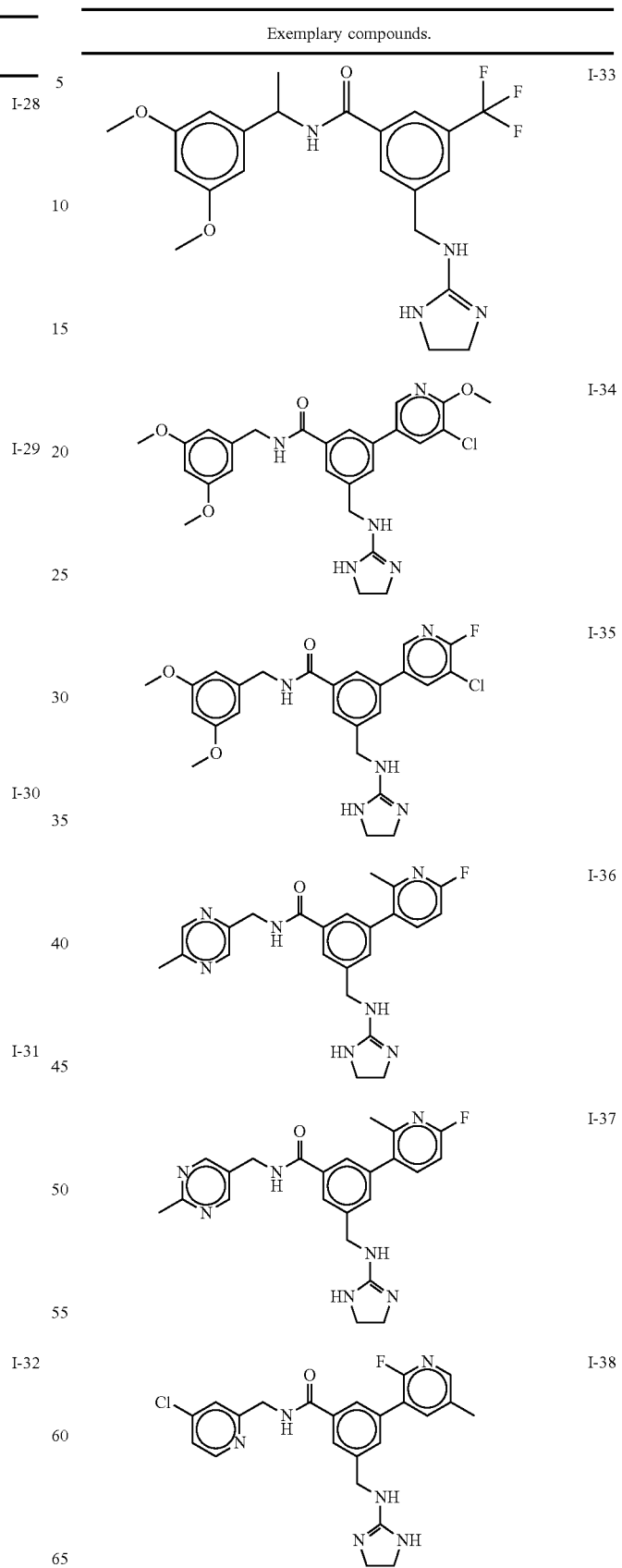

TABLE 1-continued
Exemplary compounds.
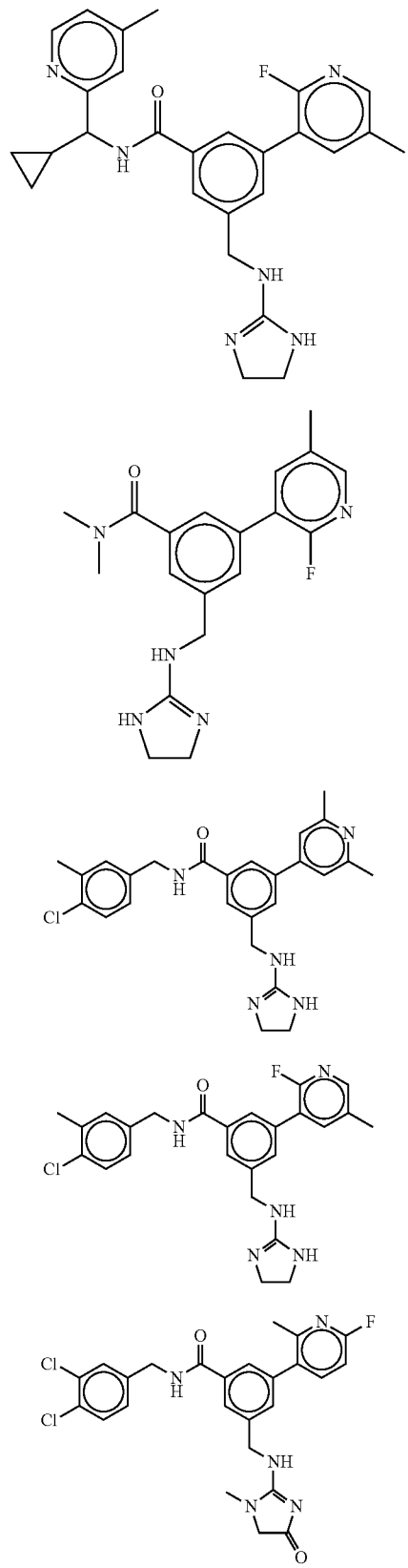
TABLE 1-continued
Exemplary compounds.
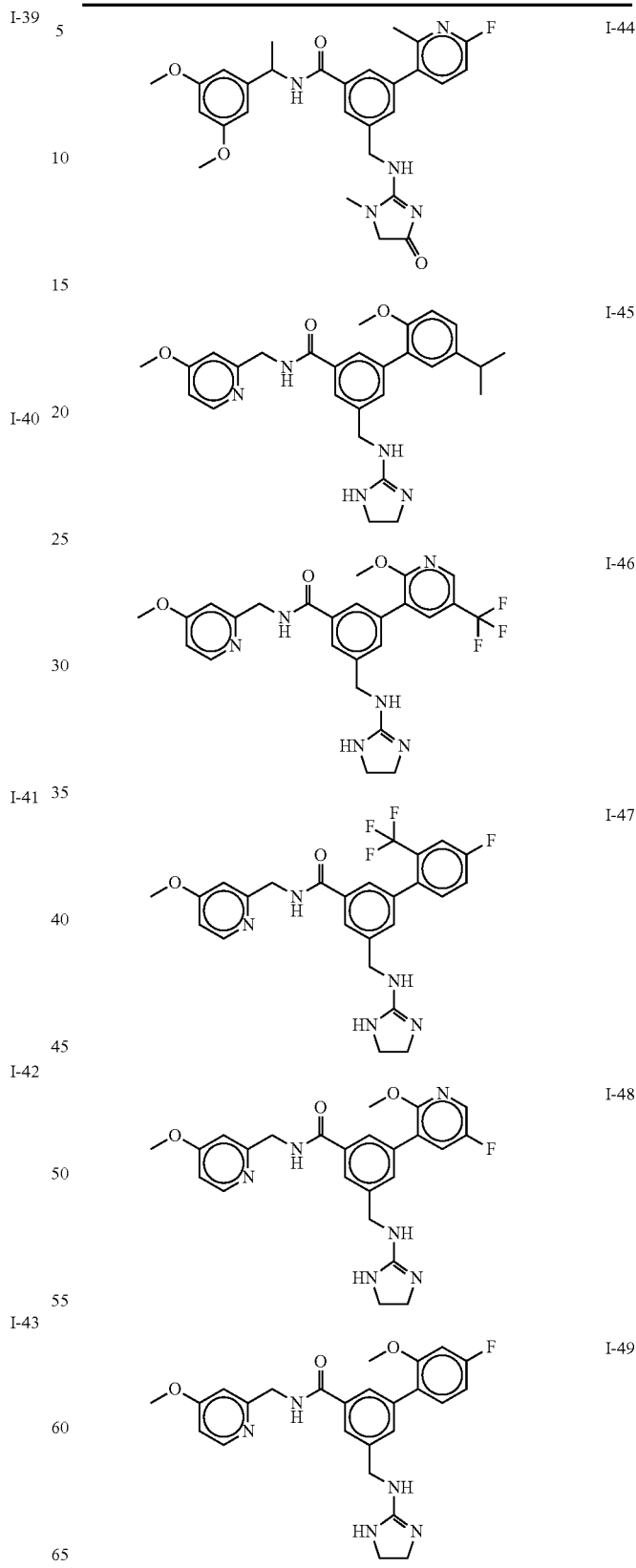

TABLE 1-continued
Exemplary compounds.
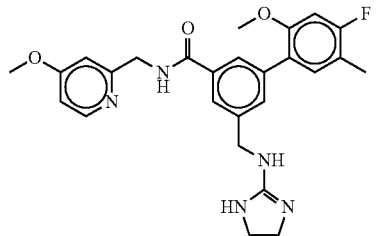 I-50
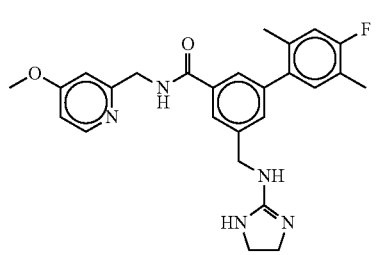 I-51
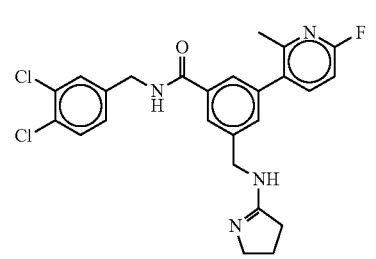 I-52
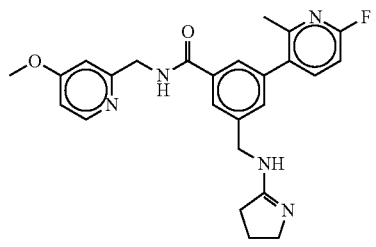 I-53
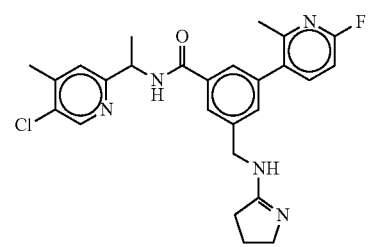 I-54
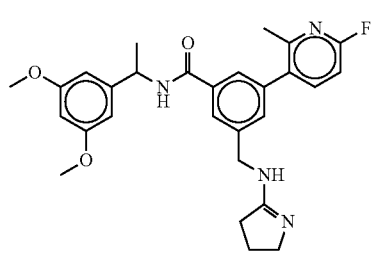 I-55
TABLE 1-continued
Exemplary compounds.
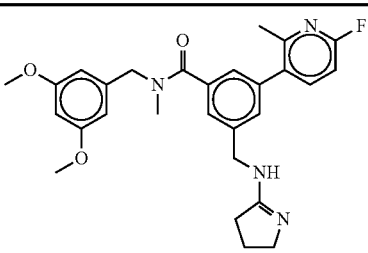 I-56
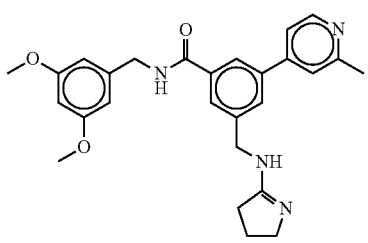 I-57
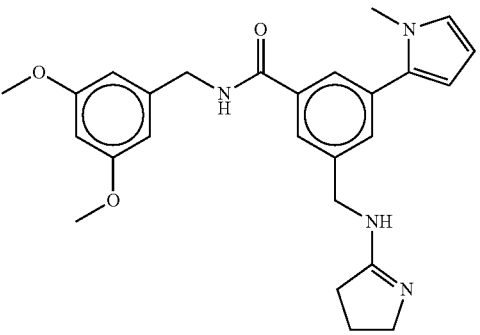 I-58
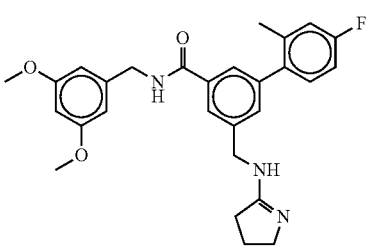 I-59
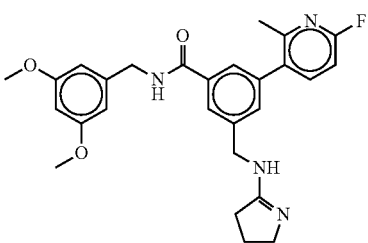 I-60
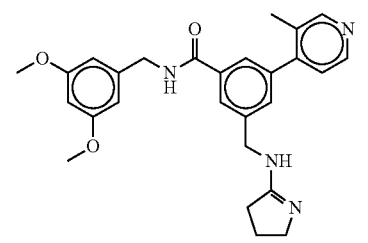 I-61

TABLE 1-continued
Exemplary compounds.
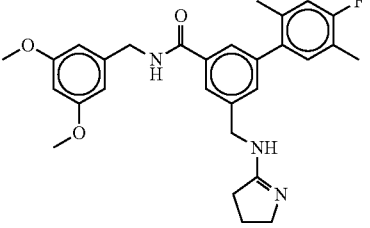 I-62
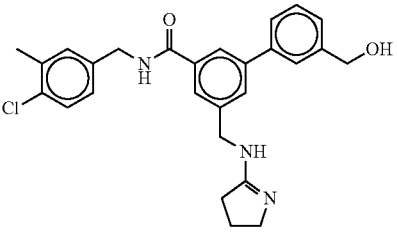 I-63
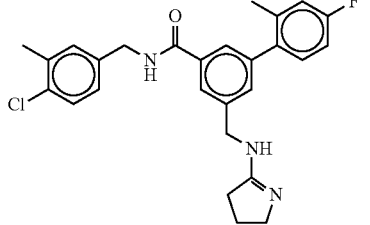 I-64
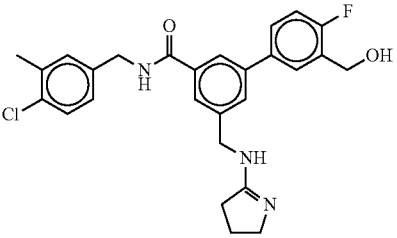 I-65
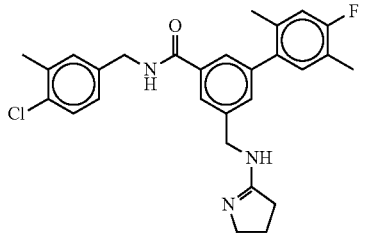 I-66
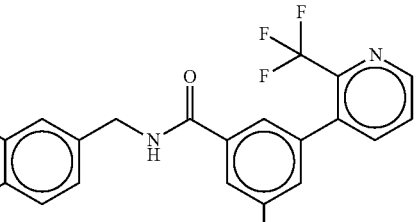 I-67
TABLE 1-continued
Exemplary compounds.
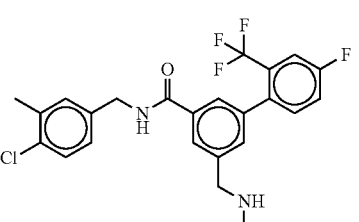 I-68
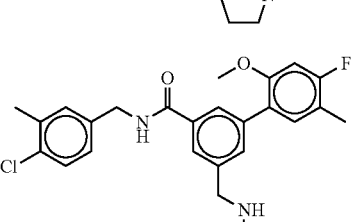 I-69
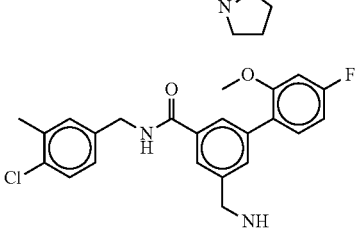 I-70
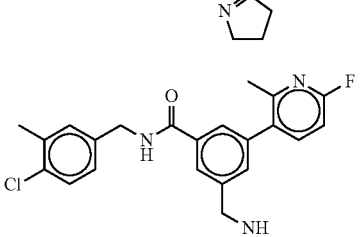 I-71
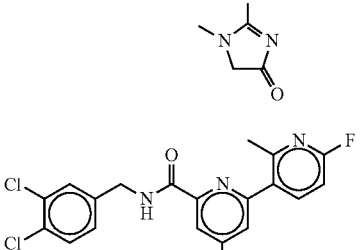 I-72
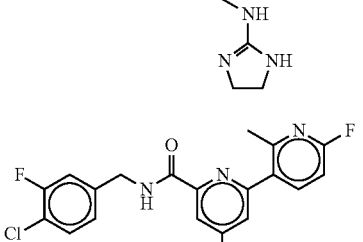 I-73

TABLE 1-continued
Exemplary compounds.
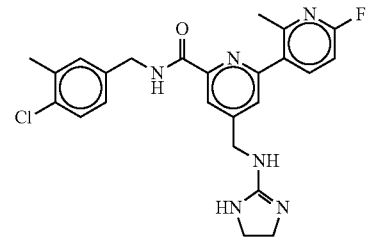 I-74
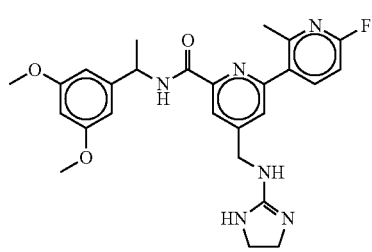 I-75
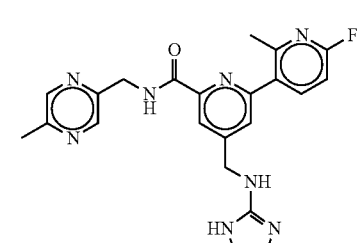 I-76
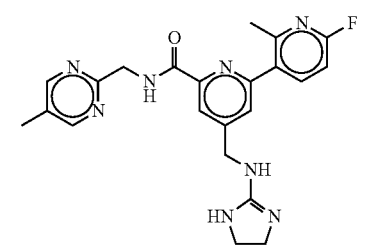 I-77
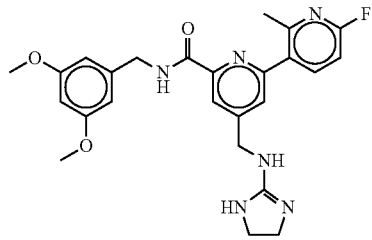 I-78
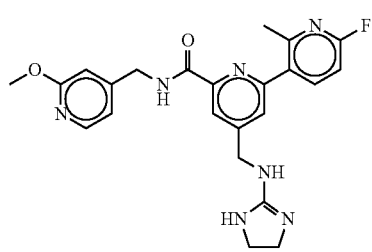 I-79
TABLE 1-continued
Exemplary compounds.
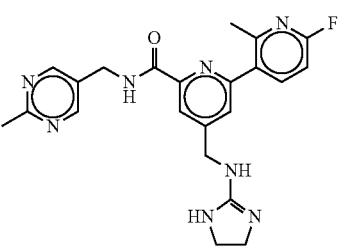 I-80
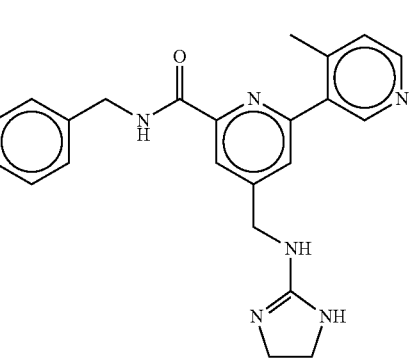 I-81
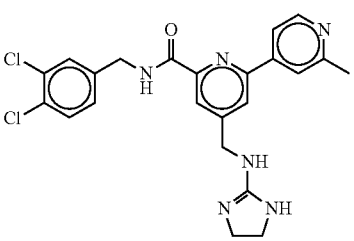 I-82
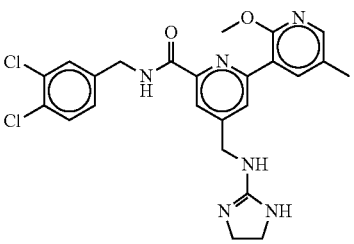 I-83
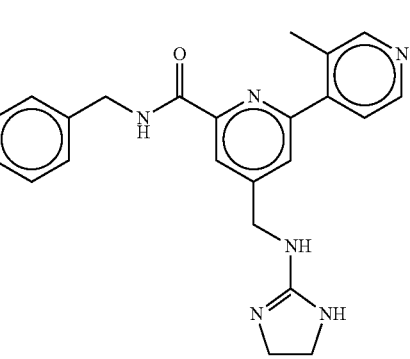 I-84

TABLE 1-continued
Exemplary compounds.
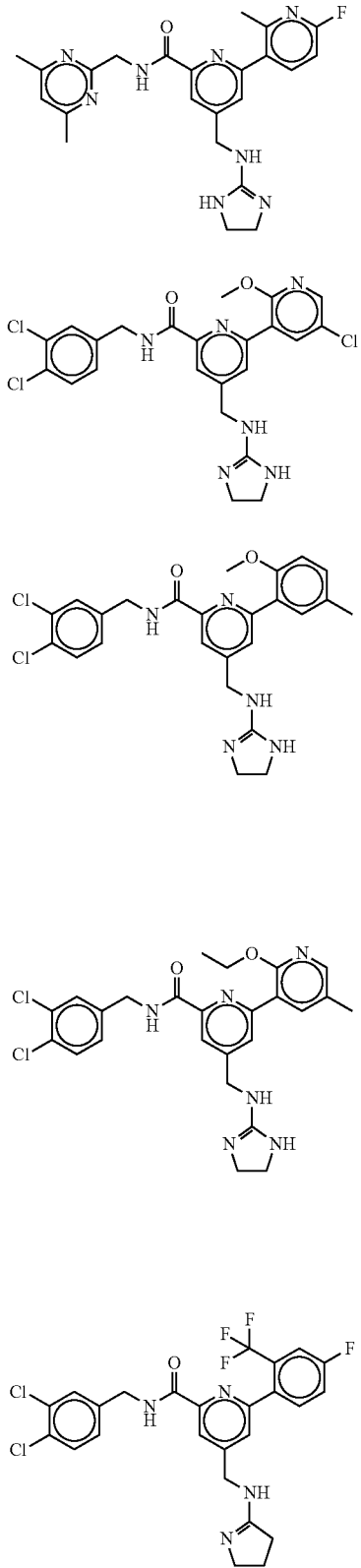
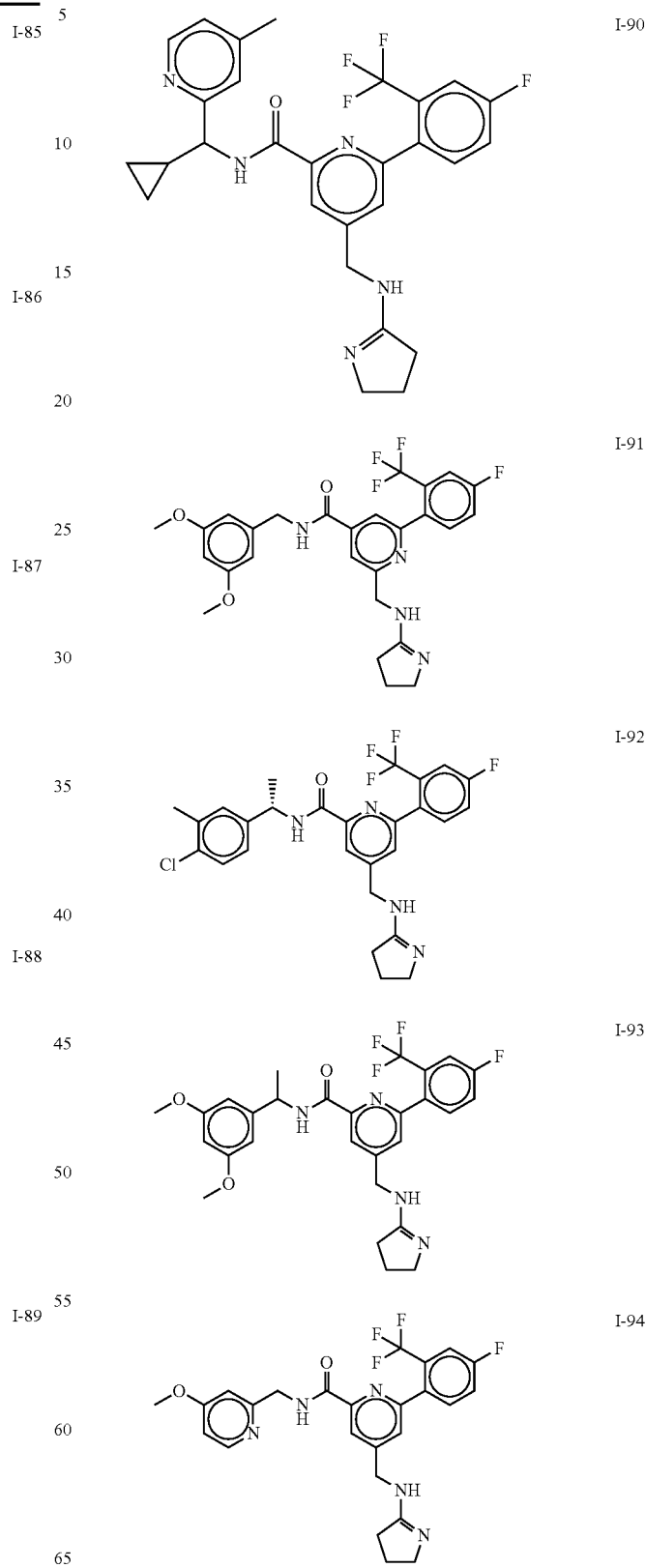

TABLE 1-continued
Exemplary compounds.
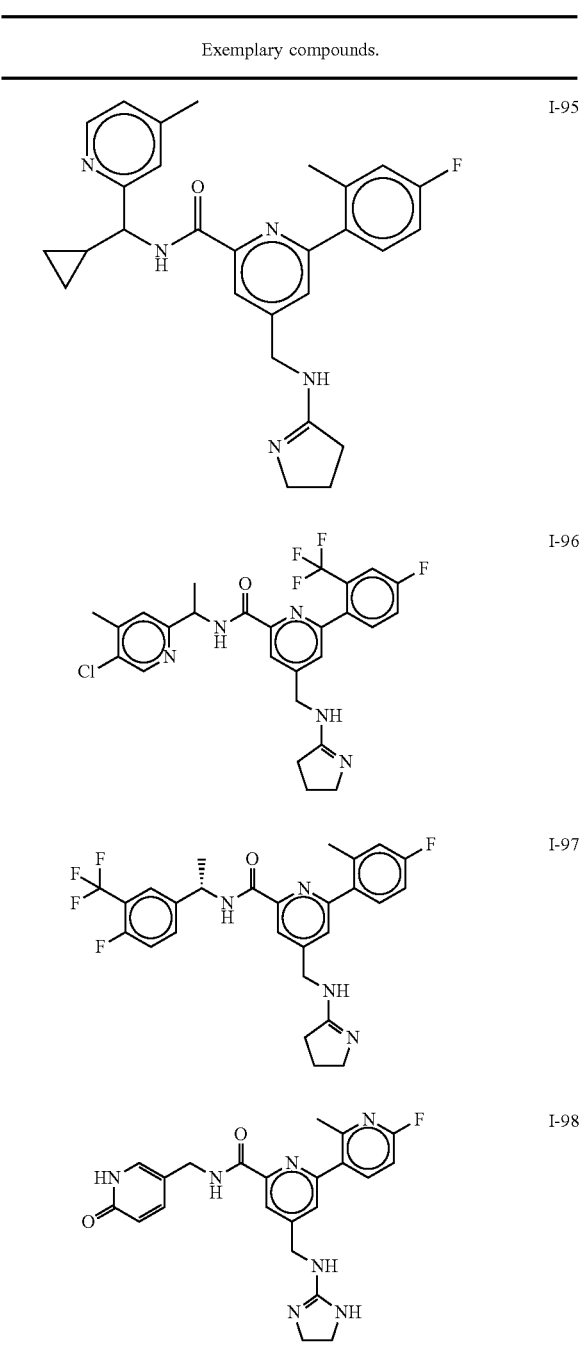
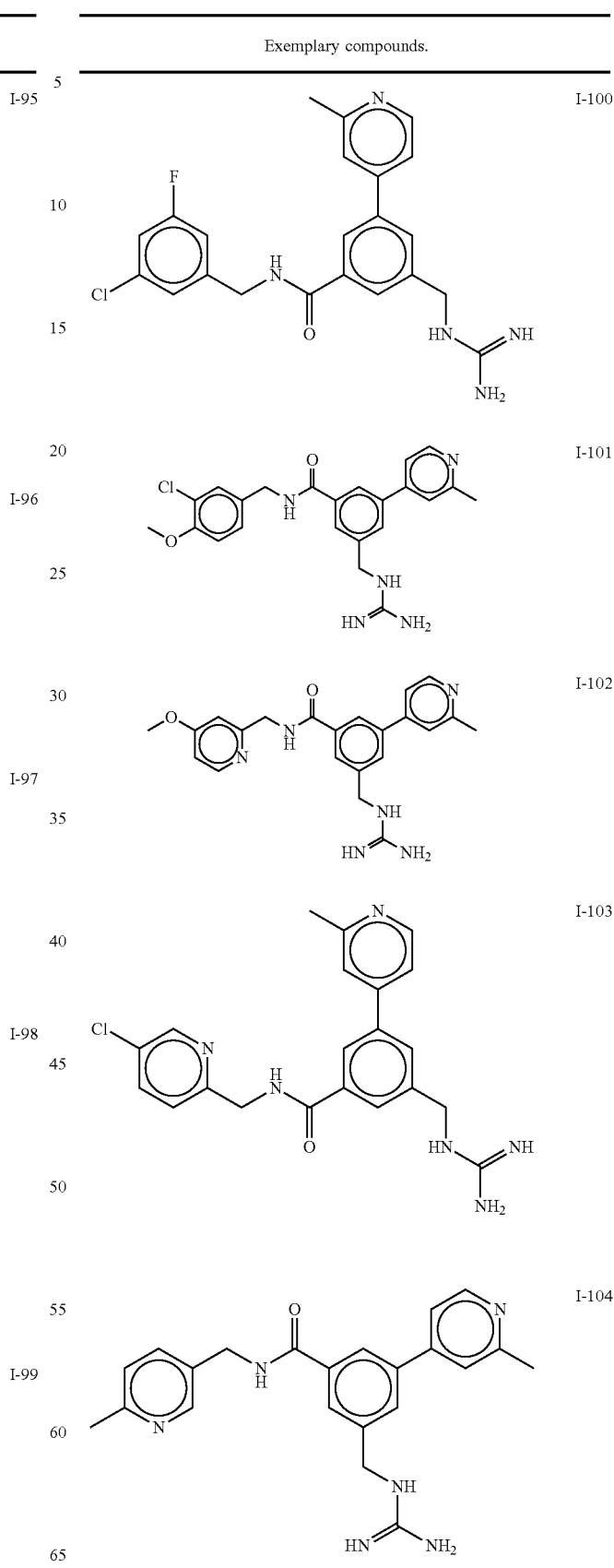

TABLE 1-continued
Exemplary compounds.
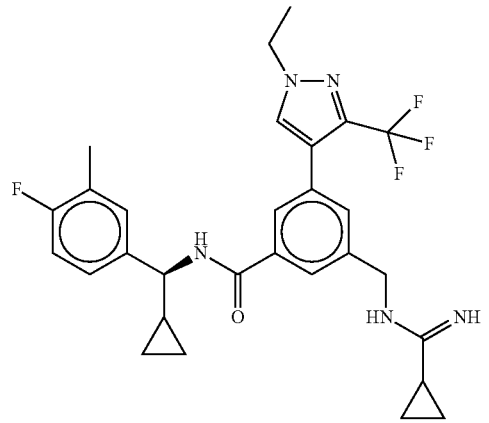
I-105
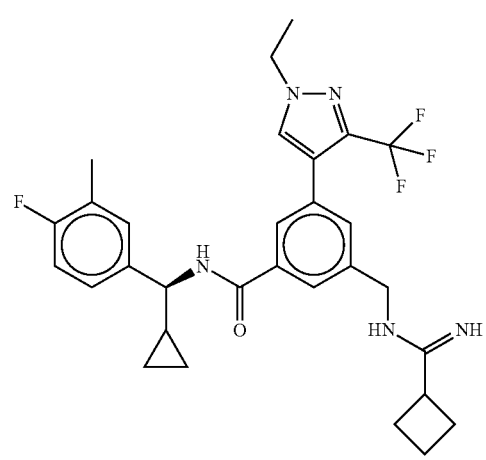
I-106
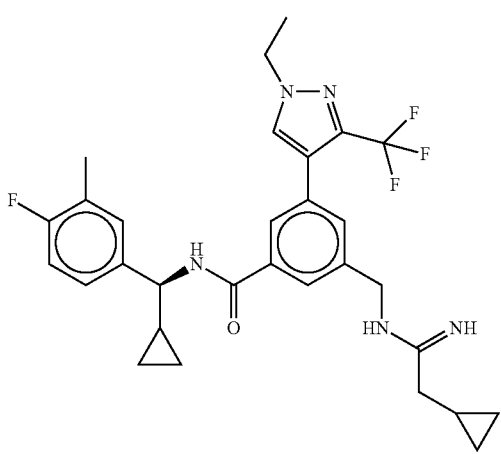
I-107
TABLE 1-continued
Exemplary compounds.
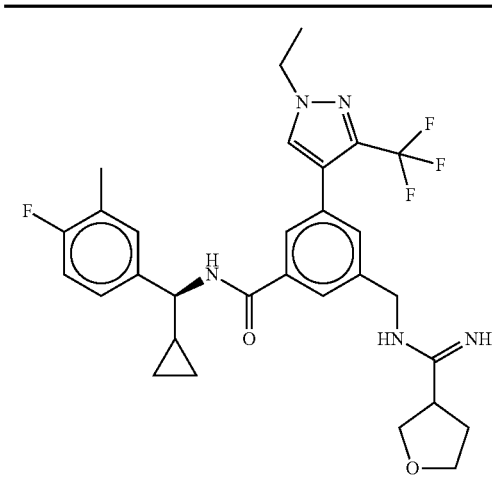
I-108
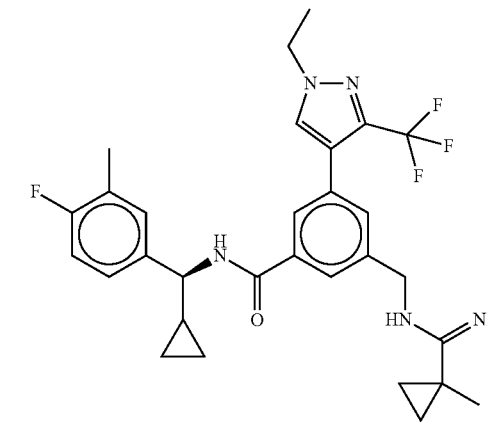
I-109
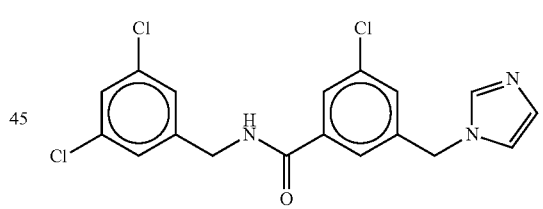
I-110
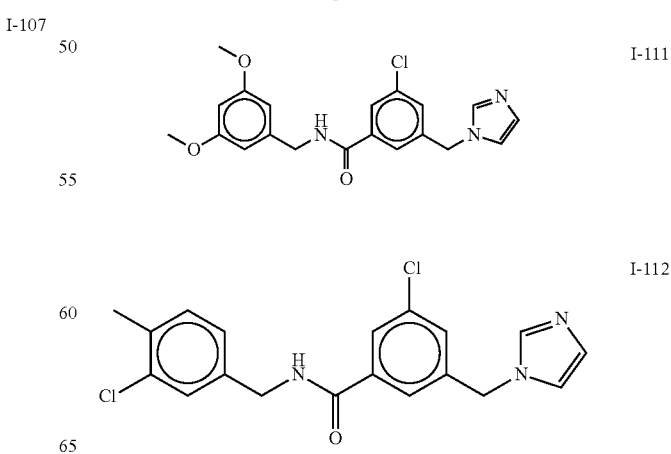
I-111
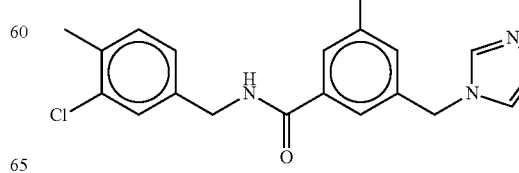
I-112

TABLE 1-continued
Exemplary compounds.
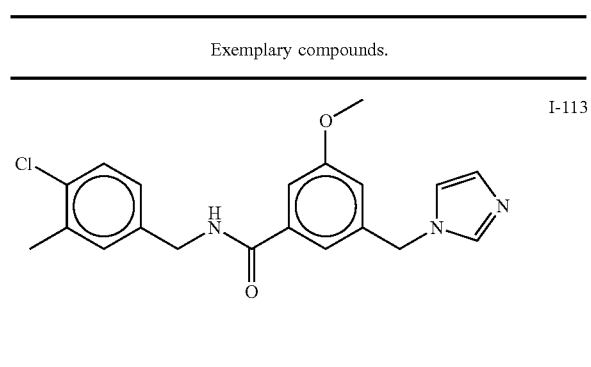 I-113
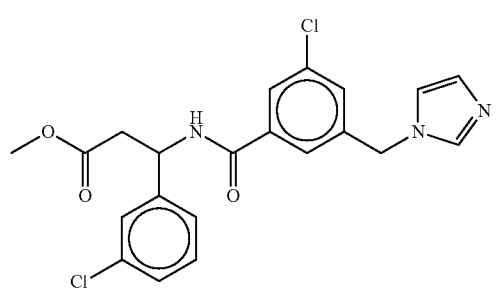 I-114
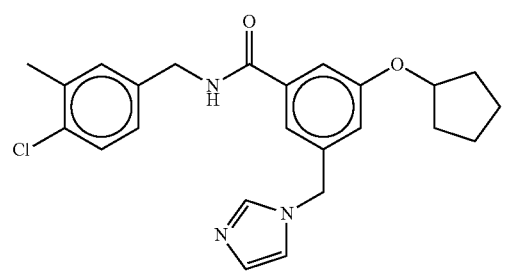 I-115
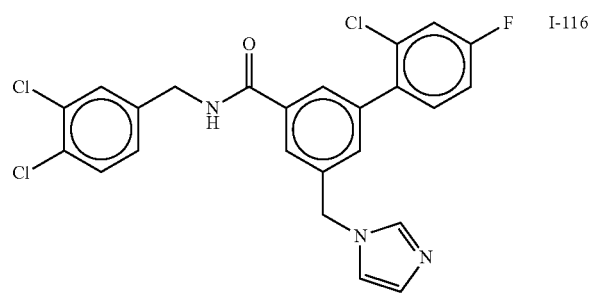 I-116
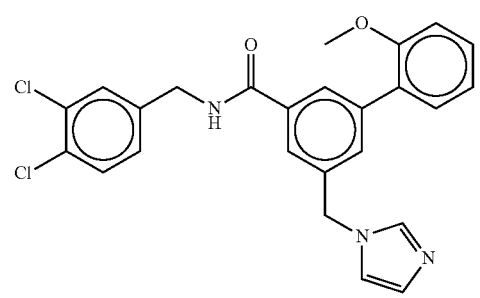 I-117
TABLE 1-continued
Exemplary compounds.
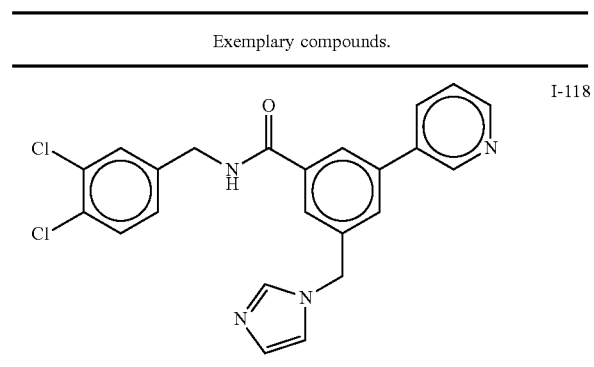 I-118
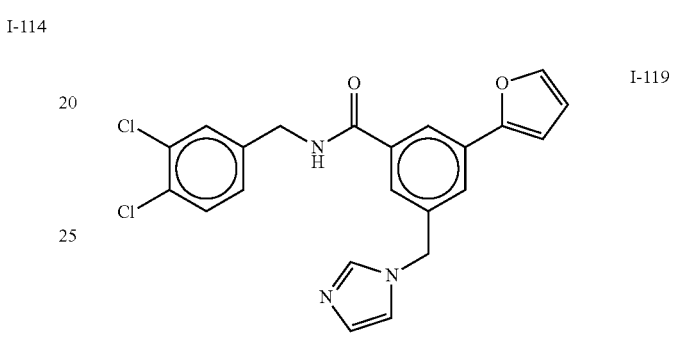 I-119
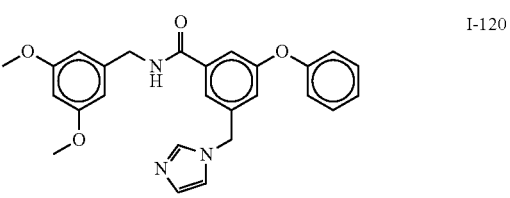 I-120
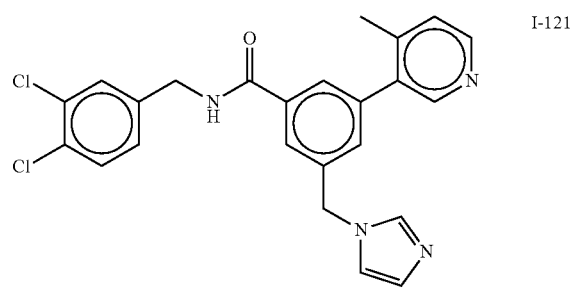 I-121
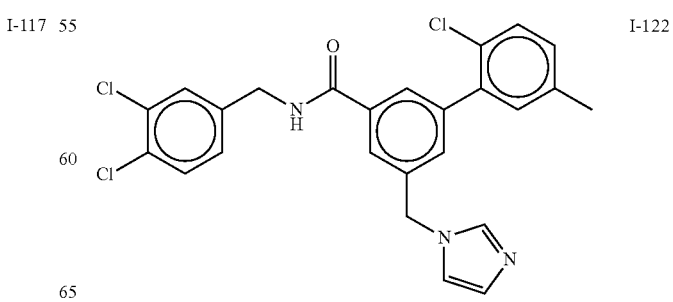 I-122

TABLE 1-continued

Exemplary compounds.

I-123

I-124

I-125

I-126

I-127

I-128

I-129

I-130

I-131

I-132

TABLE 1-continued

Exemplary compounds.

I-133

I-134

I-135

I-136

I-137

I-138

I-139

I-140

I-141

I-142

TABLE 1-continued
Exemplary compounds.
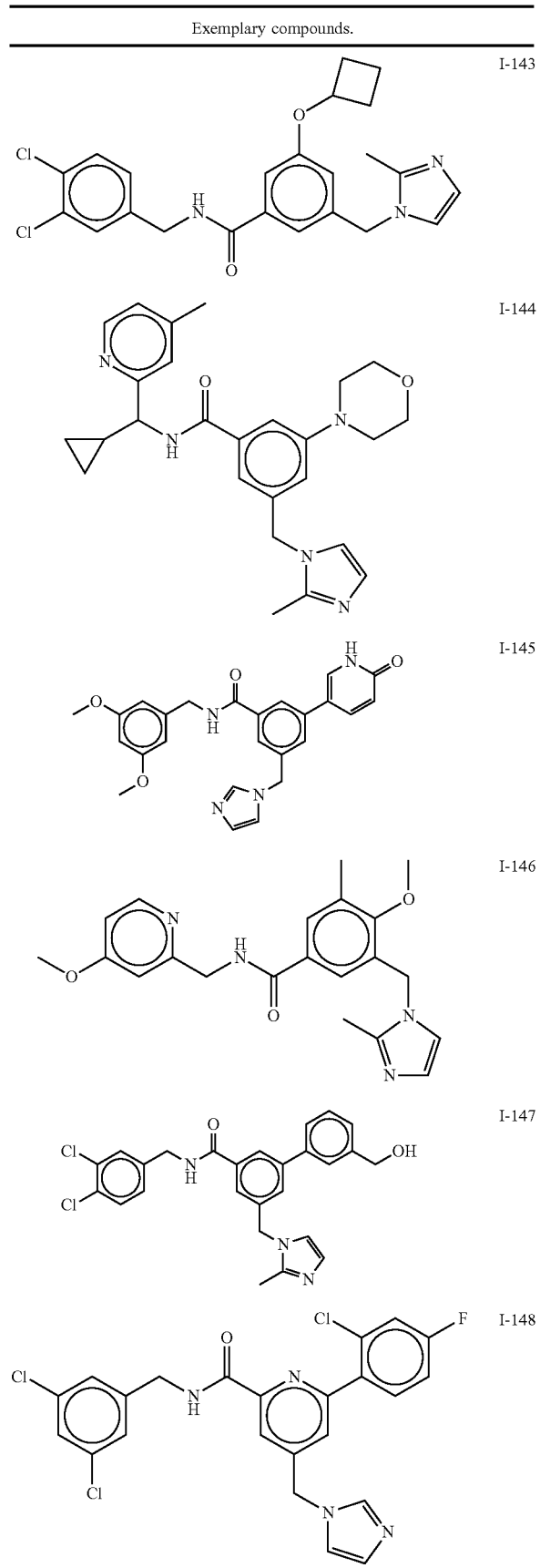
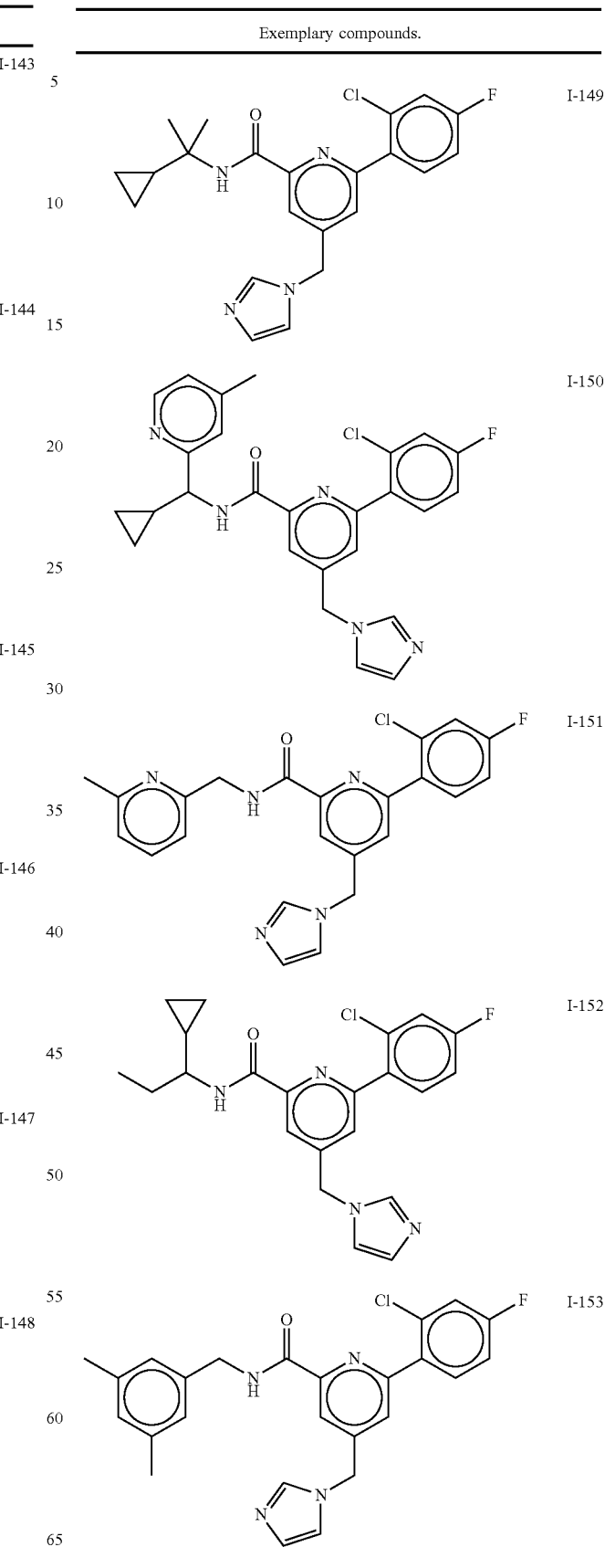

TABLE 1-continued
Exemplary compounds.
| | |
|---|---|
| 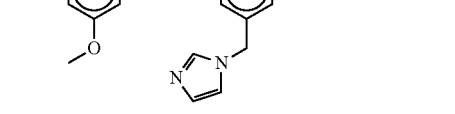 I-154 | 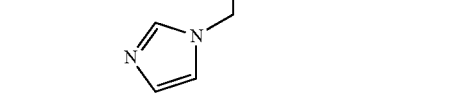 I-160 |
| 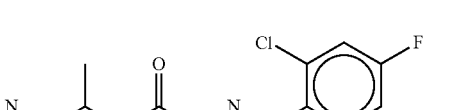 I-155 | I-161 |
| I-156 | I-162 |
| 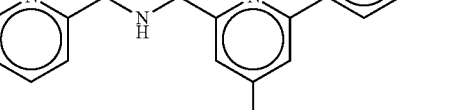 I-157 | 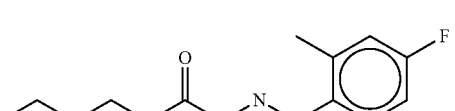 I-163 |
| I-158 | I-164 |
| I-159 | 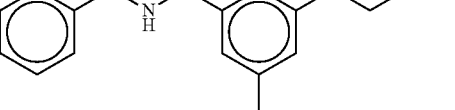 I-165 |

TABLE 1-continued

Exemplary compounds.

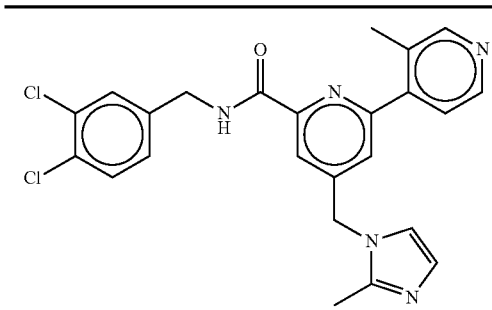 I-166

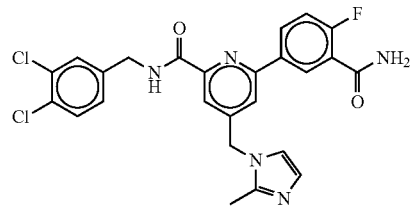 I-167

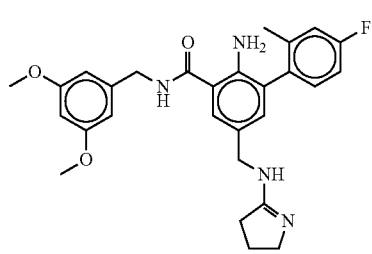 I-168

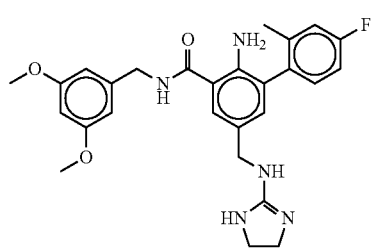 I-169

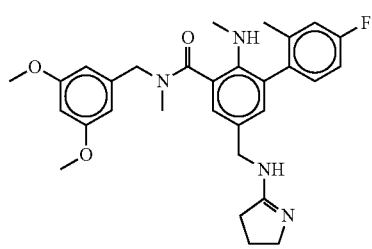 I-170

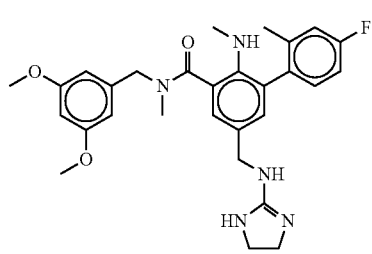 I-171

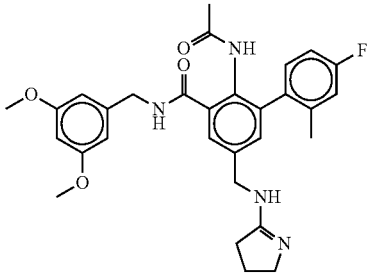 I-172

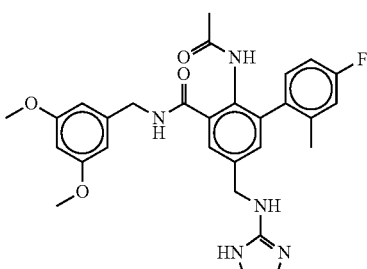 I-173

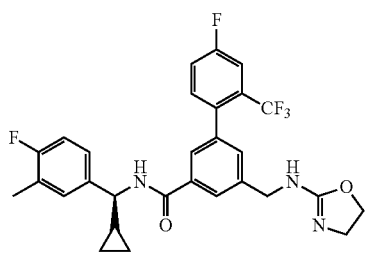 [SMILES: Cc1cc([C@@H](NC(=O)c2cc(CNC3=NCCO3)cc(-c3ccc(F)cc3C(F)(F)F)c2)C2CC2)ccc1F] I-174

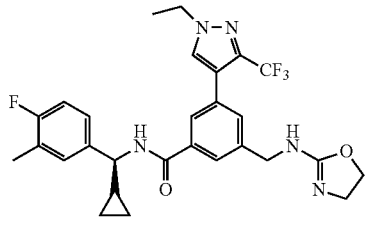 [SMILES: CCn1cc(-c2cc(CNC3=NCCO3)cc(C(=O)N[C@H](c3ccc(F)c(C)c3)C3CC3)c2)c(C(F)(F)F)n1] I-175

Compound names are assigned by using Struct=Name naming algorithm as part of CHEMDRAW® ULTRA v. 12.0 or ChemBioDraw® 14.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound and its salts may possess tautomeric forms, as well as geometric isomers, and that these also constitute an aspect of the invention. The heteroaryl

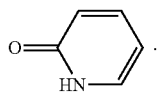

also represents the tautomeric form

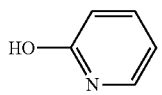

A compound of the invention or a pharmaceutically acceptable salt or tautomer thereof includes: the compound, the pharmaceutically acceptable salts of the compound, tautomers of the compound, and tautomers of the pharmaceutically acceptable salts of the compound.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. BINDING TO WDR5

The disclosed compounds may bind to WDR5 and prevent the association of MLL1 or other transcription factors and proteins dependent on WDR5. The compounds may bind to WDR5 and prevent oncogenic processes associated with MLL1, c-MYC, or other oncogenic proteins dependent on WDR5.

Compounds of formula (I) can bind to WDR5 resulting in a $K_i$ ranging from about 0.01 nM to about 250 μM. The compounds may have a $K_i$ of about 250 μM, about 200 μM, about 150 μM, about 100 μM, about 90 μM, about 80 μM, about 70 μM, about 60 μM, about 50 μM, about 40 μM, about 30 μM, about 20 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) can bind to WDR5 resulting in a $K_i$ of less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. GENERAL SYNTHESIS

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein. Compounds of formula (I) may be also prepared by metabolic processes. Preparation of the compounds by metabolic processes includes those occurring in the human or animal body (in vivo) or processes occurring in vitro.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, which are compatible with the reaction conditions, will be readily apparent to one skilled in the art and alternate methods can be used.

Scheme 1

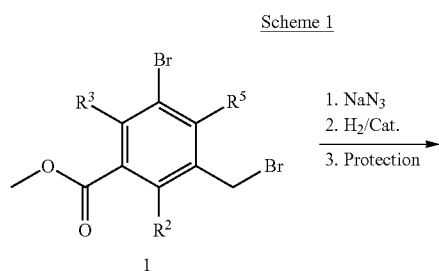

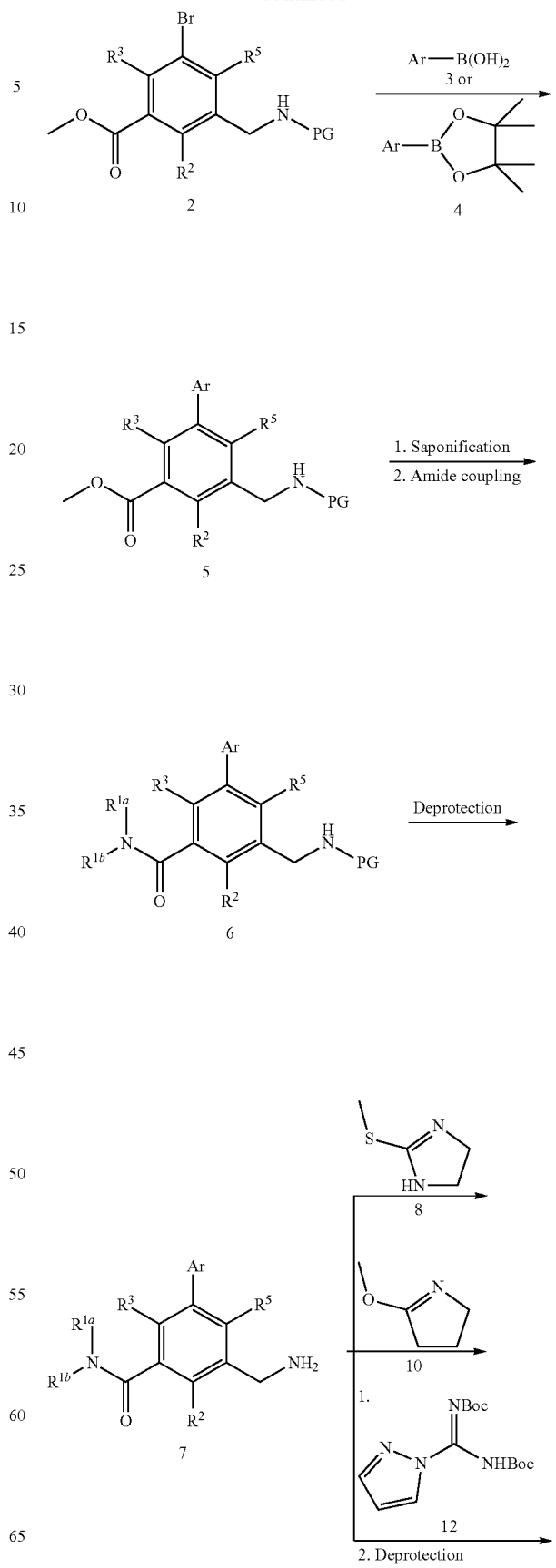

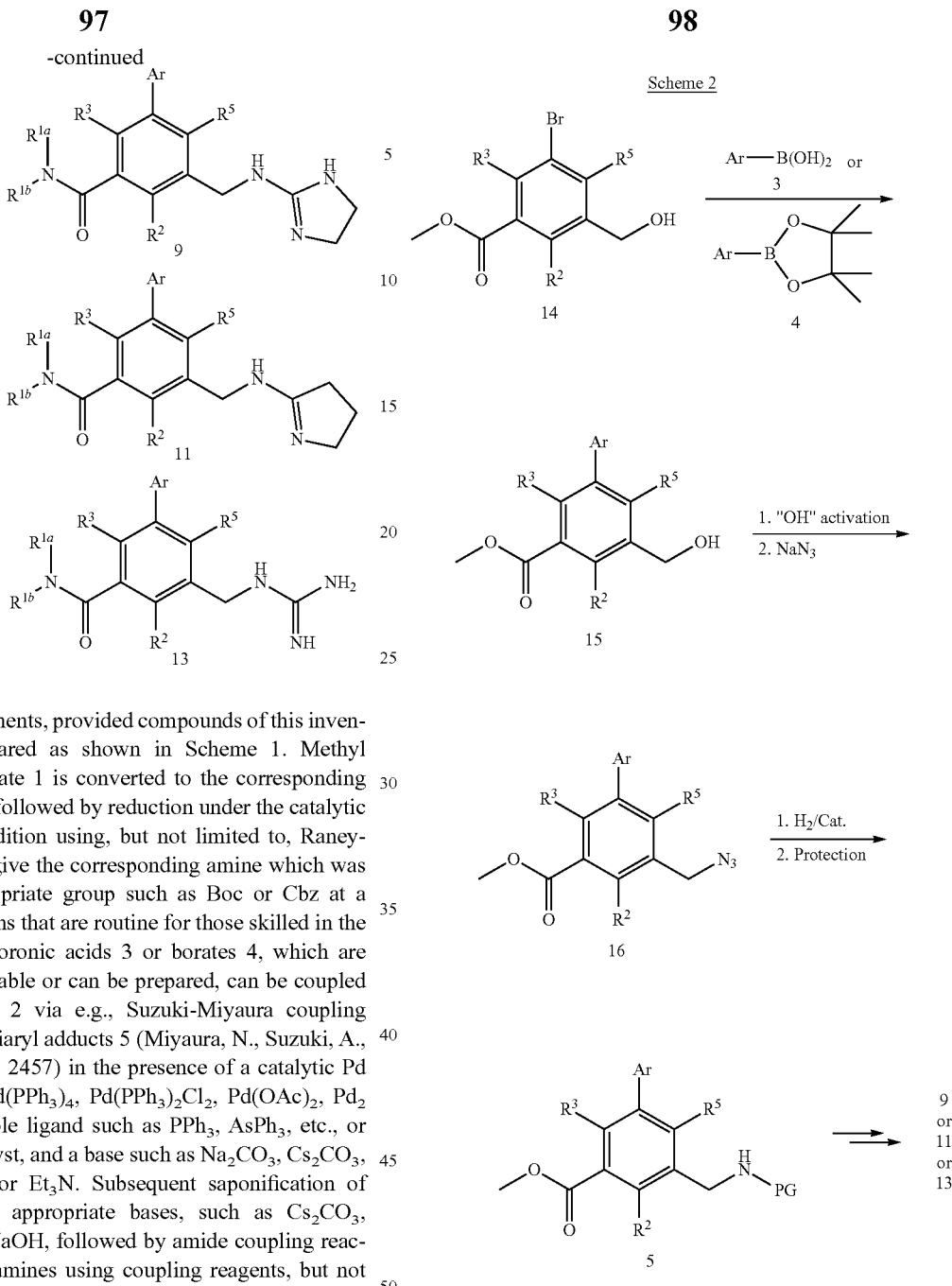

In some embodiments, provided compounds of this invention may be prepared as shown in Scheme 1. Methyl bromomethylbenzoate 1 is converted to the corresponding azide intermediate followed by reduction under the catalytic hydrogenation condition using, but not limited to, Raney-Nickel or Pd/C to give the corresponding amine which was protected by appropriate group such as Boc or Cbz at a number of conditions that are routine for those skilled in the art. A variety of boronic acids 3 or borates 4, which are commercially available or can be prepared, can be coupled with intermediates 2 via e.g., Suzuki-Miyaura coupling protocol to afford biaryl adducts 5 (Miyaura, N., Suzuki, A., Chem. Rev. (1995), 2457) in the presence of a catalytic Pd species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. Subsequent saponification of compound 5 with appropriate bases, such as $Cs_2CO_3$, $K_2CO_3$, LiOH or NaOH, followed by amide coupling reaction with suitable amines using coupling reagents, but not limited to, HATU, EDC, PyBOP, DCC, HBTU, or TBTU at a number of conditions that are routine for those skilled in the art of organic synthesis gives amide 6. The amine-protecting group was then removed under appropriate condition for using a protecting group that are routine in the art of organic synthesis to generate the versatile penultimate intermediate 7. Cyclic guanidine 9 and cyclic amidine 11 can be produced by treatment of amine 7 with an appropriate guanidinyl or amidinyl agents, but not limited to, methylthio-dihydroimidazole 8 or methoxy-dihydropyrrole 10 in an alcoholic or polar aprotic solvent with heat, respectively. Guanidine 13 can be also generated from intermediate 7 using guanidinylation agent, but not limited to, such as protected amidinopyrazole 12 followed by deprotection procedures outlined above.

In some embodiments, compounds of Formula 9, 11, or 13 may be synthesized by procedures illustrated in Scheme 2 using benzyl alcohol 14 as a starting material. Formula 15 containing Ar or heteroaryl substituent can be prepared by Suzuki-Miyaura coupling protocol outlined in Scheme 1 from compounds 14. Hydroxy group of 15 may be activated by converting to bromide, Mesylate or Tosylate group under a number of conditions that are routine for those skilled in the art of organic synthesis followed by azide substitution reaction described in Scheme 1 to give intermediate 16. It can be converted to intermediate 5 by reduction and protection protocols illustrated in Scheme 1 to generate compounds of Formula 9, 11, or 13.

Scheme 3

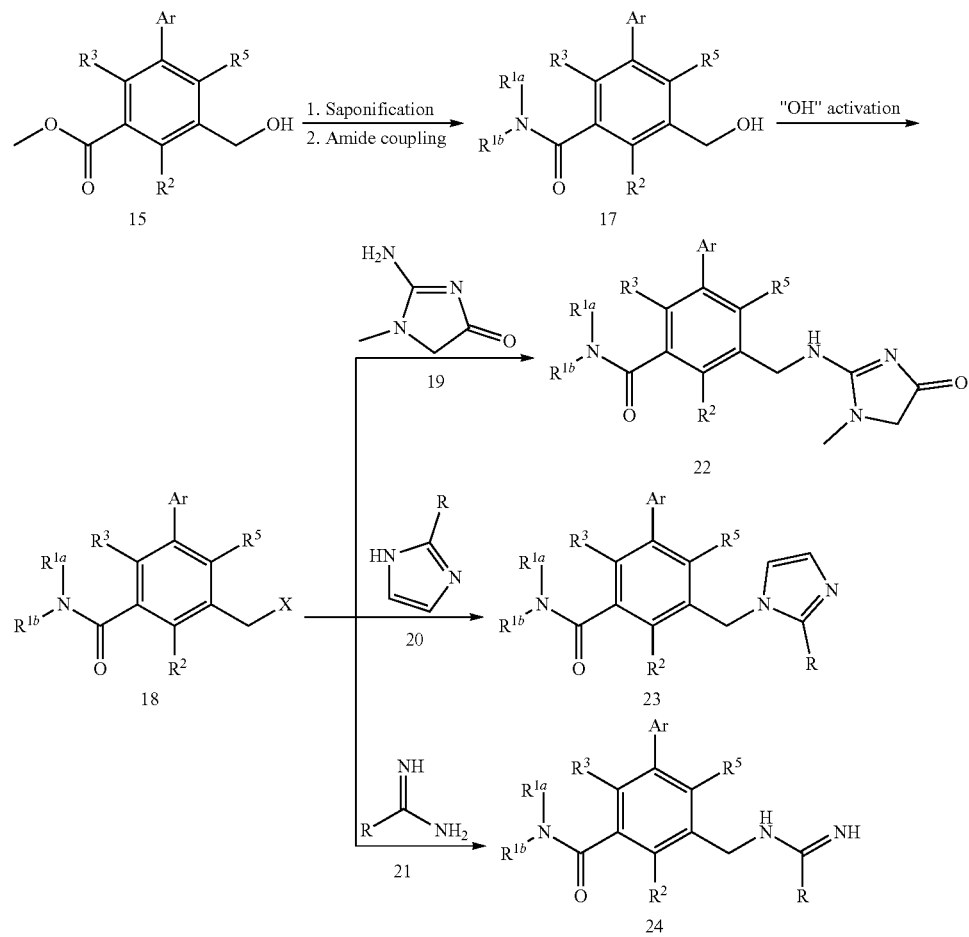

X = Br, Cl, OMs, OTs

Alternatively, compounds of Formula 15 can be subjected to saponification followed by amide coupling reactions to provide alcohol 17 by procedures illustrated in Scheme 1. Hydroxy group of 15 may be converted to bromide, chloride, Mesylate or Tosylate group by a number of conditions described in Scheme 2 to give intermediate 18 which can be reacted with nucleophiles such as aminoimidazolone 19, optionally substituted imidazole 20 or amidine 21 in the presence of appropriate bases, such as DIEA, TEA, $Cs_2CO_3$, $K_2CO_3$, LiOH or NaOH, to yield corresponding products of Formula 22, 23, and 24, respectively.

Scheme 4

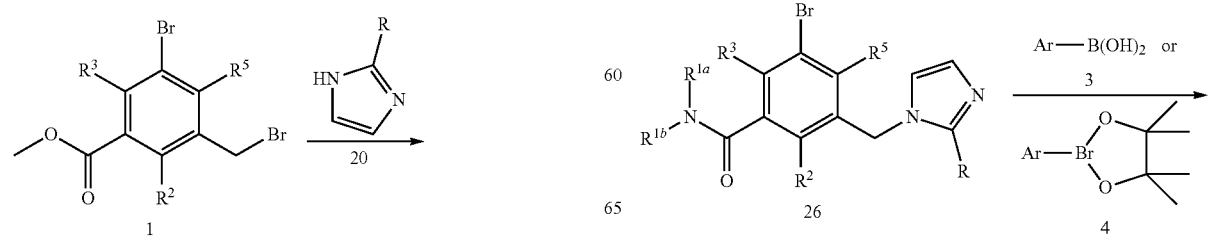

-continued

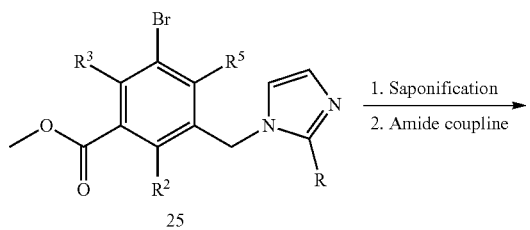

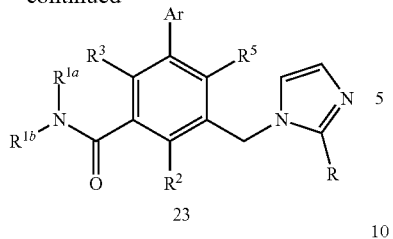

23

An alternate route to produce imidazole 23 is shown in Scheme 4 and described here. The benzyl bromide of Formula 1 can be converted to imidazole 25 by SN2 substitution reaction described in Scheme 3. Subsequent saponification followed by amide coupling reaction sequence produces intermediate 26, which can be subjected in Suzuki-Miyaura coupling protocol outlined in Scheme 1 to give imidazole 23. In some embodiments, a provided approach allows for great diversity in the introduced Ar group.

Scheme 5

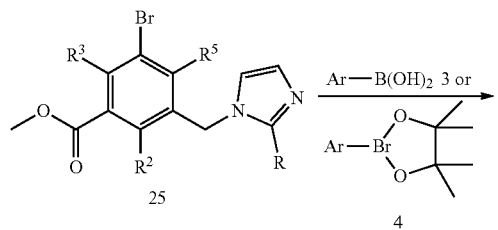

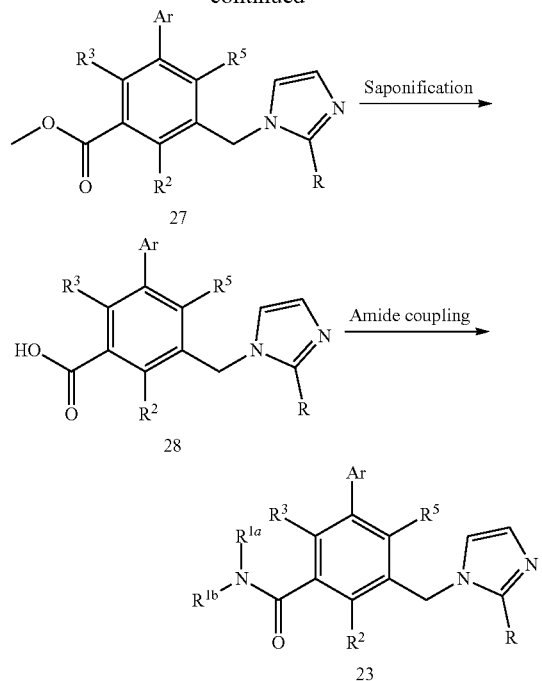

In some embodiments, the reaction sequence demonstrated in Scheme 4 can be reversed by conducting Suzuki-Miyaura coupling protocol prior to the final amide-coupling step to afford compounds of Formula 23. This method can introduce a variety of amines to achieve a maximum diversity in the amide moiety of the Formula 23.

Scheme 6

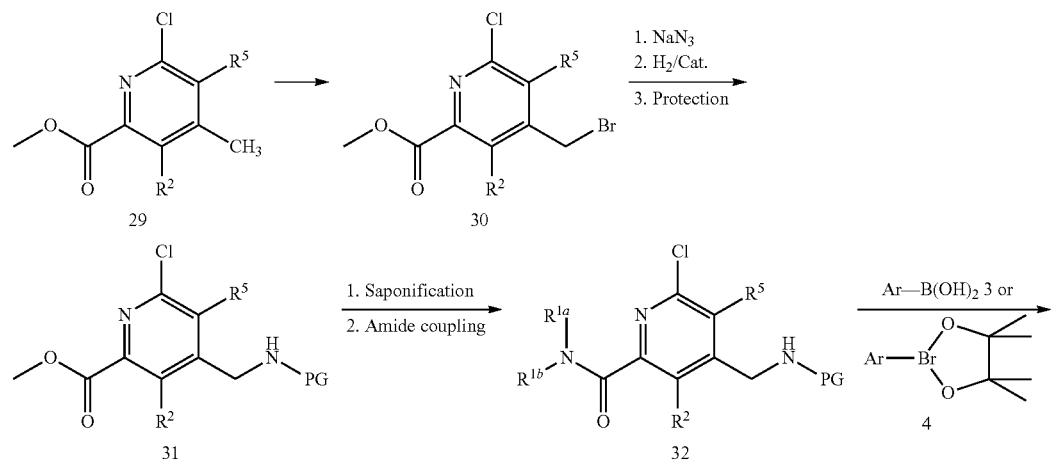

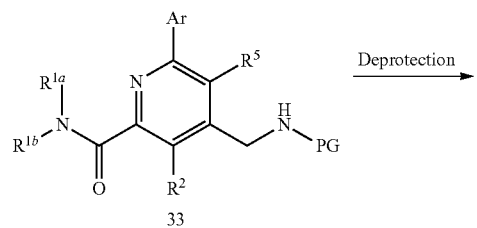

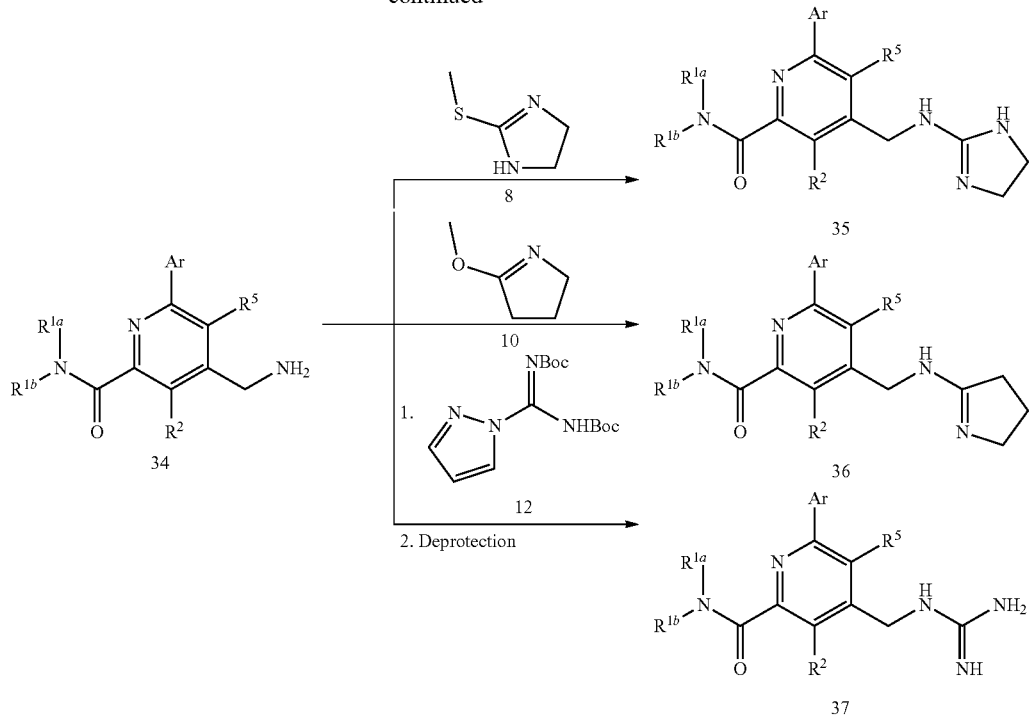

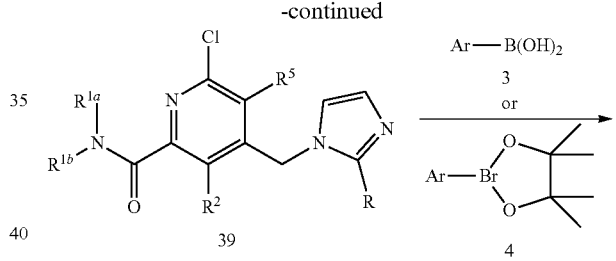

Exemplary methods for preparing compounds of Formula 35-37 containing the core pyridyl group in Scheme 6 and proceed from compounds of Formula 29. Radical bromination can be applied using, but not limited to, NBS and AIBN to generate intermediates of Formula 30. Azide introduction, followed by reduction and amine protection depicted in Scheme 1 can be performed to afford compounds of Formula 31. Amide 32 can be synthesized using saponification followed by amide-coupling protocols described above. Subsequent Suzuki-Miyaura coupling protocol followed by deprotection outlined in Scheme 1 can afford amine 34. Finally, cyclic guanidine 35, amidine 36, and Guanidine 37 can be yielded by methods depicted in Scheme 1.

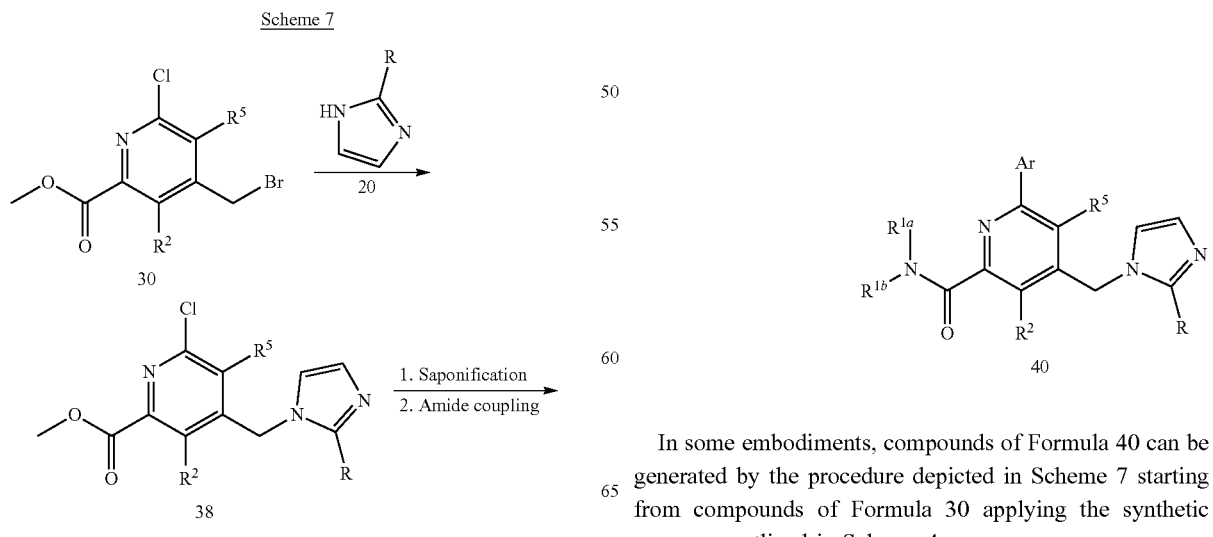

In some embodiments, compounds of Formula 40 can be generated by the procedure depicted in Scheme 7 starting from compounds of Formula 30 applying the synthetic sequence outlined in Scheme 4.

Scheme 8

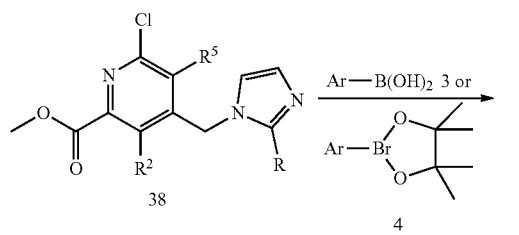

38

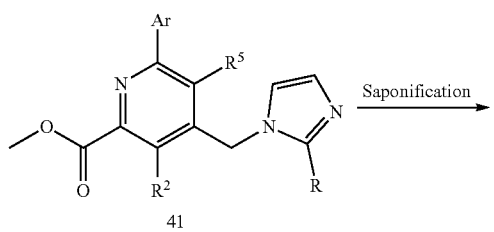

41

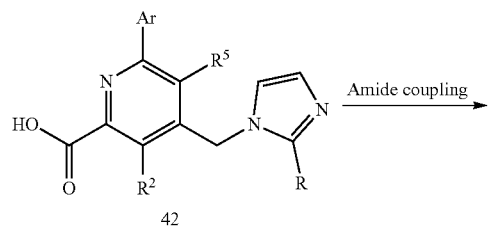

42

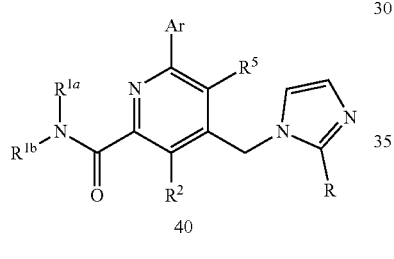

40

An alternate route to compounds of Formula 40 is shown in Scheme 8 from intermediate 38 by applying reaction sequence depicted in Scheme 5.

In another approach, example compounds of type 1.6 may be prepared according to Scheme B1. Starting from isophthalate dimethyl ester 1.1, reduction followed by ester hydrolysis affords acid carbinol 1.3. Amide coupling, activation via thionyl chloride, azide displacement, and reduction provides penultimate intermediate 1.5. Treatment of 1.5 with an appropriate amidinyl or guanidinyl agent in an alcoholic or polar aprotic solvent with heat provides final examples of type 1.6.

Scheme B1

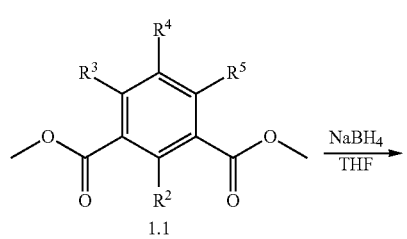

1.1

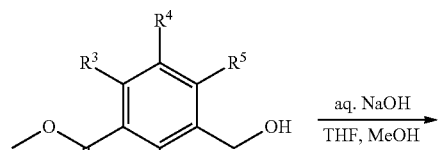

1.2

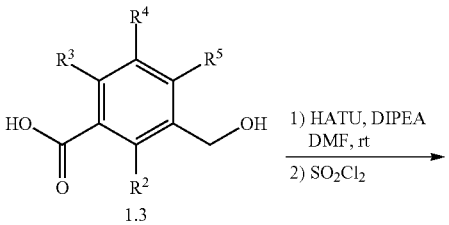

1.3

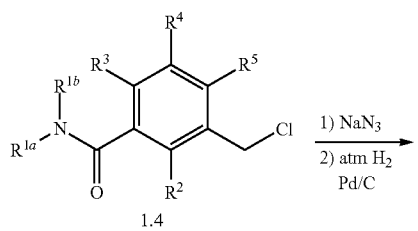

1.4

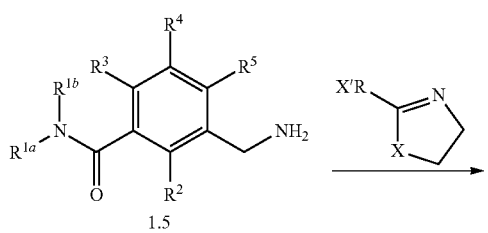

1.5

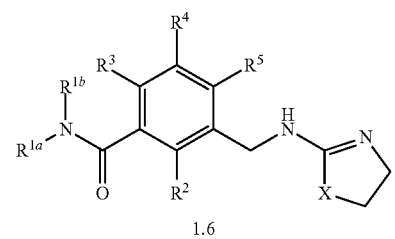

1.6

X'R = SCH$_3$ or OCH$_3$
X = NH or CH$_2$

In another synthetic strategy starting from tolyl benzoate 2.1, bromination, followed by azide displacement and saponification affords azido acid 2.4. Amide coupling with HATU or an equivalent coupling agent followed Raney-Nickel reduction with atmospheric hydrogen gives amine 2.6. Similar to Scheme B1, derivatization to give final amidine or guanidine examples can be accomplished using know activated precursors to produce final compounds 2.7.

Scheme B2

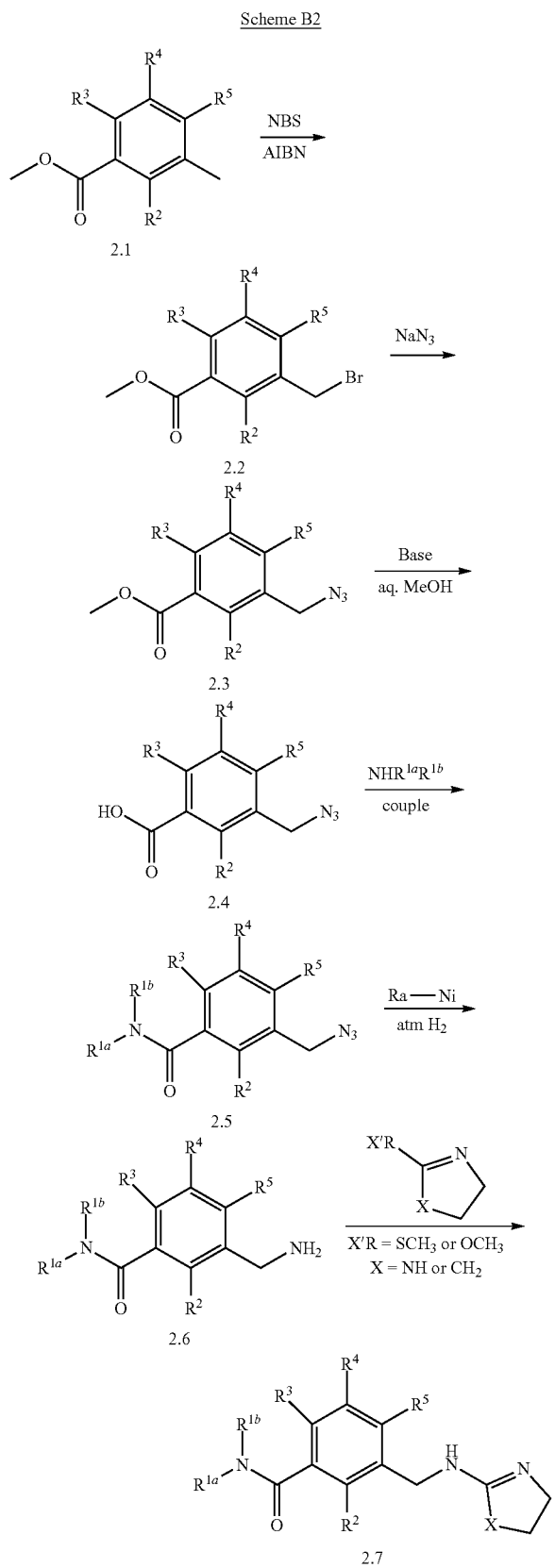

A more specific example of type 2.7 is set forth in Scheme B3 to give 3.7.

Scheme B3

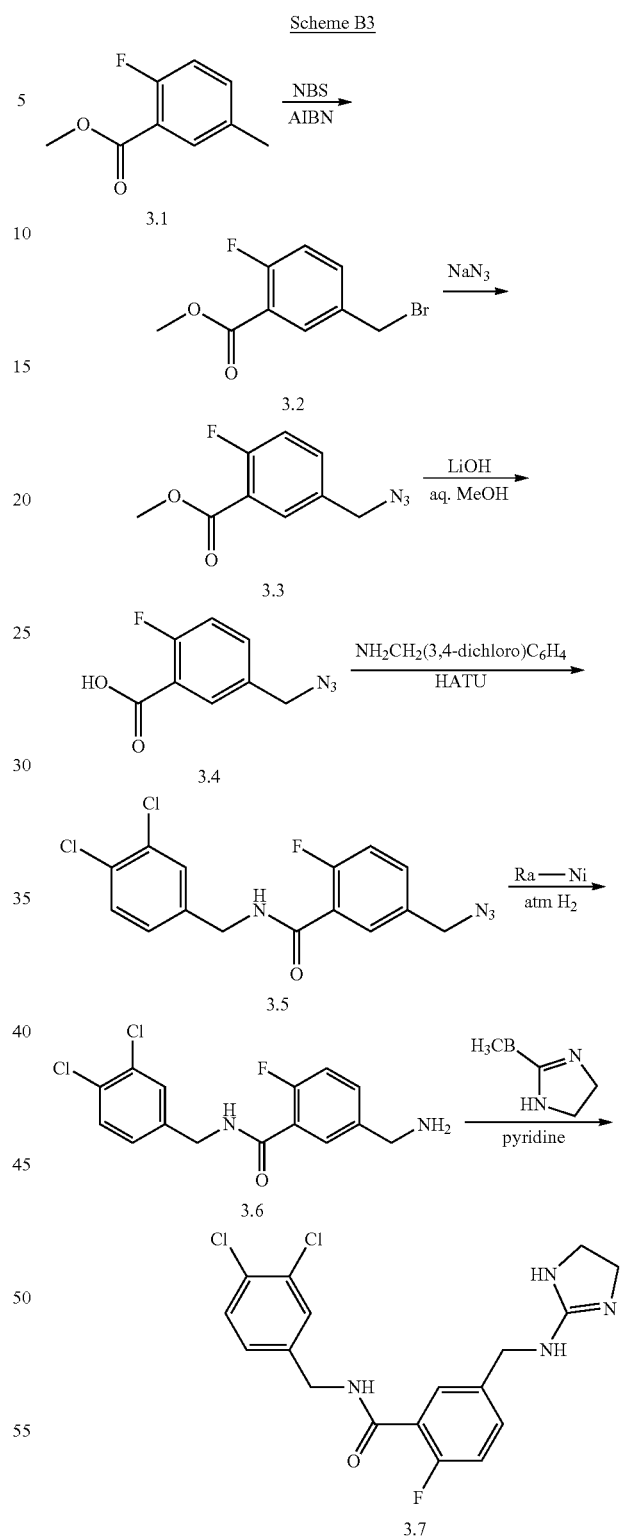

Alternatively final compounds can be prepared according to Scheme B4 using a carbamate amine protection strategy. Starting from 4.1 bromination, azide introduction, followed by reduction and one-pot Boc anhydride treatment affords 4.4. Saponification, amine coupling, followed by acid treatment to remove Boc protecting group provides penultimate compounds of type 4.6. Amidine or guanidine introduction as before affords final examples 4.7.
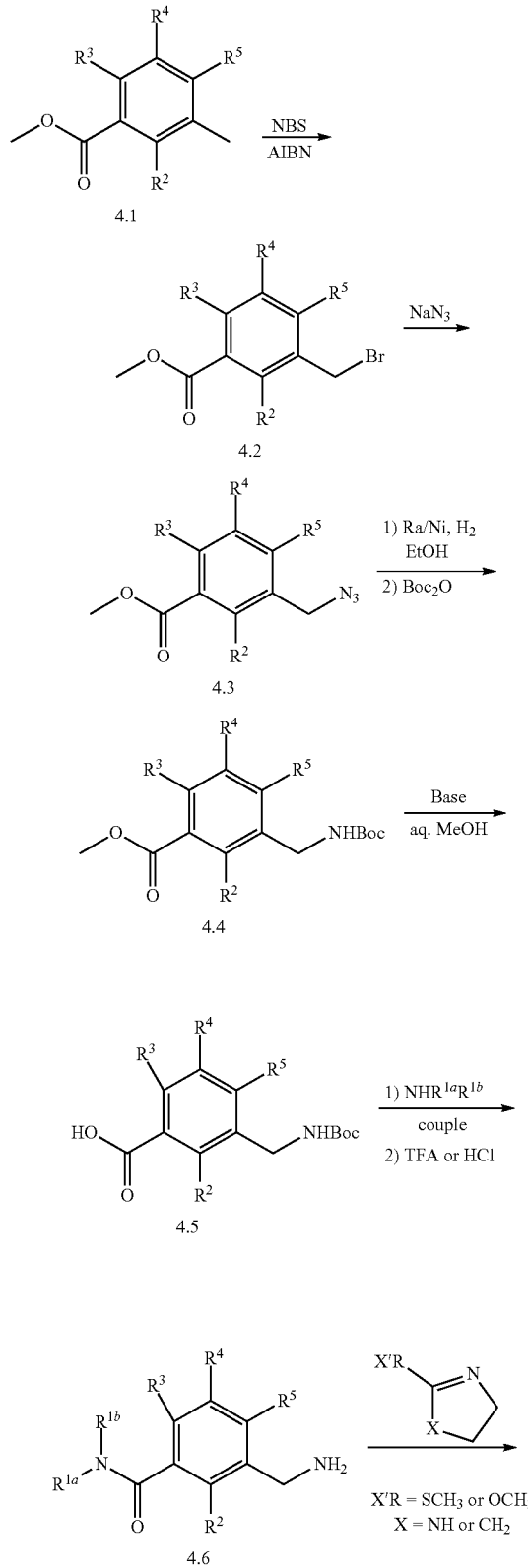
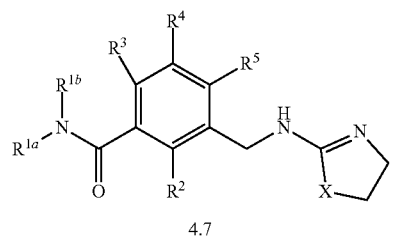
A more specific example of type 4.7 is set forth in Scheme B5.
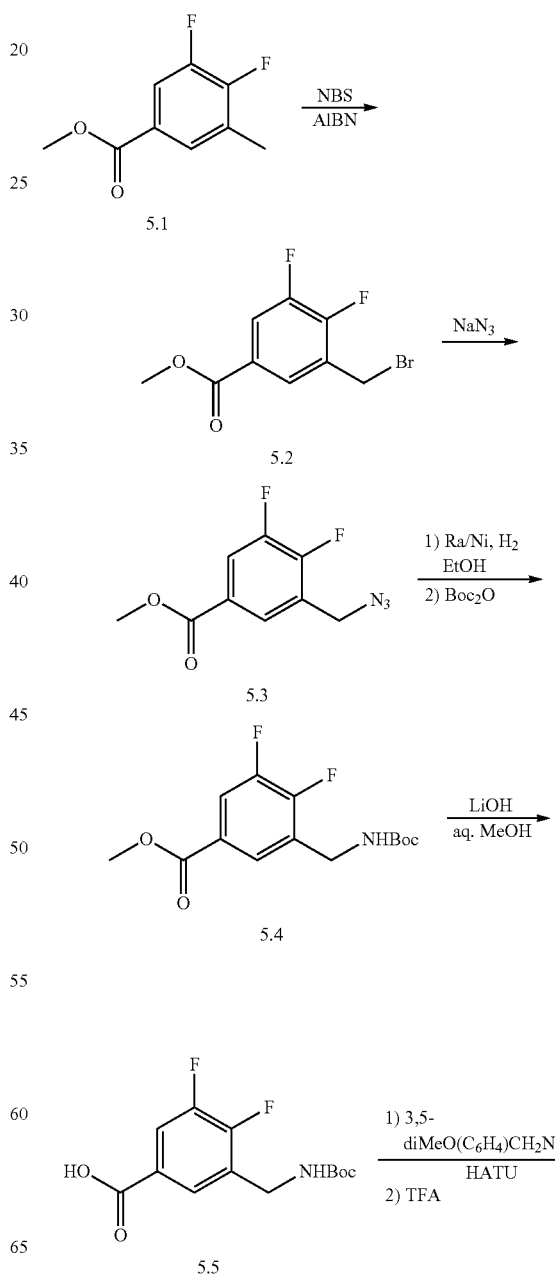

111
-continued

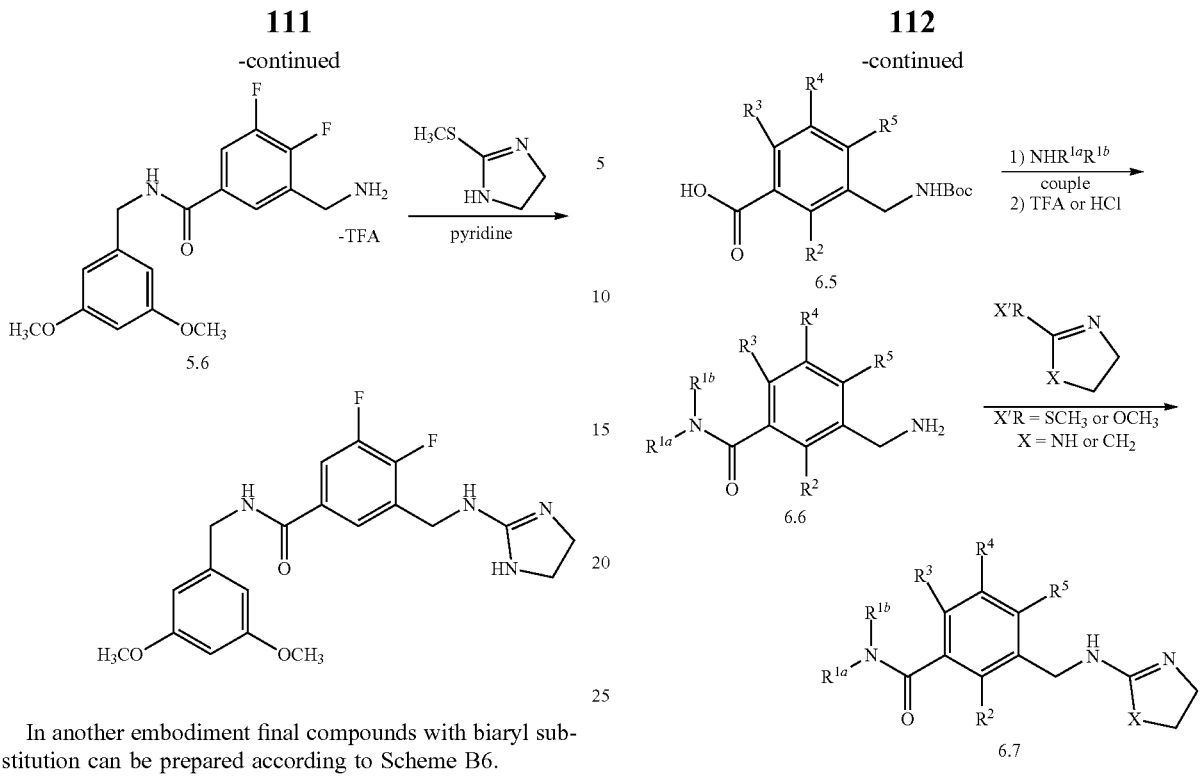

In another embodiment final compounds with biaryl substitution can be prepared according to Scheme B6.

Scheme B6

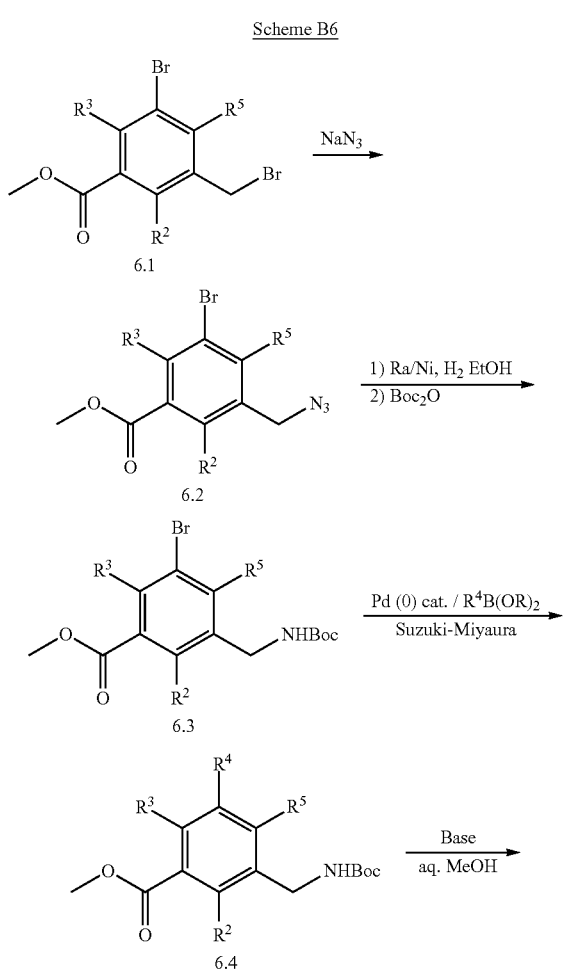

112
-continued

Starting from 6.1, azide introduction (6.2), followed by reduction and one-pot Boc anhydride treatment affords 6.3. Suzuki-Miyaura coupling, saponification, and amine coupling, followed by acid treatment provides amine 6.6. Amidine or guanidine introduction as before affords final examples 6.7. A more specific example of 6.7 is set forth in Scheme B7.

Scheme B7

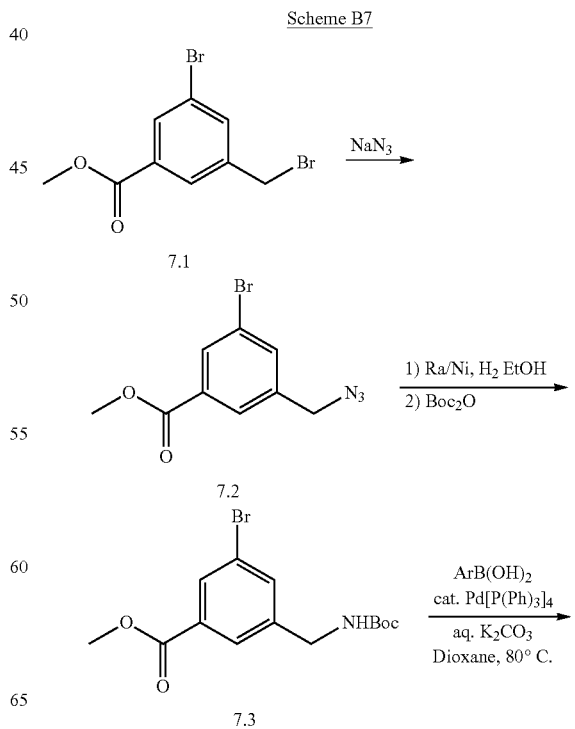

Scheme B8
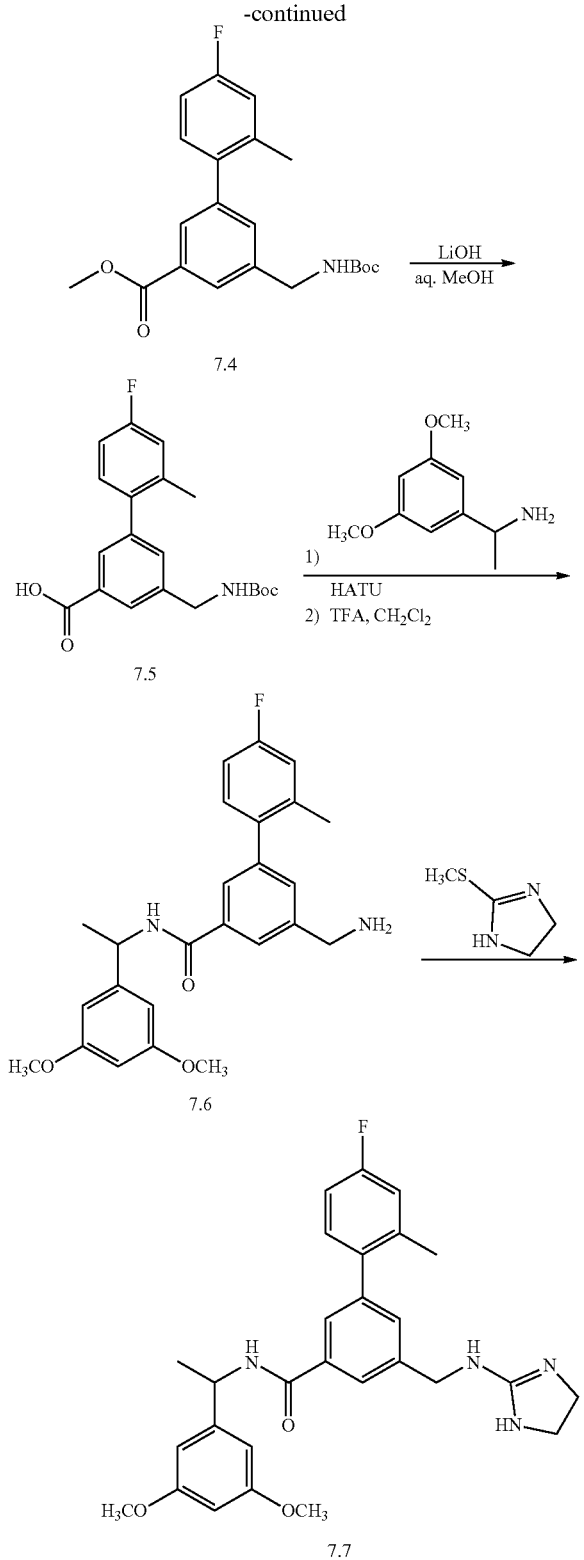
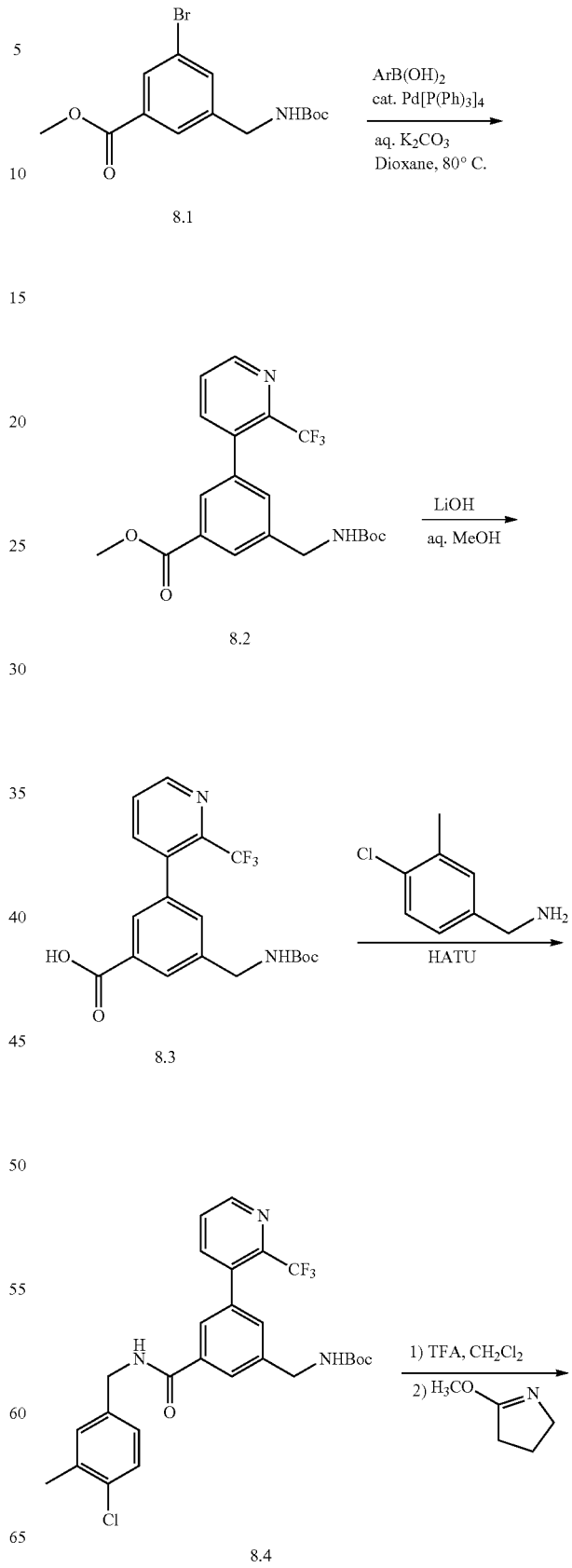
An additional example involving incorporation of an amidine in the final step is set forth in Scheme B8. Suzuki-Miyaura coupling as before via bromide 8.1 provides 8.2. Saponification and amide coupling furnishes Boc protected amide 8.4. Deprotection and treatment with 5-methoxy-3,4-dihydro-2H-pyrrole in acetic acid and methanol.

115

-continued

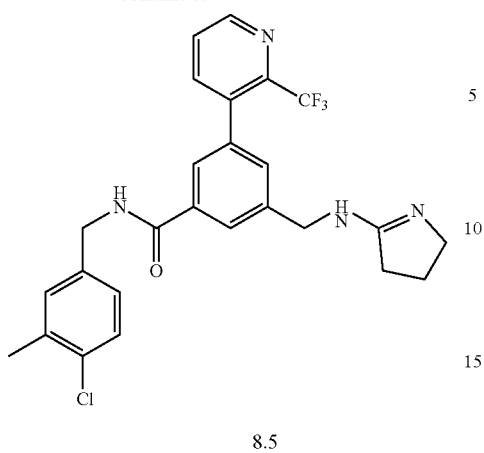

8.5

In another embodiment final compounds can be accessed via an activation-direct heterocycle displacement using a reaction sequence outlined according to Scheme B9.

Scheme B9

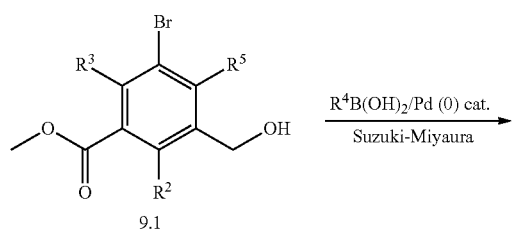

116

-continued

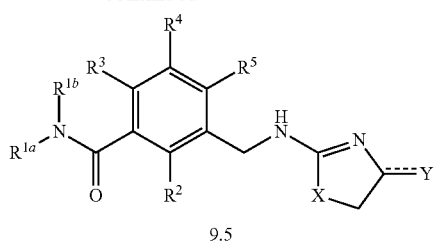

9.5

Suzuki-Miyaura coupling with intermediate alcohol 9.1, followed by hydrolysis, amide coupling and activation of the alcohol (e.g. PBr$_3$) gives bromide 9.4. Alternatively, other benzylic activation methods such as mesyl chloride in presence of a tertiary amine base such as DIPEA may be used. Displacement with an appropriate amino heterocycle gives final compound 9.5. A more specific example using 2-imino-1-methylimidazolidin-4-one is set forth below in Scheme B10.

Scheme B10

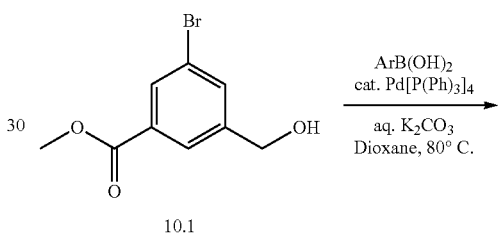

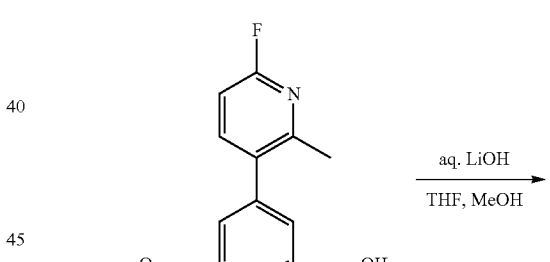

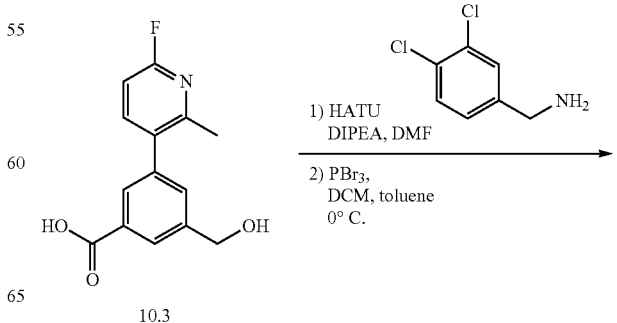

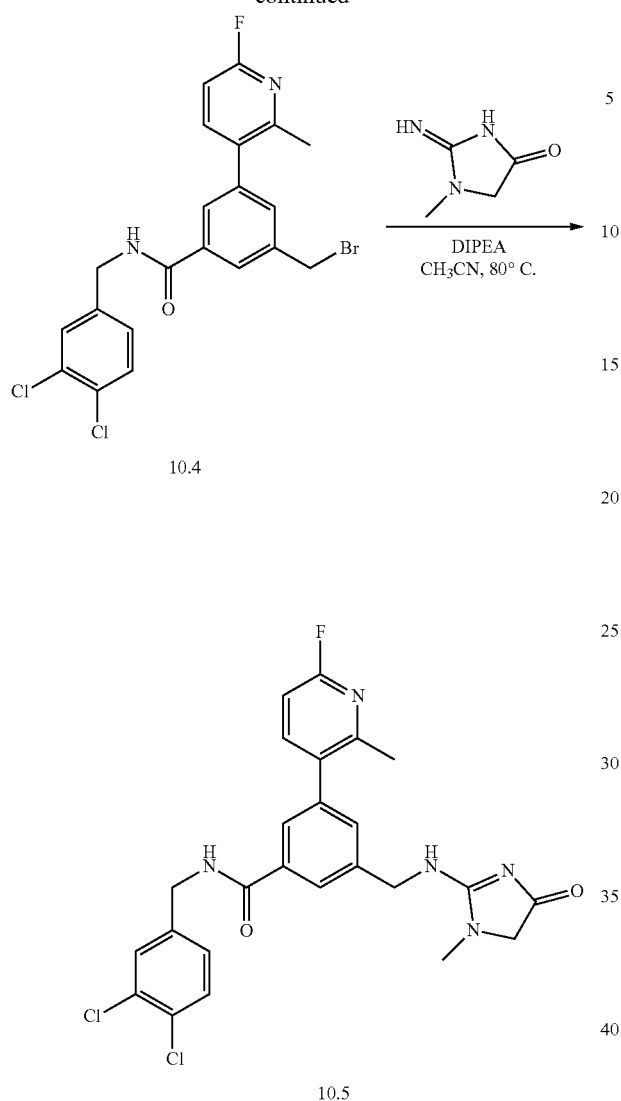

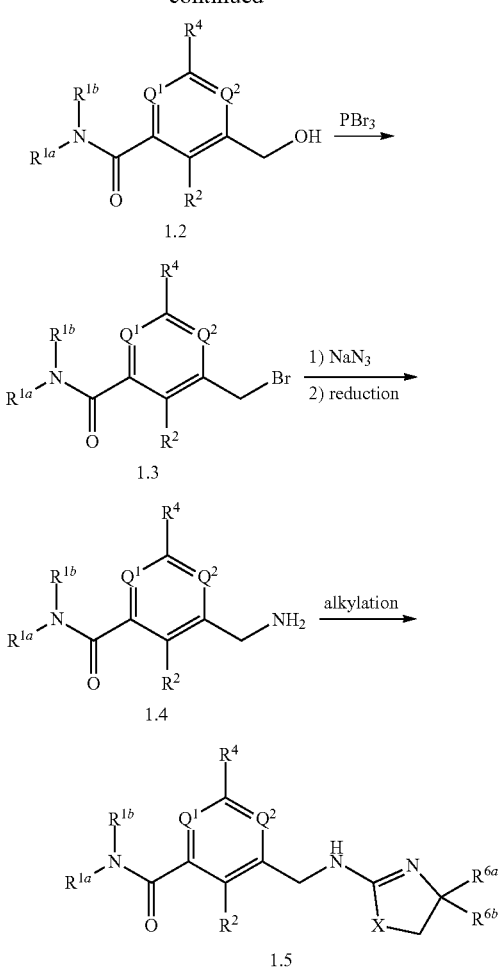

A more specific example of type 1.5 is set forth in Scheme C2 to give 2.5.

Example compounds of type 1.5 may be prepared according to Scheme C1. Starting from acid carbinol 1.1, amide coupling affords 1.2. Activation via phosphorous tribromide or a related halogenating agent, followed by azide displacement, and reduction provides penultimate intermediate 1.4. Treatment of 1.4 in an alkylation reaction using an activated amidine or imidate based heterocycle, for example such as 5-methoxy-3,4-dihydro-2H-pyrrole, provides final examples of type 1.5.

Scheme C1

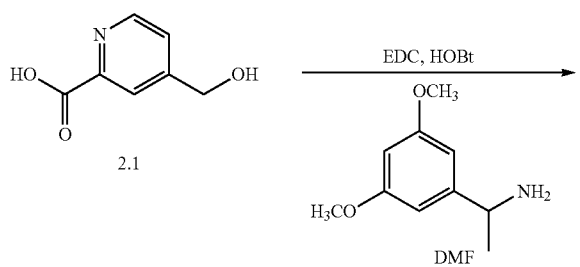

Scheme C2

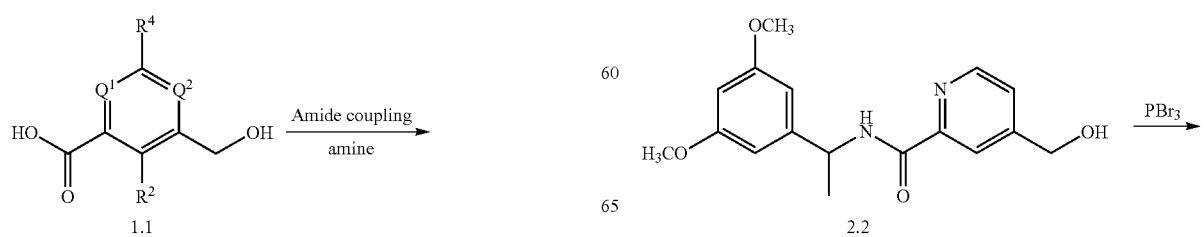

-continued

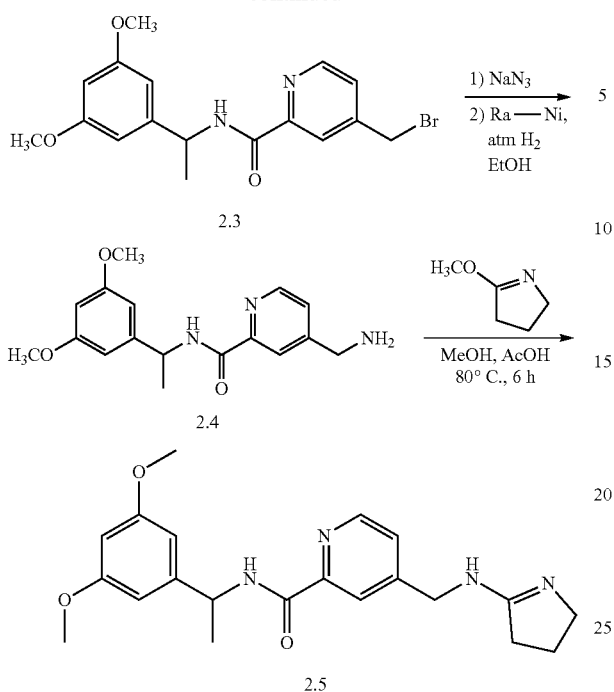

Alternatively, final compounds may be prepared according to Scheme C3 involving first azide introduction, amide coupling to give 3.4, then reduction and final heterocycle introduction via addition-elimination using an appropriate electrophilic heterocycle to give examples of type 3.5.

Scheme C3

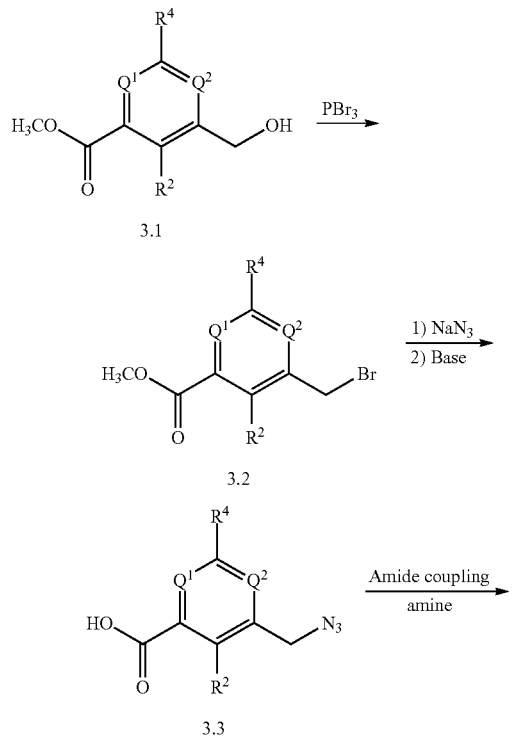

-continued

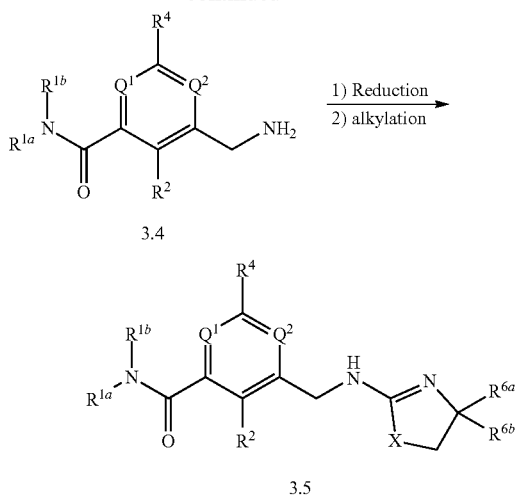

A more specific example of type 3.5 is set forth in Scheme C4 to give 4.5. Final heterocycle introduction is accomplished in the presence of amine intermediate A2 using 2-(methylthio)-4,5-dihydro-1H-imidazole using heat and pyridine as a solvent.

Scheme C4

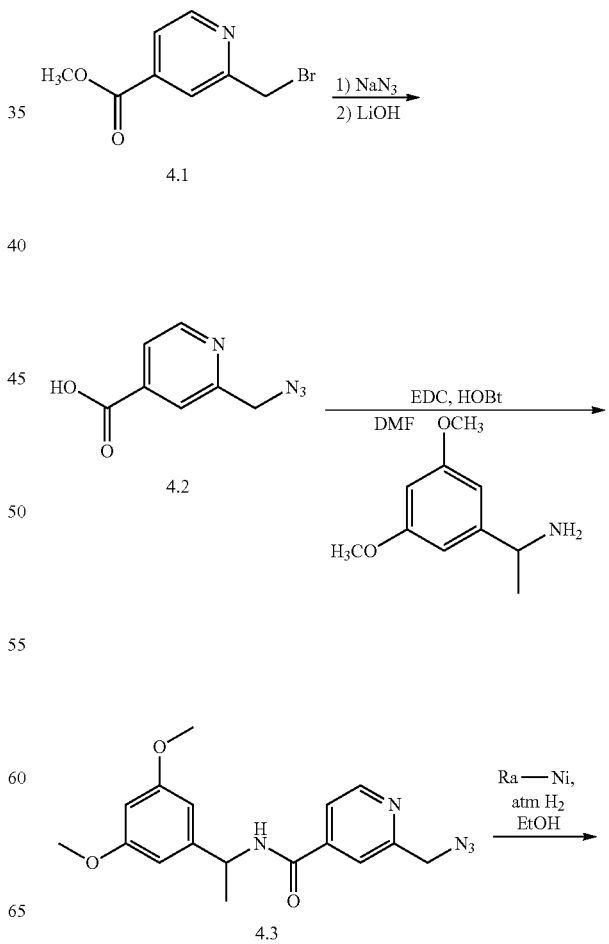

121
-continued

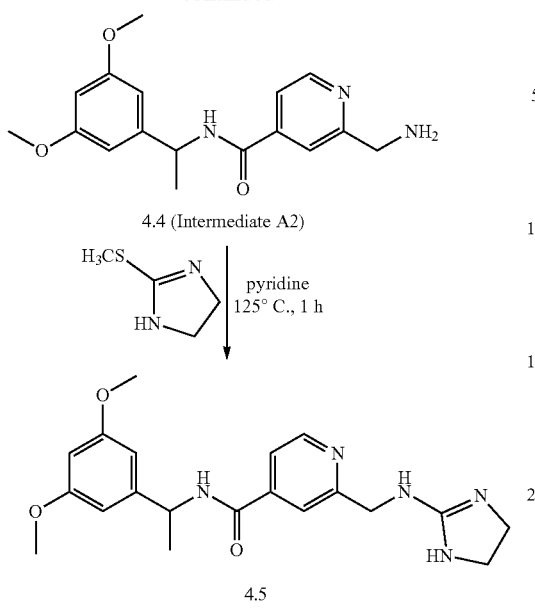

Alternatively, final compounds can be prepared according to Scheme C5 involving first azide introduction, reduction, and Boc protection to give 5.3. 5.3 can then be manipulated as before to introduce diverse amides 5.4, Boc deprotection and final treatment with an electrophilic heterocyclic precursor gives example of type 5.5.

Scheme C5

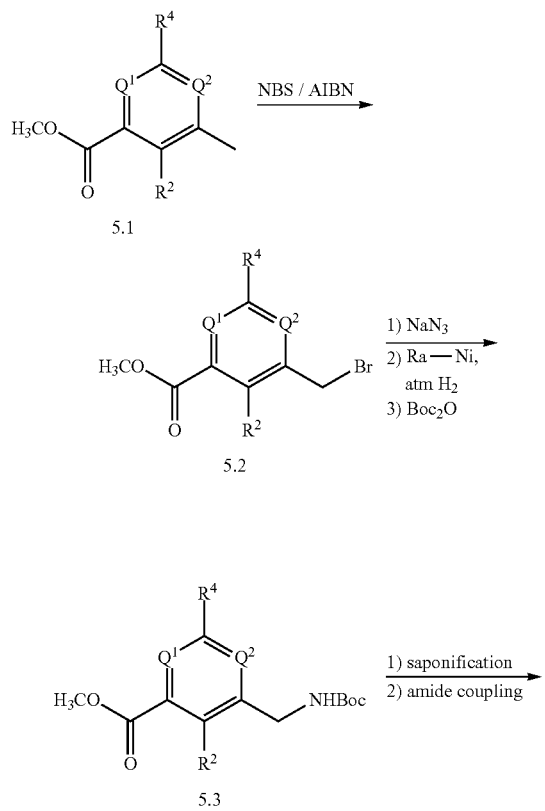

122
-continued

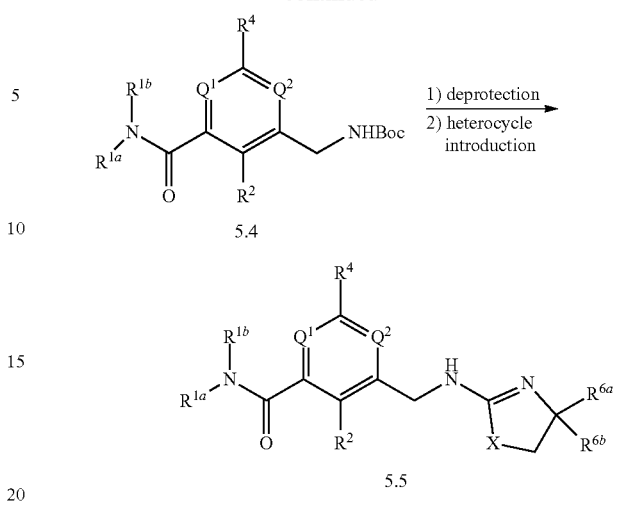

In another embodiment final compounds with biaryl $R^4$ substitution can be prepared employing a Suzuki cross-coupling according to Scheme C6.

Scheme C6

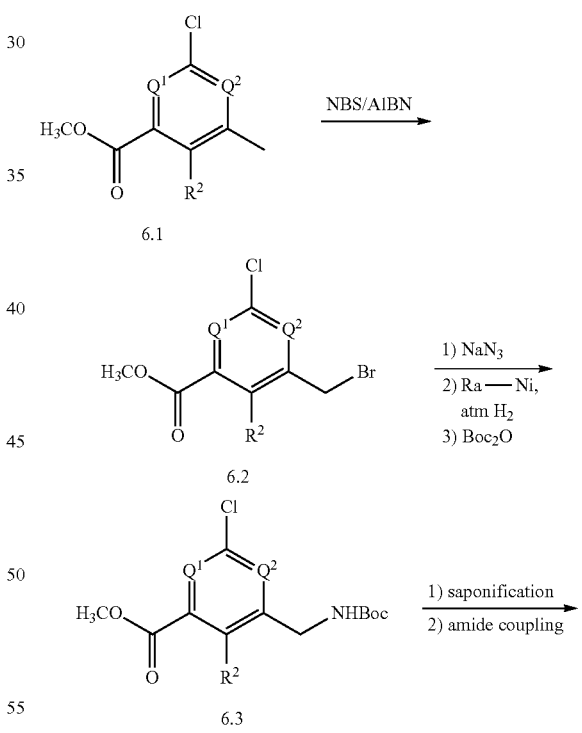

-continued

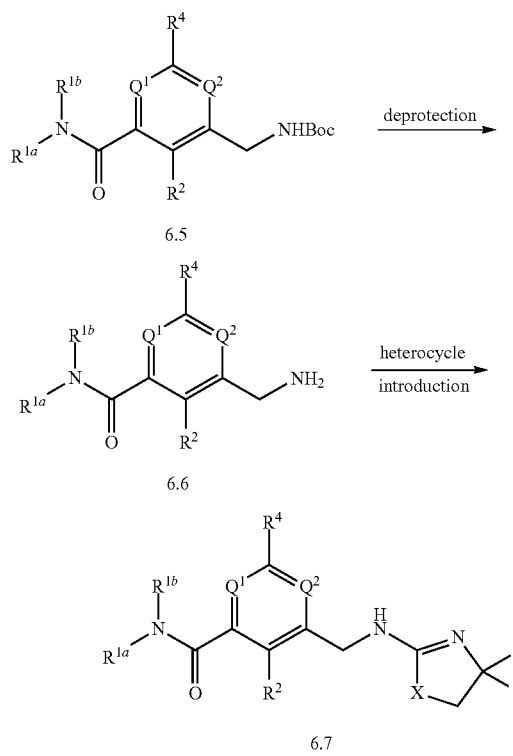

6.5

6.6

6.7

A more specific example of 6.7 is set forth in Scheme C7.

Scheme C7

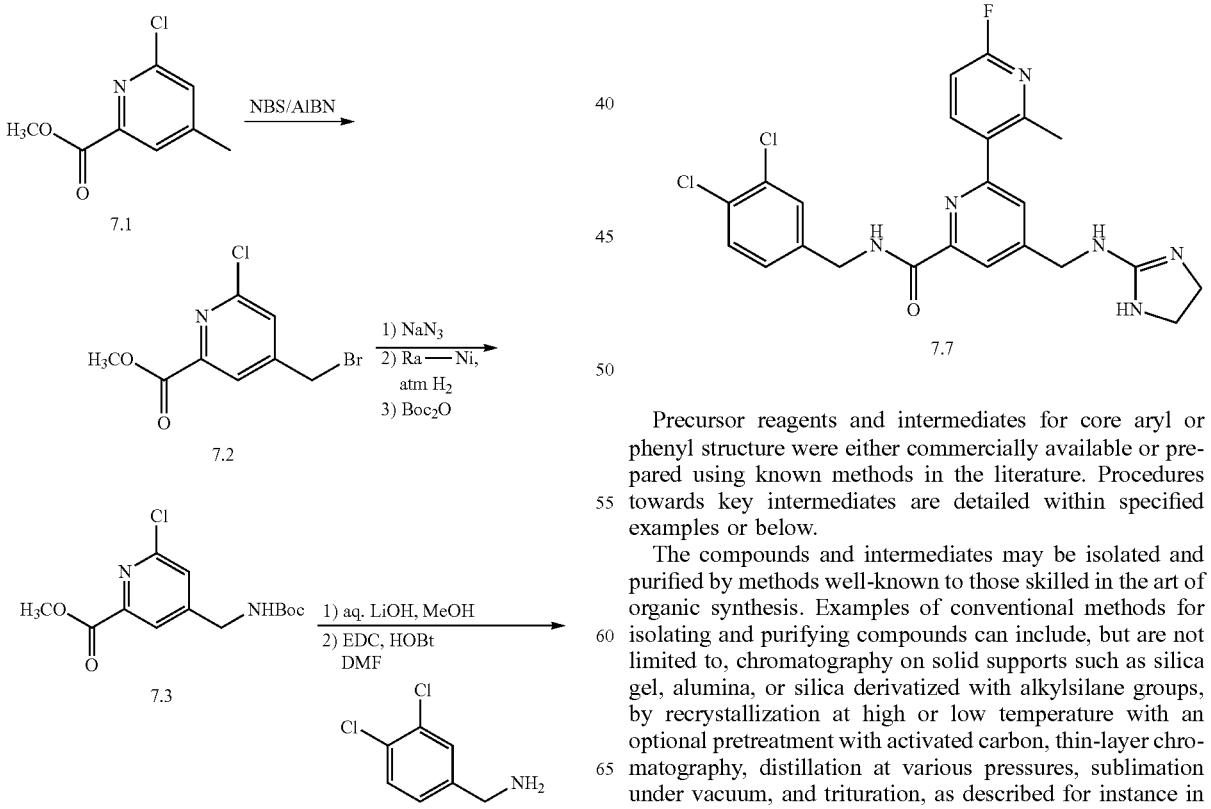

7.1

7.2

7.3

-continued

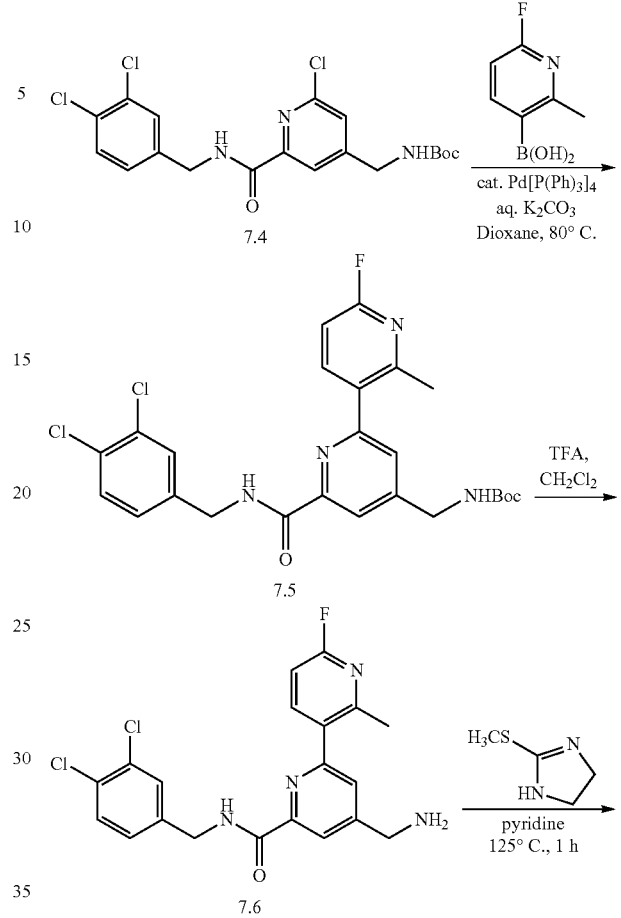

7.4

7.5

7.6

7.7

Precursor reagents and intermediates for core aryl or phenyl structure were either commercially available or prepared using known methods in the literature. Procedures towards key intermediates are detailed within specified examples or below.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

C. EXAMPLES

Abbreviations

The following abbreviations are employed in the Examples and elsewhere herein:
DCM=dichloromethane
EDC=1-Ethyl-3-(3-dimethylaminopropyl)carbodiimide
TEA=triethylamine
DMF=dimethylformamide
DMSO=dimethylsulfoxide
THF=tetrahydrofuran
$K_2CO_3$=potassium carbonate
$Cs_2CO_3$=cesium carbonate
ether=diethyl ether
NaOH=sodium hydroxide
KOH=potassium hydroxide
EtOAc=ethyl acetate
$Na_2CO_3$=sodium carbonate
$NaHCO_3$=sodium bicarbonate
$MgSO_4$=magnesium sulfate
$CH_2Cl_2$=methylene chloride
MeOH=methanol
EtOH=ethanol
Hex=hexanes
HCl=hydrochloric acid
$Pd(PPh_3)_4$=tetrakis(triphenylphosphine)palladium(0)
$Pd(OAc)_2$—Palladium(II) acetate
TFA=trifluoroacetic acid
$Et_3N$=triethylamine
DIPEA=N,N-diisopropylethylamine
NaH=sodium hydride
$NaN_3$=sodium azide
TBAF=tetrabutyl ammonium fluoride
DTBAD=di-tert-butyl azodicarboxylate
HATU=2-(7-aza-1H-benzotriazole-1-yl)-1,1,3,3-tetramethyluronium hexafluorophosphate
NBS=N-bromo succinimide
AIBN=Azobisisobutyronitrile
min=minute(s)
h or hr=hour(s)
mL or ml=milliliter
g=gram(s)
mg=milligram(s)
mmol=millimole(s)
r.t.=room temperature
LRMS=low resolution mass spectrometry
NMR=nuclear magnetic resonance
(M+H)=the protonated mass of the free base of the compound
$R_T$=retention time (in minutes)

Microwave assisted reactions are performed in a single-mode reactor: Emrys™ Optimizer microwave reactor (Personal Chemistry A.B., currently Biotage).

Hydrogenation reactions are performed using an atmospheric balloon or using a Parr hydrogenation shaker apparatus.

Normal phase flash silica gel-based column chromatography is performed using ready-to-connect cartridges from ISCO, on irregular silica gel, particle size 15-40 µm on a Combi-flash Companion chromatography system from ISCO.

Low resolution mass spectra are obtained on an Agilent 1200 series 6130 mass spectrometer. Analytical HPLC is performed on an HP1100 with UV detection at 214 and 254 nm along with ELSD detection, LC/MS (J-Sphere80-C18, 3.0×50 mm, 4.1 min gradient, 5%[0.05% TFA/CH$_3$CN]: 95%[0.05% TFA/H$_2$O] to 100% [0.05% TFA/CH$_3$CN]. Preparative RP-HPLC purification is performed on a custom HP1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient. µ

For LC-MS-characterization of the compounds of the present invention, the following methods are used.

Method 1:

The HPLC measurement is performed using an Agilent 1200 system comprising a binary pump with degasser, an autosampler, a column oven, a diode-array detector (DAD) and a column as specified in the respective methods below. Flow from the column is split to a SQ mass spectrometer and Polymer Labs ELSD. The MS detector is configured with an ES ionization source. Nitrogen is used as the nebulizer gas. The source temperature is maintained at 350° C. Data acquisition is performed with Agilent Chemstation software. Reversed phase HPLC is carried out on a Kinetex C18 column (2.6 µm, 2.1×30 µm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 2:

Using method 1 instrument and column conditions. The gradient conditions used are: 93% A (water+0.1% TFA), 7% B (acetonitrile), to 95% B in 2.0 minutes, returning to initial conditions at 2.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

$^1$H NMR spectra are recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which is used as internal standard. Coupling constants (J-values) are reported in Hz.

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

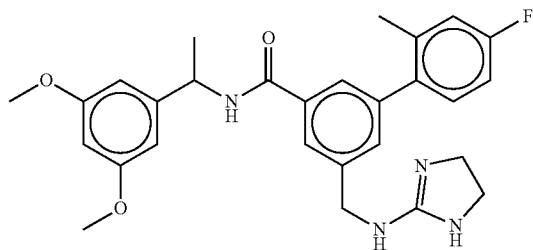

Example 1

(±)-5-(((4,5-dihydro-1H-imidazol-2-yl)amino)methyl)-N-(1-(3,5-dimethoxyphenyl)ethyl)-4'-fluoro-2'-methyl-[1,1'-biphenyl]-3-carboxamide Step A. Preparation of methyl 3-bromo-5-(((tert-butoxycarbonyl)amino)methyl)benzoate: General Procedure for Azide Formation, Reduction, and Boc Protection Steps A solution of methyl 3-bromo-5-(bromomethyl)benzoate (877624-40-3, CombiBlocks) (1.39 g, 4.54 mmol) and sodium azide (0.58 g, 8.49 mmol) in 90% methanol/water (110 mL) was refluxed for 4 h. The reaction mixture was cooled to ambient temperature and concentrated under reduced pressure. The residue was dissolved in DCM, washed with water, dried over MgSO$_4$, filtered and concentrated in vacuo to give crude methyl 3-(azidomethyl)-5-bromobenzoate. It was dissolved in ethanol (50 mL) and RaNi (0.20 g cat) was added. The reaction mixture was stirred under H$_2$ atmosphere for 2 h then filtered. The filtrate was concentrated to yield crude methyl 3-(aminomethyl)-5-bromobenzoate, which was dissolved in THF (50 mL) then DIEA (0.66 mL, 3.82 mmol) and (BOC)$_2$O (1.00 g, 4.66 mmol) were added. The reaction mixture was stirred for 18 h then concentrated in vacuo. The residue was purified by flash chromatography (Combi-flash Rf, Hex/EtOAc=0-100% gradient) to afford the title compound (1.50 g, 96%). $^1$H NMR (400 MHz, d$_6$ DMSO) δ 7.9 (s, 1H), 7.8 (s, 1H), 7.7 (s, 1H), 7.5 (t, 1H, J=5.5 Hz), 4.2 (d, 2H, J=6.1 Hz), 3.9 (s, 3H), 1.4 (s, 9H).

Step B. Preparation of methyl 5-(((tert-butoxycarbonyl)amino)methyl)-4'-fluoro-2'-methyl-[1,1'-biphenyl]-3-carboxylate: General Procedure for Suzuki Coupling Ar was bubbled into a mixture of methyl 3-bromo-5-(((tert-butoxycarbonyl)amino)methyl)benzoate (1.50 g, 4.37 mmol) and K$_2$CO$_3$ (1.60 g, 11.65 mmol) in 80% 1,4-dioxane/water (100 mL) for 5 min. Tetrakis(triphenylphosphine)palladium (0) (0.40 g, 0.35 mmol) and 4-fluoro-2-methylphenylboronic acid (1.07 g, 6.93 mmol) were added to the mixture, and the reaction mixture was stirred for 4 h at 80° C. The reaction was cooled to ambient temperature and concentrated. The residue was dissolved in DCM, washed with water, dried with MgSO$_4$, filtered and concentrated in vacuo. The residue was purified by flash chromatography (Combi-flash Rf, Hex/EtOAc=0-100% gradient) to afford the title compound (1.61 g, 99%) $^1$H NMR (400 MHz, d$_6$ DMSO) δ 7.8 (s, 1H), 7.7 (s, 1H), 7.5 (m, 1H), 7.3 (m, 1H), 7.2 (m, 2H), 4.2 (d, 2H J=6.5 Hz), 3.8 (s, 3H), 2.2 (s, 3H), 1.4 (s, 9H).

Step C. Preparation of 5-(aminomethyl)-N-(1-(3,5-dimethoxyphenyl)ethyl)-4'-fluoro-2'-methyl-[1,1'-biphenyl]-3-carboxamide: General Procedure for HATU Coupling Reaction A solution of methyl 5-(((tert-butoxycarbonyl)amino) methyl)-4'-fluoro-2'-methyl-[1,1'-biphenyl]-3-carboxylate (1.61, 4.33 mmol) in THF (50 mL)/MeOH (5 mL)/water (5 ml) was treated with 2M LiOH aq. (4.52 mL, 9.05 mmol) and stirred for 6 h. The solvent was removed under reduced pressure, and the residue was diluted with water. 1N HCl aq. was added to adjusted pH=2. The resulting solid was filtered, washed with water and dried in a vacuum oven to afford crude 5-(((tert-butoxycarbonyl)amino)methyl)-4'-fluoro-2'-methyl-[1,1'-biphenyl]-3-carboxylic acid. (1.40 g, 90%). To a solution of 5-(((tert-butoxycarbonyl)amino)methyl)-4'-fluoro-2'-methyl-[1,1'-biphenyl]-3-carboxylic acid (0.08 g, 0.22 mmol) in DMF (2 mL) was added DIEA (0.10 mL, 0.55 mmol) and HATU (0.09 g, 0.23 mmol). The reaction mixture was stirred for 5 min then 1-(3,5-dimethoxyphenyl)ethan-1-amine (0.05 g, 0.24 mmol) was added. The reaction mixture was stirred for 18 h at ambient temperature then concentrated under reduced pressure. The residue was dissolved in EtOAc, washed with water, dried over MgSO$_4$, filtered, and concentrated. The residue was purified by flash chromatography (Combi-flash Rf, Hex/EtOAc=0-100% gradient) to afford tert-butyl ((5-((1-(3,5-dimethoxyphenyl) ethyl)carbamoyl)-4'-fluoro-2'-methyl-[1,1'-biphenyl]-3-yl) methyl)carbamate. The intermediate was dissolved in DCM (2 mL), treated with TFA (1 mL), stirred for 1 h then concentrated under reduced pressure to afford the crude title compound, which was used in next step without further purification.

Step D. Example 1

The crude 5-(aminomethyl)-N-(1-(3,5-dimethoxyphenyl) ethyl)-4'-fluoro-2'-methyl-[1,1'-biphenyl]-3-carboxamide (0.22 mmol) was dissolved in pyridine (3 mL) and 2-methylthio-2-imidazoline hydroiodide (0.05 g, 0.22 mmol) was added. The reaction mixture was heated under microwave at 125° C. for 1 h. The reaction was cooled to ambient temperature and concentrated. The residue was purified by reverse phase HPLC (Phenomenex Gemini C18, H$_2$O/ CH$_3$CN gradient from 30-90% CH$_3$CN, 0.1% TFA) to yield the TFA salt of the title compound. The TFA salt was dissolve in EtOAc and washed with sat. NaHCO$_3$. The organic layer was dried and concentrated to afford the title compound (0.03 g 56%). $^1$H NMR (400 MHz, d$_6$ DMSO) δ 8.8 (d, 1H, J=5.8 Hz), 7.8 (d, 2H, J=6.6 Hz), 7.4 (s, 1H), 7.3 (m, 1H), 7.2 (m, 1H), 7.1 (m, 1H), 6.5 (d, 2H, J=2.1 Hz), 6.3 (t, 1H, J=2.2 Hz), 5.1 (m, 1H), 4.5 (s, 2H), 3.7 (s, 6H), 3.6 (s, 3H), 2.2 (s, 3H), 1.4 (d, 3H, J=7.3 Hz): LCMS: 97%. MS (ES) 491 (M+H

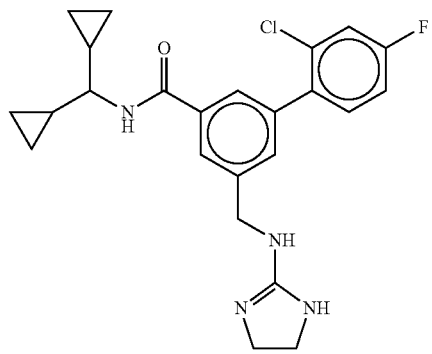

Example 2

2'-Chloro-N-(dicyclopropylmethyl)-5-(((4,5-di-hydro-1H-imidazol-2-yl)amino)methyl)-4'-fluoro-[1, 1'-biphenyl]-3-carboxamide Step A. Preparation of methyl 5-(((tert-butoxycarbonyl)amino)methyl)-2'-chloro-4'-fluoro-[1,1'-biphenyl]-3-carboxylate The title compound was prepared following the procedure described in Example 1, Step B using methyl 3-bromo-5-(((tert-butoxycarbonyl)amino)methyl)benzoate and 2-chloro-4-fluoro phenylboronic acid.

Step B. Preparation of 5-(aminomethyl)-2'-chloro-N-(dicyclopropylmethyl)-4'-fluoro-[1,1'-biphenyl]-3-carboxamide The title compound was prepared following the procedure described in Example 1, Step C using methyl 5-(((tert-butoxycarbonyl)amino)methyl)-2'-chloro-4'-fluoro-[1,1'-biphenyl]-3-carboxylate and dicyclopropylmethanamine.

Step C. Example 2

The title compound (0.01 g, 15%) was prepared following the procedure described in Example 1, Step D using 5-(aminomethyl)-2'-chloro-N-(dicyclopropylmethyl)-4'-fluoro-[1,1'-biphenyl]-3-carboxamide (0.06 g, 0.16 mmol), pyridine (3 mL) and 2-methylthio-2-imidazoline hydroiodide (0.04 g, 0.17 mmol). LCMS: 98% 254 nm R$_T$=0.81 min, MS (ES) 441 (M+H).

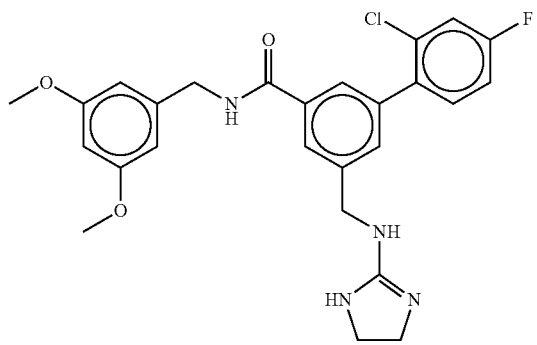

Example 3

2'-chloro-5-(((4,5-dihydro-1H-imidazol-2-yl)amino) methyl)-N-(3,5-dimethoxybenzyl)-4'-fluoro-[1,1'-biphenyl]-3-carboxamide

Step A. Preparation of 5-(aminomethyl)-2'-chloro-N-(3,5-dimethoxybenzyl)-4'-fluoro-[1,1'-biphenyl]-3-carboxamide The title compound was prepared following the procedure described in Example 1, Step C using methyl 5-(((tert-butoxycarbonyl)amino)methyl)-2'-chloro-4'-fluoro-[1,1'-biphenyl]-3-carboxylate and (3,5-dimethoxyphenyl)methanamine.

Step B. Example 3

The title compound (0.01 g, 15%) was prepared following the procedure described in Example 1, Step D using 5-(aminomethyl)-2'-chloro-N-(3,5-dimethoxybenzyl)-4'-fluoro-[1,1'-biphenyl]-3-carboxamide (0.07 g, 0.16 mmol), pyridine (3 mL) and 2-methylthio-2-imidazoline hydroiodide (0.04 g, 0.17 mmol). LCMS: 98% 254 nm $R_T$=0.79 min, MS (ES) 497 (M+H).

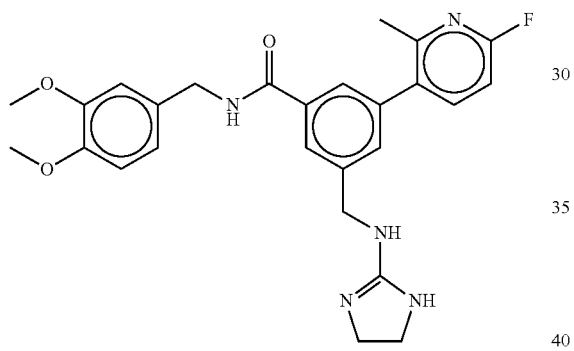

Example 4

3-(((4,5-Dihydro-1H-imidazol-2-yl)amino)methyl)-N-(3,4-dimethoxybenzyl)-5-(6-fluoro-2-methylpyridin-3-yl)benzamide

Step A. Preparation of methyl 3-((((tert-butoxycarbonyl)amino)methyl)-5-(6-fluoro-2-methylpyridin-3-yl)benzoate The title compound was prepared following the procedure described in Example 1, Step B using methyl 3-bromo-5-(((tert-butoxycarbonyl)amino)methyl)benzoate and (6-fluoro-2-methylpyridin-3-yl)boronic acid.

Step B. Preparation of 3-(aminomethyl)-N-(3,4-dimethoxybenzyl)-5-(6-fluoro-2-methylpyridin-3-yl)benzamide The title compound was prepared following the procedure described in Example 1, Step C using methyl 3-((((tert-butoxycarbonyl)amino)methyl)-5-(6-fluoro-2-methylpyridin-3-yl)benzoate (0.14 mmol), HATU (0.06 g, 0.14 mmol), DIEA ((0.06 mL, 0.35 mmol) and (3,4-dimethoxyphenyl)methanamine (0.03 g, 0.15 mmol).

Step C. Example 4

The title compound (0.03 g, 40%) was prepared following the procedure described in Example 1, Step D using 3-(aminomethyl)-N-(3,4-dimethoxybenzyl)-5-(6-fluoro-2-methylpyridin-3-yl)benzamide (0.14 mmol), pyridine (3 mL) and 2-methylthio-2-imidazoline hydroiodide (0.04 g, 0.17 mmol). $^1$H NMR (400 MHz, $d_6$ DMSO) δ8.9 (t, 1H, J=5.8 Hz), 8.5 (broad s, 2H), 7.8 (m, 2H), 7.4 (s, 1H), 7.1 (d, 1H, J=8.5 Hz), 6.9 (d, 1H, J=1.8 Hz), 6.8 (m, 3H), 4.4 (s, 2H), 4.3 (d, 2H, J=6.6 Hz), 3.7 (S, 3H), 3.6 (s, 3H), 3.5 (s, 4H), 2.3 (s, 3H). LC=98% MS=478 (M+1).; LCMS: 98% 254 nm, MS (ES) 478 (M+H).

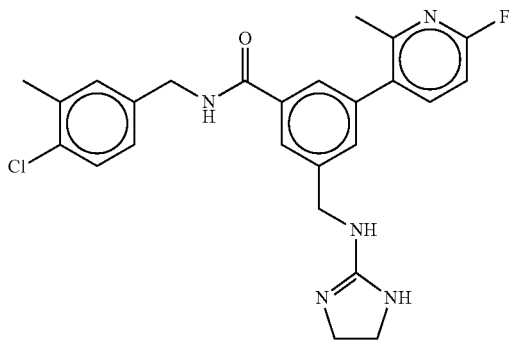

Example 5

N-(4-chloro-3-methylbenzyl)-3-(((4,5-dihydro-1H-imidazol-2-yl)amino)methyl)-5-(6-fluoro-2-methyl-pyridin-3-yl)benzamide

Step A. Preparation of 3-(aminomethyl)-N-(4-chloro-3-methylbenzyl)-5-(6-fluoro-2-methylpyridin-3-yl)benzamide The title compound was prepared following the procedure described in Example 1, Step C using methyl 3-((((tert-butoxycarbonyl)amino)methyl)-5-(6-fluoro-2-methylpyridin-3-yl)benzoate (0.14 mmol), HATU (0.06 g, 0.14 mmol), DIEA ((0.06 mL, 0.35 mmol) and (4-chloro-3-methylphenyl)methanamine (0.03 g, 0.15 mmol).

Step B. Example 5

The title compound (0.03 g, 47%) was prepared following the procedure described in Example 1, Step D using 3-(aminomethyl)-N-(4-chloro-3-methylbenzyl)-5-(6-fluoro-2-methylpyridin-3-yl)benzamide (0.05 g, 0.14 mmol), pyridine (3 mL) and 2-methylthio-2-imidazoline hydroiodide (0.04 g, 0.17 mmol). LCMS: 94% 254 nm $R_T$=0.96 min, MS (ES) 466 (M+H).

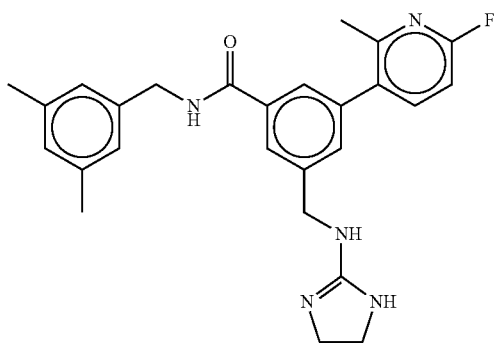

Example 6

3-(((4,5-Dihydro-1H-imidazol-2-yl)amino)methyl)-N-(3,5-dimethylbenzyl)-5-(6-fluoro-2-methylpyridin-3-yl)benzamide

Step A. Preparation of 3-(aminomethyl)-N-(3,5-dimethylbenzyl)-5-(6-fluoro-2-methylpyridin-3-yl)benzamide The title compound was prepared following the procedure described in Example 1, Step C using 3-(((tert-butoxycarbonyl)amino)methyl)-5-(6-fluoro-2-methylpyridin-3-yl)benzoic acid (0.05 g, 0.14 mmol), HATU (0.06 g, 0.14 mmol), DIEA ((0.06 mL, 0.35 mmol), and (3,4-dimethoxyphenyl)methanamine (0.02 g, 0.15 mmol)

Step B. Example 6

The title compound (0.04 g, 63%) was prepared following the procedure described in Example 1, Step D using 3-(aminomethyl)-N-(3,5-dimethylbenzyl)-5-(6-fluoro-2-methylpyridin-3-yl)benzamide (0.14 mmol), pyridine (3 mL) and 2-methylthio-2-imidazoline hydroiodide (0.04 g, 0.17 mmol). $^1$H NMR (400 MHz, d$_6$ DMSO) δ 9.1 (t, 1H, J=5.8 Hz), 8.6 broad s, 2H) 7.9 (s, 1H), 7.8 (m, 2H), 7.5 (s, 1H), 7.1 (d, 1H, J=8.2 Hz), 6.9 (s, 2H), 6.1 (s, 1H), 4.5 (s, 2H), 4.4 (d, 2H, J=4.6 Hz) 3.6 (s, 4H), 2.4 (s, 3H), 2.2 (s, 6H); LCMS: 98% 254 nm, MS (ES) 446 (M+H).

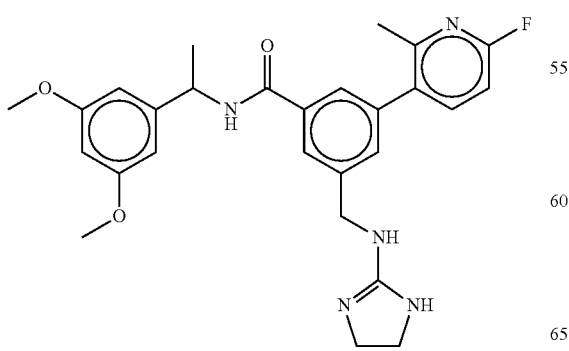

Example 7

3-(((4,5-Dihydro-1H-imidazol-2-yl)amino)methyl)-N-(1-(3,5-dimethoxyphenyl)ethyl)-5-(6-fluoro-2-methylpyridin-3-yl)benzamide

Step A. Preparation of 3-(aminomethyl)-N-(1-(3,5-dimethoxyphenyl)ethyl)-5-(6-fluoro-2-methylpyridin-3-yl)benzamide The title compound was prepared following the procedure described in Example 1, Step C using 3-(((tert-butoxycarbonyl)amino)methyl)-5-(6-fluoro-2-methylpyridin-3-yl) benzoic acid (0.05 g, 0.14 mmol), HATU (0.06 g, 0.14 mmol), DIEA ((0.06 mL, 0.35 mmol), and 1-(3,5-dimethoxyphenyl)ethan-1-amine (0.03 g, 0.15 mmol).

Step B. Example 7

The title compound (0.04 g, 56%) was prepared following the procedure described in Example 1, Step D using 3-(aminomethyl)-N-(1-(3,5-dimethoxyphenyl)ethyl)-5-(6-fluoro-2-methylpyridin-3-yl)benzamide (0.14 mmol) and 2-methylthio-2-imidazoline hydroiodide (0.04 g, 0.17 mmol). $^1$H NMR (400 MHz, d$_6$ DMSO) δ8.8 (d, 1H, J=7.0 Hz), 7.9 (m, 3H), 7.5 (s, 1H), 7.1 (d, 1H, J=8.8 Hz), 6.5 (d, 2H, i=2.0 Hz), 6.4 (t, 1H, J=2.1 Hz), 5.1 (m, 1H), 4.5 (s, 2H), 3.7 (s, 6H), 2.4 (s, 3H), 1.5 (d, 3H, J=6.8 Hz); LCMS: 98% 254 nm R$_T$=0.81 min, MS (ES) 492 (M+H).

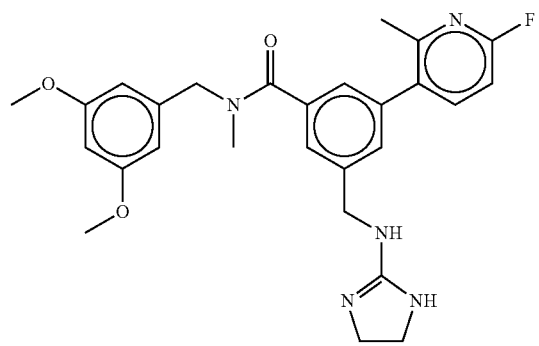

Example 8

3-(((4,5-Dihydro-1H-imidazol-2-yl)amino)methyl)-N-(3,5-dimethoxybenzyl)-5-(6-fluoro-2-methylpyridin-3-yl)-N-methylbenzamide

Step A. Preparation of 3-(aminomethyl)-N-(3,5-dimethoxybenzyl)-5-(6-fluoro-2-methylpyridin-3-yl)-N-methylbenzamide The title compound was prepared following the procedure described in Example 1, Step C using 3-(((tert-butoxycarbonyl)amino)methyl)-5-(6-fluoro-2-methylpyridin-3-yl) benzoic acid (0.05 g, 0.14 mmol), HATU (0.06 g, 0.14 mmol), DIEA ((0.06 mL, 0.35 mmol), and 1-(3,5-dimethoxyphenyl)-N-methylmethanamine (0.03 g, 0.15 mmol).

Step B. Example 8

The title compound (0.03 g, 44%) was prepared following the procedure described in Example 1, Step D using 3-(aminomethyl)-N-(3,5-dimethoxybenzyl)-5-(6-fluoro-2-methylpyridin-3-yl)-N-methylbenzamide TFA salt (0.07 g, 0.14 mmol), pyridine (3 mL) and 2-methylthio-2-imidazoline hydroiodide (0.07 g, 0.27 mmol). LCMS: 98% 254 nm $R_T$=0.89 min, MS (ES) 492 (M+H).

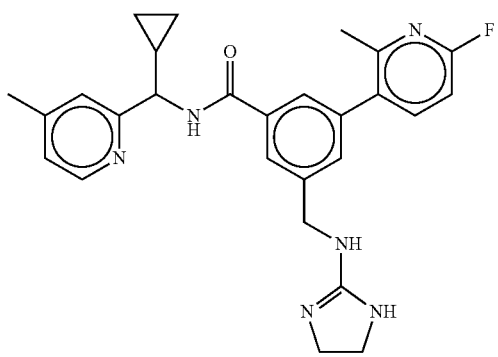

Example 9

N-(Cyclopropyl(4-methylpyridin-2-yl)methyl)-3-(((4,5-dihydro-1H-imidazol-2-yl)amino)methyl)-5-(6-fluoro-2-methylpyridin-3-yl)benzamide Step A. Preparation of 3-(aminomethyl)-N-(cyclopropyl(4-methylpyridin-2-yl)methyl)-5-(6-fluoro-2-methylpyridin-3-yl)benzamide The title compound was prepared following the procedure described in Example 1, Step C using 3-(((tert-butoxycarbonyl)amino)methyl)-5-(6-fluoro-2-methylpyridin-3-yl)benzoic acid (0.05 g, 0.14 mmol), HATU (0.06 g, 0.14 mmol), DIEA ((0.06 mL, 0.35 mmol), and cyclopropyl(4-methylpyridin-2-yl)methanamine (0.15 mmol).

Step B. Example 9

The title compound (0.03 g, 49%) was prepared following the procedure described in Example 1, Step D 3-(aminomethyl)-N-(cyclopropyl(4-methylpyridin-2-yl)methyl)-5-(6-fluoro-2-methylpyridin-3-yl)benzamide TFA salt (0.07 g, 0.14 mmol), pyridine (3 mL) and 2-methylthio-2-imidazoline hydroiodide (0.05 g, 0.20 mmol) afforded the title compound. LCMS: 98% 254 nm, MS (ES) 473 (M+H).

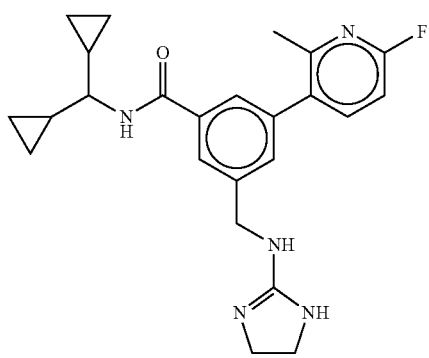

Example 10

N-(dicyclopropylmethyl)-3-(((4,5-dihydro-1H-imidazol-2-yl)amino)methyl)-5-(6-fluoro-2-methylpyridin-3-yl)benzamide Step A. Preparation of 3-(aminomethyl)-N-(dicyclopropylmethyl)-5-(6-fluoro-2-methylpyridin-3-yl)benzamide The title compound was prepared following the procedure described in Example 1, Step C using methyl 5-(((tert-butoxycarbonyl)amino)methyl)-2'-chloro-4'-fluoro-[1,1'-biphenyl]-3-carboxylate and dicyclopropylmethanamine.

Step B. Example 10

The title compound (0.01 g, 10%) was prepared following the procedure described in Example 1, Step D using 3-(aminomethyl)-N-(dicyclopropylmethyl)-5-(6-fluoro-2-methylpyridin-3-yl)benzamide TFA salt (0.06 g, 0.14 mmol), pyridine (3 mL) and 2-methylthio-2-imidazoline hydroiodide (0.07 g, 0.27 mmol). LCMS: 98% 254 nm $R_T$=0.90 min, MS (ES) 422 (M+H).

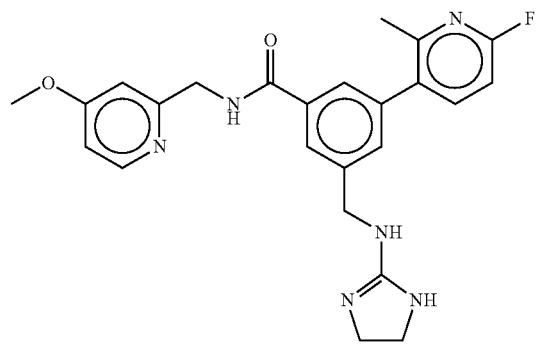

Example 11

3-(((4,5-Dihydro-1H-imidazol-2-yl)amino)methyl)-5-(6-fluoro-2-methylpyridin-3-yl)-N-((4-methoxypyridin-2-yl)methyl)benzamide Step A. Preparation of 3-(aminomethyl)-5-(6-fluoro-2-methylpyridin-3-yl)-N-((4-methoxypyridin-2-yl)methyl)benzamide The title compound was prepared following the procedure described in Example 1, Step C using methyl 5-(((tert-butoxycarbonyl)amino)methyl)-2'-chloro-4'-fluoro-[1,1'-biphenyl]-3-carboxylate and (4-methoxypyridin-2-yl)methanamine.

Step B. Example 11

The title compound (0.02 g, 31%) was prepared following the procedure described in Example 1, Step D using 3-(aminomethyl)-N-(dicyclopropylmethyl)-5-(6-fluoro-2-methylpyridin-3-yl)benzamide TFA salt (0.06 g, 0.14 mmol), pyridine (3 mL) and 2-methylthio-2-imidazoline hydroiodide (0.07 g, 0.27 mmol). LCMS: 98% 254 nm $R_T$=0.65 min, MS (ES) 449 (M+H).

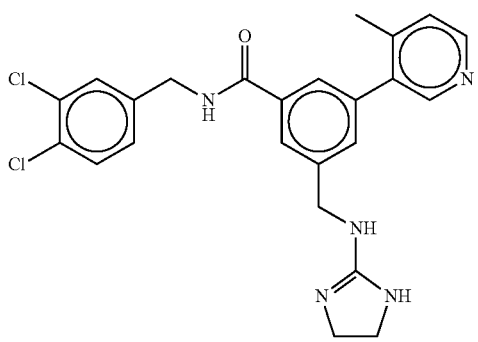

Example 12

N-(3,4-dichlorobenzyl)-3-(((4,5-dihydro-1H-imidazol-2-yl)amino)methyl)-5-(4-methylpyridin-3-yl)benzamide Step A. Preparation of methyl 3-(hydroxymethyl)-5-(4-methylpyridin-3-yl)benzoate 4-Methylpyridine-3-boronic acid (2.10 g, 15.3 mmol), Pd(PPh$_3$)$_4$ (1.18 g, 1.02 mmol) and K$_2$CO$_3$ (3.52 g, 25.5 mmol) were added to a solution of methyl 3-bromo-5-(hydroxymethyl)benzoate (2.50 g, 10.2 mmol) in dioxane/water (51.0 mL, 3:1) under Ar atmosphere (the reaction mixture was degassed using Ar gas). The reaction mixture was stirred at 85° C. for 5 h. The reaction mixture was extracted with CH$_2$Cl$_2$ (3×15 mL). The combined organic layers were dried (MgSO$_4$), filtered and concentrated. The residue was purified by flash chromatography (Combi-flash Rf, DCM/MeOH=0-2% gradient) to provide the title compound (2.20 g, 84% yield). LCMS: R$_T$=0.608 min, MS (ES) 258.1 (M+H).

Step B. Preparation of methyl 3-(azidomethyl)-5-(4-methylpyridin-3-yl)benzoate

Et$_3$N (325 µL, 2.33 mmol) and MsCl (181 µL, 2.33 mmol) were added to a solution of methyl 3-(hydroxymethyl)-5-(4-methylpyridin-3-yl)benzoate (500 mg, 1.94 mmol) in CH$_2$Cl$_2$ (9.7 mL) at 0° C. The reaction mixture was stirred at room temperature for 30 min (monitored by LC/MS). The solvent was removed under reduced pressure. The residue was dissolved in DMF (9.7 mL) and NaN$_3$ (303 mg, 4.66 mmol) was added. The reaction mixture was stirred at room temperature for 5 h. The reaction was quenched with water. The reaction mixture was extracted with EtOAc (3×15 mL). The combined organic layers were washed with water (3×10 mL) and dried (MgSO$_4$), filtered and concentrated. The crude mixture (600 mg) was used for next step without further purification. LCMS: R$_T$=0.769 min, MS (ES) 283.1 (M+H).

Step C. Preparation of methyl 3-(aminomethyl)-5-(4-methylpyridin-3-yl)benzoate

Methyl 3-(azidomethyl)-5-(4-methylpyridin-3-yl)benzoate (600 mg, 2.13 mmol) was dissolved in EtOH (21.3 mL) and the mixture was degassed using Ar. Catalytic amount of Raney nickel was added and the flask was sealed. The reaction was then purged with vacuum/H$_2$ gas. The reaction mixture was stirred at room temperature under H$_2$ gas (1 atm). After 15 h, the reaction was diluted with EtOH and CH$_2$Cl$_2$ and filtered using a syringe filter. The solution was concentrated to provide the title compound. The crude mixture (400 mg) was used for next step without further purification. LCMS: R$_T$=0.412 min, MS (ES) 257.1 (M+H).

Step D. Preparation of methyl 3-(((tert-butoxycarbonyl)amino)methyl)-5-(4-methylpyridin-3-yl)benzoate Et$_3$N (45.7 µL, 0.330 mmol) and di-tert-butyl dicarbonate (75.3 µL, 0.330 mmol) were added to a solution of methyl 3-(aminomethyl)-5-(4-methylpyridin-3-yl)benzoate (70.0 mg, 0.270 mmol) in CH$_2$Cl$_2$ (1.1 mL) at 0° C. The reaction mixture was stirred at room temperature. After 2 h, the reaction was quenched with water and extracted with CH$_2$Cl$_2$ (3×10 mL). The combined organic layers were dried (MgSO$_4$), filtered and concentrated. The residue was purified by flash chromatography (Combi-flash Rf, DCM/MeOH=0-20% gradient) to provide the title compound (50.0 mg, 51% yield). LCMS: R$_T$=0.840 min, MS (ES) 357.2 (M+H).

Step E. Preparation of 3-(((tert-butoxycarbonyl)amino)methyl)-5-(4-methylpyridin-3-yl)benzoic Acid 2 M LiOH (365 µL, 0.730 mmol) was added to a solution of methyl 3-(((tert-butoxycarbonyl)amino)methyl)-5-(4-methylpyridin-3-yl)benzoate (130 mg, 0.360 mmol) in THF/MeOH/H$_2$O (1.5 mL, 4:1:1). The reaction mixture was stirred at room temperature for 2 h. The reaction was quenched with 1 M HCl solution (pH 4, solid was formed). The mixture was filtered (washed with cold water) to obtain the title compound (50.0 mg, 40% yield). LCMS: RT=0.757 min, MS (ES) 343.1 (M+H).

Step F. Preparation of tert-butyl (3-((3,4-dichlorobenzyl)carbamoyl)-5-(4-methylpyridin-3-yl)benzyl)carbamate HATU (122 mg, 0.320 mmol), 3,4-dichlorobenzylamine (46.7 µL, 0.350 mmol) and 4-methylmorpholine (96.3 µL, 0.880 mmol) were added to a solution of 3-(((tert-butoxycarbonyl)amino)methyl)-5-(4-methylpyridin-3-yl)benzoic acid (100 mg, 0.290 mmol) in DMF (1.2 mL). The reaction mixture was stirred at room temperature for 1 h. The reaction mixture was diluted EtOAc and washed with water. The organic layer was washed with sat. aq. NH$_4$Cl and dried (MgSO$_4$), filtered and concentrated. The residue was purified by flash chromatography (Combi-flash Rf, DCM/MeOH=0-4% gradient) to provide the title compound (50.0 mg, 34% yield). LCMS: R$_T$=0.995 min, MS (ES) 500.0 (M+H).

Step G. Preparation of 3-(aminomethyl)-N-(3,4-dichlorobenzyl)-5-(4-methylpyridin-3-yl)benzamide TFA (500 µL) was added to a solution of tert-butyl (3-((3,4-dichlorobenzyl)carbamoyl)-5-(4-methylpyridin-3-yl)benzyl)carbamate (71.0 mg, 0.10 mmol) in CH$_2$Cl$_2$ (1 mL) at 0° C. The reaction mixture was stirred at 0° C. for 30 min. The reaction mixture was concentrated under reduced pressure. The residue was dissolved in EtOAc (2 mL) and sat. aq. NaHCO$_3$ was added. The organic layer was dried (MgSO$_4$), filtered and concentrated. The crude mixture (40.0 mg) was used for the next step without further purification. LCMS: $R_T$=0.784 min, MS (ES) 400.0 (M+H).

Step H. Example 12

2-Methylthio-2-imidazoline hydroiodide (30.5 mg, 0.120 mmol) was added to a solution of 3-(aminomethyl)-N-(3,4-dichlorobenzyl)-5-(4-methylpyridin-3-yl)benzamide (40.0 mg, 0.100 mmol) in pyridine (1.0 mL). The reaction mixture was stirred at 125° C. for 30 min using microwave. The reaction mixture was concentrated using air (kept inside hood). The DMSO solution was purified by reverse phase HPLC (Phenomenex Gemini C18, $H_2O/CH_3CN$ gradient from 5-40% $CH_3CN$, 0.1% TFA) to yield the title compound (29.0 mg, 62% yield). LCMS: $R_T$=0.840 min, MS (ES) 468.0 (M+H).

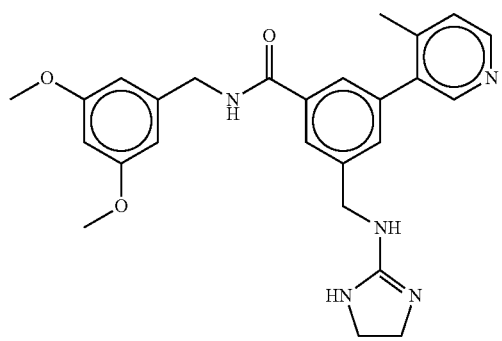

Example 13

3-(((4,5-dihydro-1H-imidazol-2-yl)amino)methyl)-N-(3,5-dimethoxybenzyl)-5-(4-methylpyridin-3-yl)benzamide Step A. Preparation of tert-butyl (3-((3,5-dimethoxybenzyl)carbamoyl)-5-(4-methylpyridin-3-yl)benzyl)carbamate The title compound (71.0 mg, 50% yield) was prepared from the procedure described in Example 12, Step F using 3,5-dimethoxybenzylamine (51.3 mg, 0.310 mmol) and 4-methylmorpholine (96.3 μL, 0.880 mmol). LCMS: $R_T$=0.929 min, MS (ES) 492.1 (M+H).

Step B. Preparation of 3-(aminomethyl)-N-(3,5-dimethoxybenzyl)-5-(4-methylpyridin-3-yl)benzamide The title compound (60.0 mg, crude mixture) was prepared from the procedure described in Example 12, Step G using tert-butyl (3-((3,5-dimethoxybenzyl)carbamoyl)-5-(4-methylpyridin-3-yl)benzyl)carbamate (71.0 mg, 0.14 mmol). LCMS: $R_T$=0.716 min, MS (ES) 392.1 (M+H).

Step C. Example 13

The title compound (53.5 mg, 76% yield) was prepared from the procedure described in Example 12, Step H using 3-(aminomethyl)-N-(3,5-dimethoxybenzyl)-5-(4-methylpyridin-3-yl)benzamide (40.0 mg, 0.100 mmol). LCMS: $R_T$=0.715 min, MS (ES) 460.0 (M+H).

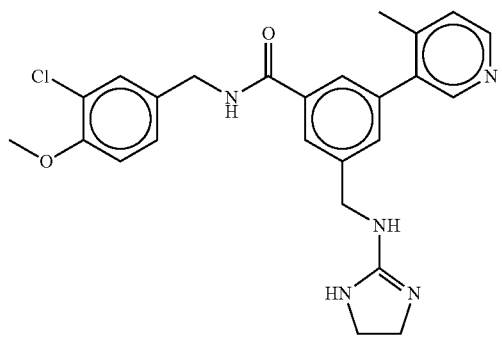

Example 14

N-(3-chloro-4-methoxybenzyl)-3-(((4,5-dihydro-1H-imidazol-2-yl)amino)methyl)-5-(4-methylpyridin-3-yl)benzamide Step A. Preparation of tert-butyl (3-((3-chloro-4-methoxybenzyl)carbamoyl)-5-(4-methylpyridin-3-yl)benzyl)carbamate The title compound (65.0 mg, 45% yield) was prepared from the procedure described in Example 12, Step F using 3-chloro-4-methoxybenzylamine (52.6 mg, 0.310 mmol). LCMS: $R_T$=0.938 min, MS (ES) 496.1 (M+H)

Step B. Preparation of 3-(aminomethyl)-N-(3-chloro-4-methoxybenzyl)-5-(4-methylpyridin-3-yl)benzamide The title compound (60.0 mg, crude mixture) was prepared from the procedure described in Example 12, Step G using tert-butyl (3-((3-chloro-4-methoxybenzyl)carbamoyl)-5-(4-methylpyridin-3-yl)benzyl)carbamate (65.0 mg, 0.14 mmol). LCMS: $R_T$=0.743 min, MS (ES) 396.1 (M+H).

Step C. Example 14

The title compound (50.4 mg, 72% yield) was prepared from the procedure described in Example 12, Step H using 3-(aminomethyl)-N-(3-chloro-4-methoxybenzyl)-5-(4-methylpyridin-3-yl)benzamide (60.0 mg, 0.150 mmol). LCMS: $R_T$=0.756 min, MS (ES) 464.1 (M+H).

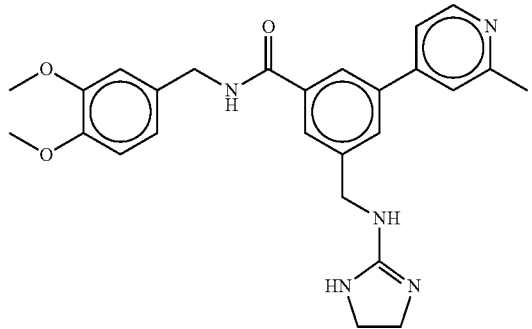

Example 15

3-(((4,5-dihydro-1H-imidazol-2-yl)amino)methyl)-N-(3,4-dimethoxybenzyl)-5-(2-methylpyridin-4-yl)benzamide Step A. Preparation of tert-butyl (3-((3,4-dimethoxybenzyl)carbamoyl)-5-(2-methylpyridin-4-yl)benzyl)carbamate The title compound (95.0 mg, 75% yield) was prepared from the procedure described in Example 12, Step F using 3,5-dimethoxybenzylamine (47.0 mg, 0.280 mmol). LCMS: $R_T$=0.872 min, MS (ES) 492.1 (M+H)

Step B. Preparation of 3-(aminomethyl)-N-(3,4-dimethoxybenzyl)-5-(2-methylpyridin-4-yl)benzamide The title compound (65.0 mg, crude mixture) was prepared from the procedure described in Example 12, Step G using tert-butyl (3-((3,4-dimethoxybenzyl)carbamoyl)-5-(2-methylpyridin-4-yl)benzyl)carbamate (95.0 mg, 0.19 mmol). LCMS: $R_T$=0.634 min, MS (ES) 392.2 (M+H).

Step C. Preparation of 3-(((4,5-dihydro-1H-imidazol-2-yl)amino)methyl)-N-(3,4-dimethoxybenzyl)-5-(2-methylpyridin-4-yl)benzamide The title compound (39.0 mg, 75% yield) was prepared from the procedure described in Example 12, Step H using 3-(aminomethyl)-N-(3,4-dimethoxybenzyl)-5-(2-methylpyridin-4-yl)benzamide (44.0 mg, 0.110 mmol). LCMS: $R_T$=0.675 min, MS (ES) 460.1 (M+H).

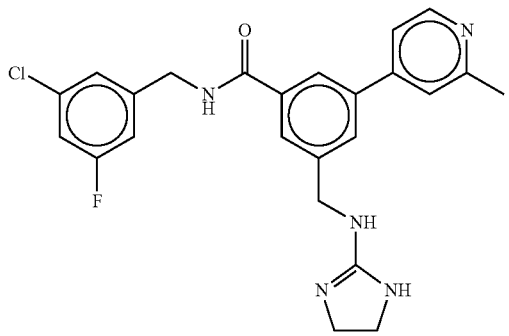

Example 16

N-(3-chloro-5-fluorobenzyl)-3-(((4,5-dihydro-1H-imidazol-2-yl)amino)methyl)-5-(2-methylpyridin-4-yl)benzamide Step A. Preparation of tert-butyl (3-((3-chloro-5-fluorobenzyl)carbamoyl)-5-(2-methylpyridin-4-yl)benzyl)carbamate The title compound (172.0 mg, 80% yield) was prepared from the procedure described in Example 12, Step F using 3-chloro-5-fluorobenzylamine (75.0 mg, 0.47 mmol). LCMS: $R_T$=0.965 min, MS (ES) 484.1 (M+H)

Step B. Preparation of 3-(aminomethyl)-N-(3-chloro-5-fluorobenzyl)-5-(2-methylpyridin-4-yl)benzamide The title compound (85.0 mg, crude mixture) was prepared from the procedure described in Example 12, Step G using tert-butyl (3-((3-chloro-5-fluorobenzyl)carbamoyl)-5-(2-methylpyridin-4-yl)benzyl)carbamate (154.0 mg, 0.32 mmol). LCMS: $R_T$=0.737 min, MS (ES) 384.1 (M+H).

Step C. Preparation of N-(3-chloro-5-fluorobenzyl)-3-(((4,5-dihydro-1H-imidazol-2-yl)amino)methyl)-5-(2-methylpyridin-4-yl)benzamide The title compound (56.0 mg, 93% yield) was prepared from the procedure described in Example 12, Step H using 3-(aminomethyl)-N-(3-chloro-5-fluorobenzyl)-5-(2-methylpyridin-4-yl)benzamide (51.0 mg, 0.130 mmol). LCMS: $R_T$=0.766 min, MS (ES) 452.1 (M+H).

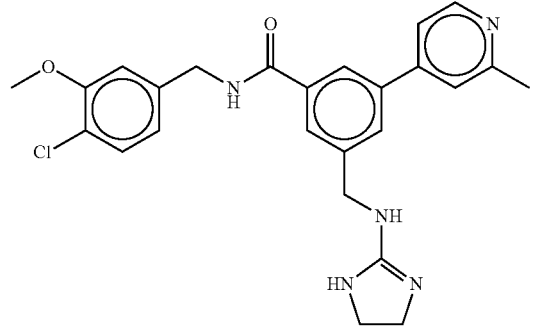

Example 17

N-(4-chloro-3-methoxybenzyl)-3-(((4,5-dihydro-1H-imidazol-2-yl)amino)methyl)-5-(2-methylpyridin-4-yl)benzamide Step A. Preparation of tert-butyl (3-((4-chloro-3-methoxybenzyl)carbamoyl)-5-(2-methylpyridin-4-yl)benzyl)carbamate The title compound (82.0 mg, 75% yield) was prepared from the procedure described in Example 12, Step F using 4-chloro-3-methoxybenzylamine (39.0 mg, 0.230 mmol). LCMS: $R_T$=0.960 min, MS (ES) 496.1 (M+H)

Step B. Preparation of 3-(aminomethyl)-N-(4-chloro-3-methoxybenzyl)-5-(2-methylpyridin-4-yl)benzamide The title compound (65.0 mg, crude mixture) was prepared from the procedure described in Example 12, Step G using tert-butyl (3-((4-chloro-3-methoxybenzyl)carbamoyl)-5-(2-methylpyridin-4-yl)benzyl)carbamate (81.0 mg, 0.16 mmol). LCMS: $R_T$=0.729 min, MS (ES) 396.1 (M+H).

Step C. Preparation of N-(4-chloro-3-methoxybenzyl)-3-(((4,5-dihydro-1H-imidazol-2-yl)amino)methyl)-5-(2-methylpyridin-4-yl)benzamide The title compound (65.0 mg, 86% yield) was prepared from the procedure described in Example 12, Step H using 3-(aminomethyl)-N-(4-chloro-3-methoxybenzyl)-5-(2-methylpyridin-4-yl)benzamide (65.0 mg, 0.160 mmol). LCMS: $R_T$=0.787 min, MS (ES) 464.1 (M+H).

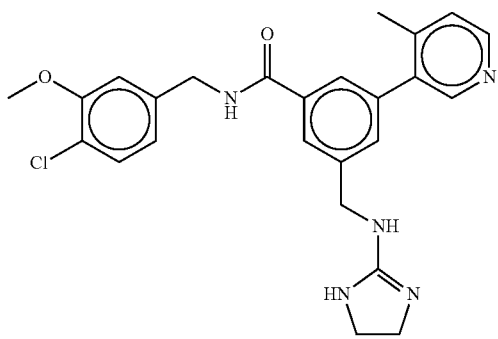

Example 18

N-(4-Chloro-3-methoxybenzyl)-3-(((4,5-dihydro-1H-imidazol-2-yl)amino)methyl)-5-(4-methylpyridin-3-yl)benzamide Step A. Preparation of tert-butyl (3-((4-chloro-3-methoxybenzyl)carbamoyl)-5-(4-methylpyridin-3-yl)benzyl)carbamate The title compound (85.0 mg, 84% yield) was prepared from the procedure described in Example 12, Step F using 4-chloro-3-methoxybenzylamine (36.8 mg, 0.210 mmol). LCMS: $R_T$=0.969 min, MS (ES) 496.1 (M+H).

Step B. Preparation of 3-(aminomethyl)-N-(4-chloro-3-methoxybenzyl)-5-(4-methylpyridin-3-yl)benzamide The title compound (65.0 mg, crude mixture) was prepared from the procedure described in Example 12, Step G using tert-butyl (3-((4-chloro-3-methoxybenzyl)carbamoyl)-5-(4-methylpyridin-3-yl)benzyl)carbamate (85.0 mg, 0.170 mmol). LCMS: $R_T$=0.747 min, MS (ES) 396.1 (M+H).

Step C. Example 18

The title compound (60.0 mg, 79% yield) was prepared from the procedure described in Example 12, Step H using 3-(aminomethyl)-N-(4-chloro-3-methoxybenzyl)-5-(4-methylpyridin-3-yl)benzamide (65.0 mg, 0.160 mmol). LCMS: $R_T$=0.775 min, MS (ES) 464.1 (M+H).

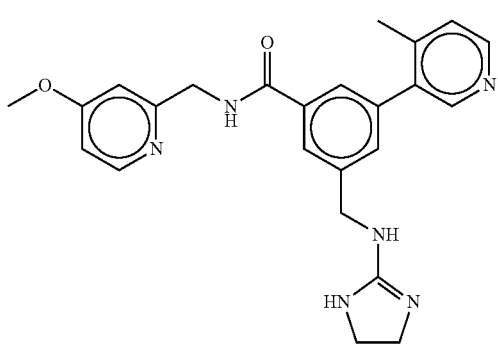

Example 19

3-(((4,5-Dihydro-1H-imidazol-2-yl)amino)methyl)-N-((4-methoxypyridin-2-yl)methyl)-5-(4-methylpyridin-3-yl)benzamide Step A. Preparation of tert-butyl (3-(((4-methoxypyridin-2-yl)methyl)carbamoyl)-5-(4-methylpyridin-3-yl)benzyl)carbamate The title compound (90.0 mg, 95% yield) was prepared from the procedure described in Example 12, Step F using (4-methoxypyridin-2-yl)methanamine (29.7 mg, 0.210 mmol). LCMS: $R_T$=0.771 min, MS (ES) 463.1 (M+H).

Step B. Preparation of 3-(aminomethyl)-N-((4-methoxypyridin-2-yl)methyl)-5-(4-methylpyridin-3-yl)benzamide The title compound (40.0 mg, crude mixture) was prepared from the procedure described in Example 12, Step G using tert-butyl (3-(((4-methoxypyridin-2-yl)methyl)carbamoyl)-5-(4-methylpyridin-3-yl)benzyl)carbamate (90.0 mg, 0.190 mmol). LCMS: $R_T$=0.209 min, MS (ES) 363.2 (M+H).

Step C. Example 19

The title compound (4.5 mg, 1% yield) was prepared from the procedure described in Example 12, Step H using 3-(aminomethyl)-N-((4-methoxypyridin-2-yl)methyl)-5-(4-methylpyridin-3-yl)benzamide (40.0 mg, 0.110 mmol). LCMS: $R_T$=0.138 min, MS (ES) 431.1 (M+H).

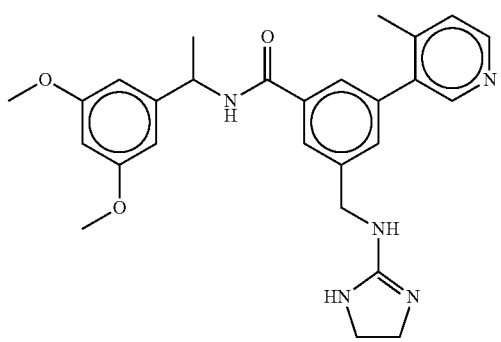

Example 20

3-(((4,5-dihydro-1H-imidazol-2-yl)amino)methyl)-N-(1-(3,5-dimethoxyphenyl)ethyl)-5-(4-methylpyridin-3-yl)benzamide Step A. Preparation of tert-butyl (3-((1-(3,5-dimethoxyphenyl)ethyl)carbamoyl)-5-(4-methylpyridin-3-yl)benzyl)carbamate The title compound (80.0 mg, 77% yield) was prepared from the procedure described in Example 12, Step F using 1-(3,5-dimethoxyphenyl)ethanamine (39.1 mg, 0.210 mmol). LCMS: $R_T$=0.971 min, MS (ES) 506.1 (M+H).

Step B. Preparation of 3-(aminomethyl)-N-(1-(3,5-dimethoxyphenyl)ethyl)-5-(4-methylpyridin-3-yl)benzamide The title compound (60.0 mg, crude mixture) was prepared from the procedure described in Example 12, Step G using tert-butyl (3-((1-(3,5-dimethoxyphenyl)ethyl)carbamoyl)-5-(4-methylpyridin-3-yl)benzyl)carbamate (80.0 mg, 0.160 mmol). LCMS: $R_T$=0.739 min, MS (ES) 406.1 (M+H).

Step C. Example 20

The title compound (60.0 mg, 85% yield) was prepared from the procedure described in Example 12, Step H using 3-(aminomethyl)-N-(1-(3,5-dimethoxyphenyl)ethyl)-5-(4-methylpyridin-3-yl)benzamide (60.0 mg, 0.150 mmol). LCMS: $R_T$=0.765 min, MS (ES) 474.2 (M+H).

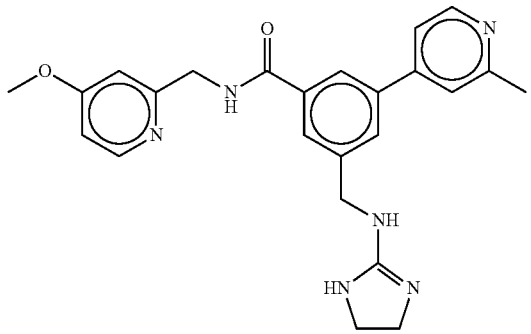

Example 21

3-(((4,5-Dihydro-1H-imidazol-2-yl)amino)methyl)-N-((4-methoxypyridin-2-yl)methyl)-5-(2-methyl-pyridin-4-yl)benzamide Step A. Preparation of tert-butyl (3-(((4-methoxy-pyridin-2-yl)methyl)carbamoyl)-5-(2-methylpyridin-4-yl)benzyl)carbamate The title compound (155.0 mg, 82% yield) was prepared from the procedure described in Example 12, Step F using (4-methoxypyridin-2-yl)-methylamine (60.0 mg, 0.430 mmol). LCMS: $R_T$=0.754 min, MS (ES) 463.2 (M+H)

Step B. Preparation of 3-(aminomethyl)-N-((4-methoxypyridin-2-yl)methyl)-5-(2-methylpyridin-4-yl)benzamide The title compound (115.0 mg, crude mixture) was prepared from the procedure described in Example 12, Step G using tert-butyl (3-(((4-methoxypyridin-2-yl)methyl)carbamoyl)-5-(2-methylpyridin-4-yl)benzyl)carbamate (155.0 mg, 0.34 mmol). LCMS: $R_T$=0.412 min, MS (ES) 363.1 (M+H).

Step C. Preparation of 3-(((4,5-Dihydro-1H-imidazol-2-yl)amino)methyl)-N-((4-methoxypyridin-2-yl)methyl)-5-(2-methylpyridin-4-yl)benzamide The title compound (49.0 mg, 65% yield) was prepared from the procedure described in Example 12, Step H using 3-(aminomethyl)-N-((4-methoxypyridin-2-yl)methyl)-5-(2-methylpyridin-4-yl)benzamide (63.0 mg, 0.170 mmol). LCMS: $R_T$=0.534 min, MS (ES) 431.2 (M+H).

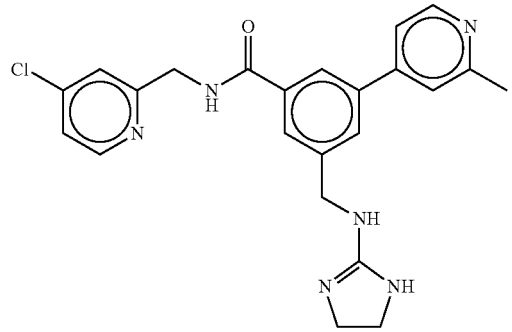

Example 22

N-((4-chloropyridin-2-yl)methyl)-3-(((4,5-dihydro-1H-imidazol-2-yl)amino)methyl)-5-(2-methylpyridin-4-yl)benzamide Step A. Preparation of tert-butyl (3-(((4-chloropyridin-2-yl)methyl)carbamoyl)-5-(2-methylpyridin-4-yl)benzyl)carbamate The title compound (151.0 mg, 73% yield) was prepared from the procedure described in Example 12, Step F using 4-chloro-2-pyridylmethylamine (67.0 mg, 0.470 mmol). LCMS: $R_T$=0.859 min, MS (ES) 467.1 (M+H).

Step B. Preparation of 3-(aminomethyl)-N-((4-chloropyridin-2-yl)methyl)-5-(2-methylpyridin-4-yl)benzamide The title compound (119.0 mg, crude mixture) was prepared from the procedure described in Example 12, Step G using tert-butyl (3-(((4-chloropyridin-2-yl)methyl)carbamoyl)-5-(2-methylpyridin-4-yl)benzyl)carbamate (151.0 mg, 0.32 mmol). LCMS: $R_T$=0.587 min, MS (ES) 367.1 (M+H).

Step C. Preparation of N-((4-chloropyridin-2-yl)methyl)-3-(((4,5-dihydro-1H-imidazol-2-yl)amino)methyl)-5-(2-methylpyridin-4-yl)benzamide The title compound (32.0 mg, 47% yield) was prepared from the procedure described in Example 12, Step H using 3-(aminomethyl)-N-((4-chloropyridin-2-yl)methyl)-5-(2-methylpyridin-4-yl)benzamide (57.0 mg, 0.160 mmol). LCMS: $R_T$=0.635 min, MS (ES) 435.1 (M+H).

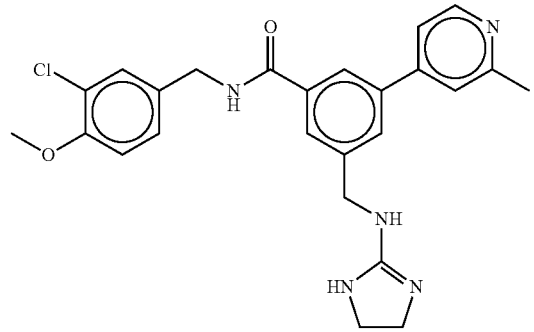

Example 23

N-(3-chloro-4-methoxybenzyl)-3-(((4,5-dihydro-1H-imidazol-2-yl)amino)methyl)-5-(2-methylpyridin-4-yl)benzamide

Step A. Preparation of tert-butyl (3-((3-chloro-4-methoxybenzyl)carbamoyl)-5-(2-methylpyridin-4-yl)benzyl)carbamate The title compound (169.0 mg, 78% yield) was prepared from the procedure described in Example 12, Step F using 3-chloro-4-methoxybenzylamine (79.0 mg, 0.460 mmol). LCMS: $R_T$=0.958 min, MS (ES) 496.1 (M+H).

Step B. Preparation of 3-(aminomethyl)-N-(3-chloro-4-methoxybenzyl)-5-(2-methylpyridin-4-yl)benzamide The title compound (134.0 mg, crude mixture) was prepared from the procedure described in Example 12, Step G using tert-butyl (3-((3-chloro-4-methoxybenzyl)carbamoyl)-5-(2-methylpyridin-4-yl)benzyl)carbamate (169.0 mg, 0.34 mmol). LCMS: $R_T$=0.727 min, MS (ES) 396.1 (M+H).

Step C. Preparation of N-(3-chloro-4-methoxybenzyl)-3-(((4,5-dihydro-1H-imidazol-2-yl)amino)methyl)-5-(2-methylpyridin-4-yl)benzamide The title compound (52.0 mg, 66% yield) was prepared from the procedure described in Example 12, Step H using 3-(aminomethyl)-N-(3-chloro-4-methoxybenzyl)-5-(2-methylpyridin-4-yl)benzamide (67.0 mg, 0.170 mmol). LCMS: $R_T$=0.780 min, MS (ES) 464.1 (M+H).

Example 24

N-(3-chloro-5-fluorobenzyl)-3-(((4,5-dihydro-1H-imidazol-2-yl)amino)methyl)-5-(4-methylpyridin-3-yl)benzamide

Step A. Preparation of tert-butyl (3-((3-chloro-5-fluorobenzyl)carbamoyl)-5-(4-methylpyridin-3-yl)benzyl)carbamate The title compound (65.0 mg, 58% yield) was prepared from the procedure described in Example 12, Step F using 4-chloro-3-methylbenzylamine (38.2 mg, 0.250 mmol). LCMS: $R_T$=0.993 min, MS (ES) 484.0 (M+H).

Step B. Preparation of 3-(aminomethyl)-N-(3-chloro-5-fluorobenzyl)-5-(4-methylpyridin-3-yl)benzamide The title compound (55.0 mg, crude mixture) was prepared from the procedure described in Example 12, Step G using tert-butyl (3-((3-chloro-5-fluorobenzyl)carbamoyl)-5-(4-methylpyridin-3-yl)benzyl)carbamate (65.0 mg, 0.130 mmol). LCMS: $R_T$=0.760 min, MS (ES) 384.1 (M+H).

Step C. Example 24

The title compound (50.0 mg, 77% yield) was prepared from the procedure described in Example 12, Step H using 3-(aminomethyl)-N-(3-chloro-5-fluorobenzyl)-5-(4-methylpyridin-3-yl)benzamide (55.0 mg, 0.140 mmol). LCMS: $R_T$=0.830 min, MS (ES) 452.2 (M+H). $^1$H NMR (400 MHz, DMSO-$d_6$) δ 9.23-9.19 (m, 1H), 8.81 (br s, 1H), 8.48 (d, J=4.9 Hz, 1H), 8.45 (s, 1H), 7.90 (d, J=8.9 Hz, 2H), 7.54 (s, 1H), 7.39 (d, J=5.0 Hz, 1H), 7.32 (d, J=8.7 Hz, 1H), 7.26-7.24 (m, 1H), 7.18-7.14 (m, 1H), 4.50-4.49 (m, 2H), 4.10-4.06 (m, 4H), 3.61 (s, 2H), 3.31 (s, 3H).

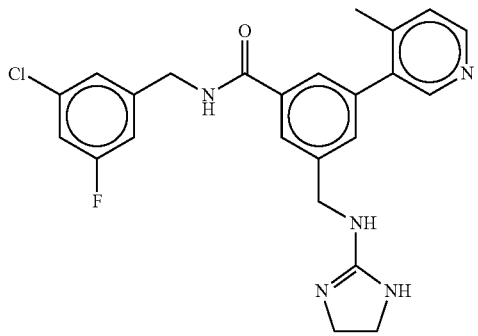

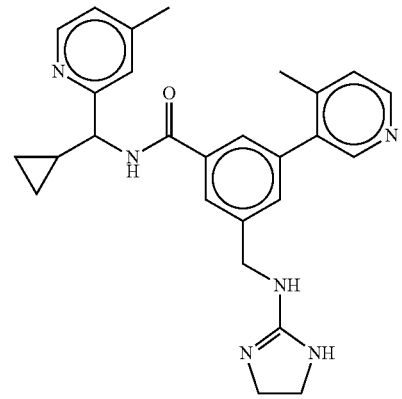

Example 25

N-(cyclopropyl(4-methylpyridin-2-yl)methyl)-3-(((4,5-dihydro-1H-imidazol-2-yl)amino)methyl)-5-(4-methylpyridin-3-yl)benzamide

Step A. Preparation of tert-butyl (3-((cyclopropyl(4-methylpyridin-2-yl)methyl)carbamoyl)-5-(4-methylpyridin-3-yl)benzyl)carbamate The title compound (100 mg, quant.) was prepared from the procedure described in Example 12, Step F using [cyclopropyl(4-methyl-2-pyridinyl)methyl]amine dihydrochloride (50.5 mg, 0.210 mmol). LCMS: $R_T$=0.805 min, MS (ES) 487.2 (M+H).

Step B. Preparation of 3-(aminomethyl)-N-(cyclopropyl(4-methylpyridin-2-yl)methyl)-5-(4-methylpyridin-3-yl)benzamide The title compound (72.0 mg, crude mixture) was prepared from the procedure described in Example 12, Step G using tert-butyl (3-((cyclopropyl(4-methylpyridin-2-yl)

methyl)carbamoyl)-5-(4-methylpyridin-3-yl)benzyl)carbamate (100 mg, 0.21 mmol). LCMS: $R_T$=0.582 min, MS (ES) 387.2 (M+H).

Step C. Example 25

The title compound (40.5 mg, 48% yield) was prepared from the procedure described in Example 12, Step H using 3-(aminomethyl)-N-(cyclopropyl(4-methylpyridin-2-yl)methyl)-5-(4-methylpyridin-3-yl)benzamide (72.0 mg, 0.190 mmol). LCMS: $R_T$=0.609 min, MS (ES) 455.2 (M+H).

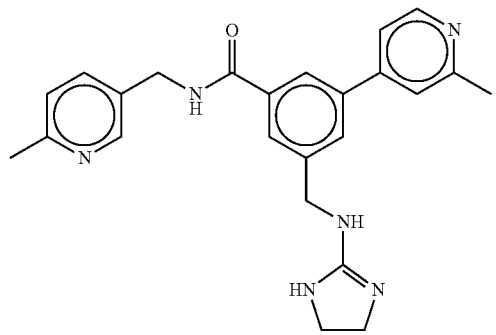

Example 26

3-(((4,5-dihydro-1H-imidazol-2-yl)amino)methyl)-N-((6-methylpyridin-3-yl)methyl)-5-(2-methylpyridin-4-yl)benzamide Step A. Preparation of tert-butyl (3-(((6-methylpyridin-3-yl)methyl)carbamoyl)-5-(2-methylpyridin-4-yl)benzyl)carbamate The title compound (143.0 mg, 76% yield) was prepared from the procedure described in Example 12, Step F using (6-methylpyridin-3-yl)-methanamine (54.0 mg, 0.420 mmol). LCMS: $R_T$=0.724 min, MS (ES) 447.2 (M+H).

Step B. Preparation of 3-(aminomethyl)-N-((6-methylpyridin-3-yl)methyl)-5-(2-methylpyridin-4-yl)benzamide The title compound (110.0 mg, crude mixture) was prepared from the procedure described in Example 12, Step G using tert-butyl (3-(((6-methylpyridin-3-yl)methyl)carbamoyl)-5-(2-methylpyridin-4-yl)benzyl)carbamate (143.0 mg, 0.32 mmol). LCMS: $R_T$=0.100 min, MS (ES) 347.2 (M+H).

Step C. Preparation of 3-(((4,5-dihydro-1H-imidazol-2-yl)amino)methyl)-N-((6-methylpyridin-3-yl)methyl)-5-(2-methylpyridin-4-yl)benzamide The title compound (23.0 mg, 35% yield) was prepared from the procedure described in Example 12, Step H using 3-(aminomethyl)-N-((6-methylpyridin-3-yl)methyl)-5-(2-methylpyridin-4-yl)benzamide (55.0 mg, 0.160 mmol). LCMS: $R_T$=0.098 min, MS (ES) 415.2 (M+H).

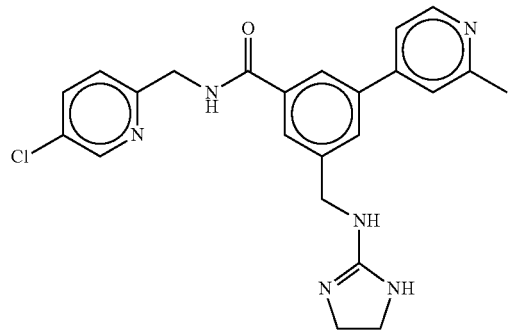

Example 27

N-((5-chloropyridin-2-yl)methyl)-3-(((4,5-dihydro-1H-imidazol-2-yl)amino)methyl)-5-(2-methylpyridin-4-yl)benzamide Step A. Preparation of tert-butyl (3-(((5-chloropyridin-2-yl)methyl)carbamoyl)-5-(2-methylpyridin-4-yl)benzyl)carbamate The title compound (173.0 mg, 85% yield) was prepared from the procedure described in Example 12, Step F using (5-chloropyridin-2-yl)-methanamine (65.0 mg, 0.460 mmol). LCMS: $R_T$=0.899 min, MS (ES) 467.1 (M+H).

Step B. Preparation of 3-(aminomethyl)-N-((5-chloropyridin-2-yl)methyl)-5-(2-methylpyridin-4-yl)benzamide The title compound (136.0 mg, crude mixture) was prepared from the procedure described in Example 12, Step G using tert-butyl (3-(((5-chloropyridin-2-yl)methyl)carbamoyl)-5-(2-methylpyridin-4-yl)benzyl)carbamate (173.0 mg, 0.37 mmol). LCMS: $R_T$=0.632 min, MS (ES) 367.1 (M+H).

Step C. Preparation of N-((5-chloropyridin-2-yl)methyl)-3-(((4,5-dihydro-1H-imidazol-2-yl)amino)methyl)-5-(2-methylpyridin-4-yl)benzamide The title compound (50.0 mg, 89% yield) was prepared from the procedure described in Example 12, Step H using 3-(aminomethyl)-N-((5-chloropyridin-2-yl)methyl)-5-(2-methylpyridin-4-yl)benzamide (47.0 mg, 0.130 mmol). LCMS: $R_T$=0.677 min, MS (ES) 435.1 (M+H).

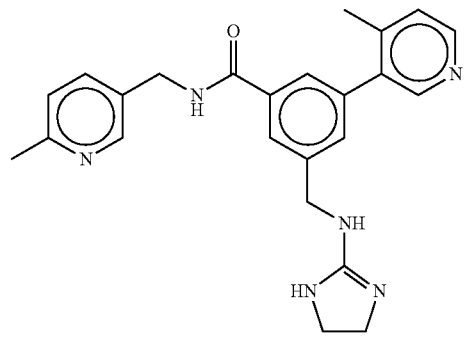

Example 28

3-(((4,5-Dihydro-1H-imidazol-2-yl)amino)methyl)-5-(4-methylpyridin-3-yl)-N-((6-methylpyridin-3-yl)methyl)benzamide

Step A. Preparation of tert-butyl (3-(4-methylpyridin-3-yl)-5-(((6-methylpyridin-3-yl)methyl)carbamoyl)benzyl)carbamate The title compound (60.0 mg, 65% yield) was prepared from the procedure described in Example 12, Step F using (6-methylpyridine-3-yl)methanamine (31.7 mg, 0.210 mmol). LCMS: $R_T$=0.717 min, MS (ES) 447.2 (M+H).

Step B. Preparation of 3-(aminomethyl)-5-(4-methylpyridin-3-yl)-N-((6-methylpyridin-3-yl)methyl)benzamide The title compound (40.0 mg, crude mixture) was prepared from the procedure described in Example 12, Step G using tert-butyl (3-(4-methylpyridin-3-yl)-5-(((6-methylpyridin-3-yl)methyl)carbamoyl)benzyl)carbamate (60.0 mg, 0.130 mmol). LCMS: $R_T$=0.090 min, MS (ES) 374.2 (M+H).

Step C. Example 28

The title compound (8.0 mg, 17% yield) was prepared from the procedure described in Example 12, Step H using 3-(aminomethyl)-5-(4-methylpyridin-3-yl)-N-((6-methylpyridin-3-yl)methyl)benzamide (40.0 mg, 0.120 mmol). LCMS: $R_T$=0.181 min, MS (ES) 415.2 (M+H).

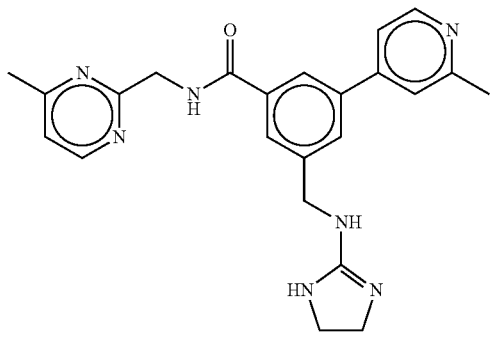

Example 29

3-(((4,5-Dihydro-1H-imidazol-2-yl)amino)methyl)-5-(2-methylpyridin-4-yl)-N-((4-methylpyrimidin-2-yl)methyl)benzamide

Step A. Preparation of tert-butyl (3-(2-methylpyridin-4-yl)-5-(((4-methylpyrimidin-2-yl)methyl)carbamoyl)benzyl)carbamate The title compound (132.0 mg, 85% yield) was prepared from the procedure described in Example 12, Step F using (4-methylpyrimidin-2-yl)-methanamine (45.0 mg, 0.360 mmol). LCMS: $R_T$=0.806 min, MS (ES) 448.2 (M+H).

Step B. Preparation of 3-(aminomethyl)-5-(2-methylpyridin-4-yl)-N-((4-methylpyrimidin-2-yl)methyl)benzamide The title compound (97.0 mg, crude mixture) was prepared from the procedure described in Example 12, Step G using tert-butyl (3-(2-methylpyridin-4-yl)-5-(((4-methylpyrimidin-2-yl)methyl)carbamoyl)benzyl)carbamate (132.0 mg, 0.29 mmol). LCMS: $R_T$=0.533 min, MS (ES) 348.2 (M+H).

Step C. Preparation of 3-(((4,5-Dihydro-1H-imidazol-2-yl(amino)methyl)-5-(2-methylpyridin-4-yl)-N-((4-methylpyrimidin-2-yl)methyl)benzamide The title compound (40.0 mg, 70% yield) was prepared from the procedure described in Example 12, Step H using 3-(aminomethyl)-5-(2-methylpyridin-4-yl)-N-((4-methylpyrimidin-2-yl)methyl)benzamide (48.0 mg, 0.140 mmol). LCMS: $R_T$=0.596 min, MS (ES) 416.1 (M+H).

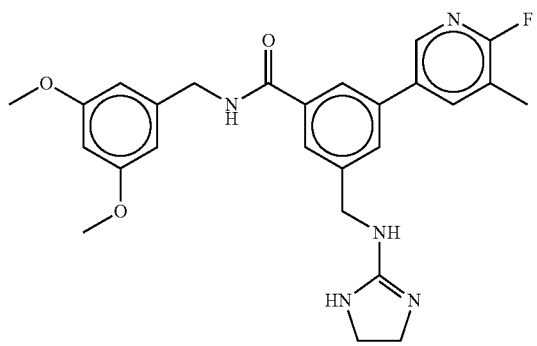

Example 30

3-(((4,5-Dihydro-1H-imidazol-2-yl)amino)methyl)-N-(3,5-dimethoxybenzyl)-5-(6-fluoro-5-methylpyridin-3-yl)benzamide

Step A. Preparation of tert-butyl (3-((3,5-dimethoxybenzyl)carbamoyl)-5-(6-fluoro-5-methylpyridin-3-yl)benzyl)carbamate The title compound (137.0 mg, 81% yield) was prepared from the procedure described in Example 12, Step F using 3,5-dimethoxybenzylamine (58.0 mg, 0.350 mmol). LCMS: $R_T$=1.17 min, MS (ES) 510.2 (M+H)

Step B. Preparation of 3-(aminomethyl)-N-(3,5-dimethoxybenzyl)-5-(6-fluoro-5-methylpyridin-3-yl)benzamide The title compound (106.0 mg, crude mixture) was prepared from the procedure described in Example 12, Step G using tert-butyl (3-((3,5-dimethoxybenzyl)carbamoyl)-5-(6-fluoro-5-methylpyridin-3-yl)benzyl)carbamate (137.0 mg, 0.27 mmol). LCMS: $R_T$=0.924 min, MS (ES) 410.1 (M+H).

Step C. Preparation of 3-(((4,5-Dihydro-1H-imidazol-2-yl)amino)methyl)-N-(3,5-dimethoxybenzyl)-5-(6-fluoro-5-methylpyridin-3-yl)benzamide The title compound (44.0 mg, 71% yield) was prepared from the procedure described in Example 12, Step H using 3-(aminomethyl)-N-(3,5-dimethoxybenzyl)-5-(6-fluoro-5-methylpyridin-3-yl)benzamide (53.0 mg, 0.130 mmol). LCMS: $R_T$=0.936 min, MS (ES) 478.1 (M+H).

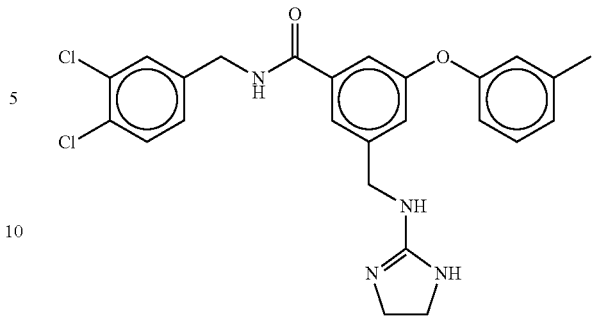

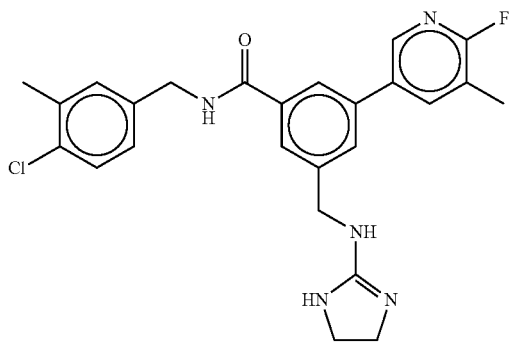

Example 31

N-(4-Chloro-3-methylbenzyl)-3-(((4,5-dihydro-1H-imidazol-2-yl)amino)methyl)-5-(6-fluoro-5-methyl-pyridin-3-yl)benzamide Step A. Preparation of tert-butyl (3-((4-chloro-3-methylbenzyl)carbamoyl)-5-(6-fluoro-5-methylpyridin-3-yl)benzyl)carbamate The title compound (137.0 mg, 84% yield) was prepared from the procedure described in Example 12, Step F using 3-methyl-4-chlorobenzylamine (54.0 mg, 0.350 mmol). LCMS: $R_T$=1.30 min, MS (ES) 498.1 (M+H)

Step B. Preparation of 3-(aminomethyl)-N-(4-chloro-3-methylbenzyl)-5-(6-fluoro-5-methylpyridin-3-yl)benzamide The title compound (107.0 mg, crude mixture) was prepared from the procedure described in Example 12, Step G using tert-butyl (3-((4-chloro-3-methylbenzyl)carbamoyl)-5-(6-fluoro-5-methylpyridin-3-yl)benzyl)carbamate (137.0 mg, 0.28 mmol). LCMS: $R_T$=0.987 min, MS (ES) 398.1 (M+H).

Step C. Preparation of N-(4-Chloro-3-methylbenzyl)-3-(((4,5-dihydro-1H-imidazol-2-yl)amino)methyl)-5-(6-fluoro-5-methylpyridin-3-yl)benzamide The title compound (45.0 mg, 73% yield) was prepared from the procedure described in Example 12, Step H using 3-(aminomethyl)-N-(4-chloro-3-methylbenzyl)-5-(6-fluoro-5-methylpyridin-3-yl)benzamide (53.0 mg, 0.130 mmol). LCMS: $R_T$=1.046 min, MS (ES) 466.1 (M+H).

Example 32

N-(3,4-Dichlorobenzyl)-3-(((4,5-dihydro-1H-imidazol-2-yl)amino)methyl)-5-(m-tolyloxy)benzamide Step A. Preparation of methyl 3-(hydroxymethyl)-5-(m-tolyloxy)benzoate NaBH$_4$ (605 mg, 16.0 mmol) was added to a solution of dimethyl 5-(m-tolyloxy)isophthalate (1.20 g, 4.00 mmol) in THF/MeOH (40 mL, 10:1) under Ar atmosphere. The reaction mixture was refluxed for 5 h. The reaction was quenched with sat. aq. NH$_4$Cl solution and concentrated. Sat. aq. NaHCO$_3$ solution was added and extracted with CH$_2$Cl$_2$ (3×20 mL). The combined organic layers were dried (MgSO$_4$), filtered and concentrated. The residue was purified by flash chromatography (Combi-flash Rf, Hex/EtOAc=0-60% gradient) to provide the title compound (720 mg, 66% yield). LCMS: $R_T$=1.503 min, MS (ES) 273.1 (M+H).

Step B. Preparation of 3-(hydroxymethyl)-5-(m-tolyloxy)benzoic Acid

The title compound (800 mg, crude mixture) was prepared from the procedure described in Example 12, Step E using methyl 3-(hydroxymethyl)-5-(m-tolyloxy)benzoate (720 mg, 2.64 mmol). LCMS: $R_T$=1.299 min, MS (ES) 259.0 (M+H).

Step C. Preparation of N-(3,4-dichlorobenzyl)-3-(hydroxymethyl)-5-(m-tolyloxy)benzamide HBTU (1.29 g, 3.41 mmol), 3,4-dichlorobenzylamine (454 μL, 3.41 mmol) and Et$_3$N (906 μL, 3.41 mmol) were added to a solution of 3-(hydroxymethyl)-5-(m-tolyloxy)benzoic acid (800 mg, 3.10 mmol) in CH$_2$Cl$_2$ (13 mL). The reaction mixture was stirred at room temperature for 5 h. The reaction mixture was quenched with water and extracted with CH$_2$Cl$_2$ (3×10 mL). The organic layer was washed with sat. aq. NH$_4$Cl and dried (MgSO$_4$), filtered and concentrated. The residue was purified by flash chromatography (Combi-flash Rf, Hex/EtOAc=0-60% gradient) to provide the title compound (1.00 g, 78% yield). LCMS: $R_T$=1.716 min, MS (ES) 415.9 (M+H).

Step D. Preparation of N-(3,4-dichlorobenzyl)-3-formyl-5-(m-tolyloxy)benzamide

Manganese(IV) oxide (1.25 g, 14.4 mmol) was added to a solution of N-(3,4-dichlorobenzyl)-3-(hydroxymethyl)-5-(m-tolyloxy)benzamide (1.00 g, 2.40 mmol) in CH$_2$Cl$_2$ (24 mL). The reaction mixture was stirred at room temperature for 5 h. The reaction mixture was filtered using Celite pad and concentrated. The residue was purified by flash chromatography (Combi-flash Rf, Hex/EtOAc=0-60% gradient) to provide the title compound (690 mg, 69% yield). LCMS: $R_T$=1.867 min, MS (ES) 414.0 (M+H).

Step E. Preparation of 3-(aminomethyl)-N-(3,4-dichlorobenzyl)-5-(m-tolyloxy)benzamide Ammonium acetate (1.71 g, 22.2 mmol) and sodium cyanoborohydride (52.3 mg, 0.830 mmol) were added to a solution of N-(3,4-dichlorobenzyl)-3-formyl-5-(m-tolyloxy)benzamide (230 mg, 0.560 mmol) in iPrOH (5.6 mL). The reaction mixture was refluxed for 2 h. The reaction mixture was filtered (to remove extra NH₄OAc) and concentrated. The residue was dissolved in water and extracted with CH₂Cl₂ (3×10 mL). The organic layer was washed with brine and dried (MgSO₄), filtered and concentrated. The residue was purified by flash chromatography (Combi-flash Rf, DCM/MeOH=0-25% gradient) to provide the title compound (50.0 mg, 22% yield). LCMS: $R_T$=1.465 min, MS (ES) 415.0 (M+H).

Step F. Example 32

The title compound (55.0 mg, 95% yield) was prepared from the procedure described in Example 12, Step H using 3-(aminomethyl)-N-(3,4-dichlorobenzyl)-5-(m-tolyloxy)benzamide (50.0 mg, 0.120 mmol). LCMS: $R_T$=1.543 min, MS (ES) 483.0 (M+H).

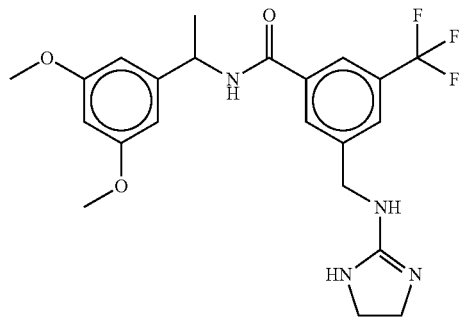

Example 33

3-(((4,5-Dihydro-1H-imidazol-2-yl)amino)methyl)-N-(1-(3,5-dimethoxyphenyl)ethyl)-5-(trifluoromethyl)benzamide Step A. Preparation of methyl 3-(bromomethyl)-5-(trifluoromethyl)benzoate A solution of methyl 3-methyl-5-(trifluoromethyl)benzoate (0.72 g, 3.32 mmol) in CCl₄ (40 mL) was refluxed through a Dean Stark trap to remove trace amounts of water. The solution was cooled to ambient temperature and treated with N-bromosuccinimide (NBS) (0.71 g, 3.98 mmol) and 2,2'azobis(2-methylpropionitrile (AIBN) (0.05 g). The solution was refluxed for 18 h then cooled to ambient temperature. The reaction mixture was filtered, and the filtrate was concentrated under reduced pressure to afford the title compound (0.98 g, quant). The crude was used without further purification.

Step B. Preparation of methyl 3-(((tert-butoxycarbonyl)amino)methyl)-5-(trifluoromethyl)benzoate A solution of the crude methyl 3-(bromomethyl)-5-(trifluoromethyl)benzoate (0.98 g, 3.32 mmol) and sodium azide (0.65 g, 9.96 mmol) in DMF (11 mL) was heated to 70° C. for 4 h.

The solution was cooled to ambient temperature and concentrated. The residue was dissolved in DCM, washed with water, dried over MgSO₄, filtered and concentrated. The crude methyl 3-(azidomethyl)-5-(trifluoromethyl)benzoate (0.36 g, 1.37 mmol) was dissolved in THF (4 mL) and treated with triphenyl phosphine (0.36 g, 1.37) and then stirred for 18 h. The reaction was diluted with water (400 mL), acidified with 1N HCl and washed with EtOAc. The aqueous layer was basified with sat. aq. NaHCO₃ and extracted with EtOAc. The organic layer was dried with MgSO₄, filtered and concentrated to afford methyl 3-(aminomethyl)-5-(trifluoromethyl)benzoate (0.16 g, 0.66 mmol). The intermediate was dissolved in THF (6 mL), and DIPEA (0.12 mL, 0.66 mmol) and (Boc)₂O (0.175 g, 0.79 mmol) were added. The resulting solution was stirred for 18 h then concentrated. The residue was purified by flash chromatography (Combi-flash Rf, Hex/EtOAc=0-80% gradient) to afford the title compound (0.190 g, 86%).

Step C. Example 33

The title compound (0.06 g, 22%) was prepared following the procedure described in Example 1, Step C and D: methyl 3-(((tert-butoxycarbonyl)amino)methyl)-5-(trifluoromethyl) benzoate (0.19 g, 0.57 mmol) was saponified to afford 3-(((tert-butoxycarbonyl)amino)methyl)-5-(trifluoromethyl) benzoic acid (0.19 g, quant). It was then coupled with 1-(3,5-dimethoxyphenyl)ethan-1-amine (0.12 g, 0.69 mmol) using DIPEA (0.30 mL, 1.71 mmol) and HATU (0.24 g, 0.63 mmol) to give tert-butyl (3-((1-(3,5-dimethoxyphenyl)ethyl) carbamoyl)-5-(trifluoromethyl)benzyl)carbamate. The Boc group was deprotected, and the resulting amine intermediate was reacted with 2-methylthio-2-imidazoline hydroiodide (0.16 g, 0.65 mmol) in pyridine (3 mL) to yield the title compound. ¹H NMR (400 MHz, d₆-DMSO) δ 7.8 (s, 1H), 7.7 (m, 2H), 6.5 (s, 1H), 6.4 (s, 1H), 6.2 (s, 1H), 4.6 (s, 1H), 4.5 (d, 2H, J=8.6), 4.4 (s, 1H), 3.7 (s, 6H), 3.6 (s, 4H), 1.4 (s, 3H). LC-MS, 95% (215, 254 nm); LCMS: $R_T$=0.9 min, MS (ES) 451.0 (M+H).

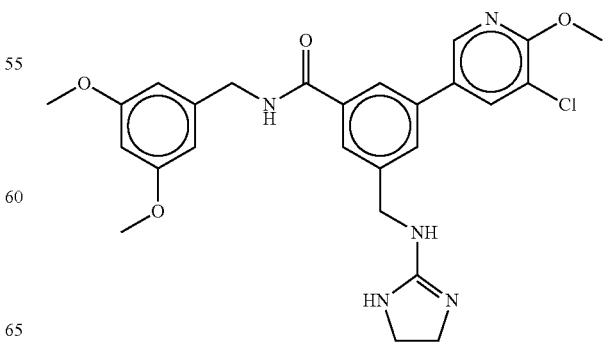

Example 34

3-(5-Chloro-6-methoxypyridin-3-yl)-5-(((4,5-dihydro-1H-imidazol-2-yl)amino)methyl)-N-(3,5-dimethoxybenzyl)benzamide

Step A. Preparation of tert-butyl (3-(5-chloro-6-methoxypyridin-3-yl)-5-((3,5-dimethoxybenzyl)carbamoyl)benzyl)carbamate The title compound (218.0 mg, 77% yield) was prepared from the procedure described in Example 12, Step F using 3,5-dimethoxybenzylamine (92.0 mg, 0.550 mmol). LCMS: $R_T$=1.24 min, MS (ES) 542.1 (M+H).

Step B. Preparation of 3-(aminomethyl)-5-(5-chloro-6-methoxypyridin-3-yl)-N-(3,5-dimethoxybenzyl)benzamide The title compound (177.0 mg, crude mixture) was prepared from the procedure described in Example 12, Step G using tert-butyl (3-(5-chloro-6-methoxypyridin-3-yl)-5-((3,5-dimethoxybenzyl)carbamoyl)benzyl)carbamate (218.0 mg, 0.52 mmol). LCMS: $R_T$=0.961 min, MS (ES) 442.1 (M+H).

Step C. Preparation of 3-(5-Chloro-6-methoxypyridin-3-yl)-5-(((4,5-dihydro-1H-imidazol-2-yl)amino)methyl)-N-(3,5-dimethoxybenzyl)benzamide The title compound (91.0 mg, 70% yield) was prepared from the procedure described in Example 12, Step H using 3-(aminomethyl)-5-(5-chloro-6-methoxypyridin-3-yl)-N-(3,5-dimethoxybenzyl)benzamide (113.0 mg, 0.260 mmol). LCMS: $R_T$=0.977 min, MS (ES) 510.1 (M+H).

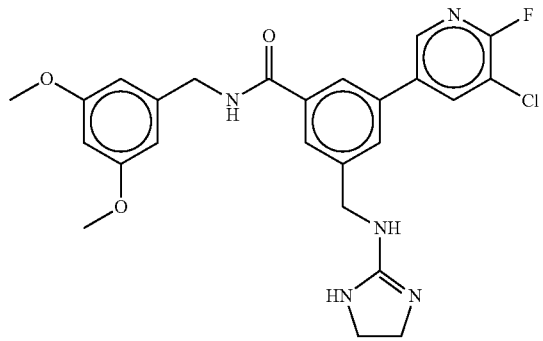

Example 35

3-(5-Chloro-6-fluoropyridin-3-yl)-5-(((4,5-dihydro-1H-imidazol-2-yl)amino)methyl)-N-(3,5-dimethoxybenzyl)benzamide

Step A. Preparation of tert-butyl (3-(5-chloro-6-fluoropyridin-3-yl)-5-((3,5-dimethoxybenzyl)carbamoyl)benzyl)carbamate The title compound (56.0 mg, 62% yield) was prepared from the procedure described in Example 12, Step F using 3,5-dimethoxybenzylamine (30.0 mg, 0.18 mmol).

Step B. Preparation of 3-(aminomethyl)-5-(5-chloro-6-fluoropyridin-3-yl)-N-(3,5-dimethoxybenzyl)benzamide The title compound (45.0 mg, crude mixture) was prepared from the procedure described in Example 12, Step G using tert-butyl (3-(5-chloro-6-fluoropyridin-3-yl)-5-((3,5-dimethoxybenzyl)carbamoyl)benzyl)carbamate (56.0 mg, 0.11 mmol).

Step C. Preparation of 3-(5-Chloro-6-fluoropyridin-3-yl)-5-(((4,5-dihydro-1H-imidazol-2-yl)amino)methyl)-N-(3,5-dimethoxybenzyl)benzamide The title compound (20.0 mg, 40% yield) was prepared from the procedure described in Example 12, Step H using 3-(aminomethyl)-5-(5-chloro-6-fluoropyridin-3-yl)-N-(3,5-dimethoxybenzyl)benzamide (56.0 mg, 0.11 mmol). LCMS: $R_T$=0.962 min, MS (ES) 498.1 (M+H).

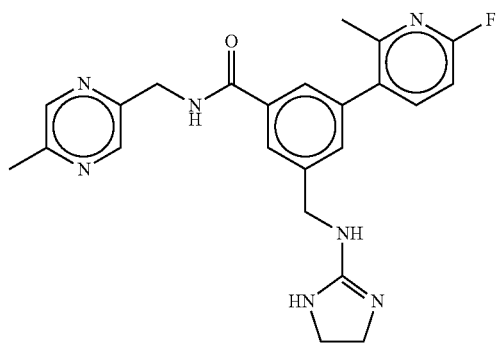

Example 36

3-(((4,5-dihydro-1H-imidazol-2-yl)amino)methyl)-5-(6-fluoro-2-methylpyridin-3-yl)-N-((5-methylpyrazin-2-yl)methyl)benzamide

Step A. Preparation of 3-(aminomethyl)-5-(6-fluoro-2-methylpyridin-3-yl)-N-((5-methylpyrazin-2-yl)methyl)benzamide The title compound was prepared following the procedure described in Example 1, Step C using methyl 3-(((tert-butoxycarbonyl)amino)methyl)-5-(6-fluoro-2-methylpyridin-3-yl)benzoate (0.20 mmol) and (5-methylpyrazin-2-yl)methanamine (0.22 mmol).

Step B. Example 36

The title compound (0.04 g, 46%) was prepared following the procedure described in Example 1, Step D using 3-(aminomethyl)-5-(6-fluoro-2-methylpyridin-3-yl)-N-((5-methylpyrazin-2-yl)methyl)benzamide TFA salt (0.09 g, 0.19 mmol), pyridine (4 mL) and 2-methylthio-2-imidazoline hydroiodide (0.09 g, 0.38 mmol) afforded the title compound. LCMS: 98% 254 nm $R_T$=0.70 min, MS (ES) 434 (M+H).

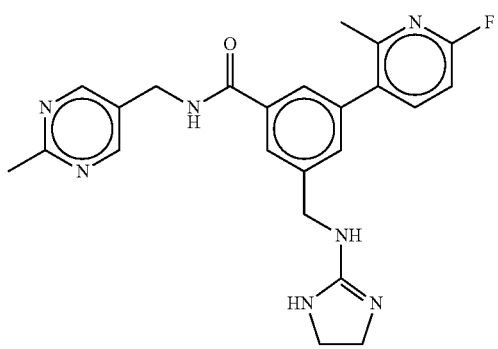

Example 37

3-(((4,5-dihydro-1H-imidazol-2-yl)amino)methyl)-5-(6-fluoro-2-methylpyridin-3-yl)-N-((2-methylpyrimidin-5-yl)methyl)benzamide Step A. Preparation of 3-(aminomethyl)-5-(6-fluoro-2-methylpyridin-3-yl)-N-((5-methylpyrazin-2-yl)methyl)benzamide The title compound was prepared following the procedure described in Example 1, Step C using methyl 3-(((tert-butoxycarbonyl)amino)methyl)-5-(6-fluoro-2-methylpyridin-3-yl)benzoate (0.20 mmol) and (2-methylpyrimidin-5-yl)methanamine (0.22 mmol).

Step B. Example 37

The title compound (0.01 g, 7%) was prepared following the procedure described in Example 1, Step D using 3-(aminomethyl)-5-(6-fluoro-2-methylpyridin-3-yl)-N-((5-methylpyrazin-2-yl)methyl)benzamide TFA salt (0.09 g, 0.19 mmol), pyridine (4 mL) and 2-methylthio-2-imidazoline hydroiodide (0.09 g, 0.38 mmol) afforded the title compound. LCMS: 98% 254 nm $R_T$=0.70 min, MS (ES) 434 (M+H).

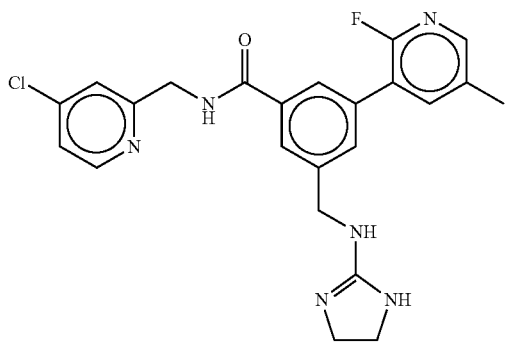

Example 38

N-((4-chloropyridin-2-yl)methyl)-3-(((4,5-dihydro-1H-imidazol-2-yl)amino)methyl)-5-(2-fluoro-5-methylpyridin-3-yl)benzamide Step A. Preparation of tert-butyl (3-(((4-chloropyridin-2-yl)methyl)carbamoyl)-5-(2-fluoro-5-methylpyridin-3-yl)benzyl)carbamate The title compound (46.0 mg, 68% yield) was prepared from the procedure described in Example 12, Step F using (4-chloropyridin-2-yl)-methanamine (22.0 mg, 0.150 mmol). LCMS: $R_T$=1.098 min, MS (ES) 485.1 (M+H).

Step B. Preparation of 3-(aminomethyl)-N-((4-chloropyridin-2-yl)methyl)-5-(2-fluoro-5-methylpyridin-3-yl)benzamide The title compound (38.0 mg, crude mixture) was prepared from the procedure described in Example 12, Step G using tert-butyl (3-(((4-chloropyridin-2-yl)methyl)carbamoyl)-5-(2-fluoro-5-methylpyridin-3-yl)benzyl)carbamate (46.0 mg, 0.10 mmol). LCMS: $R_T$=0.808 min, MS (ES) 385.1 (M+H).

Step C. Preparation of N-((4-chloropyridin-2-yl)methyl)-3-(((4,5-dihydro-1H-imidazol-2-yl)amino)methyl)-5-(2-fluoro-5-methylpyridin-3-yl)benzamide The title compound (24.0 mg, 53% yield) was prepared from the procedure described in Example 12, Step H using 3-(aminomethyl)-N-((4-chloropyridin-2-yl)methyl)-5-(2-fluoro-5-methylpyridin-3-yl)benzamide (46.0 mg, 0.10 mmol). LCMS: $R_T$=0.843 min, MS (ES) 453.1 (M+H).

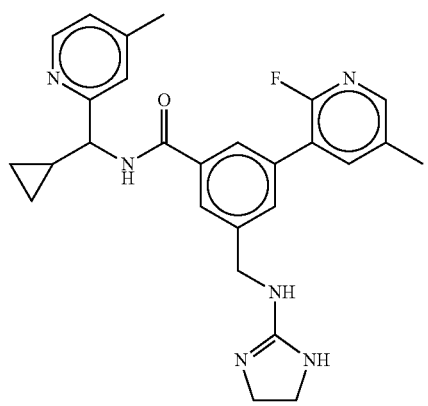

Example 39

N-(cyclopropyl(4-methylpyridin-2-yl)methyl)-3-(((4,5-dihydro-1H-imidazol-2-yl)amino)methyl)-5-(2-fluoro-5-methylpyridin-3-yl)benzamide Step A. Preparation of tert-butyl (3-((cyclopropyl(4-methylpyridin-2-yl)methyl)carbamoyl)-5-(2-fluoro-5-methylpyridin-3-yl)benzyl)carbamate The title compound (49.0 mg, 69% yield) was prepared from the procedure described in Example 12, Step F using cyclopropyl(4-methyl-pyridin-2-yl)methanamine dihydrochloride (36.0 mg, 0.15 mmol). LCMS: $R_T$=0.975 min, MS (ES) 505.2 (M+H).

Step B. 3-(aminomethyl)-N-(cyclopropyl(4-methylpyridin-2-yl)methyl)-5-(2-fluoro-5-methylpyridin-3-yl)benzamide The title compound (40.0 mg, crude mixture) was prepared from the procedure described in Example 12, Step G using tert-butyl (3-((cyclopropyl(4-methylpyridin-2-yl)methyl)carbamoyl)-5-(2-fluoro-5-methylpyridin-3-yl)benzyl)carbamate (49.0 mg, 0.10 mmol). LCMS: $R_T$=0.741 min, MS (ES) 405.2 (M+H).

Step C. Preparation of N-(cyclopropyl(4-methylpyridin-2-yl)methyl)-3-(((4,5-dihydro-1H-imidazol-2-yl)amino)methyl)-5-(2-fluoro-5-methylpyridin-3-yl)benzamide The title compound (25.0 mg, 53% yield) was prepared from the procedure described in Example 12, Step H using 3-(aminomethyl)-N-(cyclopropyl(4-methylpyridin-2-yl)methyl)-5-(2-fluoro-5-methylpyridin-3-yl)benzamide (40.0 mg, 0.10 mmol). LCMS: $R_T$=0.780 min, MS (ES) 473.2 (M+H).

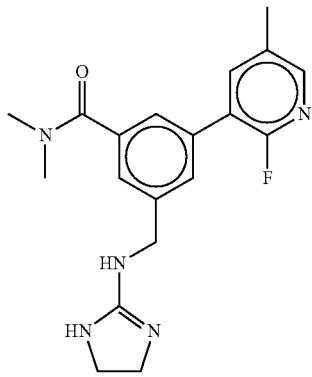

Example 40

3-(((4,5-dihydro-1H-imidazol-2-yl)amino)methyl)-5-(2-fluoro-5-methylpyridin-3-yl)-N,N-dimethylbenzamide Step A. Preparation of tert-butyl (3-(dimethylcarbamoyl)-5-(2-fluoro-5-methylpyridin-3-yl)benzyl)carbamate The title compound (24.0 mg, 35% yield) was prepared from the procedure described in Example 12, Step F using dimethylamine hydrochloride (15.0 mg, 0.19 mmol). LCMS: $R_T$=0.996 min, MS (ES) 388.2 (M+H).

Step B. Preparation of 3-(aminomethyl)-5-(2-fluoro-5-methylpyridin-3-yl)-N,N-dimethylbenzamide The title compound (18.0 mg, crude mixture) was prepared from the procedure described in Example 12, Step G using tert-butyl (3-(dimethylcarbamoyl)-5-(2-fluoro-5-methylpyridin-3-yl)benzyl)carbamate (24.0 mg, 0.06 mmol). LCMS: $R_T$=0.711 min, MS (ES) 288.1 (M+H).

Step C. Preparation of 3-(((4,5-dihydro-1H-imidazol-2-yl)amino)methyl)-5-(2-fluoro-5-methylpyridin-3-yl)-N,N-dimethylbenzamide The title compound (4.0 mg, 18% yield) was prepared from the procedure described in Example 12, Step H using 3-(aminomethyl)-5-(2-fluoro-5-methylpyridin-3-yl)-N,N-dimethylbenzamide (18.0 mg, 0.06 mmol). LCMS: $R_T$=0.767 min, MS (ES) 356.2 (M+H).

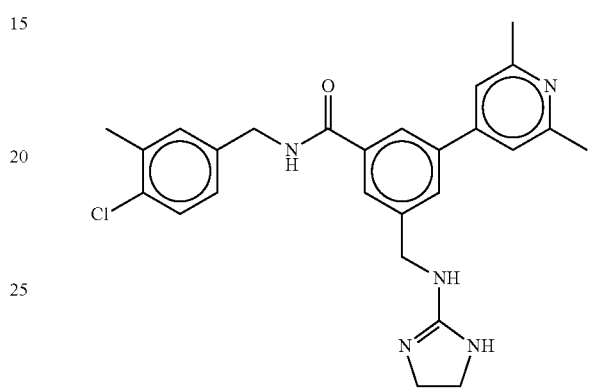

Example 41

N-(4-chloro-3-methylbenzyl)-3-(((4,5-dihydro-1H-imidazol-2-yl)amino)methyl)-5-(2,6-dimethylpyridin-4-yl)benzamide Step A. Preparation of tert-butyl (3-((4-chloro-3-methylbenzyl)carbamoyl)-5-(2,6-dimethylpyridin-4-yl)benzyl)carbamate The title compound (40.0 mg, 62% yield) was prepared from the procedure described in Example 12, Step F using 4-chloro-3-methylbenzylamine (22.0 mg, 0.14 mmol). LCMS: $R_T$=1.042 min, MS (ES) 494.1 (M+H).

Step B. Preparation of 3-(aminomethyl)-N-(4-chloro-3-methylbenzyl)-5-(2,6-dimethylpyridin-4-yl)benzamide The title compound (32.0 mg, crude mixture) was prepared from the procedure described in Example 12, Step G using tert-butyl (3-((4-chloro-3-methylbenzyl)carbamoyl)-5-(2,6-dimethylpyridin-4-yl)benzyl)carbamate (40.0 mg, 0.08 mmol). LCMS: $R_T$=0.842 min, MS (ES) 394.2 (M+H).

Step C. Preparation of N-(4-chloro-3-methylbenzyl)-3-(((4,5-dihydro-1H-imidazol-2-yl)amino)methyl)-5-(2,6-dimethylpyridin-4-yl)benzamide The title compound (32.0 mg, 84% yield) was prepared from the procedure described in Example 12, Step H using 3-(aminomethyl)-N-(4-chloro-3-methylbenzyl)-5-(2,6-dimethylpyridin-4-yl)benzamide (32.0 mg, 0.08 mmol). LCMS: $R_T$=0.878 min, MS (ES) 462.1 (M+H).

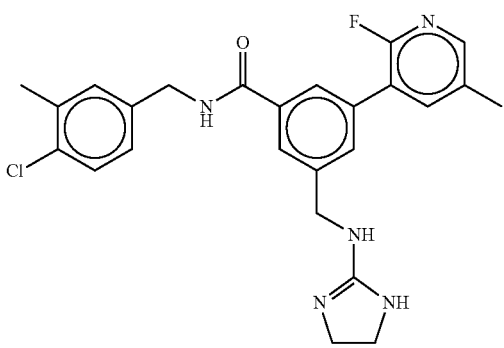

Example 42

N-(4-chloro-3-methylbenzyl)-3-(((4,5-dihydro-1H-imidazol-2-yl)amino)methyl)-5-(2-fluoro-5-methyl-pyridin-3-yl)benzamide Step A. Preparation of tert-butyl (3-((4-chloro-3-methylbenzyl)carbamoyl)-5-(2-fluoro-5-methylpyridin-3-yl)benzyl)carbamate The title compound (61.0 mg, 88% yield) was prepared from the procedure described in Example 12, Step F using 4-chloro-3-methoxybenzylamine (24.0 mg, 0.15 mmol). LCMS: $R_T$=1.23 min, MS (ES) 498.1 (M+H).

Step B. Preparation of 3-(aminomethyl)-N-(4-chloro-3-methylbenzyl)-5-(2-fluoro-5-methylpyridin-3-yl)benzamide The title compound (50.0 mg, crude mixture) was prepared from the procedure described in Example 12, Step G using tert-butyl (3-((4-chloro-3-methylbenzyl)carbamoyl)-5-(2-fluoro-5-methylpyridin-3-yl)benzyl)carbamate (61.0 mg, 0.13 mmol). LCMS: $R_T$=0.954 min, MS (ES) 398.1 (M+H).

Step C. Preparation of N-(4-chloro-3-methylbenzyl)-3-(((4,5-dihydro-1H-imidazol-2-yl)amino)methyl)-5-(2-fluoro-5-methylpyridin-3-yl)benzamide The title compound (26.0 mg, 44% yield) was prepared from the procedure described in Example 12, Step H using 3-(aminomethyl)-N-(4-chloro-3-methylbenzyl)-5-(2-fluoro-5-methylpyridin-3-yl)benzamide (50.0 mg, 0.13 mmol). LCMS: $R_T$=0.996 min, MS (ES) 466.1 (M+H).

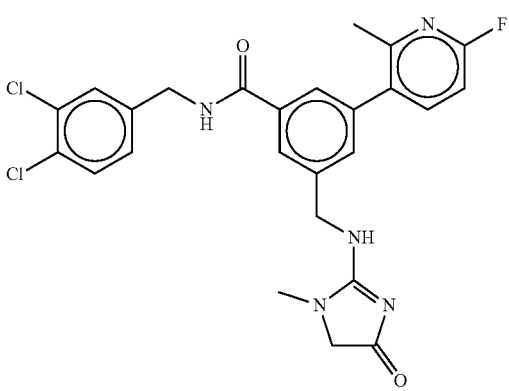

Example 43

N-(3,4-dichlorobenzyl)-3-(6-fluoro-2-methylpyridin-3-yl)-5-(((1-methyl-4-oxo-4,5-dihydro-1H-imidazol-2-yl)amino)methyl)benzamide Step A. Preparation of methyl 3-(6-fluoro-2-methylpyridin-3-yl)-5-(hydroxymethyl)benzoate The title compound (7.19 g, 83%) was prepared following the procedure described in Example 1, Step B using methyl 3-bromo-5-(hydroxymethyl)benzoate (7.50 g, 31.00 mmol), $K_2CO_3$ (10.69 g, 72.5 mmol), 80% 1,4 dioxane/water (665 mL), Tetrakis(triphenylphosphine)palladium (O) (2.68 g, 2.32 mmol), and (6-fluoro-2-methylpyridin-3-yl)boronic acid (6.4 g, 41.5 mmol). $^1$H NMR (400 MHz, $d_6$ DMSO) δ 8.0 (s, 1H), 7.8 (t, 1H, J=7.9 Hz), 7.8 (s, 1H), 7.6 (s, 1H), 5.4 (broad S, 1H), 4.6 (s, 2H), 3.9 (s, 2H), 2.8 (s, 3H), 2.3 (s, 3H).

Step B. Preparation of 3-(6-fluoro-2-methylpyridin-3-yl)-5-(hydroxymethyl)benzoic Acid A solution of methyl 3-(6-fluoro-2-methylpyridin-3-yl)-5-(hydroxymethyl)benzoate (7.19 g, 26.00 mmol) in THF (200 mL)/Methanol (50 mL)/water (50 ml) was treated with LiOH (1.13 g, 54.00 mmol) then stirred for 6 h at ambient temperature. The solvent was removed under reduced pressure and diluted with water. The aqueous solution was acidified with HCl aq. (1N) to pH=2. The resulting solid was filtered, washed with water and dried in a vacuum oven to afford the title compound (6.20 g, 91%) $^1$H NMR (400 MHz, $D_6$-DMSO) δ 7.98 (s, 1H) 7.9 (t, 1H, J=8.04 Hz), 7.8 (s, 1H), 7.6 (m, 1H), 7.56 (s, 1H), 7.1 (m, 1H) 5.40 (broad s, 1H), 4.62 (s, 2H), 2.30 (s, 3H), 7.1 (m, 1H), 5.4 (broad s, 1H), 4.6 (s, 2H), 2.4 (s, 3H).

Step C. Preparation of N-(3,4-dichlorobenzyl)-3-(6-fluoro-2-methylpyridin-3-yl)-5-(hydroxymethyl)benzamide A solution of 3-(6-fluoro-2-methylpyridin-3-yl)-5-(hydroxymethyl)benzoic acid (4.0 g, 15.3 mmol) and TEA (6.3 mL, 45.9 mmol) in DMF (70 mL) was cooled on an ice bath. EDC (3.0 g, 16.1 mmol) and HOBT (2.46 g, 16.1 mmol) were added to the reaction mixture and stirred for 5 min. (3,4-dichlorophenyl)methanamine (0.78 g, 4.2 mmol) was added and the reaction mixture was stirred for 18 h at ambient temperature. The DMF was removed under reduced pressure. The crude was dissolved in ethyl acetate, extracted with water, dried over $MgSO_4$, filtered, and the solvent removed under reduced pressure. The residue was purified by flash chromatography (Combi-flash Rf, Hex/EtOAc=0-100% gradient) to afford the title compound (3.87 g, 60%). $^1$H NMR (400 MHz, $D_6$-DMSO) δ 9.1 (t, 1H, J=5.7 Hz), 7.9 (s, 1H), 7.8 (t, 1H, J=8.2 Hz), 7.7 (s, 1H), 7.6 (m, 2H), 7.5 (s, 1H), 7.3 (m, 1H), 7.1 (m, 1H), 5.3 (t, 1H, J=5.5 Hz), 4.6 (d, 2H, J=5.6), 4.4 (d, 2H, J=5.9 Hz), 2.3 (s, 3H).

Step D. Preparation of 3-(bromomethyl)-N-(3,4-dichlorobenzyl)-5-(6-fluoro-2-methylpyridin-3-yl)benzamide A solution of N-(3,4-dichlorobenzyl)-3-(6-fluoro-2-methylpyridin-3-yl)-5-(hydroxymethyl)benzamide (3.87 g, 9.25 mmol) and DCM (100 mL)/toluene (200 mL) was cooled on an ice bath. 1N Phosphorus tribromide (9.70 mL, 9.70 mmol) was added dropwise, and the reaction mixture was stirred for 18 h at ambient temperature. The reaction was quenched with water and sat. aq. NaHCO$_3$ to adjust pH=8. The organic layer was separated, washed with water, dried over MgSO$_4$, filtered, and concentrated under reduced pressure. The residue was purified by flash chromatography (Combi-flash Rf, Hex/EtOAc=0-60% gradient) to afford the title compound (2.81 g, 63%) $^1$H NMR (400 MHz, D$_6$-DMSO) δ 9.2 (t, 1H, J=5.5), 8.0 (s, 1H), 7.9 (m, 1H), 7.8 (s, 1H), 7.7 (s, 1H), 7.6 (m, 2H), 7.3 (m, 1H), 7.1 (m, 1H), 4.8 (s, 2H), 4.5 (d, 2H, J=5.5 Hz), 2.3 (s, 3H).

Step E. Example 43

A solution of 3-(bromomethyl)-N-(3,4-dichlorobenzyl)-5-(6-fluoro-2-methylpyridin-3-yl)benzamide (0.08 g, 0.16 mmol), DIEA (0.07 mL, 0.39 mmol), 2-amino-1-methyl-1,5-dihydro-4H-imidazol-4-one HCl salt (0.05 g, 0.31 mmol) in acetonitrile (5 mL) was stirred for 18 h at 80° C. The reaction mixture was cooled to ambient temperature and concentrated under reduced pressure. The crude material was purified by reverse phase HPLC (Phenomenex Gemini C18, H$_2$O/CH$_3$CN gradient to 10-80% MeCN 0.1% TFA). The desired fractions were combined and concentrated to dryness. The residue was dissolve in ethyl acetate, washed with sat. aq. NaHCO$_3$, dried over MgSO$_4$, and concentrated to afford the title compound (0.03 g 42%). $^1$H NMR (400 MHz, D$_6$-DMSO) δ 9.1 (m, 1H), 7.9 (m, 2H), 7.8 (s, 1H), 7.6 (m, 2H), 7.5 (s, 1H), 7.3 (m, 1H), 7.1 (m, 1H), 4.8 (s, 2H), 4.5 (d, 2H, J=5.8 Hz), 3.9 (s, 2H), 2.8 (s, 3H), 2.3 (s, 3H); LCMS: 98% 254 nm R$_T$=0.94 min, MS (ES) 515 (M+H).

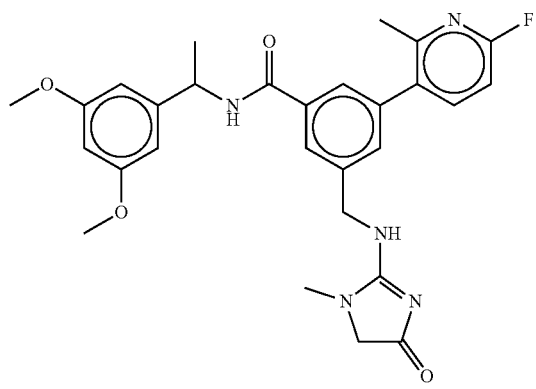

Example 44

N-(1-(3,5-dimethoxyphenyl)ethyl)-3-(6-fluoro-2-methylpyridin-3-yl)-5-(((1-methyl-4-oxo-4,5-dihydro-1H-imidazol-2-yl)amino)methyl)benzamide Step A. Preparation of N-(1-(3,5-dimethoxyphenyl)ethyl)-3-(6-fluoro-2-methylpyridin-3-yl)-5-(hydroxymethyl)benzamide The title compound was prepared following the procedure described in Example 43, Step B using 3-(6-fluoro-2-methylpyridin-3-yl)-5-(hydroxymethyl)benzoic acid, TEA, EDC, HOBT, and 1-(3,5-dimethoxyphenyl)ethan-1-amine.

Step B. Preparation of 3-(bromomethyl)-N-(1-(3,5-dimethoxyphenyl)ethyl)-5-(6-fluoro-2-methylpyridin-3-yl)benzamide The title compound was prepared following the procedure described in Example 43, Step C using N-(1-(3,5-dimethoxyphenyl)ethyl)-3-(6-fluoro-2-methylpyridin-3-yl)-5-(hydroxymethyl)benzamide and 1N Phosphorus tribromide.

Step E. Example 44

The title compound (0.02 g, 31%) was prepared following the procedure described in Example 43, Step C using 3-(bromomethyl)-N-(1-(3,5-dimethoxyphenyl)ethyl)-5-(6-fluoro-2-methylpyridin-3-yl)benzamide (0.05 g, 0.10 mmol), DIEA (0.04 mL, 0.26 mmol), 2-amino-1-methyl-1,5-dihydro-4H-imidazol-4-one HCl salt (0.02 g, 0.16 mmol) and acetonitrile (4 mL). LCMS: 95% 254 nm R$_T$=0.84 min, MS (ES) 520 (M+H).

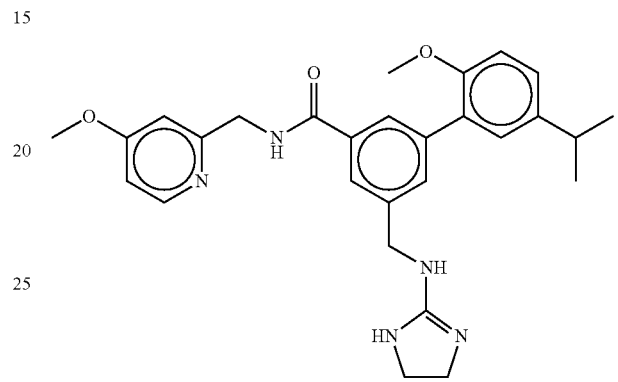

Example 45

5-(((4,5-dihydro-1H-imidazol-2-yl)amino)methyl)-5'-isopropyl-2'-methoxy-N-((4-methoxypyridin-2-yl)methyl)-[1,1'-biphenyl]-3-carboxamide Step A. Preparation of methyl 5-(((tert-butoxycarbonyl)amino)methyl)-5'-isopropyl-2'-methoxy-[1,1'-biphenyl]-3-carboxylate The title compound was prepared following the procedure described in Example 1, Step B using methyl 3-bromo-5-(((tert-butoxycarbonyl)amino)methyl)benzoate and (5-isopropyl-2-methoxyphenyl)boronic acid.

Step B. Preparation of 5-(aminomethyl)-2'-chloro-N-(dicyclopropylmethyl)-4'-fluoro-[1,1'-biphenyl]-3-carboxamide The title compound was prepared following the procedure described in Example 1, Step C using methyl 5-(((tert-butoxycarbonyl)amino)methyl)-5'-isopropyl-2'-methoxy-[1,1'-biphenyl]-3-carboxylate and (4-methoxypyridin-2-yl)methanamine.

Step C. Example 45

The title compound (0.01 g, 11%) was prepared following the procedure described in Example 1, Step D using 5-(aminomethyl)-5'-isopropyl-2'-methoxy-N-((4-methoxypyridin-2-yl)methyl)-[1,1'-biphenyl]-3-carboxamide TFA salt (0.05 g, 0.11 mmol), pyridine (2 mL) and 2-methylthio-2-imidazoline hydroiodide (0.07 g, 0.28 mmol). LCMS: >95% 254 nm R$_T$=0.829 min, MS (ES) 488 (M+H).

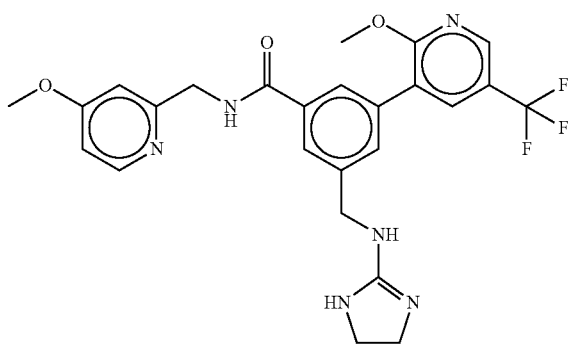

Example 46

3-(((4,5-dihydro-1H-imidazol-2-yl)amino)methyl)-5-(2-methoxy-5-(trifluoromethyl)pyridin-3-yl)-N-((4-methoxypyridin-2-yl)methyl)benzamide Step A. Preparation of methyl 3-(((tert-butoxycarbonyl)amino)methyl)-5-(2-methoxy-5-(trifluoromethyl)pyridin-3-yl)benzoate The title compound was prepared following the procedure described in Example 1, Step B using methyl 3-bromo-5-(((tert-butoxycarbonyl)amino)methyl)benzoate and (2-methoxy-5-(trifluoromethyl)pyridin-3-yl)boronic acid.

Step B. Preparation of 3-(aminomethyl)-5-(2-methoxy-5-(trifluoromethyl)pyridin-3-yl)-N-((4-methoxypyridin-2-yl)methyl)benzamide The title compound was prepared following the procedure described in Example 1, Step C using methyl 3-(((tert-butoxycarbonyl)amino)methyl)-5-(2-methoxy-5-(trifluoromethyl)pyridin-3-yl)benzoate and (4-methoxypyridin-2-yl)methanamine.

Step C. Example 46

The title compound (0.01 g, 23%) was prepared following the procedure described in Example 1, Step D using 3-(aminomethyl)-5-(2-methoxy-5-(trifluoromethyl)pyridin-3-yl)-N-((4-methoxypyridin-2-yl)methyl)benzamide TFA salt (0.07 g, 0.11 mmol), pyridine (2 mL) and 2-methylthio-2-imidazoline hydroiodide (0.07 g, 0.28 mmol). LCMS: 90% 254 nm $R_T$=0.769 min, MS (ES) 515 (M+H).

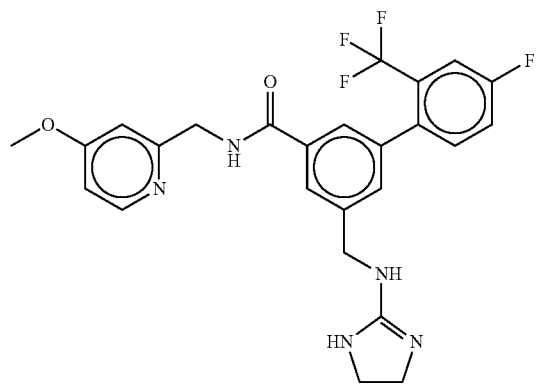

Example 47

5-(((4,5-dihydro-1H-imidazol-2-yl)amino)methyl)-4'-fluoro-N-((4-methoxypyridin-2-yl)methyl)-2'-(trifluoromethyl)-[1,1'-biphenyl]-3-carboxamide Step A. Preparation of methyl 5-(((tert-butoxycarbonyl)amino)methyl)-4'-fluoro-2'-(trifluoromethyl)-[1,1'-biphenyl]-3-carboxylate The title compound was prepared following the procedure described in Example 1, Step B using methyl 3-bromo-5-(((tert-butoxycarbonyl)amino)methyl)benzoate and (4-fluoro-2-(trifluoromethyl)phenyl)boronic acid.

Step B. Preparation of 5-(aminomethyl)-4'-fluoro-N-((4-methoxypyridin-2-yl)methyl)-2'-(trifluoromethyl)-[1,1'-biphenyl]-3-carboxamide The title compound was prepared following the procedure described in Example 1, Step C using methyl 5-(((tert-butoxycarbonyl)amino)methyl)-4'-fluoro-2'-(trifluoromethyl)-[1,1'-biphenyl]-3-carboxylate and (4-methoxypyridin-2-yl)methanamine.

Step B. Example 47

The title compound (0.01 g, 11%) was prepared following the procedure described in Example 1, Step D using 5-(aminomethyl)-4'-fluoro-N-((4-methoxypyridin-2-yl)methyl)-2'-(trifluoromethyl)-[1,1'-biphenyl]-3-carboxamide TFA salt (0.06 g, 0.11 mmol), pyridine (2 mL) and 2-methylthio-2-imidazoline hydroiodide (0.07 g, 0.28 mmol). LCMS: 90% 254 nm $R_T$=0.769 min, MS (ES) 502 (M+H).

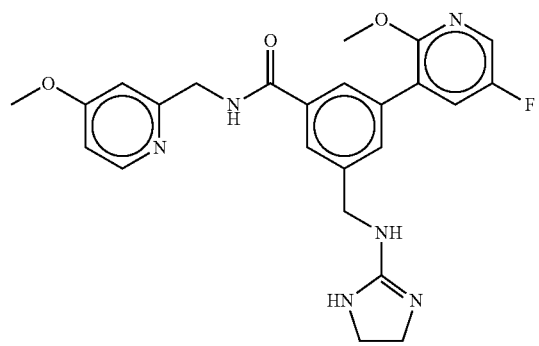

Example 48

3-(((4,5-dihydro-1H-imidazol-2-yl)amino)methyl)-5-(5-fluoro-2-methoxypyridin-3-yl)-N-((4-methoxypyridin-2-yl)methyl)benzamide Step A. Preparation of methyl 3-(((tert-butoxycarbonyl)amino)methyl)-5-(5-fluoro-2-methoxy)pyridin-3-yl)benzoate The title compound was prepared following the procedure described in Example 1, Step B using methyl 3-bromo-5-(((tert-butoxycarbonyl)amino)methyl)benzoate and (5-fluoro-2-methoxypyridin-3-yl)boronic acid.

Step B. Preparation of 3-(aminomethyl)-5-(5-fluoro-2-methoxypyridin-3-yl)-N-((4-methoxypyridin-2-yl)methyl)benzamide The title compound was prepared following the procedure described in Example 1, Step C using 3-(((tert-butoxycarbonyl)amino)methyl)-5-(5-fluoro-2-methoxy)pyridin-3-yl)benzoate and (4-methoxypyridin-2-yl)methanamine.

Step C. Example 48

The title compound (0.01 g, 11%) was prepared following the procedure described in Example 1, Step D using 3-(aminomethyl)-5-(5-fluoro-2-methoxypyridin-3-yl)-N-((4-methoxypyridin-2-yl)methyl)benzamide TFA salt (0.06 g, 0.11 mmol), pyridine (2 mL) and 2-methylthio-2-imidazoline hydroiodide (0.07 g, 0.28 mmol). LCMS: 90% 254 nm $R_T$=0.84 min, MS (ES) 465 (M+H).

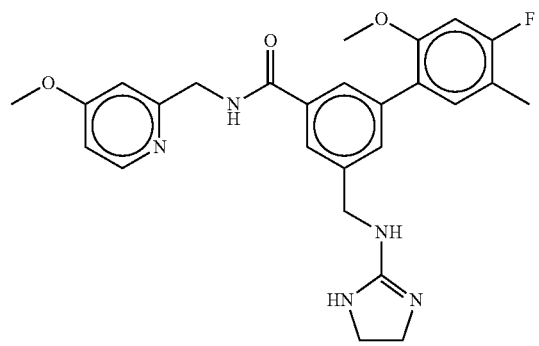

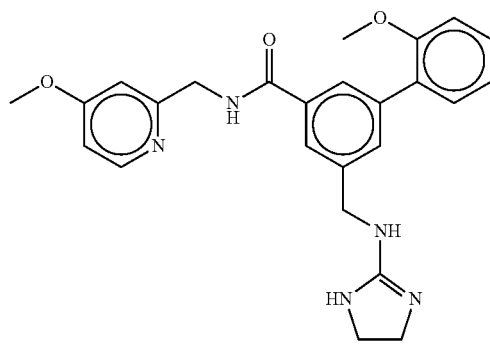

Example 49

5-(((4,5-Dihydro-1H-imidazol-2-yl)amino)methyl)-4'-fluoro-2'-methoxy-N-((4-methoxypyridin-2-yl)methyl)-[1,1'-biphenyl]-3-carboxamide Step A. Preparation of methyl 5-(((tert-butoxycarbonyl)amino)methyl)-4'-fluoro-2'-methoxy-[1,1'-biphenyl]-3-carboxylate The title compound was prepared following the procedure described in Example 1, Step B using methyl 3-bromo-5-(((tert-butoxycarbonyl)amino)methyl)benzoate and (4-fluoro-2-methoxyphenyl)boronic acid.

Step B. Preparation of 5-(aminomethyl)-4'-fluoro-2'-methoxy-N-((4-methoxypyridin-2-yl)methyl)-[1,1'-biphenyl]-3-carboxamide The title compound was prepared following the procedure described in Example 1, Step C using 5-(((tert-butoxycarbonyl)amino)methyl)-4'-fluoro-2'-methoxy-[1,1'-biphenyl]-3-carboxylate and (4-methoxypyridin-2-yl)methanamine.

Step B. Example 49

The title compound (0.01 g, 11%) was prepared following the procedure described in Example 1, Step D using 5-(aminomethyl)-4'-fluoro-2'-methoxy-N-((4-methoxypyridin-2-yl)methyl)-[1,1'-biphenyl]-3-carboxamide TFA salt (0.06 g, 0.11 mmol), pyridine (2 mL) and 2-methylthio-2-imidazoline hydroiodide (0.07 g, 0.28 mmol). LCMS: 90% 254 nm $R_T$=0.84 min, MS (ES) 464 (M+H).

Example 50

5-(((4,5-Dihydro-1H-imidazol-2-yl)amino)methyl)-4'-fluoro-2'-methoxy-N-((4-methoxypyridin-2-yl)methyl)-5'-methyl-[1,1'-biphenyl]-3-carboxamide Step A. Preparation of methyl 5-(((tert-butoxycarbonyl)amino)methyl)-4'-fluoro-2'-methoxy-5'-methyl-[1,1'-biphenyl]-3-carboxylate The title compound was prepared following the procedure described in Example 1, Step B using methyl 3-bromo-5-(((tert-butoxycarbonyl)amino)methyl)benzoate and (4-fluoro-2-methoxy-5-methylphenyl)boronic acid.

Step B. Preparation of 5-(aminomethyl)-4'-fluoro-2'-methoxy-N-((4-methoxypyridin-2-yl)methyl)-5'-methyl-[1,1'-biphenyl]-3-carboxamide The title compound was prepared following the procedure described in Example 1, Step C using 5-(((tert-butoxycarbonyl)amino)methyl)-4'-fluoro-2'-methoxy-[1,1'-biphenyl]-3-carboxylate and (4-methoxypyridin-2-yl)methanamine.

Step B. Example 50

The title compound (0.01 g, 10%) was prepared following the procedure described in Example 1, Step D using 5-(aminomethyl)-4'-fluoro-2'-methoxy-N-((4-methoxypyridin-2-yl)methyl)-5'-methyl-[1,1'-biphenyl]-3-carboxamide TFA salt (0.06 g, 0.11 mmol), pyridine (2 mL) and 2-methylthio-2-imidazoline hydroiodide (0.07 g, 0.28 mmol). LCMS: 90% 254 nm $R_T$=0.768 min, MS (ES) 478 (M+H).

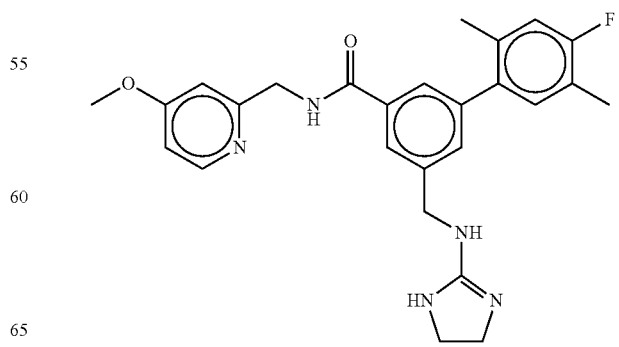

Example 51

5-(((4,5-Dihydro-1H-imidazol-2-yl)amino)methyl)-4'-fluoro-N-((4-methoxypyridin-2-yl)methyl)-2',5'-dimethyl-[1,1'-biphenyl]-3-carboxamide

Step A. Preparation of methyl 5-(((tert-butoxycarbonyl)amino)methyl)-4'-fluoro-2',5'-dimethyl-[1,1'-biphenyl]-3-carboxylate The title compound was prepared following the procedure described in Example 1, Step B using methyl 3-bromo-5-(((tert-butoxycarbonyl)amino)methyl)benzoate and (4-fluoro-2,5-dimethylphenyl)boronic acid.

Step B. Preparation of 5-(aminomethyl)-4'-fluoro-N-((4-methoxypyridin-2-yl)methyl)-2',5'-dimethyl-[1,1'-biphenyl]-3-carboxamide The title compound was prepared following the procedure described in Example 1, Step C using methyl 5-(((tert-butoxycarbonyl)amino)methyl)-4'-fluoro-2',5'-dimethyl-[1,1'-biphenyl]-3-carboxylate and (4-methoxypyridin-2-yl)methanamine.

Step C. Example 50

The title compound (0.01 g, 9%) was prepared following the procedure described in Example 1, Step D using 5-(aminomethyl)-4'-fluoro-N-((4-methoxypyridin-2-yl)methyl)-2',5'-dimethyl-[1,1'-biphenyl]-3-carboxamide TFA salt (0.06 g, 0.11 mmol), pyridine (2 mL) and 2-methylthio-2-imidazoline hydroiodide (0.07 g, 0.28 mmol). LCMS: 90% 254 nm $R_T$=0.785 min, MS (ES) 462 (M+H).

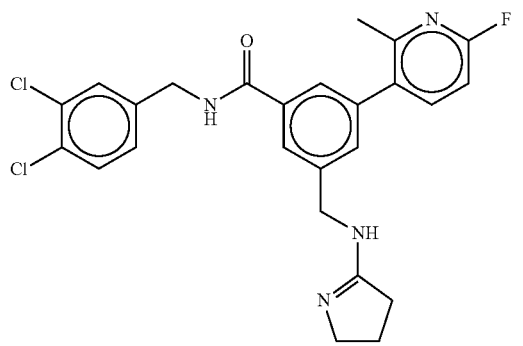

Example 52

N-(3,4-Dichlorobenzyl)-3-(((3,4-dihydro-2H-pyrrol-5-yl)amino)methyl)-5-(6-fluoro-2-methylpyridin-3-yl)benzamide

Step A. Preparation of 3-(aminomethyl)-N-(3,4-dichlorobenzyl)-5-(6-fluoro-2-methylpyridin-3-yl)benzamide The title compound was prepared following the procedure described in Example 1, Step C using methyl 3-(((tert-butoxycarbonyl)amino)methyl)-5-(6-fluoro-2-methylpyridin-3-yl)benzoate and (3,4-dichlorophenyl)methanamine.

Step B. Example 52

3-(Aminomethyl)-N-(3,4-dichlorobenzyl)-5-(6-fluoro-2-methylpyridin-3-yl)benzamide (0.18 mmol) was dissolved in Methanol (4 mL) containing 0.7% acetic acid and 5-methoxy-3,4-dihydro-2H-pyrrole (0.03 g 0.26 mmol) was added. The reaction mixture was heated to 80° C. for 6 h, cooled to ambient temperature and concentrated. The residue was purified by reverse phase HPLC (Phenomenex Gemini C18, H₂O/CH₃CN gradient to 10-40% MeCN 0.1% TFA). The desired fractions were combined and concentrated to dryness. The TFA salt was dissolve in EtOAc, washed with sat. aq. NaHCO₃, dried over MgSO₄, and concentrated to afford the title compound (0.01 g, 3%). LCMS: 98% 254 nm $R_T$=0.95 min, MS (ES) 486 (M+H).

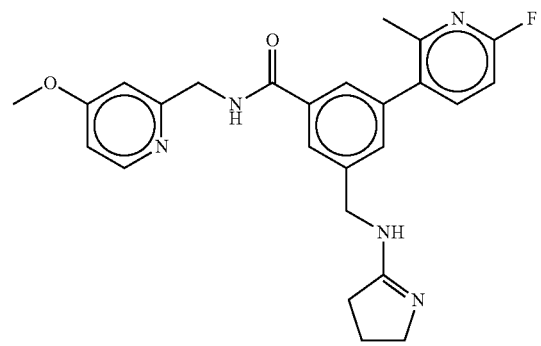

Example 53

3-(((3,4-Dihydro-2H-pyrrol-5-yl)amino)methyl)-5-(6-fluoro-2-methylpyridin-3-yl)-N-((4-methoxypyridin-2-yl)methyl)benzamide

Step A. Preparation of 3-(aminomethyl)-5-(6-fluoro-2-methylpyridin-3-yl)-N-((4-methoxypyridin-2-yl)methyl)benzamide The title compound was prepared following the procedure described in Example 1, Step C using methyl 3-(((tert-butoxycarbonyl)amino)methyl)-5-(6-fluoro-2-methylpyridin-3-yl)benzoate and (4-methoxypyridin-2-yl)methanamine.

Step B. Example 53

The title compound (0.01 g, 3%) was prepared following the procedure described in Example 52, Step B using 3-(aminomethyl)-5-(6-fluoro-2-methylpyridin-3-yl)-N-((4-methoxypyridin-2-yl)methyl)benzamide TFA salt (0.09 g, 0.18 mmol), Methanol (4 mL) containing 0.7% acetic acid and 5-methoxy-3,4-dihydro-2H-pyrrole (0.03 g 0.26 mmol). LCMS: 98% 254 nm $R_T$=0.1 min, MS (ES) 448 (M+H).

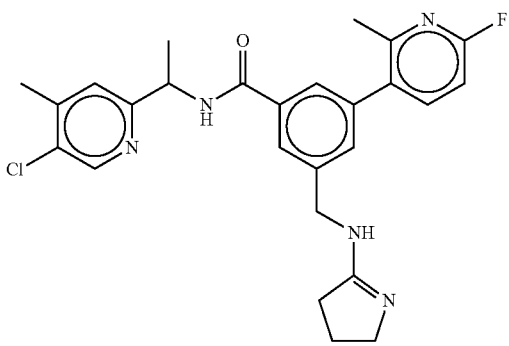

Example 54

N-(1-(5-Chloro-4-methylpyridin-2-yl)ethyl)-3-(((3, 4-dihydro-2H-pyrrol-5-yl)amino)methyl)-5-(6-fluoro-2-methylpyridin-3-yl)benzamide Step A. Preparation of 3-(aminomethyl)-N-(1-(5-chloro-4-methylpyridin-2-yl)ethyl)-5-(6-fluoro-2-methylpyridin-3-yl)benzamide The title compound was prepared following the procedure described in Example 1, Step C using methyl 3-(((tert-butoxycarbonyl)amino)methyl)-5-(6-fluoro-2-methylpyridin-3-yl)benzoate and 1-(5-chloro-4-methylpyridin-2-yl)ethan-1-amine.

Step B. Example 54

The title compound (0.05 g, 62%) was prepared following the procedure described in Example 52, Step B using 3-(aminomethyl)-N-(1-(5-chloro-4-methylpyridin-2-yl)ethyl)-5-(6-fluoro-2-methylpyridin-3-yl)benzamide TFA salt (0.09 g, 0.18 mmol), Methanol (4 mL) containing 0.7% acetic acid and 5-methoxy-3,4-dihydro-2H-pyrrole (0.03 g 0.26 mmol). LCMS: 98% 254 nm $R_T$=0.8 min, MS (ES) 480 (M+H).

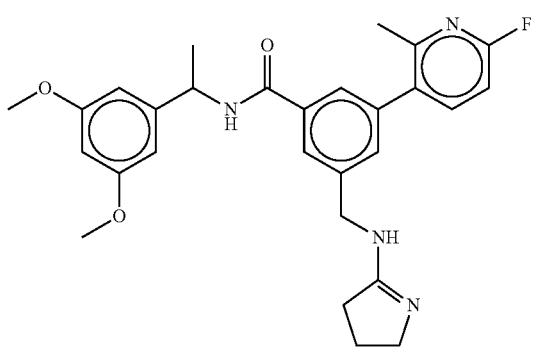

Example 55

3-(((3,4-Dihydro-2H-pyrrol-5-yl)amino)methyl)-N-(1-(3,5-dimethoxyphenyl)ethyl)-5-(6-fluoro-2-methylpyridin-3-yl)benzamide Step A. Preparation of 3-(aminomethyl)-N-(1-(3,5-dimethoxyphenyl)ethyl)-5-(6-fluoro-2-methylpyridin-3-yl)benzamide The title compound was prepared following the procedure described in Example 1, Step C using methyl 3-(((tert-butoxycarbonyl)amino)methyl)-5-(6-fluoro-2-methylpyridin-3-yl)benzoate and 1-(3,5-dimethoxyphenyl)ethan-1-amine.

Step B. Example 55

The title compound (0.04 g, 49%) was prepared following the procedure described in Example 52, Step B using 3-(aminomethyl)-N-(1-(3,5-dimethoxyphenyl)ethyl)-5-(6-fluoro-2-methylpyridin-3-yl)benzamide TFA salt (0.09 g, 0.18 mmol), Methanol (4 mL) containing 0.7% acetic acid and 5-methoxy-3,4-dihydro-2H-pyrrole (0.03 g 0.26 mmol). LCMS: 98% 254 nm $R_T$=0.8 min, MS (ES) 491 (M+H).

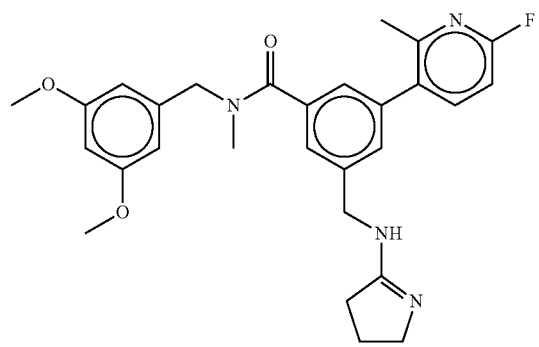

Example 56

3-(((3,4-Dihydro-2H-pyrrol-5-yl)amino)methyl)-N-(3,5-dimethoxybenzyl)-5-(6-fluoro-2-methylpyridin-3-yl)-N-methylbenzamide Step A. Preparation of 3-(aminomethyl)-N-(3,5-dimethoxybenzyl)-5-(6-fluoro-2-methylpyridin-3-yl)-N-methylbenzamide The title compound was prepared following the procedure described in Example 1, Step C using methyl 3-(((tert-butoxycarbonyl)amino)methyl)-5-(6-fluoro-2-methylpyridin-3-yl)benzoate and 1-(3,5-dimethoxyphenyl)-N-methylmethanamine.

Step B. Example 56

The title compound (0.06 g, 66%) was prepared following the procedure described in Example 52, Step B using 3-(aminomethyl)-N-(3,5-dimethoxybenzyl)-5-(6-fluoro-2-methylpyridin-3-yl)-N-methylbenzamide TFA salt (0.09 g, 0.18 mmol), Methanol (4 mL) containing 0.7% acetic acid and 5-methoxy-3,4-dihydro-2H-pyrrole (0.03 g 0.26 mmol). LCMS: 90% 254 nm $R_T$=0.8 min, MS (ES) 491 (M+H).

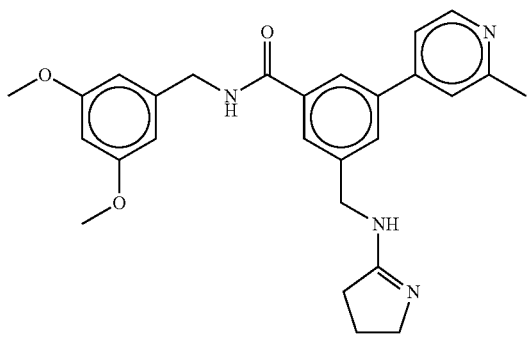

Example 57

3-(((3,4-Dihydro-2H-pyrrol-5-yl)amino)methyl)-N-(3,5-dimethoxybenzyl)-5-(2-methylpyridin-4-yl)benzamide Step A. Preparation of 3-(aminomethyl)-N-(3,5-dimethoxybenzyl)-5-(2-methylpyridin-4-yl)benzamide The title compound was prepared following the procedure described in Example 1, Step C using methyl methyl 3-(((tert-butoxycarbonyl)amino)methyl)-5-(2-methylpyridin-4-yl)benzoate and (3,5-dimethoxyphenyl)methanamine.

Step B. Example 56

The title compound (0.10 g, 55%) was prepared following the procedure described in Example 52, Step B using 3-(aminomethyl)-N-(3,5-dimethoxybenzyl)-5-(2-methyl-pyridin-4-yl)benzamide TFA salt (0.20 g, 0.40 mmol), Methanol (5 mL) containing 0.7% acetic acid and 5-methoxy-3,4-dihydro-2H-pyrrole (0.08 g 0.80 mmol). LCMS: 98% 254 nm $R_T$=1.0 min, MS (ES) 459 (M+H).

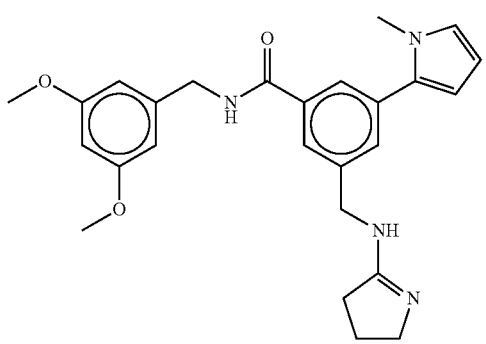

Example 58

3-(((3,4-Dihydro-2H-pyrrol-5-yl)amino)methyl)-N-(3,5-dimethoxybenzyl)-5-(1-methyl-1H-pyrrol-2-yl)benzamide Step A. Preparation of methyl 5-((((tert-butoxycarbonyl)amino)methyl)-4'-fluoro-2',5'-dimethyl-[1,1'-biphenyl]-3-carboxylate The title compound was prepared following the procedure described in Example 1, Step B using methyl 3-bromo-5-(((tert-butoxycarbonyl)amino)methyl)benzoate and 1-methyl-2-(4,4,5,5-tetramethyl-1,3,2-dioxaborolan-2-yl)-1H-pyrrole.

Step B. Preparation of 3-(aminomethyl)-N-(3,5-dimethoxybenzyl)-5-(1-methyl-1H-pyrrol-2-yl)benzamide The title compound was prepared following the procedure described in Example 1, Step C using methyl 5-(((tert-butoxycarbonyl)amino)methyl)-4'-fluoro-2',5'-dimethyl-[1,1'-biphenyl]-3-carboxylate and (3,5-dimethoxyphenyl)methanamine.

Step C. Example 58

The title compound (0.03 g, 23%) was prepared following the procedure described in Example 52, Step B 3-(aminomethyl)-N-(3,5-dimethoxybenzyl)-5-(1-methyl-1H-pyrrol-2-yl)benzamide TFA salt (0.16 g, 0.33 mmol), Methanol (5 mL) containing 0.7% acetic acid and 5-methoxy-3,4-dihydro-2H-pyrrole (0.08 g 0.80 mmol). LCMS: 90% 254 nm $R_T$=0.89 min, MS (ES) 447 (M+H).

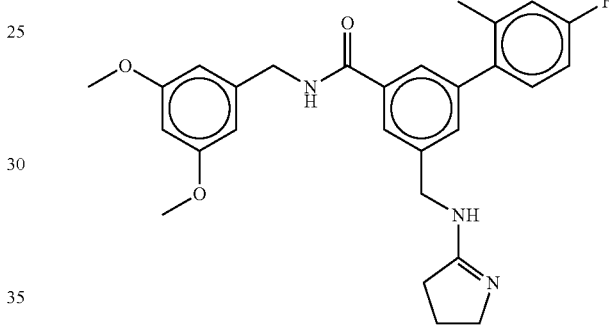

Example 59

5-(((3,4-Dihydro-2H-pyrrol-5-yl)amino)methyl)-N-(3,5-dimethoxybenzyl)-4'-fluoro-2'-methyl-[1,1'-biphenyl]-3-carboxamide The title compound (0.01 g, 6%) was prepared following the procedure described in Example 52, Step B 5-(aminomethyl)-N-(3,5-dimethoxybenzyl)-4'-fluoro-2'-methyl-[1,1'-biphenyl]-3-carboxamide TFA salt (0.21 g, 0.40 mmol), Methanol (5 mL) containing 0.7% acetic acid and 5-methoxy-3,4-dihydro-2H-pyrrole (0.08 g 0.80 mmol). LCMS: 98% 254 nm $R_T$=0.95 min, MS (ES) 476 (M+H).

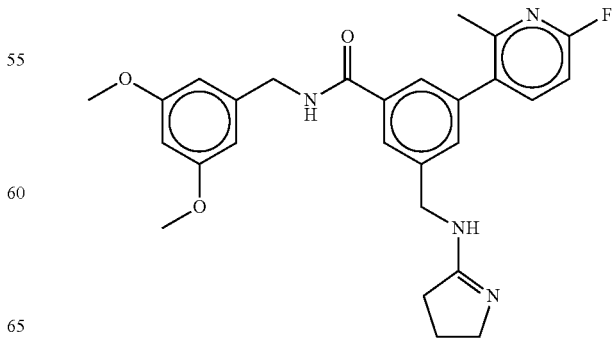

Example 60

3-(((3,4-Dihydro-2H-pyrrol-5-yl)amino)methyl)-N-(3,5-dimethoxybenzyl)-5-(6-fluoro-2-methylpyridin-3-yl)benzamide

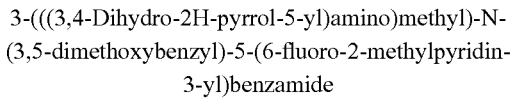

The title compound (0.03 g, 15%) was prepared following the procedure described in Example 52, Step B 3-(aminomethyl)-N-(3,5-dimethoxybenzyl)-5-(6-fluoro-2-methylpyridin-3-yl)benzamide TFA salt (0.21 g, 0.40 mmol), Methanol (5 mL) containing 0.7% acetic acid and 5-methoxy-3,4-dihydro-2H-pyrrole (0.08 g 0.80 mmol). LCMS: 90% 254 nm $R_T$=0.81 min, MS (ES) 477 (M+H).

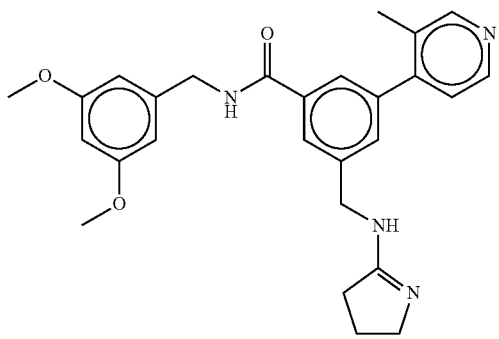

Example 61

3-(((3,4-Dihydro-2H-pyrrol-5-yl)amino)methyl)-N-(3,5-dimethoxybenzyl)-5-(3-methylpyridin-4-yl)benzamide Step A. Preparation of 3-(aminomethyl)-N-(3,5-dimethoxybenzyl)-5-(3-methylpyridin-4-yl)benzamide The title compound was prepared following the procedure described in Example 1, Step C using methyl methyl 3-(((tert-butoxycarbonyl)amino)methyl)-5-(3-methylpyridin-4-yl)benzoate and (3,5-dimethoxyphenyl)methanamine.

Step B. Example 56

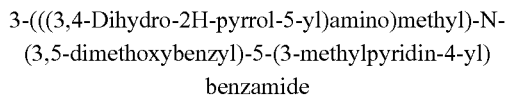

The title compound (0.01 g, 4%) was prepared following the procedure described in Example 52, Step B using 3-(aminomethyl)-N-(3,5-dimethoxybenzyl)-5-(3-methylpyridin-4-yl)benzamide TFA salt (0.20 g, 0.40 mmol), Methanol (5 mL) containing 0.7% acetic acid and 5-methoxy-3,4-dihydro-2H-pyrrole (0.08 g 0.80 mmol). LCMS: 98% 254 nm $R_T$=1.0 min, MS (ES) 459 (M+H).

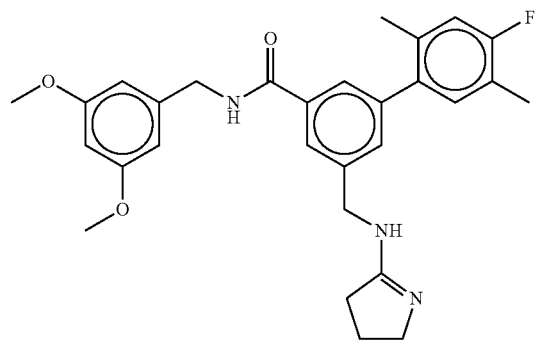

Example 62

5-(((3,4-Dihydro-2H-pyrrol-5-yl)amino)methyl)-N-(3,5-dimethoxybenzyl)-4'-fluoro-2',5'-dimethyl-[1,1'-biphenyl]-3-carboxamide Step A. Preparation of 5-(aminomethyl)-N-(3,5-dimethoxybenzyl)-4'-fluoro-2',5'-dimethyl-[1,1'-biphenyl]-3-carboxamide The title compound was prepared following the procedure described in Example 1, Step C using methyl 5-(((tert-butoxycarbonyl)amino)methyl)-4'-fluoro-2',5'-dimethyl-[1,1'-biphenyl]-3-carboxylate and (3,5-dimethoxyphenyl)methanamine.

Step B. Example 50

The title compound (0.06 g, 35%) was prepared following the procedure described in Example 52, Step B using 5-(aminomethyl)-N-(3,5-dimethoxybenzyl)-4'-fluoro-2',5'-dimethyl-[1,1'-biphenyl]-3-carboxamide TFA salt (0.19 g, 0.35 mmol), Methanol (5 mL) containing 0.7% acetic acid and 5-methoxy-3,4-dihydro-2H-pyrrole (0.08 g 0.80 mmol). LCMS: 98% 254 nm $R_T$=0.99 min, MS (ES) 490 (M+H).

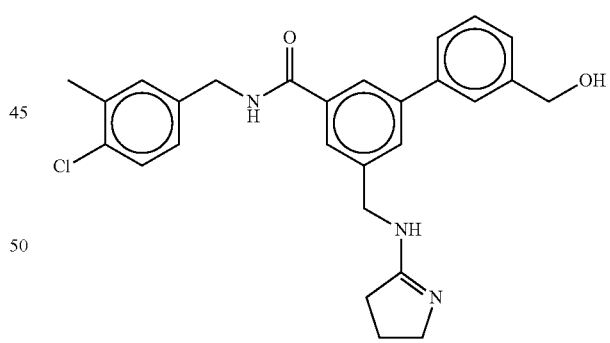

Example 63

N-(4-Chloro-3-methylbenzyl)-5-(((3,4-dihydro-2H-pyrrol-5-yl)amino)methyl)-3'-(hydroxymethyl)-[1,1'-biphenyl]-3-carboxamide Step A. Preparation of methyl 5-(((tert-butoxycarbonyl)amino)methyl)-3'-(hydroxymethyl)-[1,1'-biphenyl]-3-carboxylate The title compound was prepared following the procedure described in Example 1, Step B using methyl 3-bromo-5-

(((tert-butoxycarbonyl)amino)methyl)benzoate and (3-(hydroxymethyl)phenyl)boronic acid.

Step B. Preparation of 5-(aminomethyl)-N-(4-chloro-3-methylbenzyl)-3'-(hydroxymethyl)-[1,1'-biphenyl]-3-carboxamide The title compound was prepared following the procedure described in Example 1, Step C using methyl 5-(((tert-butoxycarbonyl)amino)methyl)-3'-(hydroxymethyl)-[1,1'-biphenyl]-3-carboxylate and (4-chloro-3-methylphenyl)methanamine.

Step C. Example 63

The title compound (0.05 g, 34%) was prepared following the procedure described in Example 52, Step B using 5-(aminomethyl)-N-(4-chloro-3-methylbenzyl)-3'-(hydroxymethyl)-[1,1'-biphenyl]-3-carboxamide TFA salt (0.15 g, 0.30 mmol), Methanol (5 mL) containing 0.7% acetic acid and 5-methoxy-3,4-dihydro-2H-pyrrole (0.06 g 0.60 mmol). LCMS: 98% 254 nm $R_T$=0.88 min, MS (ES) 464 (M+H).

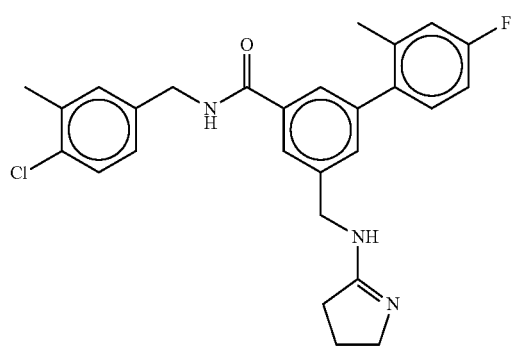

Example 64

N-(4-Chloro-3-methylbenzyl)-5-(((3,4-dihydro-2H-pyrrol-5-yl)amino)methyl)-4'-fluoro-2'-methyl-[1,1'-biphenyl]-3-carboxamide Step A. Preparation of 5-(aminomethyl)-N-(4-chloro-3-methylbenzyl)-4'-fluoro-2'-methyl-[1,1'-biphenyl]-3-carboxamide The title compound was prepared following the procedure described in Example 1, Step C using methyl 5-(((tert-butoxycarbonyl)amino)methyl)-4'-fluoro-2'-methyl-[1,1'-biphenyl]-3-carboxylate and (4-chloro-3-methylphenyl)methanamine.

Step B. Example 64

The title compound (0.07 g, 48%) was prepared following the procedure described in Example 52, Step B using 5-(aminomethyl)-N-(4-chloro-3-methylbenzyl)-4'-fluoro-2'-methyl-[1,1'-biphenyl]-3-carboxamide TFA salt (0.15 g, 0.30 mmol), Methanol (5 mL) containing 0.7% acetic acid and 5-methoxy-3,4-dihydro-2H-pyrrole (0.06 g 0.60 mmol). LCMS: 98% 254 nm $R_T$=0.90 min, MS (ES) 465 (M+H).

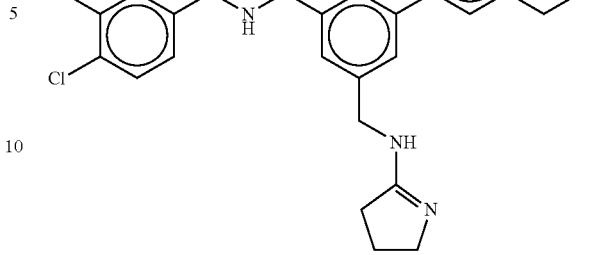

Example 65

N-(4-chloro-3-methylbenzyl)-5-(((3,4-dihydro-2H-pyrrol-5-yl)amino)methyl)-4'-fluoro-3'-(hydroxymethyl)-[1,1'-biphenyl]-3-carboxamide Step A. Preparation of methyl 5-(((tert-butoxycarbonyl)amino)methyl)-4'-fluoro-3'-(hydroxymethyl)-[1,1'-biphenyl]-3-carboxylate The title compound was prepared following the procedure described in Example 1, Step B using methyl 3-bromo-5-(((tert-butoxycarbonyl)amino)methyl)benzoate and (4-fluoro-3-(hydroxymethyl)phenyl)boronic acid.

Step B. Preparation of 5-(aminomethyl)-N-(4-chloro-3-methylbenzyl)-4'-fluoro-3'-(hydroxymethyl)-[1,1'-biphenyl]-3-carboxamide The title compound was prepared following the procedure described in Example 1, Step C using methyl 5-(((tert-butoxycarbonyl)amino)methyl)-4'-fluoro-3'-(hydroxymethyl)-[1,1'-biphenyl]-3-carboxylate and (4-chloro-3-methylphenyl)methanamine.

Step B. Example 65

The title compound (0.07 g, 46%) was prepared following the procedure described in Example 52, Step B using 5-(aminomethyl)-N-(4-chloro-3-methylbenzyl)-4'-fluoro-3'-(hydroxymethyl)-[1,1'-biphenyl]-3-carboxamide TFA salt (0.16 g, 0.30 mmol), Methanol (5 mL) containing 0.7% acetic acid and 5-methoxy-3,4-dihydro-2H-pyrrole (0.06 g 0.60 mmol). LCMS: 98% 254 nm $R_T$=0.90 min, MS (ES) 480 (M+H).

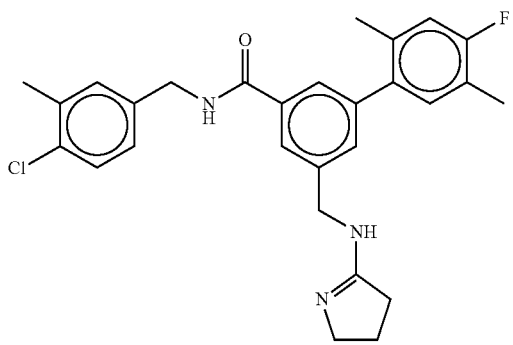

Example 66

N-(4-Chloro-3-methylbenzyl)-5-(((3,4-dihydro-2H-pyrrol-5-yl)amino)methyl)-4'-fluoro-2',5'-dimethyl-[1,1'-biphenyl]-3-carboxamide

Step A. Preparation of 5-(aminomethyl)-N-(4-chloro-3-methylbenzyl)-4'-fluoro-2'-methyl-[1,1'-biphenyl]-3-carboxamide The title compound was prepared following the procedure described in Example 1, Step C using methyl 5-(((tert-butoxycarbonyl)amino)methyl)-4'-fluoro-2',5'-dimethyl-[1,1'-biphenyl]-3-carboxylate and (4-chloro-3-methylphenyl)methanamine.

Step B. Example 66

The title compound (0.06 g, 41%) was prepared following the procedure described in Example 52, Step B using 5-(aminomethyl)-N-(4-chloro-3-methylbenzyl)-4'-fluoro-2',5'-dimethyl-[1,1'-biphenyl]-3-carboxamide TFA salt (0.16 g, 0.30 mmol), Methanol (5 mL) containing 0.7% acetic acid and 5-methoxy-3,4-dihydro-2H-pyrrole (0.06 g 0.60 mmol). LCMS:
98% 254 nm $R_T$=1.0 min, MS (ES) 480 (M+H).

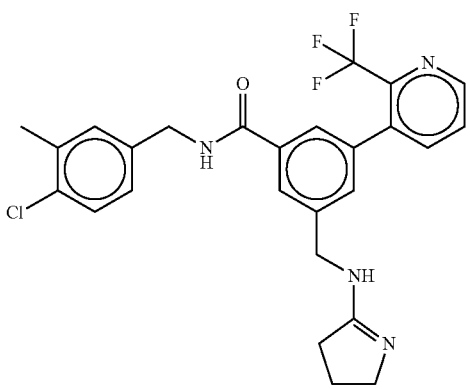

Example 67

N-(4-Chloro-3-methylbenzyl)-3-(((3,4-dihydro-2H-pyrrol-5-yl)amino)methyl)-5-(2-(trifluoromethyl)pyridin-3-yl)benzamide

Step A. Preparation of methyl 3-(((tert-butoxycarbonyl)amino)methyl)-5-(2-(trifluoromethyl)pyridin-3-yl)benzoate The title compound was prepared following the procedure described in Example 1, Step B using methyl 3-bromo-5-(((tert-butoxycarbonyl)amino)methyl)benzoate and (2-(trifluoromethyl)pyridin-3-yl)boronic acid.

Step B. Preparation of 3-(aminomethyl)-N-(4-chloro-3-methylbenzyl)-5-(2-(trifluoromethyl)pyridin-3-yl)benzamide The title compound was prepared following the procedure described in Example 1, Step C using methyl 5-(((tert-butoxycarbonyl)amino)methyl)-4'-fluoro-2',5'-dimethyl-[1,1'-biphenyl]-3-carboxylate and (4-chloro-3-methylphenyl)methanamine.

Step C. Example 67

The title compound (0.07 g, 50%) was prepared following the procedure described in Example 52, Step B using 3-(aminomethyl)-N-(4-chloro-3-methylbenzyl)-5-(2-(trifluoromethyl)pyridin-3-yl)benzamide TFA salt (0.16 g, 0.33 mmol), Methanol (5 mL) containing 0.7% acetic acid and 5-methoxy-3,4-dihydro-2H-pyrrole (0.08 g 0.80 mmol). $^1$H NMR (400 MHz, d$_6$ DMSO) δ 9.1 (t, 1H, J=6.1 Hz), 8.8 (d, 1H, J=4.2 Hz), 7.9 (m, 2H), 7.8 (m, 2H), 7.5 (s, 1H), 7.4 (d, 1H, J=8.5 Hz) 7.3, (s, 1H), 7.2 (m, 1H), 4.5 (s, 2H), 4.4 (d, 2H, J=5.8 Hz), 3.5, (t, 2H, J=7.2 Hz), 2.6 (m, 2H), 2.3 (s, 3H), 2.0 (t, 2H, J=7.2 Hz); LCMS: 98% 254 nm, MS (ES) 501 (M+H).

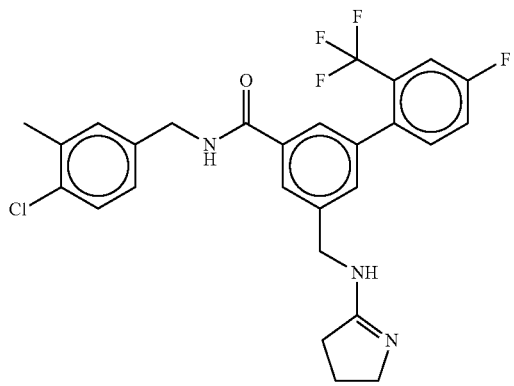

Example 68

N-(4-chloro-3-methylbenzyl)-5-(((3,4-dihydro-2H-pyrrol-5-yl)amino)methyl)-4'-fluoro-2'-(trifluoromethyl)-[1,1'-biphenyl]-3-carboxamide

Step A. Preparation of 5-(aminomethyl)-N-(4-chloro-3-methylbenzyl)-4'-fluoro-2'-(trifluoromethyl)-[1,1'-biphenyl]-3-carboxamide The title compound was prepared following the procedure described in Example 1, Step C using methyl 5-(((tert-butoxycarbonyl)amino)methyl)-4'-fluoro-2'-(trifluoromethyl)-[1,1'-biphenyl]-3-carboxylate and (4-chloro-3-methylphenyl)methanamine.

Step B. Example 68

The title compound (0.07 g, 47%) was prepared following the procedure described in Example 52, Step B using 5-(aminomethyl)-N-(4-chloro-3-methylbenzyl)-4'-fluoro-2'-(trifluoromethyl)-[1,1'-biphenyl]-3-carboxamide TFA salt (0.16 g, 0.33 mmol), Methanol (5 mL) containing 0.7% acetic acid and 5-methoxy-3,4-dihydro-2H-pyrrole (0.08 g 0.80 mmol). $^1$H NMR (400 MHz, d$_6$ DMSO) δ 9.1 (t, 1H, J=5.9), 8.0 (s, 1H), 7.8 (m, 2H), 7.7 (m, 1H), 7.5 (m, 1H), 7.4 (s, 1H), 7.3 (d, 1H, J=7.0 Hz), 7.2 (s, 1H), 7.1 (d, 1H, J=8.2 Hz), 4.6 (s, 2H), 4.4 (d, 2H, J=5.9 Hz), 3.6 (t, 2H, J=6.8 Hz), 2.7 (t, 2H, J=8.2 Hz), 2.3 (s, 3H), 2.0 (m, 2H).; LCMS: 98% 254 nm, MS (ES) 518 (M+H).

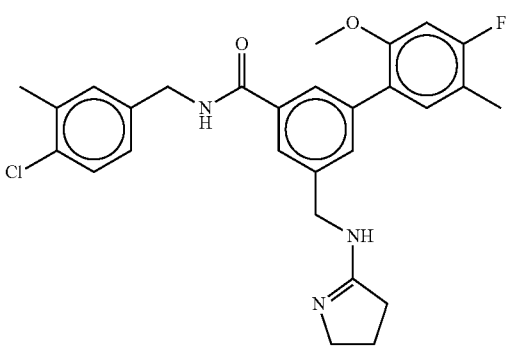

Example 69

N-(4-Chloro-3-methylbenzyl)-5-(((3,4-dihydro-2H-pyrrol-5-yl)amino)methyl)-4'-fluoro-2'-methoxy-5'-methyl-[1,1'-biphenyl]-3-carboxamide Step A. Preparation of 5-(aminomethyl)-N-(4-chloro-3-methylbenzyl)-4'-fluoro-2'-methoxy-5'-methyl-[1,1'-biphenyl]-3-carboxamide The title compound was prepared following the procedure described in Example 1, Step C using methyl 5-(((tert-butoxycarbonyl)amino)methyl)-4'-fluoro-2'-methoxy-5'-methyl-[1,1'-biphenyl]-3-carboxylate and (4-chloro-3-methylphenyl)methanamine.

Step B. Example 69

The title compound (0.02 g, 16%) was prepared following the procedure described in Example 52, Step B using 5-(aminomethyl)-N-(4-chloro-3-methylbenzyl)-4'-fluoro-2'-methoxy-5'-methyl-[1,1'-biphenyl]-3-carboxamide TFA salt (0.16 g, 0.33 mmol), Methanol (5 mL) containing 0.7% acetic acid and 5-methoxy-3,4-dihydro-2H-pyrrole (0.08 g 0.80 mmol). $^1$H NMR (400 MHz, $d_6$ DMSO) δ 9.1 (t, 1H, J=5.8 Hz), 7.9 (s, 1H), 7.8 (s, 1H), 7.5 (s, 1H), 7.4 (d, 1H, J=8.1 Hz)), 7.3 (s, 1H), 7.2 (d, 1H, J=8.1 Hz), 7.1 (d, 1H, J=8.1 Hz), 7.0 (d, 1H, J=12.2 Hz), 4.5 (s, 2H), 4.4 (d, 2H, J=6.0 Hz), 3.7 (s, 3H), 3.6 (t, 2H, J=6.9 Hz), 2.7 (t, 2H, J=8.0 Hz), 2.3 (s, 3H), 2.2 (s, 3H), 2.0 (t, 2H, J=6.9); LCMS: 98% 254 nm, MS (ES) 495 (M+H).

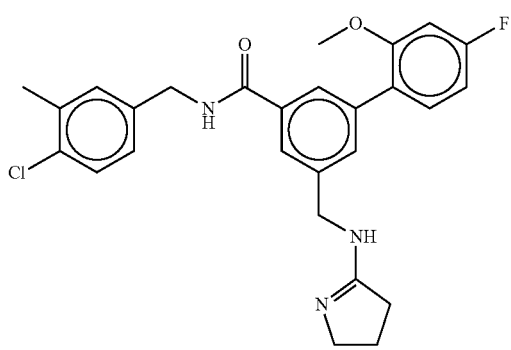

Example 70

N-(4-chloro-3-methylbenzyl)-5-(((3,4-dihydro-2H-pyrrol-5-yl)amino)methyl)-4'-fluoro-2'-methoxy-[1,1'-biphenyl]-3-carboxamide Step A. Preparation of 5-(aminomethyl)-N-(4-chloro-3-methylbenzyl)-4'-fluoro-2'-methoxy-[1,1'-biphenyl]-3-carboxamide The title compound was prepared following the procedure described in Example 1, Step C using methyl 5-(((tert-butoxycarbonyl)amino)methyl)-4'-fluoro-2'-methoxy-[1,1'-biphenyl]-3-carboxylate and (4-chloro-3-methylphenyl)methanamine.

Step B. Example 70

The title compound (0.03 g, 23%) was prepared following the procedure described in Example 52, Step B using 5-(aminomethyl)-N-(4-chloro-3-methylbenzyl)-4'-fluoro-2'-methoxy-[1,1'-biphenyl]-3-carboxamide TFA salt (0.16 g, 0.33 mmol), Methanol (5 mL) containing 0.7% acetic acid and 5-methoxy-3,4-dihydro-2H-pyrrole (0.06 g 0.60 mmol). $^1$H NMR (400 MHz, $d_6$ DMSO) δ 9.0 (t, 1H, J=5.6 Hz), 7.9 (s, 1H), 7.8 (s, 1H), 7.6 (s, 1H), 7.4 (m, 2H), 7.3 (s, 1H), 7.2 (d, 1H, J=9.4 Hz), 7.0 (d, 1H, J=11.8 Hz), 6.9 (m, 1H), 4.4 (m, 4H), 3.8 (s, 3H), 3.5 (t, 2H, J=7.1 Hz), 2.6 (t, 2H, J=8.2 Hz), 2.3 (s, 3H), 1.9 (m, 2H); LCMS: 98% 254 nm, MS (ES) 480 (M+H).

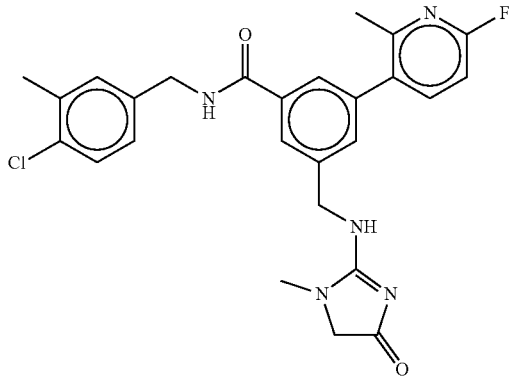

Example 71

N-(4-Chloro-3-methylbenzyl)-3-(6-fluoro-2-methylpyridin-3-yl)-5-(((1-methyl-4-oxo-4,5-dihydro-1H-imidazol-2-yl)amino)methyl)benzamide Step A. Preparation of N-(4-chloro-3-methylbenzyl)-3-(6-fluoro-2-methylpyridin-3-yl)-5-(hydroxymethyl)benzamide The title compound was prepared following the procedure described in Example 43, Step B using 3-(6-fluoro-2-methylpyridin-3-yl)-5-(hydroxymethyl)benzoic acid, TEA, EDC, HOBT, and (4-chloro-3-methylphenyl)methanamine.

Step B. Preparation of 3-(bromomethyl)-N-(4-chloro-3-methylbenzyl)-5-(6-fluoro-2-methylpyridin-3-yl)benzamide The title compound was prepared following the procedure described in Example 43, Step C using N-(4-chloro-3- methylbenzyl)-3-(6-fluoro-2-methylpyridin-3-yl)-5-(hydroxymethyl)benzamide and 1N Phosphorus tribromide.

Step C. Example 71

The title compound (0.03 g, 46%) was prepared following the procedure described in Example 43, Step D 3-(bromomethyl)-N-(4-chloro-3-methylbenzyl)-5-(6-fluoro-2-methylpyridin-3-yl)benzamide (0.06 g, 0.13 mmol), DIEA (0.06 mL, 0.26 mmol), 2-amino-1-methyl-1,5-dihydro-4H-imidazol-4-one HCl salt (0.03 g, 0.23 mmol) and acetonitrile (4 mL) afforded the title compound (0.03 g, 46%). LCMS: 98% 254 nm R$_T$=0.92 min, MS (ES) 494 (M+H).

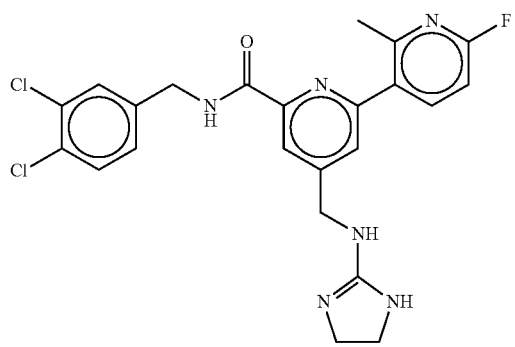

Example 72

N-(3,4-Dichlorobenzyl)-4-(((4,5-dihydro-1H-imidazol-2-yl)amino)methyl)-6'-fluoro-2'-methyl-[2,3'-bipyridine]-6-carboxamide Step A. Preparation of methyl 4-(bromomethyl)-6-chloropicolinate A solution of methyl 6-chloro-4-methylpicolinate (6.00 g, 32.40 mmol) in CCl$_4$ (350 mL) and chlorobenzene (100 mL) was refluxed through a Dean Stark trap to remove trace amount of water. The solution was cooled to ambient temperature and treated with N-Bromosuccinimide (NBS) (8.60 g, 48.6 mmol) and 2,2'azobis(2-methylpropionitrile (AIBN, 0.53 g, 3.24 mmol). The solution was heated to reflux for 18 h. An additional amount of NBS (8.00 g, 44.94 mmol) and AIBN (0.50 g, 3.0 mmol) was added and refluxing continued for an additional 6 h. The mixture was cooled to ambient temperature and concentrated under reduced pressure to approximately 25% of the original volume. The mixture was filtered and the filtrate was concentrated under reduced pressure. The residue was purified by flash chromatography (Combi-flash Rf, Hex/EtOAc=0-100% gradient) to afford the title compound (1.4 g 16%): $^1$H NMR (400 MHz, d$_6$ DMSO) δ 8.07 (s, 1H), 7.82 (s, 1H), 4.71 (s, 2H), 3.83 (s, 3H).

Step B. Preparation of methyl 4-(((tert-butoxycarbonyl)amino)methyl)-6-chloropicolinate A solution methyl 4-(bromomethyl)-6-chloropicolinate (3.70 g, 14.1 mmol) and sodium azide (1.91 g, 28.1 mmol) in 90% methanol/water (110 mL) was heated to reflux for 4 h. The solution was cooled to ambient temperature and the solvent was removed under reduced pressure. The crude was dissolved in DCM, washed with water, dried over MgSO$_4$, filtered and concentrated. The crude methyl 4-(azidomethyl)-6-chloropicolinate was dissolved in EtOH (100 mL) and treated with Ra—Ni (0.30 g, cat) and then stirred under atmospheric hydrogen for 3 h. The reaction mixture was filtered and the filtrate was concentrated under reduced pressure. The crude methyl 4-(aminomethyl)-6-chloropicolinate was dissolved in THF (100 mL), treated with DIPEA (3.20 mL, 21.0 mmol) and (Boc)$_2$O (3.37 g, 15.4 mmol). The solution was stirred for 18 h then concentrated in vacuo. The residue was purified by flash chromatography (Combi-flash Rf, Hex/EtOAc=0-100% gradient) to afford the title compound (1.1 g, 26%): $^1$H NMR (400 MHz, d$_6$ DMSO) δ 7.95 (s, 1H), 7.61 (s, 2H), 4.26 (d, 2H, J=6.76 Hz), 3.90 (s, 3H), 1.41 (s, 9H).

Step C. Preparation of 4-(((tert-butoxycarbonyl)amino)methyl)-6-chloropicolinic Acid A solution of methyl 4-(((tert-butoxycarbonyl)amino) methyl)-6-chloropicolinate (0.83, 2.76 mmol) in THF (40 mL)/MeOH (5 mL)/water (5 mL) was treated with 2M aq. LiOH (2.52 mL, 3.04 mmol). The reaction mixture was stirred for 6 h, concentrated and diluted with water. The solution was acidified with 1N HCl to pH=4 then concentrated under reduced pressure to give the crude title compound, which was used without further purification (0.75 g, 95%).

Step D. Preparation of tert-butyl ((2-chloro-6-((3,4-dichlorobenzyl)carbamoyl)pyridin-4-yl)methyl)carbamate A solution of 4-(((tert-butoxycarbonyl)amino)methyl)-6-chloropicolinic acid (0.27 g, 0.94 mmol) in DMF (5 mL) was treated with DIPEA (0.41 mL, 2.35 mmol) and HATU (0.38 g, 0.99 mmol). The solution was stirred for 5 min and then treated with (3,4-dichlorophenyl)methanamine (0.18 g, 1.03 mmol). Stirring continued for 18 h and the mixture was concentrated under reduced pressure. The crude was dissolved in EtOAc, extracted with water, dried over MgSO$_4$, filtered, and the solvent removed under reduced pressure. The residue was purified by flash chromatography (Combi-flash Rf, DCM/MeOH=0-3% gradient) to afford the title compound (0.34 g, 81%). $^1$H NMR (400 MHz, d$_6$ DMSO) δ 9.36 (t, 1H, J=6.3), 7.93 (s, 1H), 7.59 (m, 3H), 7.32 (d, 1H J=8.3), 4.47 (d, 2H, J=6.40), 4.25 (d, 2H, J=6.2), 1.40 (s, 9H).

Step E. Preparation of tert-butyl ((6-((3,4-dichlorobenzyl)carbamoyl)-6'-fluoro-2'-methyl-[2,3'-bipyridin]-4-yl)methyl)carbamate Argon gas was bubbled into a mixture of tert-butyl ((2-chloro-6-((3,4-dichlorobenzyl)carbamoyl)pyridin-4-yl) methyl)carbamate (0.74 g, 1.67 mmol), K$_2$CO$_3$ (0.57 g, 4.18 mmol) in 80% 1,4-dioxane/water (40 mL) for 5 min. Tetrakis (triphenylphosphine)palladium (0) (0.04 g, 0.04 mmol) and (6-fluoro-2-methylpyridin-3-yl)boronic acid (0.19 g, 0.17 mmol) were added to the mixture, and the reaction was heated to 80° C. for 4 h. The reaction was cooled to ambient temperature, and the solvent was removed under reduced pressure. The crude was dissolved in DCM, washed with water, dried over MgSO$_4$, filtered and concentrated under reduced pressure. The residue was purified by flash chromatography (Combi-flash Rf, Hex/EtOAc=0-80% gradient) to afford the title compound (0.64 g, 73%): $^1$H NMR (400 MHz, d$_6$ DMSO) δ 9.39 (t, 1H, J=5.97), 8.15 (t, 1H, J=8.2), 7.97 (s, 1H), 7.67 (s, 1H), 7.59 (m, 2H), 7.32 (d, 1H, J=8.7), 7.17 (d, 1H, J=8.4), 4.50 (d, 2H, J=6.4), 4.31 (d, 2H, J=5.83), 2.00 (s, 3H), 1.41 (s, 9H).

Step F. Example 72

A solution of tert-butyl ((6-((3,4-dichlorobenzyl)carbamoyl)-6'-fluoro-2'-methyl-[2,3'-bipyridin]-4-yl)methyl)carbamate (0.64 g, 1.52 mmol) in DCM (20 mL) was treated with TFA (10 mL), stirred for 1 h, and concentrated under reduced pressure. The crude was dissolved in pyridine (24 mL) and transferred to a microwave reaction vessel. The solution was treated with 2-methylthio-2-imidazoline hydroiodide (0.56 g, 2.28 mmol) and heated on a microwave reactor at 125° C. for 1 h. The reaction was cooled to ambient temperature and the solvent removed under reduced pressure. The crude material was purified by reverse phase HPLC (Phenomenex Gemini C18, $H_2O/CH_3CN$ gradient to 10-95 MeCN 0.1% TFA). The desired fractions were combined and concentrated to dryness. The product was dissolved in EtOAc and washed with sat. aq. $NaHCO_3$. The organic layer was dried and concentrated to afford the title compound (0.44 g 60%). $^1$H NMR (400 MHz, $d_6$ DMSO) δ 9.45 (t, 1H, J=6.5), 8.02 (s, 1H), 7.74 (s, 1H), 7.59 (m, 2H), 7.32 (d, 1H, J=8.3), 7.20 (d, 1H, J=8.4), 4.59 (s, 2H), 4.51 (d, 2H, J=6.3), 3.62 (s, 4H), 2.55 (s, 3H); LC-MS=98% (215, 254 nm), $R_T$=0.94 min., m/z=488.1 [M+1]. LCMS: >95% 254 nm $R_T$=0.829 min, MS (ES) 488 (M+H).

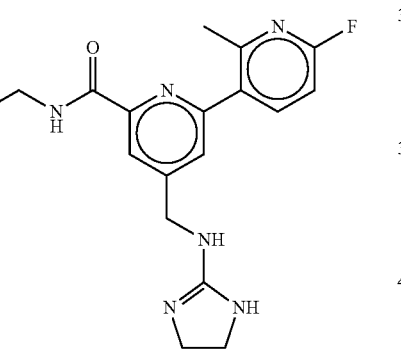

Example 73

N-(4-Chloro-3-fluorobenzyl)-4-(((4,5-dihydro-1H-imidazol-2-yl)amino)methyl)-6'-fluoro-2'-methyl-[2,3'-bipyridine]-6-carboxamide

Step A. Preparation of tert-butyl ((2-chloro-6-((4-chloro-3-fluorobenzyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (4-chloro-3-fluorophenyl)methanamine.

Step B. Preparation of tert-butyl ((6-((4-chloro-3-fluorobenzyl)-6'-fluoro-2'-methyl-[2,3'-bipyridin]-4-yl)methyl)carbamate The title compound was prepared from the procedure described in Example 72, Step E using tert-butyl ((2-chloro-6-((4-chloro-3-fluorobenzyl)carbamoyl)pyridin-4-yl)methyl)carbamate.

Step C. Example 73

The title compound (0.01 g, 17%) was prepared from the procedure described in Example 72, Step F using tert-butyl ((6-((4-chloro-3-fluorobenzyl)-6'-fluoro-2'-methyl-[2,3'-bipyridin]-4-yl)methyl)carbamate (0.09 g, 0.18 mmol). $^1$H NMR (400 MHz, $d_6$ DMSO) δ 9.4 (t, 1H, J=6.3 Hz), 8.6 (br, 2H), 8.2 (t, 1H, J=8.0 Hz), 8.0 (s, 1H), 7.7 (s, 1H), 7.5 (t, 1H J=7.7 Hz), 7.3 (d, 1H, J=10.5 Hz), 7.2 (m, 2H), 4.6 (s, 2H), 4.5 (d, 2H, J=6.3 Hz), 3.6 (s, 4H), 2.6 (s, 3H); LCMS: 98% 254 nm $R_T$=0.96 min, MS (ES) 471 (M+H).

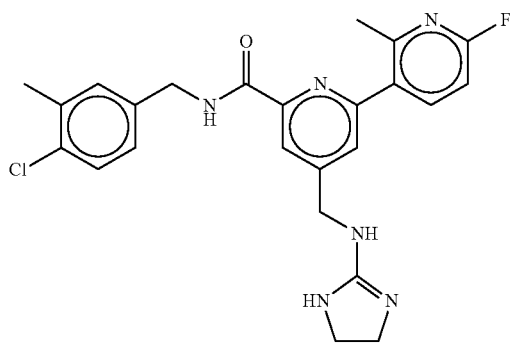

Example 74

N-(4-Chloro-3-methylbenzyl)-4-(((4,5-dihydro-1H-imidazol-2-yl)amino)methyl)-6'-fluoro-2'-methyl-[2,3'-bipyridine]-6-carboxamide

Step A. Preparation of tert-butyl ((2-chloro-6-((4-chloro-3-methylbenzyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (4-chloro-3-methylphenyl)methanamine.

Step B. Preparation of tert-butyl ((6-((4-chloro-3-methylbenzyl)-6'-fluoro-2'-methyl-[2,3'-bipyridin]-4-yl)methyl)carbamate The title compound was prepared from the procedure described in Example 72, Step E using tert-butyl ((2-chloro-6-((4-chloro-3-fluorobenzyl)carbamoyl)pyridin-4-yl)methyl)carbamate.

Step C. Example 74

The title compound (0.02 g, 20%) was prepared from the procedure described in Example 72, Step F using tert-butyl ((6-((4-chloro-3-methylbenzyl)-6'-fluoro-2'-methyl-[2,3'-bipyridin]-4-yl)methyl)carbamate (0.09 g, 0.18 mmol). LCMS: 98% 254 nm $R_T$=0.90 min, MS (ES) 467 (M+H).

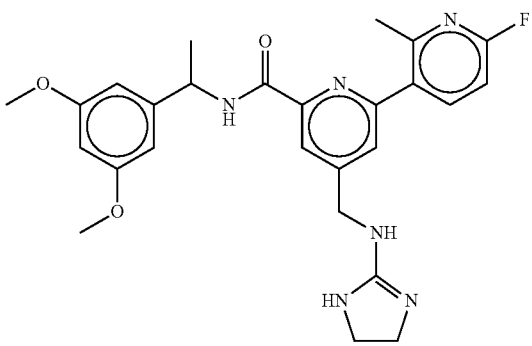

Example 75

4-(((4,5-Dihydro-1H-imidazol-2-yl)amino)methyl)-N-(1-(3,5-dimethoxyphenyl)ethyl)-6'-fluoro-2'-methyl-[2,3'-bipyridine]-6-carboxamide

Step A. Preparation of tert-butyl ((2-chloro-6-((1-(3,5-dimethoxyphenyl)ethyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and 1-(3,5-dimethoxyphenyl)ethan-1-amine.

Step B. Preparation of tert-butyl ((6-((1-(3,5-dimethoxyphenyl)ethyl)carbamoyl)-6'-fluoro-2'-methyl-[2,3'-bipyridin]-4-yl)methyl)carbamate The title compound was prepared from the procedure described in Example 72, Step E using tert-butyl ((2-chloro-6-((1-(3,5-dimethoxyphenyl)ethyl)carbamoyl)pyridin-4-yl)methyl)carbamate.

Step C. Example 75

The title compound (0.03 g, 26%) was prepared from the procedure described in Example 72, Step F using tert-butyl ((6-((1-(3,5-dimethoxyphenyl)ethyl)carbamoyl)-6'-fluoro-2'-methyl-[2,3'-bipyridin]-4-yl)methyl)carbamate (0.09 g, 0.18 mmol). $^1$H NMR (400 MHz, d$_6$ DMSO) δ 9.4 (t, 1H, J=7.0 Hz), 8.6 (br, 2H), 8.1 (t, 1H, J=7.7 Hz), 8.0 (s, 1H), 7.7 (s. 1H), 7.5 (t, 1H, J=8.2 Hz), 7.3 (d, 1H, J=10.6 Hz), 7.2 (d, 2H, J=7.4 Hz), 4.6 (s, 2H), 4.5 (d, 2H, J=5.6 Hz), 3.6 (s, 3H), 3.3 (br, 5H), 2.5 (S, 3H), 2.4 (s, 6H); LCMS: 98% 254 nm R$_T$=0.94 min, MS (ES) 493 (M+H).

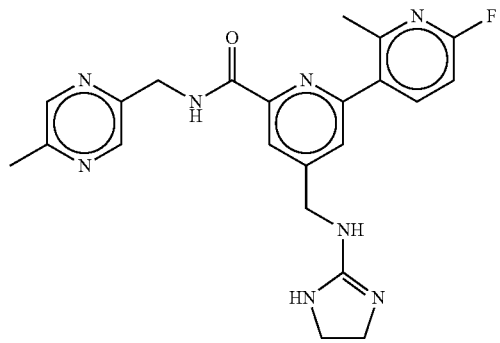

Example 76

4-(((4,5-Dihydro-1H-imidazol-2-yl)amino)methyl)-6'-fluoro-2'-methyl-N-((5-methylpyrazin-2-yl)methyl)-[2,3'-bipyridine]-6-carboxamide

Step A. Preparation of tert-butyl ((2-chloro-6-(((5-methylpyrazin-2-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (5-methylpyrazin-2-yl)methanamine.

Step B. Preparation of tert-butyl ((6'-fluoro-2'-methyl-6-(((5-methylpyrazin-2-yl)methyl)carbamoyl)-[2,3'-bipyridin]-4-yl)methyl)carbamate The title compound was prepared from the procedure described in Example 72, Step E using tert-butyl ((2-chloro-6-(((5-methylpyrazin-2-yl)methyl)carbamoyl)pyridin-4-yl)methyl)carbamate.

Step C. Example 76

The title compound (0.05 g, 60%) was prepared from the procedure described in Example 72, Step F using tert-butyl ((6'-fluoro-2'-methyl-6-(((5-methylpyrazin-2-yl)methyl)carbamoyl)-[2,3'-bipyridin]-4-yl)methyl)carbamate (0.08 g, 0.18 mmol). $^1$H NMR (400 MHz, d$_6$ DMSO) δ 9.4 (t, 1H, J=5.9 Hz), 8.4 (d, 2H, J=5.9 Hz), 8.2 (t, 1H, J=7.9 Hz), 8.0 (s, 1H), 7.8 (s, 1H), 7.2 (d, 1H J=8.2 Hz), 4.7 (d, 2H, J=5.5 Hz), 4.6 (s, 2H), 3.6 (s, 3H), 3.4 (s, 4H) 2.6 (s, 3H); LCMS: 98% 254 nm R$_T$=0.78 min, MS (ES) 435 (M+H).

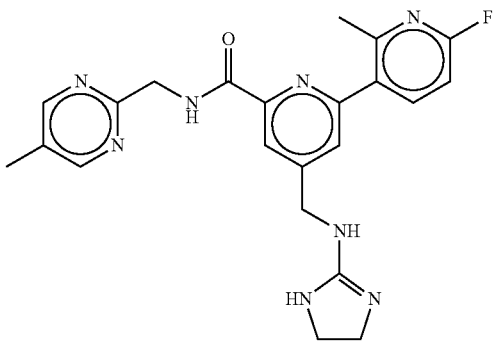

Example 77

4-(((4,5-Dihydro-1H-imidazol-2-yl)amino)methyl)-6'-fluoro-2'-methyl-N-((5-methylpyrimidin-2-yl)methyl)-[2,3'-bipyridine]-6-carboxamide

Step A. Preparation of tert-butyl ((2-chloro-6-(((5-methylpyrimidin-2-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (5-methylpyrimidin-2-yl)methanamine.

Step B. Preparation of tert-butyl ((6'-fluoro-2'-methyl-6-(((5-methylpyrimidin-2-yl)methyl)carbamoyl)-[2,3'-bipyridin]-4-yl)methyl)carbamate The title compound was prepared from the procedure described in Example 72, Step E using tert-butyl ((2-chloro-6-(((5-methylpyrimidin-2-yl)methyl)carbamoyl)pyridin-4-yl)methyl)carbamate.

Step C. Example 77

The title compound (0.02 g, 26%) was prepared from the procedure described in Example 72, Step F using tert-butyl ((6'-fluoro-2'-methyl-6-(((5-methylpyrimidin-2-yl)methyl)carbamoyl)-[2,3'-bipyridin]-4-yl)methyl)carbamate (0.08 g, 0.18 mmol). LCMS: 98% 254 nm $R_T$=0.80 min, MS (ES) 435 (M+H).

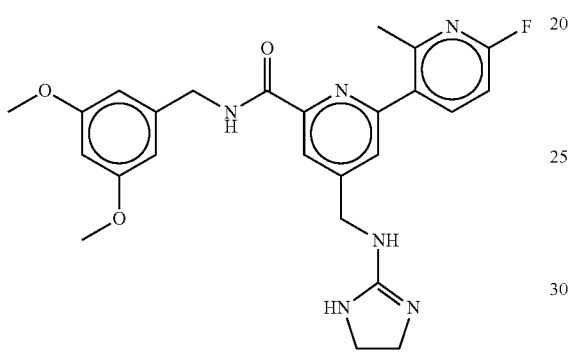

Example 78

4-(((4,5-Dihydro-1H-imidazol-2-yl)amino)methyl)-N-(3,5-dimethoxybenzyl)-6'-fluoro-2'-methyl-[2,3'-bipyridine]-6-carboxamide

Step A. Preparation of tert-butyl ((2-chloro-6-((3,5-dimethoxybenzyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (3,5-dimethoxy phenyl)methanamine.

Step B. Preparation of tert-butyl ((6-((3,5-dimethoxybenzyl)-6'-fluoro-2'-methyl-[2,3'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate.

Step C. Example 78

The title compound (0.02 g, 20%) was prepared from the procedure described in Example 72, Step F using tert-butyl ((6-((3,5-dimethoxybenzyl)-6'-fluoro-2'-methyl-[2,3'-bipyridin]-4-yl)methyl)carbamate (0.09 g, 0.18 mmol). LCMS: 98% 254 nm $R_T$=0.90 min, MS (ES) 479 (M+H).

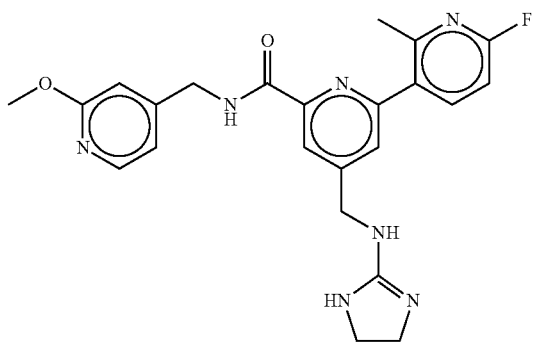

Example 79

4-(((4,5-Dihydro-1H-imidazol-2-yl)amino)methyl)-6'-fluoro-N-((2-methoxypyridin-4-yl)methyl)-2'-methyl-[2,3'-bipyridine]-6-carboxamide

Step A. Preparation of tert-butyl ((2-chloro-6-(((2-methoxypyridin-4-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (2-methoxypyridin-4-yl)methanamine.

Step B. Preparation of tert-butyl ((6'-fluoro-6-(((2-methoxypyridin-4-yl)methyl)carbamoyl)-2'-methyl-[2,3'-bipyridin]-4-yl)methyl)carbamate The title compound was prepared from the procedure described in Example 72, Step E using tert-butyl ((2-chloro-6-(((2-methoxypyridin-4-yl)methyl)carbamoyl)pyridin-4-yl)methyl)carbamate.

Step C. Example 79

The title compound (0.03 g, 30%) was prepared from the procedure described in Example 72, Step F using tert-butyl ((6'-fluoro-6-(((2-methoxypyridin-4-yl)methyl)carbamoyl)-2'-methyl-[2,3'-bipyridin]-4-yl)methyl)carbamate (0.09 g, 0.18 mmol). LCMS: 95% 254 nm $R_T$=0.76 min, MS (ES) 450 (M+H).

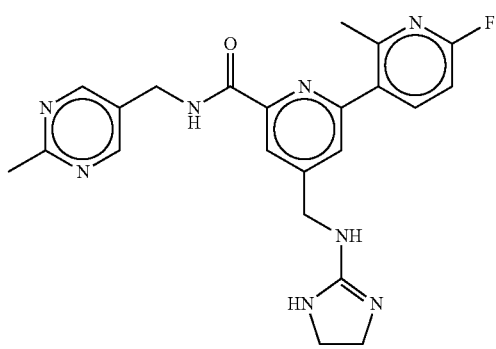

Example 80

4-(((4,5-Dihydro-1H-imidazol-2-yl)amino)methyl)-6'-fluoro-2'-methyl-N-((2-methylpyrimidin-5-yl)methyl)-[2,3'-bipyridine]-6-carboxamide

Step A. Preparation of tert-butyl ((2-chloro-6-(((2-methylpyrimidin-5-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (2-methylpyrimidin-5-yl)methanamine.

Step B. Preparation of tert-butyl ((6'-fluoro-2'-methyl-6-(((2-methylpyrimidin-5-yl)methyl)carbamoyl)-[2,3'-bipyridin]-4-yl)methyl)carbamate The title compound was prepared from the procedure described in Example 72, Step E using tert-butyl ((2-chloro-6-(((2-methylpyrimidin-5-yl)methyl)carbamoyl)pyridin-4-yl)methyl)carbamate.

Step C. Example 80

The title compound (0.01 g, 9%) was prepared from the procedure described in Example 72, Step F using tert-butyl ((6-((3,5-dimethoxybenzyl)-6'-fluoro-2'-methyl-[2,3'-bipyridin]-4-yl)methyl)carbamate (0.08 g, 0.18 mmol). LCMS: 98% 254 nm $R_T$=0.75 min, MS (ES) 435 (M+H).

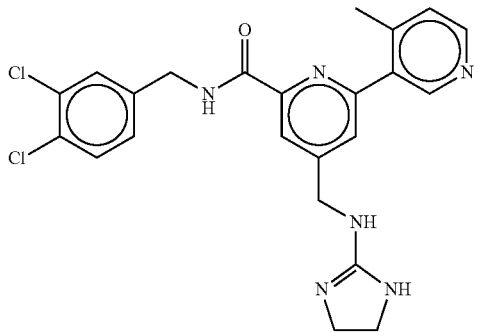

Example 81

N-(3,4-Dichlorobenzyl)-4-(((4,5-dihydro-1H-imidazol-2-yl)amino)methyl)-4'-methyl-[2,3'-bipyridine]-6-carboxamide

Step A. Preparation of tert-butyl ((6-((3,4-dichlorobenzyl)carbamoyl)-4'-methyl-[2,3'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (4-methylpyridin-3-yl)boronic acid.

Step B. Example 81

The title compound (0.04 g, 50%) was prepared from the procedure described in Example 72, Step F using tert-butyl ((6-((3,4-dichlorobenzyl)carbamoyl)-4'-methyl-[2,3'-bipyridin]-4-yl)methyl)carbamate (0.08 g, 0.16 mmol). LCMS: 98% 254 nm $R_T$=0.86 min, MS (ES) 469 (M+H).

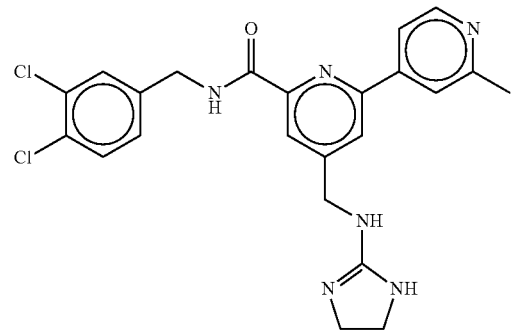

Example 82

N-(3,4-Dichlorobenzyl)-4-(((4,5-dihydro-1H-imidazol-2-yl)amino)methyl)-2'-methyl-[2,4'-bipyridine]-6-carboxamide

Step A. Preparation of tert-butyl ((6-((3,4-dichlorobenzyl)carbamoyl)-4'-methyl-[2,3'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (2-methylpyridin-4-yl)boronic acid.

Step B. Example 82

The title compound (0.01 g, 3%) was prepared from the procedure described in Example 72, Step F using tert-butyl ((6-((3,4-dichlorobenzyl)carbamoyl)-4'-methyl-[2,3'-bipyridin]-4-yl)methyl)carbamate (0.08 g, 0.16 mmol). LCMS: 98% 254 nm, MS (ES) 469 (M+H).

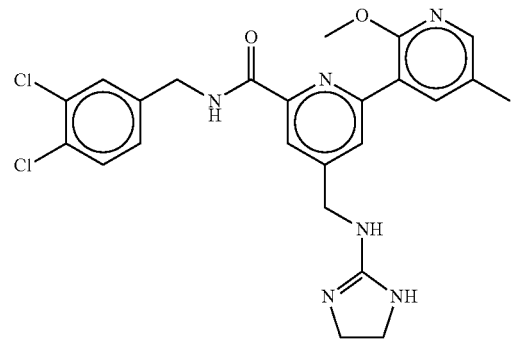

Example 83

N-(3,4-Dichlorobenzyl)-4-(((4,5-dihydro-1H-imidazol-2-yl)amino)methyl)-2'-methoxy-5'-methyl-[2,3'-bipyridine]-6-carboxamide

Step A. Preparation of tert-butyl ((6-((3,4-dichlorobenzyl)carbamoyl)-2'-methoxy-5'-methyl-[2,3'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (5-methoxy-2-methylpyridin-4-yl)boronic acid.

Step B. Example 83

The title compound (0.04 g, 47%) was prepared from the procedure described in Example 72, Step F using tert-butyl ((6-((3,4-dichlorobenzyl)carbamoyl)-2'-methoxy-5'-methyl-[2,3'-bipyridin]-4-yl)methyl)carbamate (0.08 g, 0.16 mmol). LCMS: 98% 254 nm $R_T$=1.0 min, MS (ES) 499 (M+H).

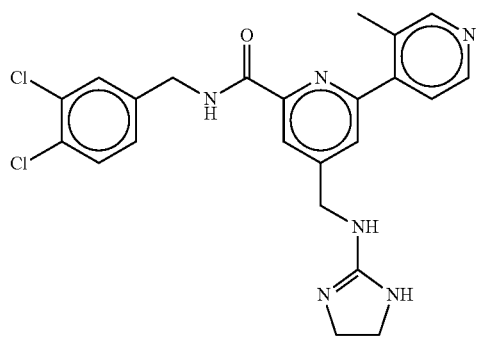

Example 84

N-(3,4-Dichlorobenzyl)-4-(((4,5-dihydro-1H-imidazol-2-yl)amino)methyl)-3'-methyl-[2,4'-bipyridine]-6-carboxamide

Step A. Preparation of tert-butyl ((6-((3,4-dichlorobenzyl)carbamoyl)-3'-methyl-[2,4'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (3-methylpyridin-4-yl)boronic acid.

Step B. Example 84

The title compound (0.01 g, 5%) was prepared from the procedure described in Example 72, Step F using tert-butyl ((6-((3,4-dichlorobenzyl)carbamoyl)-3'-methyl-[2,4'-bipyridin]-4-yl)methyl)carbamate (0.08 g, 0.16 mmol). LCMS: 98% 254 nm $R_T$=0.90 min, MS (ES) 469 (M+H).

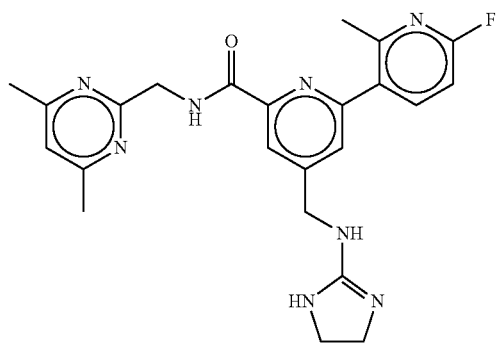

Example 85

4-(((4,5-Dihydro-1H-imidazol-2-yl)amino)methyl)-N-((4,6-dimethylpyrimidin-2-yl)methyl)-6'-fluoro-2'-methyl-[2,3'-bipyridine]-6-carboxamide

Step A. Preparation of tert-butyl ((2-chloro-6-(((4,6-dimethylpyrimidin-2-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (4,6-dimethylpyrimidin-2-yl)methanamine.

Step B. Preparation of tert-butyl ((6-(((4,6-dimethylpyrimidin-2-yl)methyl)carbamoyl)-6'-fluoro-2'-methyl-[2,3'-bipyridin]-4-yl)methyl)carbamate The title compound was prepared from the procedure described in Example 72, Step E using tert-butyl ((2-chloro-6-(((4,6-dimethylpyrimidin-2-yl)methyl)carbamoyl)pyridin-4-yl)methyl)carbamate.

Step C. Example 85

The title compound (0.04 g, 45%) was prepared from the procedure described in Example 72, Step F using tert-butyl ((6-((4,6-dimethylpyrimidin-2-yl)methyl)carbamoyl)-6'-fluoro-2'-methyl-[2,3'-bipyridin]-4-yl)methyl)carbamate (0.09 g, 0.19 mmol). LCMS: 98% 254 nm $R_T$=0.70 min, MS (ES) 448 (M+H).

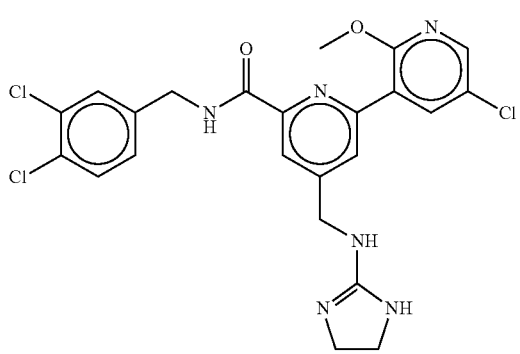

Example 86

5'-Chloro-N-(3,4-dichlorobenzyl)-4-(((4,5-dihydro-1H-imidazol-2-yl)amino)methyl)-2'-methoxy-[2,3'-bipyridine]-6-carboxamide Step A. Preparation of tert-butyl ((5'-chloro-6-((3,4-dichlorobenzyl)carbamoyl)-2'-methoxy-[2,3'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (5-chloro-2-methoxypyridin-3-yl)boronic acid.

Step B. Example 86

The title compound (0.04 g, 40%) was prepared from the procedure described in Example 72, Step F using tert-butyl ((5'-chloro-6-((3,4-dichlorobenzyl)carbamoyl)-2'-methoxy-[2,3'-bipyridin]-4-yl)methyl)carbamate (0.09 g, 0.16 mmol). LCMS: 98% 254 nm $R_T$=1.06 min, MS (ES) 519 (M+H).

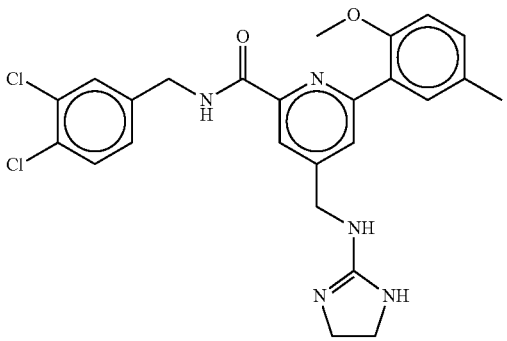

Example 87

N-(3,4-dichlorobenzyl)-4-(((4,5-dihydro-1H-imidazol-2-yl)amino)methyl)-6-(2-methoxy-5-methylphenyl)picolinamide Step A. Preparation of tert-butyl ((2-((3,4-dichlorobenzyl)carbamoyl)-6-(2-methoxy-5-methylphenyl)pyridin-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (2-methoxy-5-methylphenyl)boronic acid.

Step B. Example 87

The title compound (0.03 g, 40%) was prepared from the procedure described in Example 72, Step F using tert-butyl ((2-((3,4-dichlorobenzyl)carbamoyl)-6-(2-methoxy-5-methylphenyl)pyridin-4-yl)methyl)carbamate (0.08 g, 0.16 mmol). LCMS: 98% 254 nm $R_T$=1.08 min, MS (ES) 496 (M+H).

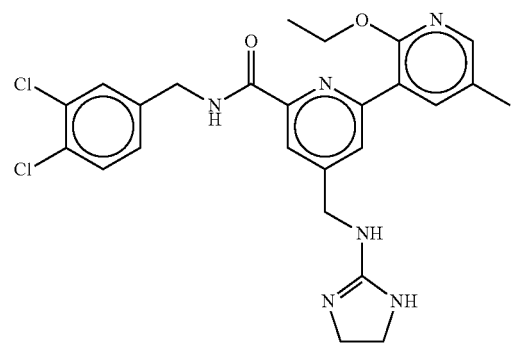

Example 88

N-(3,4-dichlorobenzyl)-4-(((4,5-dihydro-1H-imidazol-2-yl)amino)methyl)-2'-ethoxy-5'-methyl-[2,3'-bipyridine]-6-carboxamide Step A. Preparation of tert-butyl ((6-((3,4-dichlorobenzyl)carbamoyl)-2'-ethoxy-5'-methyl-[2,3'-bipyridin]-4-yl)methyl)carbamate The title compound was prepared from the procedure described in Example 72, Step E using tert-butyl ((2-chloro-6-((3,5-dimethoxybenzyl)carbamoyl)pyridin-4-yl)methyl)carbamate and (2-ethoxy-5-methylpyridin-3-yl)boronic acid.

Step B. Example 88

The title compound (0.03 g, 33%) was prepared from the procedure described in Example 72, Step F using tert-butyl ((6-((3,4-dichlorobenzyl)carbamoyl)-2'-ethoxy-5'-methyl-[2,3'-bipyridin]-4-yl)methyl)carbamate (0.09 g, 0.16 mmol). LCMS: 98% 254 nm $R_T$=1.05 min, MS (ES) 513 (M+H).

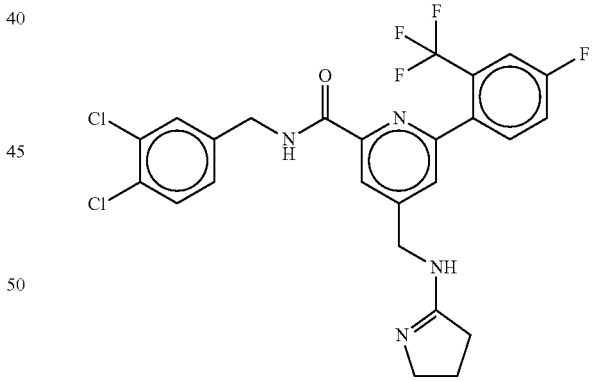

Example 89

N-(3,4-Dichlorobenzyl)-4-(((3,4-dihydro-2H-pyrrol-5-yl)amino)methyl)-6-(4-fluoro-2-(trifluoromethyl)phenyl)picolinamide Step A. Preparation of 4-(aminomethyl)-N-(3,4-dichlorobenzyl)-6-(4-fluoro-2-(trifluoromethyl)phenyl)picolinamide The title compound was prepared from the procedure described in Example 72, Step E using tert-butyl ((2-chloro- 6-((3,5-dimethoxybenzyl)carbamoyl)pyridin-4-yl)methyl) carbamate and (4-fluoro-2-(trifluoromethyl)phenyl)boronic acid followed by deprotection of Boc group by TFA in DCM.

Step B. Example 89

The title compound (0.04 g, 54%) was prepared following the procedure described in Example 52, Step B using 4-(aminomethyl)-N-(3,4-dichlorobenzyl)-6-(4-fluoro-2-(trifluoromethyl)phenyl)picolinamide TFA salt (0.07 g, 0.12 mmol), Methanol (5 mL) containing 0.7% acetic acid and 5-methoxy-3,4-dihydro-2H-pyrrole (0.03 g 0.25 mmol). LCMS: 98% 254 nm $R_T$=1.0 min, MS (ES) 540 (M+H).

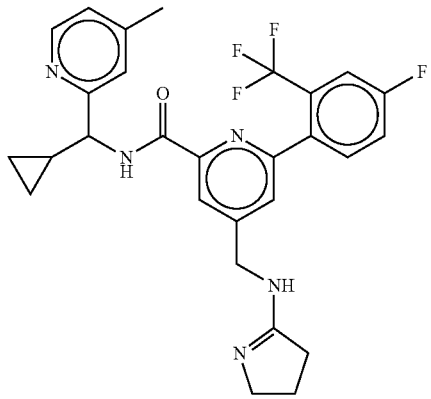

Example 90

N-(Cyclopropyl(4-methylpyridin-2-yl)methyl)-4-(((3,4-dihydro-2H-pyrrol-5-yl)amino)methyl)-6-(4-fluoro-2-(trifluoromethyl)phenyl)picolinamide Step A. Preparation of tert-butyl ((2-chloro-6-((cyclopropyl(4-methylpyridin-2-yl)methyl)carbamoyl) pyridin-4-yl)methyl)carbamate The title compound was prepared from the procedure described in Example 72, Step D using 4-(((tert-butoxycarbonyl)amino)methyl)-6-chloropicolinic acid and cyclopropyl(4-methylpyridin-2-yl)methanamine.

Step B. Preparation of 4-(aminomethyl)-N-(cyclopropyl(4-methylpyridin-2-yl)methyl)-6-(4-fluoro-2-(trifluoromethyl)phenyl)picolinamide The title compound was prepared from the procedure described in Example 72, Step E using tert-butyl ((2-chloro-6-((cyclopropyl(4-methylpyridin-2-yl)methyl)carbamoyl) pyridin-4-yl)methyl)carbamate and (4-fluoro-2-(trifluoromethyl)phenyl)boronic acid followed by deprotection of Boc group by TFA in DCM.

Step C. Example 90

The title compound (0.04 g, 57%) was prepared from the procedure described in Example 52, Step B using 4-(aminomethyl)-N-(cyclopropyl(4-methylpyridin-2-yl)methyl)-6-(4-fluoro-2-(trifluoromethyl)phenyl)picolinamide TFA salt (0.07 g, 0.12 mmol), Methanol (5 mL) containing 0.7% acetic acid and 5-methoxy-3,4-dihydro-2H-pyrrole (0.03 g 0.25 mmol). $^1$H NMR (400 MHz, $d_6$ DMSO) δ 9.7 (br, 1H), 8.9 (d, 1H, J=8.2 Hz), 8.4 (d, 1H, i=3.5 Hz), 8.1 (s, 1H), 7.9 (d, 1H, J=10 Hz), 7.8 (s, 2H), 7.7 (s, 1H), 7.3 (s, 1H), 7.1 (d, 1H, J=5.3 Hz), 4.7 (s, 2H), 4.6 (t, 1H, J=8.6 Hz), 3.6 (t, 2H, J=6.4 Hz), 2.9 (t, 2H, J=8.0 Hz), 2.3 (s, 3H), 2.1 (m, 2H), 1.2 (m, 1H), 0.5 (m, 4H); LCMS: 98% 254 nm, MS (ES) 526 (M+H).

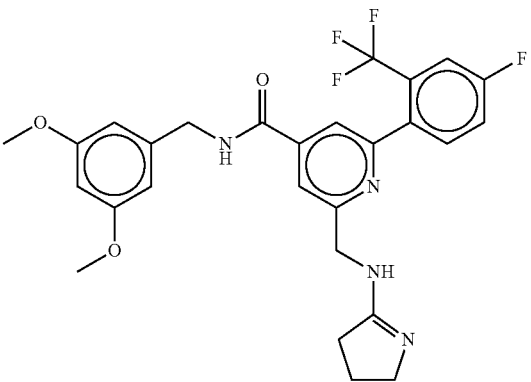

Example 91

2-(((3,4-dihydro-2H-pyrrol-5-yl)amino)methyl)-N-(3,5-dimethoxybenzyl)-6-(4-fluoro-2-(trifluoromethyl)phenyl)isonicotinamide Step A. Preparation of 4-(aminomethyl)-N-(3,5-dimethoxybenzyl)-6-(4-fluoro-2-(trifluoromethyl) phenyl)picolinamide The title compound was prepared from the procedure described in Example 72, Step E using tert-butyl ((2-chloro-6-((cyclopropyl(4-methylpyridin-2-yl)methyl)carbamoyl) pyridin-4-yl)methyl)carbamate and (3,5-dimethoxyphenyl) boronic acid followed by deprotection of Boc group by TFA in DCM.

Step B. Example 90

The title compound (0.05 g, 75%) was prepared from the procedure described in Example 52, Step B using 4-(aminomethyl)-N-(3,5-dimethoxybenzyl)-6-(4-fluoro-2-(trifluoromethyl)phenyl)picolinamide TFA salt (0.07 g, 0.12 mmol), Methanol (5 mL) containing 0.7% acetic acid and 5-methoxy-3,4-dihydro-2H-pyrrole (0.03 g 0.25 mmol). $^1$H NMR (400 MHz, $d_6$ DMSO) δ 9.0 (t, 1H, J=5.9 Hz), 8.1 (s, 1H), 7.8 (d, 1H, J=8.8 Hz), 7.7 (m, 3H), 6.5 (d, 2H, J=1.8 Hz), 6.4 (t, 1H, J=1.9 Hz), 2.7 (s, 2H), 4.5 (d, 2H, J=6.5 Hz), 3.7 (s, 6H), 3.6 (t, 2H, J=7.1 Hz), 2.8 (t, 2H, J=8.0 Hz), 2.0 (m, 2H); LCMS: 98% 254 nm, MS (ES) 531 (M+H).

201

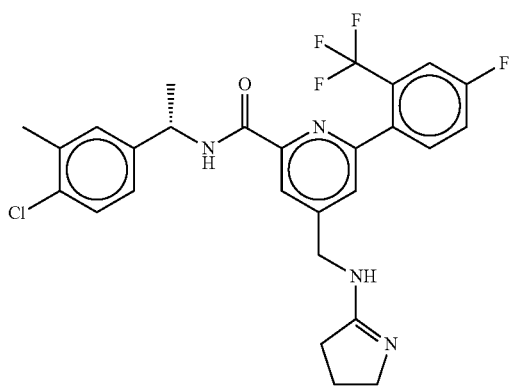

Example 92

(S)—N-(1-(4-chloro-3-methylphenyl)ethyl)-4-(((3,4-dihydro-2H-pyrrol-5-yl)amino)methyl)-6-(4-fluoro-2-(trifluoromethyl)phenyl)picolinamide Step A. Preparation of tert-butyl (S)-((2-chloro-6-((1-(4-chloro-3-methylphenyl)ethyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (S)-1-(4-chloro-3-methylphenyl)ethan-1-amine.

Step B. Preparation of (S)-4-(aminomethyl)-N-(1-(4-chloro-3-methylphenyl)ethyl)-6-(4-fluoro-2-(trifluoromethyl)phenyl)picolinamide The title compound was prepared from the procedure described in Example 72, Step E using tert-butyl (S)-((2-chloro-6-((1-(4-chloro-3-methylphenyl)ethyl)carbamoyl)pyridin-4-yl)methyl)carbamate and (4-fluoro-2-(trifluoromethyl)phenyl)boronic acid followed by deprotection of Boc group by TFA in DCM.

Step C. Example 92

The title compound (0.04 g, 67%) was prepared from the procedure described in Example 52, Step B using (S)-4-(aminomethyl)-N-(1-(4-chloro-3-methylphenyl)ethyl)-6-(4-fluoro-2-(trifluoromethyl)phenyl)picolinamide TFA salt (0.06 g, 0.12 mmol), Methanol (5 mL) containing 0.7% acetic acid and 5-methoxy-3,4-dihydro-2H-pyrrole (0.03 g 0.25 mmol). $^1$H NMR (400 MHz, d$_6$ DMSO) δ 8.6 (d, 1H, J=8.2 Hz), 8.0 (s, 1H), 7.9 (d, 1H, J=9.4 Hz), 7.8 (m, 3H), 7.4 (s, 1H), 7.3 (s, 1H), 7.2 (d, 1H, J=9.4 Hz), 5.1 (m, 1H), 4.6 (s, 2H), 3.5 (t, 2H, J=7.0 Hz), 2.7 (t, 2H, J=8.2 Hz), 2.9 (s, 3H), 2.0 (t, 2H, J=7.0 Hz), 1.5 (d, 3H, J=6.0 Hz); LCMS: 98% 254 nm, MS (ES) 533 (M+H).

202

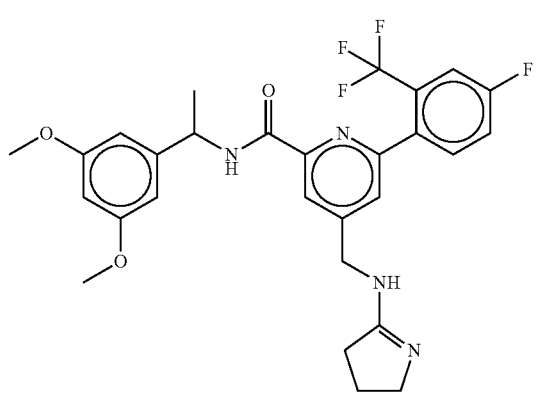

Example 93

4-(((3,4-dihydro-2H-pyrrol-5-yl)amino)methyl)-N-(1-(3,5-dimethoxyphenyl)ethyl)-6-(4-fluoro-2-(trifluoromethyl)phenyl)picolinamide Step A. Preparation of tert-butyl ((2-chloro-6-((1-(3,5-dimethoxyphenyl)ethyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and 1-(3,5-dimethoxyphenyl)ethan-1-amine.

Step B. Preparation of 4-(aminomethyl)-N-(1-(3,5-dimethoxyphenyl)ethyl)-6-(4-fluoro-2-(trifluoromethyl)phenyl)picolinamide The title compound was prepared from the procedure described in Example 72, Step E using tert-butyl ((2-chloro-6-((1-(3,5-dimethoxyphenyl)ethyl)carbamoyl)pyridin-4-yl)methyl)carbamate and (4-fluoro-2-(trifluoromethyl)phenyl)boronic acid followed by deprotection of Boc group by TFA in DCM.

Step C. Example 93

The title compound (0.04 g, 58%) was prepared from the procedure described in Example 52, Step B using 4-(aminomethyl)-N-(1-(3,5-dimethoxyphenyl)ethyl)-6-(4-fluoro-2-(trifluoromethyl)phenyl)picolinamide TFA salt (0.07 g, 0.12 mmol), Methanol (5 mL) containing 0.7% acetic acid and 5-methoxy-3,4-dihydro-2H-pyrrole (0.03 g 0.25 mmol). LCMS: 98% 254 nm R$_T$=1.0 min, MS (ES) 545 (M+H).

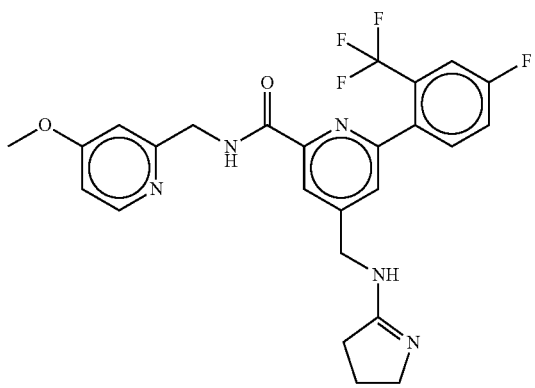
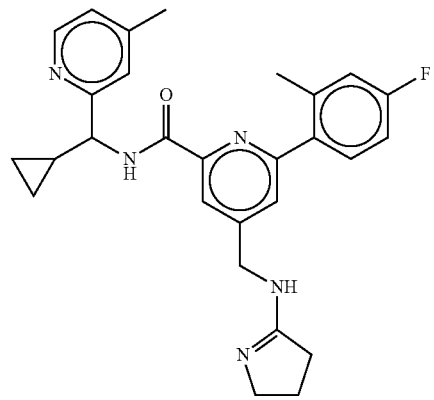

Example 94

4-(((3,4-dihydro-2H-pyrrol-5-yl)amino)methyl)-6-(4-fluoro-2-(trifluoromethyl)phenyl)-N-((4-methoxypyridin-2-yl)methyl)picolinamide Step A. Preparation of tert-butyl ((2-chloro-6-(((4-methoxypyridin-2-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (4-methoxypyridin-2-yl)methanamine.

Step B. Preparation of 4-(aminomethyl)-6-(4-fluoro-2-(trifluoromethyl)phenyl)-N-((4-methoxypyridin-2-yl)methyl)picolinamide The title compound was prepared from the procedure described in Example 72, Step E using tert-butyl ((2-chloro-6-(((4-methoxypyridin-2-yl)methyl)carbamoyl)pyridin-4-yl)methyl)carbamate and (4-fluoro-2-(trifluoromethyl)phenyl)boronic acid followed by deprotection of Boc group by TFA in DCM.

Step C. Example 94

The title compound (0.03 g, 53%) was prepared from the procedure described in Example 52, Step B using 4-(aminomethyl)-6-(4-fluoro-2-(trifluoromethyl)phenyl)-N-((4-methoxypyridin-2-yl)methyl)picolinamide TFA salt (0.07 g, 0.12 mmol), Methanol (5 mL) containing 0.7% acetic acid and 5-methoxy-3,4-dihydro-2H-pyrrole (0.03 g 0.25 mmol). LCMS: 98% 254 nm $R_T$=1.1 min, MS (ES) 502 (M+H).

Example 95

N-(Cyclopropyl(4-methylpyridin-2-yl)methyl)-4-(((3,4-dihydro-2H-pyrrol-5-yl)amino)methyl)-6-(4-fluoro-2-methylphenyl)picolinamide Step A. Preparation of 4-(aminomethyl)-N-(cyclopropyl(4-methylpyridin-2-yl)methyl)-6-(4-fluoro-2-methylphenyl)picolinamide The title compound was prepared from the procedure described in Example 72, Step E using tert-butyl ((2-chloro-6-((cyclopropyl(4-methylpyridin-2-yl)methyl)carbamoyl)pyridin-4-yl)methyl)carbamate and (4-fluoro-2-methylphenyl)boronic acid followed by deprotection of Boc group by TFA in DCM.

Step C. Example 95

The title compound (0.07 g, 84%) was prepared from the procedure described in Example 52, Step B using 4-(aminomethyl)-N-(cyclopropyl(4-methylpyridin-2-yl)methyl)-6-(4-fluoro-2-methylphenyl)picolinamide TFA salt (0.09 g, 0.17 mmol), Methanol (5 mL) containing 0.7% acetic acid and 5-methoxy-3,4-dihydro-2H-pyrrole (0.03 g 0.25 mmol), afforded the title compound. LCMS: 98% 254 nm $R_T$=1.2 min, MS (ES) 472 (M+H).

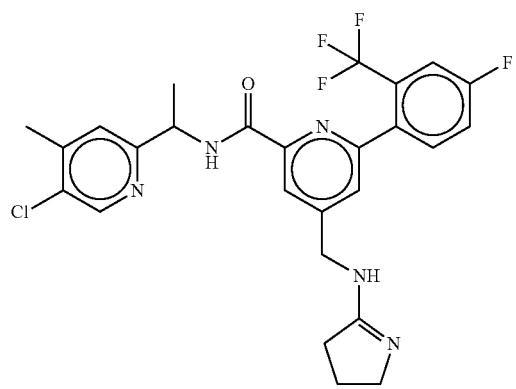

Example 96

N-(1-(5-chloro-4-methylpyridin-2-yl)ethyl)-4-(((3,4-dihydro-2H-pyrrol-5-yl)amino)methyl)-6-(4-fluoro-2-(trifluoromethyl)phenyl)picolinamide

Step A. Preparation of tert-butyl ((2-chloro-6-((1-(5-chloro-4-methylpyridin-2-yl)ethyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and 1-(5-chloro-4-methylpyridin-2-yl)ethan-1-amine.

Step B. Preparation of 4-(aminomethyl)-N-(1-(5-chloro-4-methylpyridin-2-yl)ethyl)-6-(4-fluoro-2-(trifluoromethyl)phenyl)picolinamide The title compound was prepared from the procedure described in Example 72, Step E using tert-butyl ((2-chloro-6-((1-(5-chloro-4-methylpyridin-2-yl)ethyl)carbamoyl)pyridin-4-yl)methyl)carbamate and (4-fluoro-2-(trifluoromethyl)phenyl)boronic acid followed by deprotection of Boc group by TFA in DCM.

Step C. Example 96

The title compound (0.04 g, 65%) was prepared from the procedure described in Example 52, Step B using 4-(aminomethyl)-N-(1-(5-chloro-4-methylpyridin-2-yl)ethyl)-6-(4-fluoro-2-(trifluoromethyl)phenyl)picolinamide TFA salt (0.07 g, 0.12 mmol), Methanol (5 mL) containing 0.7% acetic acid and 5-methoxy-3,4-dihydro-2H-pyrrole (0.03 g 0.25 mmol). LCMS: 98% 254 nm $R_T$=0.90 min, MS (ES) 534 (M+H).

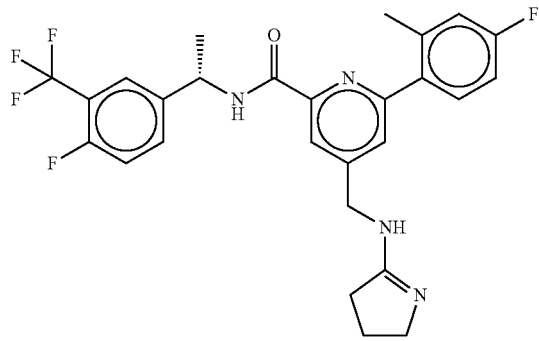

Example 97

(S)-4-(((3,4-dihydro-2H-pyrrol-5-yl)amino)methyl)-6-(4-fluoro-2-methylphenyl)-N-(1-(4-fluoro-3-(trifluoromethyl)phenyl)ethyl)picolinamide

Step A. Preparation of tert-butyl (S)-((2-chloro-6-((1-(4-fluoro-3-(trifluoromethyl)phenyl)ethyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and (S)-1-(3-fluoro-4-(trifluoromethyl)phenyl)ethan-1-amine.

Step B. Preparation of (S)-4-(aminomethyl)-6-(4-fluoro-2-methylphenyl)-N-(1-(4-fluoro-3-(trifluoromethyl)phenyl)ethyl)picolinamide The title compound was prepared from the procedure described in Example 72, Step E using (S)-((2-chloro-6-((1-(4-fluoro-3-(trifluoromethyl)phenyl)ethyl)carbamoyl)pyridin-4-yl)methyl)carbamate and (4-fluoro-2-methylphenyl)boronic acid followed by deprotection of Boc group by TFA in DCM.

Step C. Example 97

The title compound (0.06 g, 74%) was prepared from the procedure described in Example 52, Step B using (S)-4-(aminomethyl)-6-(4-fluoro-2-methylphenyl)-N-(1-(4-fluoro-3-(trifluoromethyl)phenyl)ethyl)picolinamide TFA salt (0.09 g, 0.17 mmol), Methanol (5 mL) containing 0.7% acetic acid and 5-methoxy-3,4-dihydro-2H-pyrrole (0.03 g 0.25 mmol). LCMS: 98% 254 nm $R_T$=1.0 min, MS (ES) 517 (M+H).

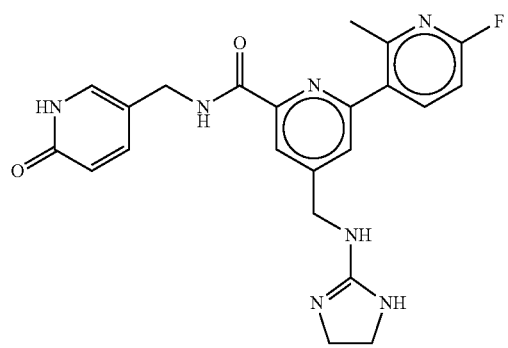

Example 98

4-(((4,5-dihydro-1H-imidazol-2-yl)amino)methyl)-6'-fluoro-2'-methyl-N-((6-oxo-1,6-dihydropyridin-3-yl)methyl)-[2,3'-bipyridine]-6-carboxamide

Step A. Preparation of tert-butyl ((2-chloro-6-(((6-oxo-1,6-dihydropyridin-3-yl)methyl)carbamoyl)pyridin-4-yl)methyl)carbamate The title compound was prepared from the procedure described in Example 72, Step D using 4-(((tert-butoxycarbonyl)amino)methyl)-6-chloropicolinic acid and 5-(aminomethyl)pyridin-2(1H)-one.

Step B. Preparation of tert-butyl ((6'-fluoro-2'-methyl-6-(((6-oxo-1,6-dihydropyridin-3-yl)methyl)carbamoyl)-[2,3'-bipyridin]-4-yl)methyl)carbamate The title compound was prepared from the procedure described in Example 72, Step E using tert-butyl ((2-chloro-6-(((6-oxo-1,6-dihydropyridin-3-yl)methyl)carbamoyl)pyridin-4-yl)methyl)carbamate.

Step C. Example 98

The title compound (0.01 g, 2%) was prepared from the procedure described in Example 72, Step F using tert-butyl ((6'-fluoro-2'-methyl-6-(((6-oxo-1,6-dihydropyridin-3-yl)

methyl)carbamoyl)-[2,3'-bipyridin]-4-yl)methyl)carbamate (0.08 g, 0.18 mmol). LCMS: 98% 254 nm $R_T$=0.69 min, MS (ES) 436 (M+H).

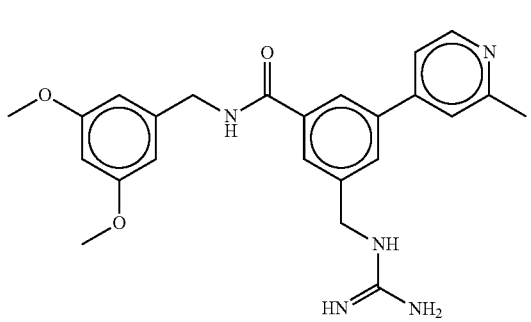

Example 99

N-(3,5-Dimethoxybenzyl)-3-(guanidinomethyl)-5-(2-methylpyridin-4-yl)benzamide

Step A. Preparation of N-(3,5-dimethoxybenzyl) (E)-3-((2,3-bis(tert-butoxycarbonyl)guanidino)methyl)-5-(2-methylpyridin-4-yl)benzamide To a stirred solution of 3,5-dimethoxybenzyl 3-(aminomethyl)-5-(2-methylpyridin-4-yl)benzoate (92.0 mg, 0.23 mmol) in THF (1.0 mL) under Ar atmosphere was added tert-butyl (E)-(((tert-butoxycarbonyl)amino)(1H-pyrazol-1-yl)methylene)carbamate (87.0 mg, 0.28 mmol). The reaction mixture was stirred at room temperature for 12 h then concentrated under vacuum. The residue was dissolved in EtOAc and sat. aq. NaHCO$_3$. The aqueous layer was separated and extracted with EtOAc (2×). The combined organic layers were washed with brine, dried (MgSO$_4$), filtered and concentrated. The residue was purified by flash chromatography (Combi-flash Rf, DCM/MeOH=0-3% gradient) to provide the title compound (105 mg, 70%). LCMS: $R_T$=1.079 min, MS (ES) 634.2 (M+H).

Step B. Preparation of N-(3,5-Dimethoxybenzyl)-3-(guanidinomethyl)-5-(2-methylpyridin-4-yl)benzamide The N-(3,5-dimethoxybenzyl) (E)-3-((2,3-bis(tert-butoxycarbonyl)guanidino)methyl)-5-(2-methylpyridin-4-yl)benzamide (105.0 mg, 0.28 mmol) was stirred in a solution of 1:1 TFA/DCM (3.0 mL) at room temperature for 3 h. The reaction mixture was concentrated under vacuum. The residue was dissolved in EtOAc and sat. aq. NaHCO$_3$. The aqueous layer was separated and extracted with EtOAc (2×). The combined organic layers were washed with brine, dried (MgSO$_4$), filtered and concentrated under vacuum at 50° C. to provide the title compound (46 mg, 64%). LCMS: $R_T$=0.732 min, MS (ES) 434.1 (M+H).

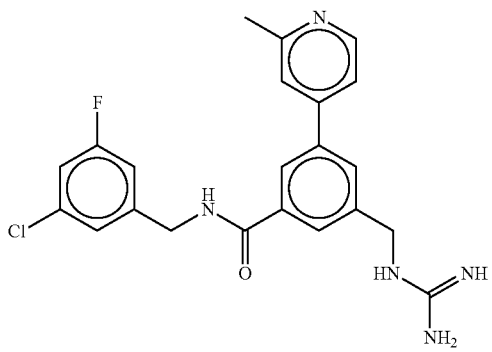

Example 100

N-(3-Chloro-5-fluorobenzyl)-3-(guanidinomethyl)-5-(2-methylpyridin-4-yl)benzamide Step A. Preparation of N-(3-chloro-5-fluorobenzyl) (E)-3-((2,3-bis(tert-butoxycarbonyl)guanidino)methyl)-5-(2-methylpyridin-4-yl)benzamide The title compound (89.0 mg, 78% yield) was prepared from the procedure described in Example 99, Step A using 3-(aminomethyl)-N-(3-chloro-5-fluorobenzyl)-5-(2-methylpyridin-4-yl)benzamide (70.0 mg, 0.18 mmol). LCMS: $R_T$=1.104 min, MS (ES) 626.1 (M+H).

Step B. Preparation of N-(3-Chloro-5-fluorobenzyl)-3-(guanidinomethyl)-5-(2-methylpyridin-4-yl)benzamide The title compound (60.0 mg, 43%) was prepared from the procedure described in Example 99, Step B using N-(3-chloro-5-fluorobenzyl) (E)-3-((2,3-bis(tert-butoxycarbonyl)guanidino)methyl)-5-(2-methylpyridin-4-yl)benzamide (89.0 mg, 0.14 mmol). LCMS: $R_T$=0.759 min, MS (ES) 426.1 (M+H).

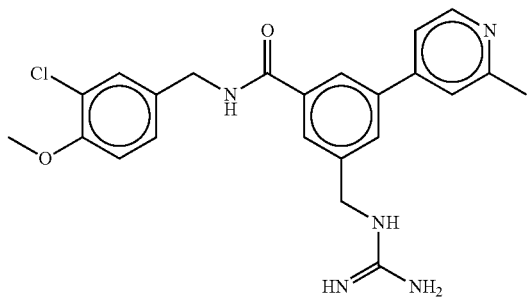

Example 101

N-(3-Chloro-4-methoxybenzyl)-3-(guanidinomethyl)-5-(2-methylpyridin-4-yl)benzamide Step A. Preparation of N-(3-chloro-4-methoxybenzyl) (E)-3-((2,3-bis(tert-butoxycarbonyl)guanidino)methyl)-5-(2-methylpyridin-4-yl)benzamide The title compound (73.0 mg, 67% yield) was prepared from the procedure described in Example 99, Step A using 3-(aminomethyl)-N-(3-chloro-4-methoxybenzyl)-5-(2-methylpyridin-4-yl)benzamide (67.0 mg, 0.17 mmol). LCMS: $R_T$=1.105 min, MS (ES) 638.1 (M+H).

Step B. Preparation of N-(3-chloro-4-methoxybenzyl)-3-(guanidinomethyl)-5-(2-methylpyridin-4-yl)benzamide The title compound (42.0 mg, 93%) was prepared from the procedure described in Example 99, Step B using N-(3-chloro-4-methoxybenzyl) (E)-3-((2,3-bis(tert-butoxycarbonyl)guanidino)methyl)-5-(2-methylpyridin-4-yl)benzamide (65.0 mg, 0.10 mmol). LCMS: $R_T$=0.758 min, MS (ES) 438.1 (M+H).

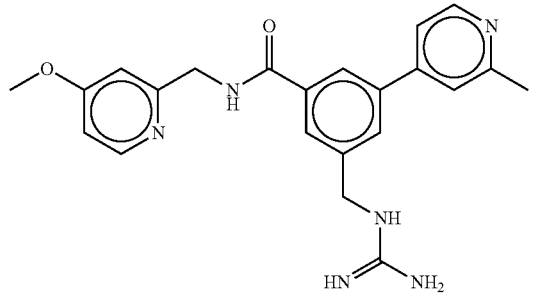

Example 102

3-(Guanidinomethyl)-N-((4-methoxypyridin-2-yl)methyl)-5-(2-methylpyridin-4-yl)benzamide Step A. Preparation of N-((4-methoxypyridin-2-yl)methyl) (E)-3-((2,3-bis(tert-butoxycarbonyl)guanidino)methyl)-5-(2-methylpyridin-4-yl)benzamide The title compound (65.0 mg, 75% yield) was prepared from the procedure described in Example 99, Step A using 3-(aminomethyl)-N-((4-methoxypyridin-2-yl)methyl)-5-(2-methylpyridin-4-yl)benzamide (52.0 mg, 0.14 mmol). LCMS: $R_T$=0.915 min, MS (ES) 605.2 (M+H).

Step B. Preparation of 3-(Guanidinomethyl)-N-((4-methoxypyridin-2-yl)methyl)-5-(2-methylpyridin-4-yl)benzamide The title compound (41.0 mg, 95%) was prepared from the procedure described in Example 99, Step B using N-((4-methoxypyridin-2-yl)methyl) (E)-3-((2,3-bis(tert-butoxycarbonyl)guanidino)methyl)-5-(2-methylpyridin-4-yl)benzamide (65.0 mg, 0.11 mmol). LCMS: $R_T$=0.462 min, MS (ES) 405.2 (M+H).

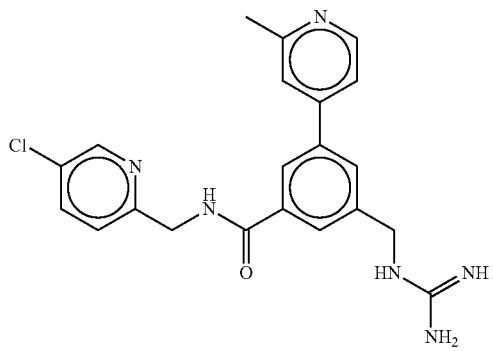

Example 103

N-((5-Chloropyridin-2-yl)methyl)-3-(guanidinomethyl)-5-(2-methylpyridin-4-yl)benzamide Step A. Preparation of N-((5-chloropyridin-2-yl)methyl) (E)-3-((2,3-bis(tert-butoxycarbonyl)guanidino)methyl)-5-(2-methylpyridin-4-yl)benzamide The title compound (56.0 mg, 70% yield) was prepared from the procedure described in Example 99, Step A using 3-(aminomethyl)-N-((5-chloropyridin-2-yl)methyl)-5-(2-methylpyridin-4-yl)benzamide (48.0 mg, 0.13 mmol). LCMS: $R_T$=1.035 min, MS (ES) 609.1 (M+H).

Step B. Preparation of N-((5-Chloropyridin-2-yl)methyl)-3-(guanidinomethyl)-5-(2-methylpyridin-4-yl)benzamide The title compound (30.0 mg, 79%) was prepared from the procedure described in Example 99, Step B using N-((5-chloropyridin-2-yl)methyl) (E)-3-((2,3-bis(tert-butoxycarbonyl)guanidino)methyl)-5-(2-methylpyridin-4-yl)benzamide (56.0 mg, 0.09 mmol). LCMS: $R_T$=0.685 min, MS (ES) 409.1 (M+H).

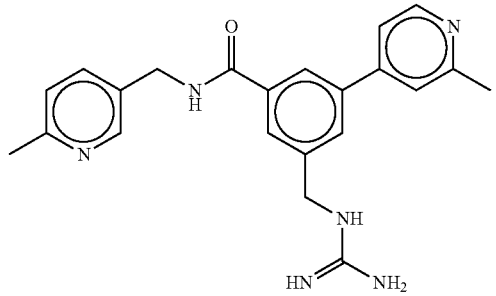

Example 104

3-(guanidinomethyl)-N-((6-methylpyridin-3-yl)methyl)-5-(2-methylpyridin-4-yl)benzamide Step A. Preparation of N-((6-methylpyridin-3-yl)methyl) (E)-3-((2,3-bis(tert-butoxycarbonyl)guanidino)methyl)-5-(2-methylpyridin-4-yl)benzamide The title compound (62.0 mg, 67% yield) was prepared from the procedure described in Example 99, Step A using 3-(aminomethyl)-N-((6-methylpyridin-3-yl)methyl)-5-(2-methylpyridin-4-yl)benzamide (55.0 mg, 0.16 mmol). LCMS: R$_T$=0.558 min, MS (ES) 389.2 (M+H).

Step B. Preparation of 3-(guanidinomethyl)-N-((6-methylpyridin-3-yl)methyl)-5-(2-methylpyridin-4-yl)benzamide The title compound (6.0 mg, 15%) was prepared from the procedure described in Example 99, Step B using N-((6-methylpyridin-3-yl)methyl) (E)-3-((2,3-bis(tert-butoxycarbonyl)guanidino)methyl)-5-(2-methylpyridin-4-yl)benzamide (62.0 mg, 0.11 mmol). LCMS: R$_T$=0.685 min, MS (ES) 409.1 (M+H).

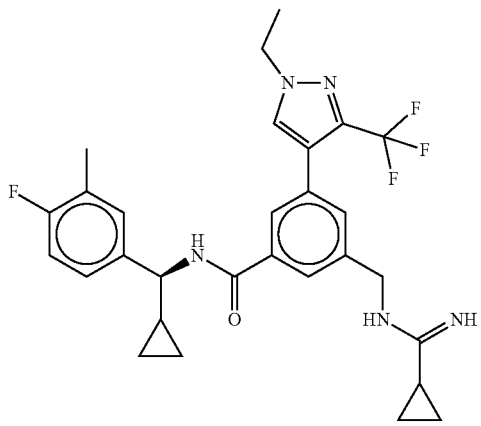

Example 105

(S)-3-(Cyclopropanecarboximidamidomethyl)-N-(cyclopropyl(4-fluoro-3-methylphenyl)methyl)-5-(1-ethyl-3-(trifluoromethyl)-1H-pyrazol-4-yl)benzamide Step A. Preparation of methyl 3-bromo-5-(((tert-butyldiphenylsilyl)oxy)methyl)benzoate TBDPS-Cl (15.9 mL, 16.8 g, 61.21 mmol) was added to a solution of methyl 3-bromo-5-(hydroxymethyl)benzoate (10 g, 40.8 mmol) in CH$_2$Cl$_2$ (408 mL) at 23° C. and stirred for 1 h. The resultant heterogeneous reaction mixture was filtered and concentrated in vacuo. The residue was purified by flash chromatography (Combi-flash Rf, Hex/EtOAc=0-10% gradient) to afford the title compound (18.2 g, 37.6 mmol, 92%) as a white solid. $^1$H NMR (400 MHz, Chloroform-d) δ 8.05 (s, 1H), 7.89 (s, 1H), 7.76-7.64 (m, 5H), 7.48-7.34 (m, 6H), 4.75 (s, 2H), 3.91 (s, 3H), 1.11 (s, 9H).

Step B. Preparation of methyl 3-(((tert-butyldiphenylsilyl)oxy)methyl)-5-(4,4,5,5-tetramethyl-1,3,2-dioxaborolan-2-yl)benzoate Bis(pinacolato)diboron (11.2 g, 44.2 mmol) was added to a mixture of methyl 3-bromo-5-(((tert-butyldiphenylsilyl)oxy)methyl)benzoate (17.6 g, 40.1 mmol), KOAc (11.8 g, 120.4 mmol) and PdCl$_2$(dppf) (3.2 g, 4.0 mmol) in Dioxane (401 mL) and degassed for 20 min; then stirred for 12 h at 85° C. The heterogeneous mixture was filtered through a pad of celite and concentrated in vacuo. The residue was purified by flash chromatography (Combi-flash Rf, Hex/EtOAc=0-15% gradient) to afford the title compound (19.7 g, 37.1 mmol, 93%) as a white solid. $^1$H NMR (400 MHz, Chloroform-d) δ 8.37 (s, 1H), 8.22 (s, 1H), 7.88 (s, 1H), 7.74-7.66 (m, 4H), 7.48-7.33 (m, 6H), 4.81 (s, 2H), 3.93 (s, 3H), 1.36 (s, 12H), 1.12 (s, 9H).

Step C. Preparation of methyl 3-(1-ethyl-3-(trifluoromethyl)-1H-pyrazol-4-yl)-5-(hydroxymethyl)benzoate Pd(PPh$_3$)$_4$ (0.19 g, 0.16 mmol) and potassium carbonate (3.3 g, 10.3 mmol) were added to a solution of 4-bromo-1-ethyl-3-(trifluoromethyl)pyrazole (1 g, 4.1 mmol, 1 equiv) and methyl 3-(((tert-butyldiphenyl silyl)oxy)methyl)-5-(4,4,5,5-tetramethyl-1,3,2-dioxaborolan-2-yl)benzoate (2.4 g, 4.5 mmol) in Dioxane/H$_2$O (97 mL, 0.04 M, 4:1) and degassed for 20 min. The reaction mixture was then placed in a preheated oil bath and stirred for 14 h at 80° C. At 23° C., brine was added to the mixture and extracted with EtOAc. The combined organic layers were dried over Na$_2$SO$_4$ and concentrated in vacuo to give crude methyl 3-(((tert-butyldiphenylsilyl)oxy)methyl)-5-(1-ethyl-3-(trifluoromethyl)-1H-pyrazol-4-yl)benzoate, which was used without further purification. Tetra-n-butylammonium fluoride (9.82 mL, 1 M in THF, 9.82 mmol) was added to a solution of crude methyl 3-(((tert-butyldiphenylsilyl)oxy)methyl)-5-(1-ethyl-3-(trifluoromethyl)-1H-pyrazol-4-yl)benzoate in THF (49 mL) at 0° C. and allowed to stir for 1 h. The reaction mixture was then concentrated in vacuo. The residue was purified by flash chromatography (Combi-flash Rf, Hex/EtOAc=0-60% gradient) to afford the title compound (1.1 g, 3.4 mmol, 81%) as a colorless oil.

Step D. Preparation of 3-(1-ethyl-3-(trifluoromethyl)-1H-pyrazol-4-yl)-5-(hydroxymethyl)benzoic Acid Lithium hydroxide (0.36 g, 15.0 mmol) was added to a solution of 3-(1-ethyl-3-(trifluoromethyl)-1H-pyrazol-4-yl)-5-(hydroxymethyl)benzoic acid (1.1 g, 3.4 mmol) in THF/H$_2$O (4:1, 38 mL) and stirred for 5 h at 23° C. The aqueous layer was then collected and the organic layer was extracted with 2.5 N NaOH. The combined aqueous extraction layers were washed with Et$_2$O and then acidified with 3 N HCl to a pH of 4. The resultant acidic aqueous solution was extracted with EtOAc and the combined organic layers were dried over Na$_2$SO$_4$ and concentrated in vacuo to afford the title compound as a white solid. (0.98 g, 0.31 mmol, 93%).

Step E. Preparation of (S)—N-(cyclopropyl(4-fluoro-3-methylphenyl)methyl)-3-(1-ethyl-3-(trifluoromethyl)-1H-pyrazol-4-yl)-5-(hydroxymethyl)benzamide N,N-Diisopropylethylamine (0.17 g, 0.22 mL, 1.3 mmol) was added to a heterogeneous mixture of 3-(1-ethyl-3-(trifluoromethyl)-1H-pyrazol-4-yl)-5-(hydroxymethyl)benzoic acid (0.1 g, 0.32 mmol) in CH$_2$Cl$_2$ (2.1 mL) at 23° C. and stirred to homogeneity. Then at −10° C., 1-[Bis(dimethylamino)methylene]-1H-1,2,3-triazolo[4,5-b]pyridinium 3-oxide hexafluorophosphate (0.19 g, 0.51 mmol) was added to the solution and allowed to stir for 20 min. Next the HCl salt of (S)-cyclopropyl(4-fluoro-3-methylphenyl)methanamine (82 mg, 0.38 mmol, 1.2 equiv) was added to the mixture and then stirred at −10° C. for 3 h. The reaction mixture was then concentrated in vacuo. The residue was purified by flash chromatography (Combi-flash Rf, Hex/

EtOAc=0-80% gradient) to afford the title compound (0.13 g, 0.29 mmol, 88%) as a white solid.

Step F. Preparation of (S)-3-(bromomethyl)-N-(cyclopropyl(4-fluoro-3-methylphenyl)methyl)-5-(1-ethyl-3-(trifluoromethyl)-1H-pyrazol-4-yl)benzamide N-Bromosuccinimide (0.15 g, 0.84 mmol) was added to a solution of triphenylphosphine (0.22 g, 0.84 mmol) and (S)—N-(cyclopropyl(4-fluoro-3-methylphenyl)methyl)-3-(1-ethyl-3-(trifluoromethyl)-1H-pyrazol-4-yl)-5-(hydroxymethyl)benzamide (0.13 g, 0.29 mmol) in THF at 23° C. and allowed to stir for 12 h. Brine was then added to the mixture and extracted with EtOAc. The combined organic layers were dried over $Na_2SO_4$ and concentrated in vacuo. The residue was purified by flash chromatography (Combiflash Rf, Hex/EtOAc=0-80% gradient) to afford the title compound (0.14 g, 0.26 mmol, 93%) as an off white solid.

Step G. Example 105

(S)-3-(Bromomethyl)-N-(cyclopropyl(4-fluoro-3-methylphenyl)methyl)-5-(1-ethyl-3-(trifluoromethyl)-1H-pyrazol-4-yl)benzamide (27 mg, 0.05 mmol), DIPEA (17 µL, 0.10 mmol), cyclopropanecarboximidamide hydrochloride (12 mg, 0.10 mmol) and KI (17 mg, 0.10 mmol) were combined in MeCN (0.5 mL) and stirred at r.t. for 16 h. The mixture was concentrated and the residue was purified by reverse phase HPLC (Phenomenex Gemini C18, $H_2O/CH_3CN$ gradient to 10-95% MeCN 0.1% TFA) to afford the title compound (3 mg, 0.005 mmol, 11%). $^1$H NMR (400 MHz, MeOH-$d_4$) δ 8.04 (d, J=1.2 Hz, 1H), 7.89 (t, J=1.7 Hz, 1H), 7.79 (t, J=1.7 Hz, 1H), 7.56 (s, 1H), 7.37-7.25 (m, 1H), 7.00 (dd, J=9.7, 8.4 Hz, 1H), 4.56 (s, 2H), 4.41 (d, J=9.4 Hz, 1H), 4.31 (q, J=7.3 Hz, 2H), 2.28 (d, J=2.0 Hz, 3H), 1.89-1.79 (m, 1H), 1.55 (t, J=7.3 Hz, 3H), 1.44-1.28 (m, 1H), 1.18-1.06 (m, 4H), 0.73-0.62 (m, 2H), 0.58-0.41 (m, 2H); $^{19}$F NMR (376 MHz, MeOH-$d_4$) δ −60.2,−122.4; LCMS (Method A): $R_T$=1.38 min, MS (ES) 542.1 (M+H).

Step G using cyclobutanecarboximidamide hydrochloride (13 mg, 0.10 mmol). LCMS (Method A): $R_T$=1.39 min, MS (ES) 556.0 (M+H).

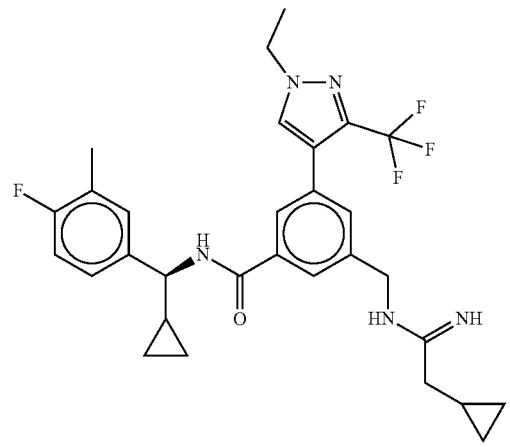

Example 107

(S)—N-(Cyclopropyl(4-fluoro-3-methylphenyl)methyl)-3-((2-cyclopropylacetimidamido)methyl)-5-(1-ethyl-3-(trifluoromethyl)-1H-pyrazol-4-yl)benzamide The title compound (9 mg, 0.016 mmol, 32%) was prepared according to procedure outlined for Example 104 Step G using 2-cyclopropylethanimidamide hydrochloride (13 mg, 0.10 mmol). LCMS (Method A): $R_T$=1.38 min, MS (ES) 556.0 (M+H).

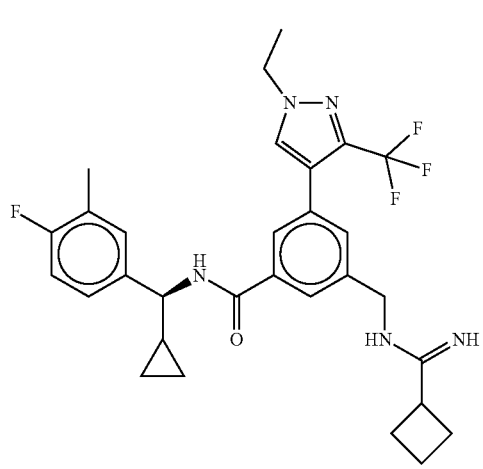

Example 106

(S)-3-(Cyclobutanecarboximidamidomethyl)-N-(cyclopropyl(4-fluoro-3-methylphenyl)methyl)-5-(1-ethyl-3-(trifluoromethyl)-1H-pyrazol-4-yl)benzamide The title compound (9 mg, 0.016 mmol, 32%) was prepared according to procedure outlined for Example 104

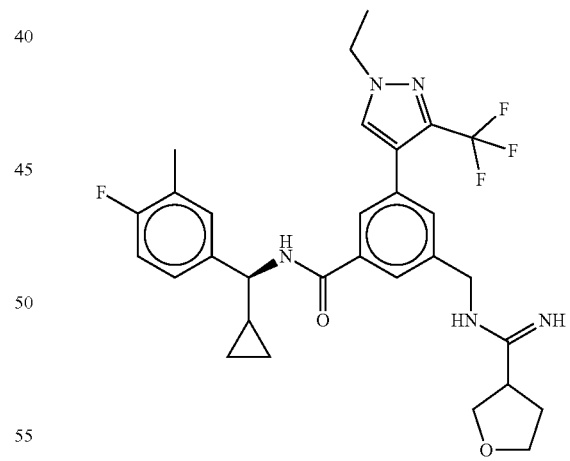

Example 108

N—((S)-Cyclopropyl(4-fluoro-3-methylphenyl)methyl)-3-(1-ethyl-3-(trifluoromethyl)-1H-pyrazol-4-yl)-5-((tetrahydrofuran-3-carboximidamido)methyl)benzamide The title compound (5 mg, 0.008 mmol, 18%) was prepared according to procedure outlined for Example 104

Step G using oxolane-3-carboximidamide hydrochloride (15 mg, 0.10 mmol). LCMS (Method A): $R_T$=1.38 min, MS (ES) 572.1 (M+H).

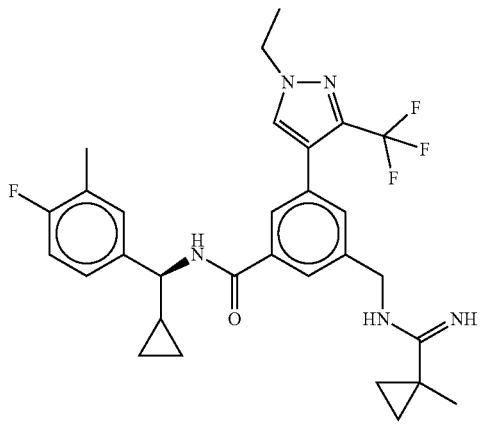

Example 109

(S)—N-(Cyclopropyl(4-fluoro-3-methylphenyl)methyl)-3-(1-ethyl-3-(trifluoromethyl)-1H-pyrazol-4-yl)-5-((1-methylcyclopropane-1-carboximidamido)methyl)benzamide The title compound (3 mg, 0.005 mmol, 10%) was prepared according to procedure outlined for Example 104 Step G, using 1-methylcyclopropane-carboximidamide hydrochloride (13 mg, 0.10 mmol). LCMS (Method A): $R_T$=1.32 min, MS (ES) 556.0 (M+H)

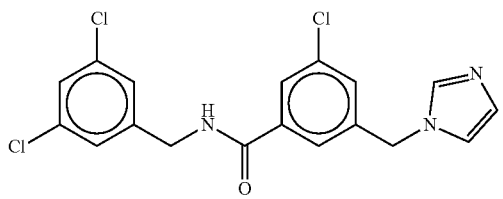

Example 110

3-((1H-Imidazol-1-yl)methyl)-5-chloro-N-(3,5-dichlorobenzyl)benzamide

Step A. Preparation of 3-((1H-imidazol-1-yl)methyl)-5-chlorobenzoic Acid

A solution of methyl 3-(bromomethyl)-5-chlorobenzoate (0.15 g, 0.57 mmol), imidazole (0.06 g, 0.85 mmol), $K_2CO_3$ (0.08 g, 0.57 mmol) in acetonitrile (10 mL) was heated to reflux for a 6 h. The solution was cooled and the solvent was removed under reduced pressure. The residue was dissolved in dichloromethane and washed with water. The organic phase was dried with $MgSO_4$, filtered and concentrated under reduced pressure. The crude (0.07 g, 0.28 mM) was dissolved in THF (5 mL)/MeOH (1 mL)/water (1 mL) and then treated with 2N LiOH (0.15 ml, 0.30 mmol). The reaction mixture was stirred for 2 h at ambient temperature then concentrated under reduced pressure. The residue was dissolved in water and acidified with 1N HCl to pH=1. The resulting solid was filtered, washed with water, and dried in a vacuum oven overnight to give the title compound 3-((1H-imidazol-1-yl)methyl)-5-chlorobenzoic acid (0.07 g, quant).

Step B. Example 110

The title compound (0.04 g, 36%) was prepared following the procedure described in Example 1, Step C using 3-((1H-imidazol-1-yl)methyl)-5-chlorobenzoic acid (0.07 g, 0.28 mmol), DMF (2 mL), DIEA (1.10 mL, 6.27 mmol), HATU (0.11 g, 0.29 mmol, and (3,5-dichlorophenyl)methanamine (0.05 g, 0.31 mmol). LCMS: 98% 254 nm $R_T$=0.87 min, MS (ES) 396 (M+H).

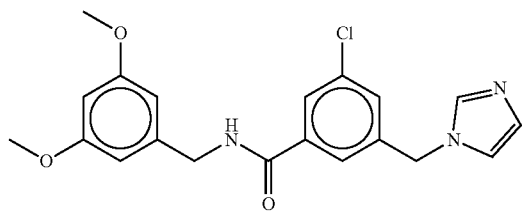

Example 111

3-((1H-Imidazol-1-yl)methyl)-5-chloro-N-(3,5-dimethoxybenzyl)benzamide

The title compound (0.01 g, 6%) was prepared following the procedure described in Example 1, Step C using 3-((1H-imidazol-1-yl)methyl)-5-chlorobenzoic acid (0.06 g, 0.25 mmol), DMF (1 mL), DIEA (0.11 mL, 0.60 mmol), HATU (0.10 g, 0.26 mmol), and (3,5-dimethoxyphenyl)methanamine (0.05 g, 0.27 mmol). LCMS: 98% 254 nm $R_T$=1.0 min, MS (ES) 396 (M+H).

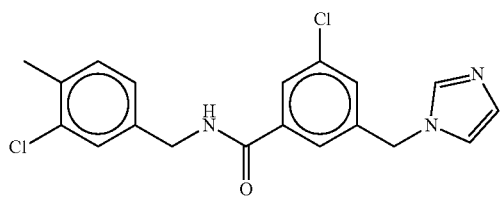

Example 112

3-((1H-Imidazol-1-yl)methyl)-5-chloro-N-(3-chloro-4-methylbenzyl)benzamide

The title compound (0.03 g, 32%) was prepared following the procedure described in Example 1, Step C using 3-((1H-imidazol-1-yl)methyl)-5-chlorobenzoic acid (0.06 g, 0.25 mmol), DMF (1 mL), DIEA (0.11 mL, 0.60 mmol), HATU (0.10 g, 0.26) mmol, and (3-chloro-4-methylphenyl)methanamine (0.04 g, 0.27 mmol). LCMS: 98% 254 nm $R_T$=0.85 min, MS (ES) 375 (M+H).

217

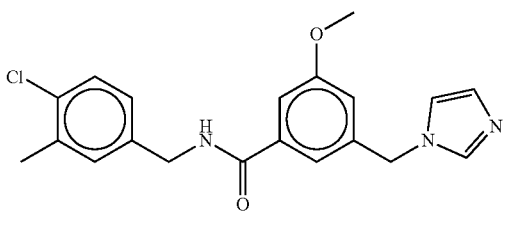

Example 113

3-((1H-Imidazol-1-yl)methyl)-N-(4-chloro-3-methylbenzyl)-5-methoxybenzamide

Step A. Preparation of 3-((1H-imidazol-1-yl)methyl)-5-methoxybenzoic Acid

The title compound (0.8 g, 58%, 2 steps) was prepared following the procedure described in Example 110, Step A substituting methyl 3-(bromomethyl)-5-chlorobenzoate with methyl 3-(bromomethyl)-5-methoxybenzoate (0.16 g, 0.62 mmol).

Step B. Example 113

The title compound (0.02 g, 27%) was prepared following the procedure described in Example 1, Step C using 3-((1H-imidazol-1-yl)methyl)-5-methoxybenzoic acid (0.04 g, 0.18 mmol), HATU (0.07 g, 0.18 mmol), DIEA (0.08 mL, 0.45 mmol), DMF (1 mL), and (4-chloro-3-methylphenyl)methanamine (0.3 g, 0.20 mmol). LCMS: 98% 254 nm $R_T$=0.84 min, MS (ES) 370 (M+H).

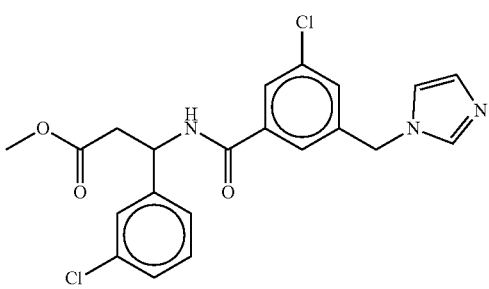

Example 114

Methyl 3-(3-((1H-imidazol-1-yl)methyl)-5-chlorobenzamido)-3-(3-chlorophenyl)propanoate The title compound (0.05 g, 35%) was prepared following the procedure described in Example 1, Step C using 3-((1H-imidazol-1-yl)methyl)-5-chlorobenzoic acid (0.08 g, 0.31 mmol), DMF (1 mL), DIEA (0.14 mL, 0.79 mmol), HATU (0.12 g, 0.32 mmol, and methyl 3-amino-3-(3-chlorophenyl) propanoate (0.08 g, 0.35 mmol). LCMS: 98% 254 nm $R_T$=0.86 min, MS (ES) 433 (M+H).

218

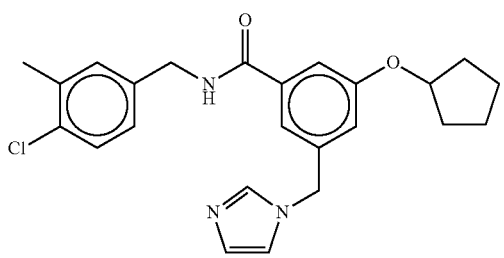

Example 115

3-((1H-Imidazol-1-yl)methyl)-N-(4-chloro-3-methylbenzyl)-5-(cyclopentyloxy)benzamide Step A. Preparation of 3-((1H-imidazol-1-yl)methyl)-5-(cyclopentyloxy)benzoic Acid The title compound was prepared following the procedure described in Example 110, Step A substituting methyl 3-(bromomethyl)-5-chlorobenzoate with methyl 3-(bromomethyl)-5-(cyclopentyloxy)benzoate.

Step B. Example 115

The title compound (0.03 g, 68%) was prepared following the procedure described in Example 1, Step C using 3-((1H-imidazol-1-yl)methyl)-5-(cyclopentyloxy)benzoic acid (0.03 g, 0.09 mmol), DMF (1 mL), DIEA (0.04 mL, 0.24 mmol), HATU (0.04 g, 0.09 mmol, and (4-chloro-3-methylphenyl)methanamine (0.02 g, 0.10 mmol). LCMS: 98% 254 nm $R_T$=0.97 min, MS (ES) 424 (M+H).

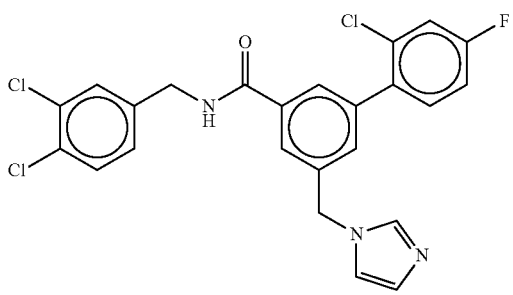

Example 116

5-((1H-Imidazol-1-yl)methyl)-2'-chloro-N-(3,4-dichlorobenzyl)-4'-fluoro-[1,1'-biphenyl]-3-carboxamide Step A. Preparation of 3-((1H-imidazol-1-yl)methyl)-5-bromobenzoic Acid The title compound was prepared following the procedure described in Example 110, Step A substituting methyl 3-(bromomethyl)-5-chlorobenzoate with methyl 3-(bromomethyl)-5-bromobenzoate.

Step B. Preparation of 3-((1H-imidazol-1-yl)methyl)-5-bromo-N-(3,4-dichlorobenzyl)benzamide The title compound was prepared following the procedure described in Example 1, Step C using 3-((1H-imidazol-1- yl)methyl)-5-bromobenzoic acid, HATU, DIEA, DMF, and (3,4-dichlorophenyl)methanamine.

Step C. Example 116

The title compound (0.02 g, 33%) was prepared following the procedure described in Example 1, Step B using 3-((1H-imidazol-1-yl)methyl)-5-bromo-N-(3,4-dichlorobenzyl) benzamide (0.06 g, 0.14 mmol) and (2-chloro-4-fluorophenyl)boronic acid (0.04 g, 0.20 mmol). LCMS: 98% 254 nm $R_T$=1.0 min, MS (ES) 489 (M+H).

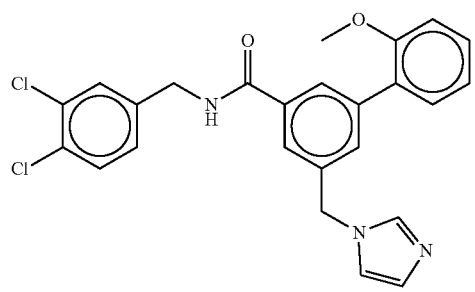

Example 117

5-((1H-imidazol-1-yl)methyl)-N-(3,4-dichlorobenzyl)-2'-methoxy-[1,1'-biphenyl]-3-carboxamide Argon gas was bubbled into a solution of 3-((1H-imidazol-1-yl)methyl)-5-bromo-N-(3,4-dichlorobenzyl)benzamide (0.05 g 0.10 mmol), di-isopropyl amine (0.04 mL, 0.26 mmol), (2-methoxyphenyl)boronic acid (0.02 g, 0.15 mmol) and 80% DMF/water (1 mL) for 5 min then triphenylphosphine-3,3',3"-trisulfonic acid trisodium salt (0.02 g, 0.03 mmol) and Pd(OAc)$_2$ (0.01 g, 0.02 mmol) were added. The reaction mixture was stirred at 80° C. for 6 h, cooled to ambient temperature and concentrated under reduced pressure. The residue was dissolved in DCM, washed with water, dried with MgSO$_4$, filtered and concentrated under reduced pressure. The residue was purified by flash chromatography (Combi-flash Rf, Hex/EtOAc=0-100% gradient) to afford the title compound (0.01 g, 29%). LCMS: 98% 254 nm $R_T$=0.9 min, MS (ES) 467 (M+H).

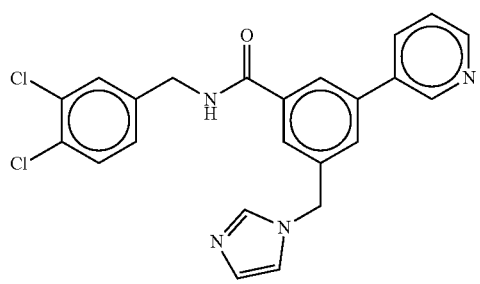

Example 118

3-((1H-Imidazol-1-yl)methyl)-N-(3,4-dichlorobenzyl)-5-(pyridin-3-yl)benzamide

The title compound (0.02 g, 36%) was prepared following the procedure described in Example 117 using 3-((1H-imidazol-1-yl)methyl)-5-bromo-N-(3,4-dichlorobenzyl) benzamide (0.05 g 0.10 mmol) and pyridin-3-ylboronic acid (0.02 g, 0.15 mmol). LCMS: 98% 254 nm $R_T$=0.7 min, MS (ES) 438 (M+H).

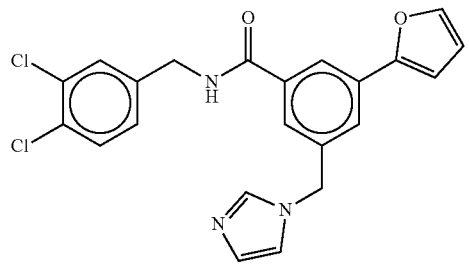

Example 119

3-((1H-Imidazol-1-yl)methyl)-N-(3,4-dichlorobenzyl)-5-(furan-2-yl)benzamide

The title compound (0.01 g, 13%) was prepared following the procedure described in Example 117 using 3-((1H-imidazol-1-yl)methyl)-5-bromo-N-(3,4-dichlorobenzyl) benzamide (0.04 g 0.09 mmol) and furan-2-ylboronic acid (0.02 g, 0.14 mmol). LCMS: 98% 254 nm $R_T$=0.73 min, MS (ES) 427 (M+H).

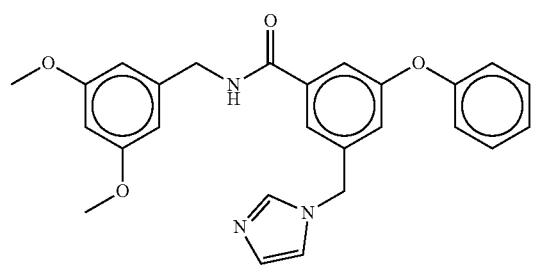

Example 120

3-((1H-imidazol-1-yl)methyl)-N-(3,5-dimethoxybenzyl)-5-phenoxybenzamide

Step A. Preparation of 3-((1H-imidazol-1-yl)methyl)-5-phenoxybenzoic Acid

The title compound was prepared following the procedure described in Example 110, Step A substituting methyl 3-(bromomethyl)-5-chlorobenzoate with methyl 3-(bromomethyl)-5-phenoxybenzoate.

Step B. Example 113

The title compound (0.03 g, 52%) was prepared following the procedure described in Example 1, Step C using 3-((1H-imidazol-1-yl)methyl)-5-phenoxybenzoic acid (0.04 g, 0.12 mmol), DMF (1 mL), DIEA (0.05 mL, 0.29 mmol), HATU (0.04 g, 0.09 mmol), and (3,5-dimethoxyphenyl)methanamine (0.02 g, 0.13 mmol). LCMS: 98% 254 nm $R_T$=0.67 min, MS (ES) 444 (M+H).

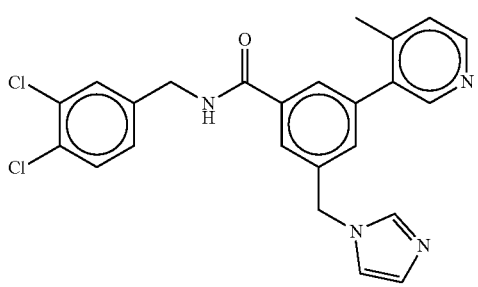

Example 121

3-((1H-imidazol-1-yl)methyl)-N-(3,4-dichlorobenzyl)-5-(4-methylpyridin-3-yl)benzamide The title compound (0.01 g, 20%) was prepared following the procedure described in Example 117 using 3-((1H-imidazol-1-yl)methyl)-5-bromo-N-(3,4-dichlorobenzyl)benzamide (0.06 g 0.13 mmol) and (4-methylpyridin-3-yl)boronic acid (0.03 g, 0.20 mmol). LCMS: 98% 254 nm $R_T$=0.54 min, MS (ES) 453 (M+H).

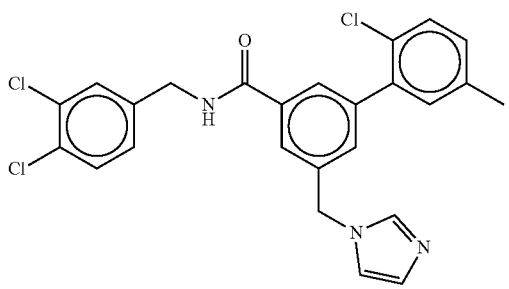

Example 122

5-((1H-Imidazol-1-yl)methyl)-2'-chloro-N-(3,4-dichlorobenzyl)-5'-methyl-[1,1'-biphenyl]-3-carboxamide The title compound (0.01 g, 23%) was prepared following the procedure described in Example 117 using 3-((1H-imidazol-1-yl)methyl)-5-bromo-N-(3,4-dichlorobenzyl)benzamide (0.06 g 0.13 mmol) and (4-methylpyridin-3-yl)boronic acid (0.03 g, 0.20 mmol). LCMS: 98% 254 nm $R_T$=0.80 min, MS (ES) 485 (M+H).

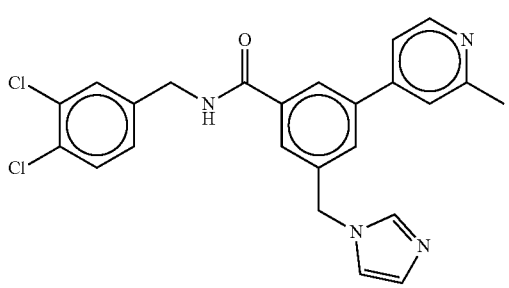

Example 123

3-((1H-Imidazol-1-yl)methyl)-N-(3,4-dichlorobenzyl)-5-(2-methylpyridin-4-yl)benzamide The title compound (0.01 g, 20%) was prepared following the procedure described in Example 117 using 3-((1H-imidazol-1-yl)methyl)-5-bromo-N-(3,4-dichlorobenzyl)benzamide (0.06 g 0.13 mmol) and (2-methylpyridin-4-yl)boronic acid (0.03 g, 0.20 mmol). LCMS: 98% 254 nm $R_T$=0.70 min, MS (ES) 451 (M+H).

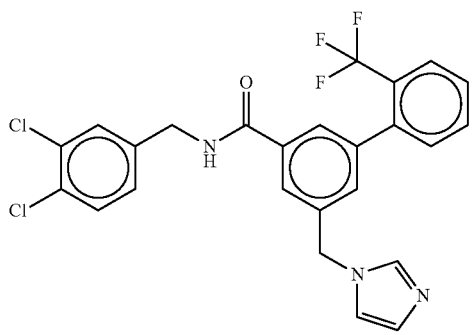

Example 124

5-((1H-Imidazol-1-yl)methyl)-N-(3,4-dichlorobenzyl)-2'-(trifluoromethyl)-[1,1'-biphenyl]-3-carboxamide The title compound (0.02 g, 25%) was prepared following the procedure described in Example 117 using 3-((1H-imidazol-1-yl)methyl)-5-bromo-N-(3,4-dichlorobenzyl)benzamide (0.06 g 0.13 mmol) and (2-(trifluoromethyl)phenyl)boronic acid (0.04 g, 0.20 mmol). LCMS: 98% 254 nm $R_T$=0.78 min, MS (ES) 505 (M+H).

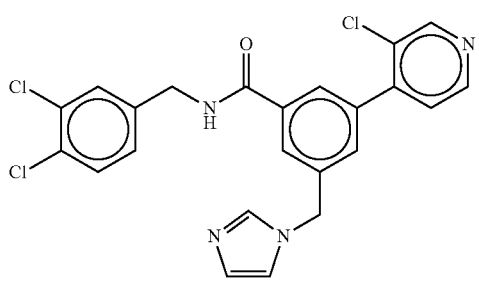

Example 125

3-((1H-Imidazol-1-yl)methyl)-5-(3-chloropyridin-4-yl)-N-(3,4-dichlorobenzyl)benzamide The title compound (0.01 g, 10%) was prepared following the procedure described in Example 117 using 3-((1H-imidazol-1-yl)methyl)-5-bromo-N-(3,4-dichlorobenzyl)benzamide (0.06 g 0.13 mmol) and (3-chloropyridin-4-yl)boronic acid (0.04 g, 0.20 mmol). LCMS: 98% 254 nm, MS (ES) 472 (M+H).

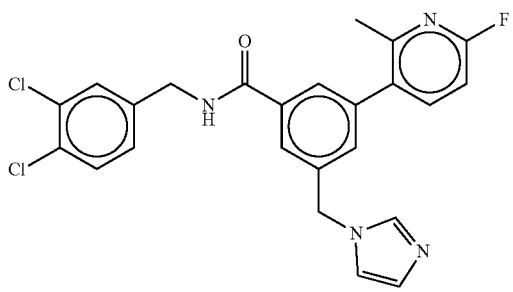

Example 126

3-((1H-Imidazol-1-yl)methyl)-N-(3,4-dichloroben-zyl)-5-(6-fluoro-2-methylpyridin-3-yl)benzamide The title compound (0.02 g, 30%) was prepared following the procedure described in Example 117 using 3-((1H-imidazol-1-yl)methyl)-5-bromo-N-(3,4-dichlorobenzyl)benzamide (0.06 g 0.13 mmol) and (6-fluoro-2-methylpyridin-3-yl)boronic acid (0.03 g, 0.20 mmol). LCMS: 98% 254 nm $R_T$=0.79 min, MS (ES) 470 (M+H).

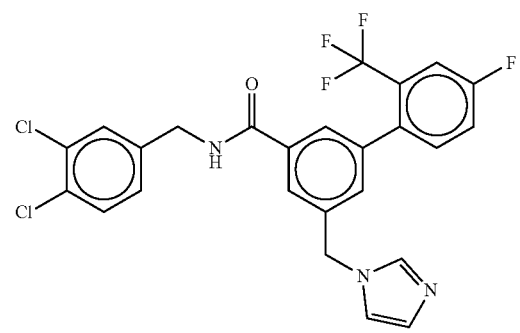

Example 127

5-((1H-Imidazol-1-yl)methyl)-N-(3,4-dichloroben-zyl)-4'-fluoro-2'-(trifluoromethyl)-[1,1'-biphenyl]-3-carboxamide The title compound (0.01 g, 20%) was prepared following the procedure described in Example 117 using 3-((1H-imidazol-1-yl)methyl)-5-bromo-N-(3,4-dichlorobenzyl)benzamide (0.06 g 0.13 mmol) and (4-fluoro-2-(trifluoromethyl)phenyl)boronic acid (0.04 g, 0.20 mmol). LCMS: 98% 254 nm $R_T$=0.94 min, MS (ES) 523 (M+H).

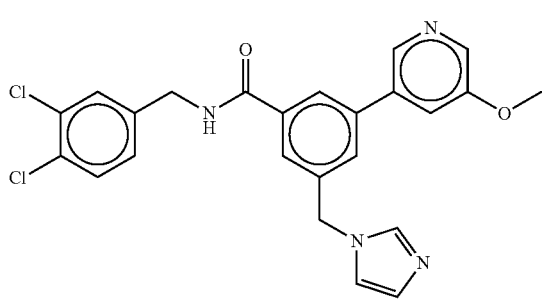

Example 128

3-((1H-Imidazol-1-yl)methyl)-N-(3,4-dichloroben-zyl)-5-(5-methoxypyridin-3-yl)benzamide The title compound (0.01 g, 14%) was prepared following the procedure described in Example 117 using 3-((1H-imidazol-1-yl)methyl)-5-bromo-N-(3,4-dichlorobenzyl)benzamide (0.06 g 0.13 mmol) and (5-methoxypyridin-3-yl)boronic acid (0.03 g, 0.20 mmol). LCMS: 98% 254 nm $R_T$=0.73 min, MS (ES) 469 (M+2H).

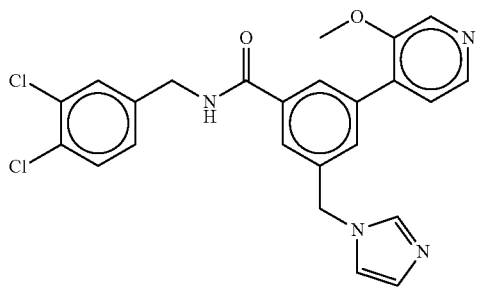

Example 129

3-((1H-Imidazol-1-yl)methyl)-N-(3,4-dichloroben-zyl)-5-(3-methoxypyridin-4-yl)benzamide The title compound (0.01 g, 19%) was prepared following the procedure described in Example 117 using 3-((1H-imidazol-1-yl)methyl)-5-bromo-N-(3,4-dichlorobenzyl)benzamide (0.06 g 0.13 mmol) and (3-methoxypyridin-4-yl)boronic acid (0.03 g, 0.20 mmol). LCMS: 98% 254 nm $R_T$=0.67 min, MS (ES) 523 (M+H).

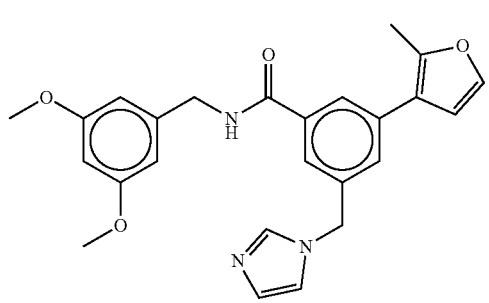

Example 130

3-((1H-Imidazol-1-yl)methyl)-N-(3,5-dimethoxy-benzyl)-5-(2-methylfuran-3-yl)benzamide Step A. Preparation of 3-((1H-imidazol-1-yl)methyl)-5-bromo-N-(3,5-dimethoxybenzyl)benz-amide The title compound was prepared following the procedure described in Example 1, Step C using 3-((1H-imidazol-1- yl)methyl)-5-bromobenzoic acid, DMF, DIEA, HATU, and (3,5-dimethoxyphenyl)methanamine.

Step B. Example 130

The title compound (0.03 g, 42%) was prepared following the procedure described in Example 117 using 3-((1H-imidazol-1-yl)methyl)-5-bromo-N-(3,5-dimethoxybenzyl)benzamide (0.06 g 0.14 mmol) and (2-methylfuran-3-yl)boronic acid (0.04 g, 0.21 mmol). LCMS: 98% 254 nm $R_T$=0.60 min, MS (ES) 432 (M+H).

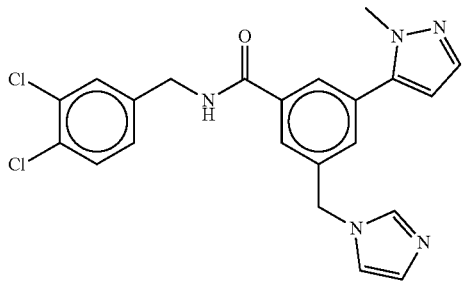

Example 131

3-((1H-Imidazol-1-yl)methyl)-N-(3,4-dichlorobenzyl)-5-(1-methyl-1H-pyrazol-5-yl)benzamide The title compound (0.02 g, 27%) was prepared following the procedure described in Example 117 using 3-((1H-imidazol-1-yl)methyl)-5-bromo-N-(3,4-dichlorobenzyl)benzamide (0.06 g 0.13 mmol) and ((1-methyl-1H-pyrazol-5-yl)boronic acid (0.03 g, 0.20 mmol). LCMS: 98% 254 nm $R_T$=0.60 min, MS (ES) 441 (M+H).

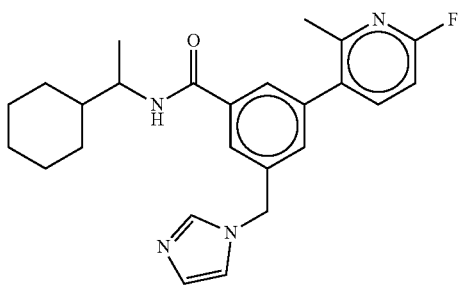

Example 132

3-((1H-Imidazol-1-yl)methyl)-N-(1-cyclohexylethyl)-5-(6-fluoro-2-methylpyridin-3-yl)benzamide Step A. Preparation of methyl 3-((1H-imidazol-1-yl)methyl)-5-(6-fluoro-2-methylpyridin-3-yl)benzoate The title compound was prepared following the procedure described in Example 117 using methyl 3-((1H-imidazol-1-yl)methyl)-5-bromobenzoate and (6-fluoro-2-methylpyridin-3-yl)boronic acid.

Step B. Preparation of 3-((1H-imidazol-1-yl)methyl)-5-(6-fluoro-2-methylpyridin-3-yl)benzoate Methyl 3(1H-imidazol-1-yl)methyl)-5-(6-fluoro-2-methylpyridin-3-yl)benzoate (1 eq.) was dissolved in THF/MeOH/water (5/1/1) and 2N LiOH (2.0 eq.) was added. The reaction mixture was stirred for 2 h at ambient temperature then concentrated under reduced pressure. The residue was dissolved in water and acidified with 1N HCl to pH=1. The resulting solid was filtered, washed with water, and dried in a vacuum oven overnight to give the title compound.

Step C. Example 132

The title compound (0.02 g, 53%) was prepared following the procedure described in Example 1, Step C using 3-((1H-imidazol-1-yl)methyl)-5-(6-fluoro-2-methylpyridin-3-yl)benzoic acid (0.03 g, 0.10 mmol), DMF (1 mL), DIEA (0.04 mL, 0.24 mmol), HATU (0.04 g, 0.10. mmol), and 1-cyclohexylethan-1-amine (0.02 g, 0.10 mmol). $^1$H NMR (400 MHz, d$_6$ DMSO) δ 8.2 (d, 1H, J=7.1 Hz), 7.9 (m, 1H), 7.8 (s, 1H), 7.7 (s, 1H), 7.4 (s, 1H), 7.3 (s, 1H), 7.1 (d, 1H, J=8.2 Hz), 6.9 (s, 1H), 5.3 (s, 2H), 3.9 (m, 1H), 2.3 (s, 3H), 1.7 (m, 6H), 1.6 (m, 1H), 1.5 (m, 1H), 1.1 (m, 6H), 1.0 (m, 1H); LCMS: 98% 254 nm $R_T$=0.93 min, MS (ES) 421 (M+H).

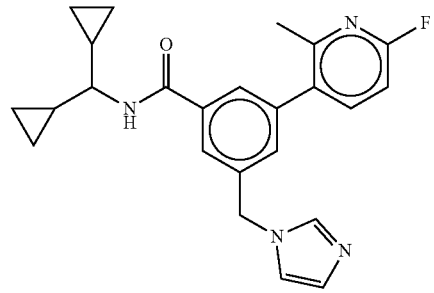

Example 133

3-((1H-imidazol-1-yl)methyl)-N-(dicyclopropylmethyl)-5-(6-fluoro-2-methylpyridin-3-yl)benzamide The title compound (0.01 g, 16%) was prepared following the procedure described in Example 1, Step C using 3-((1H-imidazol-1-yl)methyl)-5-(6-fluoro-2-methylpyridin-3-yl)benzoic acid (0.03 g, 0.10 mmol), DMF (1 mL), DIEA (0.04 mL, 0.24 mmol), HATU (0.04 g, 0.10. mmol, and dicyclopropylmethanamine (0.02 g, 0.10 mmol) afford the title compound (0.01 g, 16%). LCMS: 98% 254 nm, MS (ES) 405 (M+H).

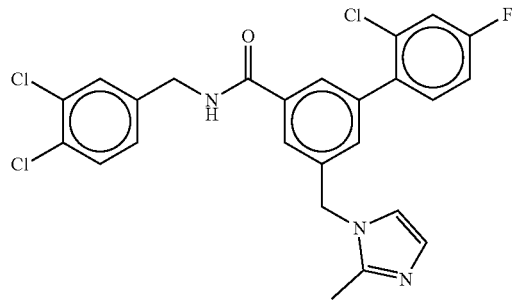

Example 134

2'-Chloro-N-(3,4-dichlorobenzyl)-4'-fluoro-5-((2-methyl-1H-imidazol-1-yl)methyl)-[1,1'-biphenyl]-3-carboxamide

Step A. Preparation of methyl 3-(2-chloro-4-fluorophenyl)-5-(hydroxymethyl)benzoate The title compound was prepared following the procedure described in Example 1, Step B using methyl 3-bromo-5-(hydroxymethyl)benzoate and (2-chloro-4-fluorophenyl)boronic acid.

Step B. Preparation of 3-(2-chloro-4-fluorophenyl)-5-(hydroxymethyl)benzoic Acid The title compound was prepared following the procedure described in Example 43, Step B using methyl 3-(2-chloro-4-fluorophenyl)-5-(hydroxymethyl)benzoate.

Step C. Preparation of 2'-chloro-N-(3,4-dichlorobenzyl)-4'-fluoro-5-(hydroxymethyl)-[1,1'-biphenyl]-3-carboxamide The title compound was prepared following the procedure described in Example 43, Step C using 3-(2-chloro-4-fluorophenyl)-5-(hydroxymethyl)benzoic acid and (3,4-dichlorophenyl)methanamine.

Step D. Preparation of 5-(bromomethyl)-2'-chloro-N-(3,4-dichlorobenzyl)-4'-fluoro-[1,1'-biphenyl]-3-carboxamide The title compound (0.79 g, 69%) was prepared following the procedure described in Example 43, Step D using 2'-chloro-N-(3,4-dichlorobenzyl)-4'-fluoro-5-(hydroxymethyl)-[1,1'-biphenyl]-3-carboxamide (1.0 g, 2.28 mmol) and 1N Phosphorus tribromide. $^1$H NMR (400 MHz, d$_6$ DMSO) δ 9.1 (M, 1H), 7.9 (s, 1H), 7.8 (s, 1H), 7.6 (s, 1H), 7.5 (m, 3H), 7.4 (m, 1H), 7.2, (m, 2H), 4.7 (s, 2H), 4.4 (d, 2H, J=5.3 Hz), 3.2 (s, 3H).

Step E. Example 134

A solution of 5-(bromomethyl)-2'-chloro-N-(3,4-dichlorobenzyl)-4'-fluoro-[1,1'-biphenyl]-3-carboxamide (0.05 g, 0.1 mmol), 2-methyl-1H-imidazole (0.02 g, 0.20 mmol) and DIEA (0.04 mL, 0.25 mmol) in acetonitrile (2 mL) was refluxed for 18 h. The reaction mixture was cooled to ambient temperature and concentrated under reduced pressure. The residue was purified by reverse phase HPLC (Phenomenex Gemini C18, H$_2$O/CH$_3$CN gradient to 10-95% MeCN 0.1% TFA) to afford the title compound (0.02 g, 48%). $^1$H NMR (400 MHz, d$_6$ DMSO) δ 9.2 (t, 1H, J=6.2 Hz), 7.9 (s, 1H), 7.8 (s, 1H), 7.6 (m, 1H), 7.5 (m, 2H), 7.5 (m, 1H), 7.3 (m, 3H), 7.2 (s, 1H), 6.8 (s, 1H), 5.3 (s, 2H), 4.5 (d, 2H, 5.3 Hz), 2.3 (s, 3H). LC=98%, MS=503 (m+1).; LCMS: 98% 254 nm R$_T$=1.03 min, MS (ES) 503 (M+H).

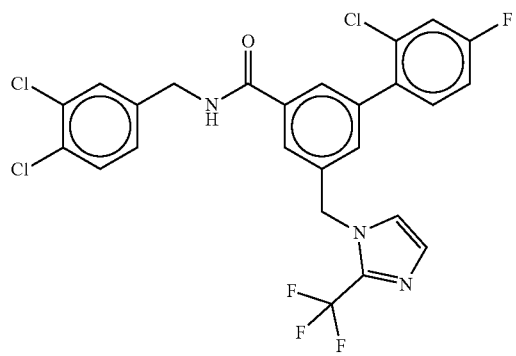

Example 135

2'-Chloro-N-(3,4-dichlorobenzyl)-4'-fluoro-5-((2-(trifluoromethyl)-1H-imidazol-1-yl)methyl)-[1,1'-biphenyl]-3-carboxamide The title compound (0.01 g, 10%) was prepared following the procedure described in Example 134, Step E using 5-(bromomethyl)-2'-chloro-N-(3,4-dichlorobenzyl)-4'-fluoro-[1,1'-biphenyl]-3-carboxamide (0.05 g, 0.10 mmol) and 2-(trifluoromethyl)-1H-imidazole (0.03 g, 0.20 mmol) and DIEA (0.04 mL, 0.25 mmol). LCMS: 95% 254 nm R$_T$=1.3 min, MS (ES) 558 (M+2H).

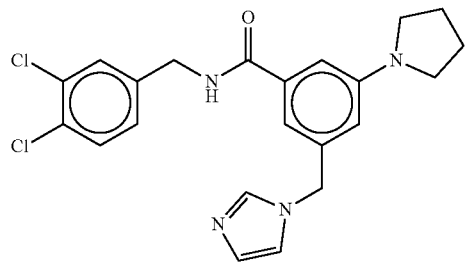

Example 136

3-((1H-Imidazol-1-yl)methyl)-N-(3,4-dichlorobenzyl)-5-(pyrrolidin-1-yl)benzamide Ar was bubbled into a mixture of 3-((1H-imidazol-1-yl)methyl)-5-bromo-N-(3,4-dichlorobenzyl)benzamide (0.05 g, 0.11 mmol), sodium tert butoxide (0.02 g, 0.15 mmol) in toluene (1 mL) for 5 min and Pd$_2$(dba)$_3$ (0.0.2 g, 0.02 mmol), BINAP (0.02 g, 0.03 mmol) and pyrrolidine (0.03 g, 0.29 mmol) were added. The reaction mixture was stirred for 18 h at 85° C., cooled to ambient temperature, filtered and concentrated under reduced pressure. The residue was purified by reverse phase HPLC (Phenomenex Gemini C18, H$_2$O/CH$_3$CN gradient to 10-95% MeCN 0.1% TFA) to afford the title compound (0.01 g, 6%). LCMS: 82% 214 nm R$_T$=0.68 min, MS (ES) 429 (M+H).

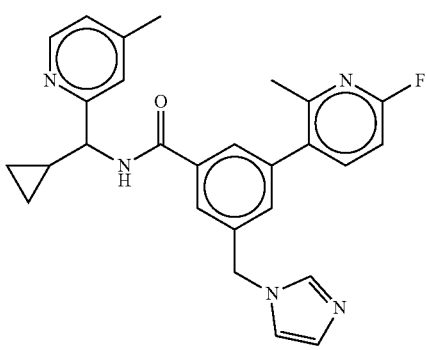

Example 137

3-((1H-Imidazol-1-yl)methyl)-N-(cyclopropyl(4-methylpyridin-2-yl)methyl)-5-(6-fluoro-2-methyl-pyridin-3-yl)benzamide The title compound (0.04 g, 56%) was prepared following the procedure described in Example 1, Step C 3-((1H-imidazol-1-yl)methyl)-5-(6-fluoro-2-methylpyridin-3-yl) benzoic acid (0.05 g, 0.15 mmol), DMF (1 mL), DIEA (0.08 mL, 0.45 mmol), HATU (0.06 g, 0.17 mmol), and cyclopropyl(4-methylpyridin-2-yl)methanamine (0.04 g, 0.20 mmol). LCMS: >95% 214 nm $R_T$=0.119 min, MS (ES) 456.1 (M+H).

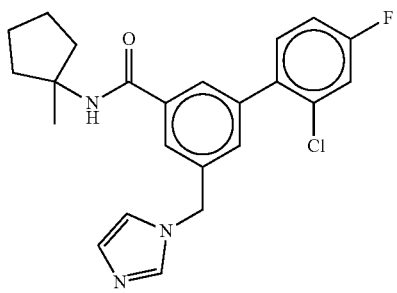

Example 138

5-((1H-Imidazol-1-yl)methyl)-2'-chloro-4'-fluoro-N-(1-methylcyclopentyl)-[1,1'-biphenyl]-3-carboxamide Step A. Preparation of 5-((1H-imidazol-1-yl)methyl)-2'-chloro-4'-fluoro-[1,1'-biphenyl]-3-carboxylic Acid The title compound was prepared following the procedure described in Example 117 using methyl 3-((1H-imidazol-1-yl)methyl)-5-bromobenzoate and (2-chloro-4-fluorophenyl) boronic acid followed by saponification procedure described in Example 132 step B.

Step C. Example 138

The title compound (0.04 g, 58%) was prepared following the procedure described in Example 1, Step C using 5-((1H-imidazol-1-yl)methyl)-2'-chloro-4'-fluoro-[1,1'-biphenyl]-3-carboxylic acid (0.05 g, 0.15 mmol), DMF (1 mL), DIEA (0.08 mL, 0.5 mmol), HATU (0.06 g, 0.17 mmol), and 1-methylcyclopentan-1-amine (0.02 g, 0.18 mmol). LCMS: >95% 254 nm $R_T$=0.73 min, MS (ES) 412 (M+H).

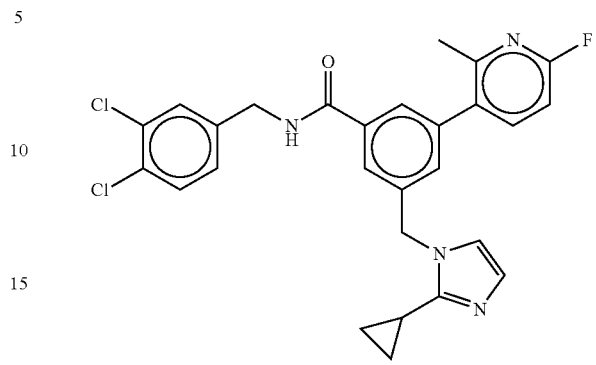

Example 139

3-((2-Cyclopropyl-1H-imidazol-1-yl)methyl)-N-(3,4-dichlorobenzyl)-5-(6-fluoro-2-methylpyridin-3-yl) benzamide The title compound (0.02 g, 36%) was prepared following the procedure described in Example 134, Step E using 3-(bromomethyl)-N-(3,4-dichlorobenzyl)-5-(6-fluoro-2-methylpyridin-3-yl)benzamide (0.06 g, 0.13 mmol), 2-cyclopropyl-1H-imidazole (0.03 g, 0.25 mmol) and DIEA (0.06 mL, 0.31 mmol). $^1$H NMR (400 MHz, d$_6$ DMSO) δ 9.2 (t, 1H, J=11.8), 7.8 (m, 3H), 7.6 (m, 2H), 7.3 (s, 1H), 7.3 (d, 1H, J=8.8), 7.2 (s, 1H), 7.1 (d, 1H, J=8.8 Hz), 6.8 (s, 1H), 5.4 (s, 2H), 4.5 (d, 2H, J=6.6 Hz), 2.3 (s, 3H), 0.8 (m, 2H), 0.7 (m, 2H); LCMS: 98% 254 nm $R_T$=0.99 min, MS (ES) 509 (M+2H).

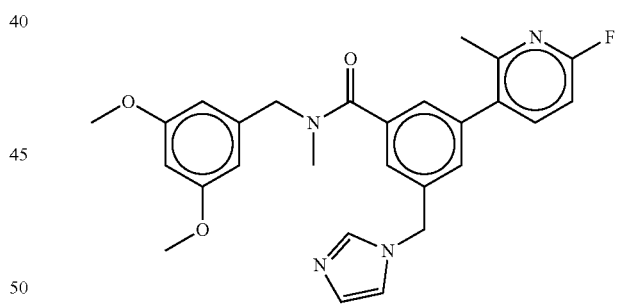

Example 140

3-((1H-Imidazol-1-yl)methyl)-N-(3,5-dimethoxy-benzyl)-5-(6-fluoro-2-methylpyridin-3-yl)-N-methylbenzamide The title compound (0.04 g, 41%) was prepared following the procedure described in Example 1, Step C 3-((1H-imidazol-1-yl)methyl)-5-(6-fluoro-2-methylpyridin-3-yl) benzoic acid (0.07 g, 0.22 mmol), DMF (1 mL), DIEA (0.12 mL, 0.66 mmol), HATU (0.09 g, 0.24 mmol) and 1-(3,5-dimethoxyphenyl)-N-methylmethanamine (0.04 g, 0.26 mmol). LCMS: >95% 214 nm RT=0.883 min, MS (ES) 475 (M+H).

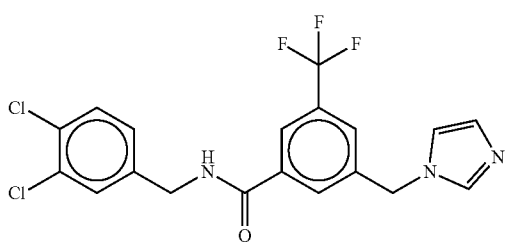

Example 141

3-((1H-Imidazol-1-yl)methyl)-N-(3,4-dichlorobenzyl)-5-(trifluoromethyl)benzamide Step A. Preparation of 3-((1H-imidazol-1-yl)methyl)-5-(trifluoromethyl)benzoic Acid The title compound was prepared following the procedure described in Example 110, Step A substituting methyl 3-(bromomethyl)-5-chlorobenzoate with methyl 3-(bromomethyl)-5-(trifluoromethyl)benzoate.

Step B. Example 141

The title compound (0.01 g, 22%) was prepared following the procedure described in Example 1, Step C using 3-((1H-imidazol-1-yl)methyl)-5-(trifluoromethyl)benzoic acid (0.04 g, 0.15 mmol), DMF (1 mL), DIEA (0.08 mL, 0.46 mmol), HATU (0.07 g, 0.17 mmol) and (3,4-dichlorophenyl)methanamine (0.04 g, 0.26 mmol). LCMS: 90% 215 nm $R_T$=1.02 min, MS (ES) 428 (M+H).

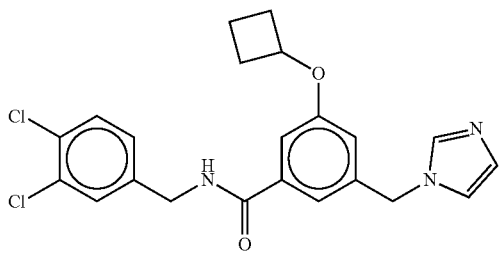

Example 142

3-((1H-Imidazol-1-yl)methyl)-5-cyclobutoxy-N-(3,4-dichlorobenzyl)benzamide

Step A. Preparation of dimethyl 5-cyclobutoxyisophthalate

K$_2$CO$_3$ (8.22 g, 59.5 mmol) and bromocyclobutane (3.4 mL, 35.7 mmol) were added to a solution of dimethyl 5-hydroxyisophthalate (5.00 g, 23.8 mmol) in DMF (95.2 mL). The reaction mixture was stirred at 95° C. for 15 h then quenched with water. The reaction mixture was extracted with EtOAc (3×15 mL). The combined organic layers were washed with water (5×15 mL) and dried (MgSO$_4$), filtered and concentrated. The crude mixture (5.70 g) was used for the next step without further purification. LCMS: $R_T$=1.668 min, MS (ES) 265.1 (M+H).

Step B. Preparation of methyl 3-cyclobutoxy-5-(hydroxymethyl)benzoate

The title compound (3.70 g, 73%) was prepared from the procedure described in Example 32, Step A using dimethyl 5-cyclobutoxyisophthalate (5.70 g, 21.6 mmol). LCMS: $R_T$=1.277 min, MS (ES) 237.1 (M+H).

Step C. Preparation of methyl 3-(bromomethyl)-5-cyclobutoxybenzoate

PBr$_3$ (1.1 mL, 11.4 mmol) was added to a solution of Methyl 3-cyclobutoxy-5-(hydroxymethyl)benzoate (900 mg, 3.81 mmol) in CH$_2$Cl$_2$ (15 mL). The reaction mixture was stirred at room temperature for 1 h. The reaction mixture was quenched with water and extracted with CH$_2$Cl$_2$ (3×10 mL). The combined organic layers were dried (MgSO$_4$), filtered and concentrated. The residue was purified by flash chromatography (Combi-flash Rf, Hex/EtOAc=0-30% gradient) to afford the title compound (180 mg, 16%). LCMS: $R_T$=1.747 min, MS (ES) 299.0 (M+H).

Step D. Preparation of methyl 3-((1H-imidazol-1-yl)methyl)-5-cyclobutoxybenzoate Imidazole (91.0 mg, 1.34 mmol) and K$_2$CO$_3$ (185 mg, 1.34 mmol) were added to a solution of methyl 3-(bromomethyl)-5-cyclobutoxybenzoate (200 mg, 0.670 mmol) in CH$_3$CN (6.7 mL). The reaction mixture was stirred at 60° C. for 5 h. The reaction mixture was filtered and concentrated. The residue was purified by flash chromatography (Combi-flash Rf, DCM/MeOH=0-4% gradient) to provide the title compound (110 mg, 58%). LCMS: $R_T$=0.953 min, MS (ES) 287.1 (M+H).

Step E. Preparation of 3-((1H-imidazol-1-yl)methyl)-5-cyclobutoxybenzoic Acid

The title compound (110 mg, crude mixture) was prepared from the procedure described in Example 12, Step E using methyl 3-((1H-imidazol-1-yl)methyl)-5-cyclobutoxybenzoate (110 mg, 0.380 mmol). LCMS: $R_T$=1.043 min, MS (ES) 273.1 (M+H).

Step F. Example 142

The title compound (27.2 mg, 17%) was prepared from the procedure described in Example 12, Step F using 3,4-dichlorobenzylamine (53.9 µL, 0.400 mmol). LCMS: $R_T$=1.438 min, MS (ES) 430.1 (M+H). $^1$H NMR (400 MHz, MeOH-d$_4$) δ 7.75 (s, 1H), 7.52-7.44 (m, 3H), 7.31-7.30 (m, 1H), 7.27-7.23 (m, 2H), 7.13-7.12 (m, 1H), 7.00-6.99 (m, 1H), 6.82 (t, J=2.0 Hz, 1H), 5.23 (s, 2H), 4.69 (quintet, J=7.2 Hz, 1H), 4.50 (s, 2H), 2.47-2.40 (m, 2H), 2.14-2.00 (m, 2H), 1.87-1.65 (m, 1H).

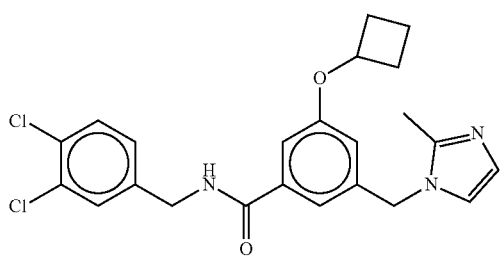

Example 143

3-Cyclobutoxy-N-(3,4-dichlorobenzyl)-5-((2-methyl-1H-imidazol-1-yl)methyl)benzamide Step A. Preparation of methyl 3-cyclobutoxy-5-((2-methyl-1H-imidazol-1-yl)methyl)benzoate The title compound (200 mg, crude mixture) was prepared from the procedure described in Example 142, Step D using 2-methylimidazole (87.8 mg, 1.07 mmol). LCMS: $R_T$=1.211 min, MS (ES) 301.1 (M+H).

Step B. Preparation of 3-cyclobutoxy-5-((2-methyl-1H-imidazol-1-yl)methyl)benzoic Acid The title compound (250 mg, crude mixture) was prepared from the procedure described in Example 12, Step E using methyl 3-cyclobutoxy-5-((2-methyl-1H-imidazol-1-yl)methyl)benzoate (200 mg, 0.670 mmol). LCMS: $R_T$=0.973 min, MS (ES) 287.1 (M+H).

Step C. Example 143

The title compound (65.0 mg, 42%) was prepared from the procedure described in Example 12, Step F using 3,4-dichlorobenzylamine (67.6 μL, 0.380 mmol). LCMS: $R_T$=1.442 min, MS (ES) 444.0 (M+H). $^1$H NMR (400 MHz, MeOH-d$_4$) δ 7.47 (d, J=2.0 Hz, 1H), 7.45 (d, J=8.4 Hz, 1H), 7.26-7.22 (m, 3H), 7.05 (d, J=1.3 Hz, 1H), 6.87 (d, J=1.2 Hz, 1H), 6.64-6.63 (m, 1H), 5.17 (s, 2H), 4.65 (quintet, J=7.9 Hz, 1H), 4.49 (s, 2H), 2.45-2.38 (m, 2H), 2.29 (s, 3H), 2.13-2.03 (m, 2H), 1.86-1.79 (m, 1H), 1.75-1.65 (m, 1H).

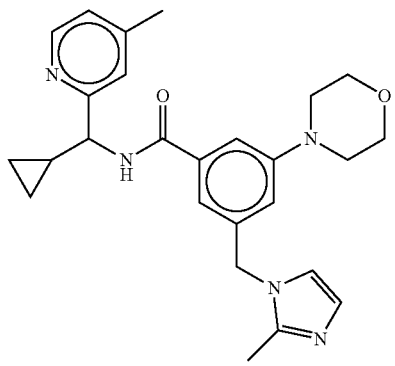

Example 144

N-(cyclopropyl(4-methylpyridin-2-yl)methyl)-3-((2-methyl-1H-imidazol-1-yl)methyl)-5-morpholinobenzamide Step A. Preparation of dimethyl 5-morpholinoisophthalate Pd(OAc)$_2$ (8.2 mg, 0.040 mmol), RuPhos (42.7 mg, 0.090 mmol), Cs$_2$CO$_3$ (1.49 g, 4.58 mmol) and morpholine (237 μL, 2.75 mmol) were added to a solution of dimethyl 5-bromoisophthalate (500 mg, 1.83 mmol) in dioxane (4.1 mL). The reaction mixture was degassed using Ar gas. The reaction mixture was stirred at 90° C. for 20 h. The reaction mixture was filtered through Celite pad (washed with EtOAc) and concentrated. The residue was purified by flash chromatography (Combi-flash Rf, Hex/EtOAc=0-40% gradient) to provide the title compound (390 mg, 76%). LCMS: $R_T$=1.339 min, MS (ES) 280.0 (M+H).

Step B. Preparation of methyl 3-(hydroxymethyl)-5-morpholinobenzoate

The title compound (400 mg, 49%) was prepared from the procedure described in Example 32, Step A using dimethyl 5-morpholinoisophthalate (660 mg, 2.36 mmol). LCMS: $R_T$=0.187 min, MS (ES) 252.1 (M+H).

Step C. Preparation of methyl 3-(bromomethyl)-5-morpholinobenzoate

Triphenylphosphine (835 mg, 3018 mmol) and NBS (567 mg, 3.18 mmol) were added to a solution of 3-(hydroxymethyl)-5-morpholinobenzoate (400 mg, 1.59 mmol) in THF (6.5 mL) under Ar atmosphere. The reaction mixture was stirred at room temperature for 15 h. The reaction was quenched with water and extracted with CH$_2$Cl$_2$ (3×15 mL). The combined organic layers were washed with sat. NHCO$_3$ solution (2×) and brine, dried (MgSO$_4$), filtered and concentrated. The residue was purified by flash chromatography (Combi-flash Rf, Hex/EtOAc=0-40% gradient) to provide the title compound (370 mg, 74%). LCMS: $R_T$=1.430 min, MS (ES) 313.9 (M+H).

Step D. Preparation of methyl 3-((2-methyl-1H-imidazol-1-yl)methyl)-5-morpholinobenzoate The title compound (100 mg, 56%) was prepared from the procedure described in Example 142, Step D using 2-methylimidazole (70.6 mg, 0.860 mmol). LCMS: $R_T$=0.922 min, MS (ES) 316.1 (M+H).

Step E. Preparation of 3-((2-methyl-1H-imidazol-1-yl)methyl)-5-morpholinobenzoic Acid The title compound (100 mg, crude mixture) was prepared from the procedure described in Example 12, Step E using methyl 3-((2-methyl-1H-imidazol-1-yl)methyl)-5-morpholinobenzoate (100 mg, 0.320 mmol). LCMS: $R_T$=0.833 min, MS (ES) 302.1 (M+H).

Step F. Example 144

The title compound (9.0 mg, 12%) was prepared from the procedure described in Example 12, Step F using [cyclopropyl(4-methyl-2-pyridinyl)methyl]amine dihydrochloride (41.0 mg, 0.170 mmol). LCMS: $R_T$=1.161 min, MS (ES) 446.1 (M+H). $^1$H NMR (400 MHz, MeOH-d$_4$) δ 8.34 (d, J=5.1 Hz, 1H), 7.42 (t, J=1.8 Hz, 1H), 7.32 (s, 1H), 7.20-7.14 (m, 3H), 7.04 (s, 1H), 6.94-6.92 (m, 1H), 5.22 (s, 2H), 4.39 (d, J=10.0 Hz, 1H), 3.84-3.81 (m, 4H), 3.21-3.18 (m, 4H), 2.42 (s, 3H), 2.39 (s, 3H), 1.38-1.29 (m, 2H), 0.68-0.47 (m, 4H).

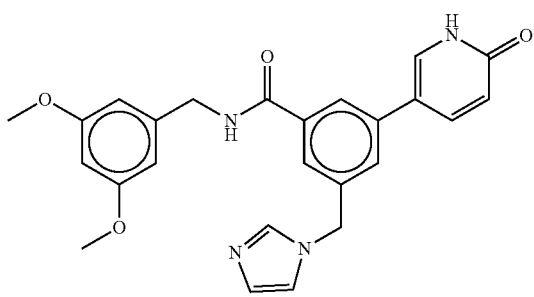

Example 145

3-((1H-Imidazol-1-yl)methyl)-N-(3,5-dimethoxy-benzyl)-5-(6-oxo-1,6-dihydropyridin-3-yl)benzamide The title compound (0.01 g, 14%) was prepared following the procedure described in Example 117 using 3-((1H-imidazol-1-yl)methyl)-5-bromo-N-(3,5-dimethoxybenzyl)benzamide (0.10 g 0.23 mmol) and (6-oxo-1,6-dihydropyridin-3-yl)boronic acid (0.11 g, 0.81 mmol). LCMS: 98% 254 nm $R_T$=0.59 min, MS (ES) 445 (M+H).

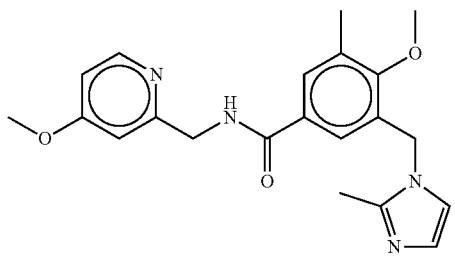

Example 146

4-Methoxy-N-((4-methoxypyridin-2-yl)methyl)-3-methyl-5-((2-methyl-1H-imidazol-1-yl)methyl)benzamide Step A. Preparation of methyl 3-(bromomethyl)-4-methoxy-5-methylbenzoate The title compound (0.51 g, 42%) was prepared following the procedure described in Example 72, Step A using 4-methoxy-3,5-dimethylbenzoate (0.86 g, 4.43 mmol).

Step B. Preparation of methyl 3-(acetoxymethyl)-4-methoxy-5-methylbenzoate

A solution of methyl 3-(bromomethyl)-4-methoxy-5-methylbenzoate (0.51 g, 1.87 mmol), NaOAc (0.30 g, 3.74 mmol) in acetonitrile (50 mL) was heated to reflux for an 18 h. The reaction was cooled, concentrated under reduced pressure. The residue was dissolved in DCM, washed with water, dried and concentrated under reduced pressure. The crude was purified by flash chromatography (Combi-flash Rf, Hex/EtOAc=0-100% gradient) to afford the title compound (0.35 g, 74%). $^1$H NMR (400 MHz, CDCl$_3$) δ 7.9 (s, 1H), 7.8 (s, 1H), 5.2 (s, 2H), 3.9 (s, 3H), 3.8 S, 3H), 2.3 (s, 3H), 2.1 (s, 3H).

Step C. Preparation of 3-hydroxy-4-methoxy-5-methylbenzoic Acid

The title compound (0.23 g, 87%) was prepared from the procedure described in Example 12, Step E using methyl 3-(acetoxymethyl)-4-methoxy-5-methylbenzoate (0.35 g, 1.37 mmol).

Step D. Preparation of 3-(hydroxymethyl)-4-methoxy-N-((4-methoxypyridin-2-yl)methyl)-5-methylbenzamide A solution of 3-hydroxy-4-methoxy-5-methylbenzoic acid (0.23 g, 1.18 mmol), DIEA (0.73 ml, 4.13 mmol) and 2-Chloro-1,3-dimethylimidazolinium chloride (0.22 g, 1.30 mmol) in THF (15 mL) was cooled on an ice bath and stirred for 30 min. (4-Methoxypyridin-2-yl)methanamine (0.19 g, 1.30 mmol) was added to the reaction mixture and stirred for 18 h then concentrated. The residue was purified by flash chromatography (Combi-flash Rf, DCM/MeOH=0-10% gradient) to afford the title compound (0.26 g, 70%).

Step E. Preparation of 3-(bromomethyl)-4-methoxy-N-((4-methoxypyridin-2-yl)methyl)-5-methylbenzamide A solution of 3-(hydroxymethyl)-4-methoxy-N-((4-methoxypyridin-2-yl)methyl)-5-methylbenzamide (0.26 g, 0.82 mmol) in THF (20 mL) was cooled on an ice bath. The solution was treated with triphenyl phosphine (0.29 g, 1.64 mmol), NBS (0.43 g, 1.64 mmol) and stirred for 4 h. The solvent was removed under reduced pressure and purified by flash chromatography (Combi-flash Rf, Hex/EtOAc=0-100% gradient) to afford the title compound (0.15 g, 48%).

Step F. Example 146

The title compound (0.02 g, 38%) was prepared from the procedure described in Example 142, Step D using of 3-(bromomethyl)-4-methoxy-N-((4-methoxypyridin-2-yl)methyl)-5-methylbenzamide (0.05 g, 0.13 mmol), DIEA (0.06 mL, 0.33 mmol) and 2-methyl-1H-imidazole (0.02 g, 0.26 mmol). LCMS: 98% 254 nm $R_T$=0.1 min, MS (ES) 381 (M+H).

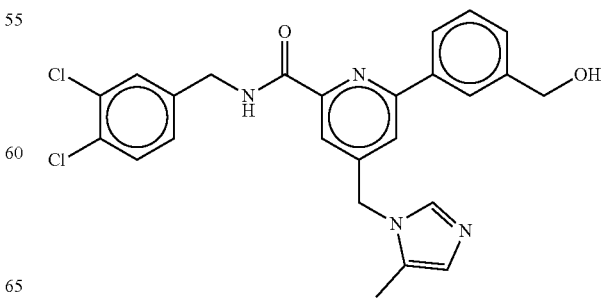

Example 147

N-(3,4-dichlorobenzyl)-3'-(hydroxymethyl)-5-((2-methyl-1H-imidazol-1-yl)methyl)-[1,1'-biphenyl]-3-carboxamide

Step A. Preparation of 3-bromo-5-((2-methyl-1H-imidazol-1-yl)methyl)benzoic Acid The title compound was prepared following the procedure described in Example 110, Step A using methyl 3-bromo-5-(bromomethyl)benzoate and 2-methyl-1H-imidazole.

Step B. Preparation of 3-bromo-N-(3,4-dichlorobenzyl)-5-((2-methyl-1H-imidazol-1-yl)methyl)benzamide The title compound was prepared following the procedure described in Example 1, Step C using 3-bromo-5-((2-methyl-1H-imidazol-1-yl)methyl)benzoic acid, HATU, DIEA, DMF, and (3,4-dichlorophenyl)methanamine.

Step C. Example 147

The title compound (0.16 g, 34%) was prepared following the procedure described in Example 1, Step B using 3-bromo-N-(3,4-dichlorobenzyl)-5-((2-methyl-1H-imidazol-1-yl)methyl)benzamide (0.45 g, 0.99 mmol) and (3-(hydroxymethyl)phenyl)boronic acid (0.23 g, 1.49 mmol). LCMS: 98% 254 nm $R_T$=0.89 min, MS (ES) 481 (M+H).

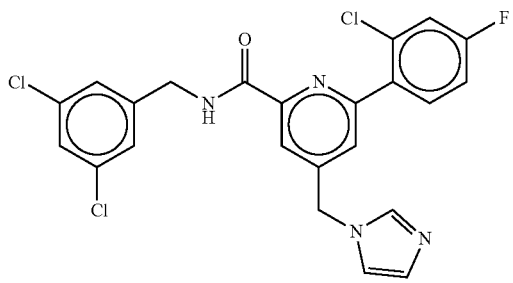

Example 148

4-((1H-imidazol-1-yl)methyl)-6-(2-chloro-4-fluorophenyl)-N-(3,5-dichlorobenzyl)picolinamide

Step A. Preparation of methyl 4-((1H-imidazol-1-yl)methyl)-6-chloropicolinate A solution of methyl 4-(bromomethyl)-6-chloropicolinate (1 eq) and 1H-imidazole (2 eq) in acetonitrile was refluxed for 6 h, cooled to ambient temperature and concentrated. After aqueous work up, the crude product was purified by flash chromatography (Combi-flash Rf, DCM/MeOH=0-10% gradient) to afford the title compound.

Step B. Preparation of 4-((1H-imidazol-1-yl)methyl)-6-(2-chloro-4-fluorophenyl)picolinic Acid (2-Chloro-4-fluorophenyl)boronic acid (1.5 eq) was coupled to 4-((1H-imidazol-1-yl)methyl)-6-chloropicolinate (1.0 eg.) following the procedure described in Example 117 to give crude methyl 4-((1H-imidazol-1-yl)methyl)-6-(2-chloro-4-fluorophenyl)picolinate. The resulting ester (1 eq) was saponified with 2M LiOH (1.5 eq) a mixture of THF/MeOH/water (4:1:1) at ambient temperature to afford the title compound.

Step B. Example 148

The title compound (0.01 g, 19%) was prepared following the procedure described in Example 72, Step D using 4-((1H-imidazol-1-yl)methyl)-6-(2-chloro-4-fluorophenyl)picolinic acid (0.03 g, 0.08 mmol) and (3,5-dichlorophenyl)methanamine (0.04 g, 0.09 mmol). LCMS: >95% 254 nm $R_T$=1.047 min, MS (ES) 488 (M+H).

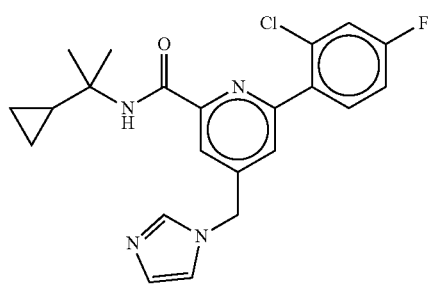

Example 149

4-((1H-imidazol-1-yl)methyl)-6-(2-chloro-4-fluorophenyl)-N-(2-cyclopropylpropan-2-yl)picolinamide The title compound (0.01 g, 13%) was prepared following the procedure described in Example 72, Step D using 4-((1H-imidazol-1-yl)methyl)-6-(2-chloro-4-fluorophenyl)picolinic acid (0.05 g, 0.15 mmol) and 2-cyclopropylpropan-2-amine (0.05 g, 0.18 mmol). LCMS: >95% 214 nm $R_T$=1.002 min, MS (ES) 413.1 (M+H).

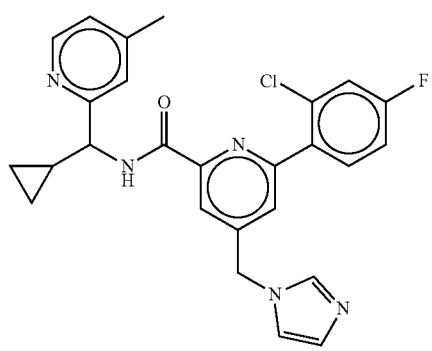

Example 150

4-((1H-Imidazol-1-yl)methyl)-6-(2-chloro-4-fluorophenyl)-N-(cyclopropyl(4-methylpyridin-2-yl)methyl)picolinamide The title compound (0.01 g, 14%) was prepared following the procedure described in Example 72, Step D using 4-((1H-imidazol-1-yl)methyl)-6-(2-chloro-4-fluorophenyl)picolinic acid (0.05 g, 0.15 mmol) and cyclopropyl(4-methylpyridin-2-yl)methanamine (0.04 g, 0.18 mmol). LCMS: >95% 214 nm $R_T$=0.131 min, MS (ES) 476.0 (M+H).

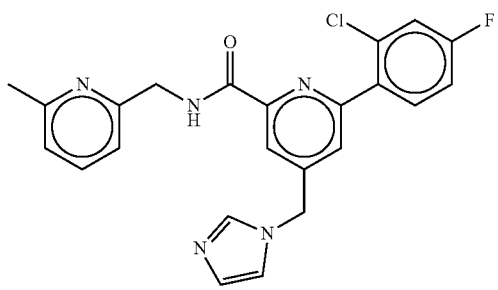

Example 151

4-((1H-Imidazol-1-yl)methyl)-6-(2-chloro-4-fluorophenyl)-N-((6-methylpyridin-2-yl)methyl)picolinamide The title compound (0.01 g, 12%) was prepared following the procedure described in Example 72, Step D using 4-((1H-imidazol-1-yl)methyl)-6-(2-chloro-4-fluorophenyl) picolinic acid (0.05 g, 0.15 mmol) and (6-methylpyridin-2-yl)methanamine (0.02 g, 0.18 mmol). LCMS: >95% 214 nm $R_T$=0.113 min, MS (ES) 436 (M+H).

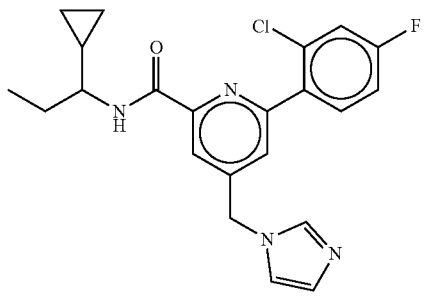

Example 152

4-((1H-Imidazol-1-yl)methyl)-6-(2-chloro-4-fluorophenyl)-N-(1-cyclopropylpropyl)picolinamide The title compound (0.01 g, 18%) was prepared following the procedure described in Example 72, Step D using 4-((1H-imidazol-1-yl)methyl)-6-(2-chloro-4-fluorophenyl) picolinic acid (0.05 g, 0.15 mmol) and 1-cyclopropylpropan-1-amine (0.02 g, 0.18 mmol). LCMS: >95% 254 nm $R_T$=1.003 min, MS (ES) 413 (M+H).

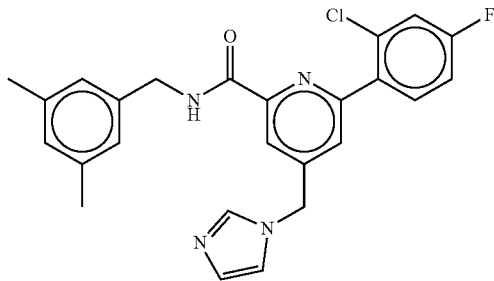

Example 153

4-((1H-Imidazol-1-yl)methyl)-6-(2-chloro-4-fluorophenyl)-N-(3,5-dimethylbenzyl)picolinamide The title compound (0.02 g, 31%) was prepared following the procedure described in Example 72, Step D using 4-((1H-imidazol-1-yl)methyl)-6-(2-chloro-4-fluorophenyl) picolinic acid (0.05 g, 0.15 mmol) and (3,5-dimethylphenyl)methanamine (0.02 g, 0.15 mmol). LCMS: >95% 254 nm $R_T$=1.016 min, MS (ES) 449.1 (M+H).

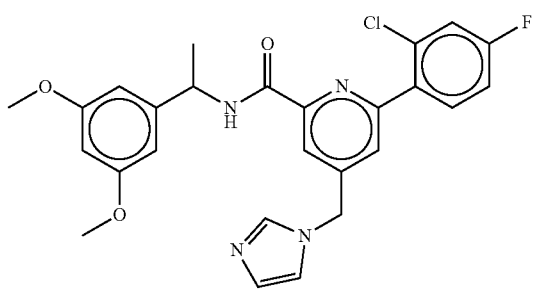

Example 154

4-((1H-Imidazol-1-yl)methyl)-6-(2-chloro-4-fluorophenyl)-N-(1-(3,5-dimethoxyphenyl)ethyl)picolinamide The title compound (0.03 g, 44%) was prepared following the procedure described in Example 72, Step D using 4-((1H-imidazol-1-yl)methyl)-6-(2-chloro-4-fluorophenyl) picolinic acid (0.05 g, 0.15 mmol) and 1-(3,5-dimethoxyphenyl)ethan-1-amine (0.03 g, 0.15 mmol). LCMS: >95% 254 nm $R_T$=0.979 min, MS (ES) 495 (M+H).

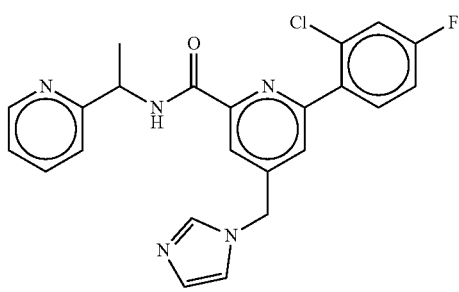

Example 155

4-((1H-Imidazol-1-yl)methyl)-6-(2-chloro-4-fluorophenyl)-N-(1-(pyridin-2-yl)ethyl)picolinamide The title compound (0.02 g, 26%) was prepared following the procedure described in Example 72, Step D using 4-((1H-imidazol-1-yl)methyl)-6-(2-chloro-4-fluorophenyl) picolinic acid (0.05 g, 0.15 mmol) and 1-(pyridin-2-yl)ethan-1-amine (0.02 g, 0.15 mmol). LCMS: >95% 214 nm $R_T$=1.002 min, MS (ES) 413.1 (M+H).

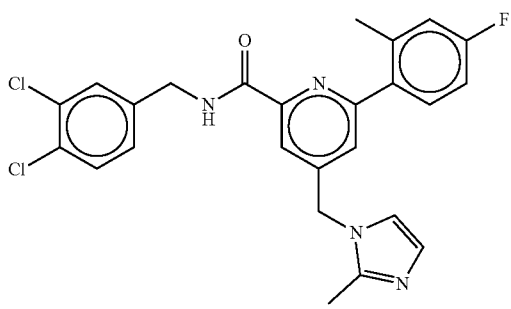

Example 156

N-(3,4-dichlorobenzyl)-6-(4-fluoro-2-methylphenyl)-4-((2-methyl-1H-imidazol-1-yl)methyl)picolinamide Step A. Preparation of 6-chloro-4-((2-methyl-1H-imidazol-1-yl)methyl)picolinic Acid A solution of methyl 4-(bromomethyl)-6-chloropicolinate (2.33 g, 9.35 mmol) and 2-methyl-1H-imidazole (1.53 g, 18.7 mmol) in acetonitrile was refluxed for 6 h, cooled to ambient temperature and concentrated. After aqueous work up, the crude product was purified by flash chromatography (Combi-flash Rf, DCM/MeOH=0-10% gradient) to afford methyl 6-chloro-4-((2-methyl-1H-imidazol-1-yl)methyl)picolinate (1.59 g, 67%). It was saponified with 2M LiOH (2.50 ml, 7.53 mmol)) a mixture of THF/MeOH/water (4:1:1) at ambient temperature to afford the title compound (1.5 g, 6.28 mmol).

Step B. Preparation of 6-chloro-N-(3,4-dichlorobenzyl)-4-((2-methyl-1H-imidazol-1-yl)methyl)picolinamide The title compound (0.63 g, 71%) was prepared following the procedure described in Example 72, Step D using 6-chloro-4-((2-methyl-1H-imidazol-1-yl)methyl)picolinic acid (0.52 g, 2.09 mmol) and (3,4-dichlorophenyl)methanamine (0.40 g, 2.30 mmol).

Step C. Example 156

The title compound was prepared following the procedure described in Example 117 using 6-chloro-N-(3,4-dichlorobenzyl)-4-((2-methyl-1H-imidazol-1-yl)methyl)picolinamide (1.0 eq) and (4-fluoro-2-methylphenyl)boronic acid (1.5 eq). LCMS: 98% 254 nm $R_T$=0.99 min, MS (ES) 484 (M+H).

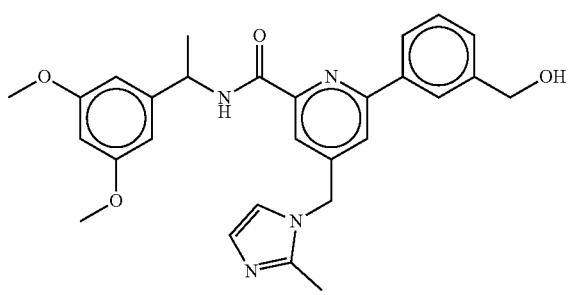

Example 157

N-(1-(3,5-dimethoxyphenyl)ethyl)-6-(3-(hydroxymethyl)phenyl)-4-((2-methyl-1H-imidazol-1-yl)methyl)picolinamide Step A. Preparation of 6-chloro-N-(1-(3,5-dimethoxyphenyl)ethyl)-4-((2-methyl-1H-imidazol-1-yl)methyl)picolinamide The title compound (0.63 g, 71%) was prepared following the procedure described in Example 72, Step D using 6-chloro-4-((2-methyl-1H-imidazol-1-yl)methyl)picolinic acid (0.52 g, 2.09 mmol) and 1-(3,5-dimethoxyphenyl)ethan-1-amine (0.41 g, 2.30 mmol).

Step B. Example 157

The title compound (0.006 g, 7%) was prepared following the procedure described in Example 1, Step B using 6-chloro-N-(1-(3,5-dimethoxyphenyl)ethyl)-4-((2-methyl-1H-imidazol-1-yl)methyl)picolinamide (0.07 g, 0.17 mmol) and ((3-(hydroxymethyl)phenyl)boronic acid (0.04 g, 0.25 mmol). LCMS: 98% 254 nm $R_T$=0.86 min, MS (ES) 487 (M+H).

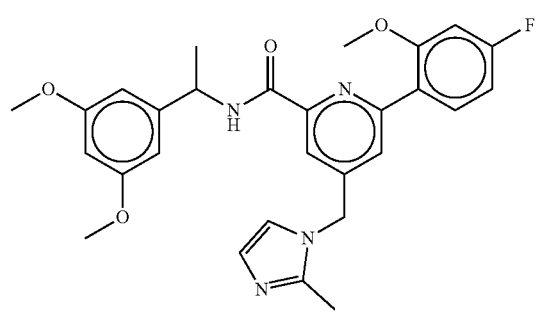

Example 158

N-(1-(3,5-dimethoxyphenyl)ethyl)-6-(4-fluoro-2-methoxyphenyl)-4-((2-methyl-1H-imidazol-1-yl)methyl)picolinamide The title compound (0.006 g, 7%) was prepared following the procedure described in Example 1, Step B using 6-chloro-N-(1-(3,5-dimethoxyphenyl)ethyl)-4-((2-methyl-1H-imidazol-1-yl)methyl)picolinamide (0.06 g 0.15 mmol) and (4-fluoro-2-methoxyphenyl)boronic acid (0.04 g, 0.25 mmol). LCMS: 98% 254 nm $R_T$=0.96 min, MS (ES) 505 (M+H).

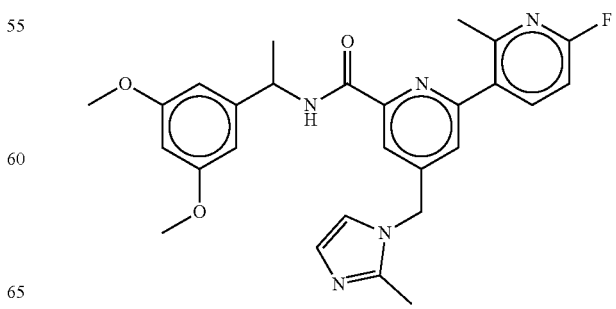

Example 159

N-(1-(3,5-Dimethoxyphenyl)ethyl)-6'-fluoro-2'-methyl-4-((2-methyl-1H-imidazol-1-yl)methyl)-[2,3'-bipyridine]-6-carboxamide The title compound (0.01 g, 5%) was prepared following the procedure described in Example 1, Step B using 6-chloro-N-(1-(3,5-dimethoxyphenyl)ethyl)-4-((2-methyl-1H-imidazol-1-yl)methyl)picolinamide (0.06 g 0.15 mmol) and (6-fluoro-2-methylpyridin-3-yl)boronic acid (0.03 g, 0.25 mmol). LCMS: 98% 254 nm $R_T$=0.89 min, MS (ES) 490 (M+H).

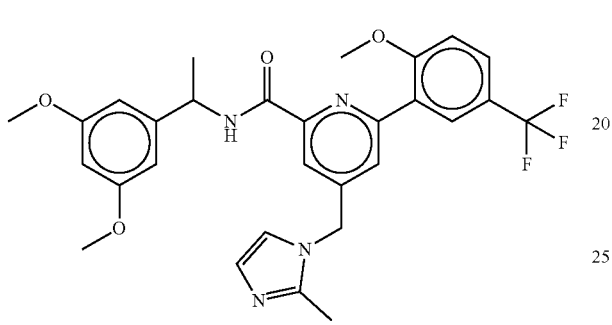

Example 160

N-(1-(3,5-Dimethoxyphenyl)ethyl)-6-(2-methoxy-5-(trifluoromethyl)phenyl)-4-((2-methyl-1H-imidazol-1-yl)methyl)picolinamide The title compound (0.01 g, 5%) was prepared following the procedure described in Example 1, Step B using 6-chloro-N-(1-(3,5-dimethoxyphenyl)ethyl)-4-((2-methyl-1H-imidazol-1-yl)methyl)picolinamide (0.06 g 0.15 mmol) and (2-methoxy-5-(trifluoromethyl)phenyl)boronic acid (0.05 g, 0.25 mmol). LCMS: 98% 254 nm $R_T$=1.0 min, MS (ES) 556 (M+H).

Example 161

6-(3-Carbamoyl-4-fluorophenyl)-N-(1-(3,5-dimethoxyphenyl)ethyl)-4-((2-methyl-1H-imidazol-1-yl)methyl)picolinamide The title compound (0.01 g, 3%) was prepared following the procedure described in Example 117 using 6-chloro-N-(1-(3,5-dimethoxyphenyl)ethyl)-4-((2-methyl-1H-imidazol-1-yl)methyl)picolinamide (0.06 g 0.15 mmol) and (3-carbamoyl-4-fluorophenyl)boronic acid (0.04 g, 0.25 mmol). LCMS: 95% 254 nm $R_T$=0.84 min, MS (ES) 518 (M+H).

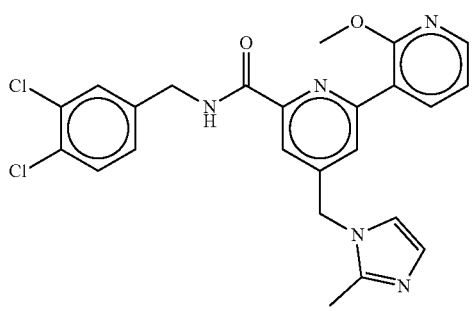

Example 162

N-(3,4-Dichlorobenzyl)-2'-methoxy-4-((2-methyl-1H-imidazol-1-yl)methyl)-[2,3'-bipyridine]-6-carboxamide The title compound (0.01 g, 5%) was prepared following the procedure described in Example 117 using 6-chloro-N-(3,4-dichlorobenzyl)-4-((2-methyl-1H-imidazol-1-yl)methyl)picolinamide (0.07 g 0.19 mmol) and (2-methoxypyridin-3-yl)boronic acid (0.04 g, 0.28 mmol). LCMS: 98% 254 nm, MS (ES) 483 (M+H).

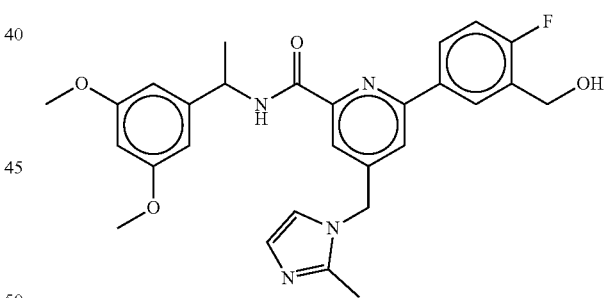

Example 163

N-(1-(3,5-dimethoxyphenyl)ethyl)-6-(4-fluoro-3-(hydroxymethyl)phenyl)-4-((2-methyl-1H-imidazol-1-yl)methyl)picolinamide The title compound (0.01 g, 4%) was prepared following the procedure described in Example 117 using 6-chloro-N-(1-(3,5-dimethoxyphenyl)ethyl)-4-((2-methyl-1H-imidazol-1-yl)methyl)picolinamide (0.06 g 0.15 mmol) and (4-fluoro-3-(hydroxymethyl)phenyl)boronic acid (0.04 g, 0.25 mmol). LCMS: 92% 254 nm $R_T$=0.88 min, MS (ES) 505 (M+H).

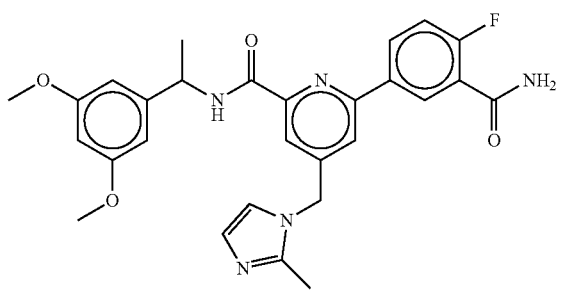

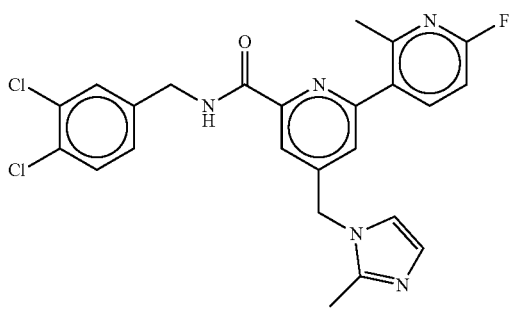

Example 164

N-(3,4-dichlorobenzyl)-6'-fluoro-2'-methyl-4-((2-methyl-1H-imidazol-1-yl)methyl)-[2,3'-bipyridine]-6-carboxamide The title compound (0.01 g, 11%) was prepared following the procedure described in Example 117 using 6-chloro-N-(3,4-dichlorobenzyl)-4-((2-methyl-1H-imidazol-1-yl)methyl)picolinamide (0.07 g 0.19 mmol) and (6-fluoro-2-methylpyridin-3-yl)boronic acid (0.04 g, 0.28 mmol). LCMS: 98% 254 nm R$_T$=0.94 min, MS (ES) 485 (M+H).

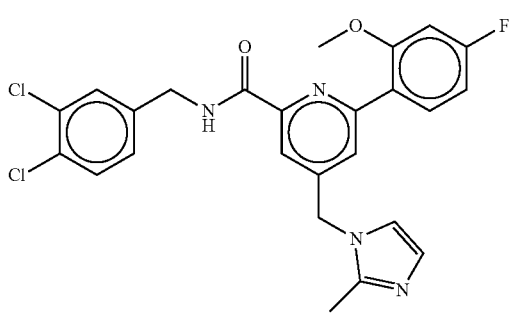

Example 165

N-(3,4-Dichlorobenzyl)-6-(4-fluoro-2-methoxyphenyl)-4-((2-methyl-1H-imidazol-1-yl)methyl)picolinamide The title compound (0.01 g, 10%) was prepared following the procedure described in Example 117 using 6-chloro-N-(3,4-dichlorobenzyl)-4-((2-methyl-1H-imidazol-1-yl)methyl)picolinamide (0.07 g 0.19 mmol) and ((4-fluoro-2-methoxyphenyl)boronic acid (0.05 g, 0.28 mmol). LCMS: 98% 254 nm R$_T$=1.01 min, MS (ES) 501 (M+2H).

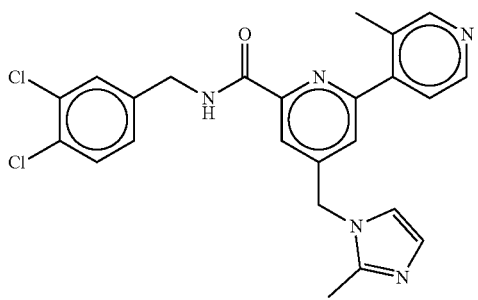

Example 166

N-(3,4-Dichlorobenzyl)-3'-methyl-4-((2-methyl-1H-imidazol-1-yl)methyl)-[2,4'-bipyridine]-6-carboxamide The title compound (0.01 g, 9%) was prepared following the procedure described in Example 117 using 6-chloro-N-(3,4-dichlorobenzyl)-4-((2-methyl-1H-imidazol-1-yl)methyl)picolinamide (0.07 g 0.19 mmol) and (3-methylpyridin-4-yl)boronic acid (0.04 g, 0.28 mmol). LCMS: 98% 254 nm R$_T$=0.75 min, MS (ES) 467 (M+H).

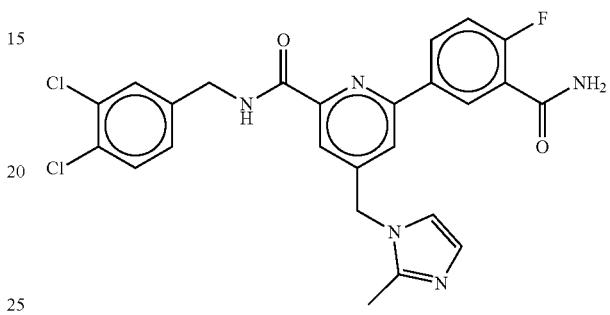

Example 167

6-(3-Carbamoyl-4-fluorophenyl)-N-(3,4-dichlorobenzyl)-4-((2-methyl-1H-imidazol-1-yl)methyl)picolinamide The title compound (0.01 g, 2%) was prepared following the procedure described in Example 117 using 6-chloro-N-(3,4-dichlorobenzyl)-4-((2-methyl-1H-imidazol-1-yl)methyl)picolinamide (0.07 g 0.19 mmol) and (3-carbamoyl-4-fluorophenyl)boronic acid (0.05 g, 0.28 mmol). LCMS: 98% 254 nm, MS (ES) 513 (M+H).

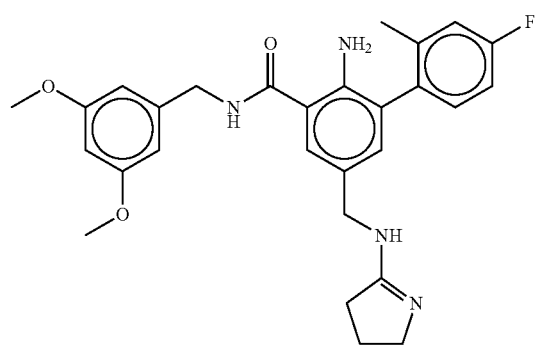

Example 168

2-Amino-5-(((3,4-dihydro-2H-pyrrol-5-yl)amino)methyl)-N-(3,5-dimethoxybenzyl)-4'-fluoro-2'-methyl-[1,1'-biphenyl]-3-carboxamide Step A. Preparation of 2-amino-3-bromo-5-chloro-N-(3,5-dimethoxybenzyl)benzamide N,N-diisopropylethylamine (5.76 mL, 33.1 mmol) was added to a solution of 2-amino-3-bromo-5-chlorobenzoic acid (4.12 g, 16.6 mmol) and 2-(1H-Benzotriazole-1-yl)-1,1,3,3-tetramethylaminium tetrafluoroborate (5.32 g, 16.6 mmol) in DMF (55.0 mL). The reaction was stirred for 10 min at room temperature and then 3,5-dimethoxybenzylamine (2.77 g, 16.6 mmol) was added. The reaction was stirred for 2 h at room temperature and then water was added. The solid was collected by vacuum filtration and washed with water. The solid was further dried in a vacuum oven overnight to provide the title compound (6.30 g, 96%) as a yellow solid. $^1$H NMR (400 MHz, DMSO) δ 9.06 (br, 1H), 7.68-7.65 (m, 2H), 6.58 (br, 2H), 6.47 (d, J=2.4 Hz, 2H), 6.38 (t, J=2.4 Hz, 1H), 4.36 (d, J=6 Hz, 2H), 3.72 (s, 6H). LCMS $R_T$=1.769 min, MS (ES) 399 [M+H].

Step B. Preparation of 2-amino-5-chloro-N-(3,5-dimethoxybenzyl-4'-fluoro-2'-methyl-[1,1'-biphenyl]-3-carboxamide Pd(dppf)Cl$_2$ (119 mg, 0.163 mmol) was added to a solution of 2-amino-3-bromo-5-chloro-N-(3,5-dimethoxybenzyl)benzamide (1.30 g, 3.27 mmol), 4-fluoro-2-methylphenylboronic acid (0.755 g, 4.90 mmol) and K$_2$CO$_3$ (1.35 g, 9.80 mmol) in 1,4-dioxane:water (12.8 mL, 3:1). The reaction was degassed for 10 min and then heated to 95° C. for 2 h under argon. The reaction was cooled to room temperature and diluted with water and extracted with EtOAc (3×). The combined organic layers were washed with brine, dried (MgSO$_4$), filtered and concentrated. The residue was purified by flash chromatography (Combi-flash Rf, Hex/EtOAc=0-35% gradient) to provide the title compound (1.32 g, 94%). $^1$H NMR (400 MHz, CDCl$_3$) δ 7.32 (d, J=2.4 Hz, 1H), 7.14-7.10 (m, 1H), 7.04-6.95 (m, 3H), 6.51 (d, J=2.4 Hz, 2H), 6.41 (t, J=2.4 Hz, 1H), 4.54 (d, J=5.2 Hz, 2H), 3.80 (s, 6H), 2.15 (s, 3H). LCMS $R_T$=1.959 min, MS (ES) 429 [M+H].

Step C. Preparation of 2-amino-N-(3,5-dimethoxybenzyl-4'-fluoro-2'-methyl-5-vinyl-[1,1'-biphenyl]-3-carboxamide Pd(PtBu$_3$)$_2$ (0.465 g, 0.911 mmol) was added to a solution of 2-amino-5-chloro-N-(3,5-dimethoxybenzyl)-4'-fluoro-2'-methyl-[1,1'-biphenyl]-3-carboxamide (1.30 g, 3.04 mmol), potassium vinyltrifluoroborate (1.22 g, 9.11 mmol), Cs$_2$CO$_3$ (2.97 g, 9.11 mmol) in 1,4-dioxane:water (12.0 mL, 3:1). The reaction was degassed for 10 min and then heated to 95° C. for 16 h under Ar. The reaction was cooled to room temperature and diluted with water and extracted with EtOAc (3×). The combined organic layers were washed with brine, dried (MgSO$_4$), filtered and concentrated. The residue was purified by flash chromatography (Combi-flash Rf, Hex/EtOAc=0-35% gradient) to provide to provide the title compound (0.455 g, 36%). LCMS $R_T$=1.930 min, MS (ES) 421 [M+H].

Step D. Preparation of 2-amino-N-(3,5-dimethoxybenzyl-4'-fluoro-5-formyl-2'-methyl-[1,1'-biphenyl]-3-carboxamide OsO$_4$ (24.2 mg, 0.0952 mmol) was added to a solution of 2-amino-N-(3,5-dimethoxybenzyl)-4'-fluoro-2'-methyl-5-vinyl-[1,1'-biphenyl]-3-carboxamide (160 mg, 0.381 mmol) and pyridine (61 µL, 0.762 mmol) in 1,4-dioxane:water (3.8 mL, 3:1) followed by the addition of NaIO$_4$ (325 mg, 1.52 mmol). The reaction was stirred at room temperature overnight and then filtered and the solvent was removed under reduced pressure. The residue was purified by flash chromatography (Combi-flash Rf, Hex/EtOAc=0-50% gradient) to provide the title compound (142 mg, 88%). $^1$H NMR (400 MHz, CDCl$_3$) δ 9.74 (s, 1H), 7.94 (d, J=1.8 Hz, 1H), 7.55 (d, J=1.8 Hz, 1H), 7.17-7.13 (m, 1H), 7.07-6.98 (m, 2H), 6.52 (d, J=2.2 Hz, 2H), 6.42 (t, J=2.2 Hz, 1H), 6.32 (br, 1H), 4.57 (d, J=5.6 Hz, 2H), 3.81 (s, 6H), 2.14 (s, 3H). LCMS $R_T$=1.745 min, MS (ES) 423 [M+H].

Step E. Preparation of 2-amino-5-(aminomethyl)-N-(3,5-dimethoxybenzyl)-4'-fluoro-2'-methyl-[1,1'-biphenyl]-3-carboxamide A solution of 2-amino-N-(3,5-dimethoxybenzyl)-4'-fluoro-5-formyl-2'-methyl-[1,1'-biphenyl]-3-carboxamide (70.0 mg, 0.166 mmol) and hydroxylammonium chloride (57.6 mg, 0.829 mmol) in methanol (1.7 mL) was stirred for 1 h at 50° C. The reaction was then cooled to room temperature and concentrated under reduced pressure. The residue was taken up in MeOH:acetic acid (0.8 mL 1:1) and zinc dust (54.2 mg, 0.829 mmol) was added. The reaction was sonicated for 1 hour and then filtered and concentrated under reduced pressure to provide the title compound (59.0 mg, 84%). LCMS $R_T$=1.351 min, MS (ES) 424 [M+H].

Step F. Example 168

5-methoxy-3,4-dihydro-2H-pyrrole (9.36 mg, 0.0945 mmol) was added to a solution of 2-amino-5-(aminomethyl)-N-(3,5-dimethoxybenzyl)-4'-fluoro-2'-methyl-[1,1'-biphenyl]-3-carboxamide (20.0 mg, 0.0472 mmol) in pyridine (0.50 mL). The reaction mixture was stirred at room temperature for 1 hour. The reaction mixture was concentrated and the residue was taken up in DMSO and purified by reverse phase HPLC (Phenomenex Gemini C18, H$_2$O/CH$_3$CN gradient from 20-95% CH$_3$CN, 0.1% TFA) to yield the title compound (6.80 mg, 29% yield). $^1$H NMR (400 MHz, CDCl$_3$) δ 7.40 (s, 1H), 7.14-7.11 (m, 1H), 7.03-6.93 (m, 3H), 6.51 (d, J=2.2 Hz, 2H), 6.39 (t, J=2.2 Hz, 1H), 5.44 (s, 2H), 4.54 (d, J=5.3 Hz, 2H), 4.32 (s, 2H), 3.79 (s, 6H), 3.79-3.63 (m, 2H), 2.47-2.43 (m, 2H), 2.14 (s, 3H), 2.04-1.93 (m, 2H). $^{19}$F NMR (376 MHz, CDCl$_3$) δ −117.88. LCMS: $R_T$=1.456 min, MS (ES) 491 (M+H).

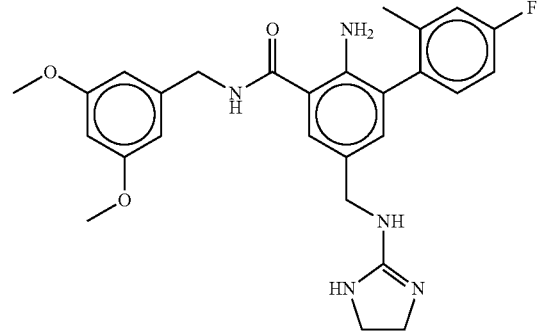

Example 169

2-Amino-5-(((4,5-dihydro-1H-imidazol-2-yl)amino)methyl)-N-(3,5-dimethoxybenzyl)-4'-fluoro-2'-methyl-[1,1'-biphenyl]-3-carboxamide 2-(methylthio)-4,5-dihydro-1H-imidazole (16.5 mg, 0.142 mmol) was added to a solution of 2-amino-5-(aminomethyl)-N-(3,5-dimethoxybenzyl)-4'-fluoro-2'-methyl-[1,1'-biphenyl]-3-carboxamide (20.0 mg, 0.0472 mmol) in pyridine (0.50 mL). The reaction mixture was stirred at 125° C. for 1 h using microwave irradiation. The reaction mixture was concentrated and the residue was taken up in DMSO and purified by reverse phase HPLC (Phenomenex Gemini C18, $H_2O/CH_3CN$ gradient from 20-95% $CH_3CN$, 0.1% TFA) to yield the title compound (8.20 mg, 35% yield). $^1H$ NMR (400 MHz, $CDCl_3$) δ 7.52 (s, 1H), 7.12-7.08 (m, 1H), 7.02-6.93 (m, 3H), 6.52 (d, J=2.2 Hz, 2H), 6.36 (t, J=2.2 Hz, 1H), 4.51 (s, 2H), 4.23 (s, 2H), 3.77 (s, 6H), 3.57-3.54 (m, 4H), 2.11 (s, 3H). $^{19}F$ NMR (376 MHz, $CDCl_3$) δ −114.75. LCMS: $R_T$=1.442 min, MS (ES) 492 [M+H].

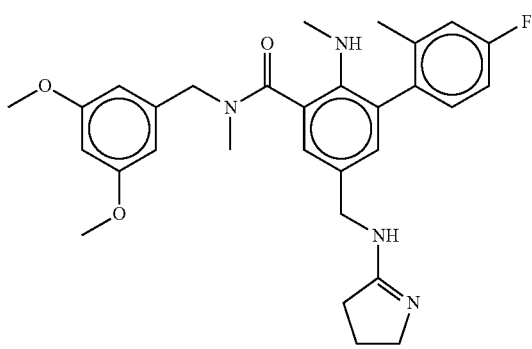

Example 170

5-(((3,4-dihydro-2H-pyrrol-5-yl)amino)methyl)-N-(3,5-dimethoxybenzyl)-4'-fluoro-N,2'-dimethyl-2-(methylamino)-[1,1'-biphenyl]-3-carboxamide Step A. Preparation of 3-bromo-5-chloro-N-(3,5-dimethoxybenzyl)-N-methyl-2-(methylamino)benzamide 2-amino-3-bromo-5-chloro-N-(3,5-dimethoxybenzyl)benzamide (490 mg, 1.23 mmol) was dissolved in THF (5.0 mL) and 60% NaH (124 mg, 3.69 mmol) was added. The reaction was stirred for 15 minutes at room temperature and then methyl iodide (190 µL, 3.08 mmol) was added and the reaction was heated to 50° C. for 4 hours. The reaction was cooled to room temperature and poured into saturated $NH_4Cl$ and extracted with EtOAc (3×). The combined organic layers were washed with brine, dried ($MgSO_4$), filtered and concentrated. Flash column chromatography on $SiO_2$ was used to purify the product eluting with 2:1 hexanes:EtOAc to provide the title compound (160 mg, 31%). LCMS $R_T$=1.770 min, MS (ES) 427 [M+H].

Step B. Preparation of 5-chloro-N-(3,5-dimethoxybenzyl)-4'-fluoro-N,2'-dimethyl-2-(methylamino)-[1,1'-biphenyl]-3-carboxamide The title compound (150 mg, 88%) was prepared following the procedure described in Example 168, Step B using 3-bromo-5-chloro-N-(3,5-dimethoxybenzyl)-N-methyl-2-(methylamino)benzamide (160 mg, 0.376 mmol) and 4-fluoro-2-methylphenylboronic acid (86.8 mg, 0.563 mmol). LCMS $R_T$=1.986 min, MS (ES) 457 [M+H].

Step C. Preparation of N-(3,5-dimethoxybenzyl)-4'-fluoro-N,2'-dimethyl-2-(methylamino)-5-vinyl-[1,1'-biphenyl]-3-carboxamide The title compound (61 mg, 41%) was prepared following the procedure described in Example 168, Step C using 5-chloro-N-(3,5-dimethoxybenzyl)-4'-fluoro-N,2'-dimethyl-2-(methylamino)-[1,1'-biphenyl]-3-carboxamide (150 mg, 0.329 mmol), and potassium vinyltrifluoroborate (132 mg, 0.986 mmol). LCMS $R_T$=1.991 min, MS (ES) 449 [M+H].

Step D. Preparation of N-(3,5-dimethoxybenzyl)-4'-fluoro-5-formyl-N,2'-dimethyl-2-(methylamino)-[1,1'-biphenyl]-3-carboxamide The title compound (31.0 mg, 51%) was prepared following the procedure described in Example 168, Step D using $OsO_4$ (17.0 mg, 0.0669 mmol) and N-(3,5-dimethoxybenzyl)-4'-fluoro-N,2'-dimethyl-2-(methylamino)-5-vinyl-[1,1'-biphenyl]-3-carboxamide (120 mg, 0.268 mmol). $^1H$ NMR (400 MHz, $CDCl_3$) δ. LCMS $R_T$=1.710 min, MS (ES) 451 [M+H].

Step E. Preparation of 5-(aminomethyl)-N-(3,5-dimethoxybenzyl)-4'-fluoro-N,2'-dimethyl-2-(methylamino)-[1,1'-biphenyl]-3-carboxamide The title compound (28.0 mg, 93%) was prepared following the procedure described in Example 168, Step E using N-(3,5-dimethoxybenzyl)-4'-fluoro-5-formyl-N,2'-dimethyl-2-(methylamino)-[1,1'-biphenyl]-3-carboxamide (30.0 mg, 0.0669 mmol) and hydroxylammonium chloride (18.6 mg, 0.268 mmol). LCMS $R_T$=1.367 min, MS (ES) 452 [M+H].

Step F. Example 170

The title compound (6.50 mg, 47%) was prepared following the procedure described in Example 168, Step F using 5-methoxy-3,4-dihydro-2H-pyrrole (13.2 mg, 0.133 mmol) and 5-(aminomethyl)-N-(3,5-dimethoxybenzyl)-4'-fluoro-N,2'-dimethyl-2-(methylamino)-[1,1'-biphenyl]-3-carboxamide (12.0 mg, 0.0266 mmol). $^1H$ NMR (400 MHz, MeOD) δ 7.16-6.99 (m, 5H), 6.57 (d, J=1.8 Hz, 1H), 6.44 (d, J=9.2 Hz, 1H), 6.31 (s, 1H), 4.68 (s, 1H), 4.46 (s, 1H), 4.38-4.34 (m, 2H), 3.78-3.76 (m, 6H), 3.74-3.67 (m, 2H), 3.04 (s, 1H), 2.92-2.82 (m, 4H), 2.66-2.60 (m, 3H), 2.24-2.2.19 (m, 2H), 2.10 (s, 3H). $^{19}F$ NMR (376 MHz, MeOD) δ −116.65. LCMS: $R_T$=1.458 min, MS (ES) 519 (M+H).

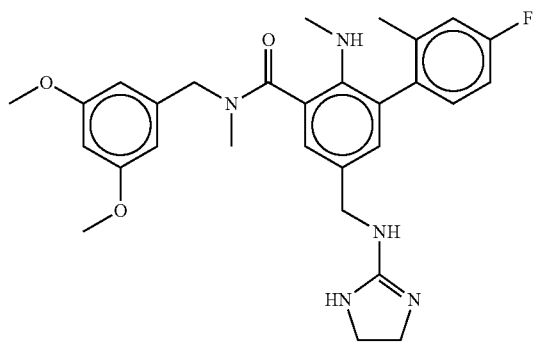

Example 171

5-(((4,5-Dihydro-1H-imidazol-2-yl)amino)methyl)-N-(3,5-dimethoxybenzyl)-4'-fluoro-N,2'-dimethyl-2-(methylamino)-[1,1'-biphenyl]-3-carboxamide The title compound (6.1 mg, 44%) was prepared following the procedure described in Example 169 using 2-(methylthio)-4,5-dihydro-1H-imidazole (15.4 mg, 0.133 mmol) and 5-(aminomethyl)-N-(3,5-dimethoxybenzyl)-4'-fluoro-N,2'-dimethyl-2-(methylamino)-[1,1'-biphenyl]-3-carboxamide (12.0 mg, 0.0266 mmol). $^1$H NMR (400 MHz, MeOD) δ 7.17-6.99 (m, 5H), 6.57 (d, J=1.8 Hz, 1H), 6.44 (d, J=10.7 Hz, 1H), 6.31 (s, 1H), 4.68 (s, 1H), 4.46 (s, 1H), 4.31-4.27 (m, 2H), 3.78-3.75 (m, 6H), 3.71-3.68 (m, 4H), 3.04-2.91 (m, 3H), 2.66-2.60 (m, 3H), 2.10 (s, 3H). $^{19}$F NMR (376 MHz, MeOD) δ −116.70. LCMS: $R_T$=1.454 min, MS (ES) 520 (M+H).

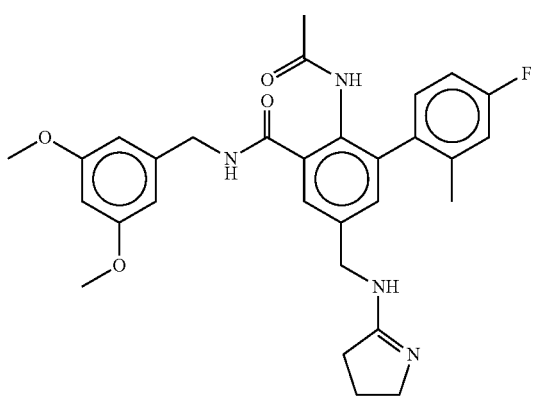

Example 172

2-Acetamido-5-(((3,4-dihydro-2H-pyrrol-5-yl)amino)methyl)-N-(3,5-dimethoxybenzyl)-4'-fluoro-2'-methyl-[1,1'-biphenyl]-3-carboxamide

Step A. Preparation of methyl 2-amino-3-bromo-5-vinylbenzoate

The title compound (0.91 g, 63%) was prepared following the procedure described in Example 168, Step B using methyl 2-amino-3-bromo-5-iodobenzoate (2.0 g, 5.64 mmol) and potassium vinyltrifluoroborate (0.981 g, 7.34 mmol). $^1$H NMR (400 MHz, CDCl$_3$) δ 7.87 (d, J=2.0 Hz, 1H), 7.71 (d, J=2.0 Hz, 1H), 6.57-6.50 (m, 1H), 6.37 (br, 2H), 5.58 (d, J=17.5 Hz, 1H), 5.12 (d, J=10.9 Hz, 1H), 3.90 (s, 3H). LCMS $R_T$=1.752 min, MS (ES) 256 [M+H].

Step B. Preparation of methyl 2-amino-3-bromo-5-formylbenzoate

The title compound (0.41 g, 45%) was prepared following the procedure described in Example 168, Step D using OsO$_4$ (0.0897 g, 0.353 mmol) and methyl 2-amino-3-bromo-5-vinylbenzoate (0.900 g, 3.53 mmol). $^1$H NMR (400 MHz, CDCl$_3$) δ 9.72 (s, 1H), 8.37 (d, J=1.9 Hz, 1H), 8.13 (d, J=1.8 Hz, 1H), 3.93 (s, 3H). LCMS $R_T$=1.375 min, MS (ES) 258 [M+H].

Step C. Preparation of methyl 2-amino-5-(aminomethyl)-3-bromobenzoate

The title compound (370 mg, 92%) was prepared following the procedure described in Example 168, Step E using methyl 2-amino-3-bromo-5-formylbenzoate (400 mg, 1.56 mmol) and hydroxylammonium chloride (433 mg, 6.23 mmol). LCMS $R_T$=0.638 min, MS (ES) 242 [M−NH$_2$].

Step D. Preparation of methyl 2-amino-3-bromo-5-(((tert-butoxycarbonyl)amino)methyl)benzoate To a solution of methyl 2-amino-5-(aminomethyl)-3-bromobenzoate (370 mg, 1.43 mmol) in DCM (6.0 mL) was added di-tert-butyl dicarbonate (344 mg, 1.58 mmol) and DMAP (17.5 mg, 0.143 mmol). The reaction was stirred at room temperature for 16 h and then concentrated. The residue was purified by flash chromatography (Combi-flash Rf, Hex/EtOAc=0-35% gradient) to provide the title compound (395 mg, 77%). $^1$H NMR (400 MHz, CDCl$_3$) δ 7.76 (d, J=2.0 Hz, 1H), 7.54 (d, J=1.8 Hz, 1H), 6.29 (br, 2H), 4.78 (br, 1H), 4.17 (d, J=4.8 Hz, 2H), 3.87 (s, 3H), 1.46 (s, 9H). LCMS $R_T$=1.661 min, MS (ES) 359 [M+H].

Step E. Preparation of methyl 2-amino-5-(((tert-butoxycarbonyl)amino)methyl)-4'-fluoro-2'-methyl-[1,1'-biphenyl]-3-carboxylate The title compound (295 mg, 68%) was prepared following the procedure described in Example 168, Step B using methyl 2-amino-3-bromo-5-(((tert-butoxycarbonyl)amino)methyl)benzoate (400 mg, 1.12 mmol) and 4-fluoro-2-methylphenylboronic acid (258 mg, 1.68 mmol). $^1$H NMR (400 MHz, CDCl$_3$) δ 7.82 (d, J=1.9 Hz, 1H), 7.14-6.94 (m, 4H), 5.64 (br, 2H), 4.76 (br, 1H), 4.21 (d, J=5.0 Hz, 2H), 3.88 (s, 3H), 2.12 (s, 3H), 1.45 (s, 9H). LCMS $R_T$=1.875 min, MS (ES) 389 [M+H].

Step F. Preparation of 2-amino-5-(((tert-butoxycarbonyl)amino)methyl)-4'-fluoro-2'-methyl-[1,1'-biphenyl]-3-carboxylic Acid To a solution of methyl 2-amino-5-(((tert-butoxycarbonyl)amino)methyl)-4'-fluoro-2'-methyl-[1,1'-biphenyl]-3-carboxylate (100 mg, 0.258 mmol) in methanol (2.5 mL) was added 2 M KOH (1.3 mL). The reaction was heated to 50° C. for 2 h. The reaction was then diluted with water and washed with EtOAc (1×). The aqueous layer was then acidified to pH~2 with 1 M HCl and extracted with EtOAc (3×). The combined organic layers were washed with brine, dried (MgSO$_4$), filtered and concentrated to provide the title compound (91 mg, 94%). LCMS $R_T$=1.670 min, MS (ES) 375 [M+H].

Step G. Preparation of tert-butyl ((6-acetamido-5-((3,5-dimethoxybenzyl)carbamoyl)-4'-fluoro-2'-methyl-[1,1'-biphenyl]-3-yl)methyl)carbamate The title compound (111 mg, 87%) was prepared following the procedure described in Example 168, Step A using 2-amino-5-(((tert-butoxycarbonyl)amino)methyl)-4'-fluoro-2'-methyl-[1,1'-biphenyl]-3-carboxylic acid (91 mg, 0.243 mmol) and 3,5-dimethoxybenzylamine (40.6 g, 0.243 mmol). $^1$H NMR (400 MHz, CDCl$_3$) δ 7.30 (d, J=5.2 Hz, 1H), 7.15-7.12 (m, 1H), 7.05-6.96 (m, 3H), 6.54 (d, J=2.2 Hz, 2H), 6.43-6.41 (m, 2H), 5.45 (s, 2H), 4.81 (s, 1H), 4.57 (d, J=5.6 Hz, 2H), 4.20 (d, 5.5 Hz, 2H), 3.81 (s, 6H), 2.15

(s, 3H), 1.44 (s, 9H). $^{19}$F NMR (376 MHz, CDCl$_3$) δ −117.83. LCMS R$_T$=1.904 min, MS (ES) 524 [M+H].

Step H. Preparation of tert-butyl ((6-acetamido-5-((3,5-dimethoxybenzyl)carbamoyl)-4'-fluoro-2'-methyl-[1,1'-biphenyl]-3-yl)methyl)carbamate To a solution of tert-butyl ((6-acetamido-5-((3,5-dimethoxybenzyl)carbamoyl)-4'-fluoro-2'-methyl-[1,1'-biphenyl]-3-yl)methyl)carbamate (42 mg, 0.0803 mmol) in THF (0.4 mL) was added 60% NaH (4.0 mg, 0.120 mmol). The reaction was stirred at room temperature for 15 min and then acetyl chloride (17.1 μL, 0.241 mmol) was added. The reaction was stirred for 30 min at room temperature and then quenched with saturated NH$_4$Cl and extracted with EtOAc (3×). The combined organic layers were washed with brine, dried (MgSO$_4$), filtered and concentrated. The residue was purified by flash chromatography (Combi-flash Rf, Hex/EtOAc=0-50% gradient) to provide the title compound (32 mg, 71%) LCMS R$_T$=1.658 min.

Step I. Preparation of 2-acetamido-5-(aminomethyl)-N-(3,5-dimethoxybenzyl)-4'-fluoro-2'-methyl-[1,1'-biphenyl]-3-carboxamide To a solution of tert-butyl ((6-acetamido-5-((3,5-dimethoxybenzyl)carbamoyl)-4'-fluoro-2'-methyl-[1,1'-biphenyl]-3-yl)methyl)carbamate (30 mg, 0.0530 mmol) in DCM (0.25 mL) was added trifluoroacetic acid (0.25 mL). The reaction was stirred at room temperature for 1 h and then concentrated to provide the title compound (23.0 mg, 93%). LCMS R$_T$=1.134 min, MS (ES) 466 [M+H].

Step J. Example 172

5-methoxy-3,4-dihydro-2H-pyrrole (11.7 mg, 0.118 mmol) was added to a solution of 2-acetamido-5-(aminomethyl)-N-(3,5-dimethoxybenzyl)-4'-fluoro-2'-methyl-[1,1'-biphenyl]-3-carboxamide (11.0 mg, 0.0236 mmol) in pyridine (0.24 mL). The reaction mixture was stirred at room temperature for 1 hour. The reaction mixture was concentrated and the residue was taken up in DMSO and purified by reverse phase HPLC (Phenomenex Gemini C18, H$_2$O/CH$_3$CN gradient from 20-95% CH$_3$CN, 0.1% TFA) to yield the title compound (6.80 mg, 54% yield). $^1$H NMR (400 MHz, MeOD) δ 7.53 (d, J=2.1 Hz, 1H), 7.33 (d, J=2.1 Hz, 1H), 7.08-7.02 (m, 2H), 6.96-6.92 (m, 1H), 6.54 (d, J=2.2 Hz, 2H), 6.40 (t, J=2.2 Hz, 1H), 4.60 (s, 2H), 4.55-4.41 (m, 2H), 3.77 (s, 6H), 3.73 (t, J=7.2 Hz, 2H), 2.92 (t, J=8.0 Hz, 2H), 2.27-2.23 (m, 2H), 2.09 (s, 3H), 1.67 (s, 3H). $^{19}$F NMR (376 MHz, MeOD) δ −116.94. LCMS: R$_T$=1.225 min, MS (ES) 533 (M+H).

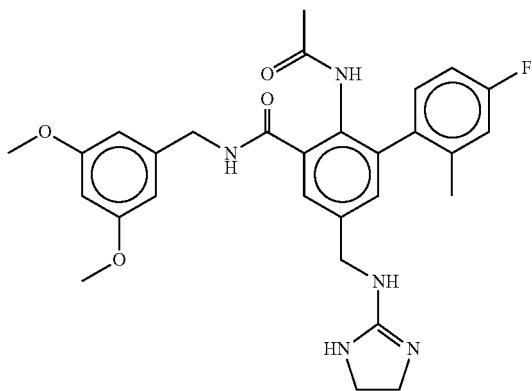

Example 173

2-Acetamido-5-(((4,5-dihydro-1H-imidazol-2-yl)amino)methyl)-N-(3,5-dimethoxybenzyl)-4'-fluoro-2'-methyl-[1,1'-biphenyl]-3-carboxamide The title compound (3.6 mg, 29%) was prepared following the procedure described in Example 169 using 2-(methylthio)-4,5-dihydro-1H-imidazole (13.7 mg, 0.118 mmol) and 2-acetamido-5-(aminomethyl)-N-(3,5-dimethoxybenzyl)-4'-fluoro-2'-methyl-[1,1'-biphenyl]-3-carboxamide (11.0 mg, 0.0236 mmol). $^1$H NMR (400 MHz, MeOD) δ 7.49 (d, J=2.1 Hz, 1H), 7.28 (d, J=2.1 Hz, 1H), 7.08-7.01 (m, 2H), 6.96-6.91 (m, 1H), 6.54 (d, J=2.2 Hz, 2H), 6.40 (t, J=2.2 Hz, 1H), 4.49-4.44 (m, 4H), 3.77 (s, 6H), 3.72 (s, 4H), 2.09 (s, 3H), 1.66 (s, 3H). $^{19}$F NMR (376 MHz, MeOD) δ −116.99. LCMS: R$_T$=1.205 min, MS (ES) 534 (M+H).

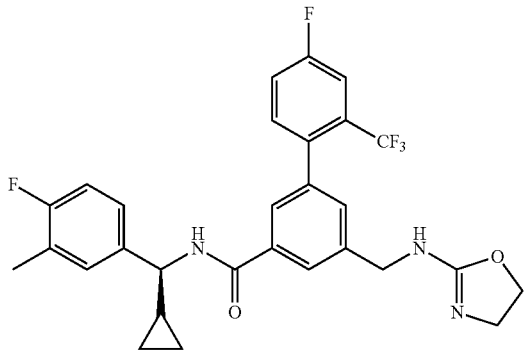 [SMILES: Cc1cc([C@@H](NC(=O)c2cc(CNC3=NCCO3)cc(-c3ccc(F)cc3C(F)(F)F)c2)C2CC2)ccc1F]

Example 174

(S)—N-(cyclopropyl(4-fluoro-3-methylphenyl)methyl)-5-(((4,5-dihydrooxazol-2-yl)amino)methyl)-4'-fluoro-2'-(trifluoromethyl)-[1,1'-biphenyl]-3-carboxamide Step A. Preparation of (S)—N-(cyclopropyl(4-fluoro-3-methylphenyl)methyl)-4'-fluoro-5-(hydroxymethyl)-2'-(trifluoromethyl)-[1,1'-biphenyl]-3-carboxamide HATU (0.54 g, 1.4 mmol) and DIEA (0.66 mL, 3.8 mmol) were added to a −20° C. solution of 4'-fluoro-5-(hydroxymethyl)-2'-(trifluoromethyl)-[1,1'-biphenyl]-3-carboxylic acid (0.30 g, 0.95 mmol) in 8 mL of DCM. This was stirred at −20° C. for 30 minutes when (5)-cyclopropyl(4-fluoro-3-methylphenyl)methanamine hydrochloride (0.19 g, 0.98 mmol) was added. The reaction was allowed to warm to RT over 16 hours. 1 M Na$_2$CO$_3$ was added and the layers were separated. The organic layer was dried with (MgSO$_4$), filtered, and concentrated. The residue was purified by silica gel chromatography with a Teledyne ISCO Combi-Flash eluting with 1 to 5% MeOH in DCM to provide the title compound (0.18 g, 51% yield). LCMS method 2: R$_T$=1.24 min, MS (ES) 405.0 (M+H).

Step B. Preparation of (S)-5-(bromomethyl)-N-(cyclopropyl(4-fluoro-3-methylphenyl)methyl)-4'-fluoro-2'-(trifluoromethyl)-[1,1'-biphenyl]-3-carboxamide Triphenylphosphine (0.50 g, 1.89 mmol) and N-Bromosuccinimide (0.34 g, 1.89 mmol) were added to a 0° C.

solution of (S)—N-(cyclopropyl(4-fluoro-3-methylphenyl) methyl)-4'-fluoro-5-(hydroxymethyl)-2'-(trifluoromethyl)-[1,1'-biphenyl]-3-carboxamide (0.45 g, 0.95 mmol) in 10 mL of THF. The reaction was allowed to warm to RT overnight. The reaction was concentrated and the residue was purified by silica gel chromatography with a Teledyne ISCO Combi-Flash eluting with 5 to 25% EtOAc in hexanes to provide the title compound (0.29 g, 57% yield).

Step C. Preparation of (S)-5-(azidomethyl)-N-(cyclopropyl(4-fluoro-3-methylphenyl)methyl)-4'-fluoro-2'-(trifluoromethyl)-[1,1'-biphenyl]-3-carboxamide Sodium azide (30 mg, 0.47 mmol) was added to a solution of (S)-5-(bromomethyl)-N-(cyclopropyl(4-fluoro-3-methylphenyl)methyl)-4'-fluoro-2'-(trifluoromethyl)-[1,1'-biphenyl]-3-carboxamide (170 mg, 0.32 mmol) in 4.5 mL of methanol and 0.5 mL of water. This was stirred at RT for 16 hours. The reaction was concentrated and the crude product was partitioned between water and DCM. The layers were separated and the organic layer was concentrated to dryness to provide the title compound (144 mg, 91% yield). LCMS method 2: $R_T$=2.07 min, MS (ES) 501.0 (M+H).

Step D. (S)-5-(aminomethyl)-N-(cyclopropyl(4-fluoro-3-methylphenyl)methyl)-4'-fluoro-2'-(trifluoromethyl)-[1,1'-biphenyl]-3-carboxamide 10% Palladium on Carbon (10 mol %) was added to a solution of (S)-5-(azidomethyl)-N-(cyclopropyl(4-fluoro-3-methylphenyl)methyl)-4'-fluoro-2'-(trifluoromethyl)-[1,1'-biphenyl]-3-carboxamide (144 mg, 0.29 mmol) in 5 mL of methanol. The reaction was degassed and placed under a hydrogen balloon atmosphere. The reaction was stirred for 30 minutes when the catalyst was filtered off and the solution was concentrated to dryness to provide the title compound (87 mg, 64% yield). LCMS method 2: $R_T$=1.46 min, MS (ES) 475.0 (M+H).

Step E. (S)—N-(cyclopropyl(4-fluoro-3-methylphenyl)methyl)-5-(((4,5-dihydrooxazol-2-yl)amino)methyl)-4'-fluoro-2'-(trifluoromethyl)-[1,1'-biphenyl]-3-carboxamide 2-chloroethyl isocyanate (19 μL, 0.22 mmol) was added to a solution of (S)-5-(aminomethyl)-N-(cyclopropyl(4-fluoro-3-methylphenyl)methyl)-4'-fluoro-2'-(trifluoromethyl)-[1,1'-biphenyl]-3-carboxamide (87 mg, 0.18 mmol) in 3 mL of DCM. This was stirred at RT for 1 hour when it was concentrated to dryness. The residue was diluted with 5 mL of acetonitrile and 1 mL of water. This solution was heated at 100 C for 2 hours. The reaction was concentrated, made basic with 1N $Na_2CO_3$ solution, and extracted with DCM. The DCM layer was concentrated to dryness and the crude product was purified by reverse phase HPLC (Phenomenex Gemini C18, $H_2O/CH_3CN$ gradient from 5-95% $CH_3CN$, 0.1% TFA) to yield the title compound (19.0 mg, 19% yield). $^1$H NMR (DMSO d6) δ 8.99 (d, J=8.5 Hz, 1H), 7.87 (s, 1H), 7.77 (dd, J=9.4, 2.9 Hz, 1H), 7.74 (s, 1H), 7.67-7.62 (m, 1H), 7.53-7.50 (m, 1H), 7.39 (s, 1H), 7.33 (d, J=7.7 Hz, 1H), 7.30-7.27 (m, 1H), 7.07 (t, J=9.9 Hz, 1H), 6.96 (bs, 1H), 4.36-4.32 (m, 3H), 4.15 (t, J=8.1 Hz, 2H), 3.54 (t, J=8.1 Hz, 2H), 2.22 (s, 3H), 1.35-1.26 (m, 1H), 0.55-0.52 (m, 2H), 0.38-0.35 (m, 2H). LCMS method 2: $R_T$=1.52 min, MS (ES) 543.9 (M+)

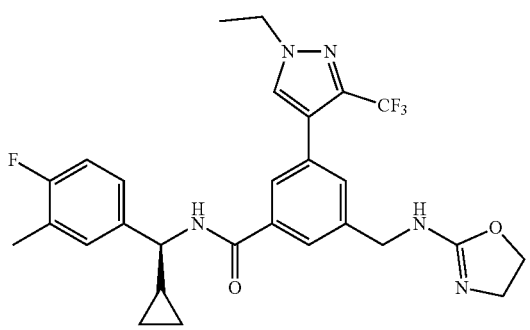 [SMILES: CCn1cc(-c2cc(CNC3=NCCO3)cc(C(=O)N[C@H](c3ccc(F)c(C)c3)C3CC3)c2)c(C(F)(F)F)n1]

Example 175

(S)—N-(cyclopropyl(4-fluoro-3-methylphenyl) methyl)-3-(((4,5-dihydrooxazol-2-yl)amino)methyl)-5-(1-ethyl-3-(trifluoromethyl)-1H-pyrazol-4-yl)benzamide The title compound was prepared according to the procedures described in Example 174, Steps A through E, substituting 3-(1-ethyl-3-(trifluoromethyl)-1H-pyrazol-4-yl)-5-(hydroxymethyl)benzoic acid for 4'-fluoro-5-(hydroxymethyl)-2'-(trifluoromethyl)-[1,1'-biphenyl]-3-carboxylic acid in Step A. $^1$H NMR (DMSO d6) δ 8.98 (d, J=8.8 Hz, 1H), 8.25 (s, 1H), 7.79 (s, 2H), 7.49 (s, 1H), 7.35 (d, J=7.34 Hz, 1H), 7.32-7.28 (m, 1H), 7.09 (t, J=9.0 Hz, 1H), 6.92 (bs, 1H), 4.37-4.24 (m, 5H), 4.17 (t, J=8.1 Hz, 2H), 3.56 (t, J=8.1 Hz, 2H), 2.23 (s, 3H), 1.45 (t, J=7.3 Hz, 3H), 1.35-1.26 (m, 1H), 0.56-0.53 (m, 2H), 0.41-0.37 (m, 2H). LCMS method 2: $R_T$=1.43 min, MS (ES) 544.0 (M+H).
Preparation of Additional Representative Compounds.

Example B1 (Table B1, B36, Scheme B2-B3)

N-(3,4-dichlorobenzyl)-5-(((4,5-dihydro-1H-imidazol-2-yl)amino)methyl)-2-fluorobenzamide

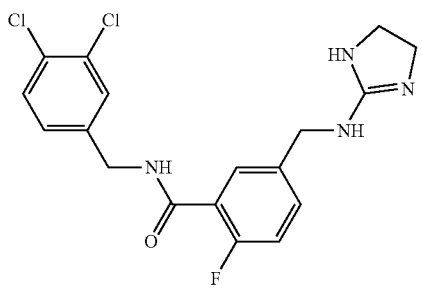 [SMILES: O=C(NCc1ccc(Cl)c(Cl)c1)c1cc(CNC2=NCCN2)ccc1F]

Bromination Step:
A solution of methyl 2-fluoro-5-methylbenzoate (2.10 g, 12.49 mmol) (CAS #2967-93-3 Combi Blocks) in $CCl_4$ (60 mL) was allowed to reflux through a Dean Stark trap to remove trace amounts of water. The solution was cooled to ambient temperature and treated with N-bromosuccinimide (NBS) (2.44 g, 13.74 mmol) and 2,2'azobis(2-methylpropionitrile (AIBN) (0.20 g, 1.20 mmol). The solution was heated to reflux for an 18 hour period. The mixture was cooled to ambient temperature, filtered and the resulting filtrate was concentrated under reduced pressure. The crude was then purified on silica gel using EtOAc/hexanes as mobile phase. The desired fractions where concentrated under reduced pressure to afford methyl 5-(bromomethyl)-2-fluorobenzoate compound 1.9 g (61%): $^1$H NMR (400 MHz, CDCl$_3$) δ 8.0 (m, 1H), 7.6 (m, 1H), 7.1 (m, 1H), 4.5 (s, 2H), 4.0 (s, 3H).

Azide Displacement and Saponification:

A solution of methyl 5-(bromomethyl)-2-fluorobenzoate (1.00 g, 8.10 mmol) and sodium azide (0.40 g, 6.09 mmol) in a 90% MeOH/water solution (40 mL) was heated to reflux for a 2 hour period. The solution was cooled and the solvent was removed under reduced pressure. The crude was dissolved in dichloromethane and extracted with water. The organic phase was dried with MgSO$_4$, filtered, and the solvent removed under reduced pressure. The crude was dissolved in a solution of THF (20 mL), MeOH (5 mL) and water (3 mL) and then treated with 2N LiOH (2.20 ml. 2N, 4.46 mmol). After 2 hours stirring, the solvent was removed under reduced pressure and then diluted with water. The mixture was acidified with HCl (1N) to pH=1. The resulting solid was removed by filtration, washed with water, and dried in a vacuum oven overnight to afford 0.35 g of 5-(azidomethyl)-4-fluorobenzoate (44%). The title compound was used without further purification.

HATU Coupling Reaction:

To an ice chilled solution of 5-(azidomethyl)-4-fluorobenzoate (0.05 g, 0.25 mmol) in DMF (1 mL) was added DIEA (0.11 mL, 0.64 mmol) and HATU (0.10 g, 0.27 mmol). The solution was allow to stir for 5 minutes and then (3,4-dichlorophenyl)methanamine (0.05 g, 0.28 mmol) was added. Stirring continued for 18 hours and the solvent was removed under reduce pressure. The crude was dissolved in ethyl acetate, extracted with water, dried over MgSO$_4$, filtered and concentrated under reduced pressure. The crude material was used in the next step without further purification.

Azide Reduction and Amine Functionalization:

A solution of crude 5-(azidomethyl)-N-(3,4-dichlorobenzyl)-2-fluorobenzamide in ethanol (10 mL) was treated with Ra—Ni (0.05 g) and then stirred under a hydrogen atmosphere for a 2 hour period. The catalyst was removed by filtration and the solvent removed under reduced pressure. The crude was then dissolved in pyridine (3 mL) and transferred to a microwave reaction vessel. The solution was then treated with 2-methylthio-2-imidazoline hydroiodide (0.10 g, 0.42 mmol) and heated on a microwave reactor at 125° C. for 1 hour. The reaction was cooled to ambient temperature and the solvent removed under reduced pressure. The crude material was purified on a reverse phase column using water (0.1% TFA) and acetonitrile. The desired fractions were combined and concentrated to dryness. The product was dissolved in EtOAc and washed with saturated aqueous NaHCO$_3$. The organic layer was dried and the solvent removed under reduced pressure to afford the title compound N-(3,4-dichlorobenzyl)-5-(((4,5-dihydro-1H-imidazol-2-yl)amino)methyl)-2-fluorobenzamide (0.03 g, 23%): $^1$H NMR (400 MHz, d$_6$ DMSO) δ 8.95 (broad s, 1H), 8.70 (broad s, 1H), 7.6 (m, 3H), 7.5 (m, 1H), 7.4 (m, 2H) 4.47 (d, 2H, J=4.47), 4.4 (s, 2H), 3.6 (s, 4H). LC-MS, 95% (254 nm), R$_f$=0.9, m/z=395.1 [M+1].

Example B2 (Table B1, B30, Scheme B4-B5)

3-(((4,5-dihydro-1H-imidazol-2-yl)amino)methyl)-N-(3,5-dimethoxybenzyl)-4,5-difluorobenzamide

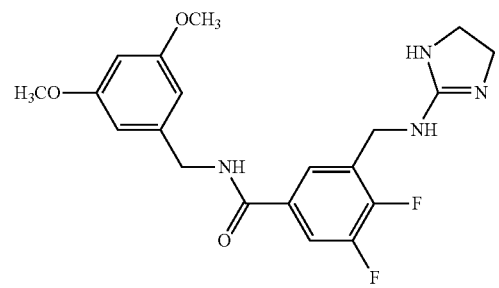 [SMILES: COc1cc(CNC(=O)c2cc(F)c(F)c(CNC3=NCCN3)c2)cc(OC)c1]

Bromination:

A solution of methyl 3,4-difluoro-5-methylbenzoate (1.00 g, 5.37 mmol)(CAS #1017778-60-7 Oakwood) in CCl$_4$ (40 mL) was allowed to reflux through a Dean Stark trap to remove trace amounts of water. The solution was cooled to ambient temperature and treated with N-bromosuccinimide (NBS) (1.10 g, 5.91 mmol) and 2,2'azobis(2-methylpropionitrile) (AIBN) (0.05 g, cat). The solution was heated to reflux for an 18 hour period. The mixture was cooled to ambient temperature, filtered and the resulting filtrate concentrated under reduced pressure to afford 0.92 g (64%): $^1$H NMR (400 MHz, CDCl$_3$) δ 7.8 (d, 1H, J=5.1), 7.7 (t, 1H, J=8.5), 4.9 (s, 1H), 4.4 (s, 2H), 3.9 (s, 3H), 1.4, (s, 9H). The crude material was used in the next step without further purification.

Azide Formation, Reduction, and BOC Protection:

A solution of the crude methyl 3-(bromomethyl)-4,5-difluorobenzoate (0.92 g, 3.48 mmol) and sodium azide (0.35 g, 5.22 mmol) in 90% methanol/water (22 mL) was heated to reflux for a 4 hour period. The solution was cooled to ambient temperature and the solvent was removed under reduced pressure. The crude was dissolved in DCM, extracted with water, dried over MgSO$_4$, filtered and the solvent removed under reduced pressure. The crude methyl 3-(azidomethyl)-4,5-difluorobenzoate was dissolved in ethanol (15 mL) and treated with Ra—Ni (0.05 g cat) and then stirred under an hydrogen atmosphere for a 2 hour period. The catalyst was removed by filtration and the solvent removed under reduced pressure. The crude methyl 3-(aminomethyl)-4,5-difluorobenzoate was dissolved in THF (20 mL), treated with DIEA (0.66 mL, 3.82 mmol) and (BOC)$_2$O (0.81 g, 3.82 mmol). The solution was stirred for an 18 hour period. The solvent was removed under reduced pressure and the crude purified on silica gel using EtOAc/hexanes as a mobile phase. The desired fractions were concentrated under reduced pressure to afford methyl 3-(((tert-butoxycarbonyl)amino)methyl)-4,5-difluorobenzoate (0.63 g, 60%).

Saponification, Amide Bond Formation, Deprotection, and Displacement:

Saponification step. A solution of methyl 3-(((tert-butoxycarbonyl)amino)methyl)-4,5-difluorobenzoate (0.63 g, 2.09 mmol) in THF (30 mL)/MeOH (5 mL)/water (5 ml) was treated with 2M LiOH aq (2.1 mL, 4.2 mmol) and allowed to stir for a 6 hour period. The solvent was removed under reduced pressure and diluted with water and the mixture acidified to pH 2 using hydrochloric acid (1N). The resulting crude was extracted with EtOAc, dried over MgSO$_4$, filtered and concentrated under reduced pressure to give 0.61 g of 3-(((tert-butoxycarbonyl)amino)methyl)-4,5-difluorobenzoate as an off-white solid (quant.).

Amide Formation.

A solution of 3-(((tert-butoxycarbonyl)amino)methyl)-4,5-difluorobenzoic acid (0.05 g, 0.17 mmol) in DMF (1 mL) was treated with DIEA (0.08 mL, 0.43 mmol) and HATU (0.07 g, 0.18 mmol). The solution was allowed to stir for 5 minutes and then treated with 3,5-dimethoxyphenyl)methanamine (0.03 g, 0.19 mmol). Stirring continued for 18 hours and the DMF was removed under reduced pressure. The crude was dissolved in EtOAc, extracted with water, dried over $MgSO_4$, filtered, and the solvent removed under reduced pressure.

Deprotection Step.

The crude amide from above was dissolved in DCM (2 mL), treated with TFA (1 mL), allowed to stir for 1 hour, and then the solvent removed under reduced pressure.

Displacement Step.

The crude was then dissolved in pyridine (3 mL) and transferred to a microwave reaction vessel. The solution was then treated with 2-methylthio-2-imidazoline hydroiodide (0.08 g, 0.35 mmol) and heated on a microwave reactor at 125° C. for a 1 hour period. The reaction was cooled to ambient temperature and the solvent removed under reduced pressure. The title compound was obtained after purification on a reverse phase column using water (0.1% TFA) and acetonitrile. The desired fractions were combined and concentrated to dryness. The product was dissolved in EtOAc and washed with sat. aq. $NaHCO_3$. The organic layer was dried and the solvent removed under reduced pressure to afford the title compound 3-(((4,5-dihydro-1H-imidazol-2-yl)amino)methyl)-N-(3,5-dimethoxybenzyl)-4,5-difluorobenzamide (0.03 g 40%): $^1$H NMR (400 MHz, $d_6$ DMSO) δ 9.1 (t, 1H, J=5.8), 8.5 (broad s, 2H), 7.9 (t, 1H, J=8.9), 7.7 (d, 1H, J=6.2), 6.4 (s, 2H), 6.3 (s, 1H), (s, 2H), 4.5 (s, 2H), 4.4 (d, 2H, J=6.2), 3.7 (s, 6H). LC-MS, >90% (254 nm), $R_t$=0.760, m/z=MS 405.1 [M+H].

Example B3 (Table B1, B15, Schemes B2-B3, Example B1)

3-(((4,5-dihydro-1H-imidazol-2-yl)amino)methyl)-N-(3,5-dimethoxybenzyl)-4-fluorobenzamide

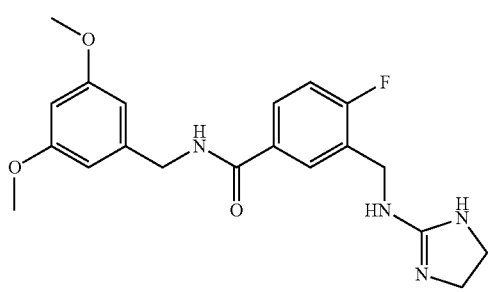 [SMILES: COc1cc(CNC(=O)c2ccc(F)c(CNC3=NCCN3)c2)cc(OC)c1]

Following the general procedures described from Example B1.

Bromination:

methyl 4-fluoro-3-methylbenzoate (5.00 g, 29.7 mmol, CAS #180636-50-4), $CCl_4$ (250 mL), N-Bromosuccinimide (NBS) (5.50 g, 30.9 mmol) and 2,2'Azobis(2-methylpropionitrile (AIBN, 0.20 g, 1.2 mmol) afforded methyl 3-(bromomethyl)-4-fluorobenzoate: 3.60 g (49%): $^1$H NMR (400 MHz, $D_6$-DMSO) δ 8.2 (dd 1H, J=2.2), 8.0 (m, 1H), 7.4 (t, 1H, J=9.1), 4.8 (s, 3H), 3.8 (s, 3H).

Displacement:

Methyl 3-(bromomethyl)-4-fluorobenzoate (2.00 g, 8.1 mmol), sodium azide (0.78 g, 12.1 mmol) and 90% MeOH/water solution (40 mL) were allowed to react as described in the procedure described in Example B1.

Saponification.

The crude material from this reaction along with THF (30 mL), MeOH (5 mL) and water (5 mL) and then treated with 2N LiOH (4.25 ml. 2N, 8.5 mmol). Upon neutralization with 1N HCl methyl 3-(bromomethyl)-4-fluorobenzoate was obtained (1.58 g, quantitative yield): $^1$H NMR (400 MHz, $CDCl_3$) δ 8.2 (m, 2H), 7.2 (t, 1H, J=8.1), 4.5 (s, 2H).

Amide Formation:

3-(azidomethyl)-4-fluorobenzoate (0.2 g, 1.02 mmol), DMF (4 mL), DIEA (0.45 mL 2.55 mmol), HATU (0.40 g, 1.04 mmol) and (3,5-dimethoxyphenyl)methanamine (0.19 g, 1.12 mmol) afforded 3-(azidomethyl)-N-(3,5-dimethoxybenzyl)-4-fluorobenzamide (0.37 g, quantitative) which was used in the next step without further purification.

Azide Reduction and Displacement:

3-(Azidomethyl)-N-(3,5-dimethoxybenzyl)-4-fluorobenzamide (0.37 g, 1.02 mmol), Ra—Ni (0.10 g cat) and ethanol (20 mL), followed by 2-methylthio-2-imidazoline hydroiodide (0.31 g, 1.28 mmol) and pyridine (15 mL) afford the title compound 3-((4,5-dihydro-1H-imidazol-2-yl)amino)methyl)-N-(3,5-dimethoxybenzyl)-4-fluorobenzamide (0.22 g, 55%): $^1$H NMR (400 MHz, $D_6$-DMSO) δ 9.0 (t, 1H, J=5.6), 7.9 (m, 2H), 7.3 (t, 1H, J=9.6), 6.5 (m, 2H), 6.4 (s, 1H), 4.5 (s, 2H), 4.4 (d, 2H, J=5.6), 3.7 (s, 6H), 3.6 (s, 4H). LC-MS, 98% (215, 254 nm), $R_t$=0.73 min., m/z=387 [M+1].

Example B4 (Table B1, B1, Schemes B2-B3, Example B1)

N-(3,5-dichlorobenzyl)-3-(((4,5-dihydro-1H-imidazol-2-yl)amino)methyl)benzamide

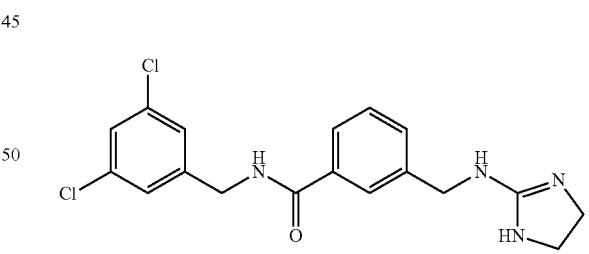

Starting from ethyl 3-(chloromethyl)benzoate (1.00 g, 5.1 mmol, CAS #134040-63-6), the final compound N-(3,5-dichlorobenzyl)-3-(((4,5-dihydro-1H-imidazol-2-yl)amino)methyl)benzamide was prepared in a manner similar to that described for Example B1 in five overall steps. Final introduction of the cyclic guanidine proceed in the presence of 2-methylthio-2-imidazoline hydroiodide and pyridine and upon workup and purification afforded the title compound: $^1$H NMR (400 MHz, $D_6$-DMSO) δ 9.1 (t, 1H, J=5.8), 7.8 (m, 2H), 7.5 (m, 3H), 7.4 (m, 2H), 4.5 (d, 2H, J=6.0), 4.4 (s, 2H), 3.6 (s, 4H). LC-MS, 98% (215, 254 nm), $R_t$=0.84 min., m/z=388.0 [M+1].

Example B5 (Table B1, B13, Schemes B2-B3, Example B1)

4-Chloro-3-(((4,5-dihydro-1H-imidazol-2-yl)amino)methyl)-N-(3,5-dimethoxybenzyl)benzamide

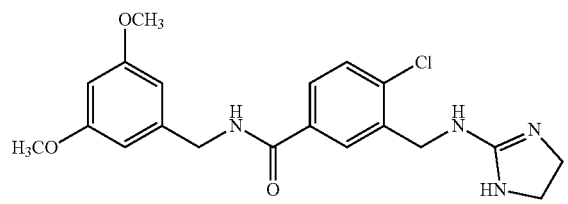 [SMILES: COc1cc(CNC(=O)c2ccc(Cl)c(CNC3=NCCN3)c2)cc(OC)c1]

Starting from methyl 4-chloro-3-methylbenzoate (2.50, 13.5 mmol, 91367-05-4) the title compound was prepared in a manner similar to that detailed in Example B1: $^1$H NMR (400 MHz, $d_6$-DMSO) δ 9.1 (t, 1H, J=5.8), 7.9 (m, 2H), 7.6 (d, 1H, J=8.5), 6.5 (s, 2H), 6.4 (s, 1H), 4.5 (s, 2H), 4.4 (d, 2H, J=5.8), 3.7 (s, 6H), 3.6 (s, 4H). LC-MS, 98% (215, 254 nm), $R_t$=0.65 min., m/z=403.2 [M+1].

Example B6 (Table B1, B27, Schemes B2-B3, Example B1)

3-(((4,5-dihydro-1H-imidazol-2-yl)amino)methyl)-N-(3,5-dimethoxybenzyl)-4-methoxybenzamide

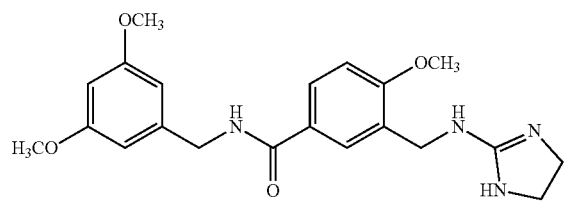 [SMILES: COc1cc(CNC(=O)c2ccc(OC)c(CNC3=NCCN3)c2)cc(OC)c1]

Starting from methyl 4-methoxy-3-methylbenzoate (1.5 g, 8.3 mmol, CAS #70347-04-5) the title compound was prepared in a manner similar to that detailed in Example B1: $^1$H NMR (400 MHz, $d_6$-DMSO) δ 8.8 (t, 1H, J=5.9), 8.5 (m, 1H), 7.9 (dd, 1H, J=3.0), 7.8 (s, 1H), 6.4 ((s, 1H), 6.3 (s, 1H), 4.4 (dd, 2H, J=6.0), 3.9 (s, 2H), 3.7 (s, 6H), 3.6 (s, 2H). LC-MS, 98% (215, 254 nM), $R_t$=0.65 min., m/z=399.0 [M+1].

Example B7 (Table B1, B51, Schemes B2-B3, Example B1)

3-(((4,5-dihydro-1H-imidazol-2-yl)amino)methyl)-N-(1-(3,5-dimethoxyphenyl)ethyl)-4-ethoxybenzamides

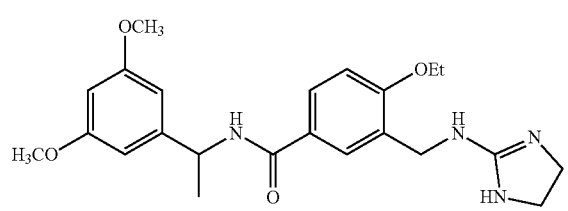 [SMILES: CCOc1ccc(C(=O)NC(C)c2cc(OC)cc(OC)c2)cc1CNC1=NCCN1]

Starting from 4-ethoxy-3-methylbenzoate (1.5 g, 8.3 mmol, CAS 93351-64-5, see BMCL, 2008, 18, 5242) the title compound was prepared in a manner similar to that detailed in Example 1: $^1$H NMR (400 MHz, $d_6$-DMSO) δ 8.6 (d, 1H, J=8.0), 7.9 (m, 1H), 7.8 (s. 1H) 7.1 (d, 1H, J=7.5), 6.5 (s, 2H), 6.4 (s, 1H), 5.1 (m, 1H), 4.3 (s, 2H), 4.2 (q, 2H, J=7.0), 3.7 (s, 6H), 3.6 (s, 4H), 1.5 (d, 3H, J=7.0), 1.4 (t, 3H, J=6.9). LC-MS, 98% (215, 254 nm), $R_t$=0.80 min., m/z=427.1 [M+1].

Example B8 (Table B1, B52, Schemes B2-B3, Example B1)

3-(((4,5-dihydro-1H-imidazol-2-yl)amino)methyl)-N-(1-(3,5-dimethoxyphenyl)ethyl)-4-isopropoxybenzamide

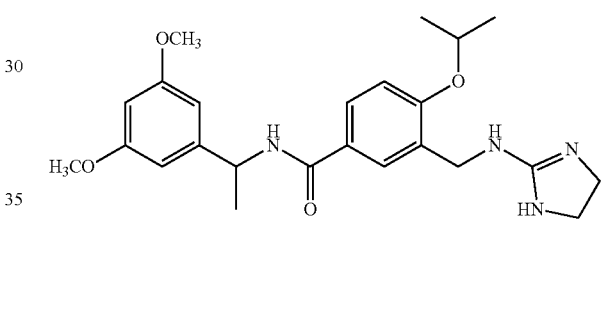

Starting from methyl 4-isopropoxy-3-methylbenzoate (0.74, 3.55 mmol, CAS 864178-56-3 see Bioorg. Med. Chem. Lett., 2008, 18, 5242) the title compound was prepared in a manner similar to that detailed in Example B1: $^1$H NMR (400 MHz, $d_6$-DMSO) δ8.6 (d, 1H J=8.4), 7.9 (m, 1H), 7.8 s, 1H), 7.1 (d, 1H, J=8.7), 6.5 (s, 2H), 6.3 (s, 1H), 5.0 (m, 1H), 4.8 (m, 1H), 4.3 (s, 2H), 3.7 (s, 6H), 3.6 (s, 4H), 1.4 (d, 3H, J=7.0), 1.3 (d, 6H, J=6.3). LC-MS, 98% (215, 254 nm), $R_t$=0.85 min., m/z=441 [M+1].

Additional Characterization of Exemplary Compounds

The compounds of formula I below in Table B1 were synthesized with methods identical or analogous to those described herein. The Synthetic Example indicated in Table B1 refers to the compound identified above and corresponding synthetic method described therein. The requisite starting materials were commercially available, described in the literature, or readily synthesized by one skilled in the art of organic synthesis. The mass spectrometry data were obtained using either General LC-MS Method 1 or General LC-MS Method 2 as described above. LC-MS [M+H] means the protonated mass of the free base of the compound.

TABLE B1

| No. | Compound | LC-MS [M + H] | Retention time | Synthetic Example, Schemes* |
|---|---|---|---|---|
| B1 | | 377.1 | 0.84 | Ex. B1, Schemes B2-B3 |
| B2 | | 385.2 | 0.86 | Ex. B1, Schemes B2-B3 |
| B3 | | 377.2 | 0.81 | Ex. B1, Schemes B2-B3 |
| B4 | | 357.1 | 0.81 | Ex. B1, Schemes B2-B3 |
| B5 | | 357.1 | 0.77 | Ex. B1, Schemes B2-B3 |
| B6 | | 395.3 | 0.85 | Ex. B1, Schemes B2-B3 |

TABLE B1-continued
| No. | Compound | LC-MS [M + H] | Retention time | Synthetic Example, Schemes* |
|---|---|---|---|---|
| B7 | 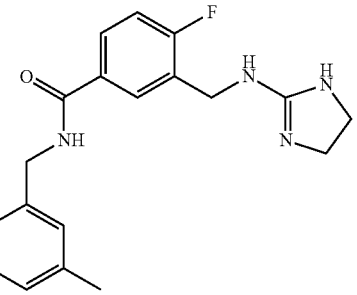 | 355.2 | 0.78 | Ex. B1, Schemes B2-B3 |
| B8 | 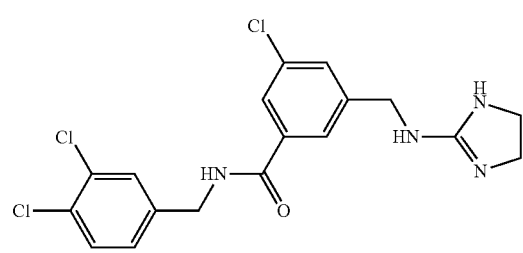 [SMILES: O=C(NCc1ccc(Cl)c(Cl)c1)c1cc(Cl)cc(CNC2=NCCN2)c1] | 411.0 | 0.90 | Ex. B1, Schemes B2-B3 |
| B9 | 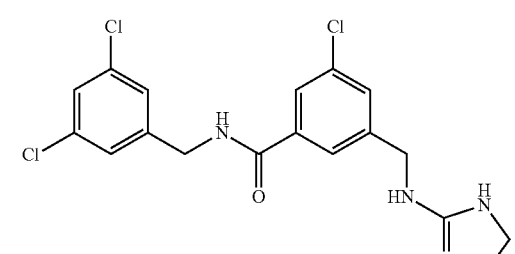 | 411.0 | 0.92 | Ex. B1, Schemes B2-B3 |
| B10 | 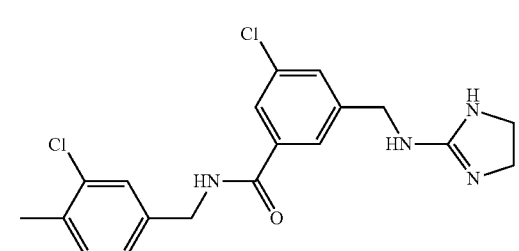 | 391.1 | 0.88 | Ex. B1, Schemes B2-B3 |
| B11 | 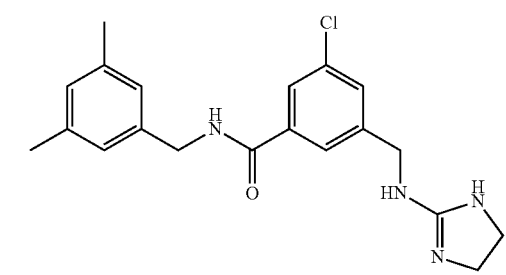 [SMILES: Cc1cc(C)cc(CNC(=O)c2cc(Cl)cc(CNC3=NCCN3)c2)c1] | 371.2 | 0.88 | Ex. B1, Schemes B2-B3 |

TABLE B1-continued

| No. | Compound | LC-MS [M + H] | Retention time | Synthetic Example, Schemes* |
|---|---|---|---|---|
| B12 | | 391.1 | 0.87 | Ex. B1, Schemes B2-B3 |
| B13 | | 404.1 | 0.65 | Ex. B1, Schemes B2-B3 |
| B14 | | 412.1 | 0.70 | Ex. B1, Schemes B2-B3 |
| B15 | | 387.2 | 0.63 | Ex. B1, Schemes B2-B3 |
| B16 | | 362.1 | 0.50 | Ex. B1, Schemes B2-B3 |

TABLE B1-continued

| No. | Compound | LC-MS [M + H] | Retention time | Synthetic Example, Schemes* |
|---|---|---|---|---|
| B17 | | 395.1 | 0.70 | Ex. B1, Schemes B2-B3 |
| B18 | | 401.2 | 0.75 | Ex. B1, Schemes B2-B3 |
| B19 | | 387.2 | 0.65 | Ex. B1, Schemes B2-B3 |
| B20 | | 382.2 | 0.78 | Ex. B1, Schemes B2-B3 |
| B21 | | 387.2 | 0.70 | Ex. B1, Schemes B2-B3 |

TABLE B1-continued
| No. | Compound | LC-MS [M + H] | Retention time | Synthetic Example, Schemes* |
|---|---|---|---|---|
| B22 | 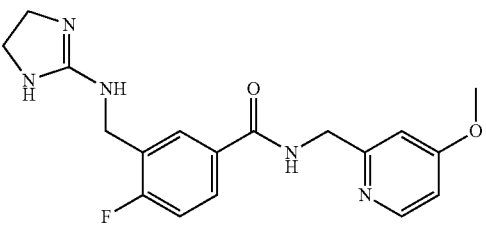 [SMILES: COc1ccnc(CNC(=O)c2ccc(F)c(CNC3=NCCN3)c2)c1] | 358.2 | 0.72 | Ex. B1, Schemes B2-B3 |
| B23 | 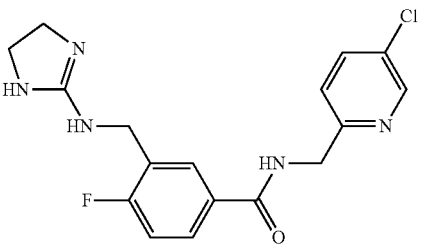 [SMILES: O=C(NCc1ccc(Cl)cn1)c1ccc(F)c(CNC2=NCCN2)c1] | 362.1 | 0.88 | Ex. B1, Schemes B2-B3 |
| B24 | 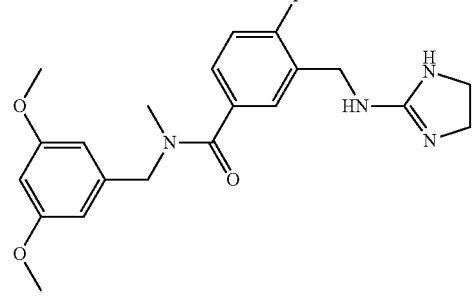 | 401.2 | 1.10 | Ex. B1, Schemes B2-B3 |
| B25 | 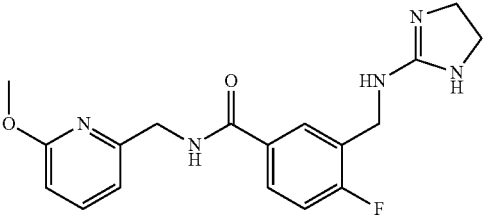 [SMILES: COc1cccc(CNC(=O)c2ccc(F)c(CNC3=NCCN3)c2)n1] | 358.2 | 0.86 | Ex. B1, Schemes B2-B3 |
| B26 | 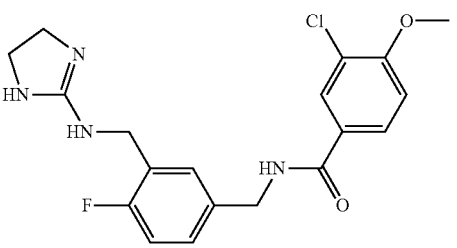 [SMILES: COc1ccc(C(=O)NCc2ccc(F)c(CNC3=NCCN3)c2)cc1Cl] | 391.1 | 0.81 | Ex. B1, Schemes B2-B3 |
| B27 | 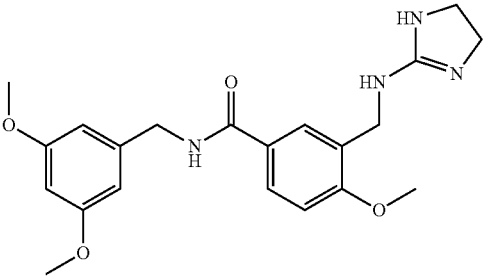 [SMILES: COc1cc(CNC(=O)c2ccc(OC)c(CNC3=NCCN3)c2)cc(OC)c1] | 399.2 | 0.77 | Ex. B1, Schemes B2-B3 |

TABLE B1-continued

| No. | Compound | LC-MS [M + H] | Retention time | Synthetic Example, Schemes* |
|---|---|---|---|---|
| B28 | | 407.1 | 0.90 | Ex. B1, Schemes B2-B3 |
| B29 | | 342.2 | 0.73 | Ex. B1, Schemes B2-B3 |
| B30 | | 405.2 | 0.76 | Ex. B2, Schemes B4-B5 |
| B31 | | 373.2 | 0.87 | Ex. B2, Schemes B4-B5 |
| B32 | | 409.1 | 0.62 | Ex. B2, Schemes B4-B5 |

TABLE B1-continued

| No. | Compound | LC-MS [M + H] | Retention time | Synthetic Example, Schemes* |
|---|---|---|---|---|
| B33 | | 413.1 | 0.91 | Ex. B2, Schemes B4-B5 |
| B34 | | 376.2 | 0.58 | Ex. B2, Schemes B4-B5 |
| B35 | | 419.2 | 0.51 | Ex. B2, Schemes B4-B5 |
| B36 | | 395.1 | 0.93 | Ex. B1, Schemes B2-3B |
| B37 | | 387.2 | 0.81 | Ex. B1, Schemes B2-B3 |

TABLE B1-continued

| No. | Compound | LC-MS [M + H] | Retention time | Synthetic Example, Schemes* |
|---|---|---|---|---|
| B38 | | 403.1 | 0.85 | Ex. B1, Schemes B2-B3 |
| B39 | | 374.1 | 0.70 | Ex. B1, Schemes B2-B3 |
| B40 | | 370.2 | 0.95 | Ex. B1, Schemes B2-B3 |
| B41 | | 391.1 | 0.89 | Ex. B1, Schemes B2-B3 |
| B42 | | 387.2 | 0.95 | Ex. B1, Schemes B2-B3 |
| B43 | | 413.2 | 1.30 | Ex. B1, Schemes B2-B3 |

TABLE B1-continued

| No. | Compound | LC-MS [M + H] | Retention time | Synthetic Example, Schemes* |
|---|---|---|---|---|
| B44 | | 374.1 | 1.14 | Ex. B1, Schemes B2-B3 |
| B45 | | 357.1 | 0.91 | Ex. B1, Schemes B2-B3 |
| B46 | | 343.2 | 0.87 | Ex. B1, Schemes B2-B3 |
| B47 | | 375.1 | 0.88 | Ex. B1, Schemes B2-B3 |
| B48 | | 400.2 | 0.80 | Ex. B2, Schemes B4-B5 |
| B49 | | 419.2 | 1.24 | Ex. B2, Schemes B4-B5 |

TABLE B1-continued

| No. | Compound | LC-MS [M + H] | Retention time | Synthetic Example, Schemes* |
|---|---|---|---|---|
| B50 | | 408.2 | 0.60 | Ex. B2, Schemes B4-B5 |
| B51 | | 427.2 | 0.80 | Ex. B1, Schemes B2-B3 |
| B52 | | 441.2 | 0.85 | Ex. B1, Schemes B2-B3 |
| B53 | | 435.1 | 0.92 | Ex. B1, Schemes B2-B3 |
| B54 | | 505.1 | 0.86 | Ex. 1, Schemes B6-B7 |

TABLE B1-continued

| No. | Compound | LC-MS [M + H] | Retention time | Synthetic Example, Schemes* |
|---|---|---|---|---|
| B55 | | 465.2 | 0.86 | Ex. 1, Schemes B6-B7 |
| B58 | | 485.1 | 0.87 | Ex. 1, Schemes B6-B7 |
| B63 | | 478.2 | 0.88 | Ex. 1, Schemes B6-B7 |
| B64 | | 486.1 | 0.96 | Ex. 1, Schemes B6-B7 |

TABLE B1-continued
| No. | Compound | LC-MS [M + H] | Retention time | Synthetic Example, Schemes* |
|-----|----------|---------------|----------------|------------------------------|
| B72 | 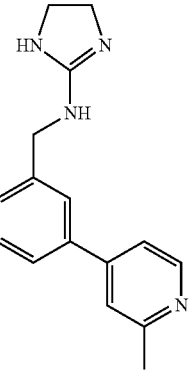 | 460.2 | 0.72 | Ex. 1, Schemes B6-B7 |
| B73 | 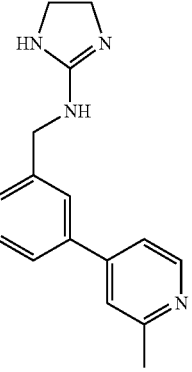 | 460.2 | 0.68 | Ex. 1, Schemes B6-B7 |
| B74 | 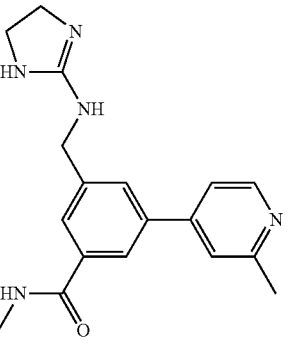 | 468.1 | 0.80 | Ex. 1, Schemes B6-B7 |
| B81 | 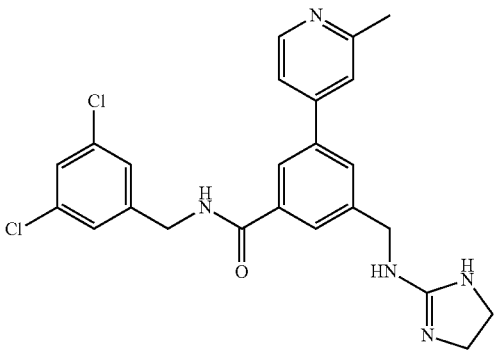 [SMILES: Cc1cc(-c2cc(CNC3=NCCN3)cc(C(=O)NCc3cc(Cl)cc(Cl)c3)c2)ccn1] | 468.1 | 0.83 | Ex. 1, Schemes B6-B7 |

TABLE B1-continued

| No. | Compound | LC-MS [M + H] | Retention time | Synthetic Example, Schemes* |
|-----|----------|---------------|----------------|----------------------------|
| B84 | | 448.2 | 0.82 | Ex. 1, Schemes B6-B7 |
| B87 | | 468.1 | 0.84 | Ex. 1, Schemes B6-B7 |
| B88 | | 448.2 | 0.80 | Ex. 1, Schemes B6-B7 |
| B89 | | 419.2 | 0.62 | Ex. 1, Schemes B6-B7 |

TABLE B1-continued

| No. | Compound | LC-MS [M + H] | Retention time | Synthetic Example, Schemes* |
|---|---|---|---|---|
| B90 | | 428.2 | 0.80 | Ex. 1, Schemes B6-B7 |
| B93 | | 404.2 | 0.74 | Ex. 1, Schemes B6-B7 |
| B95 | | 419.2 | 0.70 | Ex. 1, Schemes B6-B7 |
| B99 | | 486.1 | 1.02 | Ex. 1, Schemes B6-B7 |

TABLE B1-continued

| No. | Compound | LC-MS [M + H] | Retention time | Synthetic Example, Schemes* |
|---|---|---|---|---|
| B107 | | 478.2 | 0.89 | Ex. 1, Schemes B6-B7 |
| B109 | | 478.2 | 0.92 | Ex. 1, Schemes B6-B7 |
| B111 | | 449.2 | 0.71 | Ex. 1, Schemes B6-B7 |
| B114 | | 448.2 | 0.73 | Ex. 1, Schemes B6-B7 |

TABLE B1-continued

| No. | Compound | LC-MS [M + H] | Retention time | Synthetic Example, Schemes* |
|---|---|---|---|---|
| B115 | | 476.2 | 0.10 | Ex. 1, Schemes B6-B7 |
| B116 | | 480.2 | 0.77 | Ex. 1, Schemes B6-B7 |
| B124 | | 440.2 | 0.80 | Ex. B2, Scheme B4-B5 |
| B125 | | 434.1 | 0.90 | Ex. B2, Scheme B4-B5 |

TABLE B1-continued

| No. | Compound | LC-MS [M + H] | Retention time | Synthetic Example, Schemes* |
|---|---|---|---|---|
| B129 | 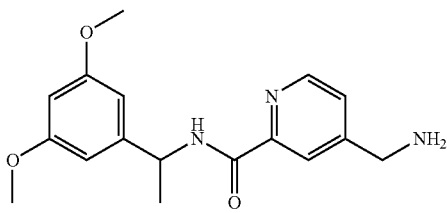 [SMILES: COc1cc(OC)cc(C(C)NC(=O)c2cc(CN)ccn2)c1] | 465.2 | 0.90 | Ex. 67, Scheme B6, B8 |

Preparation of Intermediates

Intermediate A1. 4-(aminomethyl)-N-(1-(3,5-dimethoxyphenyl)ethyl)picolinamide

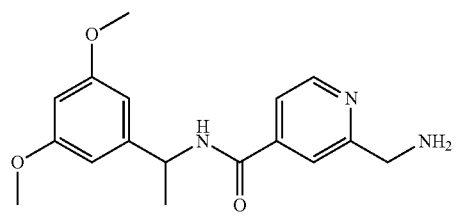 [SMILES: COc1cc(OC)cc(C(C)NC(=O)c2ccnc(CN)c2)c1]

Amide Formation.

A solution of 4-(hydroxymethyl)picolinic acid (0.50 g, 3.26 mmol) in DMF (15 mL) was treated with DIPEA (1.43 mL, 8.15 mmol) and cooled on an ice bath. The mixture was treated with EDC (0.65 g, 3.43 mmol), HOBt (0.80 g, 3.43 mmol), stirred for 5 minutes and then treated with 1-(3,5-dimethoxyphenyl)ethan-1-amine (0.65 g, 3.58 mmol). Stirring continued for 18 hours and the DMF removed under reduced pressure. The crude was dissolved in EtOAc, washed with water, dried over MgSO$_4$, filtered, and the solvent removed under reduced pressure. The crude was used purified on a silica gel column to afford N-(1-(3,5-dimethoxyphenyl)ethyl)-4-(hydroxymethyl)picolinamide (0.80 g, 78%): $^1$H NMR (400 MHz, D$_6$-DMSO) δ 8.95 (d, 1H, J=8.73), 8.59 (d, 1H, J=4.65), 7.99 (s, 1H), 7.52 (d, 1H, J=4.08), 6.59 (d, 2H, J=1.75), 6.37 (m, 1H), 5.53 (t, 1H, J=5.24), 5.10 (m, 1H), 4.62 (d, 2H, J=5.87), 3.72 (s, 6H), 1.50 (d, 3H, J=6.60).

Benzylic Activation.

A solution of N-(1-(3,5-dimethoxyphenyl)ethyl)-4-(hydroxymethyl)picolinamide (1.10 g, 3.48 mmol) and toluene (250 mL) was cooled on an ice bath and treated dropwise with PBr$_3$ (0.34 mL, 3.65 mmol) dissolved in toluene (5 mL) and allowed to stir for 18 hours. The reaction was treated with water and saturated aqueous NaHCO$_3$ until a basic pH was obtained. The organic layer was separated, washed with water, dried over MgSO$_4$, filtered, and concentrated under reduced pressure. The crude was purified on a silica gel column to afford 4-(bromomethyl)-N-(1-(3,5-dimethoxyphenyl)ethyl)picolinamide (0.40 g, 63%): $^1$H NMR (400 MHz, d$_6$-DMSO) δ 9.01 (d, 1H, J=7.5), 8.66 (d, 1H, J=5.2), 8.08 (s, 1H), 7.67 (m, 1H), 6.66 (d, 2H, J=2.3), 6.73 (t, 1H, J=2.3), 5.11 (m, 1H), 4.78 (s, 2H), 3.72 (s, 6H), 1.50 (d, 3H, J=7.1).

Azide Formation and Reduction.

A solution of 4-(bromomethyl)-N-(1-(3,5-dimethoxyphenyl)ethyl)picolinamide (0.40 g, 1.06 mmol) and sodium azide (0.15 g, 2.12 mmol) in 90% methanol/water (22 mL) was heated to reflux for 4 hours. The solution was cooled to ambient temperature and the solvent was removed under reduced pressure. The crude was dissolved in DCM, extracted with water, dried over MgSO$_4$, filtered and the solvent removed under reduced pressure. The crude was dissolved in ethanol (10 mL) and treated with Ra—Ni (0.10 g) and stirred under a hydrogen atmosphere for 2 hours. The catalyst was removed by filtration and the solvent removed under reduced pressure to afford 4-(aminomethyl)-N-(1-(3,5-dimethoxyphenyl)ethyl)picolinamide (0.25 g, 75%): LC-MS, >90% (215, 254 nm), R$_t$=0.15 min., m/z=316.1 [M+1].

Intermediate A2. 2-(aminomethyl)-N-(1-(3,5-dimethoxyphenyl)ethyl)isonicotinamide Azide Formation.

A solution of methyl 2-(bromomethyl)isonicotinate (0.23 g, 1.00 mmol, CAS #914639-05-7, CombiBlocks) and sodium azide (0.20 g, 2.98 mmol) in 90% methanol/water (22 mL) was heated to reflux for 4 hours. The solution was cooled to ambient temperature and the solvent was removed under reduced pressure. The crude was dissolved in DCM, extracted with water, dried over MgSO$_4$, filtered and the solvent removed under reduced pressure. The crude was purified on a silica gel column (Hexane/Ethyl Acetate) to afford methyl 2-(azidomethyl)isonicotinate (0.17 g, 87%): $^{1}$H NMR (400 MHz, d$_6$ DMSO) δ NMR 8.10 (d, 1H, J=4.66 Hz), 7.88 (s, 1H), 7.81 (d, 1H, J=4.97 Hz), 4.65 (s, 2H), 3.91 (s, 3H).

Saponification.

A solution of methyl 2-(azidomethyl)isonicotinate (0.17, 0.869 mmol) in THF (10 mL)/MeOH (2 mL)/water (2 mL) was treated with 2M aq. LiOH (0.86 mL, 1.74 mmol) and allowed to stir for 6 hours. The solvent was removed under reduced pressure and diluted with water. HCl (1N) was added dropwise till pH=4. The resulting solid was removed by filtration, washed with water and dried in a vacuum oven to afford 2-(azidomethyl)isonicotinic acid (0.12 g, 75%): $^{1}$H NMR (400 MHz, d$_6$ DMSO) δ 8.78 (d, 1H, J=4.66), 7.86 (s, 1H), 7.78 (d, 1H, J=5.24), 4.63 (s, 2H).

Amide Formation.

A solution of 2-(azidomethyl)isonicotinic acid (0.16 g, 0.65 mmol) in DMF (3 mL) was treated with DIPEA (0.29 mL, 0.55 mmol) and HATU (0.09 g, 0.23 mmol). The solution was allowed to stir for 5 minutes and then treated with 1-(3,5-dimethoxyphenyl)ethan-1-amine (0.05 g, 0.24 mmol). Stirring continued for 18 hours and the DMF was removed under reduced pressure. The crude was dissolved in EtOAc, washed with water, dried over MgSO$_4$, filtered, and the solvent removed under reduced pressure. The crude was purified on a silica gel column (DCM/MeOH) to afford 2-(azidomethyl)-N-(1-(3,5-dimethoxyphenyl)ethyl)isonicotinamide (0.14 g, 64%): $^{1}$H NMR (400 MHz, d$_6$ DMSO) δ 9.07 (d, 1H, J=8.72), 8.74 (d, 1H, J=5.23), 7.81 (s, 2H), 7.76 (d, 1H, J=5.20), 5.09 (m, 1H), 4.61 (s, 2H), 3.73 (s, 6H), 1.46 (D, 3H, J=6.59).

Reduction.

A solution of 2-(azidomethyl)-N-(1-(3,5-dimethoxyphenyl)ethyl)isonicotinamide (0.14 g, 0.42 mmol) ethanol (15 mL) was treated with Ra—Ni (0.05 g, cat) and then stirred under a Hydrogen atmosphere for 2 hours. The catalyst was removed by filtration and the solvent removed under reduced pressure. Crude 2-(aminomethyl)-N-(1-(3,5-dimethoxyphenyl)ethyl)isonicotinamide was used in subsequent steps without further purification. (0.13 g, quant): LC-MS, >90% (215, 254 nm), R$_f$=0.12 min., m/z=316.1 [M+1].

Preparation of Additional Representative Compounds

Example C1 (Table C1, C21, Scheme C1-C2)

4-(((3,4-dihydro-2H-pyrrol-5-yl)amino)methyl)-N-(1-(3,5-dimethoxyphenyl)ethyl)picolinamide

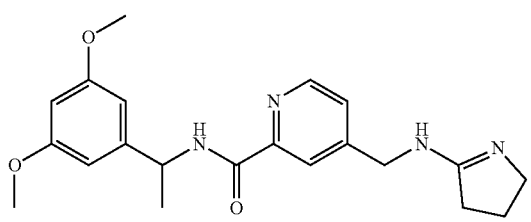 [SMILES: COc1cc(OC)cc(C(C)NC(=O)c2cc(CNC3=NCCC3)ccn2)c1]

Amidine formation. A solution of intermediate A1 4-(aminomethyl)-N-(1-(3,5-dimethoxyphenyl)ethyl) picolinamide (0.06 g, 0.19 mmol) in MeOH (5 mL) containing 0.70% AcOH was treated with 5-methoxy-3,4-dihydro-2H-pyrrole (0.03 g, 0.29 mmol). The mixture was heated at 80° C. for 6 hours. The cooled solution was concentrated under reduced pressure and purified by RP-HPLC using 0.1% TFA modifier in acetonitrile and water. The desired fractions were combined and concentrated to dryness. The product was dissolved in EtOAc and washed with saturated aqueous NaHCO$_3$. The organic layer was dried over MgSO$_4$ and the solvent removed under reduced pressure to afford the title compound 4-(((3,4-dihydro-2H-pyrrol-5-yl)amino)methyl)-N-(1-(3,5-dimethoxyphenyl)ethyl) picolinamide (0.06 g, 80%): $^{1}$H NMR (400 MHz, d$_6$ DMSO) δ 9.02 (d, 1H J=8.15), 8.67 (d, 1H, J=5.13), 7.99 (s, 1H), 7.56 (d, 1H, J=4.99), 6.59 (d, 2H, 2.19), 6.37 (m, 1H), 5.09 (m, 1H), 4.62 (s, 2H), 3.72 (s, 6H), 3.59 (t, 2H, J=7.15), 2.87 (t, 2H, J=7.90), 2.08 (m, 2H), 1.50 (d, 3H, J=7.00); LC-MS, >98% (215, 254 nm), R$_f$=0.901 min., m/z=501.1 [M+1].

Example C2 (Table C1, C20, Scheme C1-C2)

4-(((4,5-dihydro-1H-imidazol-2-yl)amino)methyl)-N-(1-(3,5-dimethoxyphenyl)ethyl)picolinamide

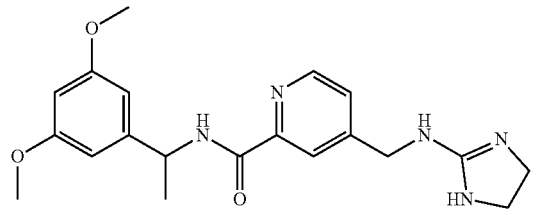 [SMILES: COc1cc(OC)cc(C(C)NC(=O)c2cc(CNC3=NCCN3)ccn2)c1]

A solution of intermediate A1 4-(aminomethyl)-N-(1-(3,5-dimethoxyphenyl)ethyl) picolinamide (0.07 g, 0.22 mmol) dissolved in pyridine (3 mL) and transferred to a microwave reaction vessel. The solution was then treated with 2-methylthio-2-imidazoline hydroiodide (0.11 g, 0.44 mmol) and heated in a microwave reactor at 125° C. for 1 hour. The reaction was cooled to ambient temperature and the solvent removed under reduced pressure. The crude compound was purified by RP-HPLC using water (0.1% TFA) and acetonitrile. The desired fractions were combined and concentrated to dryness. The product was dissolved in EtOAc and washed with saturated aqueous NaHCO$_3$. The organic layer was dried and the solvent removed under reduced pressure to afford the title compound (0.06 g, 67%): $^{1}$H NMR (400 MHz, d$_6$ DMSO) δ 9.02 (d, 1H, J=8.73), 8.66 (d, 1H, J=5.24), 7.95 (s, 1H), 7.51 (d, 1H, J=4.95), 6.60 (d, 2H, J=2.30), 6.38 (m, 1H), 5.09 (m, 1H), 4.52 (s, 2H), 3.72 (s, 6H), 3.61 (s, 4H), 1.50 (d, 3H, J=6.70); LC-MS=98% (215, 254 nm), R$_f$=0.901 min., m/z=384.1 [M+1].

Example C3 (Table C1, C34, Scheme C3-C4)

2-(((4,5-dihydro-1H-imidazol-2-yl)amino)methyl)-N-(1-(3,5-dimethoxyphenyl)ethyl)isonicotinamide

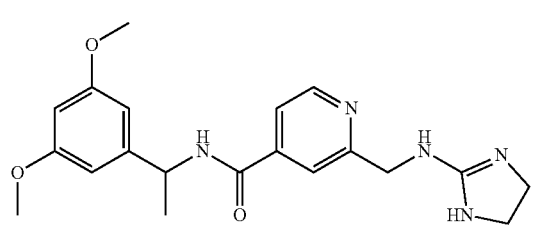 [SMILES: COc1cc(OC)cc(C(C)NC(=O)c2ccnc(CNC3=NCCN3)c2)c1]

A solution of 2-(aminomethyl)-N-(1-(3,5-dimethoxyphenyl)ethyl) isonicotinamide (0.06 g, 0.21 mmol) dissolved in pyridine (3 mL) and transferred to a microwave reaction vessel. The solution was then treated with 2-methylthio-2-imidazoline hydroiodide (0.10 g, 0.416 mmol) and heated on a microwave reactor at 125° C. for 1 hour. The reaction was cooled to ambient temperature and the solvent removed under reduced pressure. The crude compound was purified via RP-HPLC using water (0.1% TFA) and acetonitrile. The desired fractions were combined and concentrated to dryness. The product was dissolve in EtOAc and washed with saturated aqueous $NaHCO_3$. The organic layer was dried and the solvent removed under reduced pressure to afford 2-(((4,5-dihydro-1H-imidazol-2-yl)amino)methyl)-N-(1-(3,5-dimethoxyphenyl)ethyl)isonicotinamide (0.05 g, 67%): $^1$H NMR (400 MHz, $d_6$ DMSO) δ 9.10 (d, 1H J=7.39), 8.73 (d, 1H, J=5.12), 7.78 (m, 1H), 7.73 (s, 1H), 6.56 (d, 2H, J=2.15), 6.39 (t, 1H, J=2.2), 5.10 (m, 1H), 4.57 (s, 2H), 3.73 (s, 6H), 3.63 (s, 4H), 1.47 (d, 3H, J=7.17); LC-MS=98%(215, 254 nm), $R_t$=0.690 min., m/z=384.1 [M+1].

Example C4 (Table C1, C35, Schemes C3-C4)

2-(((3,4-dihydro-2H-pyrrol-5-yl)amino)methyl)-N-(1-(3,5-dimethoxyphenyl)ethyl)isonicotinamide

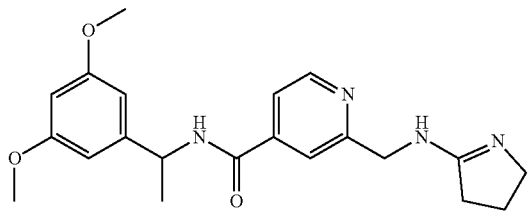 [SMILES: COc1cc(OC)cc(C(C)NC(=O)c2ccnc(CNC3=NCCC3)c2)c1]

A solution of Intermediate A2 2-(aminomethyl)-N-(1-(3,5-dimethoxyphenyl)ethyl) isonicotinamide (0.06 g, 0.21 mmol) in MeOH (5 mL) containing 0.7% AcOH was treated with 5-methoxy-3,4-dihydro-2H-pyrrole (0.04 g, 0.41 mmol). The mixture was heated to 80° C. for 6 hours. The cooled solution was concentrated under reduced pressure and the crude purified by RP-HPLC using water (0.1% TFA) and acetonitrile. The desired fractions were combined and concentrated to dryness. The product was dissolved in EtOAc and washed with aq. sat. $NaHCO_3$. The organic layer was dried and the solvent removed under reduced pressure to afford the title compound (0.04 g, 55%): $^1$H NMR (400 MHz, $d_6$ DMSO) δ 10.03 (broad s, 1 h), 9.87 (broad s, 1 h), 9.10 (d, 1H, J=7.15), 8.74 (m, 1H), 7.80 (m, 2H), 6.56 (d, 2H, J=2.14), 6.39 (t, 1H, J=2.14), 5.10 (m, 1H), 4.68 (m, 2H), 3.73 (s, 6H), 3.61 (m, 2H), 2.89 (m, 2H), 2.11 (m, 2H), 1.47 (d, 3H, J=6.96); LC-MS=98% (215, 254 nm), $R_t$=0.690 min., m/z=383.1 [M+1].

The compounds of formula I below in Table C1 were synthesized with methods identical or analogous to those described herein. The Synthetic Example indicated in Table C1 refers to the compound identified above and corresponding synthetic method described therein. The requisite starting materials were commercially available, described in the literature, or readily synthesized by one skilled in the art of organic synthesis. The mass spectrometry data were obtained using either General LC-MS Method 1 or General LC-MS Method 2 as described above. LC-MS [M+H] means the protonated mass of the free base of the compound.

TABLE C1

| No. | Compound | LC-MS [M + H] | Retention time | Synthetic Example, Schemes* |
|---|---|---|---|---|
| C2 | | 491.1 | 1.01 | Example 72, Schemes C5-C7 |
| C20 | | 384.2 | 0.70 | Example C2, Schemes C1-C2 |

TABLE C1-continued

| No. | Compound | LC-MS [M + H] | Retention time | Synthetic Example, Schemes* |
|---|---|---|---|---|
| C21 | | 383.2 | 0.74 | Example C1, Schemes C1-C2 |
| C22 | | 485.1 | 0.89 | Examples C1 and 72, Schemes C1-C2, C5-C7 |
| C23 | | 465.2 | 0.99 | Examples C1 and 72, Schemes C1-C2, C5-C7 |
| C24 | | 477.2 | 0.90 | Examples C1 and 72, Schemes C1-C2, C5-C7 |
| C27 | | 531.1 | 0.90 | Examples C1 and 72, Schemes C1-2, C5-7 |

TABLE C1-continued

| No. | Compound | LC-MS [M + H] | Retention time | Synthetic Example, Schemes* |
|---|---|---|---|---|
| C32 | 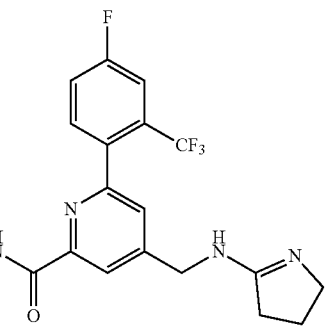 | 534.2 | 0.90 | Examples C1 and 72, Schemes C1-2, C5-7 |
| C34 | 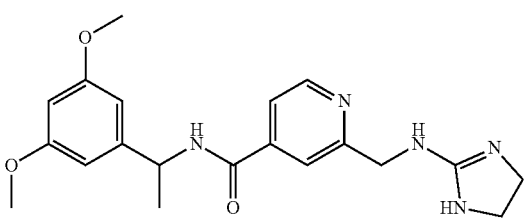 | 384.1 | 0.69 | Example C3, Scheme C3-C4 |
| C35 | 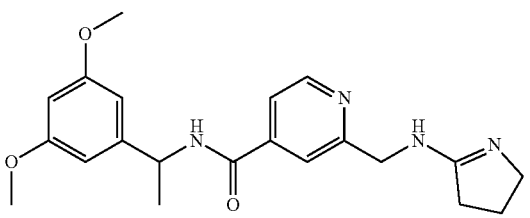 [SMILES: COc1cc(OC)cc(C(C)NC(=O)c2ccnc(CNC3=NCCC3)c2)c1] | 383.1 | 0.69 | Example C4, Scheme C3-C4 |

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizawa, 2007) and 10% of all acute leukemia cases (Marschalek, 2011). MLL leukemia patients have a poor prognosis with overall 5-year survival ratio around 35% (Dimartino, 1999; Pui, 2003; Tomizawa, 2007).

MLL is composited of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of Drosophila trithorax (Trx) (Thachuk, 1992). Wild type MLL binds to regulatory regions of homeox (HOX) genes (Milne, 2005) through the amino terminal fragment while the catalytic C-terminal domain catalyzes the Histone 3 lysine 4 (H3K4) methylation via interaction with WDR5 and up regulates target genes transcription (Nakamura, 2002; Yokoyama, 2004; Milne, 2002). Wild type MLL in conjunction with WDR5 is required for maintenance HOX genes expression and is widely expressed not only during embryo development but also in adult tissues including myeloid and lymphoid cells (Butler, 1997; Yu, 1998). Reciprocal translocations of MLL gene result in-frame fusion of 5'-end MLL with the 3'-end of another partner gene. A common feature of MLL1 abnormality in leukemia is the preservation of one wild-type MLL1 allele. Currently, more than 60 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005). The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct dysregulated target gene expression patterns and downstream events (Slany, 2009). Clinical studies reveal that MLL of different chromosomal translocations are associated with different prognosis and are treated differently under current protocols (Tamai, 2010; Balgobind, 2011; Pigazzi, 2011).

Intrinsic HMT activity of MLL1 is extremely low and requires a complex assembly of WDR5, RbBP5, ASH2L, and DPY30 protein partners for effective H3K4 trimethylation, so called WRAD complex. The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, et al. Molecular Cell, 2014, 53, 247-261.) In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. The molecules described herein will target this interaction and could provide an attractive therapeutic approach to develop novel drugs for leukemias with translocations of MLL gene and other leukemias with upregulation of target genes. It also appreciated that WDR5 has been implicated in other cancer types and may utilize the WIN-site for other chromatin regulatory complexes outside and/or overlapping with WRAD complex. As such the WIN-site inhibitors described herein may have utility in multiple cancer types through mechanisms of action involving both direct competitive WIN-site antagonism, or through allosteric inhibition of higher complexes wherein WDR5 is dependent for their proliferative activity and tumor formation. Examples include breast cancer (Dai, X. et al. PLoS One, 2015), MYC-driven tumor types (Thomas, et al. Molecular Cell, 2015), bladder cancer (Chen, X. et al. Nature, Scientific Reports, 2015), neuroblastoma (Sun, Y. et al. Cancer Research, 2015), and pancreatic cancer (Carugo, A. et al. Cell Reports, 2016).

The disclosed compounds and compositions may be used in methods for treatment of MLL related cancers. The methods of treatment may comprise administering to a subject in need of such treatment a composition comprising a therapeutically effective amount of the compound of formula (I).

In one aspect, disclosed is a method of treating cancer, the method comprising administration of a therapeutically effective amount of a compound of formula (I), or a pharmaceutically acceptable salt thereof to a subject in need thereof.

In certain embodiments, the cancer being treated is associated with dysfunction of MLL.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MLL1, the method comprising administration of a therapeutically effective amount of a compound of formula (I), or a pharmaceutically acceptable salt thereof to a subject in need thereof.

The compositions can be administered to a subject in need thereof to bind WDR5 and modulate MLL, to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL1.

The compositions may be useful for treating certain cancers in humans and animals related to MLL dysfunction. Treatment of such cancers can be effected by modulating MLL1 in a subject, by administering a compound or composition of the invention, either alone or in combination with another active agent as part of a therapeutic regimen to a subject in need thereof.

Disruption of the interaction between WDR5 and its binding partners (such as MLL1) can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof can mediate reduction, clearance or prevention of additional growth of tumor cells by disrupting the ability of MLL1, another transcription factor, or chromatin to associate with WDR5, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™.). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of different anti-cancer drugs such as chemotherapeutics, anti-tumor agents, and anti-proliferative agents.

Further, the compound of formula (I) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodynamic therapies, proteasome inhibitors, platinum containing compounds, radiation, receptor tyrosine kinase inhibitors, ribonucleotide reductase inhibitors, thrombospondin mimetics, uracil analogs, vinca alkaloids, vitamin D3 analogs, γ-radiation, DOT1L inhibitors, agents targeting epigenetic mechanisms, or an additional chemotherapeutic agent such as N-Ac-Sar-Gly-Val-D-alloIle-Thr-Nva-Ile-Arg-Pro-NHCH2CH3 or a salt thereof, actinomycin D, AG13736, 17-allylamino-17-demethoxygeldanamycin, 9-aminocamptothecin, N-(4-(3-amino-1H-indazol-4-yl)phenyl}-N-(2-fluoro-5-methylphenyl)urea or a salt thereof, N-(4-(4-aminothieno[2,3-d]pyrimidin-5-yl)phenyl}-N-(2-fluoro-5-(trifluoromethyl)phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxy-doxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN518, MLN4924, MS-275, mycophenolic acid, mitomycin C, nitrosoureas, oprelvekin, oxaliplatin, paclitaxel, PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

The in vitro modulation of WDR5 protein was determined as follows.
MLL Peptide Binding Assay
General Provided compounds of the present invention can be demonstrated to compete for binding with fluorescently labeled peptides derived from relevant MLL protein.
Fluorescence Polarization Anisotropy Competition Assay A fluorescence polarization anisotropy (FPA) assay that measures the displacement of either a FITC-labeled MLL-derived peptide or a more potent 10mer-Thr-FAM probe in response to compound treatment is performed (Karatas et al. J. Med. Chem. 2010, 5179.). The assay is run in 384-well format and is read on a BioTek Cytation. Compounds are run as 2 replicates on the left and right sides of the plate; therefore a plate can accommodate 16 compounds in a 10-point, 3-fold dilution scheme, plus positive and negative controls. Replicate values are fit to a 4-parameter fit in XLFit to generate a single $IC_{50}$ value for each compound that is then converted to a $K_i$ value. Experiments are repeated to generate a $2^{nd}$, independent $K_i$ value; values from the two experiments are averaged to produce the reported $K_i$ value for the compound. The assay performs with an average Z' value of 0.7, and is tolerant of up to 5% DMSO.

FPA Assay protocol adopted from Karatas et al. (J. Med. Chem. 2010, 5179.; J. Amer. Chem. Soc. 2013, 669.): WDR5 (Δ23, residues 24-334), is expressed and purified in sufficient quantities for screening. FITC-MLL peptide (FITC-GSARAEVHLRKS) and 10mer-Thr-FAM (ARTE-VHLRKS-(Ahx-Ahx)(Lys-(5-FAM))) were purchased from GeneScript and used without additional purification. FITC-MLL peptide is used at 50 nM, while WDR5 is added at the $K_i$ value of the protein:peptide interaction (WDR5-WIN $K_i$=2.5 μM). 10mer-Thr-FAM peptide is used at 4 nM, while WDR5 is added at the $K_i$ value of the protein:peptide interaction (WDR5-10mer-Thr $K_i$=4 nM).

Stock compounds are dispensed in barcoded 384-well plates as 30 mM solutions in DMSO. This plate is used as the source plate for the Echo Liquid Handler, which distributes the compounds to the assay plate (black, flat-bottom; Greiner) in a 10-point, 3-fold dilution scheme with a top concentration of 100 μM (5 nM low concentration) in a final volume of 50 μL. Both the top concentration and the dilution scheme can be adjusted to fit the anticipated potency of the compounds.

For the FITC-MLL assay, 2.5 μM WDR5 and 50 nM FITC-MLL peptide in assay buffer (1× Phosphate Buffered Saline, pH 6.0, 300 mM NaCl, 0.5 mM TCEP, 0.1% CHAPS) is added to all compound-containing wells and to columns 2, 24 (negative control, 0% inhibition). 2 μL of 50 nM FITC-MLL peptide alone in assay buffer is added to columns 1, 23 (positive control, 100% inhibition). For the 10mer-Thr-FAM assay, a similar addition protocol is performed, using 4 nM WDR5 and 4 nM 10mer-Thr-FAM peptide in assay buffer (1× Phosphate Buffered Saline pH 6.0, 300 mM NaCl, 0.5 mM TCEP, 0.1% CHAPS).

The plate is covered, shielded from light, and incubated for 60 min at room temperature, with rocking. Anisotropy is measured at excitation wavelength 480 nm and emission wavelength 535 nm using an EnVision Multi-label plate reader (PerkinElmer, Wellesley, Mass., USA) or a BioTek Cytation 3 (BioTek, Winooski, Vt., USA). Fluorescence anisotropy is plotted against compound concentration to generate an $IC_{50}$ (inhibitor concentration at which 50% of bound peptide is displaced) by fitting the data to a 4-parameter logistic model using XLFit software (Guildford, Surrey, UK). $IC_{50}$ is converted to a binding dissociation constant ($K_i$ value) according to the formula of Wang Z. FEBS Lett (1996) 3, 245.

$$K_i = [I]_{50}/([L]_{50}/K_d + [P]_0/K_d + 1)$$

where $[I]_{50}$ is the concentration of the free inhibitor at 50% inhibition, $[L]_{50}$ is the concentration of the free labeled ligand at 50% inhibition, $[P]_0$ is the concentration of the free protein at 0% inhibition, $K_d$ represents the dissociation constant of the FITC-MLL or 10mer-Thr-FAM probe for WDR5. Total fluorescence is also measured, to rule out compounds that are inherently fluorescent or able to act as quenchers in the assay.
TR-FRET Binding Assay A Time-Resolved Fluorescence Resonance Energy Transfer (TR-FRET) assay that measures the displacement of the 10mer-Thr-FAM probe in response to compound treatment was performed for compounds wherein the $IC_{50}$ from FPA assay using 10mer-Thr-FAM was below the lower assay $IC_{50}$ limit ~1 nM. Excess 10mer-Thr-FAM probe was utilized with His-tagged WDR5 in conjunction with a commercial anti-His antibody containing a Terbium label. The LanthaScreen™ Elite Tb-anti-HIS Antibody from ThermoFisher Scientific was used for this purpose. This Tb-anti-HIS has an excitation/emission of 340 nm and 490 nm, respectively. The 10mer-Thr-FAM probe when bound to WDR5 will undergo a FRET interaction with the Tb-anti-HIS and emit at 520 nm. The ratio of the 520 and 495 signals are then utilized to generate a dose-response curve to calculate an $IC_{50}$ value. By virtue of FRET there is little to no background fluorescence interference from 10mer-Thr-FAM probe allowing an excess of the probe to be used permitting an increase in the lower limit of the calculated $K_i$ when testing against highly potent inhibitors with $K_i \ll 1$ nM. WDR5-His Tag (423, residues 24-334) is expressed and purified in our lab in sufficient quantities for screening. 10mer-Thr-FAM peptide is used anywhere from 15 to 150 nM depending on the window of sensitivity required. WDR5-His tag protein is used at 2 nM. A source plate is prepared using an Echo Liquid Handler, which distributes the compounds to the assay plate (white, flat-bottom; Opti-Plate) in a 10-point, 3-fold dilution schemes with a top concentration of either 5 or 20 µM depending on the anticipated potency of the compounds, in a final volume of 20 µL. A final target (WDR5)/Tb-Ab concentration of 2 nM/1 nM is dispensed from appropriate stock solutions, respectively. The final DMSO concentration in each well of the assay plate is 1% or lower. As before the plate is covered, shielded from light, and incubated for 60 minutes at room temperature with rocking. Anisotropy is then measured on a Biotek Cytation 3 at excitation wavelength of 340 nm, and emission wavelengths of 495 nm and 520 nm. Working buffer conditions (pH 7.0) are similar to that in FPA above. TR-FRET signal is plotted and $IC_{50}$ and $K_i$ values are calculated in the same manner as the fluorescence polarization anisotropy based competition assays. The results for representative compounds are shown in Table 2 and 3.

TABLE 2

$K_i$ for Examplified Compounds for Inhibition of WDR5 by FPA assay

| Example | $K_i$ (nM) |
|---|---|
| 2 | 6.0 |
| 3 | 2.7 |
| 110 | 33.7 |
| 111 | 135.1 |
| 112 | 141.1 |
| 113 | 141.4 |
| 114 | 298.1 |
| 115 | 3.5 |
| 116 | 1.9 |
| 117 | 13.0 |
| 118 | 10.3 |
| 119 | 3.3 |
| 120 | 5.1 |
| 121 | 1.3 |
| 122 | 2.2 |
| 123 | 8.7 |
| 124 | 1.8 |
| 125 | 1.9 |
| 126 | <1 |
| 127 | <1 |
| 128 | 2.2 |
| 129 | 5.9 |
| 130 | 2.1 |
| 131 | <1 |
| 132 | 3.9 |
| 133 | 3.5 |
| 134 | 1.6 |
| 135 | >10000 |
| 136 | 6.5 |
| 137 | <1 |
| 148 | 1.6 |
| 149 | 8.6 |
| 150 | 1.1 |
| 151 | 8.7 |
| 152 | 13.1 |
| 153 | 4.8 |
| 154 | 5.1 |
| 155 | 21.9 |

TABLE 3

$K_i$ for Examplified Compounds for Inhibition of WDR5 by TR-FRET assay

| Example | $K_i$ (nM) |
|---|---|
| 1 | 0.46 |
| 4 | 0.36 |
| 5 | 0.02 |
| 6 | 0.14 |
| 7 | 0.11 |
| 8 | 12 |
| 9 | <0.1 |
| 10 | 2.9 |
| 11 | 0.22 |
| 12 | <0.1 |
| 13 | 0.53 |
| 14 | 0.74 |
| 15 | 1.7 |
| 16 | 0.52 |
| 17 | 3.2 |
| 18 | 3.1 |
| 19 | 0.45 |
| 20 | 0.60 |
| 21 | 0.39 |
| 22 | 0.28 |
| 23 | 1.3 |
| 24 | 0.37 |
| 25 | 0.20 |
| 26 | 3.0 |
| 27 | 1.5 |
| 28 | 7.6 |
| 29 | 13 |
| 30 | 0.33 |
| 31 | <0.1 |
| 32 | 0.91 |
| 33 | 8.9 |
| 34 | 0.37 |
| 35 | 0.36 |
| 36 | 2.8 |
| 37 | 2.1 |
| 38 | 0.26 |
| 39 | <0.1 |
| 40 | 64 |
| 41 | <0.1 |
| 42 | <0.1 |
| 43 | 15 |
| 44 | 17 |
| 45 | 1.01 |
| 46 | 0.10 |
| 47 | <0.1 |
| 48 | 0.63 |
| 49 | 0.30 |
| 50 | <0.1 |
| 51 | <0.1 |
| 53 | 0.53 |
| 54 | 0.31 |
| 55 | 11 |
| 56 | 20 |
| 57 | 3.0 |
| 58 | 5.8 |
| 59 | 0.74 |
| 60 | 0.55 |
| 61 | 1.8 |
| 62 | 0.21 |
| 63 | 0.88 |
| 64 | 0.64 |
| 65 | 4.3 |
| 66 | 0.38 |
| 67 | <0.1 |
| 68 | 0.30 |
| 69 | 1.3 |
| 70 | 0.50 |
| 71 | 6.6 |
| 72 | 0.31 |
| 73 | 0.43 |
| 74 | 0.46 |
| 75 | 0.80 |
| 76 | 32 |
| 77 | 33 |
| 78 | 0.72 |
| 79 | 5.74 |
| 80 | 22 |
| 81 | 0.24 |
| 82 | 0.46 |

TABLE 3-continued $K_i$ for Examplified Compounds for Inhibition of WDR5 by TR-FRET assay

| Example | $K_i$ (nM) |
|---|---|
| 83 | 0.31 |
| 84 | 0.15 |
| 85 | 0.99 |
| 86 | <0.1 |
| 87 | <0.1 |
| 88 | 0.12 |
| 89 | 1.9 |
| 90 | 1.2 |
| 91 | 1.6 |
| 92 | 1.5 |
| 93 | 3.3 |
| 94 | 1.2 |
| 95 | 8.6 |
| 96 | 1.5 |
| 97 | 7.3 |
| 98 | 23 |
| 99 | 1.1 |
| 100 | 2.4 |
| 101 | 2.1 |
| 102 | 1.0 |
| 103 | 3.3 |
| 104 | 12 |
| 105 | <0.1 |
| 106 | <0.1 |
| 107 | 0.15 |
| 108 | 2.0 |
| 109 | 0.13 |
| 116 | 1.3 |
| 133 | 4.6 |
| 134 | 1.0 |
| 137 | 2.0 |
| 138 | 50 |
| 139 | 1.6 |
| 140 | 95 |
| 141 | 10 |
| 142 | 0.59 |
| 143 | 0.43 |
| 144 | 4.77 |
| 145 | 22 |
| 146 | 500 |
| 147 | 0.31 |
| 150 | 5.71 |
| 151 | 32 |
| 156 | 2.15 |
| 157 | 27 |
| 158 | 8.0 |
| 159 | 3.9 |
| 160 | >33 |
| 161 | >33 |
| 162 | 6.4 |
| 163 | >33 |
| 164 | 0.28 |
| 165 | 11 |
| 166 | 2.44 |
| 167 | >33 |
| 168 | 5.2 |
| 169 | 6.1 |
| 170 | 19 |
| 171 | 19 |
| 172 | 2.1 |
| 173 | 7.2 |

Among other things, these data demonstrate the utility of representative compounds as selective inhibitors of the activity of WDR5 protein to bind peptides from relevant MLL domain.

Cellular Viability of Human Tumor Cell Lines

Anti proliferative activity using MLL-harboring cell lines. MV4:11 cells are grown in RPMI-1640 media supplemented with 10% FBS and 1% penicillin/streptomycin. Viability assays are performed by dispensing 3600 cells/ml into each well of an opaque 384-well plate and adding compounds at the indicated concentrations in a final volume of 32 μL and a final concentration of DMSO of 0.1% for all samples. After a set incubation period, 7 day protocol, the viability of cells in each well is assessed using the CellTiter-Glo assay (Promega), read on a GloMax 96 Microplane Luminometer (Promega). Serial dilutions of each cell type are included in all assays to generate standard curves and determine assay measurements are taken within the dynamic range of the instrument. $GI_{50}$ values are calculated based on three biological replicates, each with three technical replicates. Data are expressed as mean plus/minus S.E.M.

TABLE 4

$GI_{50}$ (in μM) for representative compounds on cellular proliferation of MV4:11 human cancer cell lines

| Example | $GI_{50}$ (μM) |
|---|---|
| 7 | 0.28 |
| 41 | 0.17 |
| 53 | 0.63 |
| 54 | 0.18 |
| 55 | 0.44 |
| 56 | 6.4 |
| 57 | 2.8 |
| 59 | 0.79 |
| 60 | 0.36 |
| 63 | 1.9 |
| 64 | 0.28 |
| 67 | 0.05 |
| 68 | 0.16 |
| 70 | 0.46 |
| 71 | 5.0 |
| 74 | 0.68 |
| 90 | 0.75 |
| 91 | 0.46 |
| 105 | 0.01 |
| 106 | 0.03 |
| 116 | 3.8 |
| 156 | 0.63 |
| 159 | 1.2 |
| 164 | 1.1 |
| 166 | 0.24 |
| 168 | 4.8 |
| 169 | 14 |
| 170 | 4.7 |
| 171 | 3.8 |
| 172 | 0.24 |
| 173 | 0.53 |

FPA and TR-FRET Binding Affinity of Representative WDR5 WIN-Site Inhibitors.

TABLE B2

| Example | $K_i$ (M) |
|---|---|
| B1 | 1.80E-08 |
| B2 | 4.00E-07 |
| B3 | 2.09E-07 |
| B4 | 1.19E-08 |
| B5 | 3.08E-08 |
| B6 | 4.01E-09 |
| B7 | 8.46E-09 |
| B8 | 1.07E-08 |
| B9 | 1.74E-08 |
| B10 | 5.45E-08 |
| B11 | 4.60E-08 |
| B12 | 6.51E-08 |
| B13 | 8.30E-08 |
| B14 | 5.60E-08 |
| B15 | 1.33E-09 |
| B16 | 9.05E-09 |
| B17 | 2.47E-09 |
| B18 | 1.81E-09 |
| B19 | 8.06E-09 |
| B20 | 4.60E-09 |
| B21 | 1.78E-08 |

TABLE B2-continued

| Example | $K_i$ (M) |
|---|---|
| B22 | 1.50E−09 |
| B23 | 3.03E−08 |
| B24 | 4.98E−08 |
| B25 | 7.42E−08 |
| B26 | 3.24E−09 |
| B27 | 7.52E−09 |
| B28 | 6.22E−10 |
| B29 | 2.49E−08 |
| B30 | 5.32E−09 |
| B31 | 8.11E−09 |
| B32 | 4.51E−09 |
| B33 | 4.44E−10 |
| B34 | 1.20E−08 |
| B35 | 4.22E−09 |
| B36 | 9.17E−10 |
| B37 | 8.71E−09 |
| B38 | 2.45E−08 |
| B39 | 1.39E−09 |
| B40 | 7.21E−09 |
| B41 | 1.76E−09 |
| B42 | 1.51E−09 |
| B43 | 1.82E−09 |
| B44 | 2.03E−08 |
| B45 | 1.13E−08 |
| B46 | 3.96E−09 |
| B47 | 1.89E−10 |
| B48 | 2.17E−09 |
| B49 | 1.06E−09 |
| B50 | 1.24E−08 |
| B51 | 9.77E−09 |
| B52 | 3.30E−08 |
| B53 | 4.09E−08 |
| B54 | 1.12E−09 |
| B55 | 1.27E−09 |
| B58 | 2.06E−09 |
| B63 | 1.31E−10 |
| B64 | 2.13E−11 |
| B72 | 6.34E−10 |
| B74 | 3.12E−11 |
| B81 | 3.30E−11 |
| B84 | 1.18E−10 |
| B87 | 1.98E−10 |
| B88 | 1.15E−10 |
| B89 | 4.39E−09 |
| B90 | 1.15E−10 |
| B93 | 7.59E−10 |
| B95 | 6.10E−09 |
| B99 | 8.75E−11 |
| B107 | 9.65E−11 |
| B109 | 3.85E−11 |
| B111 | 8.75E−11 |
| B114 | 2.28E−10 |
| B115 | 4.80E−10 |
| B116 | 1.06E−10 |
| B124 | >3.3E−08 |
| B125 | >3.3E−08 |
| B129 | 8.90E−11 |

$K_i$ values less than 1 nM were obtained using the TR-FRET assay.

Growth Inhibitory Activity of Representative WDR5 WIN-Site Inhibitors in MV4:11 Leukemia Cells After a 7 Day Incubation Period

TABLE B3

| Example | $GI_{50}$ (nM) |
|---|---|
| B6 | 3282 |
| B15 | 893 |
| B21 | >30,000 |
| B88 | 536 |
| B114 | 701 |
| B129 | 109 |

FPA and TR-FRET Binding Affinity of Representative WDR5 WIN-Site Inhibitors

TABLE C2

| Example | $K_i$ (M) |
|---|---|
| C2 | 3.11E−10 |
| C20 | 3.03E−08 |
| C21 | 3.30E−08 |
| C22 | 1.32E−10 |
| C23 | 3.13E−09 |
| C24 | 1.17E−08 |
| C27 | 1.58E−09 |
| C32 | 1.54E−09 |
| C34 | 3.25E−08 |
| C35 | 4.41E−08 |

$K_i$ values less than 1 nM were obtained using the TR-FRET assay.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A compound of formula (I)

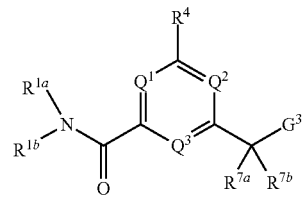

or a pharmaceutically acceptable salt or tautomer thereof, wherein:
$Q^1$ is N or $CR^3$;
$Q^2$ is N or $CR^5$;
$Q^3$ is N or $CR^2$;
$R^{1a}$ is $C_1$-$C_4$alkyl, $G^1$ or —$(CR^aR^b)_n$-$G^1$;
n is 1, 2, or 3;
$R^a$ is hydrogen, $C_1$-$C_4$alkyl, $C_1$-$C_4$haloalkyl, $C_3$-$C_6$carbocycle, or —$C_1$-$C_3$alkylene-C(O)$YR^{20}$;
Y is O, NH, or $NC_1$-$C_4$alkyl;
$R^{20}$ is H, $C_1$-$C_4$alkyl, $C_3$-$C_6$cycloalkyl, or —$C_1$-$C_3$alkylene-$R^{30}$;
$R^{30}$ is C(O)$C_1$-$C_4$alkyl, C(O)$C_3$-$C_6$cycloalkyl, or phenyl, wherein the $C_3$-$C_6$cycloalkyl and phenyl are optionally substituted with 1-4 substituents independently selected from the group consisting of halogen, $C_1$-$C_4$alkyl, —$OC_1$-$C_4$alkyl, and $C_1$-$C_4$haloalkyl;
$R^b$ is hydrogen or $C_1$-$C_4$alkyl;
optionally $R^a$ and $R^b$ together with the carbon atom to which they are attached form a ring selected from the group consisting of a 3-8 membered saturated or partially unsaturated carbocyclic ring and a 3-8 membered saturated or partially unsaturated heterocyclic ring having 1-4 heteroatoms independently selected from the group consisting of nitrogen, oxygen, or sulfur;
optionally $R^a$ and $R^b$ are taken together to form an oxo group;
$R^{1b}$ is hydrogen, $C_1$-$C_4$alkyl, $C_3$-$C_6$cycloalkyl, or —$C_1$-$C_3$alkylene-$C_3$-$C_6$cycloalkyl;
$G^1$ is 6- to 12-membered aryl, a 5- to 12-membered heteroaryl, a 4- to 12-membered heterocyclyl, or a $C_3$-$C_{10}$carbocycle optionally fused to a phenyl or to a 5- to 6-membered heteroaryl, wherein $G^1$ is optionally substituted with 1-5 substituents independently selected from the group consisting of $C_1$-$C_4$hydroxyalkyl, halogen, $C_1$-$C_6$alkyl, $C_1$-$C_6$haloalkyl, oxo, —$OR^{1c}$, —$NR^{1c}R^{1d}$, —$SR^{1c}$, cyano, —$C(O)OR^{1c}$, —$C(O)NR^{1c}R^{1d}$, —$C(O)R^{1e}$, —$SOR^{1e}$, —$SO_2R^{1e}$, —$SO_2NR^{1c}R^{1d}$, —$NR^{1c}C(O)R^{1e}$, —$NR^{1c}C(O)OR^{1d}$, —$NR^{1c}C(O)NR^{1c}R^{1d}$, —$NR^{1c}S(O)_2R^{1e}$, —$NR^{1c}S(O)_2NR^{1c}R^{1d}$, $C_3$-$C_8$cycloalkyl, and —$C_1$-$C_3$alkylene-$C_3$-$C_8$cycloalkyl, wherein the $C_3$-$C_8$cycloalkyl and $C_1$-$C_3$alkylene-$C_3$-$C_8$cycloalkyl are optionally substituted with 1-4 substituents independently selected from the group consisting of $C_1$-$C_4$alkyl and halogen;
$R^2$ is hydrogen, halo, $C_1$-$C_4$ alkyl, or $C_1$-$C_4$ haloalkyl;
$R^3$ is hydrogen, halo, $C_1$-$C_4$ alkyl, $C_1$-$C_4$ haloalkyl, —$OR^{3a}$, —$NR^{3a}R^{3b}$, —$SR^{3a}$, cyano, —$C(O)OR^{3a}$, —$C(O)NR^{3a}R^{3b}$, —$C(O)R^{3c}$, —$SOR^{3c}$, —$SO_2R^{3c}$, —$SO_2NR^{3a}R^{3b}$, —$NR^{3a}C(O)R^{3c}$, —$NR^{3a}C(O)OR^{3b}$, —$NR^{3a}C(O)NR^{3a}R^{3b}$, —$NR^{3a}S(O)_2R^{3c}$, —$NR^{3a}S(O)_2NR^{3a}R^{3b}$, $C_3$-$C_8$cycloalkyl, or —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;
$R^4$ is halo, $C_1$-$C_6$ alkyl, $C_1$-$C_6$ haloalkyl, $C_1$-$C_6$haloalkenyl, -L-$R^x$, $G^2$, -L-$G^2$, or -L-$C_1$-$C_3$alkylene-$G^2$;
L is O, S, —$NR^{4a}$—, —$S(O)$—, —$S(O)_2$—, —$S(O)_2NR^{4a}$—, —$C(O)NR^{4a}$—, —$C(O)$—, —$NR^{4a}C(O)$—, —$NR^{4a}C(O)O$—, —$NR^{4a}C(O)NR^{4a}$—, —$NR^{4a}S(O)_2$—, or —$NR^{4a}S(O)_2NR^{4a}$—;
$R^x$ is hydrogen, $C_1$-$C_6$alkyl, or $C_1$-$C_6$haloalkyl;
$G^2$ is a $C_3$-$C_{10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of $C_1$-$C_4$hydroxyalkyl, halogen, $C_1$-$C_6$alkyl, $C_1$-$C_6$haloalkyl, oxo, —$OR^{4b}$, —$NR^{4b}R^{4c}$, —$SR^{4b}$, cyano, —$C(O)OR^{4b}$, —$C(O)NR^{4b}R^{4c}$, —$C(O)R^{4d}$, —$SOR^{4d}$, —$SO_2R^{4d}$, —$SO_2NR^{4b}R^{4c}$, —$NR^{4b}C(O)R^{4d}$, —$NR^{4b}C(O)OR^{4c}$, —$NR^{4b}C(O)NR^{4b}R^{4c}$, —$NR^{4b}S(O)_2R^{4d}$, —$NR^{4b}S(O)_2NR^{4b}R^{4c}$, $C_3$-$C_8$cycloalkyl, and $C_1$-$C_3$alkylene-$C_3$-$C_8$cycloalkyl, wherein the $C_3$-$C_8$cycloalkyl and $C_1$-$C_3$alkylene-$C_3$-$C_8$cycloalkyl are optionally substituted with 1-4 substituents independently selected from the group consisting of $C_1$-$C_4$alkyl and halogen;
$R^5$ is hydrogen, halo, $C_1$-$C_4$ alkyl, $C_1$-$C_4$ haloalkyl, —$OR^{5a}$, —$NR^{5a}R^{5b}$, —$SR^{5a}$, cyano, —$C(O)OR^{5a}$, —$C(O)NR^{5a}R^{5b}$, —$C(O)R^{5c}$, —$SOR^{5c}$, —$SO_2R^{5c}$, —$SO_2NR^{5a}R^{5b}$, —$NR^{5a}C(O)R^{5c}$, —$NR^{5a}C(O)OR^{5b}$, —$NR^{5a}C(O)NR^{5a}R^{5b}$, —$NR^{5a}S(O)_2R^{5c}$, —$NR^{5a}S(O)_2NR^{5a}R^{5b}$, $C_3$-$C_8$cycloalkyl, or —$C_1$-$C_3$alkylene-$C_3$-$C_8$cycloalkyl, wherein the $C_3$-$C_8$cycloalkyl and —$C_1$-$C_3$alkylene-$C_3$-$C_8$cycloalkyl are optionally substituted with 1-4 substituents independently selected from the group consisting of $C_1$-$C_4$alkyl and halogen;

$G^3$ is

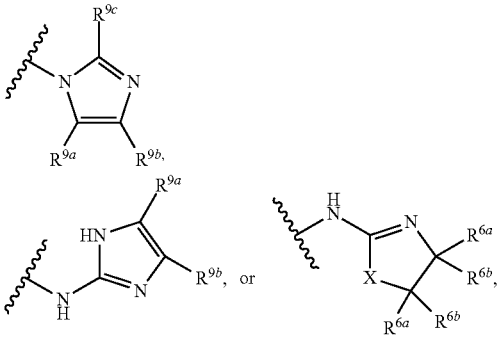

X is O, NR or $(CR^{6a}R^{6b})_{1-2}$;
R is independently hydrogen or $C_1$-$C_4$ alkyl;
$R^{6a}$ and $R^{6b}$, at each occurrence, are each independently hydrogen, $C_1$-$C_4$alkyl, $C_1$-$C_4$haloalkyl, $G^{3a}$, or —$C_1$-$C_3$alkylene-$G^{3a}$, wherein optionally each $R^{6a}$ and $R^{6b}$, independently, are taken together to form an oxo group, a 3-8 membered saturated or partially unsaturated carbocyclic ring, or a 3-8 membered saturated or partially unsaturated heterocyclic ring having 1-4 heteroatoms independently selected from the group consisting of nitrogen, oxygen, or sulfur;
$R^{7a}$ and $R^{7b}$ are independently hydrogen, halogen, $C_1$-$C_4$alkyl, or $C_1$-$C_4$haloalkyl, or $R^{7a}$ and $R^{7b}$ are taken together to form an oxo group;
$R^{9a}$, $R^{9b}$, and $R^{9c}$ are each independently hydrogen, halogen, $C_1$-$C_4$alkyl, $C_1$-$C_4$haloalkyl, or $C_3$-$C_{10}$carbocycle, wherein the $C_3$-$C_{10}$carbocycle is optionally substituted with 1-4 substituents independently selected from the group consisting of halogen, $C_1$-$C_4$alkyl, $C_1$-$C_4$haloalkyl, OH, and —$OC_1$-$C_4$alkyl;
$G^{3a}$ is $C_3$-$C_{10}$carbocycle, a 6- to 12-membered aryl, a 5- to 12-membered heteroaryl, or a 4- to 12-membered heterocycle, wherein $G^{3a}$ is optionally substituted with 1-4 substituents independently selected from the group consisting of halogen, $C_1$-$C_4$alkyl, $C_1$-$C_4$haloalkyl, OH, and —$OC_1$-$C_4$alkyl;
and
$R^{1c}$, $R^{1d}$, $R^{1e}$, $R^{3a}$, $R^{3b}$, $R^{3c}$, $R^{4a}$, $R^{4b}$, $R^{4c}$, $R^{4d}$, $R^{5a}$, $R^{5b}$, and $R^{5c}$, at each occurrence, are independently hydrogen, $C_1$-$C_6$alkyl, $C_1$-$C_6$haloalkyl, $C_3$-$C_8$cycloalkyl, or —$C_1$-$C_6$alkylene-$C_3$-$C_8$cycloalkyl, wherein the $C_3$-$C_8$cycloalkyl and —$C_1$-$C_6$alkylene-$C_3$-$C_8$cycloalkyl are optionally substituted with 1-4 substituents independently selected from the group consisting of $C_1$-$C_4$alkyl and halogen, wherein alternatively $R^{1c}$ and $R^{1d}$, $R^{3a}$ and $R^{3b}$, $R^{4b}$ and $R^{4c}$, and/or $R^{5a}$ and $R^{5b}$, each together with a common nitrogen atom to which each attaches form a 4- to 8-membered saturated or partially unsaturated heterocyclic ring, optionally substituted with 1-4 substituents independently selected from the group consisting of $C_1$-$C_4$alkyl, $C_1$-$C_4$haloalkyl, oxo, —OH, and —$OC_1$-$C_4$alkyl.

2. The compound of claim 1, or a pharmaceutically acceptable salt or tautomer thereof, wherein $G^2$ is a $C_3$-$C_7$carbocycle, a 6- to 10-membered aryl, a 5- to 10-membered heteroaryl, or a 4- to 10-membered heterocycle, wherein $G^2$ is optionally substituted with 1-3 substituents independently selected from the group consisting of C$_1$-C$_4$hydroxyalkyl, halogen, C$_1$-C$_6$alkyl, C$_1$-C$_6$haloalkyl, oxo, —OR$^{4b}$, cyano, —C(O)OR$^{4b}$, —C(O)NR$^{4b}$R$^{4c}$, and C$_3$-C$_8$cycloalkyl, wherein the C$_3$-C$_8$cycloalkyl is optionally substituted with 1-4 substituents independently selected from the group consisting of C$_1$-C$_4$alkyl and halogen.

3. The compound of claim 2, or a pharmaceutically acceptable salt or tautomer thereof, wherein:

R$^4$ is halogen, C$_1$-C$_4$alkyl, C$_1$-C$_4$haloalkyl, —O—C$_1$-C$_4$alkyl, G$^{2a}$, or —O-G$^{2b}$;

G$^{2a}$ is phenyl, a 5- to 6-membered heteroaryl, or a 4-8-membered heterocycle, wherein G$^{23}$ is optionally substituted with 1-3 substituents independently selected from the group consisting of C$_1$-C$_4$hydroxyalkyl, halogen, C$_1$-C$_4$alkyl, C$_1$-C$_4$haloalkyl, oxo, —OR$^{4b}$, and —C(O)NR$^{4b}$R$^{4c}$; and G$^{2b}$ is C$_3$-C$_7$cycloalkyl or phenyl, wherein G$^{2b}$ is optionally substituted with C$_1$-C$_4$alkyl.

4. The compound of claim 3, or a pharmaceutically acceptable salt or tautomer thereof, wherein R$^4$ is

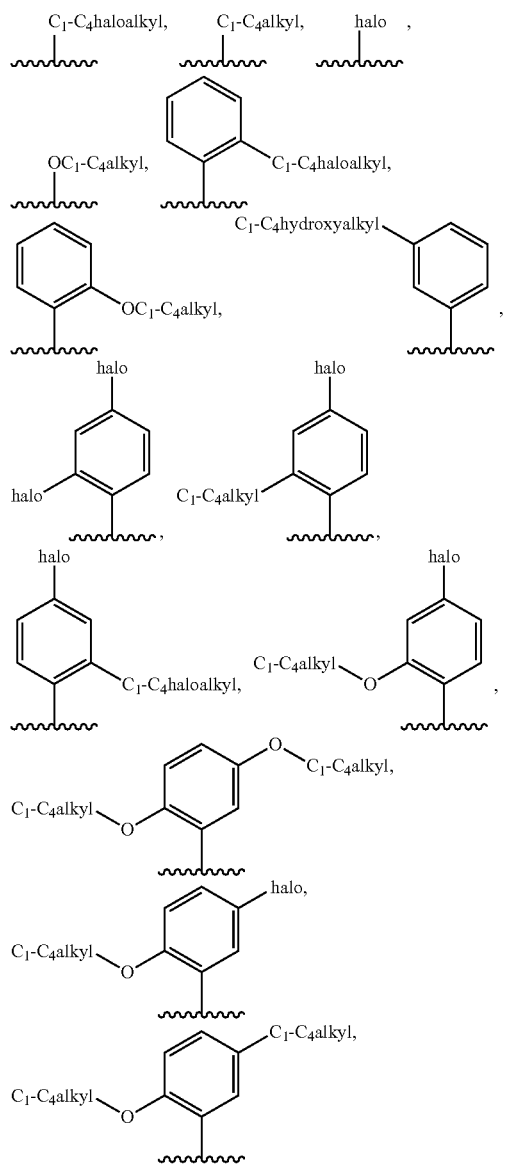

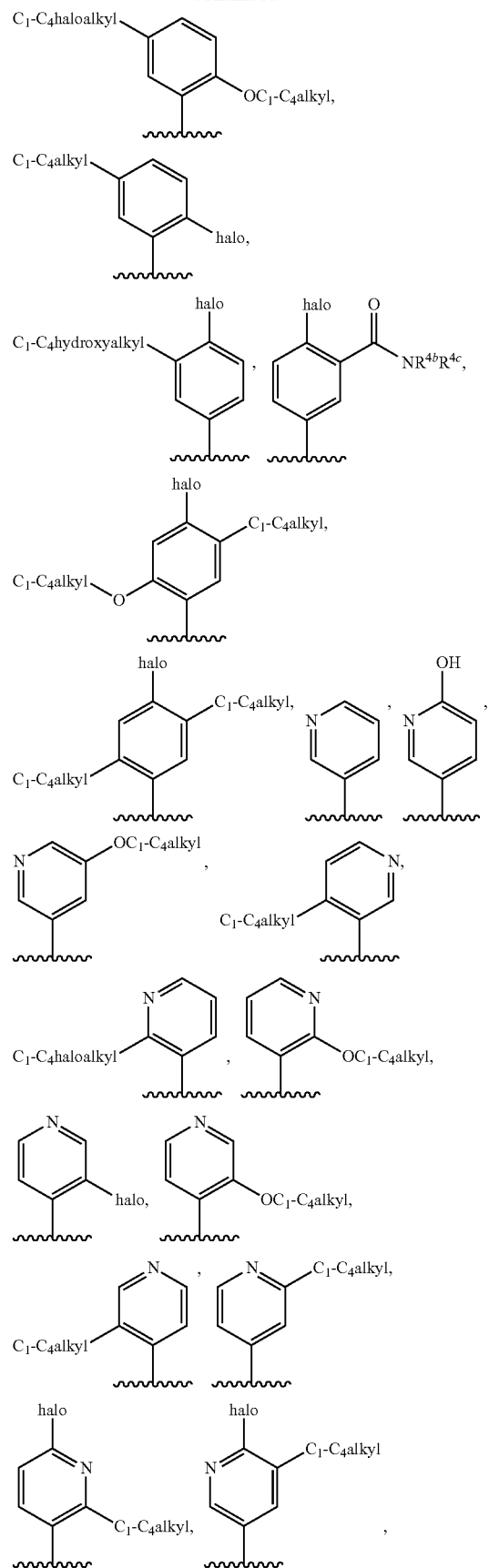

-continued

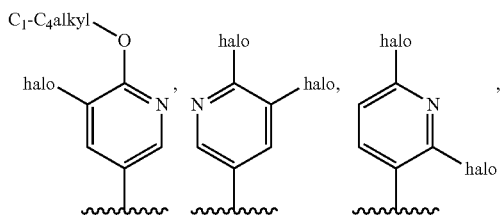
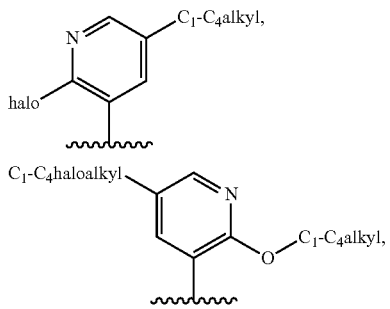
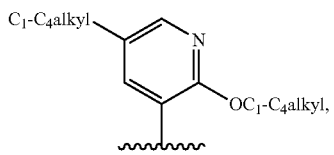
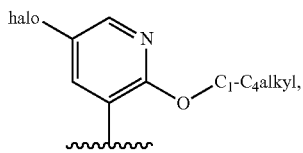
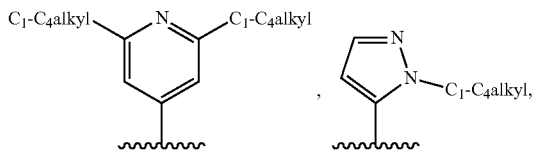
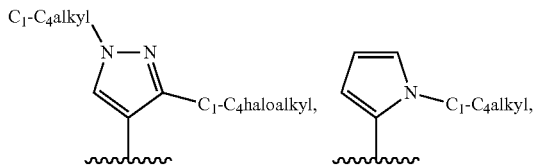
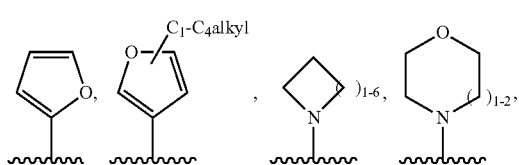
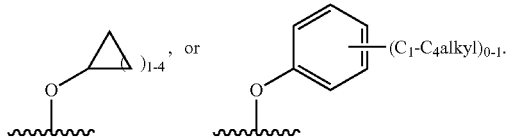

5. The compound of claim 1, or a pharmaceutically acceptable salt or tautomer thereof, wherein $G^3$ is

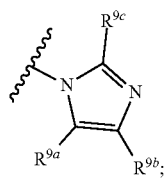

and $R^{9a}$, $R^{9b}$, and $R^{9c}$, are each independently hydrogen, $C_1$-$C_4$alkyl, $C_1$-$C_4$haloalkyl, or $C_3$-$C_6$carbocycle, wherein the $C_3$-$C_6$carbocycle is optionally substituted with 1-4 substituents independently selected from the group consisting of halogen, $C_1$-$C_4$alkyl, $C_1$-$C_4$haloalkyl, OH, and —O$C_1$-$C_4$alkyl.

6. The compound of claim 1, or a pharmaceutically acceptable salt or tautomer thereof, wherein $G^3$ is

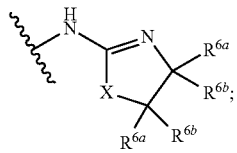

and X is NR.

7. The compound of claim 1, or a pharmaceutically acceptable salt or tautomer thereof, wherein $G^3$ is

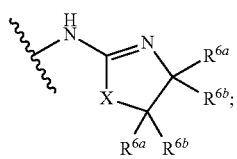

and X is $CH_2$.

8. The compound of claim 1, or a pharmaceutically acceptable salt or tautomer thereof, wherein $G^3$ is

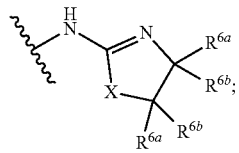

and X is O.

9. The compound of claim 1, or a pharmaceutically acceptable salt or tautomer thereof, wherein:
$Q^1$ is $CR^3$;
$Q^2$ is $CR^5$; and
$Q^3$ is $CR^2$.

10. The compound of claim 1, or a pharmaceutically acceptable salt or tautomer thereof, wherein:
$Q^1$ is N;
$Q^2$ is $CR^5$; and
$Q^3$ is $CR^2$.

11. The compound of claim 1, or a pharmaceutically acceptable salt or tautomer thereof, wherein

327

R$^{1a}$ is G$^{1a}$ or —(CR$^a$R$^b$)-G$^{1b}$;

G$^{1a}$ is C$_3$-C$_7$carbocycle wherein G$^{1a}$ is optionally substituted with 1-4 substituents independently selected from the group consisting of halogen, C$_1$-C$_6$alkyl, C$_1$-C$_6$haloalkyl, oxo, —OR$^{1c}$, —NR$^{1c}$R$^{1d}$, —SR$^{1c}$, cyano, —C(O)OR$^{1c}$, —C(O)NR$^{1c}$R$^{1d}$, —C(O)R$^{1e}$, —SOR$^{1e}$, —SO$_2$R$^{1e}$, —SO$_2$NR$^{1c}$R$^{1d}$, —NR$^{1c}$C(O)R$^{1e}$, —NR$^{1c}$C(O)OR$^{1d}$, —NR$^{1c}$C(O)NR$^{1c}$R$^{1d}$, —NR$^{1c}$S(O)$_2$R$^{1e}$, —NR$^{1c}$S(O)$_2$NR$^{1c}$R$^{1d}$, C$_3$-C$_8$cycloalkyl, and —C$_1$-C$_3$alkylene-C$_3$-C$_8$cycloalkyl, wherein the C$_3$-C$_8$cycloalkyl and C$_1$-C$_3$alkylene-C$_3$-C$_8$cycloalkyl are optionally substituted with 1-4 substituents independently selected from the group consisting of C$_1$-C$_4$alkyl and halogen; and G$^{1b}$ is C$_3$-C$_7$carbocycle, phenyl, or a 5- to 6-membered heteroaryl, wherein G$^{1b}$ is optionally substituted with 1-4 substituents independently selected from the group consisting of halogen, C$_1$-C$_6$alkyl, C$_1$-C$_6$haloalkyl, oxo, —OR$^{1c}$, —NR$^{1c}$R$^{1d}$, —SR$^{1c}$, cyano, —C(O)OR$^{1c}$, —C(O)NR$^{1c}$R$^{1d}$, —C(O)R$^{1e}$, —SOR$^{1e}$, —SO$_2$R$^{1e}$, —SO$_2$NR$^{1c}$R$^{1d}$, —NR$^{1c}$C(O)R$^{1e}$, —NR$^{1c}$C(O)OR$^{1d}$, —NR$^{1c}$C(O)NR$^{1c}$R$^{1d}$, —NR$^{1c}$S(O)$_2$R$^{1e}$, —NR$^{1c}$S(O)$_2$NR$^{1c}$R$^{1d}$, C$_3$-C$_8$cycloalkyl, and —C$_1$-C$_3$alkylene- C$_3$-C$_8$cycloalkyl, wherein the C$_3$-C$_8$cycloalkyl and —C$_1$-C$_3$alkylene-C$_3$-C$_8$cycloalkyl are optionally substituted with 1-4 substituents independently selected from the group consisting of C$_1$-C$_4$alkyl and halogen.

12. The compound of claim 1, or a pharmaceutically acceptable salt or tautomer thereof, wherein R$^b$ is hydrogen or C$_1$-C$_4$alkyl.

13. The compound of claim 1, or a pharmaceutically acceptable salt or tautomer thereof, wherein R$^{1b}$ is hydrogen or C$_1$-C$_4$alkyl.

14. The compound of claim 1, or a pharmaceutically acceptable salt or tautomer thereof, wherein R$^{1c}$, R$^{1d}$, R$^{1e}$, R$^{3a}$, R$^{3b}$, R$^{3c}$, R$^{4a}$, R$^{4b}$, R$^{4c}$, R$^{4d}$, R$^{5a}$, R$^{5b}$, and R$^{5c}$, at each occurrence, are independently hydrogen or C$_1$-C$_4$alkyl.

15. The compound of claim 1, selected from the group consisting of
  3-chloro-N-(3,4-dichlorobenzyl)-5-(((4,5-dihydro-1H-imidazol-2-yl)amino)methyl)benzamide;
  3-chloro-N-(3,5-dichlorobenzyl)-5-(((4,5-dihydro-1H-imidazol-2-yl)amino)methyl)benzamide;
  3-chloro-N-(3-chloro-4-methylbenzyl)-5-(((4,5-dihydro-1H-imidazol-2-yl)amino)methyl)benzamide;
  3-chloro-5-(((4,5-dihydro-1H-imidazol-2-yl)amino)methyl)-N-(3,5-dimethylbenzyl)benzamide;
  3-chloro-N-(1-(3-chlorophenyl)ethyl)-5-(((4,5-dihydro-1H-imidazol-2-yl)amino)methyl)benzamide;
  3-(((4,5-dihydro-1H-imidazol-2-yl)amino)methyl)-N-(3,5-dimethoxybenzyl)-4,5-difluorobenzamide;
  3-(((4,5-dihydro-1H-imidazol-2-yl)amino)methyl)-N-(3,5-dimethylbenzyl)-4,5-difluorobenzamide;
  N-(3-chloro-4-methoxybenzyl)-3-(((4,5-dihydro-1H-imidazol-2-yl)amino)methyl)-4,5-difluorobenzamide;
  N-(3,4-dichlorobenzyl)-3-(((4,5-dihydro-1H-imidazol-2-yl)amino)methyl)-4,5-difluorobenzamide;
  3-(((4,5-dihydro-1H-imidazol-2-yl)amino)methyl)-4,5-difluoro-N-((4-methoxypyridin-2-yl)methyl)benzamide;
  3-(((4,5-dihydro-1H-imidazol-2-yl)amino)methyl)-N-(1-(3,5-dimethoxyphenyl)ethyl)-4,5-difluorobenzamide;
  2'-chloro-N-(3,4-dichlorobenzyl)-5-(((4,5-dihydro-1H-imidazol-2-yl)amino)methyl)-4'-fluoro-[1,1'-biphenyl]-3-carboxamide;

328

2'-chloro-5-(((4,5-dihydro-1H-imidazol-2-yl)amino)methyl)-N-(3,5-dimethylbenzyl)-4'-fluoro-[1,1'-biphenyl]-3-carboxamide;
  2'-chloro-N-(dicyclopropylmethyl)-5-(((4,5-dihydro-1H-imidazol-2-yl)amino)methyl)-4'-fluoro-[1,1'-biphenyl]-3-carboxamide;
  2'-chloro-5-(((4,5-dihydro-1H-imidazol-2-yl)amino)methyl)-N-(3,5-dimethoxybenzyl)-4'-fluoro-[1,1'-biphenyl]-3-carboxamide;
  2'-chloro-N-(4-chloro-3-methylbenzyl)-5-(((4,5-dihydro-1H-imidazol-2-yl)amino)methyl)-4'-fluoro-[1,1'-biphenyl]-3-carboxamide;
  3-(((4,5-dihydro-1H-imidazol-2-yl)amino)methyl)-N-(3,4-dimethoxybenzyl)-5-(6-fluoro-2-methylpyridin-3-yl)benzamide;
  N-(4-chloro-3-methylbenzyl)-3-(((4,5-dihydro-1H-imidazol-2-yl)amino)methyl)-5-(6-fluoro-2-methylpyridin-3-yl)benzamide;
  3-(((4,5-dihydro-1H-imidazol-2-yl)amino)methyl)-N-(3,5-dimethylbenzyl)-5-(6-fluoro-2-methylpyridin-3-yl)benzamide;
  3-(((4,5-dihydro-1H-imidazol-2-yl)amino)methyl)-N-(1-(3,5-dimethoxyphenyl)ethyl)-5-(6-fluoro-2-methylpyridin-3-yl)benzamide;
  3-(((4,5-dihydro-1H-imidazol-2-yl)amino)methyl)-N-(3,5-dimethoxybenzyl)-5-(6-fluoro-2-methylpyridin-3-yl)benzamide;
  N-(3,4-dichlorobenzyl)-3-(((4,5-dihydro-1H-imidazol-2-yl)amino)methyl)-5-(6-fluoro-2-methylpyridin-3-yl)benzamide;
  3-(((4,5-dihydro-1H-imidazol-2-yl)amino)methyl)-N-(3,5-dimethoxybenzyl)-5-(6-fluoro-2-methylpyridin-3-yl)-N-methylbenzamide;
  N-(cyclopropyl(4-methylpyridin-2-yl)methyl)-3-(((4,5-dihydro-1H-imidazol-2-yl)amino)methyl)-5-(6-fluoro-2-methylpyridin-3-yl)benzamide;
  N-(dicyclopropylmethyl)-3-(((4,5-dihydro-1H-imidazol-2-yl)amino)methyl)-5-(6-fluoro-2-methylpyridin-3-yl)benzamide;
  3-(((4,5-dihydro-1H-imidazol-2-yl)amino)methyl)-5-(6-fluoro-2-methylpyridin-3-yl)-N-((4-methoxypyridin-2-yl)methyl)benzamide;
  N-(3,4-dichlorobenzyl)-3-(((4,5-dihydro-1H-imidazol-2-yl)amino)methyl)-5-(4-methylpyridin-3-yl)benzamide;
  3-(((4,5-dihydro-1H-imidazol-2-yl)amino)methyl)-N-(3,5-dimethoxybenzyl)-5-(4-methylpyridin-3-yl)benzamide;
  N-(3-chloro-4-methoxybenzyl)-3-(((4,5-dihydro-1H-imidazol-2-yl)amino)methyl)-5-(4-methylpyridin-3-yl)benzamide;
  3-(((4,5-dihydro-1H-imidazol-2-yl)amino)methyl)-N-(3,5-dimethoxybenzyl)-5-(2-methylpyridin-4-yl)benzamide;
  3-(((4,5-dihydro-1H-imidazol-2-yl)amino)methyl)-N-(3,4-dimethoxybenzyl)-5-(2-methylpyridin-4-yl)benzamide;
  N-(3,4-dichlorobenzyl)-3-(((4,5-dihydro-1H-imidazol-2-yl)amino)methyl)-5-(2-methylpyridin-4-yl)benzamide;
  N-(3-chloro-5-fluorobenzyl)-3-(((4,5-dihydro-1H-imidazol-2-yl)amino)methyl)-5-(2-methylpyridin-4-yl)benzamide;
  N-(4-chloro-3-methoxybenzyl)-3-(((4,5-dihydro-1H-imidazol-2-yl)amino)methyl)-5-(2-methylpyridin-4-yl)benzamide;
  N-(4-chloro-3-methoxybenzyl)-3-(((4,5-dihydro-1H-imidazol-2-yl)amino)methyl)-5-(4-methylpyridin-3-yl)benzamide;

3-(((4,5-dihydro-1H-imidazol-2-yl)amino)methyl)-N-((4-methoxypyridin-2-yl)methyl)-5-(4-methylpyridin-3-yl)benzamide;
3-(((4,5-dihydro-1H-imidazol-2-yl)amino)methyl)-N-(1-(3,5-dimethoxyphenyl)ethyl)-5-(4-methylpyridin-3-yl)benzamide;
3-(((4,5-dihydro-1H-imidazol-2-yl)amino)methyl)-N-((4-methoxypyridin-2-yl)methyl)-5-(2-methylpyridin-4-yl)benzamide;
N-(3,5-dichlorobenzyl)-3-(((4,5-dihydro-1H-imidazol-2-yl)amino)methyl)-5-(2-methylpyridin-4-yl)benzamide;
N-((4-chloropyridin-2-yl)methyl)-3-(((4,5-dihydro-1H-imidazol-2-yl)amino)methyl)-5-(2-methylpyridin-4-yl)benzamide;
N-(3-chloro-4-methoxybenzyl)-3-(((4,5-dihydro-1H-imidazol-2-yl)amino)methyl)-5-(2-methylpyridin-4-yl)benzamide;
N-(4-chloro-3-methylbenzyl)-3-(((4,5-dihydro-1H-imidazol-2-yl)amino)methyl)-5-(2-methylpyridin-4-yl)benzamide;
N-(3-chloro-5-fluorobenzyl)-3-(((4,5-dihydro-1H-imidazol-2-yl)amino)methyl)-5-(4-methylpyridin-3-yl)benzamide;
N-(cyclopropyl(4-methylpyridin-2-yl)methyl)-3-(((4,5-dihydro-1H-imidazol-2-yl)amino)methyl)-5-(4-methylpyridin-3-yl)benzamide;
N-(3,5-dichlorobenzyl)-3-(((4,5-dihydro-1H-imidazol-2-yl)amino)methyl)-5-(4-methylpyridin-3-yl)benzamide;
N-(4-chloro-3-methylbenzyl)-3-(((4,5-dihydro-1H-imidazol-2-yl)amino)methyl)-5-(4-methylpyridin-3-yl)benzamide;
3-(((4,5-dihydro-1H-imidazol-2-yl)amino)methyl)-N-((6-fluoropyridin-2-yl)methyl)-5-(4-methylpyridin-3-yl)benzamide;
3-(((4,5-dihydro-1H-imidazol-2-yl)amino)methyl)-N-(3,5-dimethylbenzyl)-5-(2-methylpyridin-4-yl)benzamide;
3-(((4,5-dihydro-1H-imidazol-2-yl)amino)methyl)-N-((6-methylpyridin-3-yl)methyl)-5-(2-methylpyridin-4-yl)benzamide;
N-((5-chloropyridin-2-yl)methyl)-3-(((4,5-dihydro-1H-imidazol-2-yl)amino)methyl)-5-(2-methylpyridin-4-yl)benzamide;
N-(dicyclopropylmethyl)-3-(((4,5-dihydro-1H-imidazol-2-yl)amino)methyl)-5-(4-methylpyridin-3-yl)benzamide;
3-(((4,5-dihydro-1H-imidazol-2-yl)amino)methyl)-5-(4-methylpyridin-3-yl)-N-((6-methylpyridin-3-yl)methyl)benzamide;
3-(((4,5-dihydro-1H-imidazol-2-yl)amino)methyl)-N-((6-fluoropyridin-2-yl)methyl)-5-(2-methylpyridin-4-yl)benzamide;
3-(((4,5-dihydro-1H-imidazol-2-yl)amino)methyl)-5-(2-methylpyridin-4-yl)-N-((4-methylpyrimidin-2-yl)methyl)benzamide;
3-(((4,5-dihydro-1H-imidazol-2-yl)amino)methyl)-N-(3,5-dimethoxybenzyl)-5-(6-fluoro-5-methylpyridin-3-yl)benzamide;
N-(4-chloro-3-methylbenzyl)-3-(((4,5-dihydro-1H-imidazol-2-yl)amino)methyl)-5-(6-fluoro-5-methylpyridin-3-yl)benzamide;
N-(3,4-dichlorobenzyl)-3-(((4,5-dihydro-1H-imidazol-2-yl)amino)methyl)-5-(6-fluoro-5-methylpyridin-3-yl)benzamide;
N-(3,4-dichlorobenzyl)-3-(((4,5-dihydro-1H-imidazol-2-yl)amino)methyl)-5-(m-tolyloxy)benzamide;
3-(((4,5-dihydro-1H-imidazol-2-yl)amino)methyl)-N-(1-(3,5-dimethoxyphenyl)ethyl)-5-(trifluoromethyl)benzamide;
3-(5-chloro-6-methoxypyridin-3-yl)-5-(((4,5-dihydro-1H-imidazol-2-yl)amino)methyl)-N-(3,5-dimethoxybenzyl)benzamide;
3-(5-chloro-6-fluoropyridin-3-yl)-5-(((4,5-dihydro-1H-imidazol-2-yl)amino)methyl)-N-(3,5-dimethoxybenzyl)benzamide;
3-(((4,5-dihydro-1H-imidazol-2-yl)amino)methyl)-5-(6-fluoro-2-methylpyridin-3-yl)-N-((5-methylpyrazin-2-yl)methyl)benzamide;
3-(((4,5-dihydro-1H-imidazol-2-yl)amino)methyl)-5-(6-fluoro-2-methylpyridin-3-yl)-N-((2-methylpyrimidin-5-yl)methyl)benzamide;
N-((4-chloropyridin-2-yl)methyl)-3-(((4,5-dihydro-1H-imidazol-2-yl)amino)methyl)-5-(2-fluoro-5-methylpyridin-3-yl)benzamide;
3-(((4,5-dihydro-1H-imidazol-2-yl)amino)methyl)-N-(3,4-dimethoxybenzyl)-5-(2-fluoro-5-methylpyridin-3-yl)benzamide;
N-(cyclopropyl(4-methylpyridin-2-yl)methyl)-3-(((4,5-dihydro-1H-imidazol-2-yl)amino)methyl)-5-(2-fluoro-5-methylpyridin-3-yl)benzamide;
3-(((4,5-dihydro-1H-imidazol-2-yl)amino)methyl)-N-(3,5-dimethoxybenzyl)-5-(2-fluoro-5-methylpyridin-3-yl)benzamide;
3-(((4,5-dihydro-1H-imidazol-2-yl)amino)methyl)-5-(2-fluoro-5-methylpyridin-3-yl)-N,N-dimethylbenzamide;
N-((4-chloropyridin-2-yl)methyl)-3-(((4,5-dihydro-1H-imidazol-2-yl)amino)methyl)-5-(2,6-dimethylpyridin-4-yl)benzamide;
N-(4-chloro-3-methylbenzyl)-3-(((4,5-dihydro-1H-imidazol-2-yl)amino)methyl)-5-(2,6-dimethylpyridin-4-yl)benzamide;
N-(4-chloro-3-methylbenzyl)-3-(((4,5-dihydro-1H-imidazol-2-yl)amino)methyl)-5-(2-fluoro-5-methylpyridin-3-yl)benzamide;
5-(((4,5-dihydro-1H-imidazol-2-yl)amino)methyl)-4'-fluoro-N-((4-methoxypyridin-2-yl)methyl)-2'-methyl-[1,1'-biphenyl]-3-carboxamide;
5-(((4,5-dihydro-1H-imidazol-2-yl)amino)methyl)-2',5'-dimethoxy-N-((4-methoxypyridin-2-yl)methyl)-[1,1'-biphenyl]-3-carboxamide;
5'-chloro-5-(((4,5-dihydro-1H-imidazol-2-yl)amino)methyl)-2'-methoxy-N-((4-methoxypyridin-2-yl)methyl)-[1,1'-biphenyl]-3-carboxamide;
5-(((4,5-dihydro-1H-imidazol-2-yl)amino)methyl)-5'-isopropyl-2'-methoxy-N-((4-methoxypyridin-2-yl)methyl)-[1,1'-biphenyl]-3-carboxamide;
3-(((4,5-dihydro-1H-imidazol-2-yl)amino)methyl)-5-(2-methoxy-5-(trifluoromethyl)pyridin-3-yl)-N-((4-methoxypyridin-2-yl)methyl)benzamide;
5-(((4,5-dihydro-1H-imidazol-2-yl)amino)methyl)-4'-fluoro-N-((4-methoxypyridin-2-yl)methyl)-2'-(trifluoromethyl)-[1,1'-biphenyl]-3-carboxamide;
3-(((4,5-dihydro-1H-imidazol-2-yl)amino)methyl)-5-(5-fluoro-2-methoxypyridin-3-yl)-N-((4-methoxypyridin-2-yl)methyl)benzamide;
5-(((4,5-dihydro-1H-imidazol-2-yl)amino)methyl)-4'-fluoro-2'-methoxy-N-((4-methoxypyridin-2-yl)methyl)-[1,1'-biphenyl]-3-carboxamide;
5-(((4,5-dihydro-1H-imidazol-2-yl)amino)methyl)-4'-fluoro-2'-methoxy-N-((4-methoxypyridin-2-yl)methyl)-5'-methyl-[1,1'-biphenyl]-3-carboxamide;

5-(((4,5-dihydro-1H-imidazol-2-yl)amino)methyl)-4'-fluoro-N-((4-methoxypyridin-2-yl)methyl)-2',5'-dimethyl-[1,1'-biphenyl]-3-carboxamide;

N-(3,4-dichlorobenzyl)-3-(((3,4-dihydro-2H-pyrrol-5-yl)amino)methyl)-5-(6-fluoro-2-methylpyridin-3-yl)benzamide;

3-(((3,4-dihydro-2H-pyrrol-5-yl)amino)methyl)-5-(6-fluoro-2-methylpyridin-3-yl)-N-((4-methoxypyridin-2-yl)methyl)benzamide;

N-(1-(5-chloro-4-methylpyridin-2-yl)ethyl)-3-(((3,4-dihydro-2H-pyrrol-5-yl)amino)methyl)-5-(6-fluoro-2-methylpyridin-3-yl)benzamide;

N-(4-chloro-3-methylbenzyl)-3-(((3,4-dihydro-2H-pyrrol-5-yl)amino)methyl)-5-(6-fluoro-2-methylpyridin-3-yl)benzamide;

3-(((3,4-dihydro-2H-pyrrol-5-yl)amino)methyl)-N-(1-(3,5-dimethoxyphenyl)ethyl)-5-(6-fluoro-2-methylpyridin-3-yl)benzamide;

3-(((3,4-dihydro-2H-pyrrol-5-yl)amino)methyl)-N-(3,5-dimethoxybenzyl)-5-(6-fluoro-2-methylpyridin-3-yl)-N-methylbenzamide;

3-(((3,4-dihydro-2H-pyrrol-5-yl)amino)methyl)-N-(3,5-dimethoxybenzyl)-5-(2-methylpyridin-4-yl)benzamide;

3-(((3,4-dihydro-2H-pyrrol-5-yl)amino)methyl)-N-(3,5-dimethoxybenzyl)-5-(1-methyl-1H-pyrrol-2-yl)benzamide;

5-(((3,4-dihydro-2H-pyrrol-5-yl)amino)methyl)-N-(3,5-dimethoxybenzyl)-4'-fluoro-2'-methyl-[1,1'-biphenyl]-3-carboxamide;

3-(((3,4-dihydro-2H-pyrrol-5-yl)amino)methyl)-N-(3,5-dimethoxybenzyl)-5-(6-fluoro-2-methylpyridin-3-yl)benzamide;

3-(((3,4-dihydro-2H-pyrrol-5-yl)amino)methyl)-N-(3,5-dimethoxybenzyl)-5-(3-methylpyridin-4-yl)benzamide;

5-(((3,4-dihydro-2H-pyrrol-5-yl)amino)methyl)-N-(3,5-dimethoxybenzyl)-4'-fluoro-2',5'-dimethyl-[1,1'-biphenyl]-3-carboxamide;

N-(4-chloro-3-methylbenzyl)-5-(((3,4-dihydro-2H-pyrrol-5-yl)amino)methyl)-3'-(hydroxymethyl)-[1,1'-biphenyl]-3-carboxamide;

N-(4-chloro-3-methylbenzyl)-5-(((3,4-dihydro-2H-pyrrol-5-yl)amino)methyl)-4'-fluoro-2'-methyl-[1,1'-biphenyl]-3-carboxamide;

N-(4-chloro-3-methylbenzyl)-5-(((3,4-dihydro-2H-pyrrol-5-yl)amino)methyl)-4'-fluoro-3'-(hydroxymethyl)-[1,1'-biphenyl]-3-carboxamide;

N-(4-chloro-3-methylbenzyl)-5-(((3,4-dihydro-2H-pyrrol-5-yl)amino)methyl)-4'-fluoro-2',5'-dimethyl-[1,1'-biphenyl]-3-carboxamide;

N-(4-chloro-3-methylbenzyl)-3-(((3,4-dihydro-2H-pyrrol-5-yl)amino)methyl)-5-(2-(trifluoromethyl)pyridin-3-yl)benzamide;

N-(4-chloro-3-methylbenzyl)-5-(((3,4-dihydro-2H-pyrrol-5-yl)amino)methyl)-4'-fluoro-2'-(trifluoromethyl)-[1,1'-biphenyl]-3-carboxamide;

N-(4-chloro-3-methylbenzyl)-5-(((3,4-dihydro-2H-pyrrol-5-yl)amino)methyl)-4'-fluoro-2'-methoxy-5'-methyl-[1,1'-biphenyl]-3-carboxamide;

N-(4-chloro-3-methylbenzyl)-5-(((3,4-dihydro-2H-pyrrol-5-yl)amino)methyl)-4'-fluoro-2'-methoxy-[1,1'-biphenyl]-3-carboxamide;

N-(4-chloro-3-methylbenzyl)-3-(6-fluoro-2-methylpyridin-3-yl)-5-(((1-methyl-4-oxo-4,5-dihydro-1H-imidazol-2-yl)amino)methyl)benzamide;

N-(1-(3,5-dimethoxyphenyl)ethyl)-3-(6-fluoro-2-methylpyridin-3-yl)-5-(((1-methyl-4-oxo-4,5-dihydro-1H-imidazol-2-yl)amino)methyl)benzamide;

N-(3,4-dichlorobenzyl)-3-(6-fluoro-2-methylpyridin-3-yl)-5-(((1-methyl-4-oxo-4,5-dihydro-1H-imidazol-2-yl)amino)methyl)benzamide;

5-(((4,5-dihydro-1H-imidazol-2-yl)amino)methyl)-N-(1-(3,5-dimethoxyphenyl)ethyl)-4'-fluoro-2'-methyl-[1,1'-biphenyl]-3-carboxamide;

2-amino-5-(((3,4-dihydro-2H-pyrrol-5-yl)amino)methyl)-N-(3,5-dimethoxybenzyl)-4'-fluoro-2'-methyl-[1,1'-biphenyl]-3-carboxamide;

2-amino-5-(((4,5-dihydro-1H-imidazol-2-yl)amino)methyl)-N-(3,5-dimethoxybenzyl)-4'-fluoro-2'-methyl-[1,1'-biphenyl]-3-carboxamide;

5-(((3,4-dihydro-2H-pyrrol-5-yl)amino)methyl)-N-(3,5-dimethoxybenzyl)-4'-fluoro-N,2'-dimethyl-2-(methylamino)-[1,1'-biphenyl]-3-carboxamide;

5-(((4,5-dihydro-1H-imidazol-2-yl)amino)methyl)-N-(3,5-dimethoxybenzyl)-4'-fluoro-N,2'-dimethyl-2-(methylamino)-[1,1'-biphenyl]-3-carboxamide;

2-acetamido-5-(((3,4-dihydro-2H-pyrrol-5-yl)amino)methyl)-N-(3,5-dimethoxybenzyl)-4'-fluoro-2'-methyl-[1,1'-biphenyl]-3-carboxamide;

2-acetamido-5-(((4,5-dihydro-1H-imidazol-2-yl)amino)methyl)-N-(3,5-dimethoxybenzyl)-4'-fluoro-2'-methyl-[1,1'-biphenyl]-3-carboxamide;

(S)—N-(cyclopropyl(4-fluoro-3-methylphenyl)methyl)-5-(((4,5-dihydrooxazol-2-yl)amino)methyl)-4'-fluoro-2'-(trifluoromethyl)-[1,1'-biphenyl]-3-carboxamide;

(S)—N-(cyclopropyl(4-fluoro-3-methylphenyl)methyl)-3-(((4,5-dihydrooxazol-2-yl)amino)methyl)-5-(1-ethyl-3-(trifluoromethyl)-1H-pyrazol-4-yl)benzamide;

N-(3,4-dichlorobenzyl)-4-(((4,5-dihydro-1H-imidazol-2-yl)amino)methyl)-6'-fluoro-2'-methyl-[2,3'-bipyridine]-6-carboxamide;

N-(3,4-dichlorobenzyl)-4-(((4,5-dihydro-1H-imidazol-2-yl)amino)methyl)-2',6'-difluoro-[2,3'-bipyridine]-6-carboxamide;

N-(4-chloro-3-fluorobenzyl)-4-(((4,5-dihydro-1H-imidazol-2-yl)amino)methyl)-6'-fluoro-2'-methyl-[2,3'-bipyridine]-6-carboxamide;

4-(((4,5-dihydro-1H-imidazol-2-yl)amino)methyl)-6'-fluoro-2'-methyl-N-((6-oxo-1,6-dihydropyridin-3-yl)methyl)-[2,3'-bipyridine]-6-carboxamide;

N-(4-chloro-3-methylbenzyl)-4-(((4,5-dihydro-1H-imidazol-2-yl)amino)methyl)-6'-fluoro-2'-methyl-[2,3'-bipyridine]-6-carboxamide;

4-(((4,5-dihydro-1H-imidazol-2-yl)amino)methyl)-N-(1-(3,5-dimethoxyphenyl)ethyl)-6'-fluoro-2'-methyl-[2,3'-bipyridine]-6-carboxamide;

4-(((4,5-dihydro-1H-imidazol-2-yl)amino)methyl)-6'-fluoro-2'-methyl-N-((5-methylpyrazin-2-yl)methyl)-[2,3'-bipyridine]-6-carboxamide;

4-(((4,5-dihydro-1H-imidazol-2-yl)amino)methyl)-6'-fluoro-2'-methyl-N-((5-methylpyrimidin-2-yl)methyl)-[2,3'-bipyridine]-6-carboxamide;

4-(((4,5-dihydro-1H-imidazol-2-yl)amino)methyl)-N-(3,5-dimethoxybenzyl)-6'-fluoro-2'-methyl-[2,3'-bipyridine]-6-carboxamide;

4-(((4,5-dihydro-1H-imidazol-2-yl)amino)methyl)-6'-fluoro-N-((2-methoxypyridin-4-yl)methyl)-2'-methyl-[2,3'-bipyridine]-6-carboxamide;

4-(((4,5-dihydro-1H-imidazol-2-yl)amino)methyl)-6'-fluoro-2'-methyl-N-((2-methylpyrimidin-5-yl)methyl)-[2,3'-bipyridine]-6-carboxamide;

N-(3,4-dichlorobenzyl)-4-(((4,5-dihydro-1H-imidazol-2-yl)amino)methyl)-4'-methyl-[2,3'-bipyridine]-6-carboxamide;
N-(3,4-dichlorobenzyl)-4-(((4,5-dihydro-1H-imidazol-2-yl)amino)methyl)-2'-methyl-[2,4'-bipyridine]-6-carboxamide;
N-(3,4-dichlorobenzyl)-4-(((4,5-dihydro-1H-imidazol-2-yl)amino)methyl)-2'-methoxy-5'-methyl-[2,3'-bipyridine]-6-carboxamide;
N-(3,4-dichlorobenzyl)-4-(((4,5-dihydro-1H-imidazol-2-yl)amino)methyl)-3'-methyl-[2,4'-bipyridine]-6-carboxamide;
4-(((4,5-dihydro-1H-imidazol-2-yl)amino)methyl)-N-((4,6-dimethylpyrimidin-2-yl)methyl)-6'-fluoro-2'-methyl-[2,3'-bipyridine]-6-carboxamide;
5'-chloro-N-(3,4-dichlorobenzyl)-4-(((4,5-dihydro-1H-imidazol-2-yl)amino)methyl)-2'-methoxy-[2,3'-bipyridine]-6-carboxamide;
N-(3,4-dichlorobenzyl)-4-(((4,5-dihydro-1H-imidazol-2-yl)amino)methyl)-6-(2-methoxy-5-methylphenyl)picolinamide;
N-(3,4-dichlorobenzyl)-4-(((4,5-dihydro-1H-imidazol-2-yl)amino)methyl)-2'-ethoxy-5'-methyl-[2,3'-bipyridine]-6-carboxamide;
N-(3,4-dichlorobenzyl)-4-(((3,4-dihydro-2H-pyrrol-5-yl)amino)methyl)-6-(4-fluoro-2-methylphenyl)picolinamide;
N-(4-chloro-3-methylbenzyl)-4-(((3,4-dihydro-2H-pyrrol-5-yl)amino)methyl)-6-(4-fluoro-2-methylphenyl)picolinamide;
4-(((3,4-dihydro-2H-pyrrol-5-yl)amino)methyl)-N-(3,5-dimethoxybenzyl)-6-(4-fluoro-2-methylphenyl)picolinamide;
N-(3,4-dichlorobenzyl)-4-(((3,4-dihydro-2H-pyrrol-5-yl)amino)methyl)-6-(4-fluoro-2-(trifluoromethyl)phenyl)picolinamide;
N-(cyclopropyl(4-methylpyridin-2-yl)methyl)-4-(((3,4-dihydro-2H-pyrrol-5-yl)amino)methyl)-6-(4-fluoro-2-(trifluoromethyl)phenyl)picolinamide;
2-(((3,4-dihydro-2H-pyrrol-5-yl)amino)methyl)-A-(3,5-dimethoxybenzyl)-6-(4-fluoro-2-(trifluoromethyl)phenyl)isonicotinamide;
4-(((3,4-dihydro-2H-pyrrol-5-yl)amino)methyl)-N-(3,5-dimethoxybenzyl)-6-(4-fluoro-2-(trifluoromethyl)phenyl)picolinamide;
(S)—N-(1-(4-chloro-3-methylphenyl)ethyl)-4-(((3,4-dihydro-2H-pyrrol-5-yl)amino)methyl)-6-(4-fluoro-2-(trifluoromethyl)phenyl)picolinamide;
4-(((3,4-dihydro-2H-pyrrol-5-yl)amino)methyl)-N-(1-(3,5-dimethoxyphenyl)ethyl)-6-(4-fluoro-2-(trifluoromethyl)phenyl)picolinamide;
4-(((3,4-dihydro-2H-pyrrol-5-yl)amino)methyl)-6-(4-fluoro-2-(trifluoromethyl)phenyl)-N-((4-methoxypyridin-2-yl)methyl)picolinamide;
N-(cyclopropyl(4-methylpyridin-2-yl)methyl)-4-(((3,4-dihydro-2H-pyrrol-5-yl)amino)methyl)-6-(4-fluoro-2-methylphenyl)picolinamide;
N-(1-(5-chloro-4-methylpyridin-2-yl)ethyl)-4-(((3,4-dihydro-2H-pyrrol-5-yl)amino)methyl)-6-(4-fluoro-2-(trifluoromethyl)phenyl)picolinamide;
N-(1-(4-chloro-5-methylpyridin-2-yl)ethyl)-4-(((3,4-dihydro-2H-pyrrol-5-yl)amino)methyl)-6-(4-fluoro-2-(trifluoromethyl)phenyl)picolinamide;
(S)-4-(((3,4-dihydro-2H-pyrrol-5-yl)amino)methyl)-6-(4-fluoro-2-methylphenyl)-N-(1-(4-fluoro-3-(trifluoromethyl)phenyl)ethyl)picolinamide;
(S)-6-(2-chloro-4-fluorophenyl)-4-(((3,4-dihydro-2H-pyrrol-5-yl)amino)methyl)-N-(1-(4-fluoro-3-methylphenyl)ethyl)picolinamide;
(S)-6-(2-chloro-4-fluorophenyl)-N-(cyclopropyl(4-fluoro-3-methylphenyl)methyl)-4-(((3,4-dihydro-2H-pyrrol-5-yl)amino)methyl)picolinamide;
(S)-6-(2-chloro-4-fluorophenyl)-N-(1-(4-fluoro-3-methylphenyl)ethyl)-4-(((1-methyl-4-oxo-4,5-dihydro-1H-imidazol-2-yl)amino)methyl)picolinamide;
(S)-6-(2-chloro-4-fluorophenyl)-N-(cyclopropyl(4-fluoro-3-methylphenyl)methyl)-4-(((1-methyl-4-oxo-4,5-dihydro-1H-imidazol-2-yl)amino)methyl)picolinamide;
3-((1H-imidazol-1-yl)methyl)-5-chloro-N-(3,5-dichlorobenzyl)benzamide;
3-((1H-imidazol-1-yl)methyl)-5-chloro-N-(3,5-dimethoxybenzyl)benzamide;
3-((1H-imidazol-1-yl)methyl)-5-chloro-N-(3-chloro-4-methylbenzyl)benzamide;
3-((1H-imidazol-1-yl)methyl)-N-(4-chloro-3-methylbenzyl)-5-methoxybenzamide;
methyl 3-(3-((1H-imidazol-1-yl)methyl)-5-chlorobenzamido)-3-(3-chlorophenyl)propanoate;
3-((1H-imidazol-1-yl)methyl)-N-(4-chloro-3-methylbenzyl)-5-(cyclopentyloxy)benzamide;
5-((1H-imidazol-1-yl)methyl)-2'-chloro-N-(3,4-dichlorobenzyl)-4'-fluoro-[1,1'-biphenyl]-3-carboxamide;
5-((1H-imidazol-1-yl)methyl)-N-(3,4-dichlorobenzyl)-2'-methoxy-[1,1'-biphenyl]-3-carboxamide;
3-((1H-imidazol-1-yl)methyl)-N-(3,4-dichlorobenzyl)-5-(pyridin-3-yl)benzamide;
3-((1H-imidazol-1-yl)methyl)-N-(3,4-dichlorobenzyl)-5-(furan-2-yl)benzamide;
3-((1H-imidazol-1-yl)methyl)-N-(3,5-dimethoxybenzyl)-5-phenoxybenzamide;
3-((1H-imidazol-1-yl)methyl)-N-(3,4-dichlorobenzyl)-5-(4-methylpyridin-3-yl)benzamide;
5-((1H-imidazol-1-yl)methyl)-2'-chloro-N-(3,4-dichlorobenzyl)-5'-methyl-[1,1'-biphenyl]-3-carboxamide;
3-((1H-imidazol-1-yl)methyl)-N-(3,4-dichlorobenzyl)-5-(2-methylpyridin-4-yl)benzamide;
5-((1H-imidazol-1-yl)methyl)-N-(3,4-dichlorobenzyl)-2'-(trifluoromethyl)-[1,1'-biphenyl]-3-carboxamide;
3-((1H-imidazol-1-yl)methyl)-5-(3-chloropyridin-4-yl)-N-(3,4-dichlorobenzyl)benzamide;
3-((1H-imidazol-1-yl)methyl)-N-(3,4-dichlorobenzyl)-5-(6-fluoro-2-methylpyridin-3-yl)benzamide;
5-((1H-imidazol-1-yl)methyl)-N-(3,4-dichlorobenzyl)-4'-fluoro-2'-(trifluoromethyl)-[1,1'-biphenyl]-3-carboxamide;
3-((1H-imidazol-1-yl)methyl)-N-(3,4-dichlorobenzyl)-5-(5-methoxypyridin-3-yl)benzamide;
3-((1H-imidazol-1-yl)methyl)-N-(3,4-dichlorobenzyl)-5-(3-methoxypyridin-4-yl)benzamide;
3-((1H-imidazol-1-yl)methyl)-N-(3,5-dimethoxybenzyl)-5-(2-methylfuran-3-yl)benzamide;
3-((1H-imidazol-1-yl)methyl)-N-(3,4-dichlorobenzyl)-5-(1-methyl-1H-pyrazol-5-yl)benzamide;
3-((1H-imidazol-1-yl)methyl)-N-(1-cyclohexylethyl)-5-(6-fluoro-2-methylpyridin-3-yl)benzamide;
3-((1H-imidazol-1-yl)methyl)-N-(dicyclopropylmethyl)-5-(6-fluoro-2-methylpyridin-3-yl)benzamide;
2'-chloro-N-(3,4-dichlorobenzyl)-4'-fluoro-5-((2-methyl-1H-imidazol-1-yl)methyl)-[1,1'-biphenyl]-3-carboxamide;

2'-chloro-N-(3,4-dichlorobenzyl)-4'-fluoro-5-((2-(trifluoromethyl)-1H-imidazol-1-yl)methyl)-[1,1'-biphenyl]-3-carboxamide;
3-((1H-imidazol-1-yl)methyl)-N-(3,4-dichlorobenzyl)-5-(pyrrolidin-1-yl)benzamide;
3-((1H-imidazol-1-yl)methyl)-N-(cyclopropyl(4-methylpyridin-2-yl)methyl)-5-(6-fluoro-2-methylpyridin-3-yl)benzamide;
5-((1H-imidazol-1-yl)methyl)-2'-chloro-4'-fluoro-N-(1-methylcyclopentyl)-[1,1'-biphenyl]-3-carboxamide;
3-((2-cyclopropyl-1H-imidazol-1-yl)methyl)-N-(3,4-dichlorobenzyl)-5-(6-fluoro-2-methylpyridin-3-yl)benzamide;
3-((1H-imidazol-1-yl)methyl)-N-(3,5-dimethoxybenzyl)-5-(6-fluoro-2-methylpyridin-3-yl)-N-methylbenzamide;
3-((1H-imidazol-1-yl)methyl)-N-(3,4-dichlorobenzyl)-5-(trifluoromethyl)benzamide;
3-((1H-imidazol-1-yl)methyl)-5-cyclobutoxy-N-(3,4-dichlorobenzyl)benzamide;
3-cyclobutoxy-N-(3,4-dichlorobenzyl)-5-((2-methyl-1H-imidazol-1-yl)methyl)benzamide;
N-(cyclopropyl(4-methylpyridin-2-yl)methyl)-3-((2-methyl-1H-imidazol-1-yl)methyl)-5-morpholinobenzamide;
3-((1H-imidazol-1-yl)methyl)-N-(3,5-dimethoxybenzyl)-5-(6-oxo-1,6-dihydropyridin-3-yl)benzamide;
4-methoxy-N-((4-methoxypyridin-2-yl)methyl)-3-methyl-5-((2-methyl-1H-imidazol-1-yl)methyl)benzamide;
N-(3,4-dichlorobenzyl)-3'-(hydroxymethyl)-5-((2-methyl-1H-imidazol-1-yl)methyl)-[1,1'-biphenyl]-3-carboxamide;
4-((1H-imidazol-1-yl)methyl)-6-(2-chloro-4-fluorophenyl)-N-(3,5-dichlorobenzyl)picolinamide;
4-((1H-imidazol-1-yl)methyl)-6-(2-chloro-4-fluorophenyl)-N-(2-cyclopropylpropan-2-yl)picolinamide;
4-((1H-imidazol-1-yl)methyl)-6-(2-chloro-4-fluorophenyl)-N-(cyclopropyl(4-methylpyridin-2-yl)methyl)picolinamide;
4-((1H-imidazol-1-yl)methyl)-6-(2-chloro-4-fluorophenyl)-N-((6-methylpyridin-2-yl)methyl)picolinamide;
4-((1H-imidazol-1-yl)methyl)-6-(2-chloro-4-fluorophenyl)-N-(1-cyclopropylpropyl)picolinamide;
4-((1H-imidazol-1-yl)methyl)-6-(2-chloro-4-fluorophenyl)-N-(3,5-dimethylbenzyl)picolinamide;
4-((1H-imidazol-1-yl)methyl)-6-(2-chloro-4-fluorophenyl)-N-(1-(3,5-dimethoxyphenyl)ethyl)picolinamide;
4-((1H-imidazol-1-yl)methyl)-6-(2-chloro-4-fluorophenyl)-N-(1-(pyridin-2-yl)ethyl)picolinamide;
N-(3,4-dichlorobenzyl)-6-(4-fluoro-2-methylphenyl)-4-((2-methyl-1H-imidazol-1-yl)methyl)picolinamide;
N-(1-(3,5-dimethoxyphenyl)ethyl)-6-(3-(hydroxymethyl)phenyl)-4-((2-methyl-1H-imidazol-1-yl)methyl)picolinamide;
N-(1-(3,5-dimethoxyphenyl)ethyl)-6-(4-fluoro-2-methoxyphenyl)-4-((2-methyl-1H-imidazol-1-yl)methyl)picolinamide;
N-(1-(3,5-dimethoxyphenyl)ethyl)-6'-fluoro-2'-methyl-4-((2-methyl-1H-imidazol-1-yl)methyl)-[2,3'-bipyridine]-6-carboxamide;
N-(1-(3,5-dimethoxyphenyl)ethyl)-6-(2-methoxy-5-(trifluoromethyl)phenyl)-4-((2-methyl-1H-imidazol-1-yl)methyl)picolinamide;
6-(3-carbamoyl-4-fluorophenyl)-N-(1-(3,5-dimethoxyphenyl)ethyl)-4-((2-methyl-1H-imidazol-1-yl)methyl)picolinamide;
N-(3,4-dichlorobenzyl)-2'-methoxy-4-((2-methyl-1H-imidazol-1-yl)methyl)-[2,3'-bipyridine]-6-carboxamide;
N-(1-(3,5-dimethoxyphenyl)ethyl)-6-(4-fluoro-3-(hydroxymethyl)phenyl)-4-((2-methyl-1H-imidazol-1-yl)methyl)picolinamide;
N-(3,4-dichlorobenzyl)-6'-fluoro-2'-methyl-4-((2-methyl-1H-imidazol-1-yl)methyl)-[2,3'-bipyridine]-6-carboxamide;
N-(3,4-dichlorobenzyl)-6-(4-fluoro-2-methoxyphenyl)-4-((2-methyl-1H-imidazol-1-yl)methyl)picolinamide;
N-(3,4-dichlorobenzyl)-3'-methyl-4-((2-methyl-1H-imidazol-1-yl)methyl)-[2,4'-bipyridine]-6-carboxamide; and
6-(3-carbamoyl-4-fluorophenyl)-N-(3,4-dichlorobenzyl)-4-((2-methyl-1H-imidazol-1-yl)methyl)picolinamide;
or a pharmaceutically acceptable salt or tautomer thereof.

16. A pharmaceutical composition comprising the compound of claim 1, or a pharmaceutically acceptable salt or tautomer thereof, and a pharmaceutically acceptable carrier.

17. A method of treating cancer comprising administering to a subject in need thereof, a therapeutically effective amount of the compound of claim 1, or pharmaceutically acceptable salt or tautomer thereof wherein the cancer is selected from the group consisting of leukemia, ovarian cancer, breast cancer, gastric cancer, lung cancer, cancers of the blood, cancers of the lymphatic system, and neuroblastoma.

18. A method of inhibiting cancer cell proliferation comprising administering to a subject in need thereof, a therapeutically effective amount of the compound of claim 1, or a pharmaceutically acceptable salt or tautomer thereof wherein the cancer cell is from a cancer selected from the group consisting of leukemia, ovarian cancer, breast cancer, gastric cancer, lung cancer, cancers of the blood, cancers of the lymphatic system, and neuroblastoma.

* * * * *